(12) United States Patent
Greenwood et al.

(10) Patent No.: US 11,053,241 B2
(45) Date of Patent: Jul. 6, 2021

(54) TYK2 INHIBITORS AND USES THEREOF

(71) Applicant: Nimbus Lakshmi, Inc., Cambridge, MA (US)

(72) Inventors: Jeremy Robert Greenwood, Brooklyn, NY (US); Craig E. Masse, Cambridge, MA (US)

(73) Assignee: Nimbus Lakshmi, Inc., Cambridge, MA (US)

(*) Notice: Subject to any disclaimer, the term of this patent is extended or adjusted under 35 U.S.C. 154(b) by 71 days.

(21) Appl. No.: 16/697,371

(22) Filed: Nov. 27, 2019

(65) Prior Publication Data

US 2020/0172540 A1 Jun. 4, 2020

Related U.S. Application Data

(60) Provisional application No. 62/773,620, filed on Nov. 30, 2018.

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC .......................... C07D 471/04; C07D 519/00
USPC ...................................................... 514/210.18
See application file for complete search history.

(56) References Cited

U.S. PATENT DOCUMENTS

| | | | |
|---|---|---|---|
| 4,650,750 A | 3/1987 | Giese | |
| 4,709,016 A | 11/1987 | Giese | |
| 5,360,819 A | 11/1994 | Giese | |
| 5,516,931 A | 5/1996 | Giese | |
| 5,602,273 A | 2/1997 | Giese | |
| 5,604,104 A | 2/1997 | Giese | |
| 5,610,020 A | 3/1997 | Giese | |
| 5,650,270 A | 7/1997 | Giese | |
| 6,552,065 B2 | 4/2003 | Remiszewski | |
| 7,390,799 B2 | 6/2008 | Bruncko | |
| 7,589,206 B2 * | 9/2009 | Eatherton | A61P 35/00 546/113 |
| 8,138,347 B2 | 3/2012 | Knight | |
| 2017/0057968 A1 | 3/2017 | Li | |
| 2018/0037570 A1 | 2/2018 | Sherer | |

FOREIGN PATENT DOCUMENTS

| | | |
|---|---|---|
| WO | WO 2001/042246 | 6/2001 |
| WO | WO 2002/088112 | 11/2002 |
| WO | WO 2003/063794 | 8/2003 |
| WO | WO 2004/019973 | 3/2004 |
| WO | WO 2004/089925 | 10/2004 |
| WO | WO 2004/106328 | 12/2004 |
| WO | WO 2005/007623 | 1/2005 |
| WO | WO 2005/113554 | 12/2005 |
| WO | WO 2006/078846 | 7/2006 |
| WO | WO 2006/122806 | 11/2006 |
| WO | WO 2007/016176 | 2/2007 |
| WO | WO 2007/044729 | 4/2007 |
| WO | WO 2007/053452 | 5/2007 |
| WO | WO 2007/070514 | 6/2007 |
| WO | WO 2007/084786 | 7/2007 |
| WO | WO 2007/129161 | 11/2007 |
| WO | WO 2008/039218 | 4/2008 |
| WO | WO 2008/109943 | 9/2008 |
| WO | WO 2008/118802 | 10/2008 |
| WO | WO 2009/114512 | 9/2009 |
| WO | WO 2011/090760 | 7/2011 |
| WO | WO 2014/074660 A1 | 5/2014 |
| WO | WO 2014/074661 A1 | 5/2014 |
| WO | WO 2015/089143 A1 | 6/2015 |
| WO | WO 2015/131080 A1 | 9/2015 |
| WO | WO 2018/089695 | 5/2018 |

OTHER PUBLICATIONS

Bacon et al., "Interleukin 12 (IL-12) induces tyrosine phosphorylation of Jak2 and Tyk2: differential use of Janus family kinases by IL-2 and IL-12," The Journal of Experimental Medicine, vol. 181, No. 1, Jan. 1995 (pp. 399-404).
Ban et al., "Replication analysis identifies TYK2 as a multiple sclerosis susceptibility factor," European Journal of Human Genetics, vol. 17, No. 10, Oct. 2009 (pp. 1309-1313).
Berge et al., "Pharmaceutical salts," Journal Pharmaceutical Sciences, vol. 66, No. 1, Jan. 1977 (pp. 1-19).
Cho et al., "Genomics and the multifactorial nature of human auto-immune disease," The New England Journal Medicine, vol. 365, No. 17, Oct. 2011 (pp. 1612-1623).
Cortes et al., "Identification of multiple risk variants for ankylosing spondylitis through high-density genotyping of immune-related loci," Nature Genetics, vol. 45, No. 7, Jul. 2013 (pp. 730-738).
Duerr et al., "A Genome-Wide Association Study Identifies IL23R as an Inflammatory Bowel Disease Gene," Science, vol. 314, No. 5804, Dec. 2006 (pp. 1461-1463).
Finbloom et al., "IL-10 induces the tyrosine phosphorylation of Tyk2 and Jak1 and the differential assembly of Stat1 and Stat3 complexes in human T cells and monocytes," Journal immunology, vol. 155, No. 3, Aug. 1995 (pp. 1079-1090).
Fontan et al. "Discovering What Makes STAT Signaling TYK in T-ALL," Cancer Discovery, vol. 3, No. 5, May 2013 (pp. 494-496).
Graham et al., "Association of NCF2, IKZF1, IRF8, IFIH1, and TYK2 with Systemic Lupus Erythematosus," PLoS Genetics, vol. 7, No. 10, Oct. 2011 (9 pages).
Harel et al., "Pharmacologic inhibition of JAK-STAT signaling promotes hair growth," Science Advances, vol. 1, No. 9, Oct. 2015 (12 pages).
International Search Report and Written Opinion for Application No. PCT/US2019/063510, dated Mar. 11, 2020 (16 pages).

(Continued)

*Primary Examiner* — Niloofar Rahmani
(74) *Attorney, Agent, or Firm* — Andrea L. C. Reid; Paul R. Fleming; Dechert LLP

(57) ABSTRACT

The present invention provides compounds, compositions thereof, and methods of using the same for the inhibition of TYK2, and the treatment of TYK2-mediated disorders.

20 Claims, No Drawings

(56) References Cited

OTHER PUBLICATIONS

Ishizaki et al., "Tyk2 deficiency protects joints against destruction in anti-type II collagen antibody-induced arthritis in mice," International Immunology, vol. 23, No. 9, Sep. 2011 (pp. 575-582).

Ishizaki et al., "Tyk2 is a therapeutic target for psoriasis-like skin inflammation," International Immunology, vol. 26, No. 5, Dec. 2013 (pp. 257-267).

Oyamada et al., "Tyrosine Kinase 2 Plays Critical Roles in the Pathogenic CD4 T Cell Responses for the Development of Experimental Autoimmune Encephalomyelitis," Journal of Immunology, vol. 183, No. 11, Dec. 2009 (pp. 7539-7546).

Parham et al., "A receptor for the heterodimeric cytokine IL-23 is composed of IL-12Rβ1 and a novel cytokine receptor subunit, IL-23R," Journal of Immunology, vol. 168, No. 11, Jun. 2002 (pp. 5699-5708).

Ramirez et al., "Defining causative factors contributing in the activation of hedgehog signaling in diffuse large B-cell lymphoma," Leukemia Research, vol. 36, No. 10, Oct. 2012 (pp. 1267-1273).

Remmers et al., "Genome-wide association study identifies variants in the MHC class I, IL10, and IL23R-IL12RB2 regions associated with Behçet's disease," Nature Genetics, vol. 42, No. 8, Aug. 2010 (pp. 698-702).

Rostovtsev et al., "A Stepwise Huisgen Cycloaddition Process: Copper(I)-Catalyzed Regioselective "Ligation" of Azides and Terminal Alkynes," Angew. Chem. Int. Ed., vol. 41, No. 14, Jul. 2002 (pp. 2596-2599).

Sanda et al. "TYK2-STAT1-BCL2 Pathway Dependence in T-Cell Acute Lymphoblastic Leukemia," Cancer Discovery, vol. 3, No. 5, May 2013 (pp. 564-577).

Sigurdsson et al., "Polymorphisms in the Tyrosine Kinase 2 and Interferon Regulatory Factor 5 Genes Are Associated with Systemic Lupis Erythematosus," American Journal of Human Genetics, vol. 76, No. 3, Mar. 2005 (pp. 528-537).

Simma et al., "Identification of an Indispensable Role for Tyrosine Kinase 2 in CTL-Mediated Tumor Surveillance," Cancer Research, vol. 69, No. 1, Jan. 2009 (pp. 203-211).

Stahl et al., "Association and activation of Jak-Tyk kinases by CNTF-LIF-OSM-IL-6β receptor components," Science, vol. 263, No. 5143, Jan. 1994 (pp. 92-95).

Strange et al., "A genome-wide association study identifies new psoriasis susceptibility loci and an interaction between HLA-C and ERAP1," Nature Genetics, vol. 42, No. 11, Nov. 2010 (pp. 985-990).

Sun et al., "Carbohydrate and protein immobilization onto solid surfaces by sequential Diels-Alder and azide-alkyne cycloadditions," Bioconjugate Chemistry, vol. 17, No. 1, Jan.-Feb. 2006 (52-57).

Velasquez et al., "A protein kinase in the interferon α/β signaling pathway," Cell, vol. 70, No. 2, Jul. 1992 (pp. 313-322).

Wan et al. "Tyk/STAT3 Signaling Mediates β-Amyloid-Induced Neuronal Cell Death: Implications in Alzheimer's Disease," Journal of Neuroscience, vol. 30, No. 20, May 2010 (pp. 6873-6881).

Welham et al., "Interleukin-13 signal transduction in lymphohemopoietic cells: similarities and differences in signal transduction with interleukin-4 and insulin," The Journal of Biological chemistry, vol. 270, No. 20, May 1995 (pp. 12286-12296).

Xing et al., "Alopecia areata is driven by cytotoxic T lymphocytes and is reversed by JAK inhibition," Nature Medicine, vol. 20, No. 9, Sep. 2014 (pp. 1043-1049).

Zhang et al., "Docking protein Gab2 regulates mucin expression and goblet cell hyperplasia through TYK2/STAT6 pathway," The FASEB Journal, vol. 26, No. 11, Nov. 2012 (pp. 4603-4613).

* cited by examiner

TYK2 INHIBITORS AND USES THEREOF

CROSS-REFERENCE TO RELATED APPLICATIONS

The present application claims priority to U.S. provisional patent application Ser. No. 62/773,620, filed Nov. 30, 2018, the entirety of which is incorporated herein by reference.

TECHNICAL FIELD OF THE INVENTION

The present invention relates to compounds and methods useful for inhibiting non-receptor tyrosine-protein kinase 2 ("TYK2"), also known as Tyrosine kinase 2. The invention also provides pharmaceutically acceptable compositions comprising compounds of the present invention and methods of using said compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is the protein kinase family.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxins, and $H_2O_2$), cytokines (e.g., interleukin-1 (IL-1), interleukin-8 (IL-8), and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by kinase-mediated events. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there remains a need to find protein kinase inhibitors useful as therapeutic agents.

SUMMARY OF THE INVENTION

It has now been found that compounds of this invention, and pharmaceutically acceptable compositions thereof, are effective as inhibitors of TYK2 kinase.

Compounds of the present invention, and pharmaceutically acceptable compositions thereof, are useful for treating a variety of diseases, disorders or conditions, associated with regulation of signaling pathways implicating TYK2 kinases. Such diseases, disorders, or conditions include those described herein.

Compounds provided by this invention are also useful for the study of TYK2 enzymes in biological and pathological phenomena; the study of intracellular signal transduction pathways occurring in bodily tissues; and the comparative evaluation of new TYK2 inhibitors or other regulators of kinases, signaling pathways, and cytokine levels in vitro or in vivo.

DETAILED DESCRIPTION OF CERTAIN EMBODIMENTS

1. General Description of Certain Embodiments of the Invention

Compounds of the present invention, and compositions thereof, are useful as inhibitors of TYK2 protein kinase.

The pseudokinase binding pocket of TYK2 contains a plurality of hydration sites, each of which is occupied by a single molecule of water. Each of these water molecules has a stability rating associated with it. As used herein, the term "stability rating" refers to a numerical calculation which incorporates the enthalpy, entropy, and free energy values associated with each water molecule. This stability rating allows for a measurable determination of the relative stability of water molecules that occupy hydration sites in the binding pocket of TYK2.

Water molecules occupying hydration sites in the binding pocket of TYK2 having a stability rating of >2.5 kcal/mol are referred to as "unstable waters."

Without wishing to be bound by any particular theory, it is believed that displacement or disruption of an unstable water molecule (i.e., a water molecule having a stability rating of >2.5 kcal/mol), or replacement of a stable water (i.e., a water molecule having a stability rating of <1 kcal/mol), by an inhibitor results in tighter binding of that inhibitor. Accordingly, inhibitors designed to displace one or more unstable water molecules (i.e., those unstable water molecules not displaced by any known inhibitor) will be a tighter binder and, therefore, more potent inhibitor as compared to an inhibitor that does not displace unstable water molecules.

It was surprisingly found that provided compounds displace or disrupt one or more unstable water molecules. In some embodiments, a provided compound displaces or disrupts at least two unstable water molecules.

In certain embodiments, the present invention provides a compound of formula I:

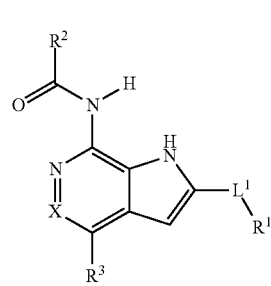

or a pharmaceutically acceptable salt thereof, wherein each of X, $L^1$, $R^1$, $R^2$, and $R^3$ is as defined below and described in embodiments herein, both singly and in combination.

In some embodiments, the present invention provides a pharmaceutical composition comprising a compound of formula I, and a pharmaceutically acceptable carrier, adjuvant, or diluent.

In some embodiments, the present invention provides a method of treating a TYK2-mediated disease, disorder, or condition comprising administering to a patient in need thereof, a a compound of formula I or a pharmaceutically acceptable salt thereof.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

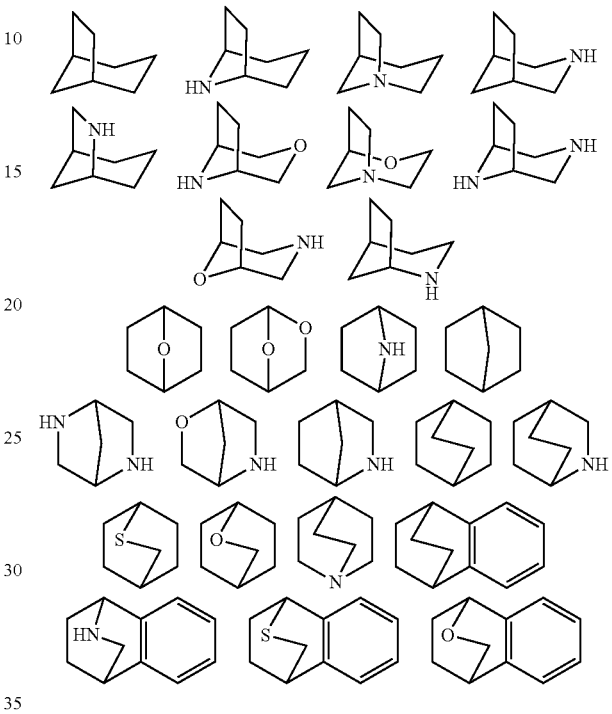

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where unless otherwise specified, the radical or point of attachment is on the heteroaromatic ring or on one of the rings to which the heteroaromatic ring is fused. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, 2-oxa-6-azaspiro[3.3]heptane, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R°$; $-(CH_2)_{0-4}OR°$; $-O(CH_2)_{0-4}R°$, $-O-(CH_2)_{0-4}C(O)OR°$; $-(CH_2)_{0-4}CH(OR°)_2$; $-(CH_2)_{0-4}SR°$; $-(CH_2)_{0-4}Ph$, which may be substituted with $R°$; $-(CH_2)_{0-4}O(CH_2)_{0-1}Ph$ which may be substituted with $R°$; $-CH=CHPh$, which may be substituted with $R°$; $-(CH_2)_{0-4}O(CH_2)_{0-1}$-pyridyl which may be substituted with $R°$; $-NO_2$; $-CN$; $-N_3$; $-(CH_2)_{0-4}N(R°)_2$; $-(CH_2)_{0-4}N(R°)C(O)R°$; $-N(R°)C(S)R°$; $-(CH_2)_{0-4}N(R)C(O)NR°_2$; $-N(R°)C(S)NR°_2$; $-(CH_2)_{0-4}N(R°)C(O)OR°$; $-N(R°)N(R°)C(O)R°$; $-N(R°)N(R°)C(O)NR°_2$; $-N(R°)N(R°)C(O)OR°$; $-N(R°)C(NR°)N(R°)_2$; $-(CH_2)_{0-4}C(O)R°$; $-C(S)R°$; $-(CH_2)_{0-4}C(O)OR°$; $-(CH_2)_{0-4}C(O)SR°$; $-(CH_2)_{0-4}C(O)OSiR°_3$; $-(CH_2)_{0-4}OC(O)R°$; $-OC(O)(CH_2)_{0-4} SR°$; $-SC(S)SR°$; $-(CH_2)_{0-4}SC(O)R°$; $-(CH_2)_{0-4}C(O)NR°_2$; $-C(S)NR°_2$; $-C(S)SR°$; $-SC(S)SR°$, $-(CH_2)_{0-4}OC(O)NR°_2$; $-C(O)N(OR°)R°$; $-C(O)C(O)R°$; $-C(O)CH_2C(O)R°$; $-C(NOR°)R°$; $-(CH_2)_{0-4}SSR°$; $-(CH_2)_{0-4}S(O)_2R°$; $-(CH_2)_{0-4}S(O)_2OR°$; $-(CH_2)_{0-4}OS(O)_2R°$; $-S(O)_2NR°_2$; $-(CH_2)_{0-4}S(O)R$; $-N(R°)S(O)_2NR°_2$; $-N(R°)S(O)_2R$; $-N(OR)R°$; $-C(NH)NR°_2$; $-P(O)_2R°$; $-P(O)$ R°$_2$; —OP(O)R°$_2$; —OP(O)(OR°)$_2$; —SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR*$_3$, —OSiR$^\bullet_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In certain embodiments, a warhead moiety, $R^1$, of a provided compound comprises one or more deuterium atoms. In certain embodiments, Ring B of a provided compound may be substituted with one or more deuterium atoms.

As used herein, the term "inhibitor" is defined as a compound that binds to and/or inhibits TYK2 with measurable affinity. In certain embodiments, an inhibitor has an $IC_{50}$ and/or binding constant of less than about 50 µM, less than about 1 µM, less than about 500 nM, less than about 100 nM, less than about 10 nM, or less than about 1 nM.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}$P, $^{33}$P, $^{35}$S, or $^{14}$C), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360, 8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in a TYK2 protein kinase activity between a sample comprising a compound of the present invention, or composition thereof, and a TYK2 protein kinase, and an equivalent sample comprising an TYK2 protein kinase, in the absence of said compound, or composition thereof.

3. Description of Exemplary Embodiments

As described above, in certain embodiments, the present invention provides a compound of formula I:

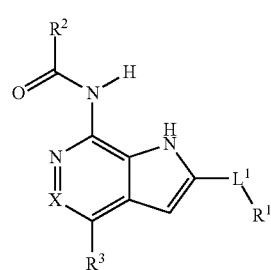

I or a pharmaceutically acceptable salt thereof, wherein:
X is N or CH;
$L^1$ is a covalent bond or a $C_{1-4}$ bivalent saturated or unsaturated, straight or branched hydrocarbon chain wherein one or two methylene units of the chain are optionally and independently replaced by —C(R$^4$)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—;

R$^4$ is independently R$^A$ or R$^B$;

each instance of R$^A$ is independently halogen, —CN, —NO$_2$, —OR, —SR, —NR$_2$, —S(O)$_2$R, —S(O)(NR)R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, or —P(O)R$_2$; or two instances of R$^A$ are optionally taken together to form an oxo;

each instance of R$^B$ is independently C$_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by q instances of R$^C$;

each instance of R$^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR or —P(O)R$_2$ or an optionally substituted group selected from C$_{1-6}$ aliphatic; phenyl; naphthalenyl; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; a 6-11 membered saturated or partially unsaturated bicyclic heterocyclic ring having 1-2 heteroatoms independently selected from nitrogen, oxygen, and sulfur; a 3-7 membered saturated or partially unsaturated monocyclic heterocyclic ring having 1-2 heteroatoms independently selected from nitrogen, oxygen, phosphorous, silicon and sulfur; and a 5-6 membered monocyclic heteroaryl ring having 1-4 heteroatoms independently selected from nitrogen, oxygen, and sulfur; or for each instance of R$^B$, optionally:

two R$^C$ groups on the same atom are taken together with the atom to form an optionally substituted 4-7 membered saturated, spirocyclic heterocyclic ring having 1-2 heteroatoms, independently selected from nitrogen, oxygen, and sulfur;

two R$^C$ groups are taken together with their intervening atoms to form an optionally substituted 4-7 membered saturated or partially unsaturated, fused ring having 0-2 heteroatoms, independently selected from nitrogen, oxygen, and sulfur; or two R$^C$ groups are taken together with their intervening atoms to form an optionally substituted 5-6 membered fused aryl ring having 0-3 heteroatoms, independently selected from nitrogen, oxygen, and sulfur;

each R is independently hydrogen, or an optionally substituted group selected from C$_{1-6}$ aliphatic; phenyl; naphthalenyl; an 8-10 membered bicyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur; and a 5-6 membered monocyclic heteroaryl ring having 1-4 heteroatoms independently selected from nitrogen, oxygen, and sulfur; or:

two R groups on the same nitrogen are taken together with the nitrogen to form an optionally substituted 4-7 membered monocyclic saturated, partially unsaturated, or heteroaryl ring having, in addition to the nitrogen, 0-3 heteroatoms independently selected from nitrogen, oxygen, and sulfur;

R$^1$ is Cy$^1$;

Cy$^1$ is phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; a 3-7 membered saturated or partially unsaturated monocyclic carbocyclic ring; or a 7-12 membered saturated or partially unsaturated bicyclic heterocyclic ring having 1-4 heteroatoms independently selected from nitrogen, oxygen, and sulfur; wherein Cy$^1$ is substituted with p instances of R$^{1A}$;

each instance of R$^{1A}$, is independently R$^A$ or R$^B$;

R$^2$ is C$_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by q instances of R$^C$;

R$^3$ is —C(O)NH$_2$, —C(O)NHCH$_3$, or —C(O)NHCD$_3$; and each of p and q is independently 0, 1, 2, 3, or 4.

As described above, in certain embodiments, the present invention provides a compound of formula I':

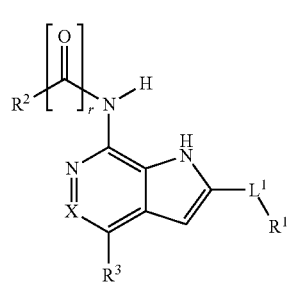

I' or a pharmaceutically acceptable salt thereof, wherein:

X is N or CH;

$L^1$ is a covalent bond or a $C_{1-4}$ bivalent saturated or unsaturated, straight or branched hydrocarbon chain wherein one or two methylene units of the chain are optionally and independently replaced by —C(R$^4$)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—;

$R^4$ is independently $R^A$ or $R^B$;

each instance of $R^A$ is independently halogen, —CN, —NO$_2$, —OR, —SR, —NR$_2$, —S(O)$_2$R, —S(O)(NR)R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, or —P(O)R$_2$; or two instances of $R^A$ are optionally taken together to form an oxo;

each instance of $R^B$ is independently $C_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by q instances of $R^C$;

each instance of $R^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR or —P(O)R$_2$ or an optionally substituted group selected from $C_{1-6}$ aliphatic; phenyl; naphthalenyl; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; a 6-11 membered saturated or partially unsaturated bicyclic heterocyclic ring having 1-2 heteroatoms independently selected from nitrogen, oxygen, and sulfur; a 3-7 membered saturated or partially unsaturated monocyclic heterocyclic ring having 1-2 heteroatoms independently selected from nitrogen, oxygen, phosphorous, silicon and sulfur; and a 5-6 membered monocyclic heteroaryl ring having 1-4 heteroatoms independently selected from nitrogen, oxygen, and sulfur; or for each instance of $R^B$, optionally:

two $R^C$ groups on the same atom are taken together with the atom to form an optionally substituted 4-7 membered saturated, spirocyclic heterocyclic ring having 1-2 heteroatoms, independently selected from nitrogen, oxygen, and sulfur;

two $R^C$ groups are taken together with their intervening atoms to form an optionally substituted 4-7 membered saturated or partially unsaturated, fused ring having 0-2 heteroatoms, independently selected from nitrogen, oxygen, and sulfur; or two $R^C$ groups are taken together with their intervening atoms to form an optionally substituted 5-6 membered fused aryl ring having 0-3 heteroatoms, independently selected from nitrogen, oxygen, and sulfur;

each R is independently hydrogen, or an optionally substituted group selected from $C_{1-6}$ aliphatic; phenyl; naphthalenyl; an 8-10 membered bicyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur; and a 5-6 membered monocyclic heteroaryl ring having 1-4 heteroatoms independently selected from nitrogen, oxygen, and sulfur; or:

two R groups on the same nitrogen are taken together with the nitrogen to form an optionally substituted 4-7 membered monocyclic saturated, partially unsaturated, or heteroaryl ring having, in addition to the nitrogen, 0-3 heteroatoms independently selected from nitrogen, oxygen, and sulfur;

$R^1$ is Cy$^1$;

Cy$^1$ is phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; a 3-7 membered saturated or partially unsaturated monocyclic carbocyclic ring; or a 7-12 membered saturated or partially unsaturated bicyclic heterocyclic ring having 1-4 heteroatoms independently selected from nitrogen, oxygen, and sulfur; wherein Cy$^1$ is substituted with p instances of $R^{1A}$;

each instance of $R^{1A}$, is independently $R^A$ or $R^B$;

$R^2$ is $C_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by q instances of $R^C$;

$R^3$ is —C(O)NH$_2$, —C(O)NHCH$_3$, or —C(O)NHCD$_3$;

each of p and q is independently 0, 1, 2, 3, or 4; and r is 0 or 1.

As defined generally above, X is N or CH. In some embodiments, X is N. In some embodiments, X is CH.

In some embodiments, X is selected from those depicted in Table 1, below.

As defined generally above, $L^1$ is a covalent bond or a $C_{1-4}$ bivalent saturated or unsaturated, straight or branched hydrocarbon chain wherein one or two methylene units of the chain are optionally and independently replaced by —C(R$^4$)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—.

In some embodiments, L$^1$ is a covalent bond.

In some embodiments, L$^1$ is a C$_{1-4}$ bivalent saturated or unsaturated, straight or branched hydrocarbon chain wherein one or two methylene units of the chain are optionally and independently replaced by —C(R$^4$)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—.

In some embodiments, L$^1$ is a C$_{1-4}$ bivalent saturated, straight or branched hydrocarbon chain wherein one or two methylene units of the chain are optionally and independently replaced by —C(R$^4$)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—. In some embodiments, L$^1$ is a C$_{1-4}$ bivalent unsaturated, straight or branched hydrocarbon chain wherein one or two methylene units of the chain are optionally and independently replaced by —C(R$^4$)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—.

In some embodiments, L$^1$ is a C$_{1-4}$ bivalent saturated, straight or branched hydrocarbon chain wherein one methylene unit of the chain is optionally replaced by —C(R$^4$)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—. In some embodiments, L$^1$ is a C$_{1-4}$ bivalent unsaturated, straight or branched hydrocarbon chain wherein one methylene unit of the chain is optionally replaced by —C(R$^4$)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—.

In some embodiments, L$^1$ is a C$_{1-4}$ bivalent saturated or unsaturated, straight or branched hydrocarbon chain. In some embodiments, L$^1$ is a C$_{1-4}$ bivalent saturated, straight or branched hydrocarbon chain. In some embodiments, L$^1$ is a C$_{1-4}$ bivalent unsaturated, straight or branched hydrocarbon chain.

In some embodiments, L$^1$ is a covalent bond, —C(R$^4$)$_2$—, —N(R)—, or —O—. In some embodiments, L$^1$ is a covalent bond or —N(R)—. In some embodiments, L$^1$ is —C(R$^4$)$_2$—, —N(R)—, or —O—. In some embodiments, L$^1$ is a covalent bond, —C(H)$_2$—, —N(H)—, or —O—. In some embodiments, L$^1$ is a covalent bond or —N(H)—. In some embodiments, L$^1$ is —C(H)$_2$—, —N(H)—, or —O—.

In some embodiments, L$^1$ is selected from those depicted in Table 1, below.

As defined generally above, each instance of R$^4$ is independently R$^A$ or R$^B$. In some embodiments, R$^4$ is R$^A$. In some embodiments, R$^4$ is R$^B$.

In some embodiments, R$^4$ is halogen; —OR; C$_{1-6}$ aliphatic, optionally substituted by q instances of R$^C$; or two instances of R$^4$ are taken together to form an oxo. In some embodiments, two instances of R$^4$ are taken together to form an oxo. In some embodiments, R$^4$ is halogen. In some embodiments, R$^4$ is —OR. In some embodiments, R$^4$ is C$_{1-6}$ aliphatic, optionally substituted by q instances of R$^C$. In some embodiments, R$^4$ is C$_{1-3}$ aliphatic.

In some embodiments, R$^4$ is selected from those depicted in Table 1, below.

As defined generally above, each instance of R$^A$ is independently halogen, —CN, —NO$_2$, —OR, —SR, —NR$_2$, —S(O)$_2$R, —S(O)(NR)R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, or —P(O)R$_2$, or two instances of R$^A$ are optionally taken together to form an oxo.

In some embodiments, each instance of R$^A$ is independently halogen, —CN, —NO$_2$, —OR, —SR, —NR$_2$, —S(O)$_2$R, —S(O)(NR)R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)NR$_2$, —N(R)C(NR)NR$_2$, —N(R)S(O)$_2$NR$_2$, —N(R)S(O)$_2$R, or —P(O)R$_2$. In some embodiments, two instances of R$^A$ are taken together to form an oxo.

In some embodiments, R$^A$ is halogen. In some embodiments, R$^A$ is —CN. In some embodiments, R$^A$ is —NO$_2$. In some embodiments, R$^A$ is —OR. In some embodiments, R$^A$ is —SR. In some embodiments, R$^A$ is —NR$_2$. In some embodiments, R$^A$ is —S(O)$_2$R. In some embodiments, R$^A$ is —S(O)(NR)R. In some embodiments, R$^A$ is —S(O)$_2$NR$_2$. In some embodiments, R$^A$ is —S(O)R. In some embodiments, R$^A$ is —S(O)NR$_2$. In some embodiments, R$^A$ is —C(O)R. In some embodiments, R$^A$ is —C(O)OR. In some embodiments, R$^A$ is —C(O)NR$_2$. In some embodiments, R$^A$ is —C(O)N(R)OR. In some embodiments, R$^A$ is —OC(O)R. In some embodiments, R$^A$ is —OC(O)NR$_2$. In some embodiments, R$^A$ is —N(R)C(O)OR. In some embodiments, R$^A$ is —N(R)C(O)NR$_2$. In some embodiments, R$^A$ is —N(R)C(NR)NR$_2$. In some embodiments, R$^A$ is —N(R)S(O)$_2$NR$_2$. In some embodiments, R$^A$ is —N(R)S(O)$_2$R. In some embodiments, R$^A$ is —P(O)R$_2$.

In some embodiments, R$^A$ is halogen, —CN, or —NO$_2$. In some embodiments, R$^A$ is —OR, —SR, or —NR$_2$. In some embodiments, R$^A$ is —S(O)$_2$R, —S(O)(NR)R, —S(O)$_2$NR$_2$, —S(O)R, or —S(O)NR$_2$. In some embodiments, R$^A$ is —C(O)R, —C(O)OR, —C(O)NR$_2$, or —C(O)N(R)OR. In some embodiments, R$^A$ is —OC(O)R or —OC(O)NR$_2$. In some embodiments, R$^A$ is —N(R)C(O)OR, —N(R)C(O)NR$_2$, or —N(R)C(NR)NR$_2$. In some embodiments, R$^A$ is —N(R)S(O)$_2$NR$_2$ or —N(R)S(O)$_2$R.

In some embodiments, R$^A$ is —S(O)$_2$R, —S(O)$_2$NR$_2$, —S(O)R, or —S(O)NR$_2$. In some embodiments, R$^A$ is —N(R)C(O)OR or —N(R)C(O)NR$_2$.

In some embodiments, R$^A$ is halogen, —CN, —OR, —SR, —NR$_2$, —OC(O)R, —OC(O)NR$_2$, or two instances of R$^A$ are taken together to form an oxo. In some embodiments, R$^A$ is halogen, —OR, or two instances of R$^A$ are taken together to form an oxo.

In some embodiments, R$^A$ is halogen, —CN, —OR, —SR, —NR$_2$, —C(O)R, —C(O)OR, —C(O)NR$_2$, —C(O)N(R)OR, or two instances of R$^A$ are taken together to form an oxo. In some embodiments, R$^A$ is halogen, —CN, —OR, —NR$_2$, —C(O)NR$_2$, or two instances of R$^A$ are taken together to form an oxo.

In some embodiments, R$^A$ is selected from those depicted in Table 1, below.

As defined generally above, each instance of R$^B$ is independently C$_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by q instances of $R^C$.

In some embodiments, $R^B$ is $C_{1-6}$ aliphatic, substituted by q instances of $R^C$. In some embodiments, $R^B$ is $C_{1-6}$ aliphatic. In some embodiments, $R^B$ is $C_{1-3}$ aliphatic, optionally substituted by q instances of $R^C$. In some embodiments, $R^B$ is $C_{1-3}$ aliphatic.

In some embodiments, $R^B$ is phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by q instances of $R^C$.

In some embodiments, $R^B$ is phenyl, substituted with q instances of $R^C$. In some embodiments, $R^B$ is a 5-6 membered monocyclic heteroaryl ring having 1-4 heteroatoms independently selected from nitrogen, oxygen, and sulfur; substituted with q instances of $R^C$. In some embodiments, $R^B$ is an 8-10 membered bicyclic heteroaryl ring having 1-4 heteroatoms independently selected from nitrogen, oxygen, and sulfur; substituted with q instances of $R^C$. In some embodiments, $R^B$ is a 3-7 membered saturated or partially unsaturated monocyclic heterocyclic ring having 1-2 heteroatoms independently selected from nitrogen, oxygen, and sulfur; substituted with q instances of $R^C$. In some embodiments, $R^B$ is a 3-7 membered saturated or partially unsaturated monocyclic carbocyclic ring; substituted with q instances of $R^C$. In some embodiments, $R^B$ is a 7-12 membered saturated or partially unsaturated bicyclic heterocyclic ring having 1-4 heteroatoms independently selected from nitrogen, oxygen, and sulfur; substituted with q instances of $R^C$.

In some embodiments, $R^B$ is phenyl or a 3-7 membered saturated or partially unsaturated monocyclic carbocyclic ring; each of which is substituted with q instances of $R^C$. In some embodiments, $R^B$ is a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted with q instances of $R^C$. In some embodiments, $R^B$ is a 5-6 membered monocyclic heteroaryl ring having 1-4 heteroatoms independently selected from nitrogen, oxygen, and sulfur; or an 8-10 membered bicyclic heteroaryl ring having 1-4 heteroatoms independently selected from nitrogen, oxygen, and sulfur; each of which is substituted with q instances of $R^C$. In some embodiments, $R^B$ is a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted with q instances of $R^C$.

In some embodiments, $R^B$ is phenyl; a 5-6 membered monocyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; a 3-7 membered saturated or partially unsaturated monocyclic carbocyclic ring; each of which is substituted with q instances of $R^C$. In some embodiments, $R^B$ is an 8-10 membered bicyclic heteroaryl ring having 1-4 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted with q instances of $R^C$.

In some embodiments, $R^B$ is a 3-7 membered saturated monocyclic carbocyclic ring, substituted by q instances of $R^C$. In some embodiments, $R^B$ is a 3-7 membered partially unsaturated monocyclic carbocyclic ring, substituted by q instances of $R^C$. In some embodiments, $R^B$ is a 3-7 membered saturated or partially unsaturated monocyclic carbocyclic ring. In some embodiments, $R^B$ is cyclopropyl.

In some embodiments, $R^B$ is $C_{1-6}$ aliphatic; phenyl; a 5-6 membered monocyclic heteroaryl ring having 1-4 heteroatoms independently selected from nitrogen, oxygen, and sulfur; a 3-7 membered saturated or partially unsaturated monocyclic carbocyclic ring; or a 3-7 membered saturated or partially unsaturated monocyclic heterocyclic ring having 1-2 heteroatoms independently selected from nitrogen, oxygen, and sulfur; each of which is substituted with q instances of $R^C$.

In some embodiments, $R^B$ is $C_{1-6}$ aliphatic; phenyl; or a 3-7 membered saturated or partially unsaturated monocyclic carbocyclic ring; each of which is substituted with q instances of $R^C$. In some embodiments, $R^B$ is a 5-6 membered monocyclic heteroaryl ring having 1-4 heteroatoms independently selected from nitrogen, oxygen, and sulfur; or a 3-7 membered saturated or partially unsaturated monocyclic heterocyclic ring having 1-2 heteroatoms independently selected from nitrogen, oxygen, and sulfur; each of which is substituted with q instances of $R^C$.

In some embodiments, $R^B$ is a 5-6 membered monocyclic heteroaryl ring having 1-4 heteroatoms independently selected from nitrogen, oxygen, and sulfur; a 3-7 membered saturated or partially unsaturated monocyclic carbocyclic ring; or a 3-7 membered saturated or partially unsaturated monocyclic heterocyclic ring having 1-2 heteroatoms independently selected from nitrogen, oxygen, and sulfur; each of which is substituted with q instances of $R^C$.

In some embodiments, $R^B$ is selected from those depicted in Table 1, below.

As defined generally above, $R^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR or —P(O)R$_2$ or an optionally substituted group selected from $C_{1-6}$ aliphatic; phenyl; naphthalenyl; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; a 6-11 membered saturated or partially unsaturated bicyclic heterocyclic ring having 1-2 heteroatoms independently selected from nitrogen, oxygen, and sulfur; a 3-7 membered saturated or partially unsaturated monocyclic heterocyclic ring having 1-2 heteroatoms independently selected from nitrogen, oxygen, phosphorous, silicon and sulfur; and a 5-6 membered monocyclic heteroaryl ring having 1-4 heteroatoms independently selected from nitrogen, oxygen, and sulfur; or for each instance of $R^B$, optionally:

two $R^C$ groups on the same atom are taken together with the atom to form an optionally substituted 4-7 membered saturated, spirocyclic heterocyclic ring having 1-2 heteroatoms, independently selected from nitrogen, oxygen, and sulfur;

two $R^C$ groups are taken together with their intervening atoms to form an optionally substituted 4-7 membered saturated or partially unsaturated, fused ring having 0-2 heteroatoms, independently selected from nitrogen, oxygen, and sulfur; or two $R^C$ groups are taken together with their intervening atoms to form an optionally substituted 5-6 membered fused aryl ring having 0-3 heteroatoms, independently selected from nitrogen, oxygen, and sulfur.

In some embodiments, $R^C$ is oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR or —P(O)R$_2$ or an optionally substituted group selected from C$_{1-6}$ aliphatic; phenyl; naphthalenyl; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; a 6-11 membered saturated or partially unsaturated bicyclic heterocyclic ring having 1-2 heteroatoms independently selected from nitrogen, oxygen, and sulfur; a 3-7 membered saturated or partially unsaturated monocyclic heterocyclic ring having 1-2 heteroatoms independently selected from nitrogen, oxygen, phosphorous, silicon and sulfur; and a 5-6 membered monocyclic heteroaryl ring having 1-4 heteroatoms independently selected from nitrogen, oxygen, and sulfur.

In some embodiments, two $R^C$ groups on the same atom are taken together with the atom to form an optionally substituted 4-7 membered saturated, spirocyclic heterocyclic ring having 1-2 heteroatoms, independently selected from nitrogen, oxygen, and sulfur.

In some embodiments, two $R^C$ groups are taken together with their intervening atoms to form an optionally substituted 4-7 membered saturated or partially unsaturated, fused ring having 0-2 heteroatoms, independently selected from nitrogen, oxygen, and sulfur.

In some embodiments, two $R^C$ groups are taken together with their intervening atoms to form an optionally substituted 5-6 membered fused aryl ring having 0-3 heteroatoms, independently selected from nitrogen, oxygen, and sulfur.

In some embodiments, $R^C$ is oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —N(R)C(O)R, —N(R)C(O)NR$_2$, —N(R)C(NR)NR$_2$, —N(R)S(O)$_2$NR$_2$, —N(R)S(O)$_2$R, or —N(R)S(O)R, or an optionally substituted C$_{1-6}$ aliphatic. In some embodiments, $R^C$ is oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, or an optionally substituted C$_{1-6}$ aliphatic. In some embodiments, $R^C$ is oxo, halogen, —CN, —NO$_2$, —OR, —SR, —NR$_2$, —S(O)$_2$R, —S(O)$_2$NR$_2$, —S(O)R, —S(O)NR$_2$, or an optionally substituted C$_{1-6}$ aliphatic. In some embodiments, $R^C$ is oxo, halogen, —CN, —OR, —SR, —S(O)$_2$R, —S(O)R, or an optionally substituted C$_{1-6}$ aliphatic. In some embodiments, $R^C$ is oxo, —OR, —S(O)$_2$R, or an optionally substituted C$_{1-6}$ aliphatic.

In some embodiments, $R^C$ is methyl.

In some embodiments, $R^C$ is selected from those depicted in Table 1, below.

As defined generally above, each R is independently hydrogen, or an optionally substituted group selected from C$_{1-6}$ aliphatic; phenyl; naphthalenyl; an 8-10 membered bicyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur; and a 5-6 membered monocyclic heteroaryl ring having 1-4 heteroatoms independently selected from nitrogen, oxygen, and sulfur; or:

two R groups on the same nitrogen are taken together with the nitrogen to form an optionally substituted 4-7 membered monocyclic saturated, partially unsaturated, or heteroaryl ring having, in addition to the nitrogen, 0-3 heteroatoms independently selected from nitrogen, oxygen, and sulfur.

In some embodiments, R is hydrogen, or an optionally substituted group selected from C$_{1-6}$ aliphatic; phenyl; naphthalenyl; an 8-10 membered bicyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur; and a 5-6 membered monocyclic heteroaryl ring having 1-4 heteroatoms independently selected from nitrogen, oxygen, and sulfur.

In some embodiments, two R groups on the same nitrogen are taken together with the nitrogen to form an optionally substituted 4-7 membered monocyclic saturated, partially unsaturated, or heteroaryl ring having, in addition to the nitrogen, 0-3 heteroatoms independently selected from nitrogen, oxygen, and sulfur.

In some embodiments, R is hydrogen. In some embodiments, R is an optionally substituted group selected from $C_{1-6}$ aliphatic; phenyl; naphthalenyl; an 8-10 membered bicyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur; and a 5-6 membered monocyclic heteroaryl ring having 1-4 heteroatoms independently selected from nitrogen, oxygen, and sulfur.

In some embodiments, R is an optionally substituted group selected from $C_{1-6}$ aliphatic; phenyl; and naphthalenyl. In some embodiments, R is an optionally substituted group selected from an 8-10 membered bicyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur; and a 5-6 membered monocyclic heteroaryl ring having 1-4 heteroatoms independently selected from nitrogen, oxygen, and sulfur.

In some embodiments, R is hydrogen, an optionally substituted $C_{1-6}$ aliphatic, or two R groups on the same nitrogen are taken together with the nitrogen to form an optionally substituted 4-7 membered monocyclic saturated, partially unsaturated, or heteroaryl ring having, in addition to the nitrogen, 0-3 heteroatoms independently selected from nitrogen, oxygen, and sulfur. In some embodiments, R is hydrogen, an optionally substituted $C_{1-6}$ aliphatic, or two R groups on the same nitrogen are taken together with the nitrogen to form an optionally substituted 4-7 membered monocyclic saturated ring having, in addition to the nitrogen, 0-1 heteroatoms independently selected from nitrogen, oxygen, and sulfur. In some embodiments, R is hydrogen or an optionally substituted $C_{1-6}$ aliphatic. In some embodiments, R is hydrogen or an optionally substituted $C_{1-3}$ aliphatic.

In some embodiments, R is selected from those depicted in Table 1, below.

As defined generally above, $R^1$ is $Cy^1$.

In some embodiments, $R^1$ is selected from those depicted in Table 1, below.

As defined generally above, $Cy^1$ is phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; a 3-7 membered saturated or partially unsaturated monocyclic carbocyclic ring; or a 7-12 membered saturated or partially unsaturated bicyclic heterocyclic ring having 1-4 heteroatoms independently selected from nitrogen, oxygen, and sulfur; wherein $Cy^1$ is substituted with p instances of $R^{1A}$.

In some embodiments, $Cy^1$ is phenyl, substituted with p instances of $R^{1A}$. In some embodiments, $Cy^1$ is a 5-6 membered monocyclic heteroaryl ring having 1-4 heteroatoms independently selected from nitrogen, oxygen, and sulfur; substituted with p instances of $R^{1A}$. In some embodiments, $Cy^1$ is an 8-10 membered bicyclic heteroaryl ring having 1-4 heteroatoms independently selected from nitrogen, oxygen, and sulfur; substituted with p instances of $R^{1A}$. In some embodiments, $Cy^1$ is a 3-7 membered saturated or partially unsaturated monocyclic heterocyclic ring having 1-2 heteroatoms independently selected from nitrogen, oxygen, and sulfur; substituted with p instances of $R^{1A}$. In some embodiments, $Cy^1$ is a 3-7 membered saturated or partially unsaturated monocyclic carbocyclic ring; substituted with p instances of $R^{1A}$. In some embodiments, $Cy^1$ is a 7-12 membered saturated or partially unsaturated bicyclic heterocyclic ring having 1-4 heteroatoms independently selected from nitrogen, oxygen, and sulfur; substituted with p instances of $R^{1A}$.

In some embodiments, $Cy^1$ is phenyl or a 3-7 membered saturated or partially unsaturated monocyclic carbocyclic ring; wherein $Cy^1$ is substituted with p instances of $R^{1A}$. In some embodiments, $Cy^1$ is a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; wherein $Cy^1$ is substituted with p instances of $R^{1A}$. In some embodiments, $Cy^1$ is a 5-6 membered monocyclic heteroaryl ring having 1-4 heteroatoms independently selected from nitrogen, oxygen, and sulfur; or an 8-10 membered bicyclic heteroaryl ring having 1-4 heteroatoms independently selected from nitrogen, oxygen, and sulfur; wherein $Cy^1$ is substituted with p instances of $R^{1A}$. In some embodiments, $Cy^1$ is a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; wherein $Cy^1$ is substituted with p instances of $R^{1A}$.

In some embodiments, $Cy^1$ is phenyl; a 5-6 membered monocyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; a 3-7 membered saturated or partially unsaturated monocyclic carbocyclic ring; wherein $Cy^1$ is substituted with p instances of $R^{1A}$. In some embodiments, $Cy^1$ is an 8-10 membered bicyclic heteroaryl ring having 1-4 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; wherein $Cy^1$ is substituted with p instances of $R^{1A}$.

In some embodiments, $Cy^1$ is phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; or a 3-7 membered saturated or partially unsaturated monocyclic heterocyclic ring having 1-2 heteroatoms independently selected from nitrogen, oxygen, and sulfur; wherein $Cy^1$ is substituted with p instances of $R^{1A}$. In some embodiments, $Cy^1$ is phenyl; a 5-6 membered monocyclic heteroaryl ring having 1-4 heteroatoms independently selected from nitrogen, oxygen, and sulfur; or a 3-7 membered saturated or partially unsaturated monocyclic heterocyclic ring having 1-2 heteroatoms independently selected from nitrogen, oxygen, and sulfur; wherein $Cy^1$ is substituted with p instances of $R^{1A}$. In some embodiments, $Cy^1$ is phenyl or a 5-6 membered monocyclic heteroaryl ring having 1-4 heteroatoms independently selected from nitrogen, oxygen, and sulfur; wherein $Cy^1$ is substituted with p instances of $R^{1A}$.

In some embodiments, $Cy^1$ is phenyl; a 6 membered monocyclic heteroaryl ring having 1-2 nitrogen atoms; or a 6 membered saturated or partially unsaturated monocyclic heterocyclic ring having 1-2 nitrogen atoms; wherein $Cy^1$ is substituted with p instances of $R^{1A}$. In some embodiments, $Cy^1$ is phenyl or a 6 membered monocyclic heteroaryl ring having 1-2 nitrogen atoms; wherein $Cy^1$ is substituted with p instances of $R^{1A}$. In some embodiments, $Cy^1$ is phenyl or pyridyl, substituted with p instances of $R^{1A}$. In some embodiments, $Cy^1$ is pyridyl, substituted with p instances of $R^{1A}$.

In some embodiments, $Cy^1$ is selected from the following:

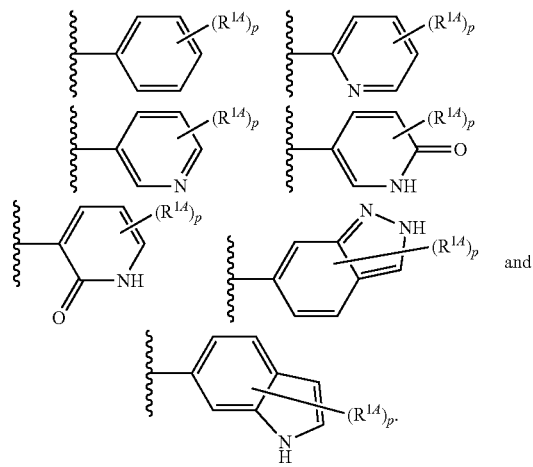

In some embodiments, $Cy^1$ is selected from the following:

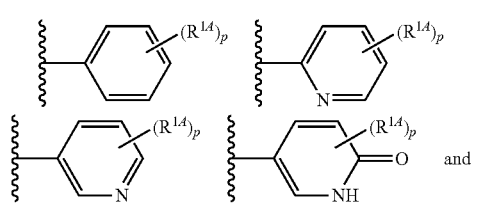

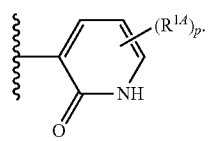

In some embodiments, $Cy^1$ is

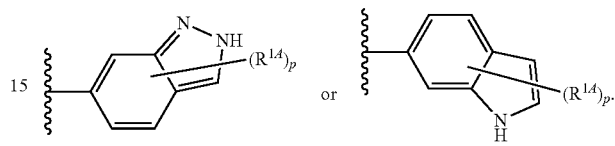

In some embodiments, $Cy^1$ is

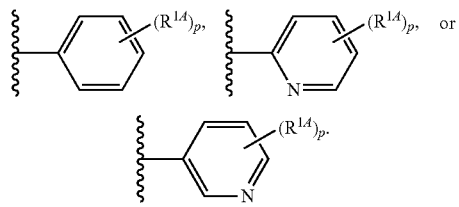

In some embodiments, $Cy^1$ is

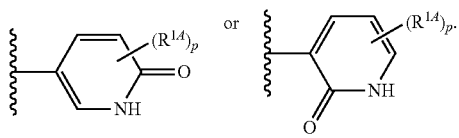

In some embodiments, $Cy^1$ is

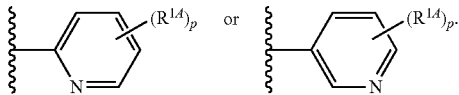

In some embodiments, $Cy^1$ is

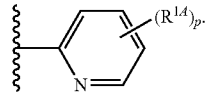

In some embodiments, $Cy^1$ is

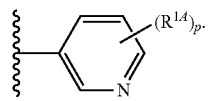

In some embodiments, Cy¹ is

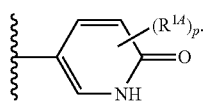

In some embodiments, Cy¹ is

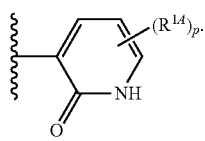

In some embodiments, Cy¹ is

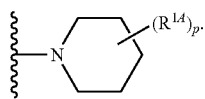

In some embodiments, Cy¹ is

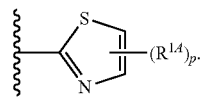

In some embodiments, Cy¹ is

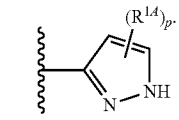

In some embodiments, Cy¹ is

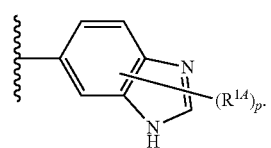

In some embodiments, Cy¹ is substituted with 0-2 instances of $R^A$ and 1 instance of $R^B$. In some embodiments, Cy¹ is substituted with 0-1 instances of $R^A$ and 1 instance of $R^B$.

In some embodiments, Cy¹ together with its $R^{1A}$ substituents is selected from the following:

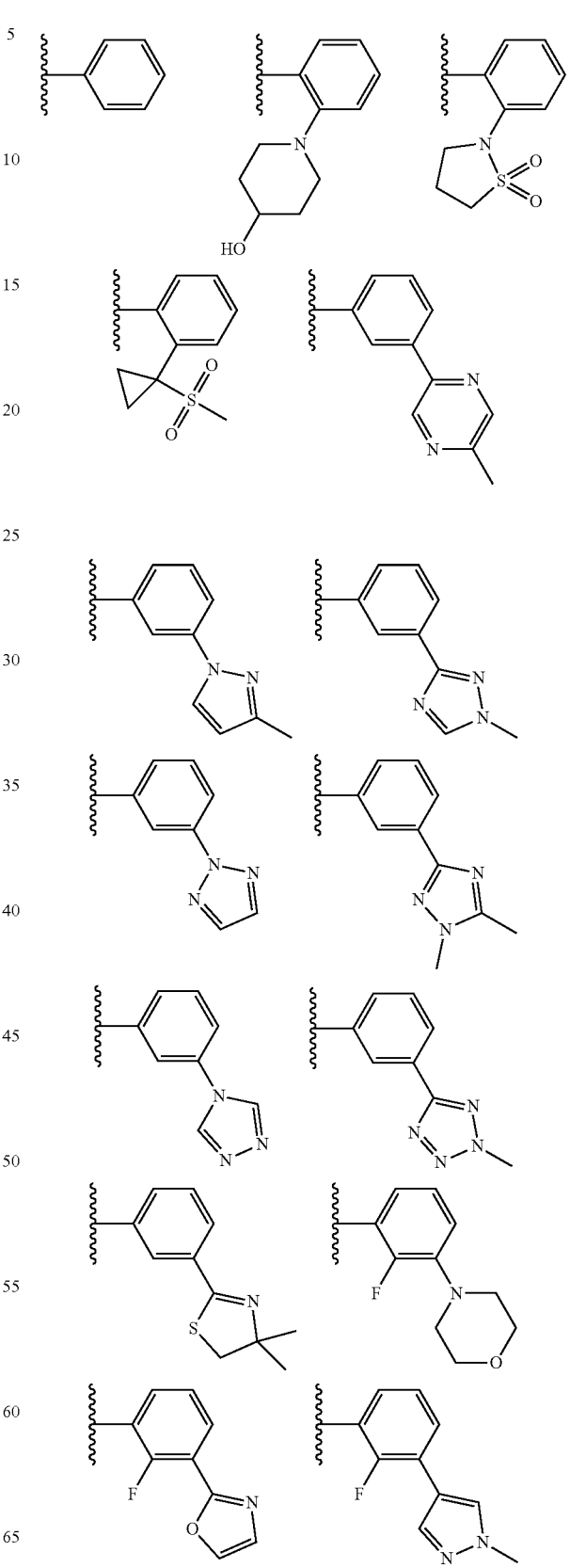

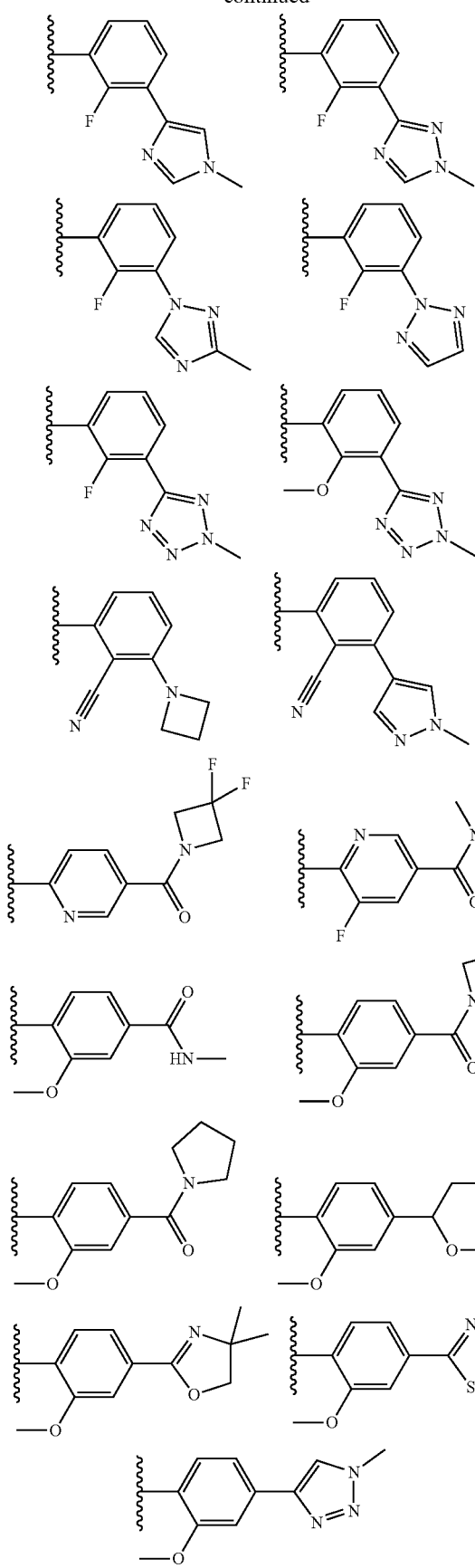
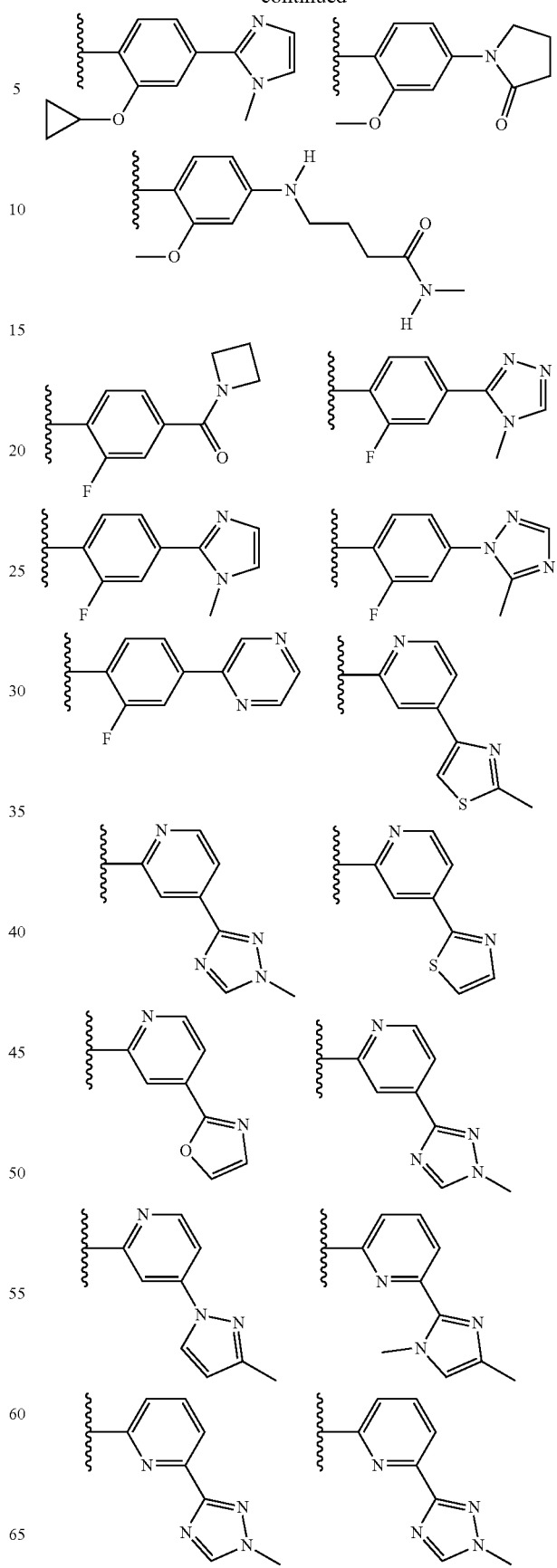

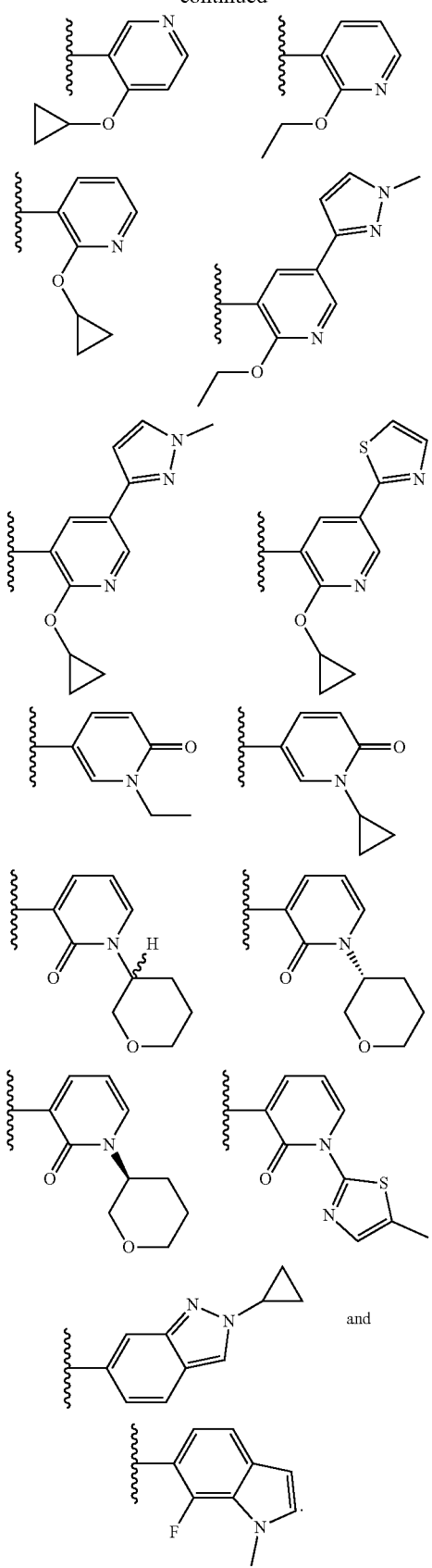
In some embodiments, $Cy^1$ together with its $R^{1A}$ substituents is selected from the following:
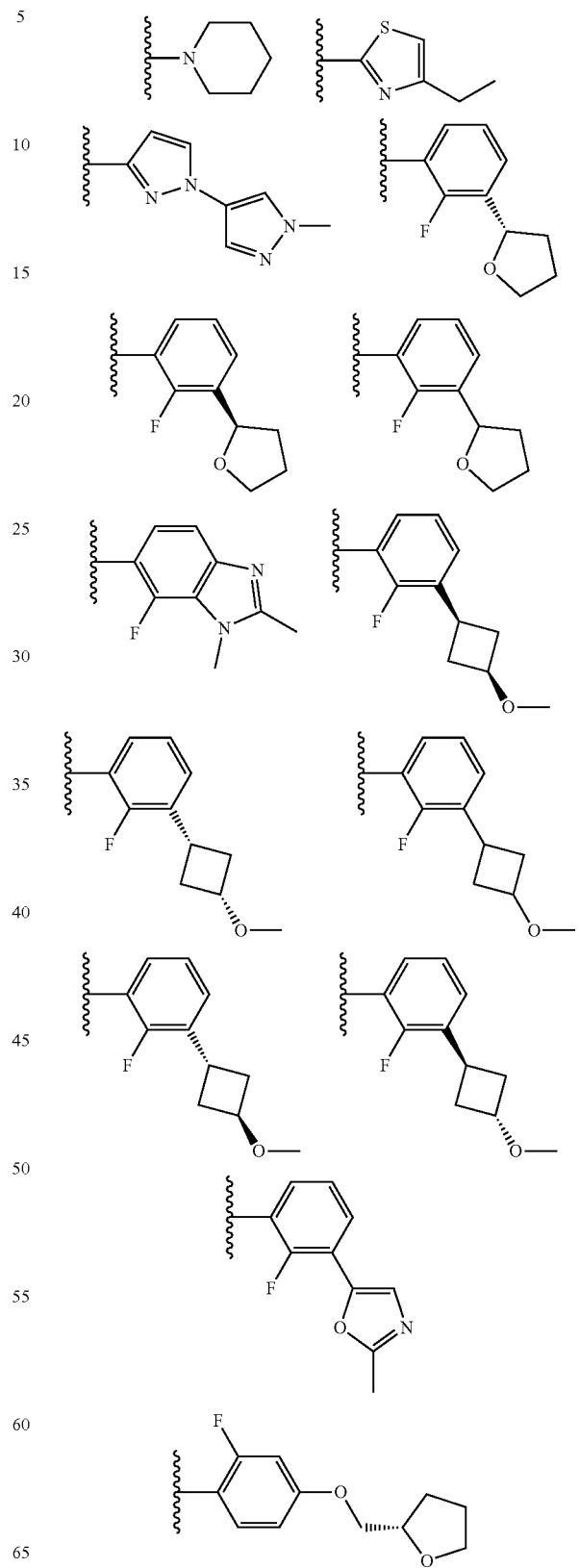

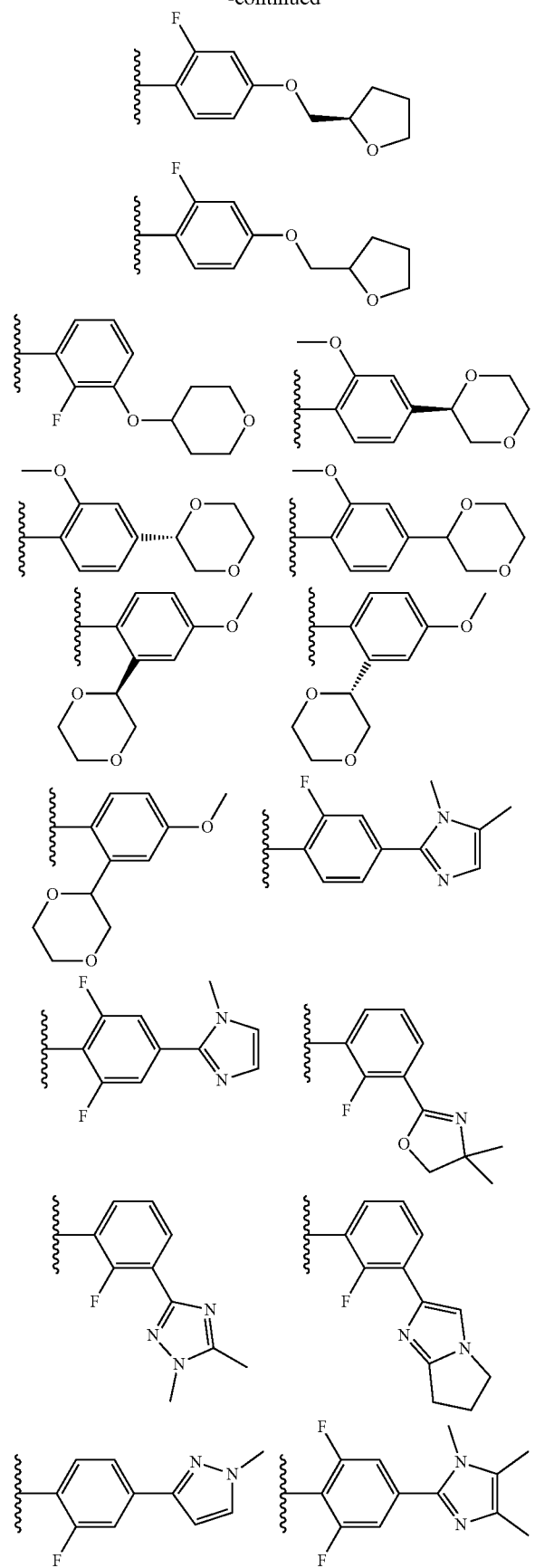
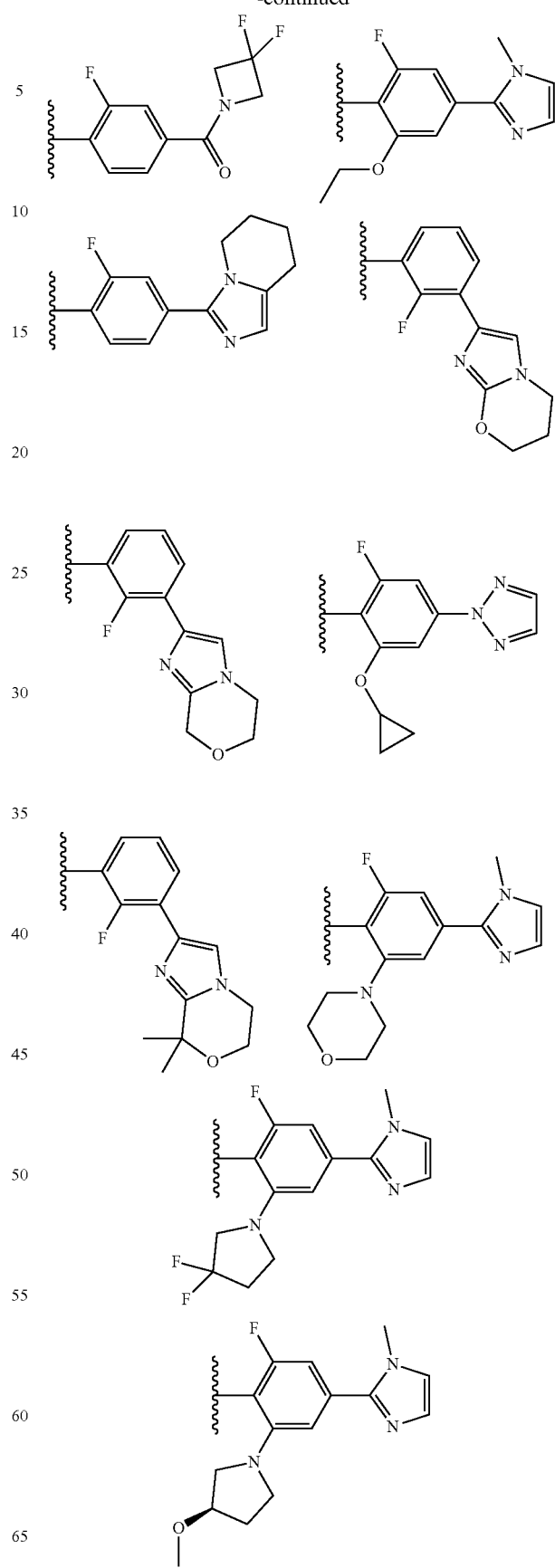

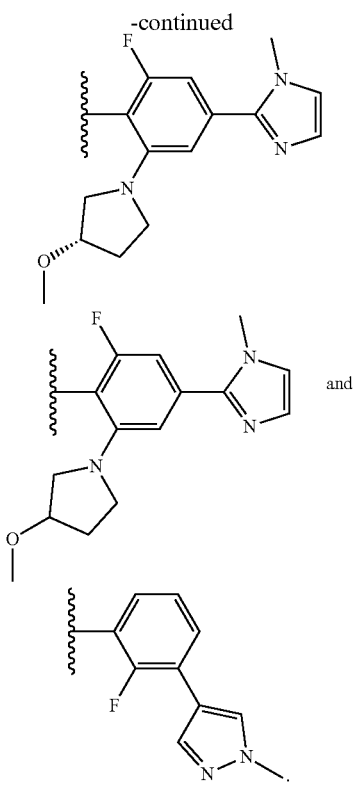

In some embodiments, Cy¹ is selected from those depicted in Table 1, below.

As defined generally above, each instance of $R^{14}$ is independently $R^A$ or $R^B$. In some embodiments, $R^{14}$ is $R^A$. In some embodiments, $R^{14}$ is $R^B$.

In some embodiments, $R^{14}$ is $R^A$ or $R^B$ selected from $C_{1-6}$ aliphatic; phenyl; a 5-6 membered monocyclic heteroaryl ring having 1-4 heteroatoms independently selected from nitrogen, oxygen, and sulfur; a 3-7 membered saturated or partially unsaturated monocyclic carbocyclic ring; and a 3-7 membered saturated or partially unsaturated monocyclic heterocyclic ring having 1-2 heteroatoms independently selected from nitrogen, oxygen, and sulfur; wherein each $R^B$ is substituted with q instances of $R^C$; or two instances of $R^{14}$ are taken together to form an oxo.

In some embodiments, two instances of $R^{14}$ are taken together to form an oxo. In some embodiments, $R^{14}$ is $R^A$ or $R^B$ selected from $C_{1-6}$ aliphatic; phenyl; a 5-6 membered monocyclic heteroaryl ring having 1-4 heteroatoms independently selected from nitrogen, oxygen, and sulfur; a 3-7 membered saturated or partially unsaturated monocyclic carbocyclic ring; and a 3-7 membered saturated or partially unsaturated monocyclic heterocyclic ring having 1-2 heteroatoms independently selected from nitrogen, oxygen, and sulfur; wherein each $R^B$ is substituted with q instances of $R^C$.

In some embodiments, $R^{14}$ is $R^A$ or $R^B$ selected from $C_{1-6}$ aliphatic; phenyl; and a 3-7 membered saturated or partially unsaturated monocyclic carbocyclic ring; wherein each $R^B$ is substituted with q instances of $R^C$. In some embodiments, $R^{14}$ is $R^A$ or $R^B$ selected from a 5-6 membered monocyclic heteroaryl ring having 1-4 heteroatoms independently selected from nitrogen, oxygen, and sulfur; and a 3-7 membered saturated or partially unsaturated monocyclic heterocyclic ring having 1-2 heteroatoms independently selected from nitrogen, oxygen, and sulfur; wherein each $R^B$ is substituted with q instances of $R^C$.

In some embodiments, $R^{14}$ is halogen; —CN; —OR; —NR₂; —C(O)NR₂; or $R^B$ selected from $C_{1-6}$ aliphatic; phenyl; a 5-6 membered monocyclic heteroaryl ring having 1-4 heteroatoms independently selected from nitrogen, oxygen, and sulfur; a 3-7 membered saturated or partially unsaturated monocyclic carbocyclic ring; and a 3-7 membered saturated or partially unsaturated monocyclic heterocyclic ring having 1-2 heteroatoms independently selected from nitrogen, oxygen, and sulfur; wherein each $R^B$ is substituted with q instances of $R^C$.

In some embodiments, $R^{14}$ is halogen; —CN; —OR; —NR₂; —C(O)NR₂; or $R^B$ selected from $C_{1-6}$ aliphatic; phenyl; and a 3-7 membered saturated or partially unsaturated monocyclic carbocyclic ring; wherein each $R^B$ is substituted with q instances of $R^C$. In some embodiments, $R^{14}$ is halogen; —CN; —OR; —NR₂; —C(O)NR₂; or $R^B$ selected from a 5-6 membered monocyclic heteroaryl ring having 1-4 heteroatoms independently selected from nitrogen, oxygen, and sulfur; and a 3-7 membered saturated or partially unsaturated monocyclic heterocyclic ring having 1-2 heteroatoms independently selected from nitrogen, oxygen, and sulfur; wherein each $R^B$ is substituted with q instances of $R^C$.

In some embodiments, at least one instance of $R^{14}$ is —C(O)NR₂ or $R^B$. In some embodiments, at least one instance of $R^{14}$ is —C(O)NR₂. In some embodiments, at least one instance of $R^{14}$ is $R^B$.

In some embodiments, at least one instance of $R^{14}$ is —C(O)NR₂ or $R^B$ selected from a 5-6 membered monocyclic heteroaryl ring having 1-4 heteroatoms independently selected from nitrogen, oxygen, and sulfur; a 3-7 membered saturated or partially unsaturated monocyclic carbocyclic ring; and a 3-7 membered saturated or partially unsaturated monocyclic heterocyclic ring having 1-2 heteroatoms independently selected from nitrogen, oxygen, and sulfur; wherein each $R^B$ is substituted with q instances of $R^C$. In some embodiments, at least one instance of $R^{14}$ is a 5-6 membered monocyclic heteroaryl ring having 1-4 heteroatoms independently selected from nitrogen, oxygen, and sulfur; a 3-7 membered saturated or partially unsaturated monocyclic carbocyclic ring; or a 3-7 membered saturated or partially unsaturated monocyclic heterocyclic ring having 1-2 heteroatoms independently selected from nitrogen, oxygen, and sulfur; each of which is substituted with q instances of $R^C$.

In some embodiments, at least one instance of $R^{14}$ is —C(O)NR₂ or $R^B$; wherein the two R groups are taken together with the nitrogen to form an optionally substituted 4-7 membered monocyclic saturated, partially unsaturated, or heteroaryl ring having, in addition to the nitrogen, 0-3 heteroatoms independently selected from nitrogen, oxygen, and sulfur. In some embodiments, at least one instance of $R^{14}$ is —C(O)NR₂; wherein the two R groups are taken together with the nitrogen to form an optionally substituted 4-7 membered monocyclic saturated, partially unsaturated, or heteroaryl ring having, in addition to the nitrogen, 0-3 heteroatoms independently selected from nitrogen, oxygen, and sulfur.

In some embodiments, at least one instance of $R^{14}$ is —C(O)NR₂ or $R^B$; wherein the two R groups are taken together with the nitrogen to form an optionally substituted 4-7 membered monocyclic saturated ring optionally having, in addition to the nitrogen, one heteroatom selected from nitrogen, oxygen, and sulfur. In some embodiments, at least one instance of $R^{14}$ is —C(O)NR₂; wherein the two R groups are taken together with the nitrogen to form an optionally substituted 4-7 membered monocyclic saturated ring optionally having, in addition to the nitrogen, one heteroatom selected from nitrogen, oxygen, and sulfur.

In some embodiments, at least one instance of $R^{14}$ is —C(O)NR$_2$ or $R^B$ selected from a 5-6 membered monocyclic heteroaryl ring having 1-4 heteroatoms independently selected from nitrogen, oxygen, and sulfur; a 3-7 membered saturated or partially unsaturated monocyclic carbocyclic ring; and a 3-7 membered saturated or partially unsaturated monocyclic heterocyclic ring having 1-2 heteroatoms independently selected from nitrogen, oxygen, and sulfur; wherein each $R^B$ is substituted with q instances of $R^C$; and wherein the two R groups are taken together with the nitrogen to form an optionally substituted 4-7 membered monocyclic saturated ring optionally having, in addition to the nitrogen, one heteroatom selected from nitrogen, oxygen, and sulfur.

In some embodiments, $R^{14}$ is selected from the following:

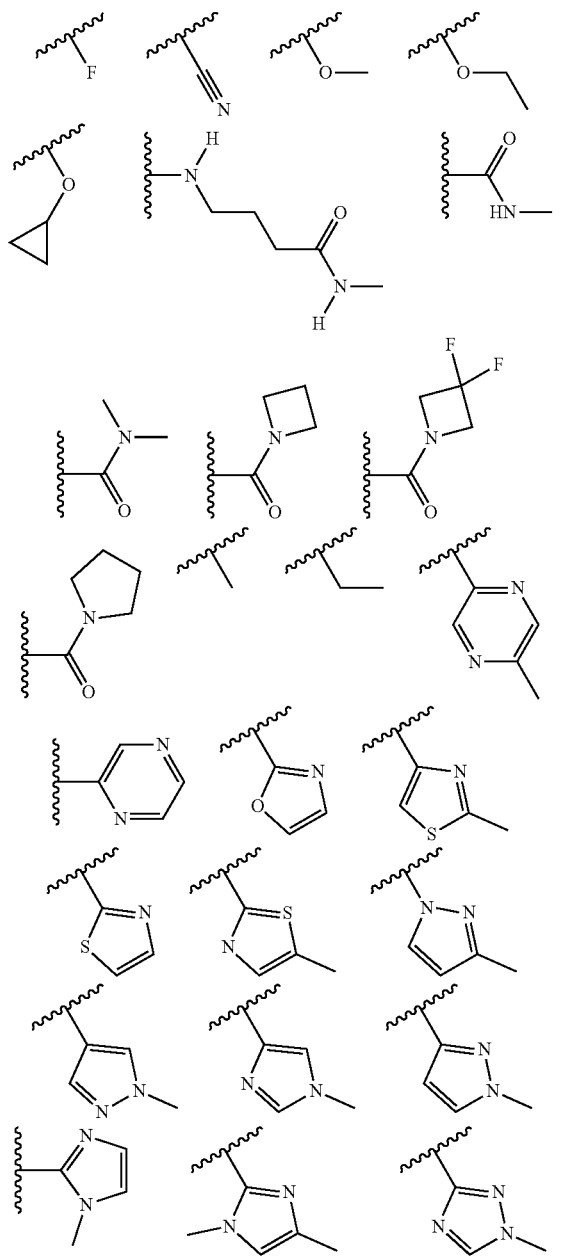
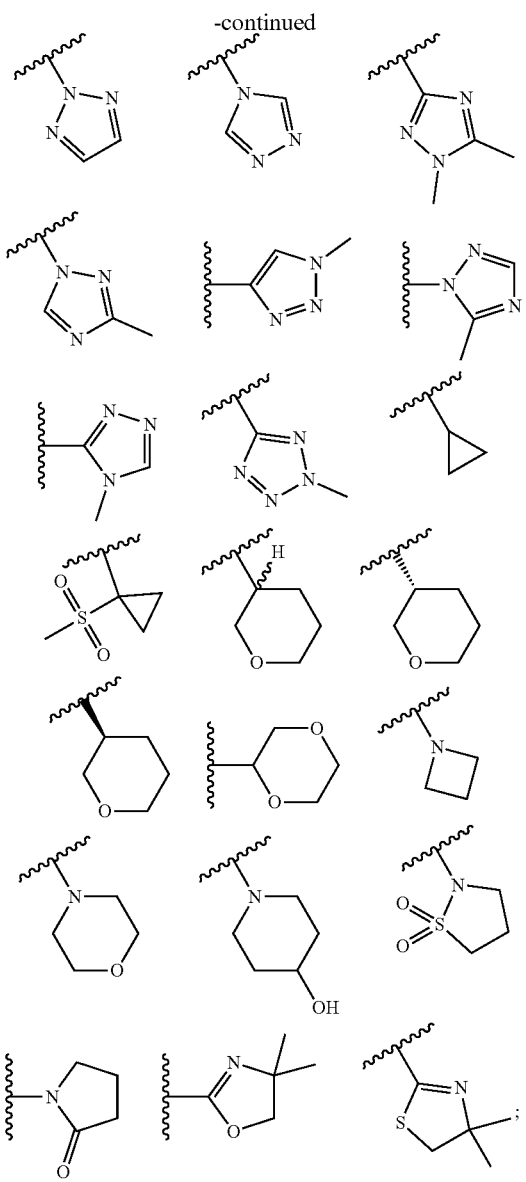

or two instances of $R^{14}$ are taken together to form an oxo.

In some embodiments, $R^{14}$ is selected from the following:

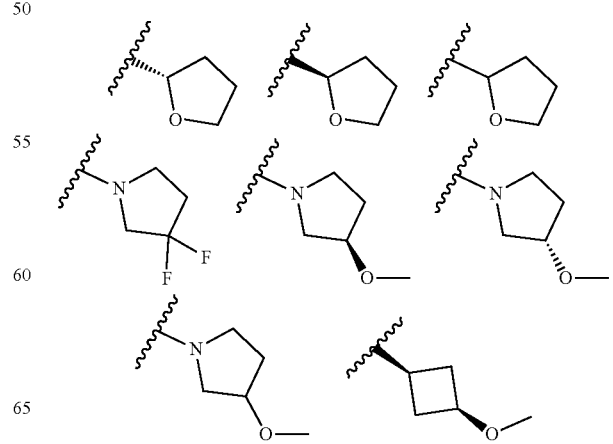

heteroaryl ring having 1-4 heteroatoms independently selected from nitrogen, oxygen, and sulfur which is substituted by q instances of $R^C$. In certain embodiments, $R^2$ is an 8-10 membered bicyclic heteroaryl ring having 1-4 heteroatoms independently selected from nitrogen, oxygen, and sulfur which is substituted by q instances of $R^C$. In certain embodiments, $R^2$ is a 3-7 membered saturated or partially unsaturated monocyclic carbocyclic ring which is substituted by q instances of $R^C$. In certain embodiments, $R^2$ is a 3-7 membered saturated or partially unsaturated monocyclic heterocyclic ring having 1-2 heteroatoms independently selected from nitrogen, oxygen, and sulfur which is substituted by q instances of $R^C$. In certain embodiments, $R^2$ is a 7-12 membered saturated or partially unsaturated bicyclic heterocyclic ring having 1-4 heteroatoms independently selected from nitrogen, oxygen, and sulfur which is substituted by q instances of $R^C$.

In some embodiments, $R^2$ is a 3-7 membered saturated or partially unsaturated monocyclic carbocyclic ring, substituted by q instances of $R^C$. In some embodiments, $R^2$ is a 3-7 membered saturated monocyclic carbocyclic ring, substituted by q instances of $R^C$. In some embodiments, $R^2$ is a 3-7 membered partially unsaturated monocyclic carbocyclic ring, substituted by q instances of $R^C$. In some embodiments, $R^2$ is a 3-7 membered saturated or partially unsaturated monocyclic carbocyclic ring.

In some embodiments, $R^2$ is cyclopropyl, cyclobutyl, cyclopentyl, cyclohexyl, cycloheptyl, or cyclooctyl; each of which is independently substituted by q instances of $R^C$.

In some embodiments, $R^2$ is cyclopropyl.

In some embodiments, $R^2$ is

In some embodiments, $R^2$ together with its $R^C$ substituents is

In some embodiments, $R^2$ is selected from those depicted in Table 1, below.

As defined generally above, $R^3$ is —C(O)NH$_2$, —C(O)NHCH$_3$, or —C(O)NHCD$_3$.

In some embodiments, $R^3$ is —C(O)NH$_2$. In some embodiments, $R^3$ is —C(O)NHCH$_3$ or —C(O)NHCD$_3$. In some embodiments, $R^3$ is —C(O)NHCH$_3$. In some embodiments, $R^3$ is —C(O)NHCD$_3$.

In some embodiments, $R^3$ is selected from those depicted in Table 1, below.

As defined generally above, p is 0, 1, 2, 3, or 4. In some embodiments, p is 0. In some embodiments, p is 1, 2, 3, or 4. In some embodiments, p is 1. In some embodiments, p is 2. In some embodiments, p is 3. In some embodiments, p is 4.

In some embodiments, p is 1, 2, or 3. In some embodiments, p is 1 or 2. In some embodiments, p is 1 or 3. In some embodiments, p is 2 or 3. In some embodiments, p is 2 or 4.

In some embodiments, p is 1, 2, or 4. In some embodiments, p is 1, 3, or 4. In some embodiments, p is 2, 3, or 4.

In some embodiments, p is selected from those depicted in Table 1, below.

As defined generally above, q is 0, 1, 2, 3, or 4. In some embodiments, q is 0. In some embodiments, q is 1, 2, 3, or 4. In some embodiments, q is 1. In some embodiments, q is 2. In some embodiments, q is 3. In some embodiments, q is 4.

In some embodiments, q is 1, 2, or 3. In some embodiments, q is 1 or 2. In some embodiments, q is 1 or 3. In some embodiments, q is 2 or 3. In some embodiments, q is 2 or 4. In some embodiments, q is 1, 2, or 4. In some embodiments, q is 1, 3, or 4. In some embodiments, q is 2, 3, or 4.

In some embodiments, q is selected from those depicted in Table 1, below.

As defined generally above, r is 0 or 1. In some embodiments, r is 0. In some embodiments, r is 1.

In some embodiments, r is selected from those depicted in Table 1, below.

In some embodiments, the present invention provides a compound of formula I' wherein $L^1$ is a covalent bond and r is 1, thereby forming a compound of formula II:

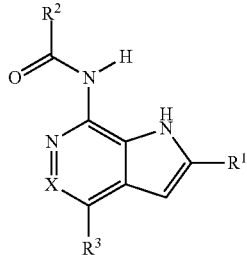

II or a pharmaceutically acceptable salt thereof, wherein each of X, $R^1$, $R^2$, and $R^3$ is as defined above and described in embodiments herein, both singly and in combination.

In some embodiments, the present invention provides a compound of formula II wherein $R^1$ is

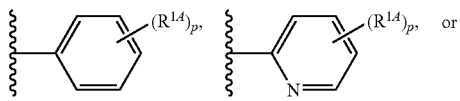

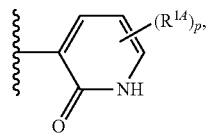

thereby forming a compound of formula III, IV, or V respectively:

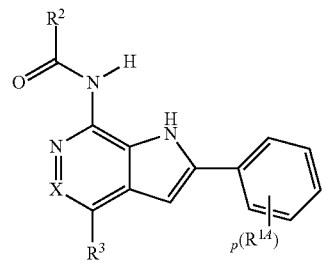

III

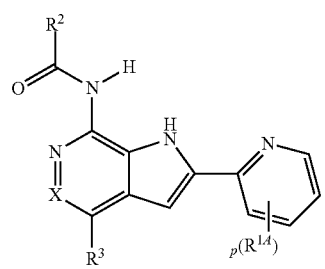

IV

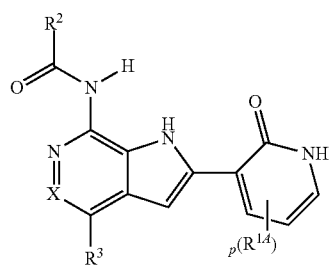

V or a pharmaceutically acceptable salt thereof, wherein each of X, $R^{14}$, $R^2$, $R^3$, and p is as defined above and described in embodiments herein, both singly and in combination.

In some embodiments, the present invention provides a compound of formula I', II, III, IV, or V wherein r is 1 and X is CH, thereby forming a compound of formula I-a, II-a, III-a, IV-a, or V-a respectively:

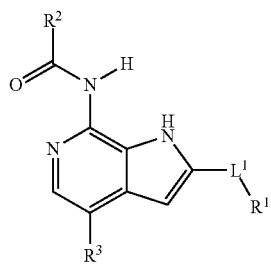

I-a

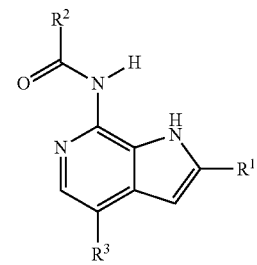

II-a

-continued

III-a
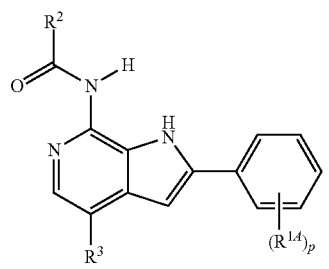

IV-a
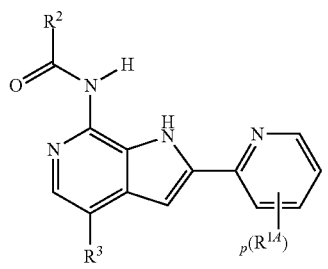

V-a
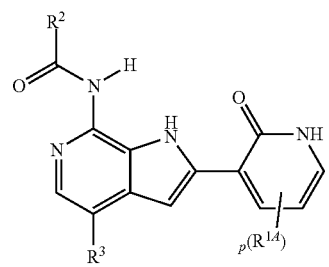

or a pharmaceutically acceptable salt thereof, wherein each of $L^1$, $R^1$, $R^{1A}$, $R^2$, $R^3$, and p is as defined above and described in embodiments herein, both singly and in combination.

In some embodiments, the present invention provides a compound of formula I', II, III, IV, V, I-a, II-a, III-a, IV-a, or V-a wherein $R^3$ is —C(O)NH$_2$.

In some embodiments, the present invention provides a compound of formula I', II, III, IV, V, I-a, II-a, III-a, IV-a, or V-a wherein $R^3$ is —C(O)NHCH$_3$ or —C(O)NHCD$_3$.

In some embodiments, the present invention provides a compound of formula I' wherein $L^1$ is a covalent bond and r is 0, thereby forming a compound of formula VI:

VI
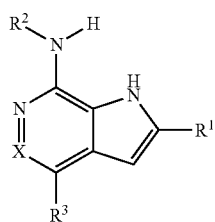

or a pharmaceutically acceptable salt thereof, wherein each of X, $R^1$, $R^2$, and $R^3$ is as defined above and described in embodiments herein, both singly and in combination.

In some embodiments, the present invention provides a compound of formula VI wherein $R^1$ is

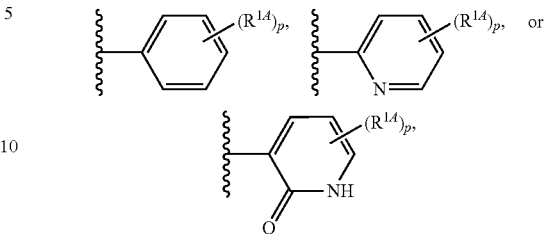

thereby forming a compound of formula VII, VIII, or IX respectively:

VII
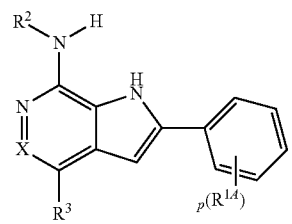

VIII
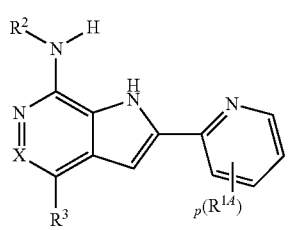

IX
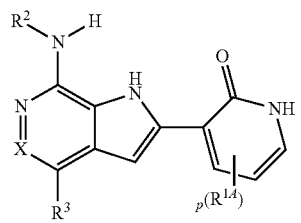

or a pharmaceutically acceptable salt thereof, wherein each of X, $R^{1A}$, $R^2$, $R^3$, and p is as defined above and described in embodiments herein, both singly and in combination.

In some embodiments, the present invention provides a compound of formula I', VI, VII, VIII, or IX wherein r is 1 and X is CH, thereby forming a compound of formula I'-a, VI-a, VII-a, VIII-a, or IX-a respectively:

I'-a
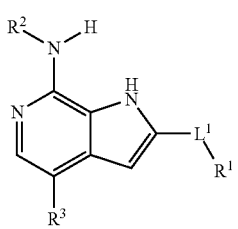

-continued

VI-a

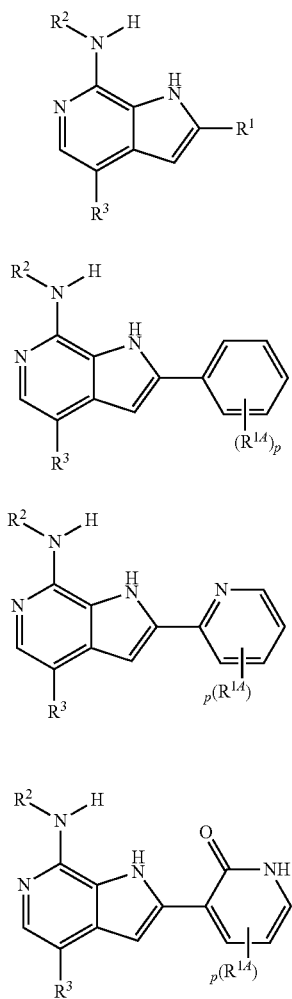

VII-a

VIII-a

IX-a or a pharmaceutically acceptable salt thereof, wherein each of $L^1$, $R^1$, $R^{14}$, $R^2$, $R^3$, and p is as defined above and described in embodiments herein, both singly and in combination.

In some embodiments, the present invention provides a compound of formula I'-a, VI-a, VII-a, VIII-a, or IX-a wherein $R^3$ is —C(O)NH$_2$.

In some embodiments, the present invention provides a compound of formula I'-a, VI-a, VII-a, VIII-a, or IX-a wherein $R^3$ is —C(O)NHCH$_3$ or —C(O)NHCD$_3$.

In some embodiments, the present invention provides a compound of formula I' wherein $L^1$ is a covalent bond, r is 0, and $R^2$ is

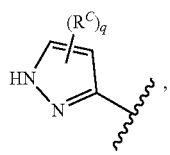

thereby forming a compound of formula X:

X

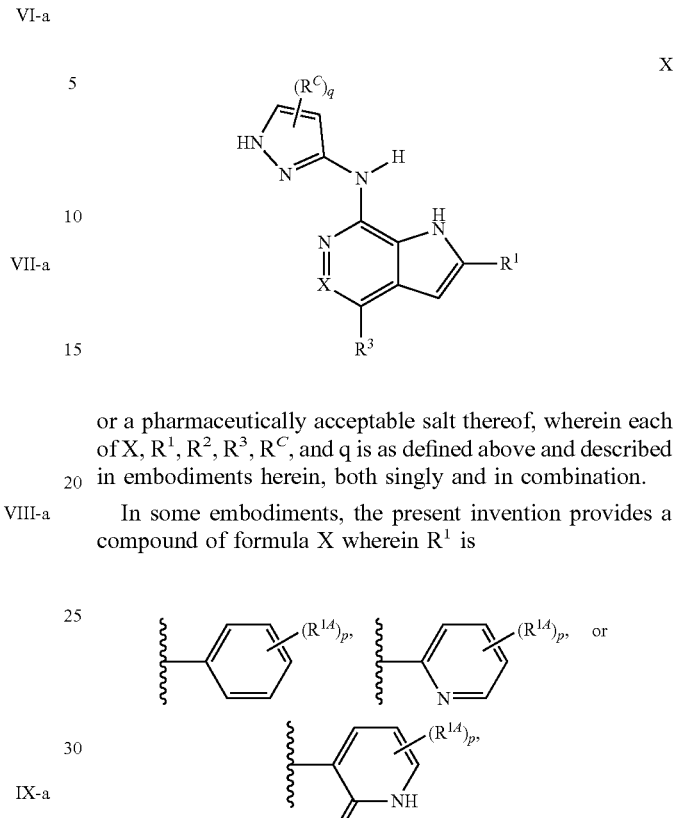

or a pharmaceutically acceptable salt thereof, wherein each of X, $R^1$, $R^2$, $R^3$, $R^C$, and q is as defined above and described in embodiments herein, both singly and in combination.

In some embodiments, the present invention provides a compound of formula X wherein $R^1$ is

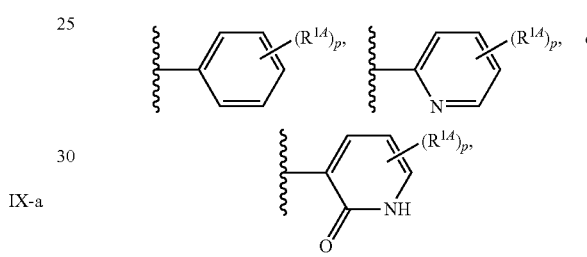

thereby forming a compound of formula XI, XII, or XIII respectively:

XI

XII

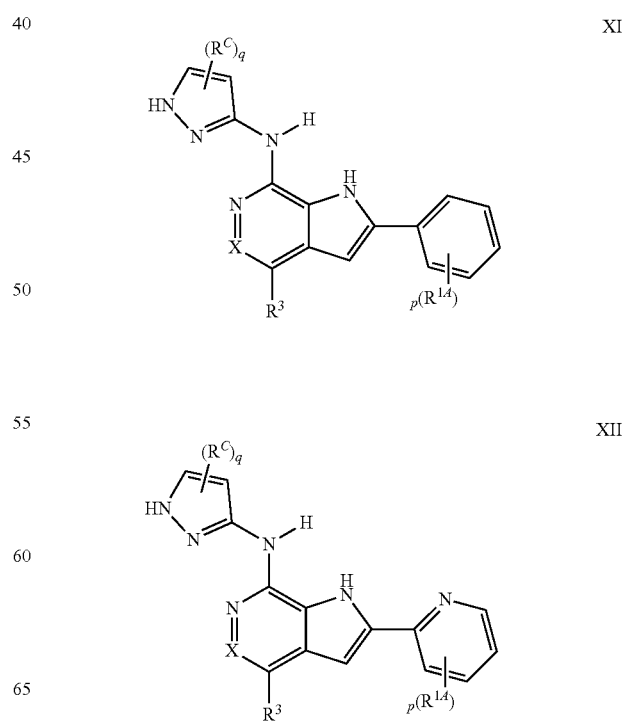

-continued

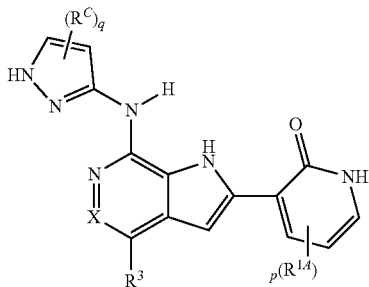
XIII or a pharmaceutically acceptable salt thereof, wherein each of X, $R^{1A}$, $R^2$, $R^3$, $R^C$, p and q is as defined above and described in embodiments herein, both singly and in combination.

In some embodiments, the present invention provides a compound of formula I', X, XI, XII, or XIII wherein r is 1 and X is CH, thereby forming a compound of formula I"-a, X-a, XI-a, XII-a, or XIII-a respectively:

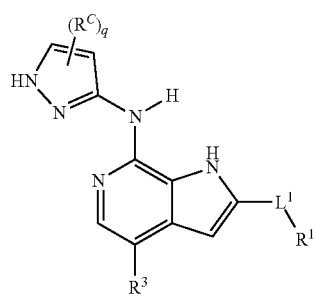
X"-a

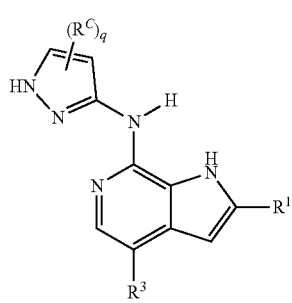
X-a

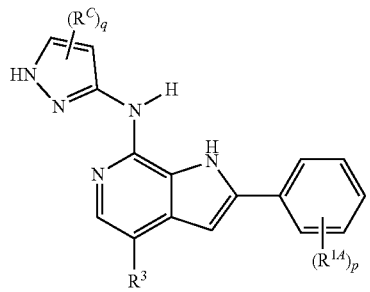
XI-a

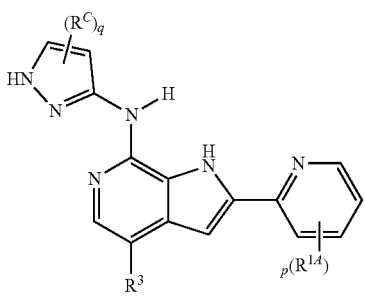
XII-a

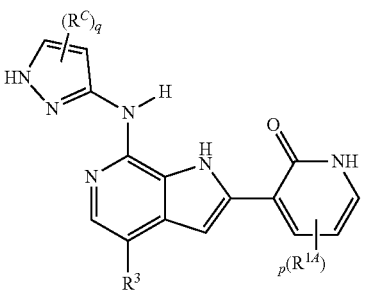
XIII-a or a pharmaceutically acceptable salt thereof, wherein each of $L^1$, $R^1$, $R^{1A}$, $R^2$, $R^3$, $R^C$, p and q is as defined above and described in embodiments herein, both singly and in combination.

In some embodiments, the present invention provides a compound of formula I"-a, X-a, XI-a, XII-a, or XIII-a wherein $R^3$ is —C(O)NH$_2$.

In some embodiments, the present invention provides a compound of formula I"-a, X-a, XI-a, XII-a, or XIII-a wherein $R^3$ is —C(O)NHCH$_3$ or —C(O)NHCD$_3$.

Exemplary compounds of the invention are set forth in Table 1, below.

TABLE 1

| Selected Compounds | |
|---|---|
| Compound | Structure |
| I-1 | |
| I-2 | |
| I-3 | |
| I-4 | |

TABLE 1-continued

Selected Compounds

| Compound | Structure |
|---|---|
| I-5 | 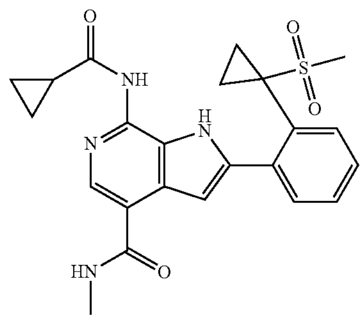 [SMILES: CNC(=O)c1cnc(NC(=O)C2CC2)c2[nH]c(-c3ccccc3C3(S(C)(=O)=O)CC3)cc12] |
| I-6 | 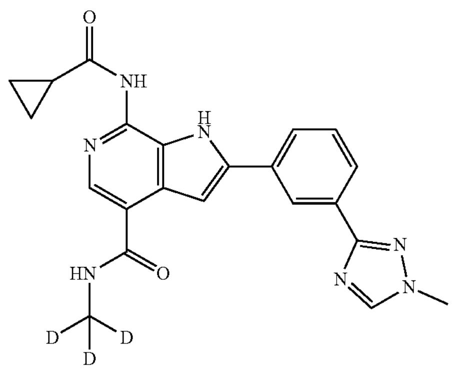 |
| I-7 | 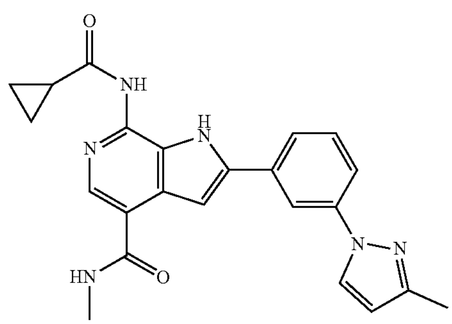 |
| I-8 | 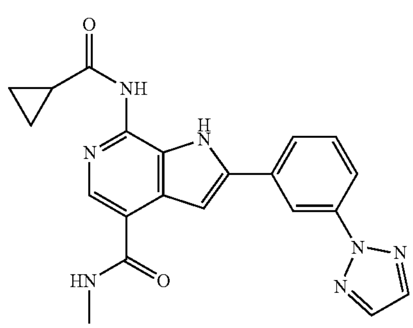 [SMILES: CNC(=O)c1cnc(NC(=O)C2CC2)c2[nH]c(-c3cccc(-n4nccn4)c3)cc12] |

TABLE 1-continued
Selected Compounds
| Compound | Structure |
|---|---|
| I-9 | 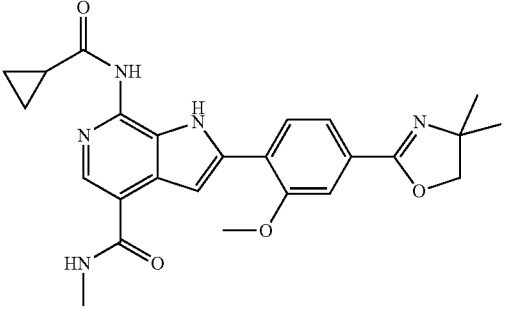 [SMILES: CNC(=O)c1cnc(NC(=O)C2CC2)c2[nH]c(-c3ccc(C4=NC(C)(C)CO4)cc3OC)cc12] |
| I-10 | 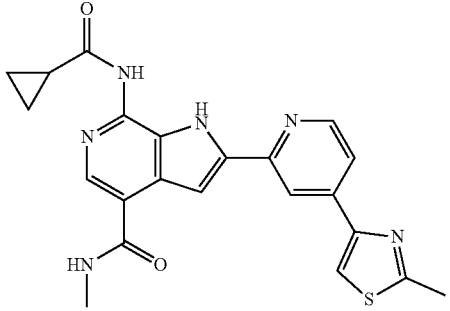 [SMILES: CNC(=O)c1cnc(NC(=O)C2CC2)c2[nH]c(-c3cc(-c4csc(C)n4)ccn3)cc12] |
| I-11 | 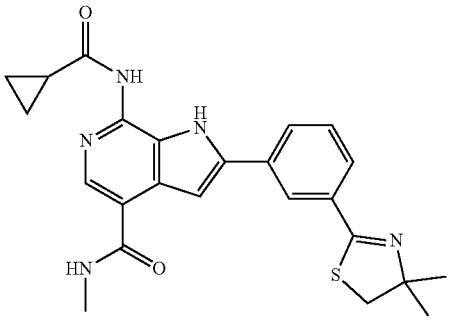 [SMILES: CNC(=O)c1cnc(NC(=O)C2CC2)c2[nH]c(-c3cccc(C4=NC(C)(C)CS4)c3)cc12] |
| I-12 | 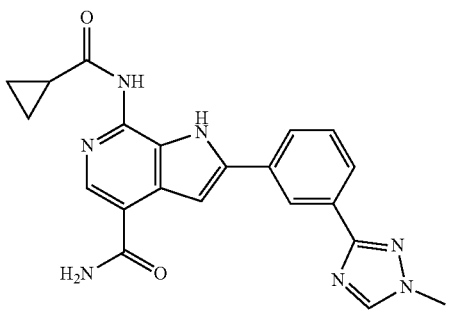 [SMILES: Cn1cnc(-c2cccc(-c3cc4c(C(N)=O)cnc(NC(=O)C5CC5)c4[nH]3)c2)n1] |

TABLE 1-continued

| Selected Compounds | |
|---|---|
| Compound | Structure |
| I-13 | |
| I-14 | |
| I-15 | |
| I-16 | |

TABLE 1-continued

Selected Compounds

| Compound | Structure |
|---|---|
| I-17 | (structure) |
| I-18 | (structure) |
| I-19 | (structure) |
| I-20 | (structure) |

TABLE 1-continued

Selected Compounds

| Compound | Structure |
|---|---|
| I-21 | 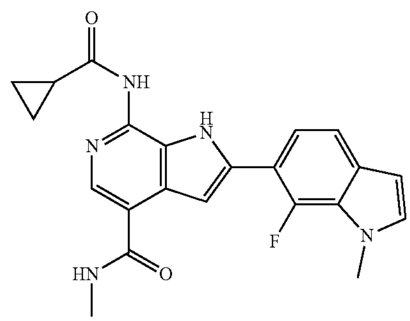 [SMILES: CNC(=O)c1cnc(NC(=O)C2CC2)c2[nH]c(-c3ccc4ccn(C)c4c3F)cc12] |
| I-22 | 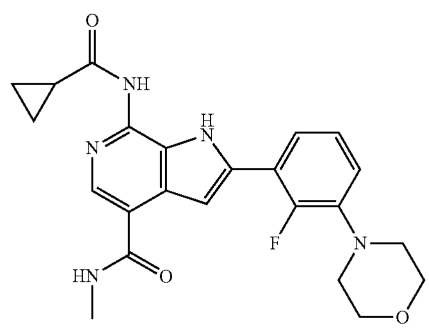 [SMILES: CNC(=O)c1cnc(NC(=O)C2CC2)c2[nH]c(-c3cccc(N4CCOCC4)c3F)cc12] |
| I-23 | 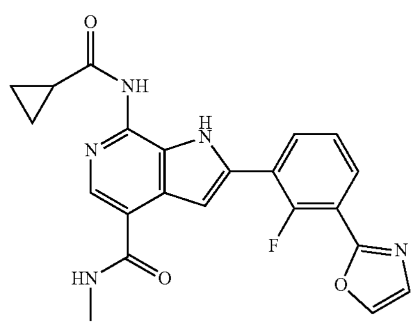 [SMILES: CNC(=O)c1cnc(NC(=O)C2CC2)c2[nH]c(-c3cccc(-c4ncco4)c3F)cc12] |
| I-24 | 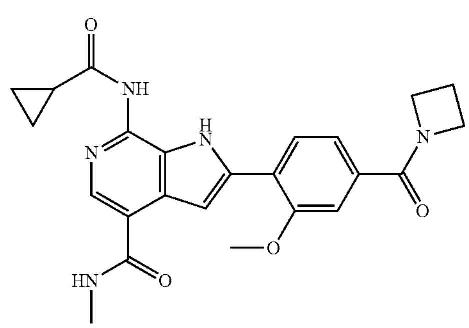 [SMILES: CNC(=O)c1cnc(NC(=O)C2CC2)c2[nH]c(-c3ccc(C(=O)N4CCC4)cc3OC)cc12] |

TABLE 1-continued
Selected Compounds
| Compound | Structure |
|---|---|
| I-25 | 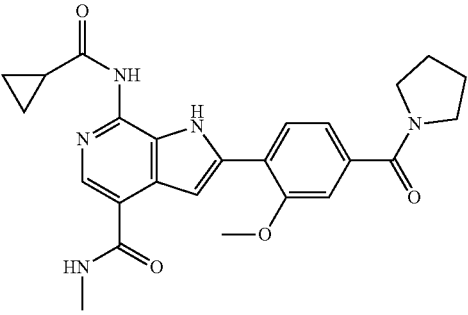 [SMILES: CNC(=O)c1cnc(NC(=O)C2CC2)c2[nH]c(-c3ccc(C(=O)N4CCCC4)cc3OC)cc12] |
| I-26 | 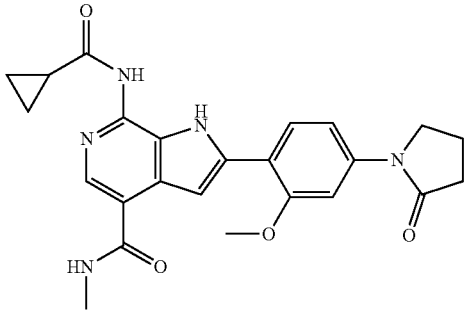 [SMILES: CNC(=O)c1cnc(NC(=O)C2CC2)c2[nH]c(-c3ccc(N4CCCC4=O)cc3OC)cc12] |
| I-27 | 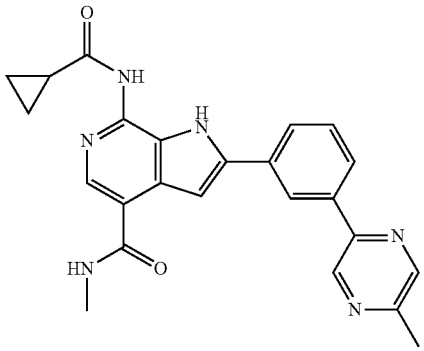 [SMILES: CNC(=O)c1cnc(NC(=O)C2CC2)c2[nH]c(-c3cccc(-c4cnc(C)cn4)c3)cc12] |
| I-28 | 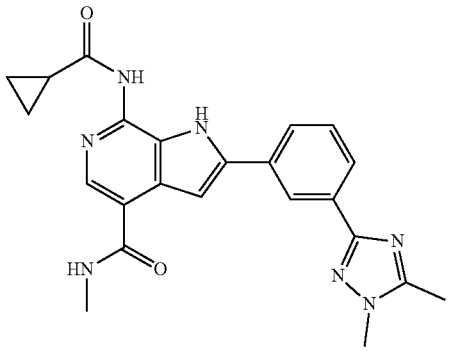 [SMILES: CNC(=O)c1cnc(NC(=O)C2CC2)c2[nH]c(-c3cccc(-c4nc(C)n(C)n4)c3)cc12] |

TABLE 1-continued

Selected Compounds

| Compound | Structure |
|---|---|
| I-29 | 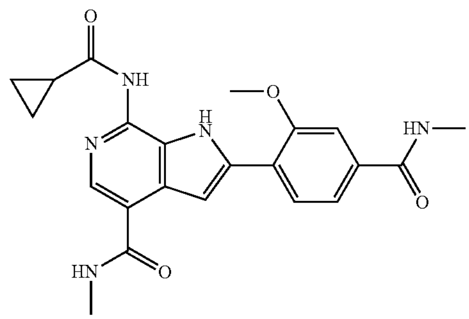 [SMILES: CNC(=O)c1ccc(-c2cc3c(C(=O)NC)cnc(NC(=O)C4CC4)c3[nH]2)c(OC)c1] |
| I-30 | 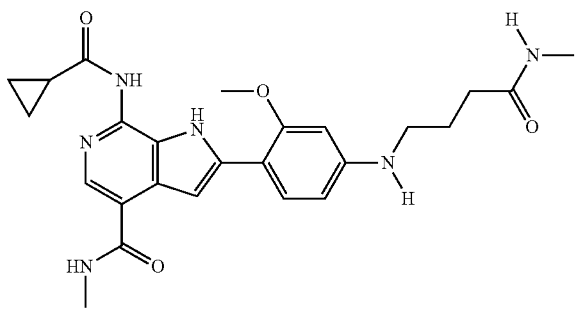 [SMILES: CNC(=O)CCCNc1ccc(-c2cc3c(C(=O)NC)cnc(NC(=O)C4CC4)c3[nH]2)c(OC)c1] |
| I-31 | 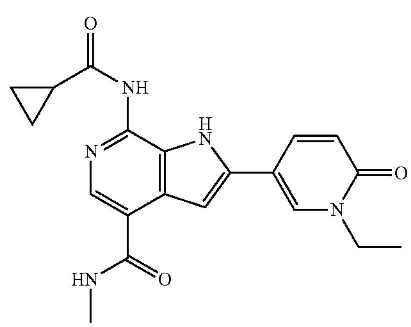 [SMILES: CCn1cc(-c2cc3c(C(=O)NC)cnc(NC(=O)C4CC4)c3[nH]2)ccc1=O] |
| I-32 | 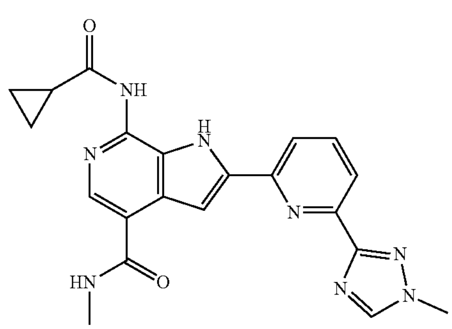 [SMILES: CNC(=O)c1cnc(NC(=O)C2CC2)c2[nH]c(-c3cccc(-c4ncn(C)n4)n3)cc12] |

TABLE 1-continued
Selected Compounds
| Compound | Structure |
|---|---|
| I-33 | 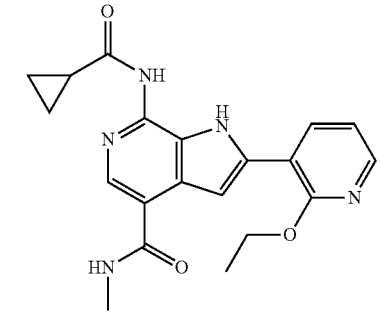 [SMILES: CCOc1ncccc1-c1cc2c(C(=O)NC)cnc(NC(=O)C3CC3)c2[nH]1] |
| I-34 | 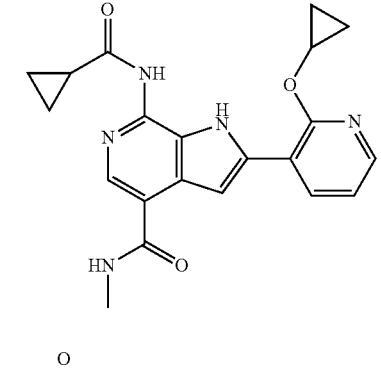 |
| I-35 | 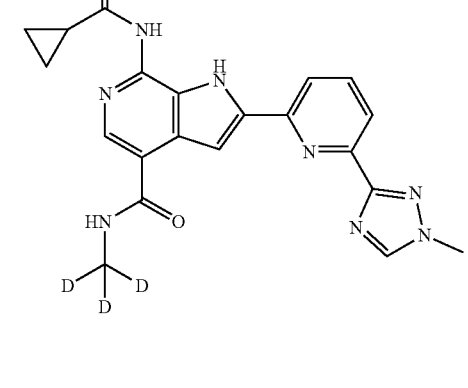 |
| I-36 | 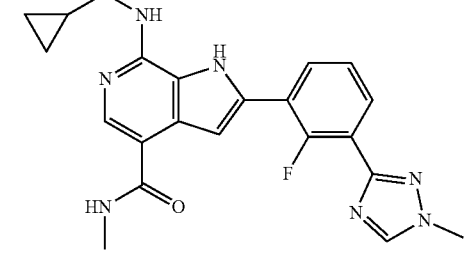 |

TABLE 1-continued

Selected Compounds

| Compound | Structure |
|---|---|
| I-37 | 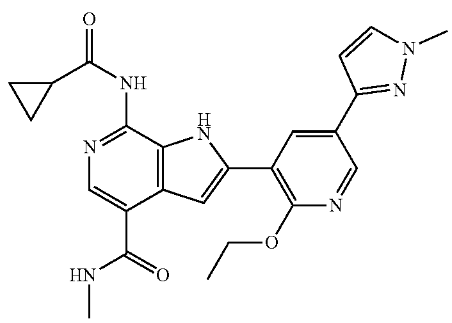 [SMILES: CCOc1ncc(-c2ccn(C)n2)cc1-c1cc2c(C(=O)NC)cnc(NC(=O)C3CC3)c2[nH]1] |
| I-38 | 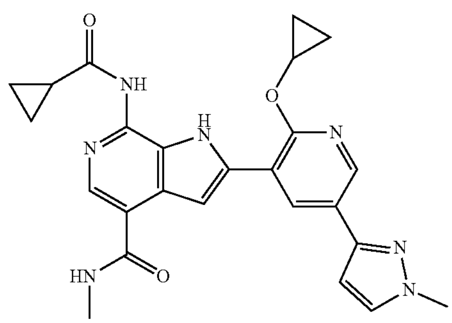 [SMILES: CNC(=O)c1cnc(NC(=O)C2CC2)c2[nH]c(-c3cc(-c4ccn(C)n4)cnc3OC3CC3)cc12] |
| I-39 | 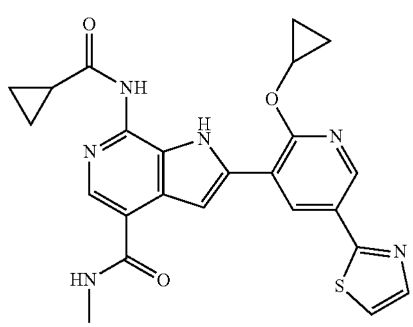 [SMILES: CNC(=O)c1cnc(NC(=O)C2CC2)c2[nH]c(-c3cc(-c4nccs4)cnc3OC3CC3)cc12] |
| I-40 | 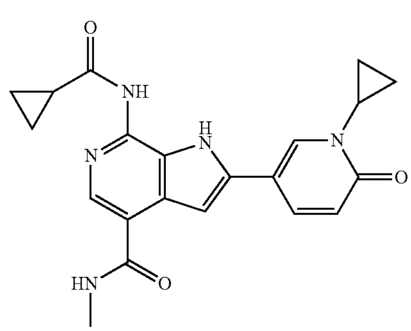 [SMILES: CNC(=O)c1cnc(NC(=O)C2CC2)c2[nH]c(-c3ccc(=O)n(C4CC4)c3)cc12] |

TABLE 1-continued

| Compound | Structure |
|---|---|
| I-41 | 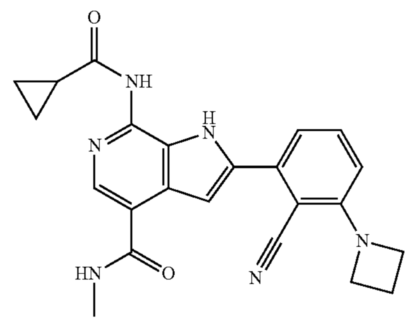 [SMILES: CNC(=O)c1cnc(NC(=O)C2CC2)c2[nH]c(-c3cccc(N4CCC4)c3C#N)cc12] |
| I-42 | 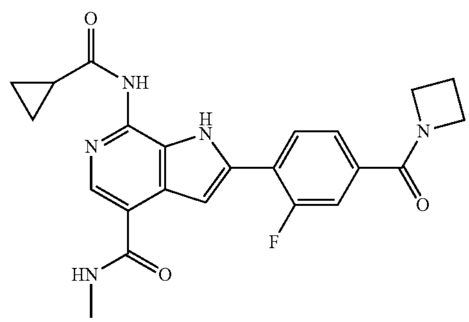 [SMILES: CNC(=O)c1cnc(NC(=O)C2CC2)c2[nH]c(-c3ccc(C(=O)N4CCC4)cc3F)cc12] |
| I-43 | 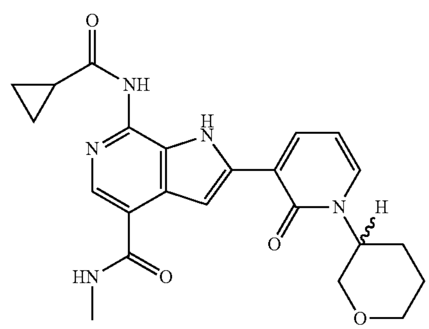 |
| I-44 | 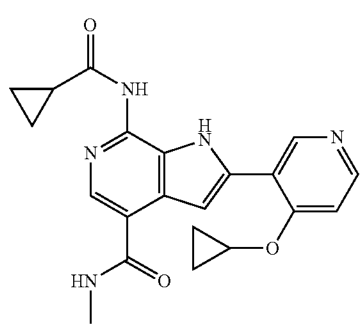 [SMILES: CNC(=O)c1cnc(NC(=O)C2CC2)c2[nH]c(-c3cnccc3OC3CC3)cc12] |

TABLE 1-continued
Selected Compounds
| Compound | Structure |
|---|---|
| I-45 | 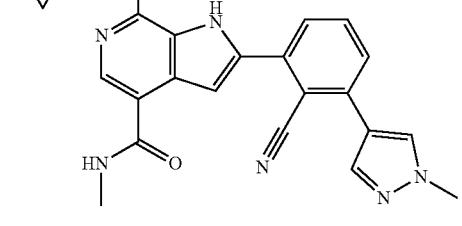 |
| I-46 | 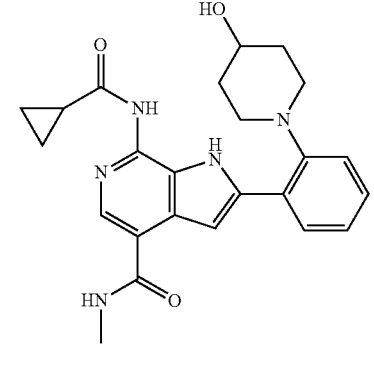 [SMILES: CNC(=O)c1cnc(NC(=O)C2CC2)c2[nH]c(-c3ccccc3N3CCC(O)CC3)cc12] |
| I-47 | 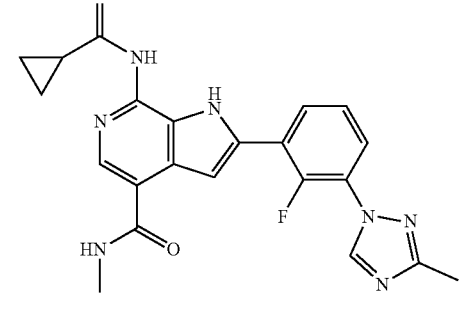 |
| I-48 | 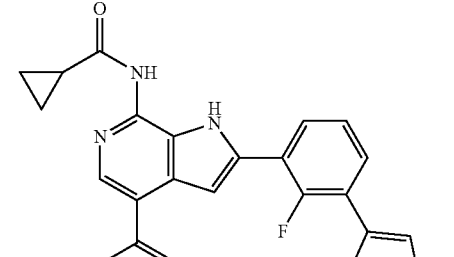 |

TABLE 1-continued
Selected Compounds
| Compound | Structure |
|---|---|
| I-49 | 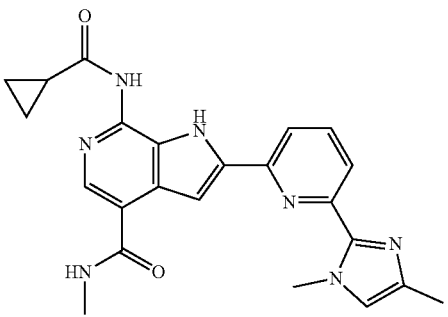 [SMILES: CNC(=O)c1cnc(NC(=O)C2CC2)c2[nH]c(-c3cccc(-c4nc(C)cn4C)n3)cc12] |
| I-50 | 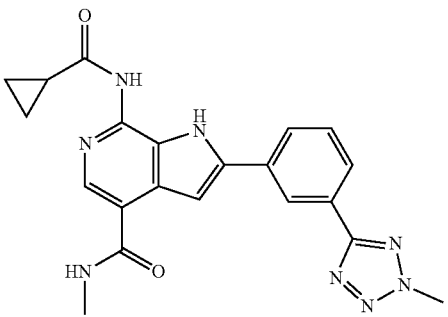 |
| I-51 | 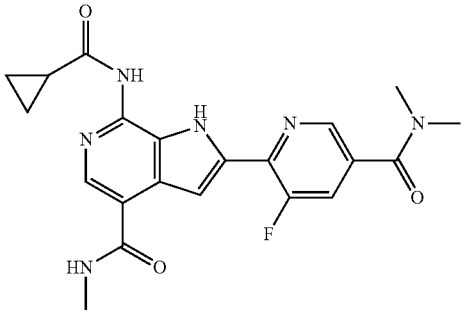 [SMILES: CNC(=O)c1cnc(NC(=O)C2CC2)c2[nH]c(-c3ncc(C(=O)N(C)C)cc3F)cc12] |
| I-52 | 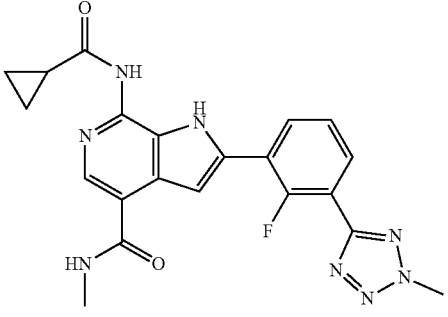 [SMILES: CNC(=O)c1cnc(NC(=O)C2CC2)c2[nH]c(-c3cccc(-c4nnn(C)n4)c3F)cc12] |

TABLE 1-continued

Selected Compounds

| Compound | Structure |
|---|---|
| I-53 | 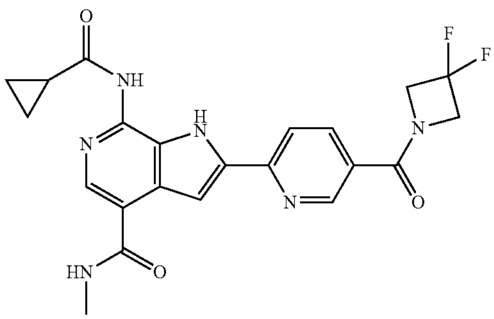 [SMILES: CNC(=O)c1cnc(NC(=O)C2CC2)c2[nH]c(-c3ccc(C(=O)N4CC(F)(F)C4)cn3)cc12] |
| I-54 | 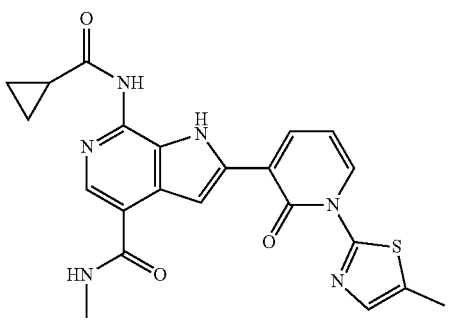 [SMILES: CNC(=O)c1cnc(NC(=O)C2CC2)c2[nH]c(-c3cccn(-c4ncc(C)s4)c3=O)cc12] |
| I-55 | 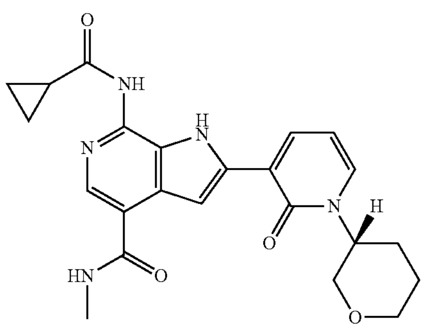 [SMILES: CNC(=O)c1cnc(NC(=O)C2CC2)c2[nH]c(-c3cccn([C@@H]4CCCOC4)c3=O)cc12] |
| I-56 | 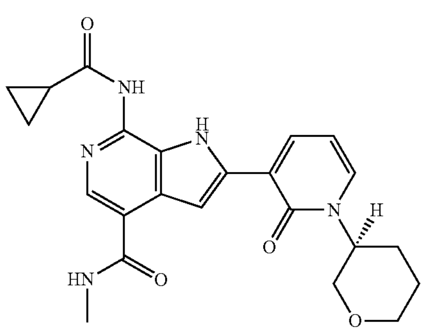 [SMILES: CNC(=O)c1cnc(NC(=O)C2CC2)c2[nH]c(-c3cccn([C@H]4CCCOC4)c3=O)cc12] |

TABLE 1-continued
Selected Compounds
| Compound | Structure |
|---|---|
| I-57 | 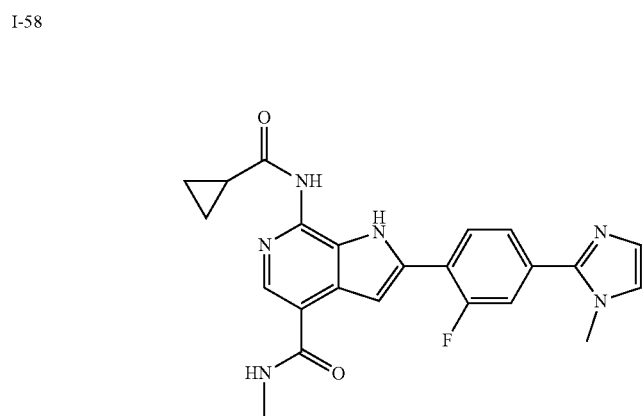 |
| I-58 | 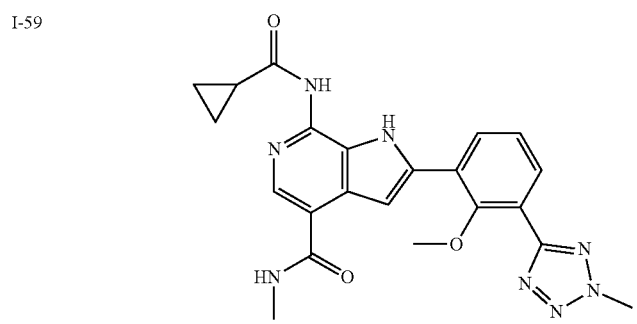 |
| I-59 | 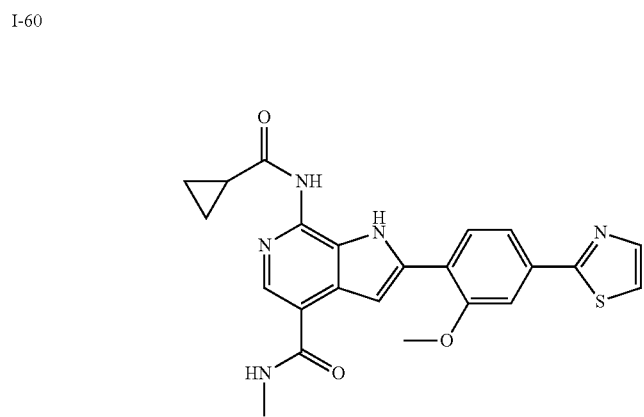 |
| I-60 | 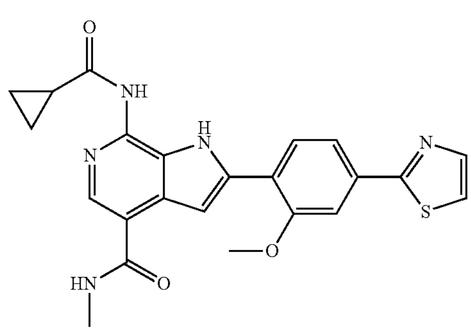 [SMILES: CNC(=O)c1cnc(NC(=O)C2CC2)c2[nH]c(-c3ccc(-c4nccs4)cc3OC)cc12] |

TABLE 1-continued
Selected Compounds
| Compound | Structure |
|---|---|
| I-61 | 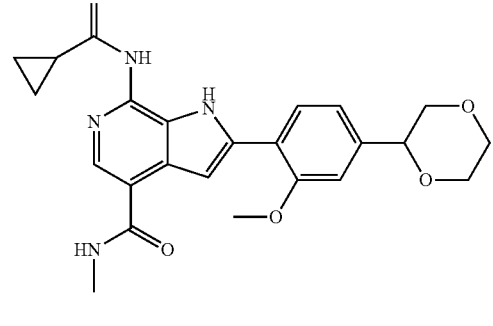 |
| I-62 | 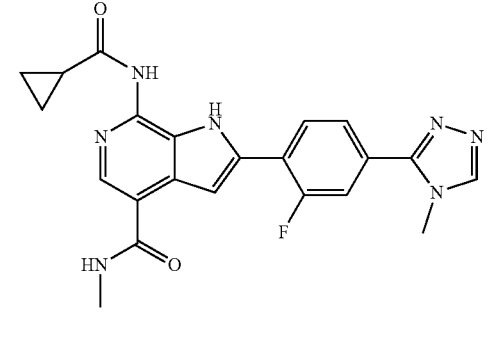 [SMILES: CNC(=O)c1cnc(NC(=O)C2CC2)c2[nH]c(-c3ccc(-c4nncn4C)cc3F)cc12] |
| I-63 | 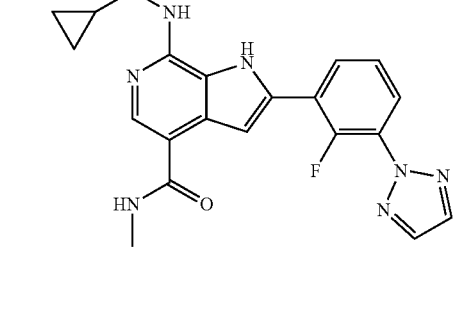 |
| I-64 | 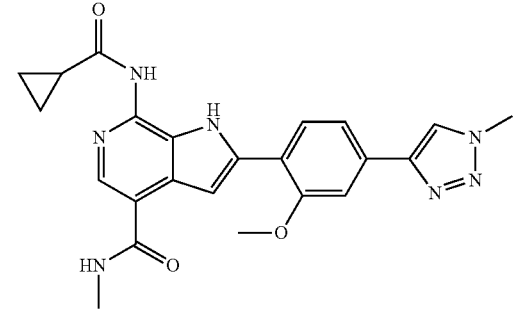 [SMILES: CNC(=O)c1cnc(NC(=O)C2CC2)c2[nH]c(-c3ccc(-c4cn(C)nn4)cc3OC)cc12] |

TABLE 1-continued

Selected Compounds

| Compound | Structure |
|---|---|
| I-65 | (structure) |
| I-66 | (structure) |
| I-67 | (structure) |
| I-68 | (structure) |

TABLE 1-continued
Selected Compounds
| Compound | Structure |
|---|---|
| I-69 | 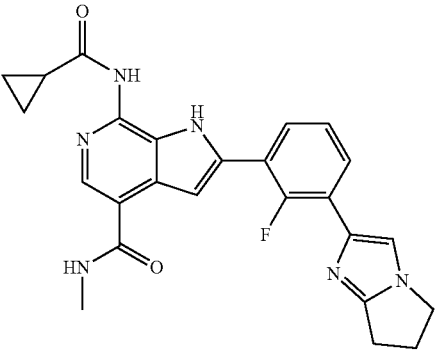 [SMILES: CNC(=O)c1cnc(NC(=O)C2CC2)c2[nH]c(-c3cccc(-c4cn5c(n4)CCC5)c3F)cc12] |
| I-70 | 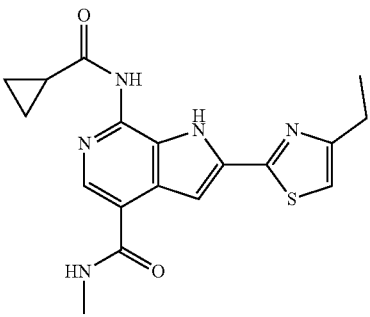 [SMILES: CCc1csc(-c2cc3c(C(=O)NC)cnc(NC(=O)C4CC4)c3[nH]2)n1] |
| I-71 | 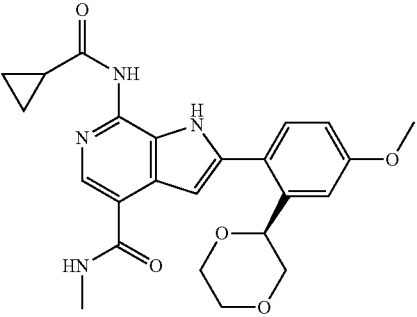 [SMILES: CNC(=O)c1cnc(NC(=O)C2CC2)c2[nH]c(-c3ccc(OC)cc3[C@H]3COCCO3)cc12] |
| I-72 | 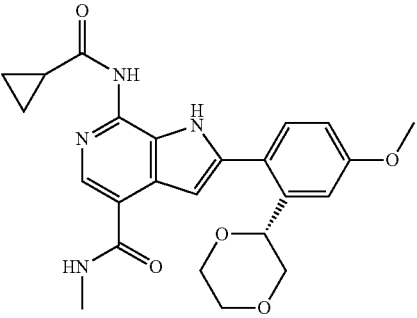 [SMILES: CNC(=O)c1cnc(NC(=O)C2CC2)c2[nH]c(-c3ccc(OC)cc3[C@@H]3COCCO3)cc12] |

TABLE 1-continued

| Compound | Structure |
|---|---|
| I-73 | 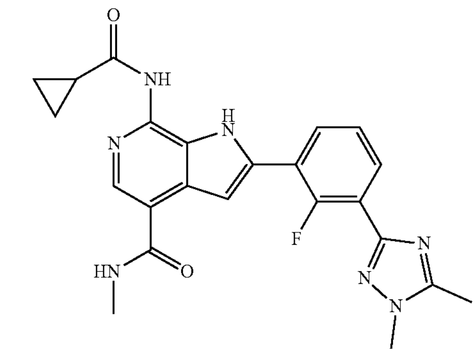 [SMILES: CNC(=O)c1cnc(NC(=O)C2CC2)c2[nH]c(-c3cccc(-c4nc(C)n(C)n4)c3F)cc12] |
| I-74 | 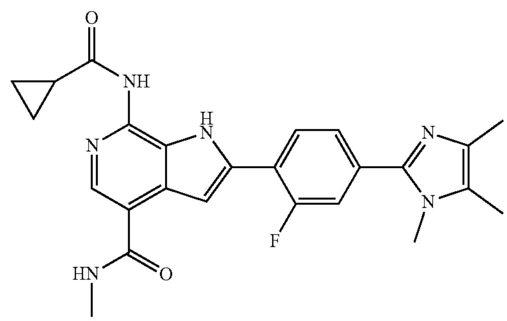 [SMILES: CNC(=O)c1cnc(NC(=O)C2CC2)c2[nH]c(-c3ccc(-c4nc(C)c(C)n4C)cc3F)cc12] |
| I-75 | 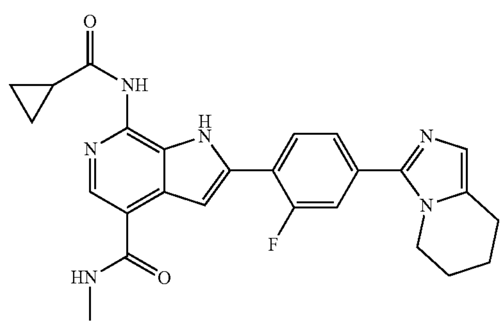 [SMILES: CNC(=O)c1cnc(NC(=O)C2CC2)c2[nH]c(-c3ccc(-c4ncc5n4CCCC5)cc3F)cc12] |
| I-76 | 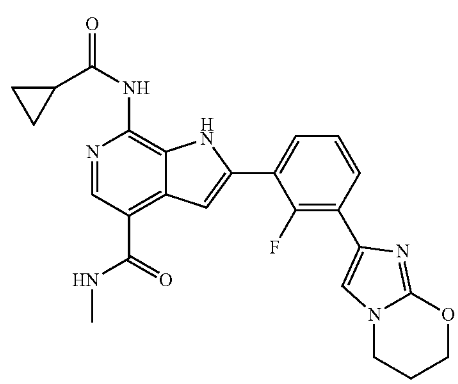 [SMILES: CNC(=O)c1cnc(NC(=O)C2CC2)c2[nH]c(-c3cccc(-c4cn5c(n4)OCCC5)c3F)cc12] |

TABLE 1-continued
Selected Compounds
| Compound | Structure |
|---|---|
| I-77 | 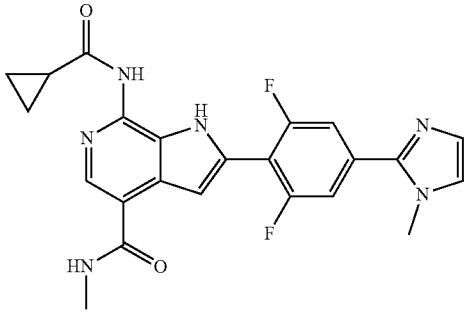 [SMILES: CNC(=O)c1cnc(NC(=O)C2CC2)c2[nH]c(-c3c(F)cc(-c4nccn4C)cc3F)cc12] |
| I-78 | 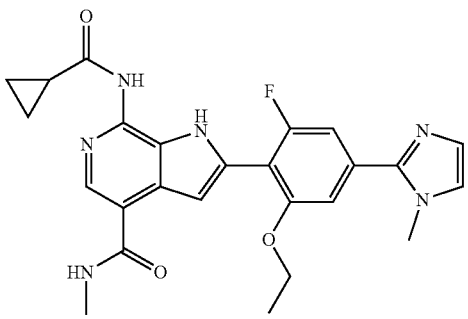 [SMILES: CCOc1cc(-c2nccn2C)cc(F)c1-c1cc2c(C(=O)NC)cnc(NC(=O)C3CC3)c2[nH]1] |
| I-79 | 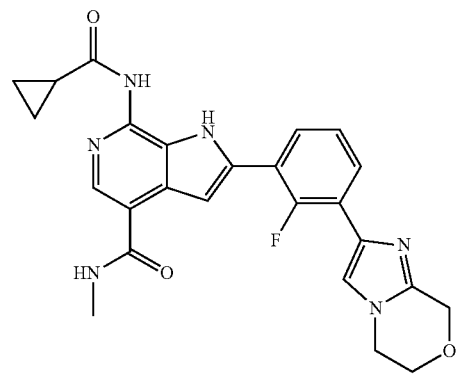 [SMILES: CNC(=O)c1cnc(NC(=O)C2CC2)c2[nH]c(-c3cccc(-c4cn5c(n4)COCC5)c3F)cc12] |
| I-80 | 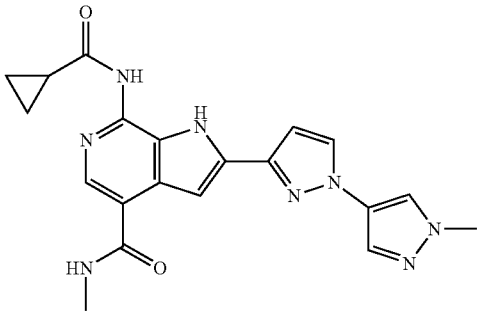 [SMILES: CNC(=O)c1cnc(NC(=O)C2CC2)c2[nH]c(-c3ccn(-c4cnn(C)c4)n3)cc12] |

TABLE 1-continued

Selected Compounds

| Compound | Structure |
|---|---|
| I-81 | 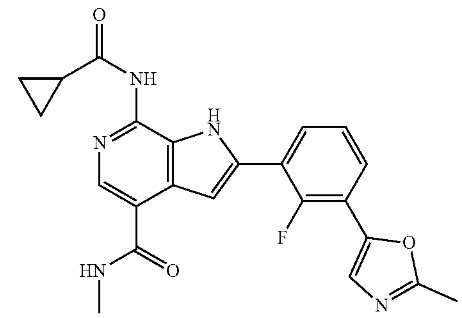 [SMILES: CNC(=O)c1cnc(NC(=O)C2CC2)c2[nH]c(-c3cccc(-c4cnc(C)o4)c3F)cc12] |
| I-82 | 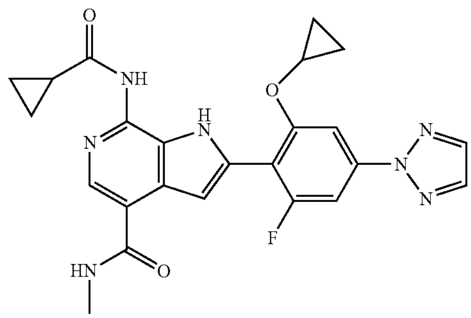 [SMILES: CNC(=O)c1cnc(NC(=O)C2CC2)c2[nH]c(-c3c(F)cc(-n4nccn4)cc3OC3CC3)cc12] |
| I-83 | 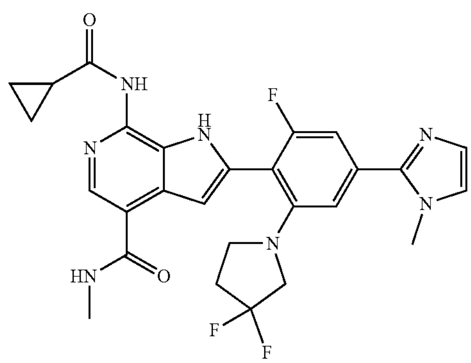 [SMILES: CNC(=O)c1cnc(NC(=O)C2CC2)c2[nH]c(-c3c(F)cc(-c4nccn4C)cc3N3CCC(F)(F)C3)cc12] |
| I-84 | 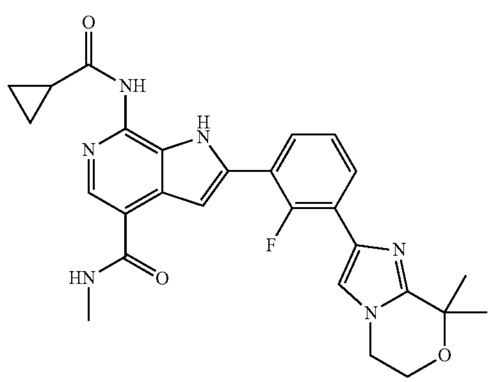 [SMILES: CNC(=O)c1cnc(NC(=O)C2CC2)c2[nH]c(-c3cccc(-c4cn5c(n4)C(C)(C)OCC5)c3F)cc12] |

TABLE 1-continued

Selected Compounds

| Compound | Structure |
|---|---|
| I-85 | 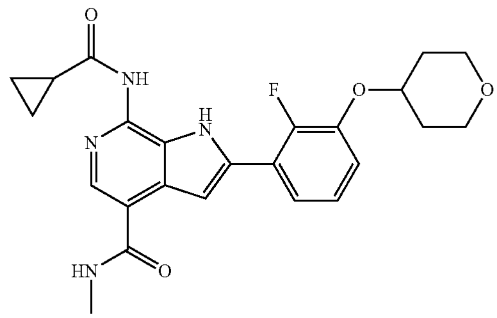 [SMILES: CNC(=O)c1cnc(NC(=O)C2CC2)c2[nH]c(-c3cccc(OC4CCOCC4)c3F)cc12] |
| I-86 | 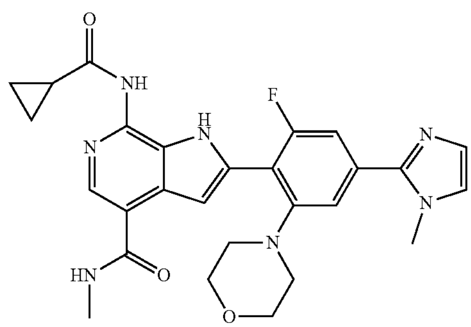 [SMILES: CNC(=O)c1cnc(NC(=O)C2CC2)c2[nH]c(-c3c(F)cc(-c4nccn4C)cc3N3CCOCC3)cc12] |
| I-87 | 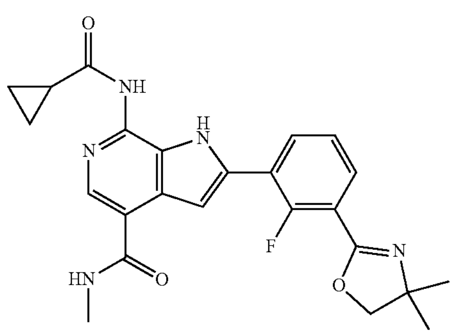 [SMILES: CNC(=O)c1cnc(NC(=O)C2CC2)c2[nH]c(-c3cccc(C4=NC(C)(C)CO4)c3F)cc12] |
| I-88 | 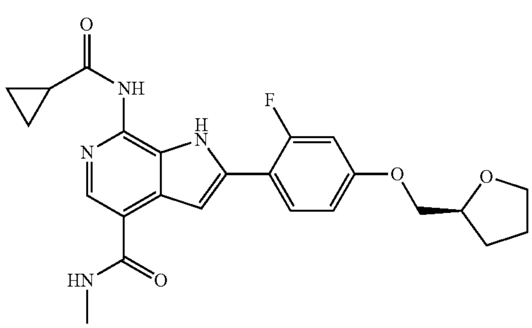 [SMILES: CNC(=O)c1cnc(NC(=O)C2CC2)c2[nH]c(-c3ccc(OC[C@@H]4CCCO4)cc3F)cc12] |

TABLE 1-continued

Selected Compounds

| Compound | Structure |
|---|---|
| I-89 | 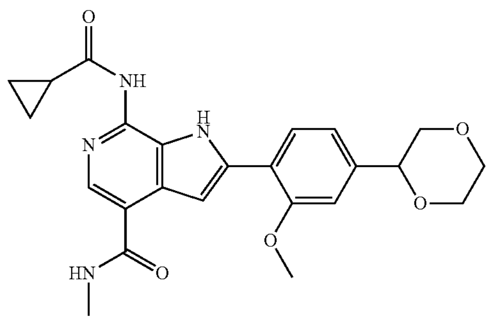 [SMILES: CNC(=O)c1cnc(NC(=O)C2CC2)c2[nH]c(-c3ccc(C4COCCO4)cc3OC)cc12] |
| I-90 | 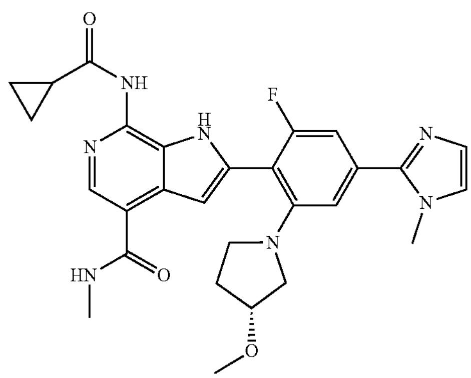 [SMILES: CNC(=O)c1cnc(NC(=O)C2CC2)c2[nH]c(-c3c(F)cc(-c4nccn4C)cc3N3CC[C@@H](OC)C3)cc12] |
| I-91 | 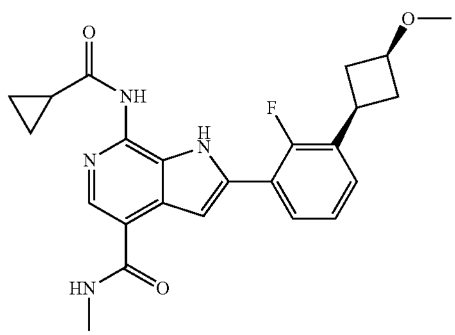 [SMILES: CNC(=O)c1cnc(NC(=O)C2CC2)c2[nH]c(-c3cccc([C@H]4C[C@@H](OC)C4)c3F)cc12] |
| I-92 | 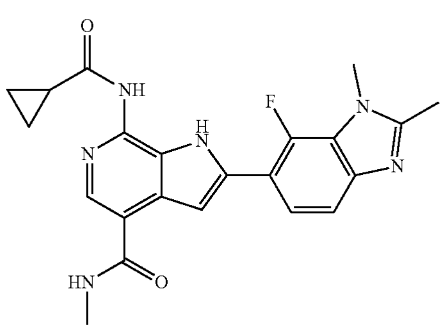 [SMILES: CNC(=O)c1cnc(NC(=O)C2CC2)c2[nH]c(-c3ccc4nc(C)n(C)c4c3F)cc12] |

TABLE 1-continued

Selected Compounds

| Compound | Structure |
|---|---|
| I-93 | 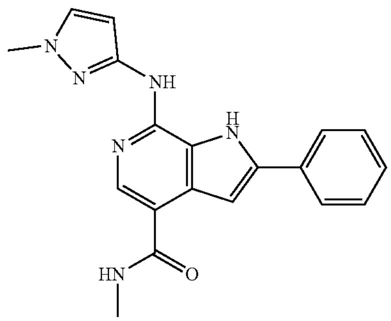 [SMILES: CNC(=O)c1cnc(Nc2ccn(C)n2)c2[nH]c(-c3ccccc3)cc12] |
| I-94 | 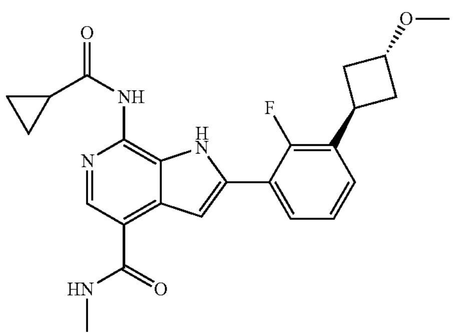 [SMILES: CNC(=O)c1cnc(NC(=O)C2CC2)c2[nH]c(-c3cccc([C@H]4C[C@H](OC)C4)c3F)cc12] |
| I-95 | 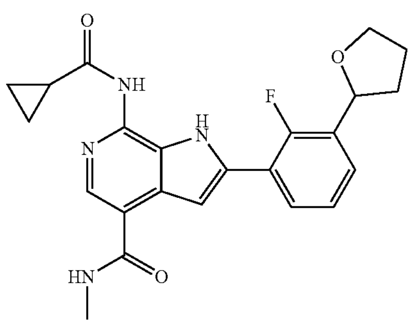 [SMILES: CNC(=O)c1cnc(NC(=O)C2CC2)c2[nH]c(-c3cccc(C4CCCO4)c3F)cc12] |
| I-96 | 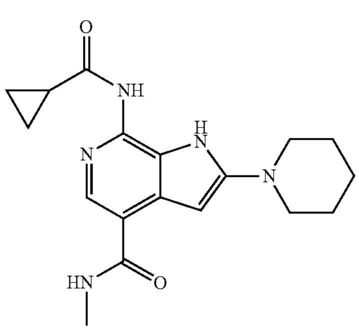 [SMILES: CNC(=O)c1cnc(NC(=O)C2CC2)c2[nH]c(N3CCCCC3)cc12] |

TABLE 1-continued

Selected Compounds

| Compound | Structure |
|---|---|
| I-97 | 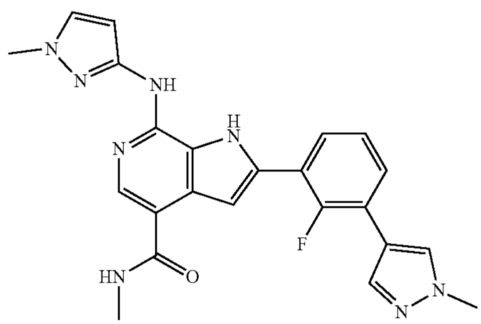 |
| I-98 | 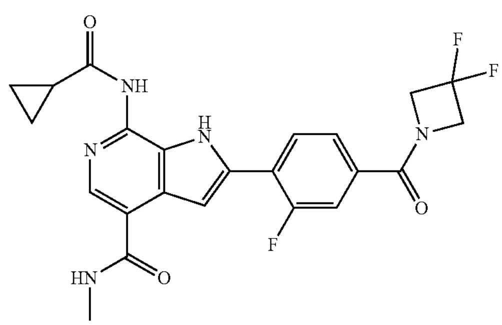 [SMILES: CNC(=O)c1cnc(NC(=O)C2CC2)c2[nH]c(-c3ccc(C(=O)N4CC(F)(F)C4)cc3F)cc12] |
| I-99 | 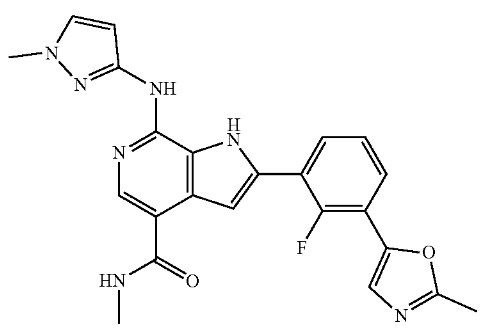 |
| I-100 | 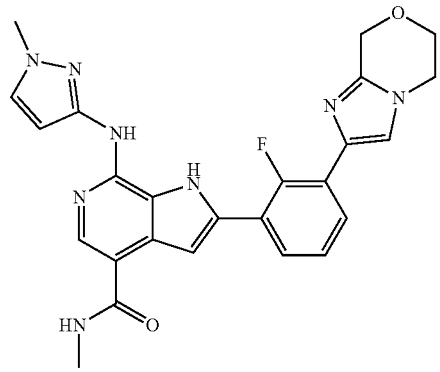 [SMILES: CNC(=O)c1cnc(Nc2ccn(C)n2)c2[nH]c(-c3cccc(-c4cn5c(n4)COCC5)c3F)cc12] |

TABLE 1-continued

Selected Compounds

| Compound | Structure |
|---|---|
| I-101 | 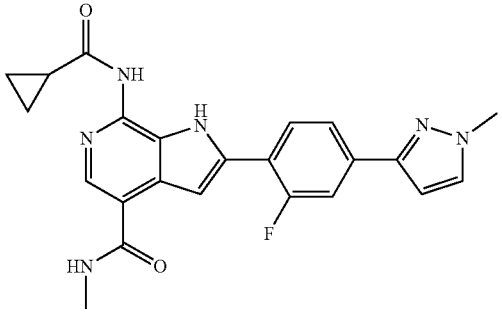 [SMILES: CNC(=O)c1cnc(NC(=O)C2CC2)c2[nH]c(-c3ccc(-c4ccn(C)n4)cc3F)cc12] |

In some embodiments, the present invention provides a compound set forth in Table 1, above, or a pharmaceutically acceptable salt thereof. In some embodiments, the present invention provides a compound set forth in Table 1, above. In some embodiments, the present invention provides a pharmaceutical composition comprising a compound set forth in Table 1 above, or a pharmaceutically acceptable salt thereof, together with a pharmaceutically acceptable carrier, excipient, or diluent.

In some embodiments, the present invention provides a compound of formula I or I' as described above, wherein the compound is denoted as "A" as set forth in Table 2. In some embodiments, the present invention provides a compound of formula I or I' as described above, wherein the compound is denoted as "B" as set forth in Table 2. In some embodiments, the present invention provides a compound of formula I or I' as described above, wherein the compound is denoted as "C" as set forth in Table 2. In some embodiments, the present invention provides a compound of formula I or I' as described above, wherein the compound is denoted as "D" as set forth in Table 2. In some embodiments, the present invention provides a compound of formula I or I' as described above, wherein the compound is denoted as "A" or "B" as set forth in Table 2. In some embodiments, the present invention provides a compound of formula I or I' as described above, wherein the compound is denoted as "A" or "B" or "C" as set forth in Table 2. In some embodiments, the present invention provides a compound of formula I or I' as described above, wherein the compound is denoted as "A" or "B" or "C" or "D" as set forth in Table 2.

In some embodiments, the present invention provides a compound of formula I or I' as defined above, or a pharmaceutically acceptable salt thereof, or a pharmaceutical composition comprising a compound of formula I or I' as defined above, or a pharmaceutically acceptable salt thereof, and a pharmaceutically acceptable carrier, adjuvant, or vehicle for use as a medicament.

Without wishing to be bound by any particular theory, it is believed that proximity of an inhibitor compound, or pendant moiety of an inhibitor compound, to the water of interest facilitates displacement or disruption of that water by the inhibitor compound, or pendant moiety of an inhibitor compound. In some embodiments, a water molecule displaced or disrupted by an inhibitor compound, or pendant moiety of an inhibitor compound, is an unstable water molecule.

In certain embodiments, the method employs a complex comprising TYK2 and an inhibitor, wherein at least one unstable water of TYK2 is displaced or disrupted by the inhibitor. In some embodiments, at least two unstable waters selected are displaced or disrupted by the inhibitor.

4. General Methods of Providing the Present Compounds

The compounds of this invention may be prepared or isolated in general by synthetic and/or semi-synthetic methods known to those skilled in the art for analogous compounds and by methods described in detail in the Examples, herein.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit a TYK2 protein kinase, or a mutant thereof, in a biological sample or in a patient. In certain embodiments, the amount of compound in compositions of this invention is such that is effective to measurably inhibit a TYK2 protein kinase, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of a TYK2 protein kinase, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of kinase activity of one or more enzymes. In some embodiments the kinase inhibited by the compounds and methods of the invention is TYK2.

TYK2 is a non-receptor tyrosine kinase member of the Janus kinase (JAKs) family of protein kinases. The mammalian JAK family consists of four members, TYK2, JAK1, JAK2, and JAK3. JAK proteins, including TYK2, are integral to cytokine signaling. TYK2 associates with the cytoplasmic domain of type I and type II cytokine receptors, as well as interferon types I and III receptors, and is activated by those receptors upon cytokine binding. Cytokines implicated in TYK2 activation include interferons (e.g. IFN-α, IFN-β, IFN-κ, IFN-δ, IFN-ε, IFN-τ, IFN-ω, and IFN-ζ (also known as limitin), and interleukins (e.g. IL-4, IL-6, IL-10, IL-11, IL-12, IL-13, IL-22, IL-23, IL-27, IL-31, oncostatin M, ciliary neurotrophic factor, cardiotrophin 1, cardiotrophin-like cytokine, and LIF). Velasquez et al., "A protein kinase in the interferon α/β signaling pathway," Cell (1992) 70:313; Stahl et al., "Association and activation of Jak-Tyk kinases by CNTF-LIF-OSM-IL-6β receptor components," Science (1994) 263:92; Finbloom et al., "IL-10 induces the tyrosine phosphorylation of Tyk2 and Jak1 and the differential assembly of Stat1 and Stat3 complexes in human T cells and monocytes," J. Immunol. (1995) 155:1079; Bacon et al., "Interleukin 12 (IL-12) induces tyrosine phosphorylation of Jak2 and Tyk2: differential use of Janus family kinases by IL-2 and IL-12," J. Exp. Med. (1995) 181:399; Welham et al., "Interleukin-13 signal transduction in lymphohemopoietic cells: similarities and differences in signal transduction with interleukin-4 and insulin," J. Biol. Chem. (1995) 270:12286; Parham et al., "A receptor for the heterodimeric cytokine IL-23 is composed of IL-12R31 and a novel cytokine receptor subunit, IL-23R," J. Immunol. (2002) 168:5699. The activated TYK2 then goes on to phosphorylate further signaling proteins such as members of the STAT family, including STAT1, STAT2, STAT4, and STAT6.

TYK2 activation by IL-23, has been linked to inflammatory bowel disease (IBD), Crohn's disease, and ulcerative colitis. Duerr et al., "A Genome-Wide Association Study Identifies IL23R as an Inflammatory Bowel Disease Gene," Science (2006) 314:1461-1463. As the downstream effector of IL-23, TYK2 also plays a role in psoriasis, ankylosing spondylitis, and Behçet's disease. Cho et al., "Genomics and the multifactorial nature of human auto-immune disease," N. Engl. J. Med (2011) 365:1612-1623; Cortes et al., "Identification of multiple risk variants for ankylosing spondylitis through high-density genotyping of immune-related loci," Nat. Genet. (2013) 45(7):730-738; Remmers et al., "Genome-wide association study identifies variants in the MHC class I, IL10, and IL23R-IL12RB2 regions associated with Behçet's disease," Nat. Genet. (2010) 42:698-702. A genome-wide association study of 2,622 individuals with psoriasis identified associations between disease susceptibility and TYK2. Strange et al., "A genome-wide association study identifies new psoriasis susceptibility loci and an interaction between HLA-C and ERAP1," Nat. Genet. (2010) 42:985-992. Knockout or tyrphostin inhibition of TYK2 significantly reduces both IL-23 and IL-22-induced dermatitis. Ishizaki et al., "Tyk2 is a therapeutic target for psoriasis-like skin inflammation," Intl. Immunol. (2013), doi: 10.1093/intimm/dxt062.

TYK2 also plays a role in respiratory diseases such as asthma, chronic obstructive pulmonary disease (COPD), lung cancer, and cystic fibrosis. Goblet cell hyperplasia (GCH) and mucous hypersecretion is mediated by IL-13-induced activation of TYK2, which in turn activates STAT6. Zhang et al., "Docking protein Gab2 regulates mucin expression and goblet cell hyperplasia through TYK2/STAT6 pathway," FASEB J. (2012) 26:1-11.

Decreased TYK2 activity leads to protection of joints from collagen antibody-induced arthritis, a model of human rheumatoid arthritis. Mechanistically, decreased Tyk2 activity reduced the production of $T_h1/T_h17$-related cytokines and matrix metalloproteases, and other key markers of inflammation. Ishizaki et al., "Tyk2 deficiency protects joints against destruction in anti-type II collagen antibody-induced arthritis in mice," Intl. Immunol. (2011) 23(9):575-582.

TYK2 knockout mice showed complete resistance in experimental autoimmune encephalomyelitis (EAE, an animal model of multiple sclerosis (MS)), with no infiltration of CD4 T cells in the spinal cord, as compared to controls, suggesting that TYK2 is essential to pathogenic CD4-mediated disease development in MS. Oyamada et al., "Tyrosine Kinase 2 Plays Critical Roles in the Pathogenic CD4 T Cell Responses for the Development of Experimental Autoimmune Encephalomyelitis," J. Immunol. (2009) 183: 7539-7546. This corroborates earlier studies linking increased TYK2 expression with MS susceptibility. Ban et al., "Replication analysis identifies TYK2 as a multiple sclerosis susceptibility factor," Eur J. Hum. Genet. (2009) 17:1309-1313. Loss of function mutation in TYK2, leads to decreased demyelination and increased remyelination of neurons, further suggesting a role for TYK2 inhibitors in the treatment of MS and other CNS demyelination disorders.

TYK2 is the sole signaling messenger common to both IL-12 and IL-23. TYK2 knockout reduced methylated BSA injection-induced footpad thickness, imiquimod-induced psoriasis-like skin inflammation, and dextran sulfate sodium or 2,4,6-trinitrobenzene sulfonic acid-induced colitis in mice.

Joint linkage and association studies of various type I IFN signaling genes with systemic lupus erythematosus (SLE, an autoimmune disorder), showed a strong, and significant correlation between loss of function mutations to TYK2 and decreased prevalence of SLE in families with affected members. Sigurdsson et al., "Polymorphisms in the Tyrosine Kinase 2 and Interferon Regulatory Factor 5 Genes Are Associated with Systemic Lupis Erythematosus," Am. J. Hum. Genet. (2005) 76:528-537. Genome-wide association studies of individuals with SLE versus an unaffected cohort showed highly significant correlation between the TYK2 locus and SLE. Graham et al., "Association of NCF2, IKZF1, IRF8, IFIH1, and TYK2 with Systemic Lupus Erythematosus," PLoS Genetics (2011) 7(10):e1002341.

TYK2 has been shown to play an important role in maintaining tumor surveillance and TYK2 knockout mice showed compromised cytotoxic T cell response, and accelerated tumor development. However, these effects were linked to the efficient suppression of natural killer (NK) and cytotoxic T lymphocytes, suggesting that TYK2 inhibitors would be highly suitable for the treatment of autoimmune disorders or transplant rejection. Although other JAK family members such as JAK3 have similar roles in the immune system, TYK2 has been suggested as a superior target because of its involvement in fewer and more closely related signaling pathways, leading to fewer off-target effects. Simma et al. "Identification of an Indispensable Role for Tyrosine Kinase 2 in CTL-Mediated Tumor Surveillance," Cancer Res. (2009) 69:203-211.

However, paradoxically to the decreased tumor surveillance observed by Simma et al., studies in T-cell acute lymphoblastic leukemia (T-ALL) indicate that T-ALL is highly dependent on IL-10 via TYK2 via STAT1-mediated signal transduction to maintain cancer cell survival through upregulation of anti-apoptotic protein BCL2. Knockdown of TYK2, but not other JAK family members, reduced cell growth. Specific activating mutations to TYK2 that promote cancer cell survival include those to the FERM domain (G36D, S47N, and R425H), the JH2 domain (V731II), and the kinase domain (E957D and R1027H). However, it was also identified that the kinase function of TYK2 is required for increased cancer cell survival, as TYK2 enzymes featuring kinase-dead mutations (M978Y or M978F) in addition to an activating mutation (E957D) resulted in failure to transform. Sanda et al. "TYK2-STAT1-BCL2 Pathway Dependence in T-Cell Acute Lymphoblastic Leukemia," Cancer Disc. (2013) 3(5):564-577.

Thus, selective inhibition of TYK2 has been suggested as a suitable target for patients with IL-10 and/or BCL2-addicted tumors, such as 70% of adult T-cell leukemia cases. Fontan et al. "Discovering What Makes STAT Signaling TYK in T-ALL," Cancer Disc. (2013) 3:494-496.

TYK2 mediated STAT3 signaling has also been shown to mediate neuronal cell death caused by amyloid-β (Aβ) peptide. Decreased TYK2 phosphorylation of STAT3 following Aβ administration lead to decreased neuronal cell death, and increased phosphorylation of STAT3 has been observed in postmorterm brains of Alzheimer's patients. Wan et al. "Tyk/STAT3 Signaling Mediates β-Amyloid-Induced Neuronal Cell Death: Implications in Alzheimer's Disease," J. Neurosci. (2010) 30(20):6873-6881.

Inhibition of JAK-STAT signaling pathways is also implicated in hair growth, and the reversal of the hair loss associated with alopecia areata. Xing et al., "Alopecia areata is driven by cytotoxic T lymphocytes and is reversed by JAK inhibition," Nat. Med. (2014) 20: 1043-1049; Harel et al., "Pharmacologic inhibition of JAK-STAT signaling promotes hair growth," Sci. Adv. (2015) 1(9):e1500973.

Accordingly, compounds that inhibit the activity of TYK2 are beneficial, especially those with selectivity over JAK2. Such compounds should deliver a pharmacological response that favorably treats one or more of the conditions described herein without the side-effects associated with the inhibition of JAK2.

Even though TYK2 inhibitors are known in the art, there is a continuing need to provide novel inhibitors having more effective or advantageous pharmaceutically relevant properties. For example, compounds with increased activity, selectivity over other JAK kinases (especially JAK2), and ADMET (absorption, distribution, metabolism, excretion, and/or toxicity) properties. Thus, in some embodiments, the present invention provides inhibitors of TYK2 which show selectivity over JAK2.

The activity of a compound utilized in this invention as an inhibitor of TYK2, or a mutant thereof, may be assayed in vitro, in vivo or in a cell line. In vitro assays include assays that determine inhibition of either the phosphorylation activity and/or the subsequent functional consequences, or ATPase activity of activated TYK2, or a mutant thereof. Alternate in vitro assays quantitate the ability of the inhibitor to bind to TYK2. Inhibitor binding may be measured by radiolabeling the inhibitor prior to binding, isolating the inhibitor/TYK2 complex and determining the amount of radiolabel bound. Alternatively, inhibitor binding may be determined by running a competition experiment where new inhibitors are incubated with TYK2 bound to known radioligands. Representative in vitro and in vivo assays useful in assaying a TYK2 inhibitor include those described and disclosed in, e.g., each of which is herein incorporated by reference in its entirety. Detailed conditions for assaying a compound utilized in this invention as an inhibitor of TYK2, or a mutant thereof, are set forth in the Examples below.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of TYK2 and are therefore useful for treating one or more disorders associated with activity of TYK2 or mutants thereof. Thus, in certain embodiments, the present invention provides a method for treating a TYK2-mediated disorder comprising the step of administering to a patient in need thereof a compound of the present invention, or pharmaceutically acceptable composition thereof.

As used herein, the term "TYK2-mediated" disorders, diseases, and/or conditions as used herein means any disease or other deleterious condition in which TYK2 or a mutant thereof is known to play a role. Accordingly, another embodiment of the present invention relates to treating or lessening the severity of one or more diseases in which TYK2, or a mutant thereof, is known to play a role. Such TYK2-mediated disorders include but are not limited to autoimmune disorders, inflammatory disorders, proliferative disorders, endocrine disorders, neurological disorders and disorders associated with transplantation.

In some embodiments, the present invention provides a method for treating one or more disorders, wherein the disorders are selected from autoimmune disorders, inflammatory disorders, proliferative disorders, endocrine disorders, neurological disorders, and disorders associated with transplantation, said method comprising administering to a patient in need thereof, a pharmaceutical composition comprising an effective amount of a compound of the present invention, or a pharmaceutically acceptable salt thereof.

In some embodiments, the disorder is an autoimmune disorder. In some embodiments the disorder is selected from type 1 diabetes, cutaneous lupus erythematosus, systemic lupus erythematosus, multiple sclerosis, psoriasis, Behçet's disease, POEMS syndrome, Crohn's disease, ulcerative colitis, and inflammatory bowel disease.

In some embodiments, the disorder is an inflammatory disorder. In some embodiments, the inflammatory disorder is rheumatoid arthritis, asthma, chronic obstructive pulmonary disease, psoriasis, hepatomegaly, Crohn's disease, ulcerative colitis, inflammatory bowel disease.

In some embodiments, the disorder is a proliferative disorder. In some embodiments, the proliferative disorder is a hematological cancer. In some embodiments the proliferative disorder is a leukemia. In some embodiments, the leukemia is a T-cell leukemia. In some embodiments the T-cell leukemia is T-cell acute lymphoblastic leukemia (T-ALL). In some embodiments the proliferative disorder is polycythemia vera, myelofibrosis, essential or thrombocytosis.

In some embodiments, the disorder is an endocrine disorder. In some embodiments, the endocrine disorder is polycystic ovary syndrome, Crouzon's syndrome, or type 1 diabetes.

In some embodiments, the disorder is a neurological disorder. In some embodiments, the neurological disorder is Alzheimer's disease.

In some embodiments the proliferative disorder is associated with one or more activating mutations in TYK2. In some embodiments, the activating mutation in TYK2 is a mutation to the FERM domain, the JH2 domain, or the kinase domain. In some embodiments the activating mutation in TYK2 is selected from G36D, S47N, R425H, V731I, E957D, and R1027H.

In some embodiments, the disorder is associated with transplantation. In some embodiments the disorder associated with transplantation is transplant rejection, or graft versus host disease.

In some embodiments the disorder is associated with type I interferon, IL-10, IL-12, or IL-23 signaling. In some embodiments the disorder is associated with type I interferon signaling. In some embodiments the disorder is associated with IL-10 signaling. In some embodiments the disorder is associated with IL-12 signaling. In some embodiments the disorder is associated with IL-23 signaling.

Compounds of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, cutaneous lupus erythematosus, systemic lupus erythematosus, pemphigus vulgaris, pemphigus foliaceus, paraneoplastic pemphigus, epidermolysis bullosa acquisita, acne vulgaris, and other inflammatory or allergic conditions of the skin.

Compounds of the invention may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), cutaneous lupus erythematosus, systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments the inflammatory disease which can be treated according to the methods of this invention is selected from acute and chronic gout, chronic gouty arthritis, psoriasis, psoriatic arthritis, rheumatoid arthritis, Juvenile rheumatoid arthritis, Systemic jubenile idiopathic arthritis (SJIA), Cryopyrin Associated Periodic Syndrome (CAPS), and osteoarthritis.

In some embodiments the inflammatory disease which can be treated according to the methods of this invention is a $T_h1$ or $T_h17$ mediated disease. In some embodiments the $T_h17$ mediated disease is selected from cutaneous lupus erythematosus, Systemic lupus erythematosus, Multiple sclerosis, and inflammatory bowel disease (including Crohn's disease or ulcerative colitis).

In some embodiments the inflammatory disease which can be treated according to the methods of this invention is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis.

Furthermore, the invention provides the use of a compound according to the definitions herein, or a pharmaceutically acceptable salt, or a hydrate or solvate thereof for the preparation of a medicament for the treatment of an autoimmune disorder, an inflammatory disorder, or a proliferative disorder, or a disorder commonly occurring in connection with transplantation.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of formula I or I' and one or more additional therapeutic agents. The therapeutic agent may be administered together with a compound of formula I or I', or may be administered prior to or following administration of a compound of formula I or I'. Suitable therapeutic agents are described in further detail below. In certain embodiments, a compound of formula I or I' may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of formula I or I' may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a compound of formula I or I' and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating rheumatoid arthritis comprising administering to a patient in need thereof a compound of formula I or I' and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a compound of formula I or I' and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating cutaneous lupus erythematosus or systemic lupus erythematosus comprising administering to a patient in need thereof a compound of formula I or I' and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating Crohn's disease, ulcerative colitis, or inflammatory bowel disease comprising administering to a patient in need thereof a compound of formula I or I' and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a compound of formula I or I' and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-bid®, Uniphyl®, Theo-24®) and aminophylline, and IgE antibodies such as omalizumab (Xolair®).

In some embodiments, the present invention provides a method of treating COPD comprising administering to a patient in need thereof a compound of formula I or I' and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In another embodiment, the present invention provides a method of treating a hematological malignancy comprising administering to a patient in need thereof a compound of formula I or I' and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a solid tumor comprising administering to a patient in need thereof a compound of formula I or I' and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a hematological malignancy comprising administering to a patient in need thereof a compound of formula I or I' and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a compound of formula I or I' and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a compound of formula I or I' and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating or lessening the severity of a disease comprising administering to a patient in need thereof a compound of formula I or I' and a BTK inhibitor, wherein the disease is selected from inflammatory bowel disease, arthritis, cutaneous lupus erythematosus, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behçet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, cutaneous lupus erythematosus, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a compound of formula I or I' and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a compound of formula I or I' and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/ PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), cutaneous lupus erythematosus, systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

In some embodiments the present invention provides a method of treating or lessening the severity of a disease comprising administering to a patient in need thereof a compound of formula I or I' and a Bcl-2 inhibitor, wherein the disease is an inflammatory disorder, an autoimmune disorder, a proliferative disorder, an endocrine disorder, a neurological disorder, or a disorder associated with transplantation. In some embodiments, the disorder is a proliferative disorder, lupus, or lupus nephritis. In some embodiments, the proliferative disorder is chronic lymphocytic leukemia, diffuse large B-cell lymphoma, Hodgkin's disease, small-cell lung cancer, non-small-cell lung cancer, myelodysplastic syndrome, lymphoma, a hematological neoplasm, or solid tumor.

In some embodiments, the present invention provides a method of treating or lessening the severity of a disease, comprising administering to a patient in need thereof a TYK2 pseudokinase (JH2) domain binding compound and a TYK2 kinase (JH1) domain binding compound. In some embodiments, the disease is an autoimmune disorder, an inflammatory disorder, a proliferative disorder, an endocrine disorder, a neurological disorder, or a disorder associated with transplantation. In some embodiments the JH2 binding compound is a compound of formula I or I'. Other suitable JH2 domain binding compounds include those described in WO2014074660A1, WO2014074661A1, WO2015089143A1, the entirety of each of which is incorporated herein by reference. Suitable JH1 domain binding compounds include those described in WO2015131080A1, the entirety of which is incorporated herein by reference.

The compounds and compositions, according to the method of the present invention, may be administered using any amount and any route of administration effective for treating or lessening the severity of an autoimmune disorder, an inflammatory disorder, a proliferative disorder, an endocrine disorder, a neurological disorder, or a disorder associated with transplantation. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting TYK2, or a mutant thereof, activity in a biological sample comprising the step of contacting said biological sample with a compound of this invention, or a composition comprising said compound. In certain embodiments, the invention relates to a method of irreversibly inhibiting TYK2, or a mutant thereof, activity in a biological sample comprising the step of contacting said biological sample with a compound of this invention, or a composition comprising said compound.

In another embodiment, the invention provides a method of selectively inhibiting TYK2 over one or more of JAK1, JAK2, and JAK3. In some embodiments, a compound of the present invention is more than 2-fold selective over JAK1/2/3. In some embodiments, a compound of the present invention is more than 5-fold selective over JAK1/2/3. In some embodiments, a compound of the present invention is more than 10-fold selective over JAK1/2/3. In some embodiments, a compound of the present invention is more than 50-fold selective over JAK1/2/3. In some embodiments, a compound of the present invention is more than 100-fold selective over JAK1/2/3.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of TYK2 (or a mutant thereof) activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting activity of TYK2, or a mutant thereof, in a patient comprising the step of administering to said patient a compound of the present invention, or a composition comprising said compound. According to certain embodiments, the invention relates to a method of reversibly or irreversibly inhibiting one or more of TYK2, or a mutant thereof, activity in a patient comprising the step of administering to said patient a compound of the present invention, or a composition comprising said compound. In other embodiments, the present invention provides a method for treating a disorder mediated by TYK2, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other therapeutic compounds. In some embodiments, the other therapeutic compounds are antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™ Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; *vinca* alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine derivative, such as imatinib or nilotinib (AMN107); PD 180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, C1-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; ALK inhibitors, which are compounds which target, decrease or inhibit anaplastic lymphoma kinase, and Bcl-2 inhibitors.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412. In some embodiments, the present invention provides a method of treating AML associated with an ITD and/or D835Y mutation, comprising administering a compound of the present invention together with a one or more FLT3 inhibitors. In some embodiments, the FLT3 inhibitors are selected from quizartinib (AC220), a staurosporine derivative (e.g. midostaurin or lestaurtinib), sorafenib, tandutinib, LY-2401401, LS-104, EB-10, famitinib, NOV-110302, NMS-P948, AST-487, G-749, SB-1317, S-209, SC-110219, AKN-028, fedratinib, tozasertib, and sunitinib. In some embodiments, the FLT3 inhibitors are selected from quizartinib, midostaurin, lestaurtinib, sorafenib, and sunitinib.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl] phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BITL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl] tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein. Additional compounds of the invention were prepared by methods substantially similar to those described herein in the Examples and methods known to one skilled in the art.

General Procedure A (Suzuki Coupling)

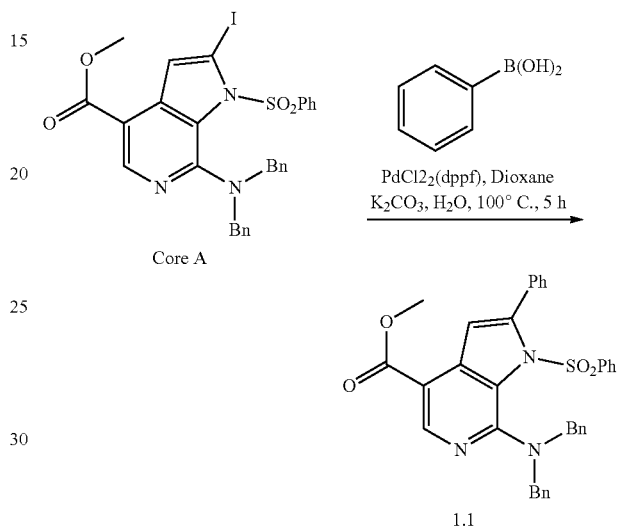

Core A

Synthesis of Compound 1.1

Argon was purged for 15 min through a stirring solution of Core A (0.2 g, 0.313 mmol, 1.0 eq), phenyl boronic acid (0.049 g, 0.406 mmol, 1.3 eq) and potassium carbonate (0.107 g, 0.782 mmol, 2.5 eq) in 1,4-dioxane:water (10 mL, 9:1). [1,1'-Bis(diphenylphosphino)ferrocene]palladium(II) dichloride (0.022 g, 0.0313 mmol, 0.1 eq) was added to it and further purging done for 10 min. Reaction was allowed to stir at 100° C. for 5 h. After completion of reaction, reaction mixture was transferred into water and product was extracted with ethyl acetate. Organic layer was combined, washed with brine solution, dried over sodium sulfate and concentrated under reduced pressure to obtain 1.1. (0.140 g, 75.93%). MS (ES): m/z 588.19 [M+H]$^+$.

General Procedure B (Deprotection with Triflic Acid)

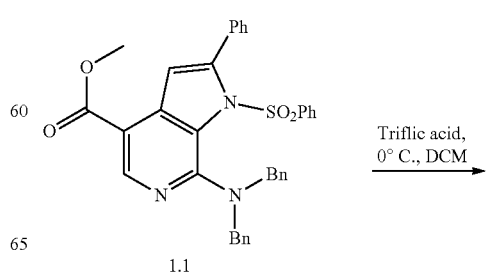

1.1

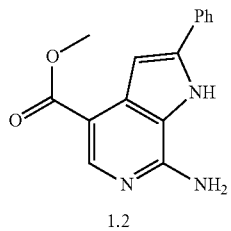

1.2

Synthesis of Compound 1.2

To a cooled solution of 1.1 (0.140 g, 0.238 mmol, 1.0 eq) in dichloromethane (2 mL), triflic acid (1 mL) was added at 0° C. Reaction mixture was stirred at same temperature for 10 min. After completion of reaction, reaction mixture was transferred into 1N sodium hydroxide solution and product was extracted with dichloromethane. Organic layer was combined, dried over sodium sulfate and concentrated under reduced pressure to obtain crude material. This was further purified by trituration with diethyl ether to a obtain 1.2. (0.063 g, 98.94%), MS (ES): m/z 268.10 [M+H]$^+$.

General Procedure C (Amide Formation with Acid Chloride)

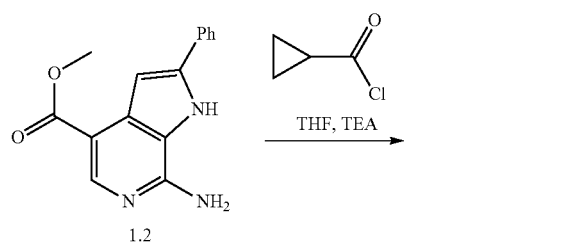

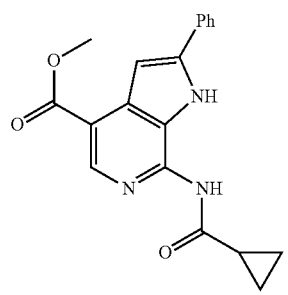

1.3

Synthesis of Compound 1.3

To a solution of compound 1.2 (0.070 g, 0.26 mmol, 1.0 eq) in tetrahydrofuran (2 mL) at 0° C. was added triethylamine (0.078 g, 0.78 mmol, 3.0 eq) and stirred for 10 min followed by addition of cyclopropanecarbonyl chloride (0.041 g, 0.39 mmol, 1.5 eq). The reaction mixture was stirred at 0° C. for 30 min. After completion of reaction, reaction mixture was transferred into ice cold water and product was extracted with ethyl acetate. Organic layer was combined, washed with saturated sodium bicarbonate solution followed by brine solution and water, dried over sodium sulfate and concentrated under reduced pressure to obtain crude material. This was further purified by column chromatography using 20% ethyl acetate in hexane to obtain 1.3. (0.025 g, Yield: 28.46%). MS (ES): m/z 336.13 [M+H]$^+$.

General Procedure D (Amide Formation Mediated by Trimethylaluminum)

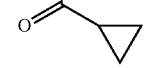

1.3

I-1

Synthesis of compound I-1

To a solution of compound 1.3 (0.025 g, 0.074 mmol, 1.0 eq) and methylamine (2M in THF, 0.11 mL, 0.22 mmol, 3.0 eq) in tetrahydrofuran (2 mL) was added N,N-diisopropylethylamine (0.028 g, 0.22 mmol, 3.0 eq) followed by trimethylaluminum (2M, 0.18 mL, 0.37 mmol, 5.0 eq) at 0° C. Reaction mixture was stirred at 70° C. for 5 h. After completion of reaction, reaction mixture was transferred to ice cold water and product was extracted with ethyl acetate. Organic layer was combined, washed with brine solution, dried over sodium sulfate and concentrated under reduced pressure to obtain crude material. This was further purified by column chromatography eluting with 2.5% methanol in dichloromethane to obtain I-1 (0.010 g, 40.12%). MS (ES): m/z 335.30 [M+H]$^+$.

General Procedure E (Stille Coupling)

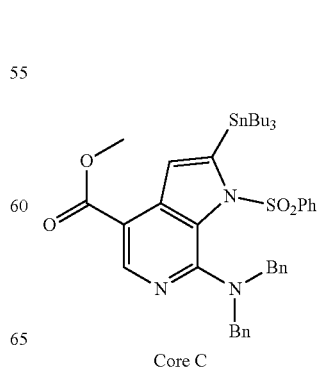

Core C

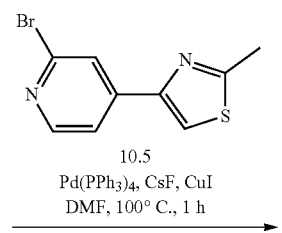

10.5

Pd(PPh$_3$)$_4$, CsF, CuI
DMF, 100° C., 1 h

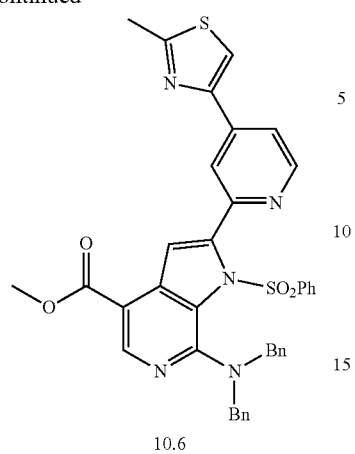

10.6

Synthesis of Compound 10.6

Argon was purged for 15 min through a stirring mixture of Core C (0.9 g, 1.12 mmol, 1.0 eq), compound 10.5 (0.368 g, 1.45 mmol, 1.0 eq), and cesium fluoride (0.338 g, 2.24 mmol, 2.0 eq) in dimethylformamide (10 mL). Copper(I) iodide (0.021 g, 1.1 mmol, 0.1 eq) and tetrakis(triphenylphosphine)palladium(0) (0.064 g, 0.056 mmol, 0.05 eq) was added to it and further purging done for 10 min. Reaction mixture was allowed to stir at 100° C. for 1 h. After completion of reaction, reaction mixture was transferred into water and product was extracted with ethyl acetate. Organic layer was combined, washed with brine solution, dried over sodium sulfate and concentrated under reduced pressure to obtain 10.6. (0.120 g, 15.57%). MS (ES): m/z 686.19 [M+H]$^+$.

General Procedure F (Boronate Ester Preparation—Pd$_2$(dba)$_3$ and Ligand)

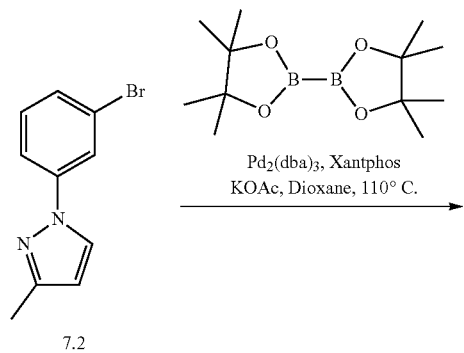

7.2

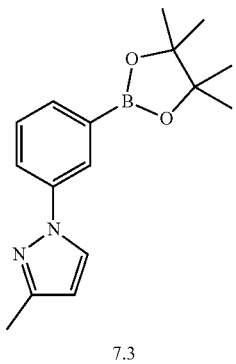

7.3

Synthesis of Compound 7.3

To a solution of 7.2 (1.3 g, 5.48 mmol, 1.0 eq) in 1,4-dioxane (48 mL) was added bis(pinacolato)diboron (1.6 g, 6.57 mmol, 1.2 eq) and potassium acetate (1.0 g, 10.96 mmol, 2.0 eq). The reaction mixture was degassed for 10 min. under argon atmosphere, then tris(dibenzylideneacetone)dipalladium(0) (0.250 g, 0.274 mmol, 0.05 eq) and 4,5-bis(diphenylphosphino)-9,9-dimethylxanthene (0.312 g, 0.54 mmol, 0.1 eq) were added, again degassed for 5 min. The reaction was stirred at 110° C. for 4 h. After completion of reaction, reaction mixture was cooled to room temperature, transferred into water and product was extracted with ethyl acetate. Organic layer was combined, washed with brine solution, dried over sodium sulfate and concentrated under reduced pressure to obtain crude material. This was further purified by combi flash using 3% methanol in dichloromethane as eluant to obtain pure 7.3. (1.0 g, 64.18%). MS (ES): m/z 285.17 [M+H]$^+$.

General Procedure G (Boronate Ester Preparation—Pd(dppf)Cl$_2$)

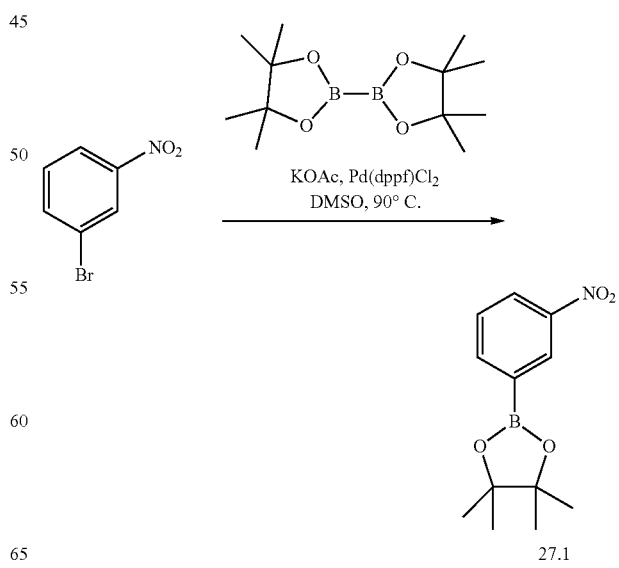

27.1

Synthesis of Compound 27.1

To a solution of 1-bromo-3-nitrobenzene (1.0 g, 4.95 mmol, 1.0 eq) in dimethyl sulfoxide (20 mL) was added bis(pinacolato)diboron (1.5 g, 5.94 mmol, 1.2 eq) and potassium acetate (0.970 g, 9.9 mmol, 2.0 eq). The reaction mixture was degassed for 10 min. under argon atmosphere, then [1,1'-bis(diphenylphosphino)ferrocene]dichloropalladium(II) (0.358 g, 0.49 mmol, 0.1 eq) was added, again degassed for 5 min. The reaction was stirred at 90° C. for 4 h. After completion of reaction, reaction mixture was cooled to room temperature, transferred into water and product was extracted with ethyl acetate. Organic layer was combined, washed with brine solution, dried over sodium sulfate and concentrated under reduced pressure to obtain crude material. This was further purified by combi flash using 3% methanol in dichloromethane as eluant to obtain pure 27.1. (0.32 g, Yield: 25.95%). MS (ES): m/z 250.12 [M+H]$^+$.

General Procedure H (Amide Coupling with HATU)

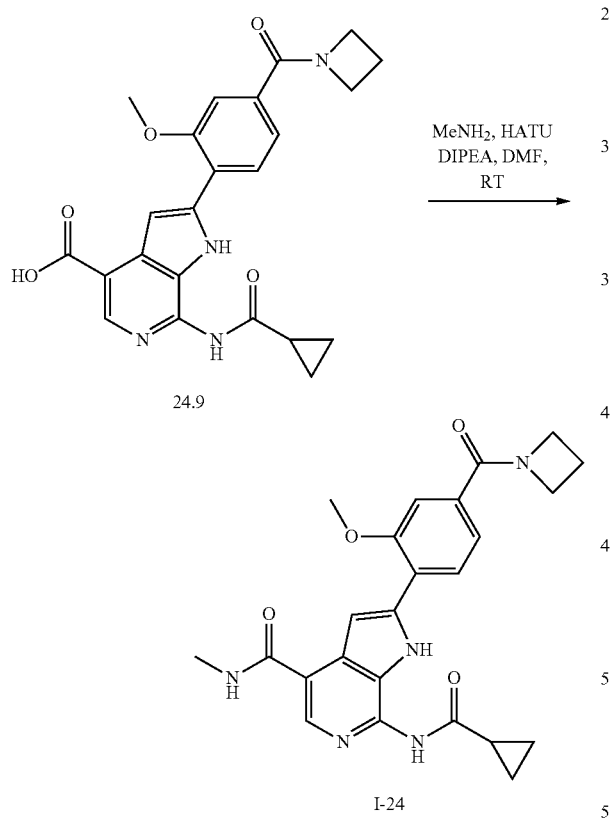

Synthesis of Compound I-24

To a solution of compound 24.9 (0.060 g, 0.13 mmol, 1.0 eq), in N,N-dimethylformamide (2 mL) was added 1-[bis(dimethylamino)methylene]-1H-1,2,3-triazolo[4,5-b]pyridinium 3-oxid hexafluorophosphate (0.098 g, 0.26 mmol, 2.0 eq) and stirred at room temperature for 15 min. To this added diisopropylethylamine (0.050 g, 0.39 mmol, 3.0 eq) followed by addition of methylamine (2M in THF 0.078 mL, 0.13 mmol, 1.2 eq). The reaction mixture was stirred at room temperature for 5 min. After completion of reaction, reaction mixture was transferred into water and product was extracted with ethyl acetate. Organic layer was combined, washed with brine solution, dried over sodium sulfate and concentrated under reduced pressure to obtain crude material. This was further purified by column chromatography and the compound was eluted in 40% ethyl acetate in hexane to obtain I-24 (0.030 g, Yield: 48.54%). MS (ES): m/z 448.37 [M+H]$^+$.

Preparation of Core A: Methyl 7-(dibenzylamino)-2-iodo-1-(phenylsulfonyl)-1H-pyrrolo[2,3-c]pyridine-4-carboxylate

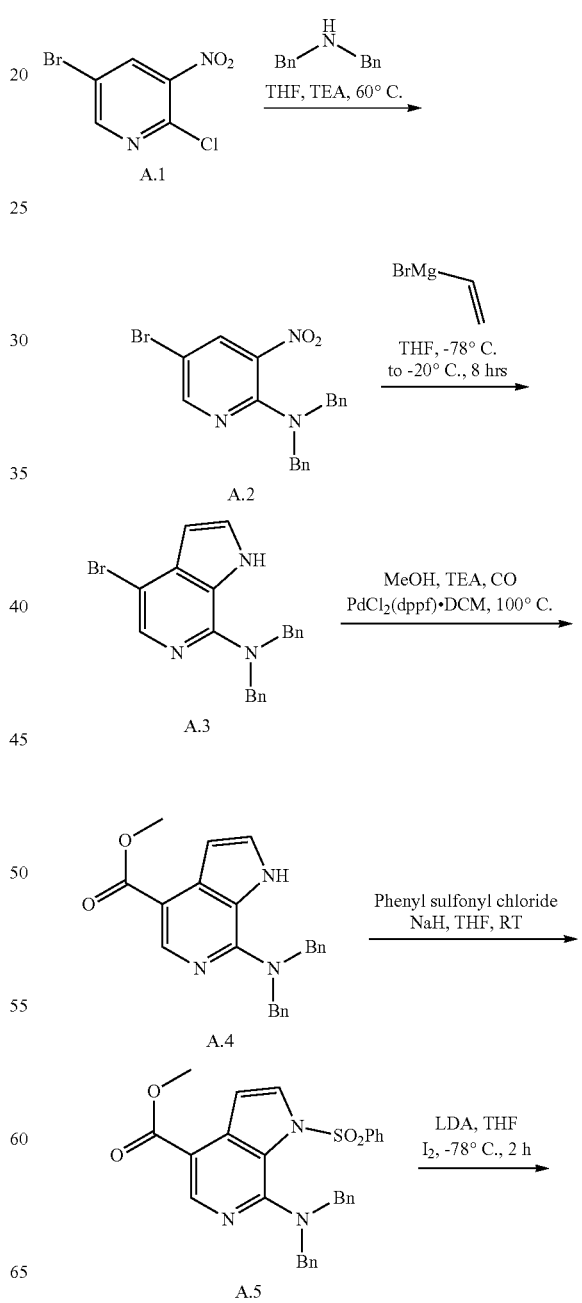

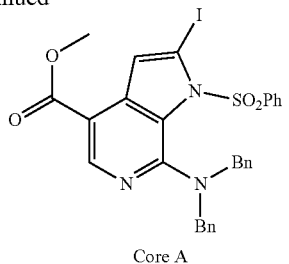

Core A

Synthesis of Compound A.2

To a solution of compound A.1 (25.0 g, 105.48 mmol, 1.0 eq) in tetrahydrofuran (800 mL) was added N,N-dibenzyl amine (33.85 g, 316.44 mmol, 3.0 eq) and triethylamine (31.96 g, 316.44 mmol, 3.0 eq). The reaction mixture was stirred at 60° C. for 1 h. After completion of reaction, reaction mixture was transferred to ice cold water and product was extracted with ethyl acetate. Organic layer was combined, washed with brine solution, dried over sodium sulfate and concentrated under reduced pressure to obtain crude material. This was further purified by column chromatography eluting with 2.5% methanol in dichloromethane to obtain A.2. (32 g, Yield: 76.31%). MS (ES): m/z 399.04 [M+H]$^+$.

Synthesis of Compound A.3

To a solution of compound A.2 (10.0 g, 25.12 mmol, 1.0 eq) in tetrahydrofuran (200 mL) was added vinyl magnesium bromide (1M in THF, 75 mL, 75.36 mmol, 3.0 eq) at −78° C. The reaction mixture was stirred at −78° C. for 1 h. After completion of reaction, reaction mixture was transferred to ice cold water and product was extracted with ethyl acetate. Organic layer was combined, washed with brine solution, dried over sodium sulfate and concentrated under reduced pressure to obtain crude material. This was further purified by column chromatography eluting with 10% ethyl acetate in hexane to obtain A.3. (2.5 g, Yield: 25.58%). MS (ES): m/z 393.07 [M+H]$^+$.

Synthesis of Compound A.4 carbon monoxide was purged for 15 min through a stirred solution of compound A.3 (1.5 g, 3.82 mmol, 1.0 eq) in methanol (70 mL) followed by addition of triethylamine (1.1 g, 11.46 mmol, 3.0 eq) and [1,1'-bis(diphenylphosphino)ferrocene]palladium(II) dichloride, complex with dichloromethane (0.310 g, 0.38 mmol, 0.1 eq). Further purging done for 10 min and reaction mixture was allowed to stir at 100° C. for 5 h. After completion of reaction, reaction mixture was transferred into water and product was extracted with ethyl acetate. Organic layer was combined, washed with brine solution, dried over sodium sulfate and concentrated under reduced pressure to obtain A.4. (1.0 g, 73.93%). MS (ES): m/z 372.17 [M+H]$^+$.

Synthesis of Compound A.5

To a suspension of sodium hydride (0.131 g, 5.38 mmol, 2.0 eq) in tetrahydrofuran (10 mL) was added a solution of compound A.4 (1.0 g, 2.69 mmol, 1.0 eq) in tetrahydrofuran (10 mL) (1.0 g, 2.69 mmol, 1.0 eq) dropwise at 0° C. The reaction mixture was stirred at 0° C. for 30 min and phenyl sulfonyl chloride (0.710 g, 4.03 mmol, 1.5 eq) was added slowly dropwise. The reaction mixture was stirred at room temperature for 1 h. After completion of reaction, reaction mixture was transferred to ice cold water and product was extracted with ethyl acetate. Organic layer was combined, washed with brine solution, dried over sodium sulfate and concentrated under reduced pressure to obtain crude material. This was further purified by column chromatography eluting with 15% ethyl acetate in hexane to obtain A.5. (0.800 g, Yield: 58.08%). MS (ES): m/z 512.16 [M+H]$^+$.

Synthesis of Core A

To the solution of compound A.5 (0.8 g, 1.56 mmol, 1.0 eq) in tetrahydrofuran (10 mL) was added lithium diisopropylamide (2.0M, 2.34 mL, 4.68 mmol, 3.0 eq) at −78° C. The reaction mixture was stirred at −78° C. for 1 h. Then a solution of iodine (0.475 g, 1.87 mmol, 2.0 eq) in tetrahydrofuran (2 mL) was added to reaction mixture and stirred for 2 h at same temperature. After completion of reaction, reaction mixture was transferred to ice cold water and product was extracted with ethyl acetate. Organic layer was combined, washed with brine solution, dried over sodium sulfate and concentrated under reduced pressure to obtain crude material. This was further purified by column chromatography eluting with 7% ethyl acetate in hexane to obtain Core A. (0.620 g, Yield: 63.39%). MS (ES): m/z 626.06 [M+H]$^+$.

Preparation of Core B: (7-(dibenzylamino)-4-(methylcarbamoyl)-1H-pyrrolo[2,3-c]pyridin-2-yl)boronic acid

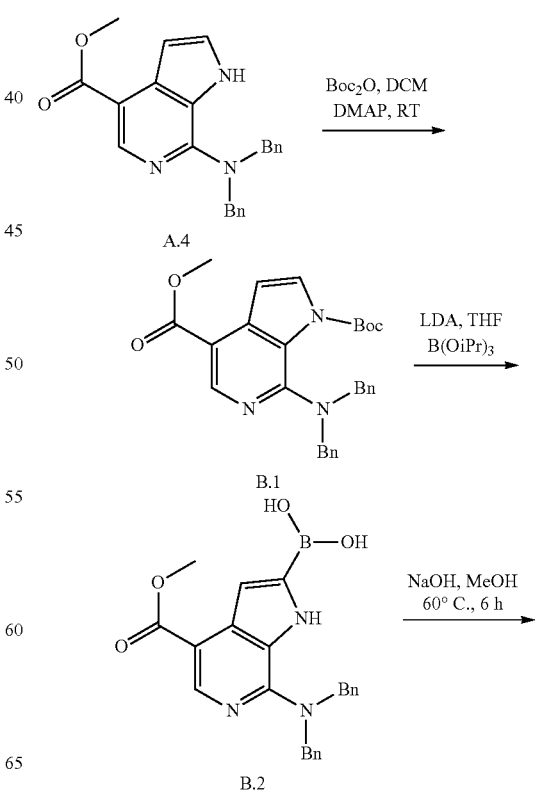

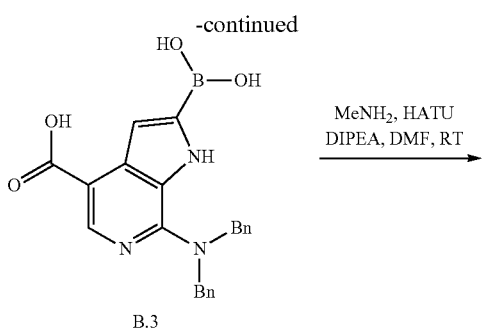

B.3

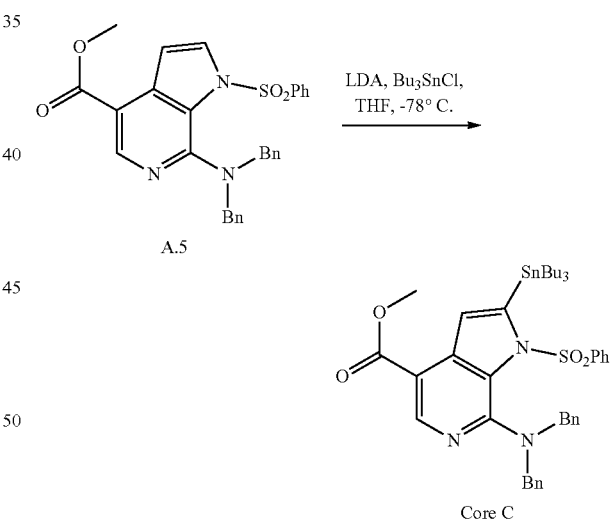

Core B

Synthesis of Compound B.1

To a solution of compound A.4 (8.0 g, 21.56 mmol, 1.0 eq) in dichloromethane (80 mL) were added di-tert-butyl dicarbonate (8.4 g, 38.80 mmol, 1.8 eq) and 4-dimethylaminopyridine (0.263 g, 2.15 mmol, 0.1 eq) and stirred at room temperature for 4 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by column chromatography and compound was eluted in 20% ethyl acetate in hexane to obtain pure B.1. (7.5 g, 73.85%). MS (ES): m/z 472.22 [M+H]$^+$.

Synthesis of Compound B.2

To a solution of compound B.1 (7.0 g, 14.86 mmol, 1.0 eq) in tetrahydrofuran (170 mL) was added lithium diisopropylamide (2.0M, 14.8 mL, 29.72 mmol, 3.0 eq) at −78° C. The reaction was stirred at −78° C. for 1 h. Then a solution of triisopropyl borate (5.5 g, 29.72 mmol, 2.0 eq) was added to reaction mixture. The reaction mixture was stirred for 2 h at 0° C. After completion of reaction, reaction mixture was transferred to ice cold water and product was extracted with ethyl acetate. Organic layer was combined, washed with brine solution, dried over sodium sulfate and concentrated under reduced pressure to obtain crude material. This was further purified by column chromatography eluting with 7% ethyl acetate in hexane to obtain B.2. (4.1 g, 66.51%). MS (ES): m/z 416.17 [M+H]$^+$.

Synthesis of Compound B.3

To a solution of compound B.2 (1.0 g, 2.40 mmol, 1.0 eq), in methanol (10 mL) was added sodium hydroxide (0.480 g, 12 mmol, 5 eq). The reaction was stirred at 60° C. for 6 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulfate and concentrated under reduced pressure to obtain crude material. This was further purified by column chromatography and compound was eluted in 2.1% methanol in dichloromethane to obtain pure B.3. (0.650 g, 67.27%). MS (ES): m/z 402.16 [M+H]$^+$.

Synthesis of Core B

To a solution of compound B.3 (0.650 g, 1.62 mmol, 1.0 eq), in N,N-dimethylformamide (7 mL) was added 1-[bis(dimethylamino)methylene]-1H-1,2,3-triazolo[4,5-b]pyridinium 3-oxid hexafluorophosphate (1.2 g, 3.24 mmol, 2.0 eq) and stirred at room temperature for 15 min. To this added diisopropylethylamine (0.8 mL, 4.86 mmol, 3.0 eq) followed by addition of methylamine (2M in THF 1.05 mL, 2.10 mmol, 1.3 eq). The reaction mixture was stirred at room temperature for 5 min. After completion of reaction, reaction mixture was transferred into water and product was extracted with ethyl acetate. Organic layer was combined, washed with brine solution, dried over sodium sulfate and concentrated under reduced pressure to obtain crude material. This was further purified by column chromatography and the compound was eluted in 40% ethyl acetate in hexane to obtain Core B. (0.400 g, 59.60%). MS(ES): m/z 415.19 [M+H]$^+$.

Preparation of Core C: Methyl 7-(dibenzylamino)-1-(phenylsulfonyl)-2-(tributylstannyl)-1H-pyrrolo[2,3-c]pyridine-4-carboxylate

Synthesis of Core C

To a solution of compound A.5 (3.0 g, 5.87 mmol, 1.0 eq) in tetrahydrofuran (30 mL) was added lithium diisopropylamide (2.0M, 8.8 mL, 17.61 mmol, 3.0 eq) dropwise at −78° C. The reaction mixture was stirred at same temperature for 30 min. Then tributyltin chloride (1.90 mL, 7.04 mmol, 1.2 eq) was added dropwise to the reaction mixture and stirred for 1 h at same temperature. After completion of reaction, reaction mixture was transferred into ice cold water and product was extracted with ethyl acetate. Organic layer was combined, washed with brine solution, dried over sodium sulfate and concentrated under reduced pressure to obtain crude material. This was further purified by column chromatography eluting with 7% ethyl acetate in hexane to obtain Core C. (3.1 g, Yield: 66.03%). MS (ES): m/z 801.26 [M+H]⁺.

Example 1: 7-(cyclopropanecarboxamido)-N-methyl-2-phenyl-1H-pyrrolo[2,3-c]pyridine-4-carboxamide (I-1)

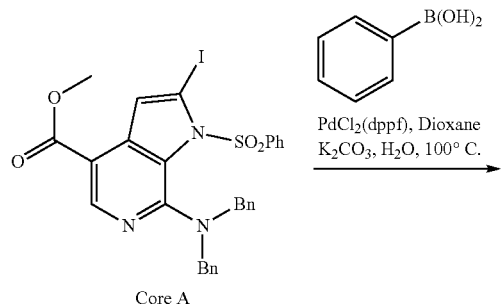

Core A

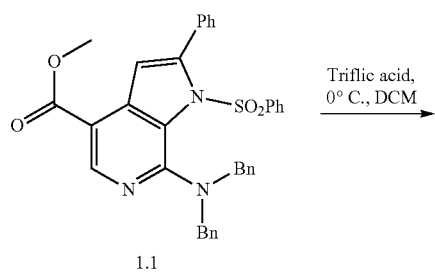

1.1

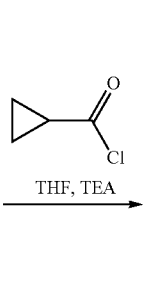

1.2

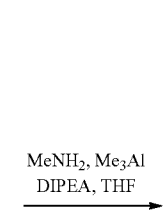

1.3

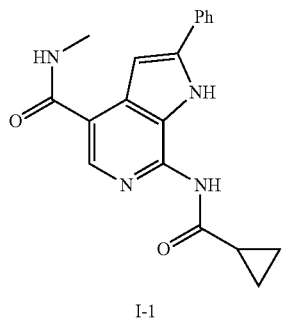

I-1

Synthesis of Compound 1.1

The compound was synthesized from Core A and phenylboronic acid using General Procedure A to obtain 1.1. (0.140 g, 75.93%). MS (ES): m/z 588.19 [M+H]⁺.

Synthesis of Compound 1.2

The compound was synthesized from compound 1.1 using General Procedure B to obtain 1.2. (0.063 g, 98.94%), MS (ES): m/z 268.10 [M+H]⁺.

Synthesis of Compound 1.3

The compound was synthesized from compound 1.2 using General Procedure C to obtain 1.3. (0.025 g, Yield: 28.46%). MS (ES): m/z 336.13 [M+H]⁺.

Synthesis of Compound I-1

The compound was synthesized from compound 1.3 and methylamine using General Procedure D. The material was further purified by column chromatography eluting with 2.5% methanol in dichloromethane to obtain I-1 (0.010 g, 40.12%). MS (ES): m/z 335.30 [M+H]⁺ LCMS purity: 96.55%, HPLC purity: 97.65%, ¹H NMR (DMSO-d₆, 400 MHZ): 8.34 (bs, 1H), 8.29 (s, 1H), 7.89 (bs, 1H), 7.87 (bs, 1H), 7.56-7.52 (t, J=7.6 Hz, 2H), 7.46-7.42 (t, J=7.6 Hz, 1H), 7.36 (s, 1H), 2.85-2.84 (d, J=4.4 Hz, 3H), 1.47 (s, 2H), 1.35-1.34 (d, J=7.2 Hz, 3H), 0.99 (bs, 2H).

Example 2: 7-(cyclopropanecarboxamido)-N-methyl-2-(3-(1-methyl-1H-1,2,4-triazol-3-yl)phenyl)-1H-pyrrolo[2,3-c]pyridine-4-carboxamide (I-2)

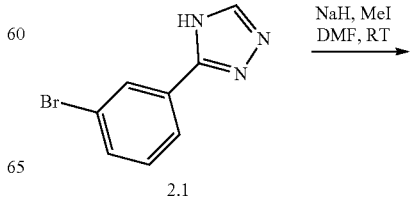

2.1

141
-continued

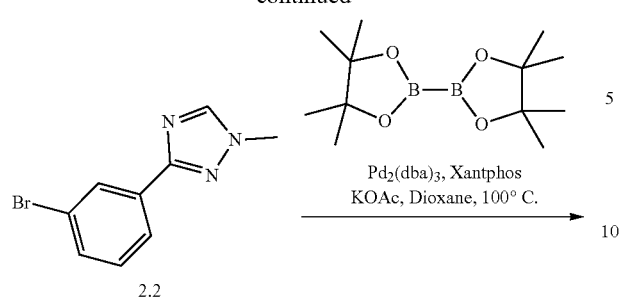

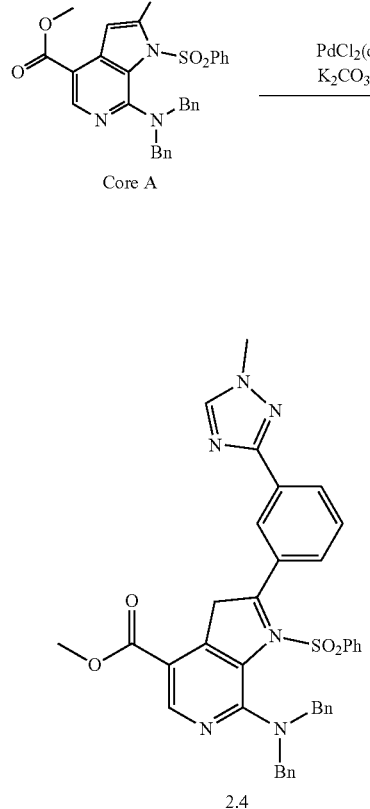

142
-continued

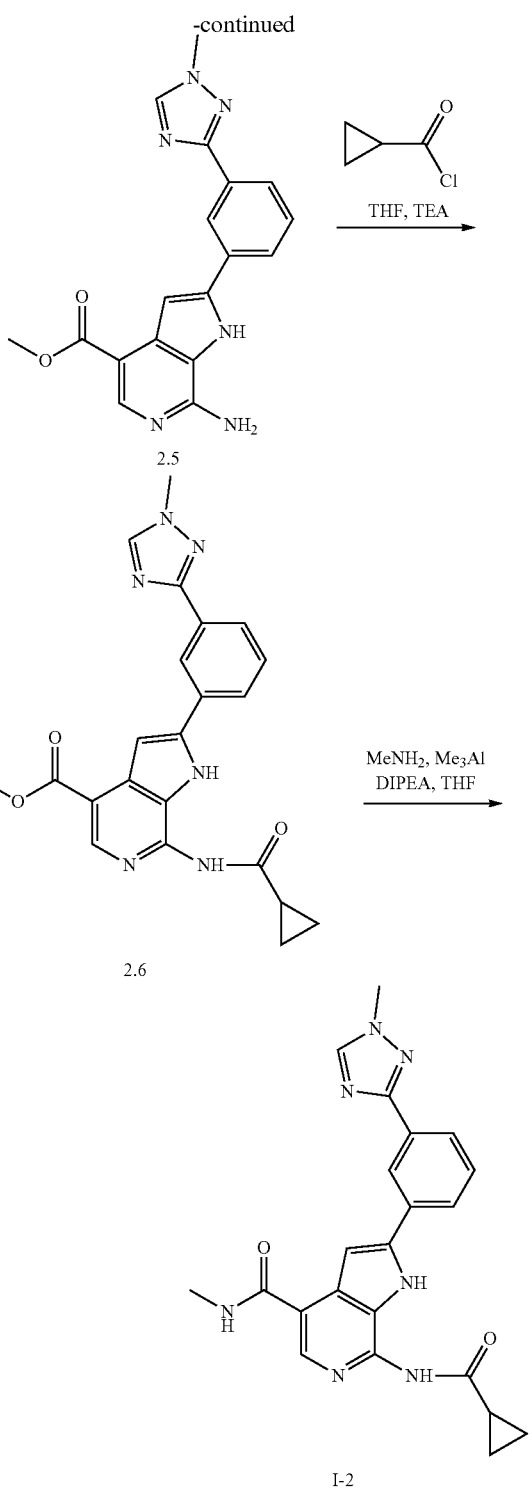

Synthesis of Compound 2.2

To a solution of compound 2.1 (3.0 g, 13.39 mmol, 1.0 eq) in dimethylformamide (30 mL), was added methyl iodide (2.0 g, 14.72 mmol, 1.1 eq). Sodium hydride (0.642 g, 26.78 mmol, 2 eq) was added at 0° C. Reaction mixture was stirred at room temperature for 2 h. After completion of reaction, reaction mixture was transferred into ice, stirred and extracted with diethyl ether. Organic layer was combined, dried over sodium sulfate and concentrated under reduced pressure to obtain crude material. This was further purified by distillation to obtain pure 2.2. (2.7 g, Yield: 84.70%). MS (ES): m/z 237.99 [M+H]⁺.

Synthesis of Compound 2.3

To a solution of compound 2.2 (0.8 g, 3.36 mmol, 1.0 eq) in 1,4-dioxane (30 mL) was added bis(pinacolato)diboron (1.0 g, 4.03 mmol, 1.2 eq) and potassium acetate (0.659 g, 6.72 mmol, 2.0 eq). The reaction mixture was degassed for 10 min. under argon atmosphere, then tris(dibenzylideneacetone)dipalladium(0) (0.153 g, 0.016 mmol, 0.05 eq) and 4,5-bis(diphenylphosphino)-9,9-dimethylxanthene (0.159 g, 0.033 mmol, 0.1 eq) were added, again degassed for 5 min. The reaction was stirred at 100° C. for 4 h. After completion of reaction, reaction mixture was cooled to room temperature, transferred into water and product was extracted with ethyl acetate. Organic layer was combined, washed with brine solution, dried over sodium sulfate and concentrated under reduced pressure to obtain crude material. This was further purified by combi flash using 3% methanol in dichloromethane as eluant to obtain pure 2.3 (0.7 g, 73.06%). MS(ES): m/z 286.17 [M+H]⁺.

Synthesis of Compound 2.4

The compound was synthesized from Core A and compound 2.3 using General Procedure A to obtain 2.4. (0.210 g, 84.58%), MS (ES): m/z 528.22 [M+H]⁺.

Synthesis of Compound 2.5

The compound was synthesized from compound 2.4 using General Procedure B to obtain 2.5. (0.1 g, 72.12%), MS (ES): m/z 349.14 [M+H]⁺.

Synthesis of Compound 2.6

The compound was synthesized from compound 2.5 using General Procedure C to obtain 2.6. (0.070 g, 58.56%), MS (ES): m/z 417.16 [M+H]⁺.

Synthesis of Compound I-2

The compound was synthesized from compound 2.6 and methylamine using General Procedure D. This was further purified by column chromatography eluting with 2.5% methanol in dichloromethane to obtain I-2 (0.030 g, 42.96%), MS (ES): m/z 416.38 [M+H]⁺ LCMS purity: 100%, HPLC purity: 99.87%, ¹H NMR (DMSO-d₆, 400 MHZ): 8.61 (bs, 1H), 8.46 (bs, 1H), 8.37-8.36 (d, J=4.4 Hz, 1H), 8.33 (s, 1H), 8.07-8.05 (d, J=8 Hz, 1H), 7.91-7.89 (d, J=7.6 Hz, 1H), 7.67-7.63 (t, J=8 Hz, 1H), 7.42 (s, 1H), 3.98 (s, 4H), 3.58 (s, 1H), 2.87-2.86 (d, J=4.4 Hz, 4H), 1.01 (bs, 2H), 0.96-0.94 (d, J=7.6 Hz, 2H).

Example 3: 7-(cyclopropanecarboxamido)-N-(methyl-d₃)-2-phenyl-1H-pyrrolo[2,3-c]pyridine-4-carboxamide (I-3)

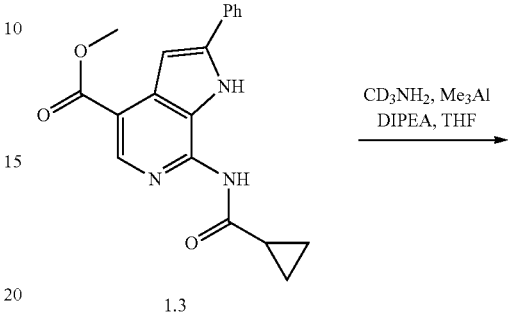

1.3

CD₃NH₂, Me₃Al
DIPEA, THF

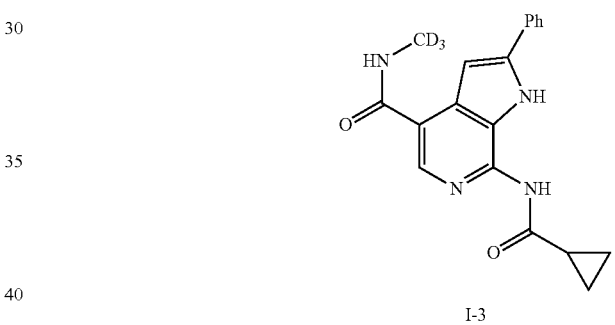

I-3

Synthesis of Compound I-3

To a solution of compound 1.3 (0.050 g, 0.14 mmol, 1.0 eq) and methyl-d₃-amine hydrochloride (0.029 g, 0.42 mmol, 3.0 eq) in tetrahydrofuran (2 mL) was added N,N-diisopropylethylamine (0.054 g, 0.42 mmol, 3.0 eq) followed by trimethylaluminum (2M, 0.35 mL, 0.7 mmol, 5.0 eq) at 0° C. Reaction mixture was stirred at 70° C. for 5 h. After completion of reaction, reaction mixture was transferred to ice cold water and product was extracted with ethyl acetate. Organic layer was combined, washed with brine solution, dried over sodium sulfate and concentrated under reduced pressure to obtain crude material. The material was further purified by column chromatography eluting with 2.5% methanol in dichloromethane to obtain I-3 (0.027 g, 53.67%), MS (ES): 338.38 [M+H]⁺ LCMS purity: 100%, HPLC purity: 99.52%, ¹H NMR (DMSO-d₆, 400 MHZ): 11.53 (bs, 1H), 11.10 (bs, 1H), 7.94-7.93 (d, J=5.6 Hz, 1H), 7.83 (s, 1H), 7.50-7.49 (d, J=4.4 Hz, 4H), 7.41-7.38 (m, 1H), 7.34-7.33 (d, J=5.6 Hz, 1H), 2.20 (bs, 1H), 1.92 (s, 2H), 0.97 (bs, 1H), 0.94-0.92 (m, 1H).

Example 4: 7-(cyclopropanecarboxamido)-2-(2-(1,1-dioxidoisothiazolidin-2-yl)phenyl)-N-methyl-1H-pyrrolo[2,3-c]pyridine-4-carboxamide (I-4)

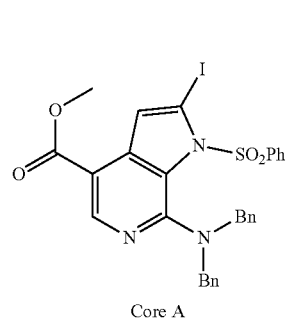
Core A

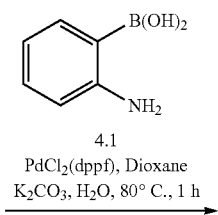
4.1
PdCl₂(dppf), Dioxane
K₂CO₃, H₂O, 80° C., 1 h

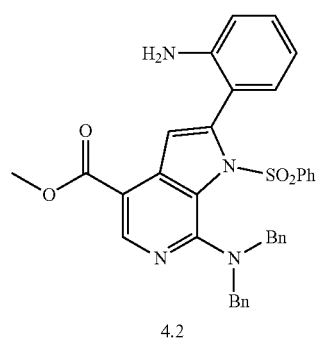
4.2

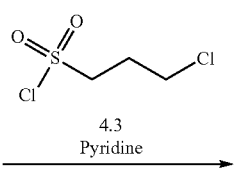
4.3
Pyridine

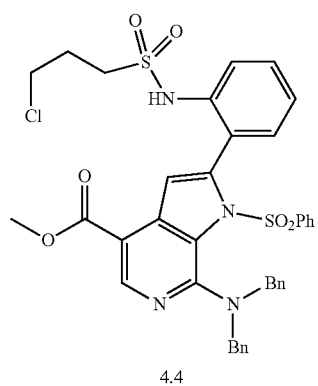
4.4

K₂CO₃
DMF, 50° C.

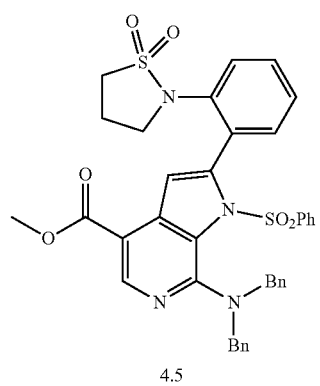
4.5

Triflic acid,
0° C., DCM

-continued

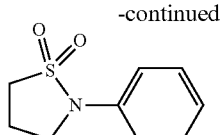
4.6

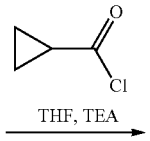
THF, TEA

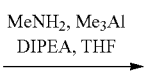
4.7

MeNH₂, Me₃Al
DIPEA, THF

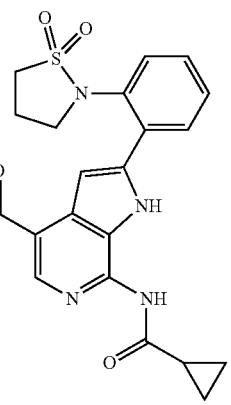
I-4

Synthesis of Compound 4.2

The compound was synthesized from Core A and compound 4.1 using General Procedure A to obtain 4.2. (0.160 g, Yield: 73.66%), MS (ES): m/z 603.20 [M+H]⁺.

Synthesis of Compound 4.4

To a solution of 4.2 (0.430 g, 0.93 mmol, 1.0 eq) in pyridine (4 mL) was added compound 4.3 (0.197 g, 1.11 mmol, 1.2 eq) at 0° C. The reaction mixture was stirred at room temperature for 3 h. After completion of reaction, reaction mixture was concentrated under reduced pressure to obtain crude material. This was further purified by column chromatography eluting with 25% ethylacetate in hexane to obtain 4.4. (0.320 g, Yield: 46.21%). MS (ES): m/z 744.17 [M+H]⁺.

Synthesis of Compound 4.5

To a solution of 4.4 (0.320 g, 0.43 mmol, 1.0 eq) in dimethylformamide (3 mL) was added potassium carbonate (0.178 g, 1.29 mmol, 3.0 eq) at room temperature. The reaction mixture was degassed for 10 min and heated at 50° C. for 8 h. After completion of reaction, reaction mixture was transferred to ice cold water and product was extracted with ethylacetate. Organic layer was combined, washed with brine solution, dried over sodium sulfate and concentrated under reduced pressure to obtain crude material. This was further purified by column chromatography eluting with 20% ethylacetate in hexane to obtain 4.5. (0.260 g, Yield: 85.44%). MS (ES): m/z 707.20 [M+H]$^+$.

Synthesis of Compound 4.6

The compound was synthesized from compound 4.5 using General Procedure B to obtain 4.6. (0.1 g, Yield: 70.35%), MS (ES): m/z 387.11 [M+H]$^+$.

Synthesis of Compound 4.7

The compound was synthesized from compound 4.6 using General Procedure C to obtain 4.7. (0.064 g, 54.41%), MS (ES): m/z 455.13 [M+H]$^+$.

Synthesis of Compound I-4

The compound was synthesized from compound 4.7 and methylamine using General Procedure D. The material was further purified by column chromatography eluting with 2.5% methanol in dichloromethane to obtain I-4 (0.025 g, 39.15%), MS (ES): 454.46 [M+H]$^+$ LCMS purity: 100%, HPLC purity: 98.36%, $^1$H NMR (DMSO-d$_6$, 400 MHZ): 11.77 (s, 1H), 11.29 (s, 1H), 8.39-8.36 (m, 3H), 7.98-7.96 (m, 1H), 7.68-7.66 (m, 1H), 7.55-7.52 (m, 1H), 7.40 (s, 1H), 3.68-3.64 (t, J=6.4 Hz, 2H), 3.55-3.51 (d, J=7.6 Hz, 2H), 3.41-3.36 (m, 1H), 2.85-2.84 (d, J=4 Hz, 3H), 2.22 (bs, 1H), 1.11-1.07 (t, J=7.2 Hz, 2H), 0.95-0.93 (m, 3H).

Example 5: 7-(cyclopropanecarboxamido)-N-methyl-2-(2-(1-(methylsulfonyl)cyclopropyl) phenyl)-1H-pyrrolo[2,3-c]pyridine-4-carboxamide (I-5)

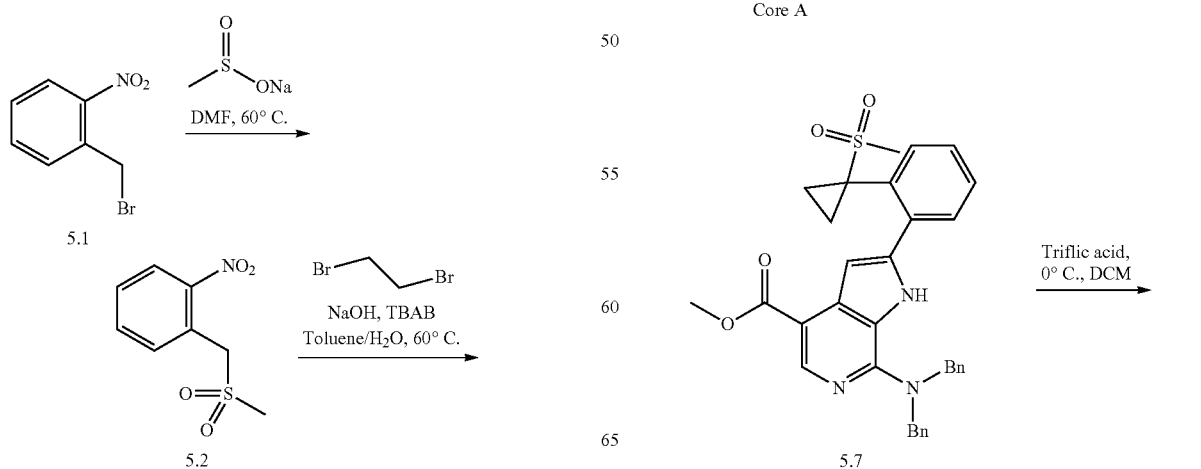

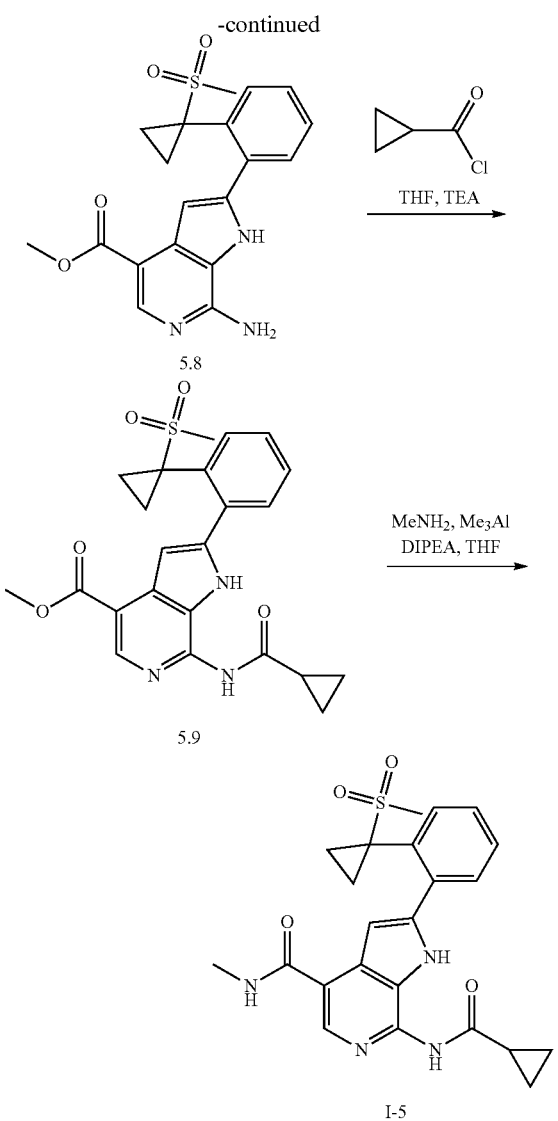

Synthesis of Compound 5.2

To a solution of compound 5.1 (10.0 g, 46.29 mmol, 1.0 eq) in dimethylformamide (100 mL) was added sodium methansulfinate (5.1 g, 50.91 mmol, 1.1 eq). The reaction mixture was stirred at 60° C. for 1 h. After completion of reaction, reaction mixture was transferred into water to obtain precipitate which was filtered and dried to obtain 5.2. (8.0 g, Yield: 80.30%), MS(ES): m/z 216.03 [M+H]$^+$.

Synthesis of Compound 5.3

To a solution of compound 5.2 (8.0 g, 37.20 mmol, 1.0 eq) in toluene (80 mL) was added 1,2-dibromoethane (10.4 g, 55.8 mmol, 1.5 eq) and tetra-n-butylammonium bromide (1.79 g, 5.58 mmol, 0.15 eq). The reaction mixture was stirred and aqueous sodium hydroxide (10N) (4.46 g, 111.6 mmol, 3.0 eq) was added. The reaction mixture was stirred at 60° C. for 16 h. After completion of reaction, reaction mixture was transferred into water to obtain precipitate which was filtered, washed with hexane and dried to obtain 5.3. (2.1 g, Yield: 23.42%), MS(ES): m/z 242.04 [M+H]$^+$.

Synthesis of Compound 5.4

To a solution of compound 5.3 (2.1 g, 8.71 mmol, 1.0 eq) in methanol (40 ml), 10% palladium on charcoal (1.0 g) was added. Hydrogen was purged through reaction mixture for 4 h at room temperature. After completion of reaction, reaction mixture was filtered through Celite-bed and washed with methanol. Filtrate was concentrated under reduced pressure to obtain crude material. This was further purified by trituration with n-pentane to obtain pure 5.4. (1.6 g, Yield: 87.00%). MS (ES): m/z 212.07 [M+H]$^+$.

Synthesis of Compound 5.5

To compound 5.4 (1.6 g, 7.58 mmol, 1.0 eq) was added hydrobromic acid (48% aq, 3.2 mL) dropwise at 0° C. Then a solution of sodium nitrite in 5 mL water (1.0 g, 15.16 mmol, 2.0 eq) was added followed by acetone (13 mL) at 0° C. Reaction mixture was stirred at 0° C. for 5 min and add copper(I) bromide (2.1 g, 15.16 mmol, 2.0 eq). The reaction mixture was stirred at 0° C. for 1 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by column chromatography and the compound was eluted in 7% ethyl acetate in hexane to obtain 5.5. (1.3 g, Yield: 62.39%). MS(ES): m/z 274.97 [M+H]$^+$.

Synthesis of Compound 5.6

To a solution of compound 5.5 (0.5 g, 1.82 mmol, 1.0 eq) in dry tetrahydrofuran (15 mL) was added n-butyllithium (1.6M in hexane, 1.25 mL, 2.00 mmol, 1.1 eq) dropwise at −78° C. Then stirred reaction mixture at same temperature for 15 min. Then after was added tributyltin chloride (1.14 g, 3.64 mmol, 2.0 eq) at −78° C. The reaction mixture was stirred at −78° C. for 2 h. After completion of reaction, to the reaction mixture was added 1N hydrochloric acid and reaction mixture brought to room temperature and extracted with ethyl acetate. Organic layer was combined, washed with brine solution, dried over sodium sulfate and concentrated under reduced pressure to obtain crude material. This was further purified by column chromatography and the compound was eluted in 4% ethyl acetate in hexane to obtain 5.6. (0.1 g, Yield: 11.34%). MS(ES): m/z 486.16 [M+H]$^+$.

Synthesis of Compound 5.7

To a degassed solution of Core A (0.8 g, 1.25 mmol, 1.0 eq) and compound 5.6 (0.668 g, 1.37 mmol, 1.1 eq) in toluene (40 mL) was added tetrakis (triphenylphosphine) palladium(0) (0.144 g, 0.12 mmol, 0.1 eq) and the reaction mixture was heated at 100° C. for 1 h under $N_2$ atmosphere. Reaction mixture was cooled to room temperature and purified by column chromatography using 5.0% ethyl acetate in hexane as eluant to obtain pure 5.7. (0.320 g, Yield: 51.85%). MS(ES): m/z 566.21 [M+H]$^+$.

Synthesis of Compound 5.8

The compound was synthesized from compound 5.7 using General Procedure B to obtain 5.8. (0.1 g, 57.23%), MS (ES): m/z 386.11 [M+H]$^+$.

Synthesis of Compound 5.9

The compound was synthesized from compound 5.8 using General Procedure C to obtain 5.9. (0.085 g, 72.24%), MS (ES): m/z 454.14 [M+H]+.

Synthesis of Compound I-5

The compound was synthesized from compound 5.9 and methylamine using General Procedure D. The material was further purified by column chromatography eluting with 2.5% methanol in dichloromethane to obtain I-5 (0.027 g, 31.83%), MS (ES): m/z 453.30 [M+H]+ LCMS purity: 100%, HPLC purity: 96.44%, $^1$H NMR (DMSO-$d_6$, 400 MHZ): 11.05 (s, 1H), 10.90 (s, 1H), 8.35-8.33 (m, 2H), 7.84-7.82 (m, 1H), 7.66-7.64 (m, 1H), 7.59-7.56 (m, 2H), 7.06 (bs, 1H), 3.14 (s, 3H), 2.83-2.82 (d, J=4.4 Hz, 3H), 2.04 (bs, 1H), 1.60 (s, 2H), 0.96 (bs, 3H), 0.83-0.81 (m, 3H).

Example 6: 7-(cyclopropanecarboxamido)-N-(methyl-$d_3$)-2-(3-(1-methyl-1H-1,2,4-triazol-3-yl)phenyl)-1H-pyrrolo[2,3-c]pyridine-4-carboxamide (I-6)

Synthesis of Compound I-6

The compound was synthesized from compound 2.6 and methyl-$d_3$-amine using General Procedure D. The material was further purified by column chromatography eluting with 2.5% methanol in dichloromethane to obtain I-6 (0.025 g, 31.10%), MS (ES): m/z 419.45 [M+H]+ LCMS purity: 100%, HPLC purity: 99.74%, $^1$H NMR (DMSO-$d_6$, 400 MHz): 11.92 (s, 1H), 11.15 (s, 1H), 8.62 (s, 1H), 8.46 (s, 1H), 8.35 (s, 1H), 8.32 (s, 1H), 8.06-8.05 (d, J=7.6 Hz, 1H), 7.92-7.90 (d, J=7.6 Hz, 1H), 7.67-7.63 (t, J=7.6 Hz, 1H), 7.41 (s, 1H), 3.98 (s, 3H), 3.44-3.41 (m, 1H), 1.01-0.94 (m, 4H).

Example 7: 7-(cyclopropanecarboxamido)-N-methyl-2-(3-(3-methyl-1H-pyrazol-1-yl) phenyl)-1H-pyrrolo[2,3-c]pyridine-4-carboxamide (I-7)

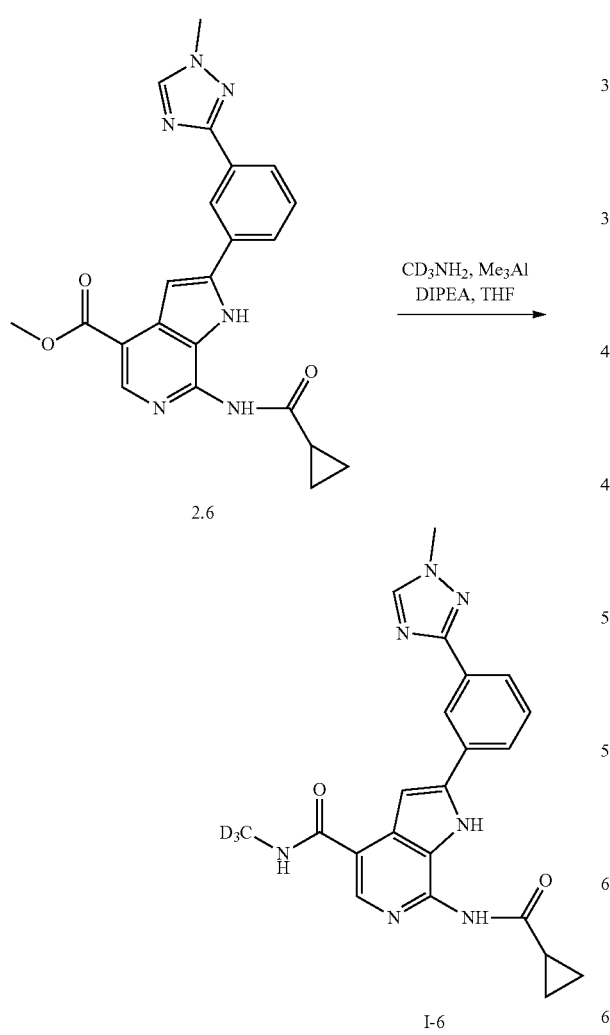

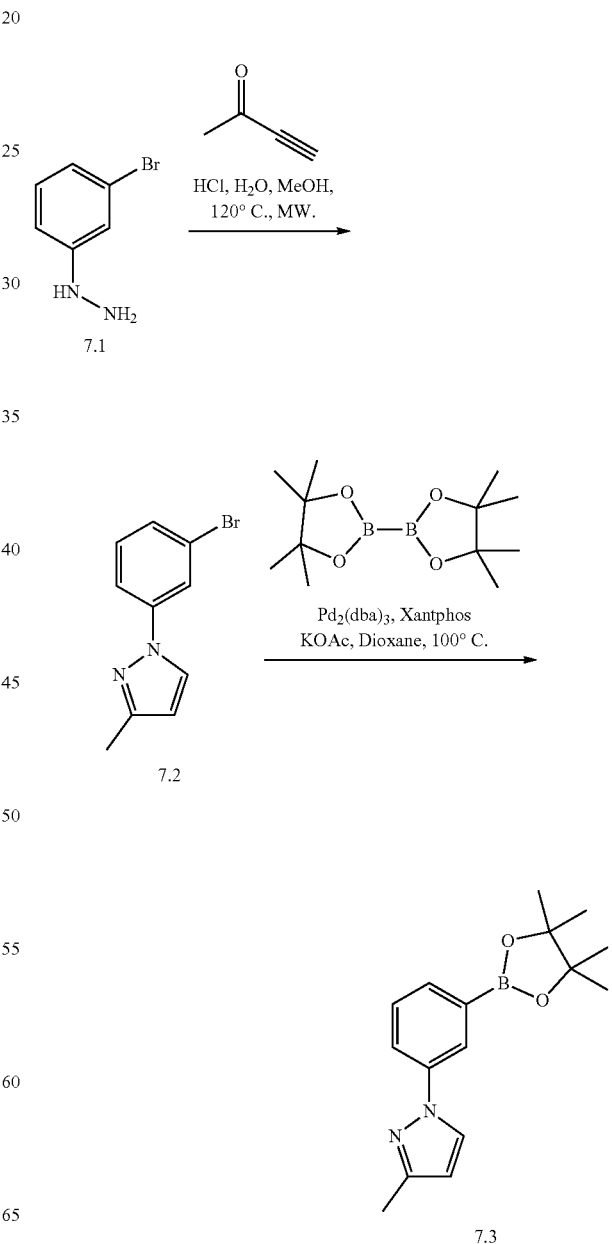

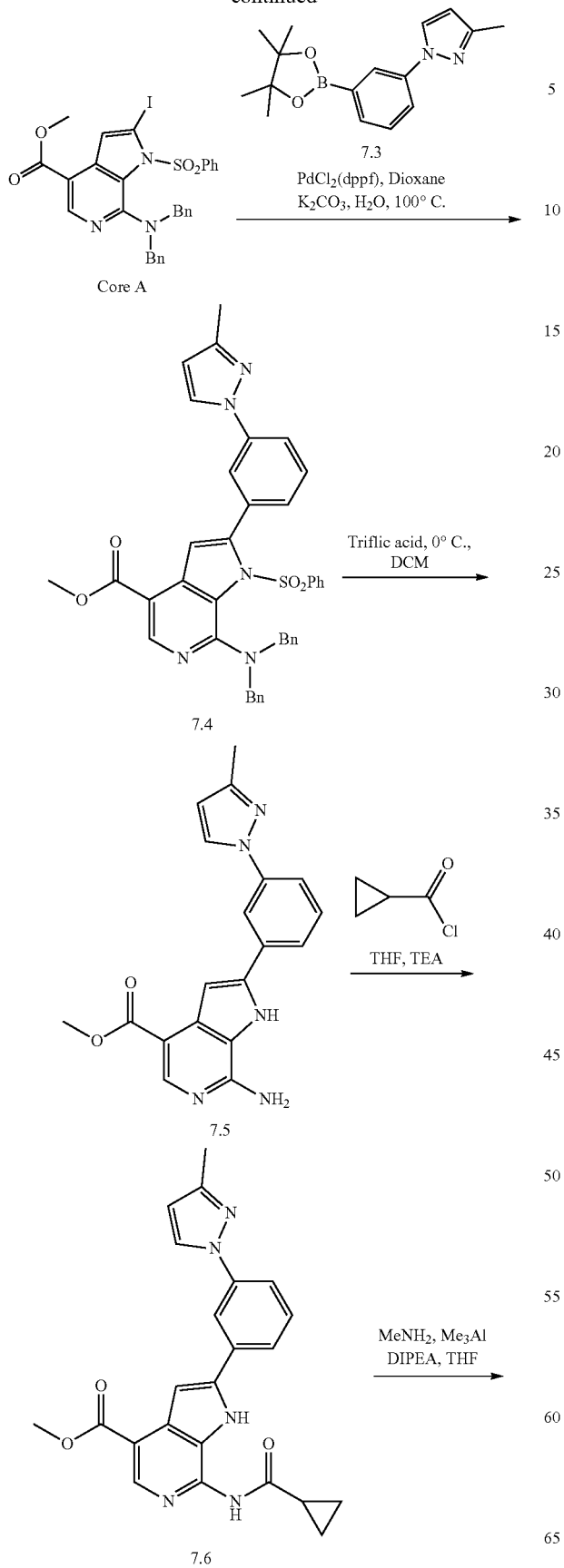
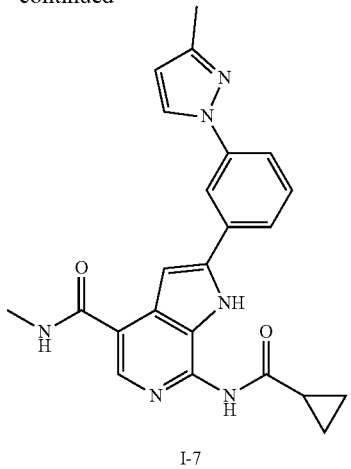

Synthesis of Compound 7.2

To a solution of compound 7.1 (3.0 g, 16.04 mmol, 1.0 eq) and but-3-yn-2-one (1.0 g, 16.04 mmol, 1.0 eq) in methanol (30 mL) was added hydrochloric acid (4.0M in water, 0.4 mL, 16.04 mmol, 1.0 eq). The reaction mixture was heated in microwave for 15 min at 120° C. After completion of reaction, reaction mixture was concentrated under reduced pressure to obtain residue. To this added water and was extracted with dichloromethane. Organic layer was combined, washed with brine solution, dried over sodium sulfate and concentrated under reduced pressure to obtain crude material. This was further purified by combi flash using 7% ethyl acetate in hexane as eluant to obtain pure 7.2. (1.3 g, Yield: 34.18%). MS (ES): m/z 237.99 [M+H]$^+$.

Synthesis of Compound 7.3

The compound was synthesized from compound 7.2 using General Procedure F to obtain 7.3. (1.0 g, 64.18%). MS(ES): m/z 285.17 [M+H]$^+$.

Synthesis of Compound 7.4

The compound was synthesized from Core A and compound 7.3 using General Procedure A to obtain 7.4. (0.160 g, Yield: 76.37%), MS (ES): m/z 668.23 [M+H]$^+$.

Synthesis of Compound 7.5

The compound was synthesized from compound 7.4 using General Procedure B to obtain 7.5. (0.070 g, Yield: 84.10%), MS (ES): m/z 348.14 [M+H]$^+$.

Synthesis of Compound 7.6

The compound was synthesized from compound 7.5 using General Procedure C to obtain 7.6. (0.050 g, 59.72%), MS (ES): m/z 416.17 [M+H]$^+$.

Synthesis of Compound I-7

The compound was synthesized from compound 7.6 and methylamine using General Procedure D. The material was further purified by column chromatography eluting with 2.5% methanol in dichloromethane to obtain I-7 (0.020 g, 40.09%), MS (ES): m/z 415.27 [M+H]⁺ LCMS purity: 96.18%, HPLC purity: 95.44%, ¹H NMR (DMSO-d₆, 400 MHz): 11.79 (s, 1H), 11.11 (s, 1H), 8.56 (s, 1H), 8.39 (bs, 1H), 8.31 (s, 2H), 7.87-7.85 (d, J=8 Hz, 1H), 7.71-7.70 (d, J=7.2 Hz, 1H), 7.65-7.61 (t, J=8 Hz, 1H), 7.48 (bs, 1H), 6.40 (s, 1H), 2.86-2.85 (d, J=4.4 Hz, 3H), 2.32 (s, 3H), 1.23 (bs, 1H), 1.00-0.93 (m, 4H).
Example 8: 2-(3-(2H-1,2,3-triazol-2-yl)phenyl)-7-(cyclopropanecarboxamido)-N-methyl-1H-pyrrolo[2,3-c]pyridine-4-carboxamide (I-8)
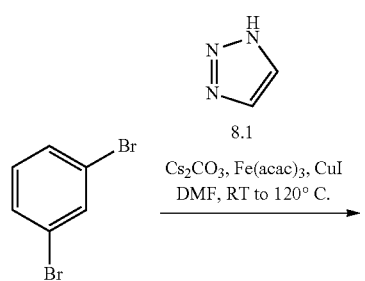
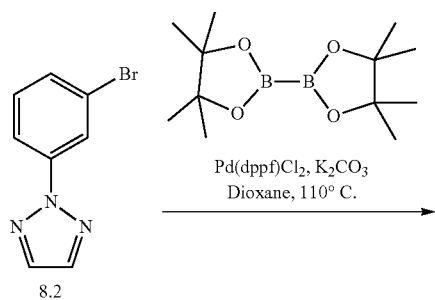
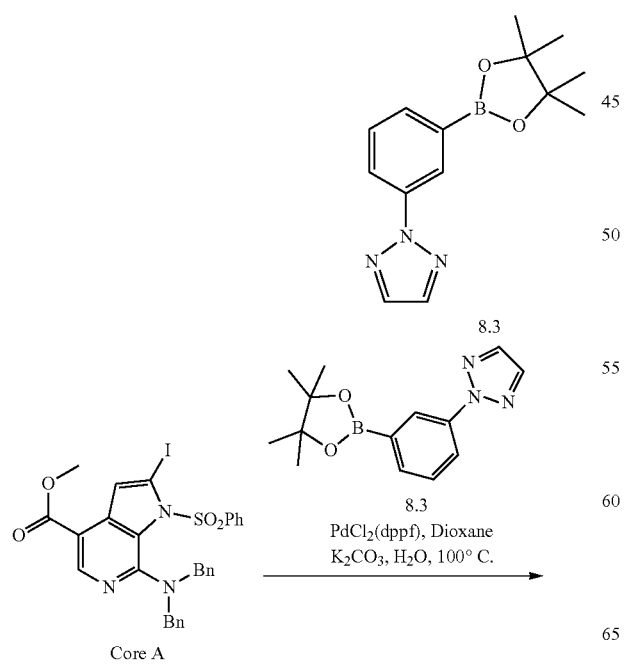
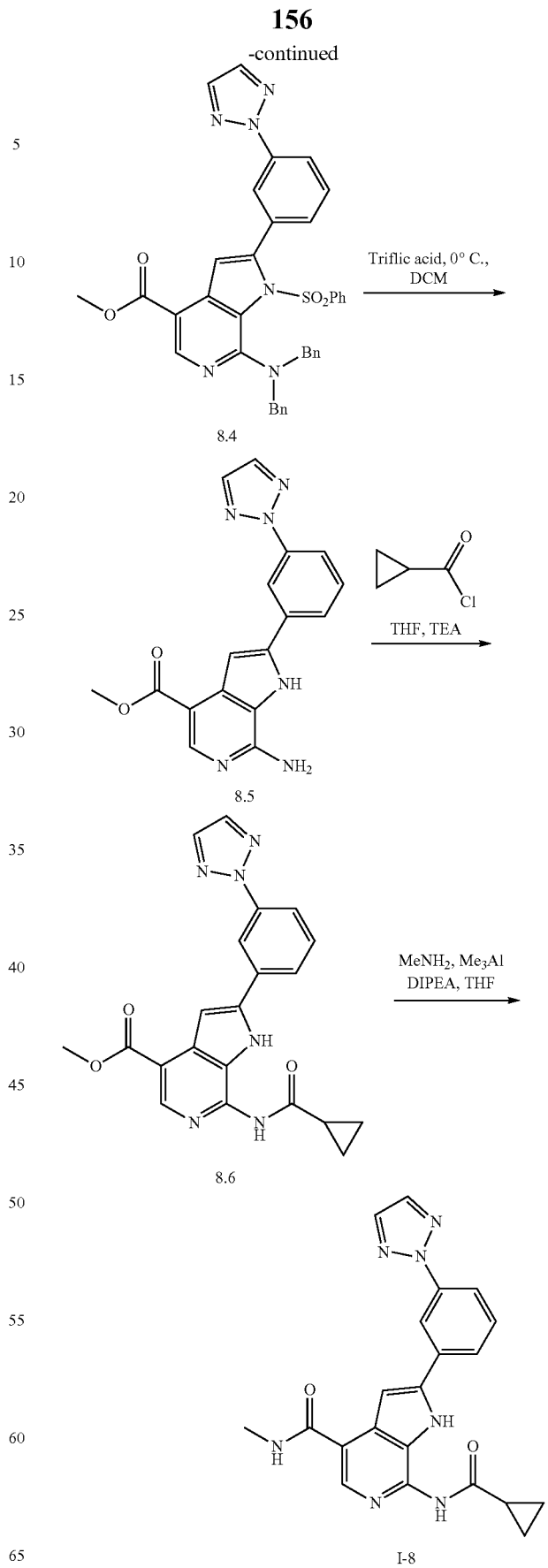

Synthesis of Compound 8.2

To a solution of 1,3-dibromobenzene (2.0 g, 8.47 mmol, 1.0 eq) in dimethylformamide (20 mL) was added compound 8.1 (0.701 g, 10.16 mmol, 1.2 eq), copper (I) iodide (0.161 g, 0.84 mmol, 0.1 eq), tris(acetylacetonato)iron(III) (0.896 g, 2.54 mmol, 0.3 eq) and cesium carbonate (5.5 g, 16.94 mmol, 2.0 eq). The reaction mixture was heated at 120° C. for 16 h under $N_2$ atmosphere. After completion of reaction, reaction mixture was concentrated under reduced pressure to obtain crude. This was further purified by combi flash using 15% ethyl acetate in hexane as eluant to obtain pure 8.2. (0.450 g, Yield: 23.69%). MS (ES): m/z 224.97 [M+H]$^+$.

Synthesis of Compound 8.3

Argon was purged for 15 min through a stirring solution of 8.2 (0.450 g, 2.00 mmol, 1.0 eq) and potassium carbonate (0.828 g, 6.00 mmol, 3.0 eq) in 1,4-dioxane (16 mL). Then bis(pinacolato)diboron (0.609 g, 2.4 mmol, 1.2 eq) and [1,1'-bis(diphenylphosphino)ferrocene]palladium(II) dichloride (0.146 g, 0.2 mmol, 0.1 eq) were added to it and further purging done for 10 min. Reaction was allowed to stir at 110° C. for 5 h. After completion of reaction, reaction mixture was transferred into water and product was extracted with ethyl acetate. Organic layer was combined, washed with brine solution, dried over sodium sulfate and concentrated under reduced pressure to obtain 8.3. (0.350 g, 64.28%). MS(ES): m/z 272.15 [M+H]$^+$.

Synthesis of Compound 8.4

The compound was synthesized from Core A and compound 8.3 using General Procedure A to obtain 8.4. (0.220 g, Yield: 71.40%), MS (ES): m/z 655.21 [M+H]$^+$.

Synthesis of Compound 8.5

The compound was synthesized from compound 8.4 using General Procedure B to obtain 8.5. (0.105 g, Yield: 93.47%), MS (ES): m/z 335.12 [M+H]$^+$.

Synthesis of Compound 8.6

The compound was synthesized from compound 8.5 using General Procedure C to obtain 8.6. (0.1 g, Yield: 79.13%), MS (ES): m/z 403.15 [M+H]$^+$.

Synthesis of Compound I-8

The compound was synthesized from compound 8.6 and methylamine using General Procedure D. The material was further purified by column chromatography eluting with 2.5% methanol in dichloromethane to obtain I-8 (0.025 g, 25.06%), MS (ES): m/z 402.55 [M+H]$^+$ LCMS purity: 100%, HPLC purity: 98.21%, $^1$H NMR (DMSO-$d_6$, 400 MHz): 11.82 (s, 1H), 11.12 (s, 1H), 9.03 (s, 1H), 8.45 (s, 1H), 8.39-8.38 (d, J=4.4 Hz, 1H), 8.31 (s, 1H), 8.05 (s, 1H), 7.98-7.94 (m, 2H), 7.79-7.75 (t, J=7.6 Hz, 1H), 7.56 (s, 1H), 2.86-2.85 (d, J=4.4 Hz, 3H), 2.24 (bs, 1H), 1.00 (bs, 2H), 0.95-0.93 (m, 2H).

Example 9: 7-(cyclopropanecarboxamido)-2-(4-(4,4-dimethyl-4,5-dihydrooxazol-2-yl)-2-methoxyphenyl)-N-methyl-1H-pyrrolo[2,3-c]pyridine-4-carboxamide (I-9)

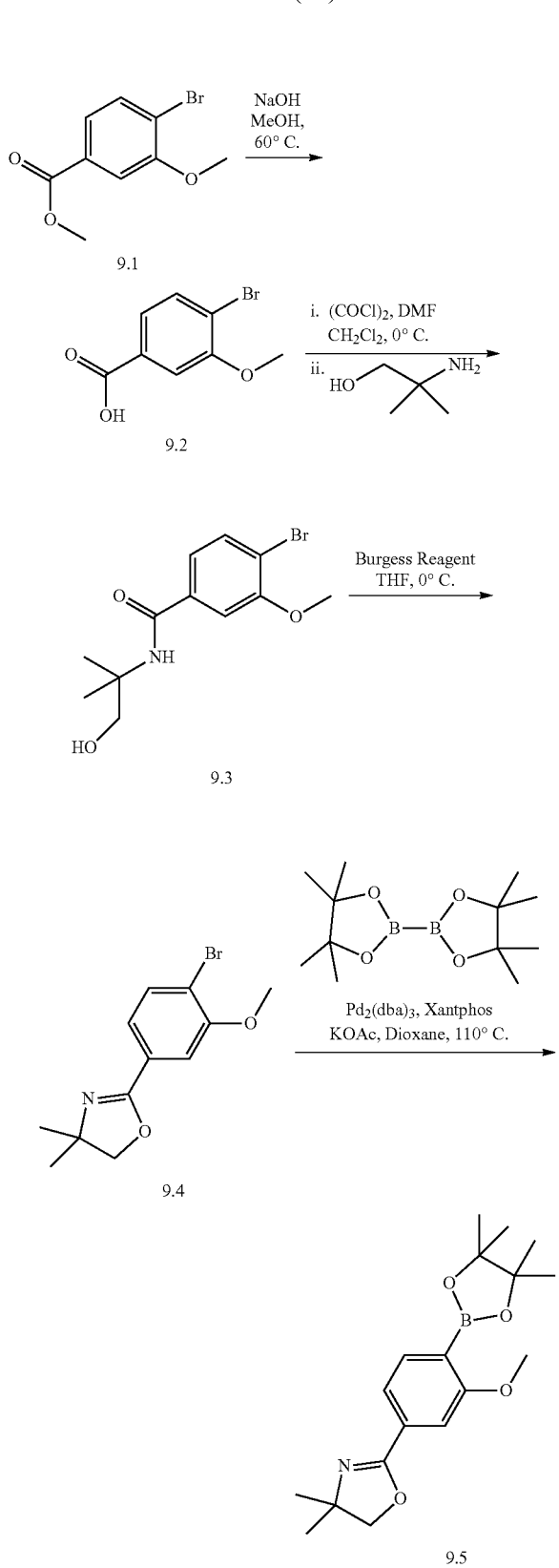

-continued

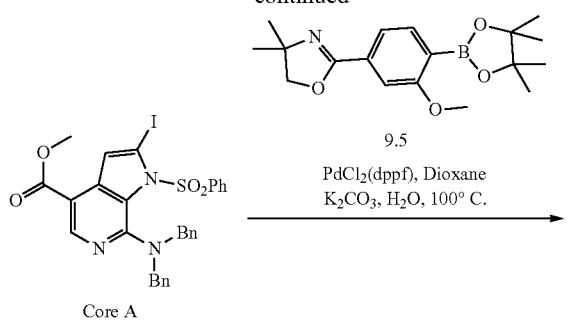

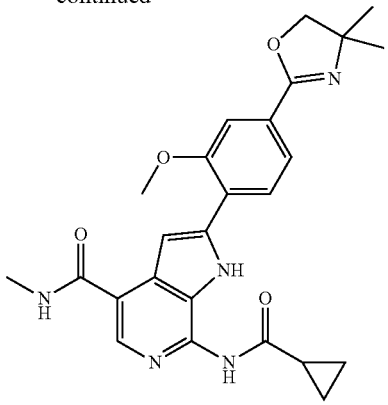

I-9

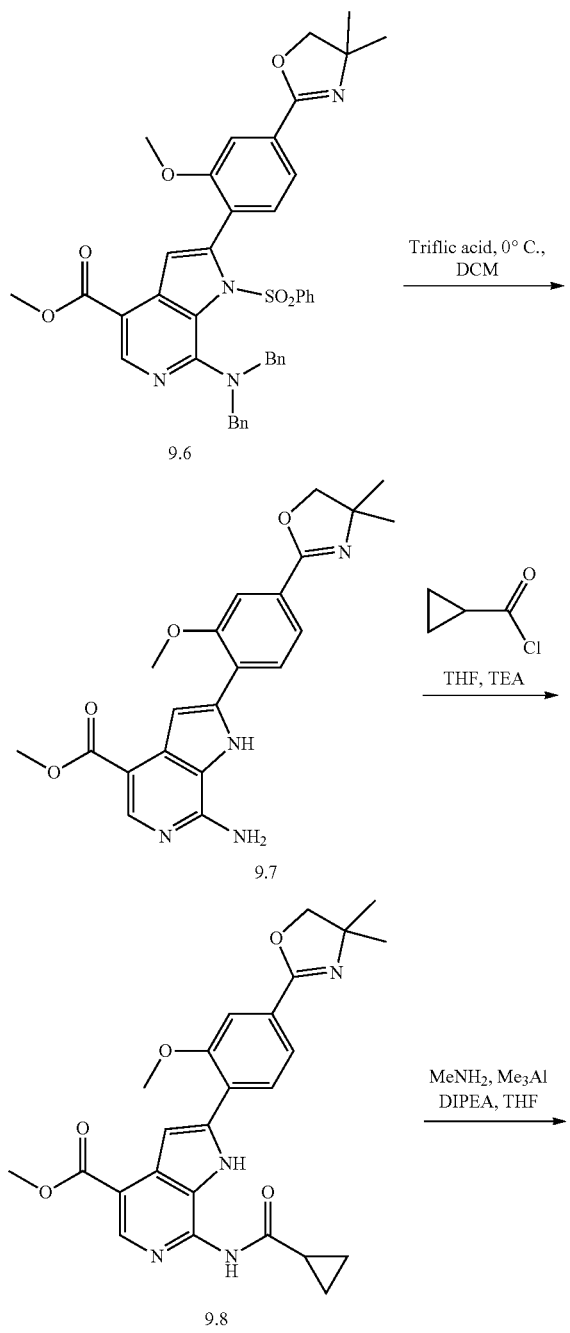

Synthesis of Compound 9.2

To a solution of 9.1 (3.0 g, 12.24 mmol, 1.0 eq), in methanol (25 mL) was added sodium hydroxide (2.4 g, 61.2 mmol, 5.0 eq). The reaction mixture was stirred at 60° C. for 1 h. After completion of reaction, reaction mixture was concentrated under reduced pressure to obtain residue. To this added water and acidified with 1N hydrochloric acid to adjust pH~6 at 10° C. Product was extracted with dichloromethane. Organic layer was combined, washed with brine solution, dried over sodium sulfate and concentrated under reduced pressure to obtain crude material. This was further purified by column chromatography and compound was eluted in 2.1% methanol in dichloromethane to obtain pure 9.2. (2.4 g, 84.86%). MS(ES): m/z 231.96 [M+H]⁺.

Synthesis of Compound 9.3

To the solution of compound 9.2 (2.4 g, 10.38 mmol, 1.0 eq) in dichloromethane (25 mL) was added catalytic dimethylformamide (1 mL) and oxalyl chloride (1.3 mL, 15.57 mmol, 1.5 eq) was added dropwise at 0° C. The reaction mixture was stirred at 0° C. for 1 h. After completion of reaction, reaction mixture was concentrated under reduced pressure to obtain crude material. To this added tetrahydrofuran (10 mL) followed by triethylamine (3.1 g, 31.14 mmol, 3.0 eq) and 2-amino-2-methyl-1-propanol (1.8 g, 20.76 mmol, 2.0 eq) at 0° C. The reaction mixture was stirred at room temperature for 2 h, transferred into ice cold water and product was extracted with ethyl acetate. Organic layer was combined, washed with brine solution, dried over sodium sulfate and concentrated under reduced pressure to obtain crude material. This was further purified by column chromatography eluting with 2.5% methanol in dichloromethane to obtain 9.3. (1.6 g, Yield: 50.97%). MS (ES): m/z 302.03 [M+H]⁺.

Synthesis of Compound 9.4

To a solution of 9.3 (1.6 g, 5.29 mmol, 1.0 eq) in tetrahydrofuran (20 mL) was added Burgess Reagent (2.5 g, 10.58 mmol, 2.0 eq) at 0° C. The reaction was stirred at 0° C. for 4 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by combi flash using 3% methanol in dichloromethane as eluant to obtain pure 9.4. (0.7 g, 46.52%). MS(ES): m/z 285.02 [M+H]⁺.

Synthesis of Compound 9.5

The compound was synthesized from compound 9.4 using General Procedure F to obtain 9.5. (0.5 g, 61.28%). MS(ES): m/z 332.20 [M+H]⁺.

Synthesis of Compound 9.6

The compound was synthesized from Core A and compound 9.5 using General Procedure A to obtain 9.6. (0.140 g, Yield: 49.94%), MS (ES): m/z 715.25 [M+H]⁺.

Synthesis of Compound 9.7

The compound was synthesized from compound 9.6 using General Procedure B to obtain 9.7. (0.075 g, Yield: 97.09%), MS (ES): m/z 395.17 [M+H]⁺.

Synthesis of Compound 9.8

The compound was synthesized from compound 9.7 using General Procedure C to obtain 9.8. (0.070 g, 74.62%), MS (ES): m/z 463.19 [M+H]⁺.

Synthesis of Compound I-9

The compound was synthesized from compound 9.8 and methylamine using General Procedure D. The material was further purified by column chromatography eluting with 2.5% methanol in dichloromethane to obtain I-9 (0.028 g, 40.09%), MS (ES): m/z 462.45 [M+H]⁺ LCMS purity: 95.00%, HPLC purity: 95.13%, ¹H NMR (DMSO-$d_6$, 400 MHz): 12.59 (s, 1H), 11.35 (s, 1H), 8.34 (bs, 1H), 8.29 (s, 1H), 8.12-8.10 (d, J=8.4 Hz, 1H), 7.59-7.58 (d, J=6.4 Hz, 2H), 7.53 (s, 1H), 4.17 (s, 2H), 4.07 (s, 2H), 2.87-2.85 (d, J=4.4 Hz, 1H), 2.52 (bs, 3H), 2.26 (bs, 1H), 1.33 (s, 6H), 1.02 (bs, 2H), 0.99-0.97 (d, J=7.6 Hz, 2H).

Example 10: 7-(cyclopropanecarboxamido)-N-methyl-2-(4-(2-methylthiazol-4-yl)pyridin-2-yl)-1H-pyrrolo[2,3-c]pyridine-4-carboxamide (I-10)

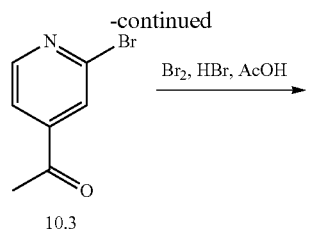

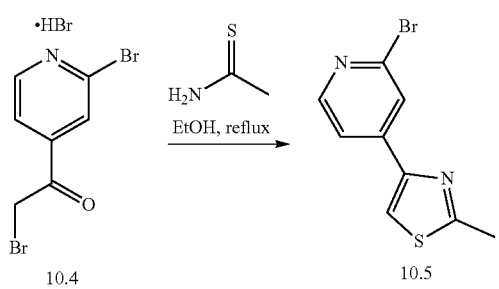

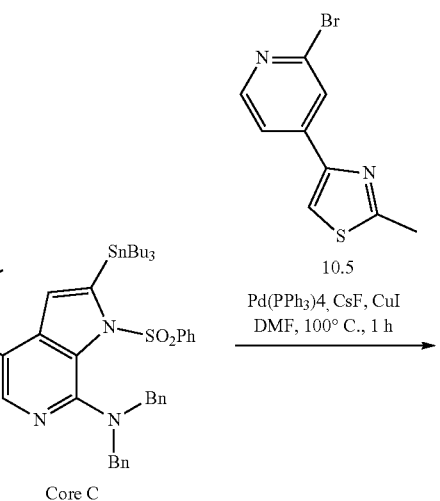

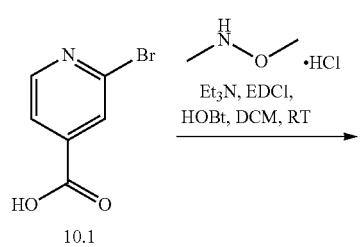

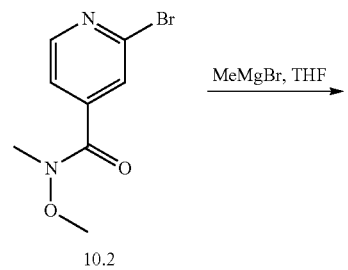

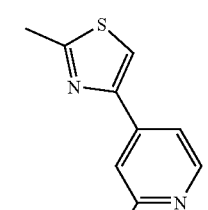

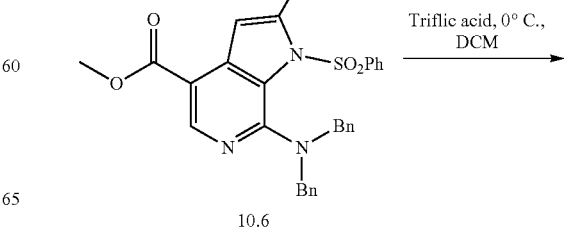

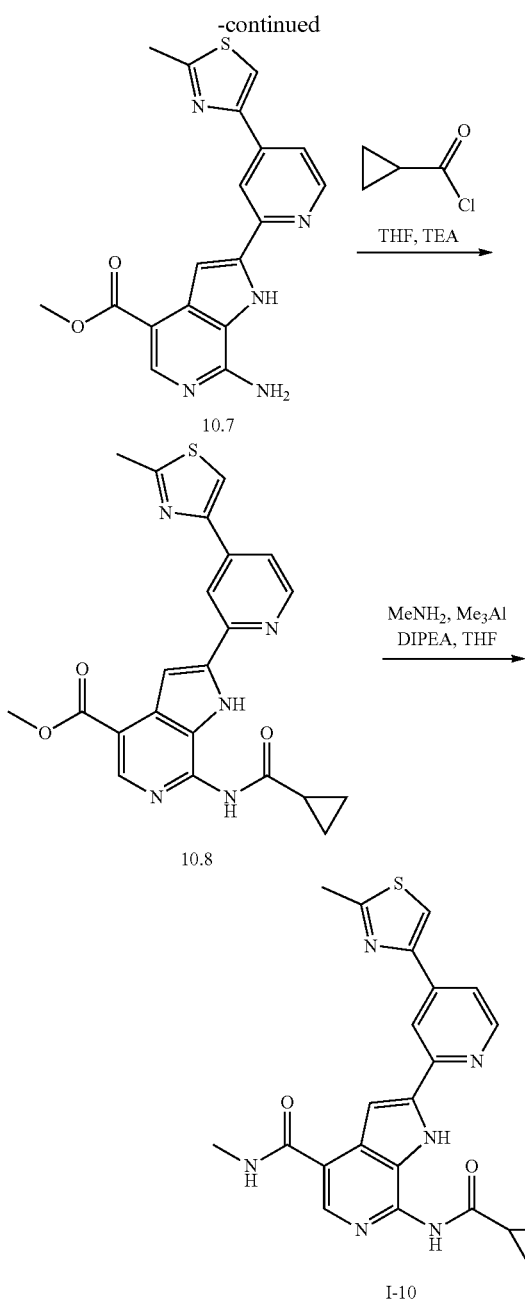

pound was eluted in 40% ethyl acetate in hexane to obtain 10.2. (1.8 g, 74.18%). MS(ES): m/z 244.9 [M+H]$^+$.

Synthesis of Compound 10.3

To a solution of compound 10.2 (1.8 g, 7.37 mmol, 1.0 eq), in tetrahydrofuran (35 mL) was added methylmagnesium bromide solution (3M in hexane, 3.68 mL, 11.05 mmol, 1.5 eq) dropwise at 0° C. The reaction mixture was stirred at room temperature for 1 h. After completion of reaction, 1N hydrochloric acid was added to the reaction mixture and extracted with ethyl acetate. Organic layer was combined, washed with brine solution, dried over sodium sulfate and concentrated under reduced pressure to obtain crude material. This was further purified by column chromatography and the compound was eluted in 15% ethyl acetate in hexane to obtain 10.3. (1.35 g, 91.89%). MS(ES): m/z 199.97 [M+H]$^+$.

Synthesis of Compound 10.4

To compound 10.3 (1.35 g, 6.75 mmol, 1.0 eq) added hydrogen bromide solution 30% in acetic acid (10 mL) followed by bromine (0.34 mL, 6.75 mmol, 1.0 eq) dropwise at 15° C. The reaction mixture was stirred at 60° C. for 2 h. After completion of reaction, reaction mixture was cooled to 20° C., diluted with diethyl ether and stirred for 30 min. The precipitated product was filtered, washed with diethyl ether and dried under vacuum to obtain pure 10.4. (1.1 g, 58.43%). MS(ES): m/z 278.87 [M+H]$^+$.

Synthesis of Compound 10.5

To a solution of compound 10.4 (1.1 g, 3.95 mmol, 1.0 eq), in ethanol (30 mL) was added ethanethioamide (0.296 g, 3.95 mmol, 1.0 eq). The reaction mixture was refluxed for 1 h. After completion of reaction, reaction mixture was cooled to obtain the precipitate which was filtered and dried to obtain 10.5. (0.650 g, 64.60%). MS(ES): m/z 254.95 [M+H]$^+$.

Synthesis of Compound 10.6

The compound was synthesized from Core C and compound 10.5 using General Procedure E to obtain 10.6. (0.120 g, 15.57%). MS (ES): m/z 686.19 [M+H]$^+$.

Synthesis of Compound 10.7

The compound was synthesized from compound 10.6 using General Procedure B to obtain 10.7. (0.063 g, 98.53%), MS (ES): m/z 366.10 [M+H]$^+$.

Synthesis of Compound 10.8

The compound was synthesized from compound 10.7 using General Procedure C to obtain 10.8. (0.060 g, 72.25%), MS (ES): m/z 434.12 [M+H]$^+$.

Synthesis of Compound I-10

The compound was synthesized from compound 10.8 and methylamine using General Procedure D. The material was further purified by column chromatography eluting with 2.5% methanol in dichloromethane to obtain I-10 (0.016 g, 26.73%), MS (ES): m/z 433.32 [M+H]$^+$ LCMS purity: 100%, HPLC purity: 97.41%, $^1$H NMR (DMSO-d$_6$, 400

Synthesis of Compound 10.2

To a solution of compound 10.1 (2.0 g, 9.90 mmol, 1.0 eq), in dichloromethane (40 mL) was added N,O-dimethylhydroxylamine hydrochloride (1.4 g, 14.85 mmol, 1.5 eq), 1-ethyl-3-(3-dimethylaminopropyl)carbodiimide (1.6 g, 10.89 mmol, 1.1 eq), hydroxybenzotriazole (1.4 g, 10.89 mmol, 1.1 eq) and triethylamine (3.9 g, 39.6 mmol, 4.0 eq) at 0° C. The reaction mixture was stirred at room temperature for 16 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by column chromatography and the com- MHz): 12.14 (s, 1H), 11.33 (s, 1H), 8.76-8.74 (d, J=5.2 Hz, 1H), 8.63 (bs, 1H), 8.60 (s, 1H), 8.44-8.43 (d, J=4.4 Hz, 1H), 8.31 (s, 1H), 7.94-7.93 (d, J=5.2 Hz, 1H), 7.77-7.77 (d, J=2 Hz, 1H), 2.88-2.87 (d, J=4.4 Hz, 3H), 2.80 (s, 3H), 1.35 (bs, 1H), 1.24 (m, 4H).
Example 11: 7-(cyclopropanecarboxamido)-2-(3-(4,4-dimethyl-4,5-dihydrothiazol-2-yl) phenyl)-N-methyl-1H-pyrrolo[2,3-c]pyridine-4-carboxamide (I-11)
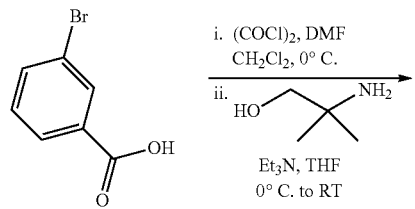
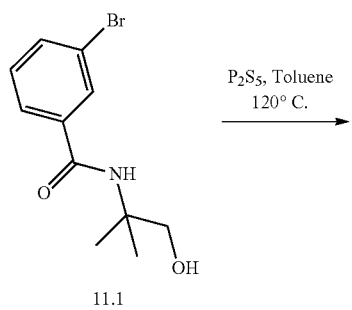
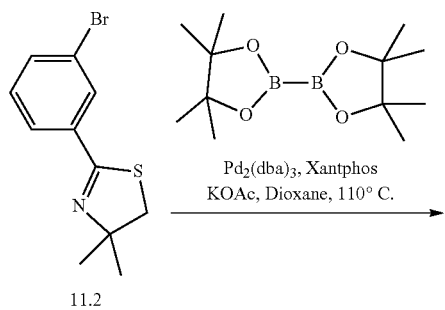
-continued
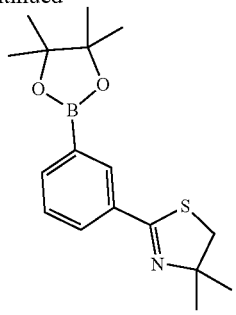
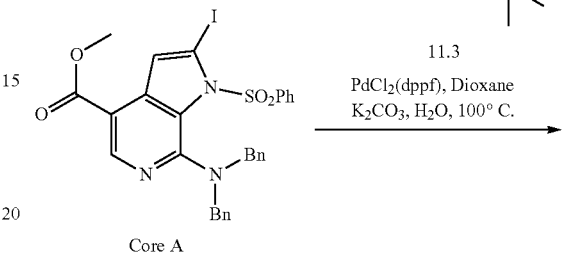
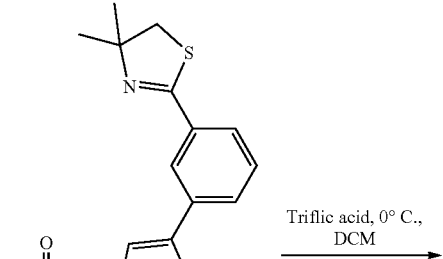
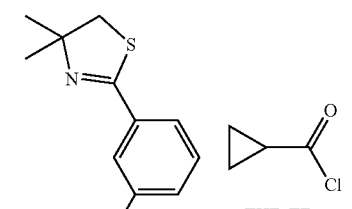
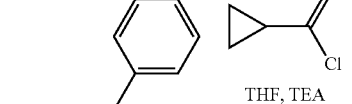
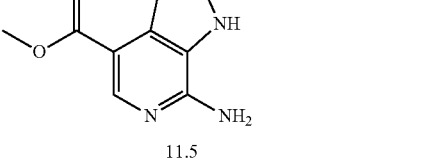

-continued

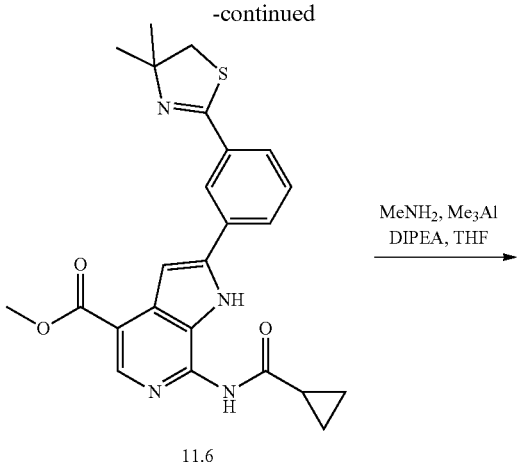

11.6

MeNH₂, Me₃Al
DIPEA, THF
→

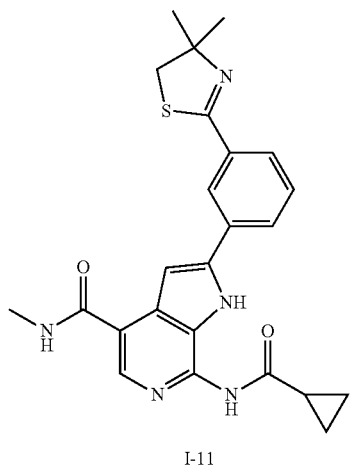

I-11

Synthesis of Compound 11.1

To the solution of 3-bromobenzoic acid (3.0 g, 14.92 mmol, 1.0 eq) in dichloromethane (30 mL) was added catalytic dimethylformamide (1 mL) and oxalyl chloride (1.9 mL, 22.38 mmol, 1.5 eq) dropwise at 0° C. The reaction mixture was stirred at 0° C. for 1 h. After completion of reaction, reaction mixture was concentrated under reduced pressure to obtain crude material. To this added tetrahydrofuran (15 mL) followed by triethylamine (4.5 g, 44.76 mmol, 3.0 eq) and 2-amino-2-methylpropan-1-ol (2.6 g, 29.84 mmol, 2.0 eq) at 0° C. The reaction mixture was stirred at room temperature for 2 h, then transferred to ice cold water and product was extracted with ethyl acetate. Organic layer was combined, washed with brine solution, dried over sodium sulfate and concentrated under reduced pressure to obtain crude material. This was further purified by column chromatography eluting with 2.5% methanol in dichloromethane to obtain 11.1. (2.8 g, Yield: 68.94%). MS (ES): m/z 273.02 [M+H]⁺.

Synthesis of Compound 11.2

To a solution of 11.1 (2.8 g, 10.29 mmol, 1.0 eq), in toluene (40 mL) was added phosphorus pentasulfide (1.4 g, 5.14 mmol, 0.5 eq). The reaction mixture was stirred at 120° C. for 3 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by column chromatography and the compound was eluted in 3% methanol in dichloromethane to obtain 11.2. (1.0 g, 35.97%). MS (ES): m/z 270.99 [M+H]⁺.

Synthesis of Compound 11.3

The compound was synthesized from compound 11.2 using General Procedure F to obtain 11.3. (0.650 g, 55.36%). MS (ES): m/z 318.17 [M+H]⁺.

Synthesis of Compound 11.4

The compound was synthesized from Core A and compound 11.3 using General Procedure A to obtain 11.4. (0.190 g, Yield: 44.39%), MS (ES): m/z 546.22 [M+H]⁺.

Synthesis of Compound 11.5

The compound was synthesized from compound 11.4 using General Procedure B to obtain 11.5. (0.090 g, Yield: 67.94%), MS (ES): m/z 381.13 [M+H]⁺.

Synthesis of Compound 11.6

The compound was synthesized from compound 11.5 using General Procedure C to obtain 11.6. (0.070 g, Yield: 65.97%), MS (ES): m/z 449.16 [M+H]⁺.

Synthesis of compound I-11. The compound was synthesized from compound 11.6 and methylamine using General Procedure D. The material was further purified by column chromatography eluting with 2.5% methanol in dichloromethane to obtain I-11 (0.025 g, 35.79%), MS (ES): m/z 448.27 [M+H]⁺ LCMS purity: 99.55%, HPLC purity: 95.11%, ¹H NMR (DMSO-d₆, 400 MHz): 11.92 (s, 1H), 11.14 (s, 1H), 8.40 (bs, 1H), 8.32 (s, 1H), 8.21 (s, 1H), 8.03-8.01 (d, J=8 Hz, 1H), 7.79-7.77 (d, J=7.6 Hz, 1H), 7.67-7.64 (t, J=7.6 Hz, 1H), 7.40 (s, 1H), 2.87-2.85 (d, J=4.4 Hz, 3H), 2.51 (s, 2H), 2.27 (bs, 1H), 1.44 (s, 6H), 0.99 (bs, 2H), 0.95-0.93 (d, J=7.6 Hz, 2H).

Example 12: 7-(cyclopropanecarboxamido)-2-(3-(1-methyl-1H-1,2,4-triazol-3-yl)phenyl)-1H-pyrrolo[2,3-c]pyridine-4-carboxamide (I-12)

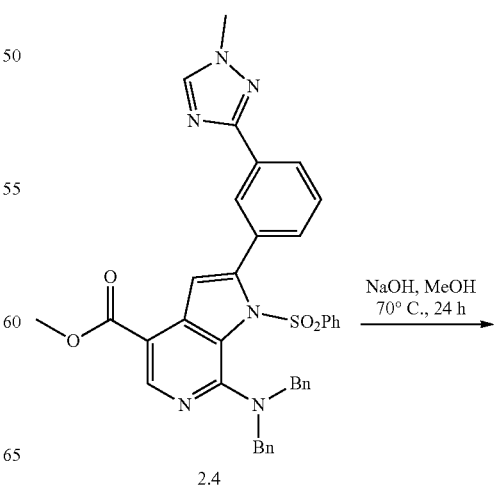

2.4

NaOH, MeOH
70° C., 24 h
→

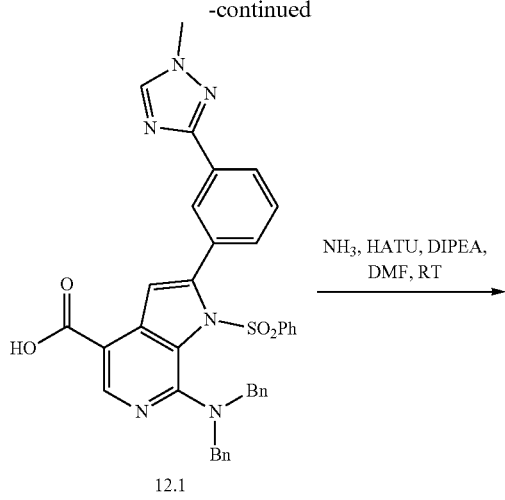

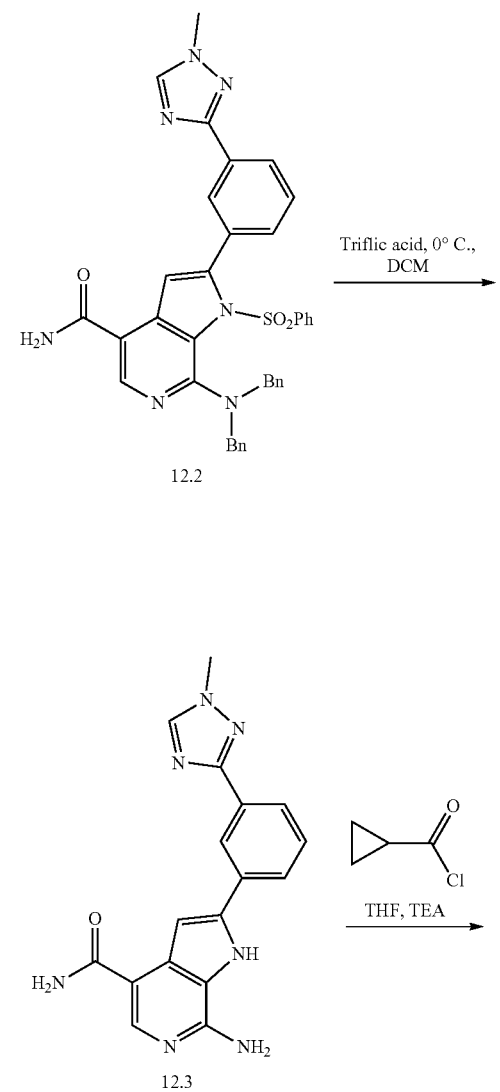

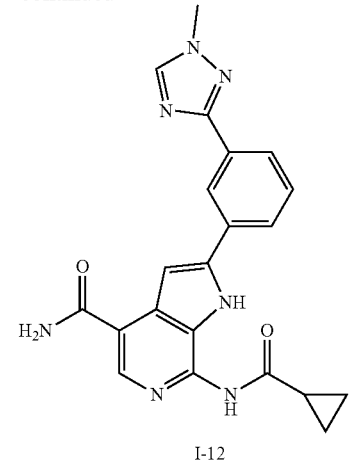

Synthesis of Compound 12.1

To a solution of compound 2.4 (0.190 g, 0.28 mmol, 1.0 eq), in methanol (3 mL) was added sodium hydroxide (0.056 g, 1.4 mmol, 5.0 eq). The reaction mixture was stirred at 70° C. for 24 h. After completion of reaction, reaction mixture was concentrated under reduced pressure to obtain residue. To this added water and acidified with 1N hydrochloric acid to adjust pH~6 at 10° C. Product was extracted with dichloromethane. Organic layer was combined, washed with brine solution, dried over sodium sulfate and concentrated under reduced pressure to obtain crude material. This was further purified by column chromatography and compound was eluted in 2.1% methanol in dichloromethane to obtain pure 12.1. (0.110 g, 59.14%). MS(ES): m/z 655.21 [M+H]$^+$.

Synthesis of Compound 12.2

To a solution of compound 12.1 (0.080 g, 0.12 mmol, 1.0 eq), in N,N-dimethylformamide (2 mL) was added 1-[bis(dimethylamino)methylene]-1H-1,2,3-triazolo[4,5-b]pyridinium 3-oxid hexafluorophosphate (0.091 g, 0.24 mmol, 2.0 eq) and stirred at room temperature for 15 min. To this added diisopropylethylamine (0.046 g, 0.36 mmol, 3.0 eq) followed by addition of 30% aqueous ammonia (0.033 mL, 0.12 mmol, 1.3 eq). The reaction mixture was stirred at room temperature for 5 min. After completion of reaction, reaction mixture was transferred into water and product was extracted with ethyl acetate. Organic layer was combined, washed with brine solution, dried over sodium sulfate and concentrated under reduced pressure to obtain crude material. This was further purified by column chromatography and the compound was eluted in 40% ethyl acetate in hexane to obtain 12.2. (0.070 g, 87.63%). MS(ES): m/z 654.22 [M+H]$^+$.

Synthesis of Compound 12.3

The compound was synthesized from compound 12.2 using General Procedure B to obtain 12.3. (0.035 g, 98.06%), MS (ES): m/z 334.14 [M+H]$^+$.

Synthesis of Compound I-12

The compound was synthesized from compound 12.3 using General Procedure C to obtain I-12 (0.030 g, 62.28%), MS (ES): m/z 402.12 [M+H]+ LCMS purity: 99.30%, HPLC purity: 97.73%, ¹H NMR (DMSO-d₆, 400 MHz): 11.90 (s, 1H), 11.13 (s, 1H), 8.61 (s, 1H), 8.46 (s, 1H), 8.41 (s, 1H), 8.07-8.05 (d, J=7.6 Hz, 1H), 7.93-7.91 (d, J=7.2 Hz, 3H), 7.67-7.63 (t, J=7.6 Hz, 2H), 7.47 (bs, 2H), 7.42 (s, 1H), 2.29 (bs, 1H), 1.01 (bs, 2H), 0.96-0.95 (d, J=7.6 Hz, 2H).

Example 13: 7-(cyclopropanecarboxamido)-N-methyl-2-(4-(1-methyl-1H-1,2,4-triazol-3-yl) pyridin-2-yl)-1H-pyrrolo[2,3-c]pyridine-4-carboxamide (I-13)

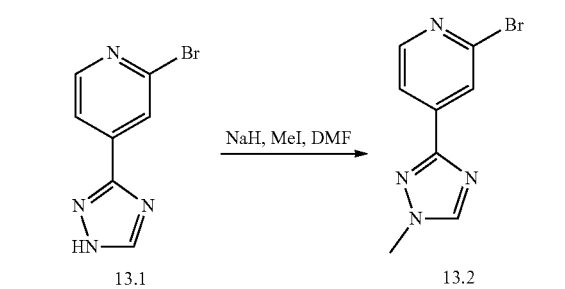

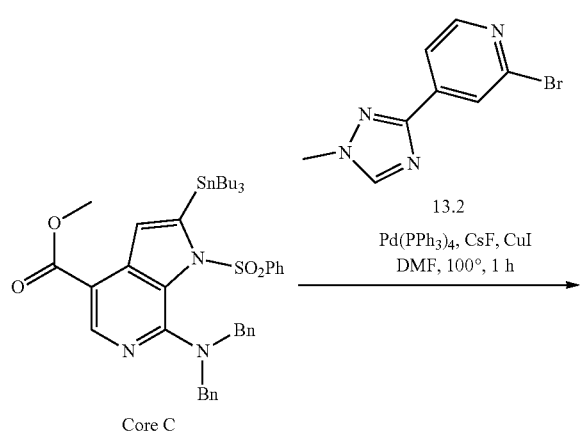

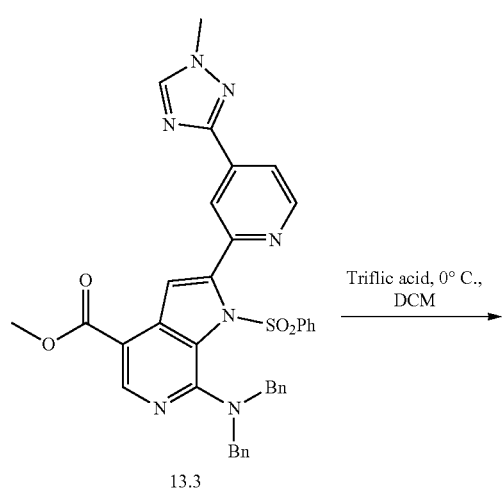

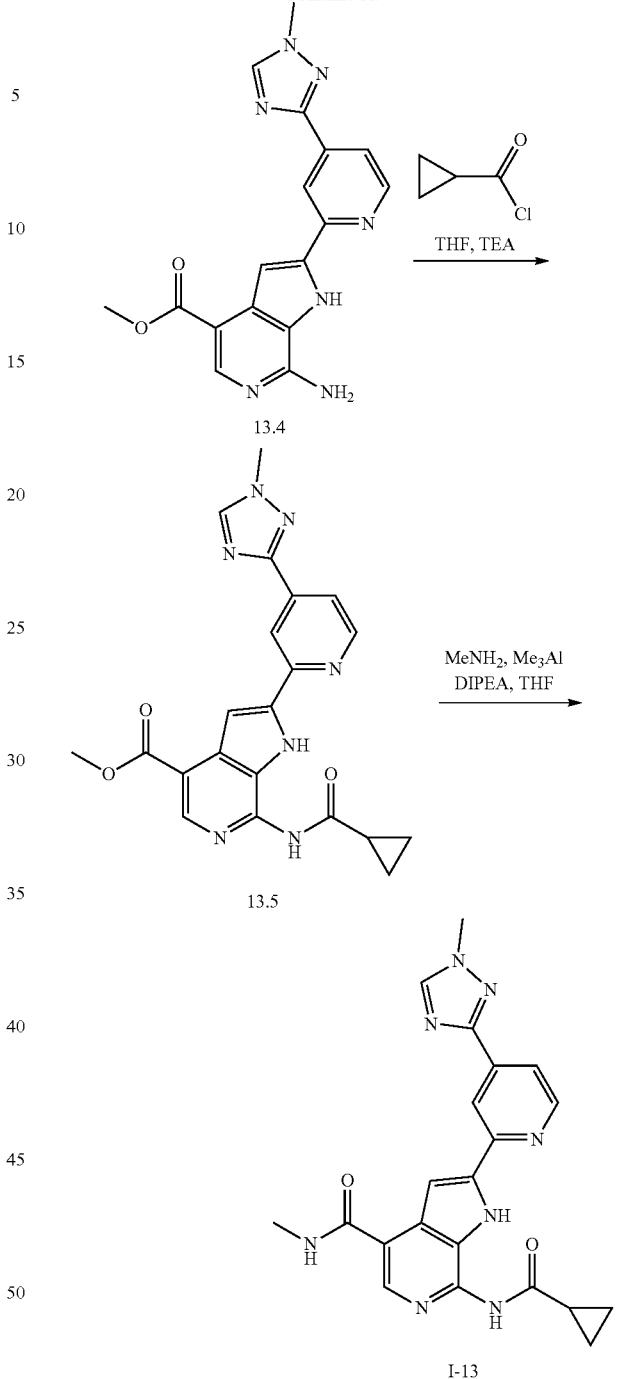

Synthesis of Compound 13.2

To a solution of compound 13.1 (2.8 g, 12.44 mmol, 1.0 eq) in dimethylformamide (30 mL), was added sodium hydride (0.597 g, 24.88 mmol, 2 eq) at 0° C. and stirred for 20 min. Methyl iodide (1.9 g, 13.68 mmol, 1.1 eq) was added and reaction mixture was stirred at room temperature for 2 h. After completion of reaction, reaction mixture was transferred into ice, stirred and extracted with diethyl ether. Organic layer was combined, dried over sodium sulfate and concentrated under reduced pressure to obtain crude material. This was further purified by distillation to obtain pure 13.2. (1.0 g, Yield: 33.62%). MS (ES): m/z 238.99 [M+H]⁺.

Synthesis of Compound 13.3

The compound was synthesized from Core C and compound 13.2 using General Procedure E to obtain 13.3. (0.130 g, 15.54%). MS (ES): m/z 670.22 [M+H]⁺.

Synthesis of Compound 13.4

The compound was synthesized from compound 13.3 using General Procedure B to obtain 13.4. (0.067 g, Yield: 98.81%), MS (ES): m/z 350.13 [M+H]⁺.

Synthesis of Compound 13.5

The compound was synthesized from compound 13.4 using General Procedure C to obtain 13.5. (0.045 g, 50.22%), MS (ES): m/z 418.16 [M+H]⁺.

Synthesis of Compound I-13

The compound was synthesized from compound 13.5 and methylamine using General Procedure D. The material was further purified by column chromatography eluting with 2.5% methanol in dichloromethane to obtain I-13 (0.027 g, 60.14%), MS (ES): m/z 417.47 [M+H]⁺ LCMS purity: 98.74%, HPLC purity: 95.00%, ¹H NMR (DMSO-d₆, 400 MHz): 12.21 (s, 1H), 11.34 (s, 1H), 8.81 (bs, 1H), 8.54 (s, 1H), 8.38 (bs, 1H), 7.94 (bs, 1H), 7.69 (bs, 1H), 7.08 (bs, 1H), 6.84 (bs, 1H), 4.02 (s, 3H), 2.88 (s, 3H), 1.56 (bs, 1H), 1.01-0.97 (m, 4H).

Example 14: 7-(cyclopropanecarboxamido)-N-methyl-2-(4-(thiazol-2-yl)pyridin-2-yl)-1H-pyrrolo[2,3-c]pyridine-4-carboxamide (I-14)

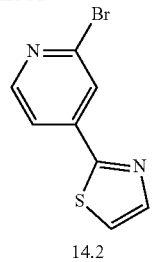

14.2

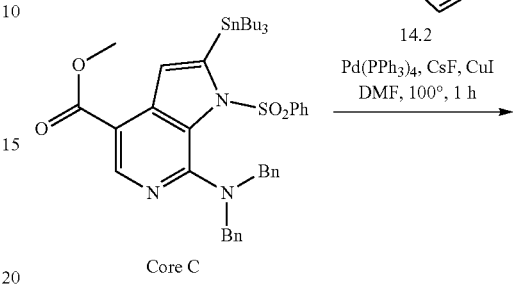

Core C

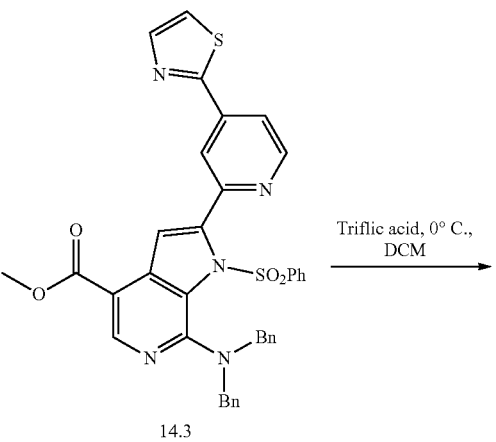

14.3

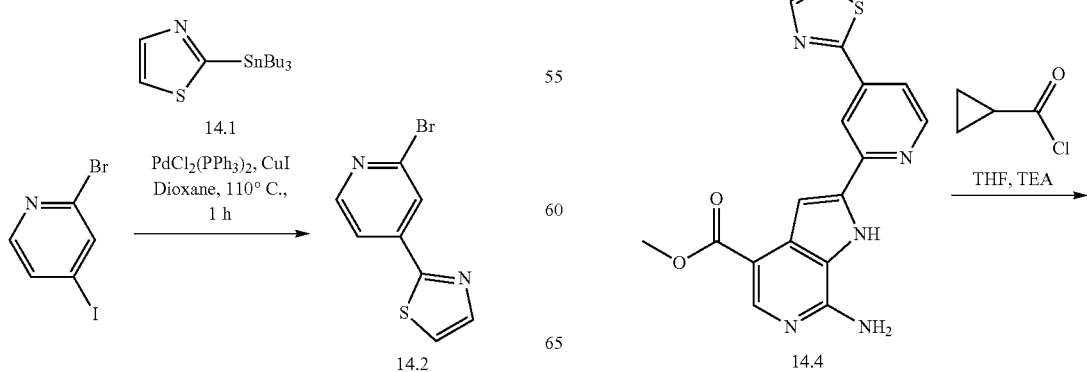

14.2

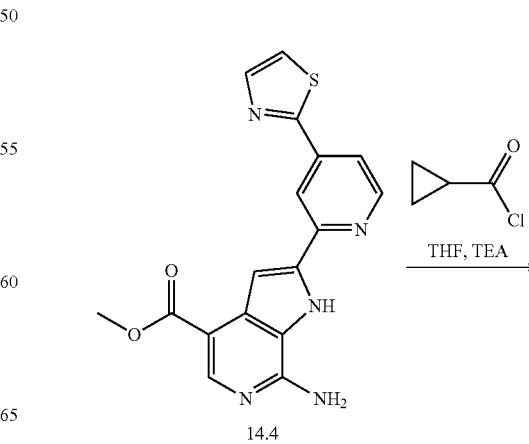

14.4

175

-continued

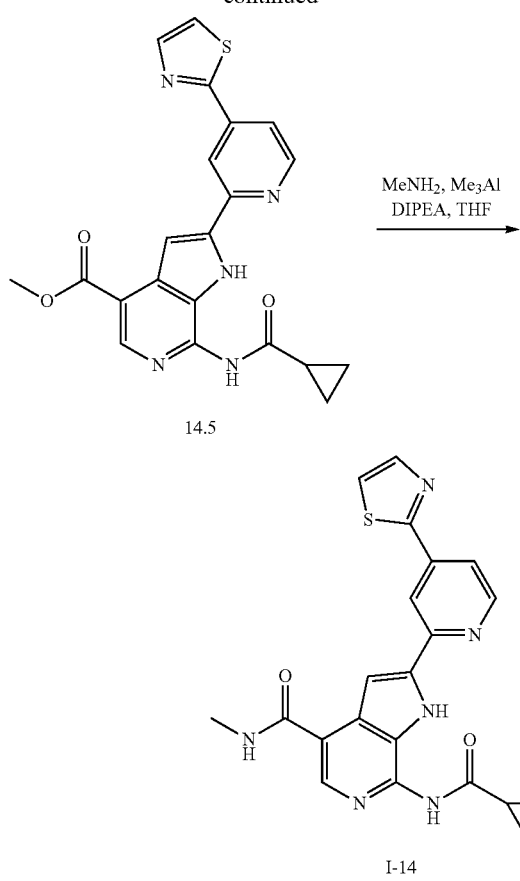

14.5

I-14

Synthesis of Compound 14.2

Argon was purged for 15 min through a stirred solution of 2-bromo-4-iodopyridine (3.0 g, 10.60 mmol, 1.0 eq), compound 14.1 (5.1 g, 13.78 mmol, 1.3 eq) and copper(I) iodide (0.201 g, 1.06 mmol, 0.1 eq) in 1,4-dioxane (50 mL). Bis(triphenylphosphine)palladium(II) dichloride (0.743 g, 1.06 mmol, 0.1 eq) was added to it and further purging done for 10 min. Reaction was allowed to stir at 110° C. for 1 h. After completion of reaction, reaction mixture was transferred into water and product was extracted with ethyl acetate. Organic layer was combined, washed with brine solution, dried over sodium sulfate and concentrated under reduced pressure to obtain 14.2. (0.7 g, 27.47%). MS (ES): m/z 241.93 [M+H]$^+$.

Synthesis of Compound 14.3

The compound was synthesized from Core C and compound 14.2 using General Procedure E to obtain 14.3. (0.130 g, 15.49%). MS (ES): m/z 672.17 [M+H]$^+$.

Synthesis of Compound 14.4

The compound was synthesized from compound 14.3 using General Procedure B to obtain 14.4. (0.067 g, Yield: 98.53%), MS (ES): m/z 352.08 [M+H]$^+$.

176

Synthesis of Compound 14.5

The compound was synthesized from compound 14.4 using General Procedure C to obtain 14.5. (0.058 g, 63.10%), MS (ES): m/z 420.11 [M+H]$^+$.

Synthesis of Compound I-14

The compound was synthesized from compound 14.5 and methylamine using General Procedure D. The material was further purified by column chromatography eluting with 2.5% methanol in dichloromethane to obtain I-14 (0.023 g, 39.75%), MS (ES): m/z 419.80 [M+H]$^+$ LCMS purity: 97.05%, HPLC purity: 98.91%, $^1$H NMR (DMSO-d$_6$, 400 MHz): 12.20 (s, 1H), 11.35 (s, 1H), 8.84-8.83 (d, J=5.2 Hz, 1H), 8.57 (bs, 1H), 8.41-8.40 (d, J=4.4 Hz, 1H), 8.14-8.13 (d, J=3.2 Hz, 1H), 7.96-7.95 (m, 1H), 7.81 (d, J=2 Hz, 1H), 7.08 (bs, 1H), 6.84 (bs, 1H), 2.89-2.88 (d, J=4.4 Hz, 3H), 1.56 (bs, 1H), 1.01-0.96 (m, 4H).

Example 15: 7-(cyclopropanecarboxamido)-N-methyl-2-(4-(oxazol-2-yl)pyridin-2-yl)-1H-pyrrolo[2,3-c]pyridine-4-carboxamide (I-15)

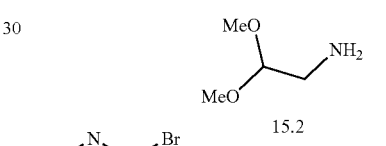

15.1

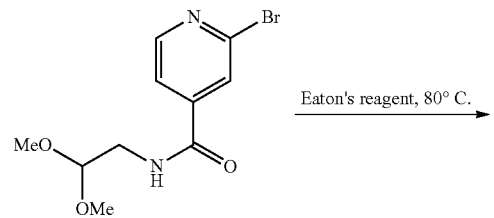

15.3

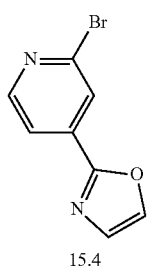

15.4

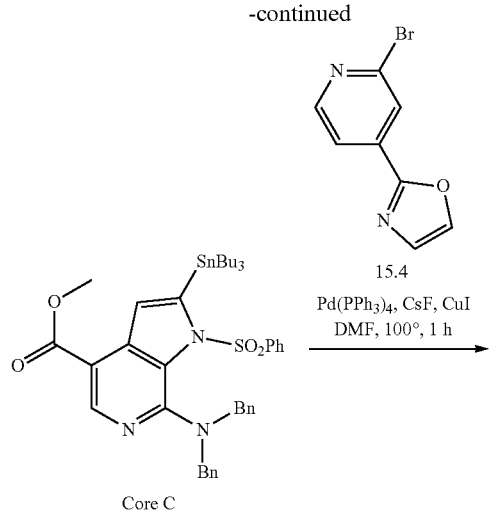

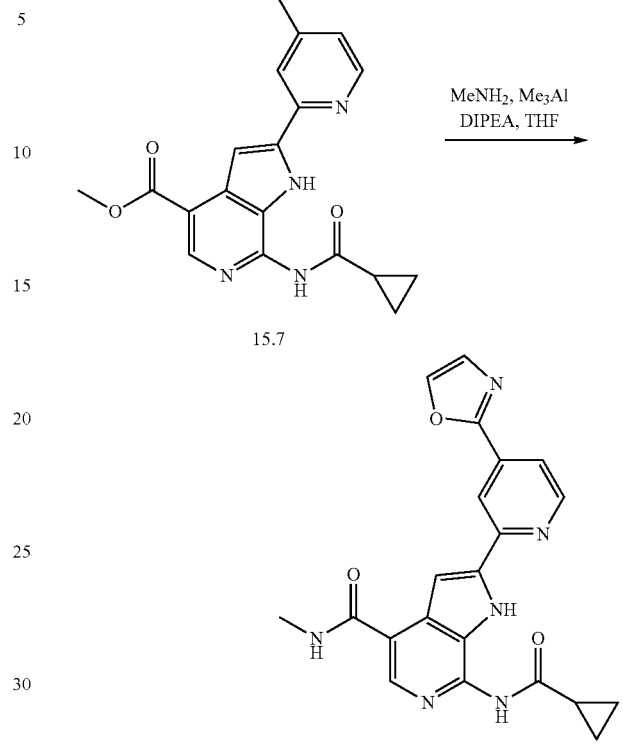

Synthesis of Compound 15.3

To a solution of 15.1 (6.0 g, 29.70 mmol, 1.0 eq) and 15.2 (3.12 g, 29.70 mmol, 1.0 eq) in tetrahydrofuran (70 mL), was added triethylamine (5.0 g, 50.49 mmol, 1.7 eq) and carbonyldiimidazole (5.7 g, 35.64 mmol, 1.2 eq). Reaction mixture was stirred at 100° C. for 2 h. After completion of reaction, reaction mixture was transferred into ice, stirred and extracted with diethyl ether. Organic layer was combined, dried over sodium sulfate and concentrated under reduced pressure to obtain crude material. This was further purified by distillation to obtain pure 15.3. (4.6 g, Yield: 53.57%). MS (ES): m/z 290.01 [M+H]$^+$.

Synthesis of Compound 15.4

To the compound 15.3 (0.045 g, 0.10 mmol, 1.0 eq) was added Eaton's Reagent (7.7 wt % phosphorus pentoxide solution in methanesulfonic acid) (0.5 mL). Then reaction mixture was stirred at 80° C. for 2 h. After completion of reaction, reaction mixture was transferred to ice cold water and product was extracted with ethyl acetate. Organic layer was combined, washed with brine solution, dried over sodium sulfate and concentrated under reduced pressure to obtain 15.4. (0.640 g, Yield: 17.87%). MS (ES): m/z 225.96 [M+H]$^+$.

Synthesis of Compound 15.5

The compound was synthesized from Core C and compound 15.4 using General Procedure E to obtain 15.5. (0.150 g, 18.32%). MS (ES): m/z 656.19 [M+H]$^+$.

Synthesis of Compound 15.6

The compound was synthesized from compound 15.5 using General Procedure B to obtain 15.6. (0.076 g, Yield: 99.08%), MS (ES): m/z 336.11 [M+H]$^+$.

Synthesis of Compound 15.7

The compound was synthesized from compound 15.6 using General Procedure C to obtain 15.7. (0.046 g, 68.46%), MS (ES): m/z 404.13 [M+H]$^+$.

Synthesis of Compound I-15

The compound was synthesized from compound 15.7 and methylamine using General Procedure D. The material was further purified by column chromatography eluting with 2.5% methanol in dichloromethane to obtain I-15 (0.025 g, 35.80%), MS (ES): m/z 403.42 [M+H]$^+$ LCMS purity: 97.14%, HPLC purity: 95.00%, $^1$H NMR (DMSO-$d_6$, 400 MHz): 12.08 (s, 1H), 10.99 (s, 1H), 8.88-8.87 (d, J=5.2 Hz, 1H), 8.51 (s, 1H), 8.34-8.33 (d, J=4.4 Hz, 2H), 8.06 (bs, 1H), 7.91-7.90 (d, J=4.2 Hz, 1H), 7.73 (s, 1H), 7.53 (s, 1H), 2.92-2.91 (d, J=4.4 Hz, 3H), 1.32-1.29 (m, 1H), 1.04-0.95 (m, 4H).

Example 16: 7-(cyclopropanecarboxamido)-N-(methyl-d3)-2-(4-(1-methyl-1H-1,2,4-triazol-3-yl)pyridin-2-yl)-1H-pyrrolo[2,3-c]pyridine-4-carboxamide (I-16)

Synthesis of Compound I-16

The compound was synthesized from compound 13.5 and methyl-$d_3$-amine using General Procedure D. The material was further purified by column chromatography eluting with 2.5% methanol in dichloromethane to obtain I-16 (0.025 g, 38.28%), MS (ES): m/z 420.80 [M+H]$^+$ LCMS purity: 95.11%, HPLC purity: 97.40%, $^1$H NMR (DMSO-$d_6$, 400 MHz): 12.01 (s, 1H), 10.92 (s, 1H), 8.80-8.78 (d, J=4.8 Hz, 1H), 8.62 (s, 1H), 8.51 (s, 1H), 8.33 (s, 1H), 8.02 (bs, 1H), 7.93-7.91 (d, J=4.4 Hz, 1H), 7.65 (s, 1H), 4.02 (s, 3H), 1.27 (bs, 1H), 1.04-0.94 (m, 4H).

Example 17: 7-(cyclopropanecarboxamido)-N-methyl-2-(4-(3-methyl-1H-pyrazol-1-yl) pyridin-2-yl)-1H-pyrrolo[2,3-c]pyridine-4-carboxamide (I-17)

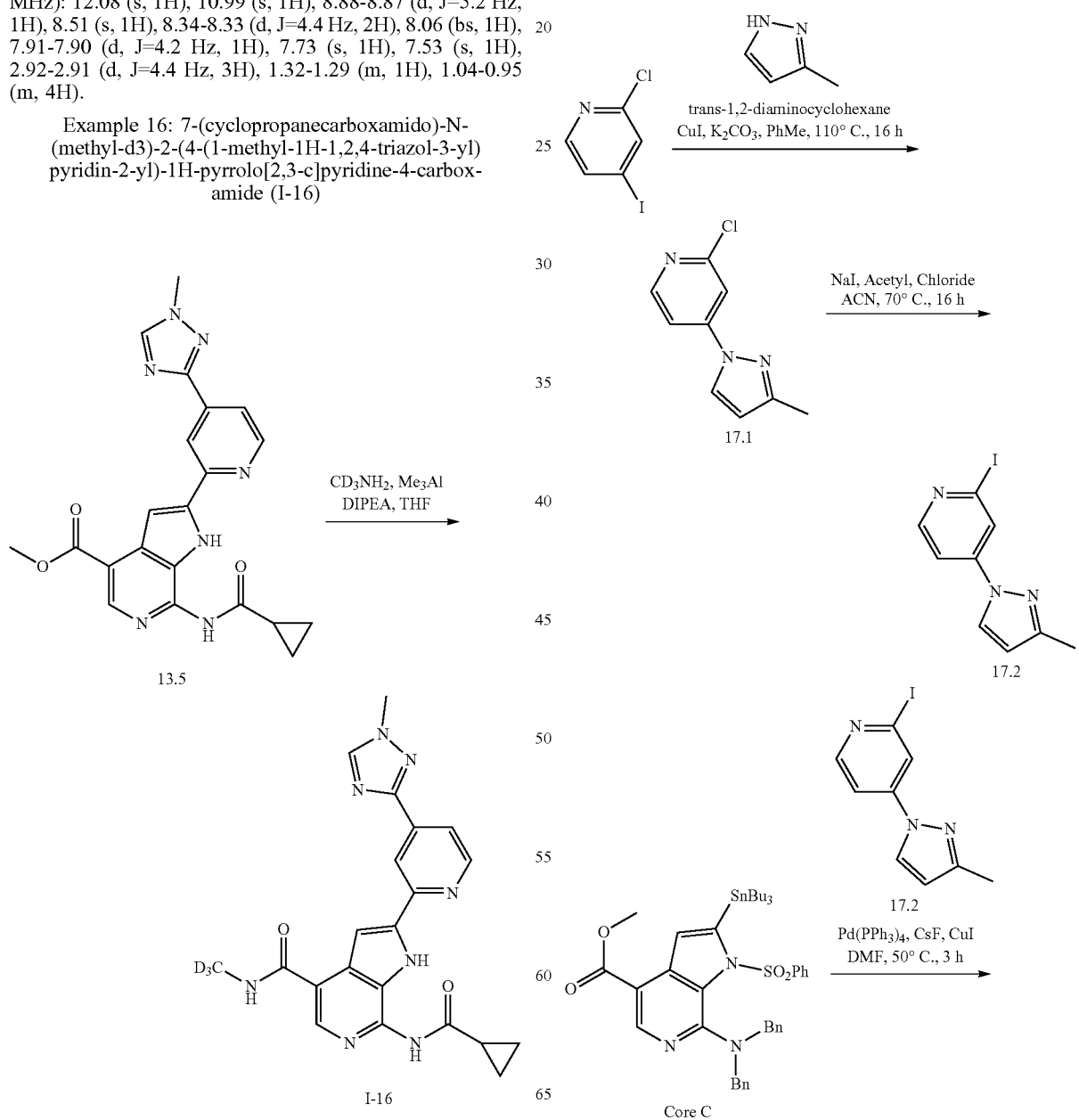

-continued

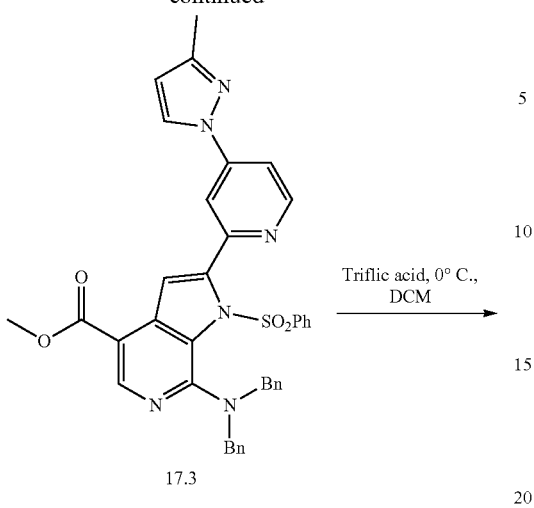

17.3

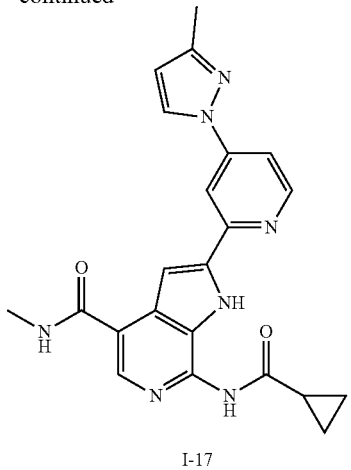

I-17

Synthesis of Compound 17.1

To a solution of 2-chloro-4-iodopyridine (1.0 g, 4.18 mmol, 1.0 eq) and potassium carbonate (1.73 g, 12.54 mmol, 3.0 eq) in toluene (15 mL) was added 3-methyl-1H-pyrazole (1.0 g, 12.54 mmol, 3.0 eq), trans-1,2-diaminocyclohexane (0.190 g, 1.67 mmol, 0.4 eq) and copper(I) iodide (0.159 g, 0.83 mmol, 0.2 eq). The reaction mixture was heated at 110° C. for 16 h. After completion of reaction, reaction mixture was transferred into ice cold water and product was extracted with ethyl acetate. Organic layer was combined, washed with brine solution, dried over sodium sulfate and concentrated under reduced pressure to obtain crude material. This was further purified by column chromatography eluting with 20% ethyl acetate in hexane to obtain 17.1. (0.320 g, 39.57%), MS (ES): m/z 194.04 [M+H]+.

Synthesis of Compound 17.2

To a solution of compound 17.1 (0.320 g, 1.65 mmol, 1.0 eq) in acetonitrile (5 mL) was added sodium iodide (1.2 g, 8.25 mmol, 5 eq) and acetyl chloride (0.194 g, 2.47 mmol, 1.5 eq). The reaction mixture was heated at 70° C. for 16 h. After completion of reaction, reaction mixture was transferred into ice cold water and product was extracted with ethyl acetate. Organic layer was combined, washed with brine solution, dried over sodium sulfate and concentrated under reduced pressure to obtain crude material. This was further purified by column chromatography eluting with 20% ethyl acetate in hexane to obtain 17.2. (0.3 g, 63.68%), MS (ES): m/z 285.97 [M+H]+.

Synthesis of Compound 17.3

The compound was synthesized from Core C and compound 17.2 using General Procedure E to obtain 17.3. (0.110 g, 13.17%). MS (ES): m/z 669.22 [M+H]+.

Synthesis of Compound 17.4

The compound was synthesized from compound 17.3 using General Procedure B to obtain 17.4. (0.057 g, Yield: 99.48%), MS (ES): m/z 349.14 [M+H]+.

Synthesis of Compound 17.5

The compound was synthesized from compound 17.4 using General Procedure C to obtain 17.5. (0.056 g, 71.70%), MS (ES): m/z 417.16 [M+H]+.

Synthesis of Compound I-17

The compound was synthesized from compound 17.5 and methylamine using General Procedure D. The material was further purified by column chromatography eluting with 2.5% methanol in dichloromethane to obtain I-17 (0.025 g, 38.28%), MS (ES): m/z 416.32 [M+H]+ LCMS purity: 97.43%, HPLC purity: 98.38%, $^1$H NMR (DMSO-$d_6$, 400 MHz): 11.97 (s, 1H), 10.92 (s, 1H), 8.69 (s, 2H), 8.43 (s, 1H), 8.30 (s, 1H), 8.08 (s, 1H), 7.81 (s, 1H), 7.75 (s, 1H), 6.47 (bs, 1H), 2.91-2.90 (d, J=4.8 Hz, 3H), 2.35 (s, 3H), 1.27 (bs, 1H), 1.03-0.94 (m, 4H).

Example 18: 2-(3-(4H-1,2,4-triazol-4-yl)phenyl)-7-(cyclopropanecarboxamido)-N-methyl-1H-pyrrolo[2,3-c]pyridine-4-carboxamide (I-18)

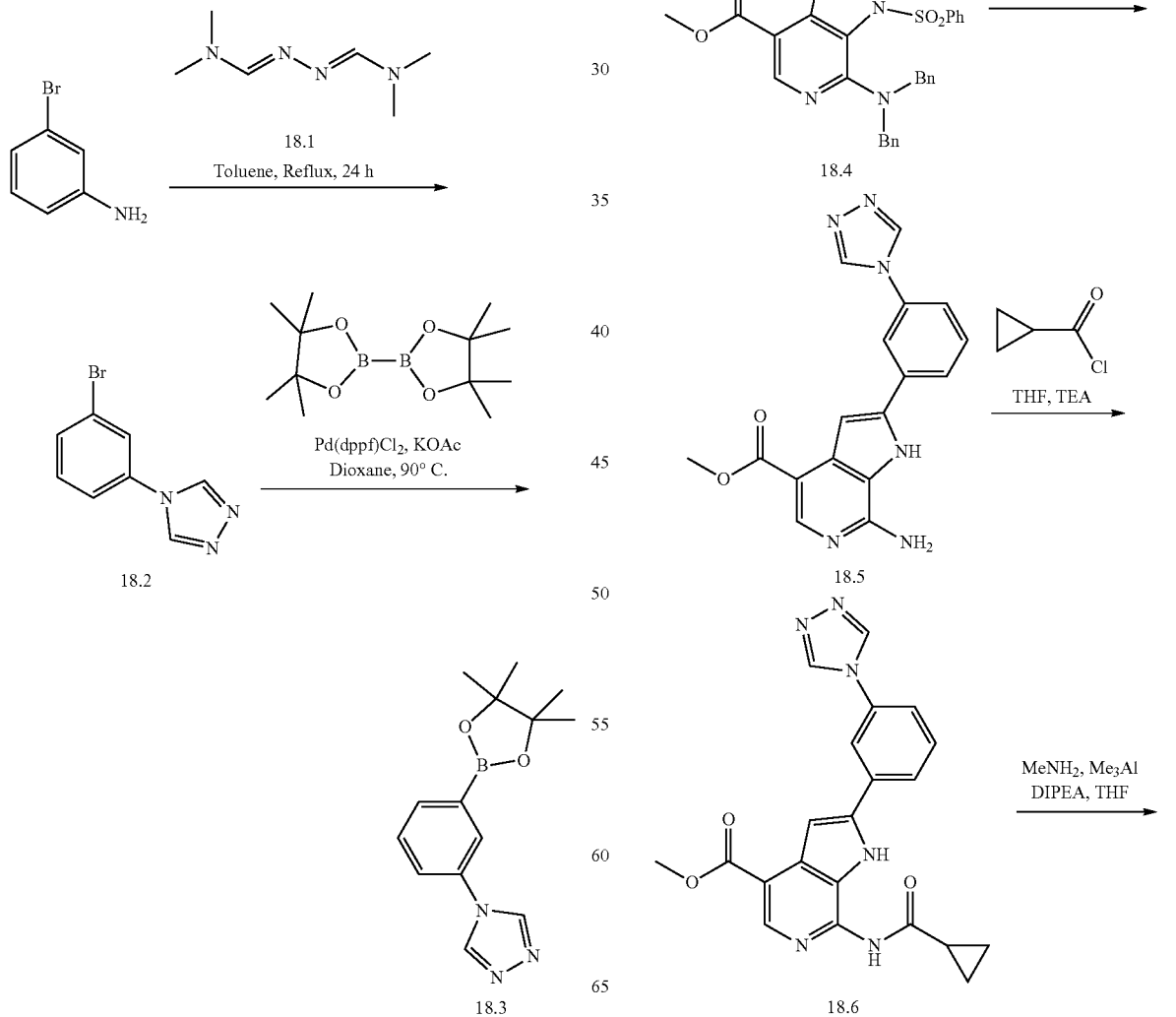

185

-continued

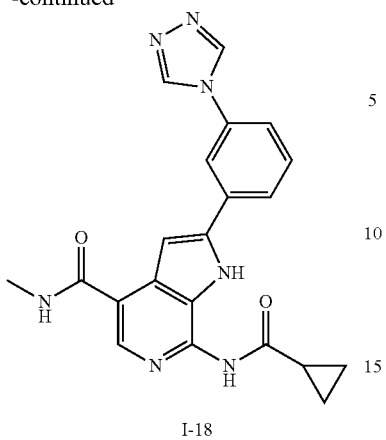

I-18

Synthesis of Compound 18.2

To a suspension of 3-bromoaniline (2.0 g, 11.62 mmol, 1.0 eq) in toluene (30 mL) was added compound 18.1 (3.3 g, 23.24 mmol, 2.0 eq) and reaction mixture was heated at 120° C. for 24 h. After completion of reaction, reaction mixture was concentrated under reduced pressure to obtain residue which was dissolved in saturated sodium bicarbonate solution and washed with hexane. Aqueous layer separated and acidified with 1N hydrochloric acid to pH~5-6 and extracted with ethyl acetate. Organic layer was combined, dried over sodium sulfate and concentrated under reduced pressure to obtain solid which was triturated with hexane to obtain pure 18.2. (0.650 g, Yield: 24.95%). MS (ES): m/z 224.97 [M+H]$^+$.

Synthesis of Compound 18.3

To a solution of 18.2 (0.650 g, 2.90 mmol, 1.0 eq) in 1,4-dioxane (20 mL) was added bis(pinacolato)diboron (0.883 g, 3.48 mmol, 1.2 eq) and potassium acetate (0.568 g, 5.8 mmol, 2.0 eq). The reaction mixture was degassed for 10 min. under argon atmosphere, then [1,1'-bis(diphenylphosphino)ferrocene]dichloropalladium(II) (0.211 g, 0.29 mmol, 0.1 eq) was added, again degassed for 5 min. The reaction was stirred at 90° C. for 4 h. After completion of reaction, reaction mixture was cooled to room temperature, transferred into water and product was extracted with ethyl acetate. Organic layer was combined, washed with brine solution, dried over sodium sulfate and concentrated under reduced pressure to obtain crude material. This was further purified by combi flash using 3% methanol in dichloromethane as eluant to obtain pure 18.3. (0.4 g, Yield: 50.86%). MS(ES): m/z 272.15 [M+H]$^+$.

Synthesis of Compound 18.4

The compound was synthesized from Core A and compound 18.3 using General Procedure A to obtain 18.4. (0.210 g, Yield: 40.89%), MS (ES): m/z 655.21 [M+H]$^+$.

186

Synthesis of Compound 18.5

The compound was synthesized from compound 18.4 using General Procedure B to obtain 18.5. (0.106 g, Yield: 98.85%), MS (ES): m/z 335.12 [M+H]$^+$.

Synthesis of Compound 18.6

The compound was synthesized from compound 18.5 using General Procedure C to obtain 18.6. (0.070 g, Yield: 67.39%), MS (ES): m/z 403.13 [M+H]$^+$.

Synthesis of Compound I-18

The compound was synthesized from compound 18.6 and methylamine using General Procedure D. The material was further purified by column chromatography eluting with 2.5% methanol in dichloromethane to obtain I-18 (0.025 g, 34.55%), MS (ES): m/z 402.79 [M+H]$^+$ LCMS purity: 100%, HPLC purity: 98.95%, $^1$H NMR (DMSO-d$_6$, 400 MHz): 11.74 (s, 1H), 11.15 (s, 1H), 9.30 (s, 2H), 8.41-8.40 (d, J=4.8 Hz, 1H), 8.31 (s, 2H), 7.89-7.88 (d, J=7.6 Hz, 1H), 7.80-7.72 (m, 2H), 7.60 (bs, 1H), 2.87-2.86 (d, J=4.4 Hz, 3H), 1.31 (bs, 1H), 1.01-0.94 (m, 4H).

Example 19: 7-(cyclopropanecarboxamido)-2-(2-fluoro-3-(1-methyl-1H-pyrazol-4-yl) phenyl)-N-methyl-1H-pyrrolo[2,3-c]pyridine-4-carboxamide (I-19)

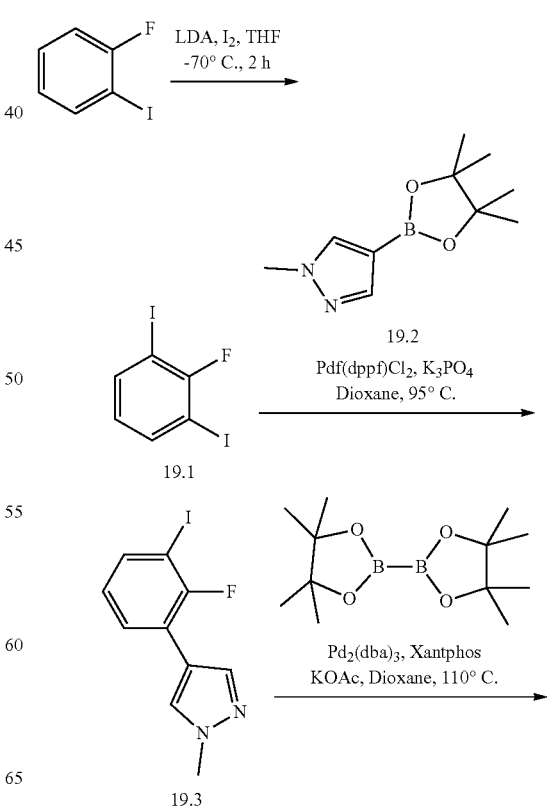

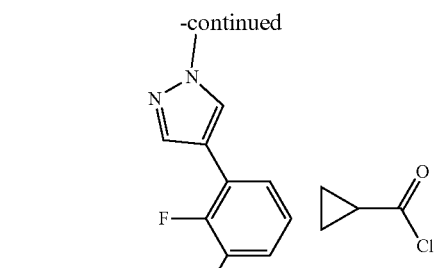

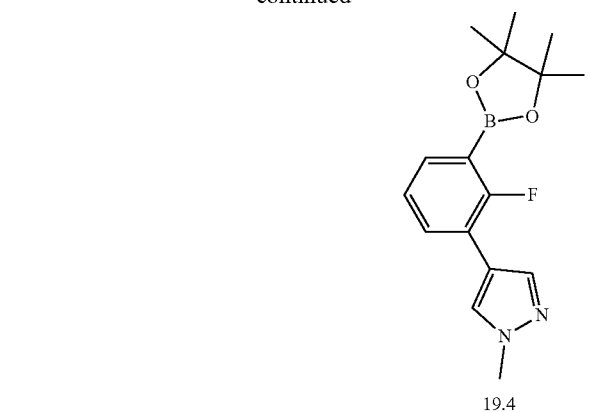

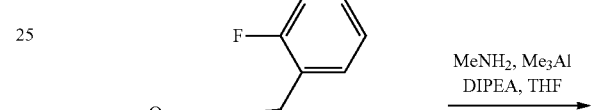

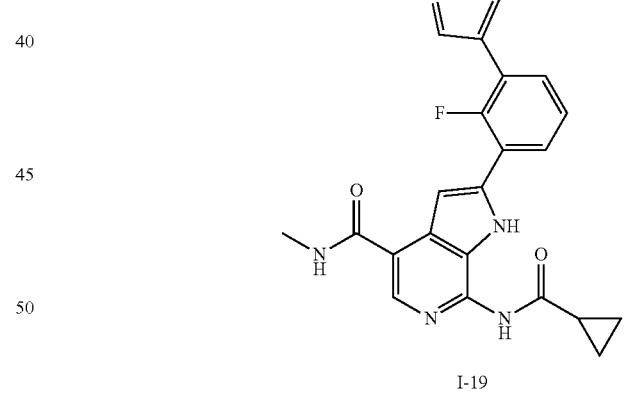

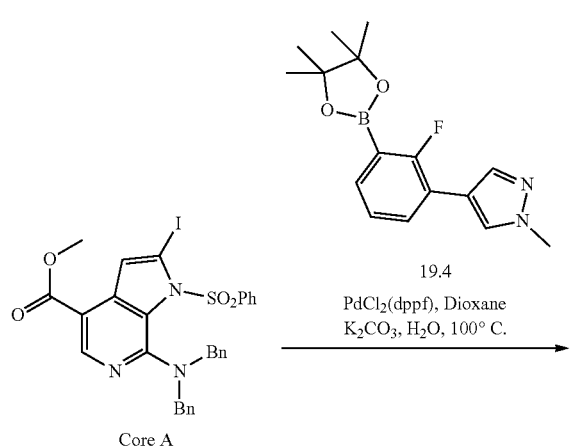

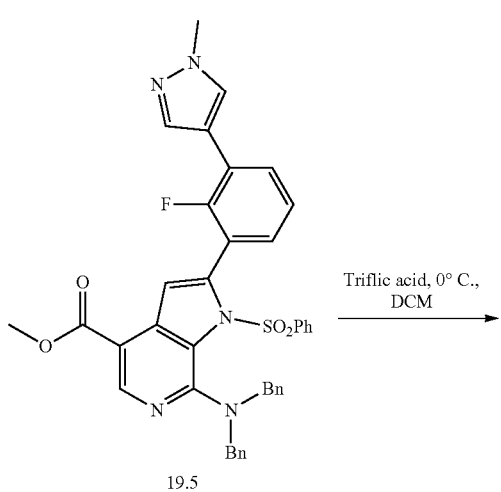

Synthesis of Compound 19.1

To a solution of 1-fluoro-2-iodobenzene (2.0 g, 9.00 mmol, 1.0 eq) in tetrahydrofuran (20 mL) was added lithium diisopropylamide (2M) (9.0 mL, 18.0 mmol, 2.0 eq) at −78° C. The reaction mixture was stirred at −78° C. for 1 h. Then a solution of iodine (2.2 g, 18.0 mmol, 2.0 eq) in tetrahydrofuran (12 mL) was added to reaction mixture and stirred for 2 h at same temperature. After completion of reaction, reaction mixture was transferred to ice cold water and product was extracted with ethyl acetate. Organic layer was combined, washed with brine solution, dried over sodium sulfate and concentrated under reduced pressure to obtain crude material. This was further purified by column chromatography eluting with 7% ethyl acetate in hexane to obtain 19.1. (1.8 g, Yield: 57.43%). MS (ES): m/z 348.83 [M+H]$^+$.

Synthesis of Compound 19.3

Argon was purged for 15 min through a stirred mixture of compound 19.1 (1.6 g, 4.61 mmol, 1.0 eq), compound 19.2 (1.2 g, 5.99 mmol, 1.3 eq) and tripotassium phosphate (2.4 g, 11.52 mmol, 2.5 eq) in 1,4-dioxane (60 mL). [1,1'-Bis(diphenylphosphino)ferrocene]palladium(II) dichloride (0.336 mg, 046 mmol, 0.1 eq) was added to it and further purging done for 10 min. Reaction was stirred at 95° C. for 6 h. After completion of reaction, reaction mixture was poured over water and product was extracted with ethyl acetate. Organic layer was combined, washed with brine solution, dried over sodium sulfate and concentrated under reduced pressure to obtain 19.3. (0.650 g, Yield: 46.79%). MS (ES): m/z 302.97 [M+H]$^+$.

Synthesis of Compound 19.4

The compound was synthesized from compound 19.3 using General Procedure F to obtain 19.4. (0.4 g, Yield: 61.53%). MS(ES): m/z 303.16 [M+H]$^+$.

Synthesis of Compound 19.5

The compound was synthesized from Core A and compound 19.4 using General Procedure A to obtain 19.5. (0.260 g, Yield: 53.71%), MS (ES): m/z 686.22 [M+H]$^+$.

Synthesis of Compound 19.6

The compound was synthesized from compound 19.5 using General Procedure B to obtain 19.6. (0.120 g, Yield: 86.63%), MS (ES): m/z 366.13 [M+H]$^+$.

Synthesis of Compound 19.7

The compound was synthesized from compound 19.6 using General Procedure C to obtain 19.7. (0.110 g, Yield: 77.27%), MS (ES): m/z 434.16 [M+H]$^+$.

Synthesis of Compound I-19

The compound was synthesized from compound 19.7 and methylamine using General Procedure D. The material was further purified by column chromatography eluting with 2.5% methanol in dichloromethane to obtain I-19 (0.025 g, Yield: 22.78%), MS (ES): m/z 433.51 [M+H]$^+$ LCMS purity: 98.70%, HPLC purity: 97.71%, $^1$H NMR (DMSO-d$_6$, 400 MHz): 12.18 (s, 1H), 11.47 (s, 1H), 8.57 (s, 1H), 8.27 (s, 1H), 8.00 (s, 1H), 7.84-7.80 (m, 1H), 7.51 (s, 1H), 7.43-7.39 (t, J=7.6 Hz, 1H), 7.10 (bs, 1H), 6.82 (bs, 1H), 3.95 (bs, 3H), 1.56 (bs, 3H), 1.24 (bs, 1H), 1.03-0.97 (m, 4H).

Example 20: 7-(cyclopropanecarboxamido)-2-(2-cyclopropyl-2H-indazol-6-yl)-N-methyl-1H-pyrrolo[2,3-c]pyridine-4-carboxamide (I-20)

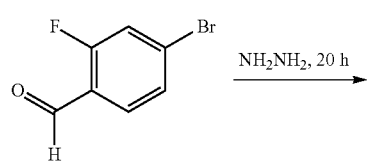

NH$_2$NH$_2$, 20 h

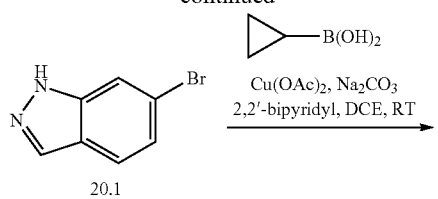

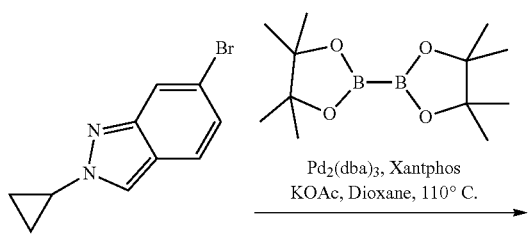

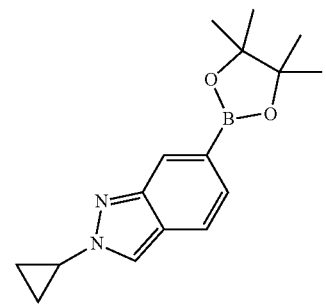

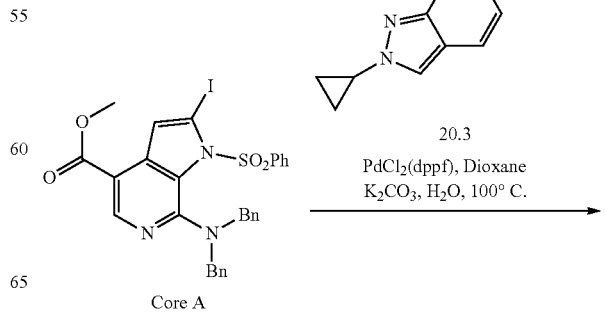

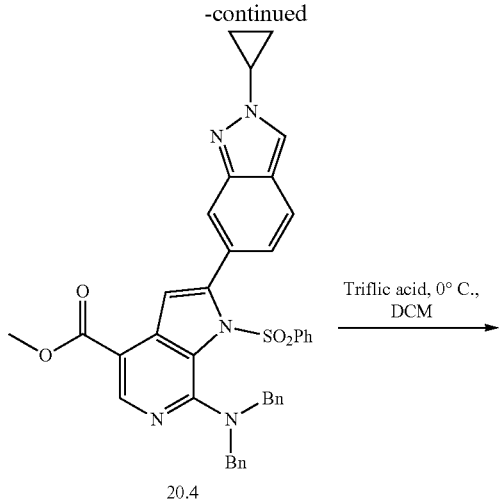

20.4

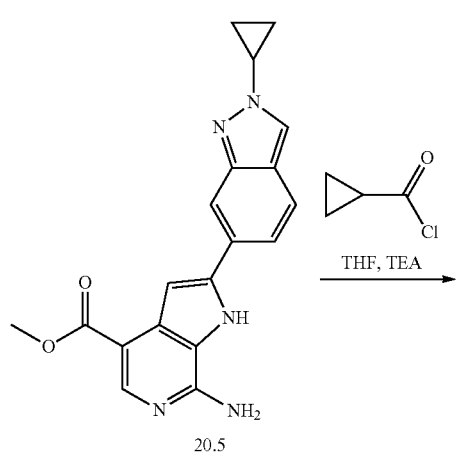

20.5

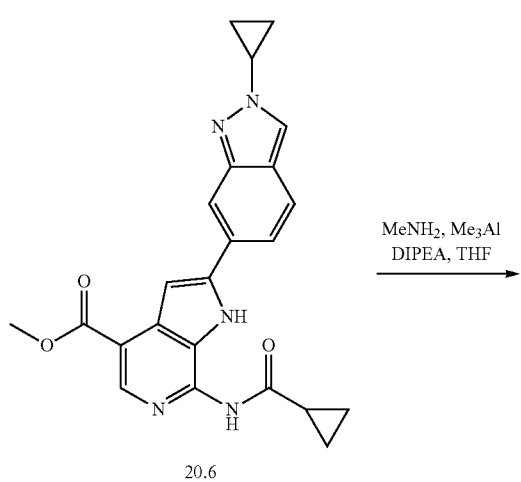

20.6

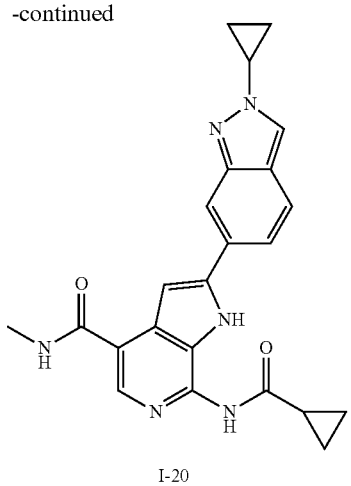

I-20

Synthesis of Compound 20.1

To 4-bromo-2-fluorobenzaldehyde (3.0 g, 14.77 mmol, 1.0 eq) was added hydrazine hydrate (0.850 g, 26.58 mmol, 1.8 eq). The reaction mixture was stirred at room temperature for 20 h. After completion of reaction, reaction mixture was transferred into ice cold water and product was extracted with ethyl acetate. Organic layer was combined, washed with brine solution, dried over sodium sulfate and concentrated under reduced pressure to obtain crude material. This was further purified by column chromatography eluting with 2.5% methanol in dichloromethane to obtain 20.1. (1.9 g, 65.25%), MS (ES): m/z 196.97 [M+H]$^+$.

Synthesis of Compound 20.2

To a solution of compound 20.1 (1 g, 5.12 mmol, 1.0 eq) in 1,2-dichloroethane (10 mL) was added cyclopropylboronic acid (0.528 g, 6.14 mmol, 1.8 eq), sodium carbonate (1.3 g, 12.8 mmol, 2.5 eq), cupric acetate (1.3 g, 7.68 mmol, 1.5 eq), and bipyridine (1.5 g, 10.24 mmol, 2.0 eq). The reaction mixture was stirred at room temperature for 6 h. After completion of reaction, reaction mixture was transferred into ice cold water and product was extracted with ethyl acetate. Organic layer was combined, washed with brine solution, dried over sodium sulfate and concentrated under reduced pressure to obtain crude material. This was further purified by column chromatography eluting with 2% methanol in dichloromethane to obtain 20.2. (0.820 g, 68.14%), MS (ES): m/z 237.99 [M+H]$^+$.

Synthesis of Compound 20.3

The compound was synthesized from compound 20.2 using General Procedure F to obtain 20.3. (0.4 g, 47.68%). MS(ES): m/z 285.17 [M+H]$^+$.

Synthesis of Compound 20.4

The compound was synthesized from Core A and compound 20.3 using General Procedure A to obtain 20.4. (0.210 g, 44.55%), MS (ES): m/z 668.23 [M+H]$^+$.

Synthesis of Compound 20.5

The compound was synthesized from compound 20.4 using General Procedure B to obtain 20.5. (0.1 g, 91.54%), MS (ES): m/z 348.14 [M+H]$^+$.

193

Synthesis of Compound 20.6

The compound was synthesized from compound 20.5 using General Procedure C to obtain 20.6. (0.1 g, 83.61%), MS (ES): m/z 416.17 [M+H]⁺.

Synthesis of Compound I-20

The compound was synthesized from compound 20.6 and methylamine using General Procedure D. The material was further purified by column chromatography eluting with 2.5% methanol in dichloromethane to obtain I-20 (0.032 g, 32.08%), MS (ES): m/z 415.27 [M+H]⁺ LCMS purity: 95.82%, HPLC purity: 96.09%, ¹H NMR (DMSO-d₆, 400 MHz): 11.88 (s, 1H), 11.14 (s, 1H), 8.38-8.37 (d, J=4.4 Hz, 1H), 8.30 (s, 1H), 8.19 (s, 1H), 8.07 (s, 1H), 7.92-7.90 (d, J=8.4 Hz, 1H), 7.63-7.61 (d, J=8.4 Hz, 1H), 7.49-7.48 (d, J=2 Hz, 1H), 2.86-2.85 (d, J=4 Hz, 3H), 2.26 (bs, 1H), 1.54 (bs, 1H), 1.23-1.17 (m, 4H), 1.01-0.93 (m, 4H).

Example 21: 7-(cyclopropanecarboxamido)-2-(7-fluoro-1-methyl-1H-indol-6-yl)-N-methyl-1H-pyrrolo[2,3-c]pyridine-4-carboxamide (I-21)

194

-continued

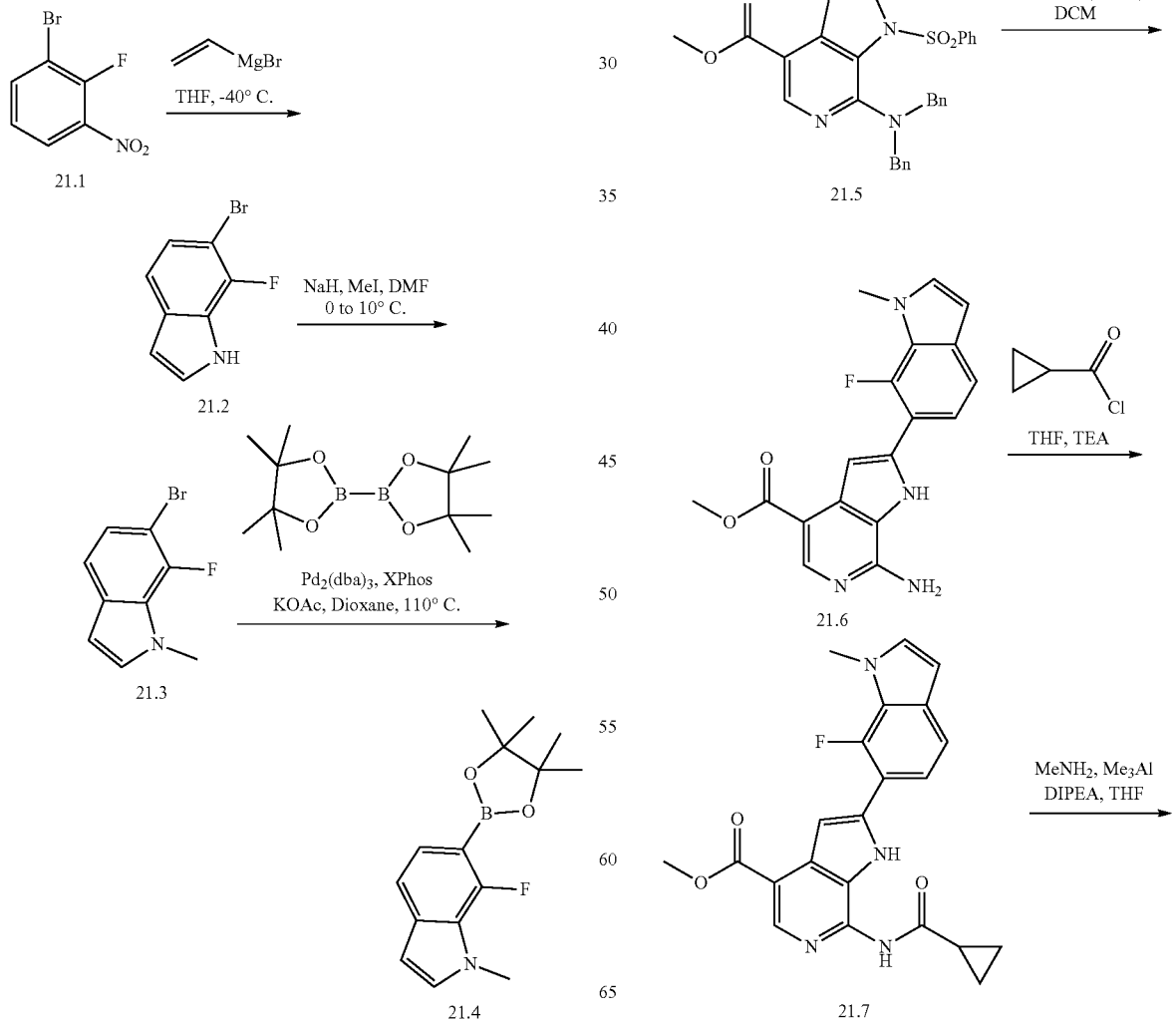

195
-continued

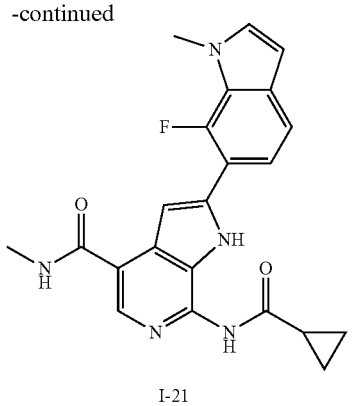

I-21

Synthesis of Compound 21.2

To a solution of compound 21.1 (10.0 g, 45.45 mmol, 1.0 eq) in tetrahydrofuran (200 mL) was added vinyl magnesium bromide (1M in THF, 136 mL, 136.35 mmol, 3.0 eq) at −78° C. The reaction mixture was stirred at −40° C. for 1 h. After completion of reaction, reaction mixture was transferred to ice cold water and product was extracted with ethyl acetate. Organic layer was combined, washed with brine solution, dried over sodium sulfate and concentrated under reduced pressure to obtain crude material. This was further purified by column chromatography eluting with 10% ethyl acetate in hexane to obtain 21.2. (1.5 g, Yield: 15.42%). MS (ES): m/z 214.96 [M+H]$^+$.

Synthesis of Compound 21.3

To a solution of 21.2 (1.5 g, 7.00 mmol, 1.0 eq) in dimethylformamide (15 mL), was added sodium hydride (0.336 g, 14.00 mmol, 2 eq) at 0° C. and stirred for 20 min. Methyl iodide (1.0 g, 7.7 mmol, 1.1 eq) was added and reaction mixture was stirred at 10° C. for 2 h. After completion of reaction, reaction mixture was transferred into ice, stirred and extracted with diethyl ether. Organic layer was combined, dried over sodium sulfate and concentrated under reduced pressure to obtain crude material. This was further purified by distillation to obtain pure 21.3. (1.2 g, Yield: 75.08%). MS (ES): m/z 228.97 [M+H]$^+$.

Synthesis of Compound 21.4

The compound was synthesized from compound 21.3 using General Procedure F, using 2-dicyclohexylphosphino-2',4',6'-triisopropylbiphenyl instead of 4,5-bis(diphenylphosphino)-9,9-dimethylxanthene, to obtain 21.4. (0.6 g, 41.45%). MS (ES): m/z 276.15 [M+H]$^+$.

Synthesis of Compound 21.5

The compound was synthesized from Core A and compound 21.4 using General Procedure A to obtain 21.5. (0.190 g, 40.86%), MS (ES): m/z 659.21 [M+H]$^+$.

Synthesis of Compound 21.6

The compound was synthesized from compound 21.5 using General Procedure B to obtain 21.6. (0.090 g, 92.23%), MS (ES): m/z 339.12 [M+H]$^+$.

196

Synthesis of Compound 21.7

The compound was synthesized from compound 21.6 using General Procedure C to obtain 21.7. (0.090 g, 83.25%), MS (ES): m/z 407.15 [M+H]$^+$.

Synthesis of Compound I-21

The compound was synthesized from compound 21.7 and methylamine using General Procedure D. The material was further purified by column chromatography eluting with 2.5% methanol in dichloromethane to obtain I-21 (0.030 g, 33.41%), MS (ES): m/z 406.20 [M+H]$^+$ LCMS purity: 98.45%, HPLC purity: 95.07%, $^1$H NMR (DMSO-d$_6$, 400 MHz): 11.98 (s, 1H), 11.30 (s, 1H), 8.38-8.37 (d, J=4 Hz, 1H), 7.53-7.49 (m, 2H), 7.43 (s, 1H), 7.09-7.07 (d, J=8 Hz, 1H), 6.84-6.82 (d, J=7.6 Hz, 1H), 6.55 (s, 1H), 4.07 (s, 3H), 2.86-2.85 (d, J=4.4 Hz, 3H), 1.56 (bs, 1H), 1.01-0.95 (m, 4H).

Example 22: 7-(cyclopropanecarboxamido)-2-(2-fluoro-3-morpholinophenyl)-N-methyl-1H-pyrrolo[2,3-c]pyridine-4-carboxamide (I-22)

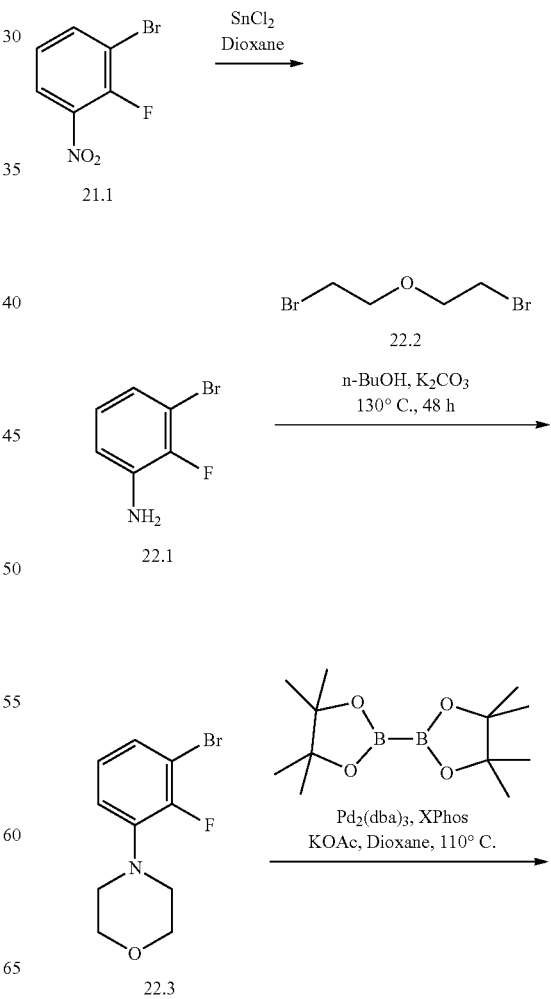

-continued

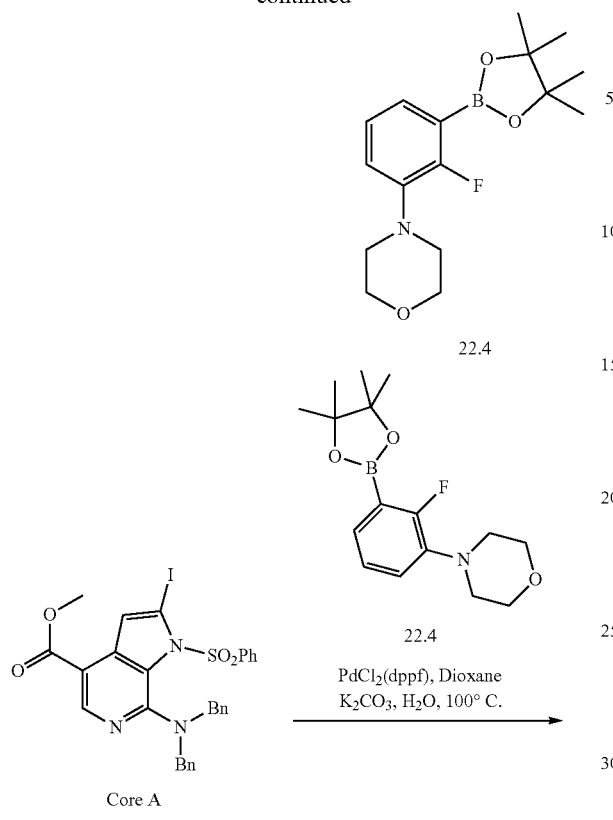

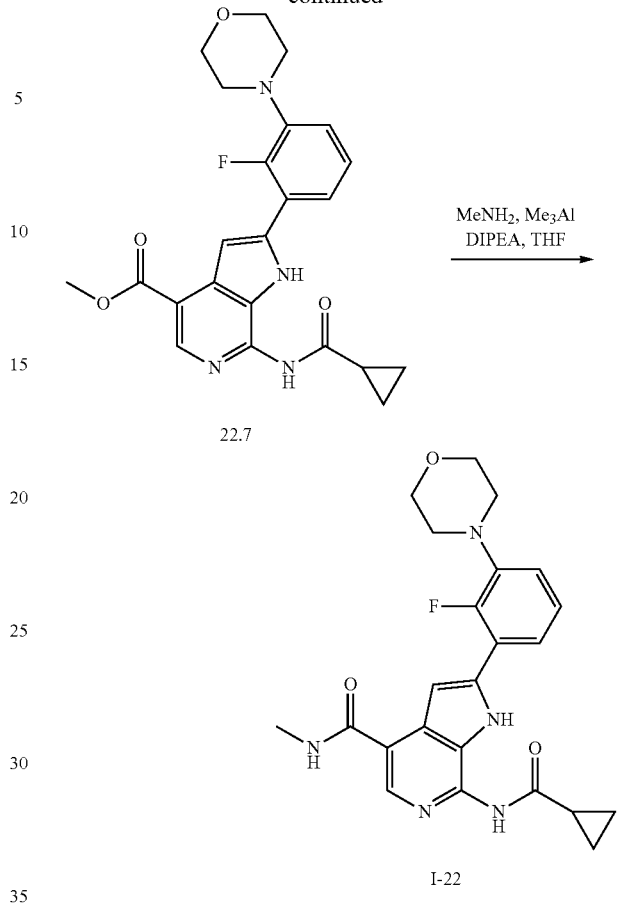

Synthesis of Compound 22.1

To the solution of compound 21.1 (10.0 g, 45.45 mmol, 1.0 eq) in 1,4-dioxane (300 mL) was added tin(II) chloride (43.0 g, 227.25 mmol, 5.0 eq). The reaction mixture was stirred at room temperature for 3 h. After completion of reaction, reaction mixture was transferred to ice cold water and product was extracted with ethyl acetate. Organic layer was combined, washed with brine solution, dried over sodium sulfate and concentrated under reduced pressure to obtain crude material. This was further purified by column chromatography eluting with 2.5% methanol in dichloromethane to obtain 22.1. (5.0 g, 57.89%). MS (ES): m/z 190.96 [M+H]$^+$.

Synthesis of Compound 22.3

To a cooled solution of compounds 22.1 (5.0 g, 26.31 mmol, 1.0 eq) and 22.2 (7.2 g, 31.57 mmol, 1.2 eq) in n-butanol (150 mL) at 0° C. was added potassium carbonate (9.0 g, 65.77 mmol, 2.5 eq). The reaction was stirred at 130° C. for 48 h. After completion of reaction, reaction mixture was transferred into water and product was extracted with ethyl acetate. Organic layer was combined and dried over sodium sulfate and concentrated under reduced pressure to obtain crude material. This was further purified by column chromatography and compound was eluted in 20% ethyl acetate in hexane to obtain pure 22.3. (0.9 g, 13.15%). MS (ES): m/z 261.00 [M+H]$^+$.

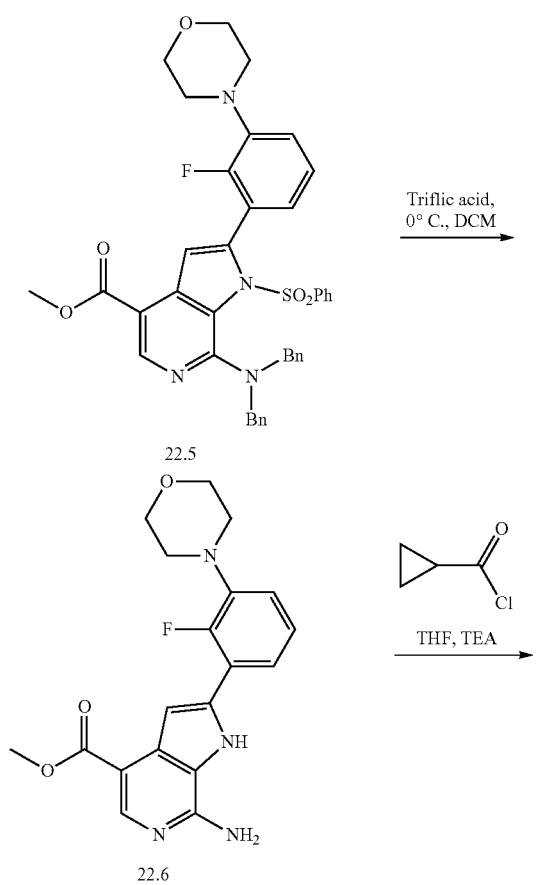

Synthesis of Compound 22.4

The compound was synthesized from compound 22.3 using General Procedure F, using 2-dicyclohexylphosphino-2',4',6'-triisopropylbiphenyl instead of 4,5-bis(diphenylphosphino)-9,9-dimethylxanthene, to obtain 22.4. (0.650 g, 61.16%). MS (ES): m/z 308.18 [M+H]$^+$.

Synthesis of Compound 22.5

The compound was synthesized from Core A and compound 22.4 using General Procedure A to obtain 22.5. (0.220 g, 45.12%), MS (ES): m/z 691.23 [M+H]$^+$.

Synthesis of Compound 22.6

The compound was synthesized from compound 22.5 using General Procedure B to obtain 22.6. (0.115 g, 97.49%), MS (ES): m/z 371.15 [M+H]$^+$.

Synthesis of Compound 22.7

The compound was synthesized from compound 22.6 using General Procedure C to obtain 22.7. (0.110 g, 71.48%), MS (ES): m/z 439.17 [M+H]$^+$.

Synthesis of Compound I-22

The compound was synthesized from compound 22.7 and methylamine using General Procedure D. The material was further purified by column chromatography eluting with 2.5% methanol in dichloromethane to obtain I-22 (0.050 g, 45.56%), MS (ES): m/z 438.42 [M+H]$^+$ LCMS purity: 100%, HPLC purity: 99.42%, $^1$H NMR (DMSO-d$_6$, 400 MHz): 11.94 (s, 1H), 11.28 (s, 1H), 8.38-8.37 (d, J=4.4 Hz, 1H), 8.30 (s, 1H), 7.52-7.49 (t, J=7.2 Hz, 1H), 7.41 (bs, 1H), 7.31-7.27 (t, J=8 Hz, 1H), 7.17-7.13 (t, J=7.6 Hz, 1H), 3.79 (bs, 4H), 3.06 (bs, 4H), 2.84-2.83 (d, J=4.4 Hz, 3H), 2.24 (bs, 1H), 0.98-0.93 (m, 4H).

Example 23: 7-(cyclopropanecarboxamido)-2-(2-fluoro-3-(oxazol-2-yl)phenyl)-N-methyl-1H-pyrrolo[2,3-c]pyridine-4-carboxamide (I-23)

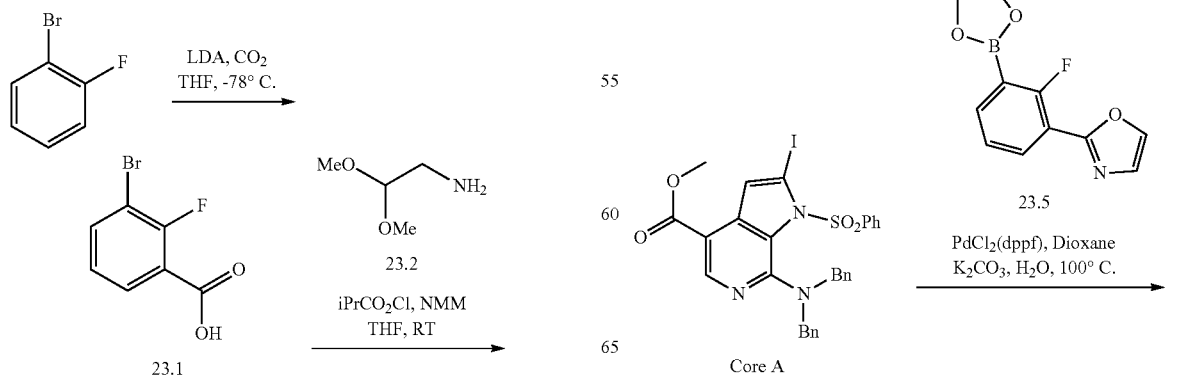

-continued

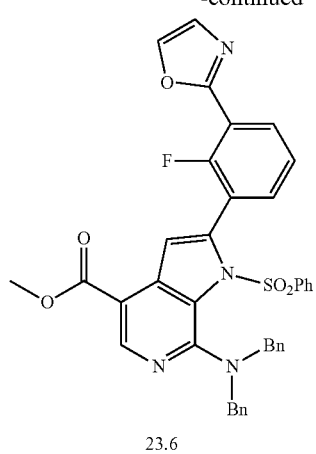

23.6

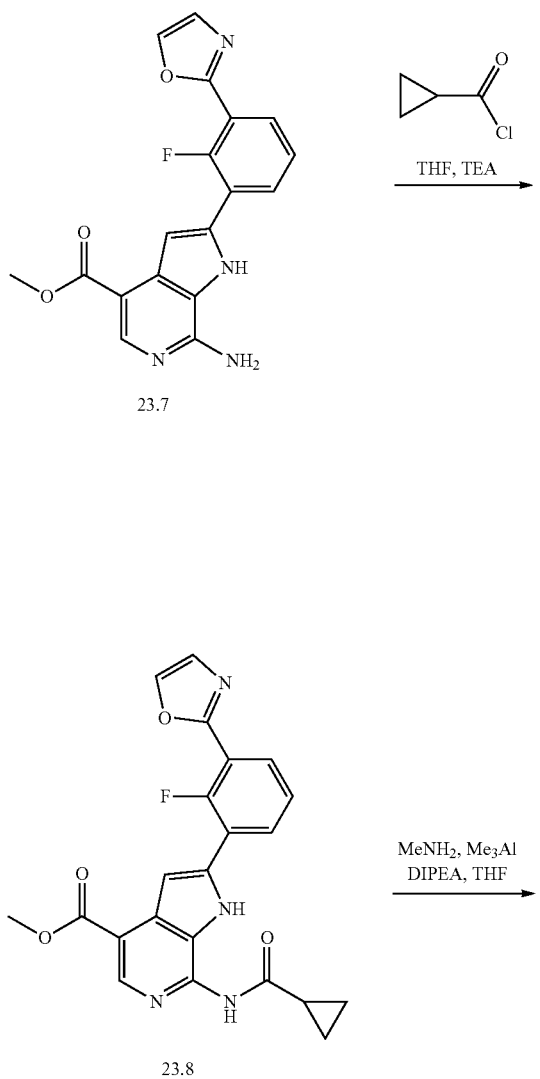

23.7

23.8

-continued

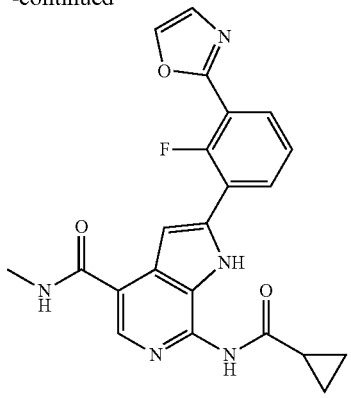

I-23

Synthesis of Compound 23.1

Carbon dioxide was purged for 15 min through a stirred solution of 1-bromo-2-fluorobenzene (5.0 g, 28.57 mmol, 1.0 eq) in tetrahydrofuran (70 mL) followed by addition of lithium diisopropylamide (2M) (42.8 mL, 85.71 mmol, 3.0 eq) at −78° C. The reaction mixture was stirred at −78° C. for 1 h. After completion of reaction, reaction mixture was transferred to ice cold water and product was extracted with ethyl acetate. Organic layer was combined, washed with brine solution, dried over sodium sulfate and concentrated under reduced pressure to obtain crude material. This was further purified by column chromatography eluting with 7% ethyl acetate in hexane to obtain 23.1. (1.3 g, Yield: 20.78%). MS (ES): m/z 218.94 [M+H]$^+$.

Synthesis of Compound 23.3

To a solution of compound 23.1 (1.3 g, 5.96 mmol, 1.0 eq), in tetrahydrofuran (40 mL) was added isopropyl carbonyl chloride (1.1 g, 11.92 mmol, 2.0 eq) and stirred at room temperature for 15 min. To this added N-methylmorpholine (1.80 g, 17.88 mmol, 3.0 eq) followed by addition of compound 23.2 (0.625 g, 5.96 mmol, 1.0 eq). The reaction mixture was stirred at room temperature for 5 min. After completion of reaction, reaction mixture was transferred into water and product was extracted with ethyl acetate. Organic layer was combined, washed with brine solution, dried over sodium sulfate and concentrated under reduced pressure to obtain crude material. This was further purified by column chromatography and the compound was eluted in 40% ethyl acetate in hexane to obtain 23.3 (0.9 g, Yield: 49.53%). MS (ES): m/z 307.00 [M+H]$^+$.

Synthesis of Compound 23.4

To a solution of 23.3 (0.9 g, 2.94 mmol, 1.0 eq), in toluene (10 mL) was added phosphorus pentoxide (0.652 g, 1.47 mmol, 0.5 eq). The reaction mixture was stirred at 110° C. for 3 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by column chromatography and the compound was eluted in 3% methanol in dichloromethane to obtain 23.4. (0.6 g, Yield: 84.32%). MS (ES): m/z 242.95 [M+H]$^+$.

Synthesis of Compound 23.5

The compound was synthesized from compound 23.4 using General Procedure F, using 2-dicyclohexylphosphino-2',4',6'-triisopropylbiphenyl instead of 4,5-bis(diphenylphosphino)-9,9-dimethylxanthene, to obtain 23.5. (0.450, Yield: 62.79%). MS (ES): m/z 290.13 [M+H]$^+$.

Synthesis of Compound 23.6

The compound was synthesized from Core A and compound 23.5 using General Procedure A to obtain 23.6. (0.210 g, Yield: 44.22%), MS (ES): m/z 673.19 [M+H]$^+$.

Synthesis of Compound 23.7

The compound was synthesized from compound 23.6 using General Procedure B to obtain 23.7. (0.115 g, Yield: 87.63%), MS (ES): m/z 352.12 [M+H]$^+$.

Synthesis of Compound 23.8

The compound was synthesized from compound 23.7 using General Procedure C to obtain 23.8. (0.100 g, Yield: 86.96%), MS (ES): m/z 421.14 [M+H]$^+$.

Synthesis of Compound I-23

The compound was synthesized from compound 23.8 and methylamine using General Procedure D. The material was further purified by column chromatography eluting with 2.5% methanol in dichloromethane to obtain I-23 (0.027 g, Yield: 27.06%), MS (ES): m/z 420.32 [M+H]$^+$ LCMS purity: 95.56%, HPLC purity: 97.22%, $^1$H NMR (DMSO-d$_6$, 400 MHz): 12.14 (s, 1H), 11.33 (s, 1H), 8.40 (s, 1H), 8.34 (s, 1H), 8.16-8.07 (m, 1H), 7.55 (s, 1H), 7.09 (bs, 2H), 6.84 (bs, 2H), 2.87-2.86 (d, J=4.4 Hz, 3H), 1.56 (bs, 1H), 1.01-0.95 (m, 4H).

Example 24: 2-(4-(azetidine-1-carbonyl)-2-methoxyphenyl)-7-(cyclopropanecarboxamido)-N-methyl-1H-pyrrolo[2,3-c]pyridine-4-carboxamide (I-24)

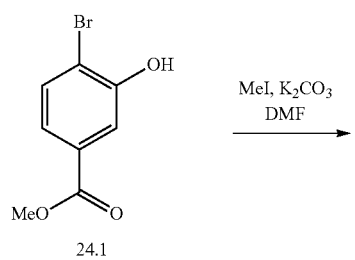

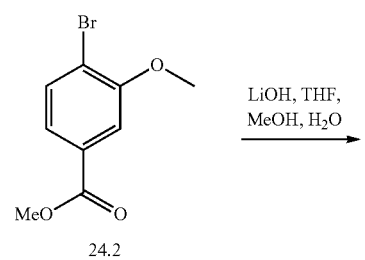

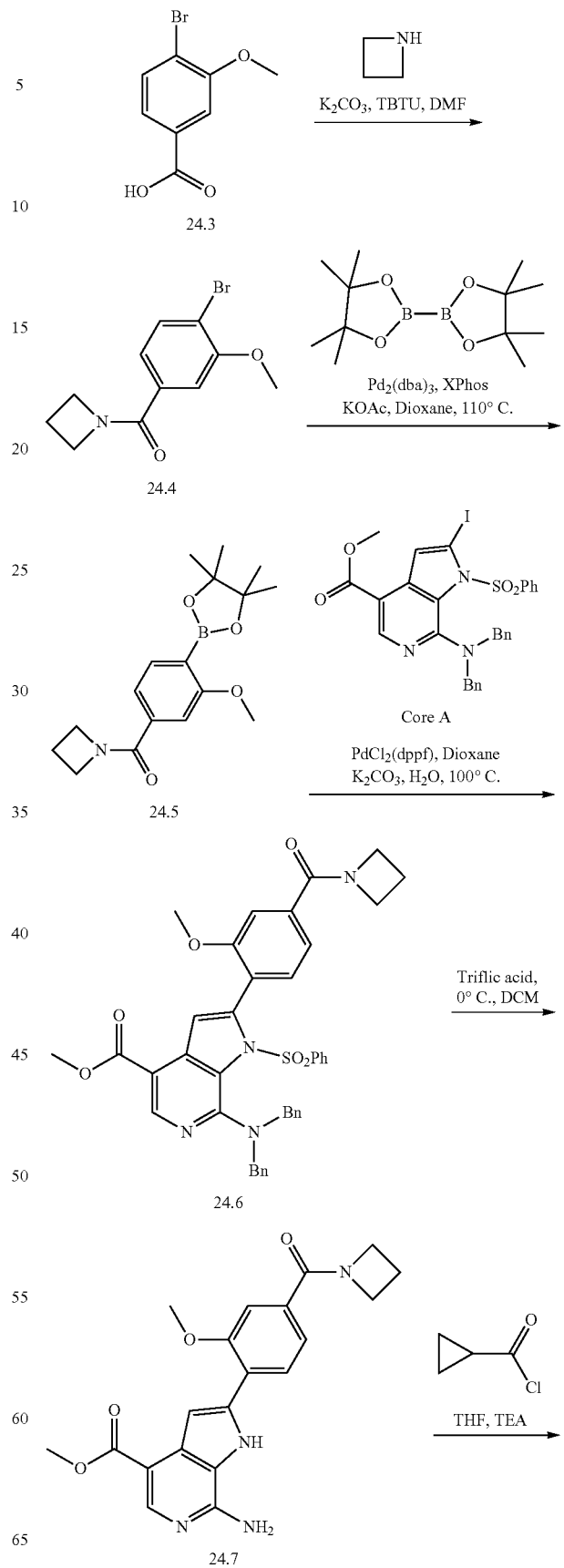

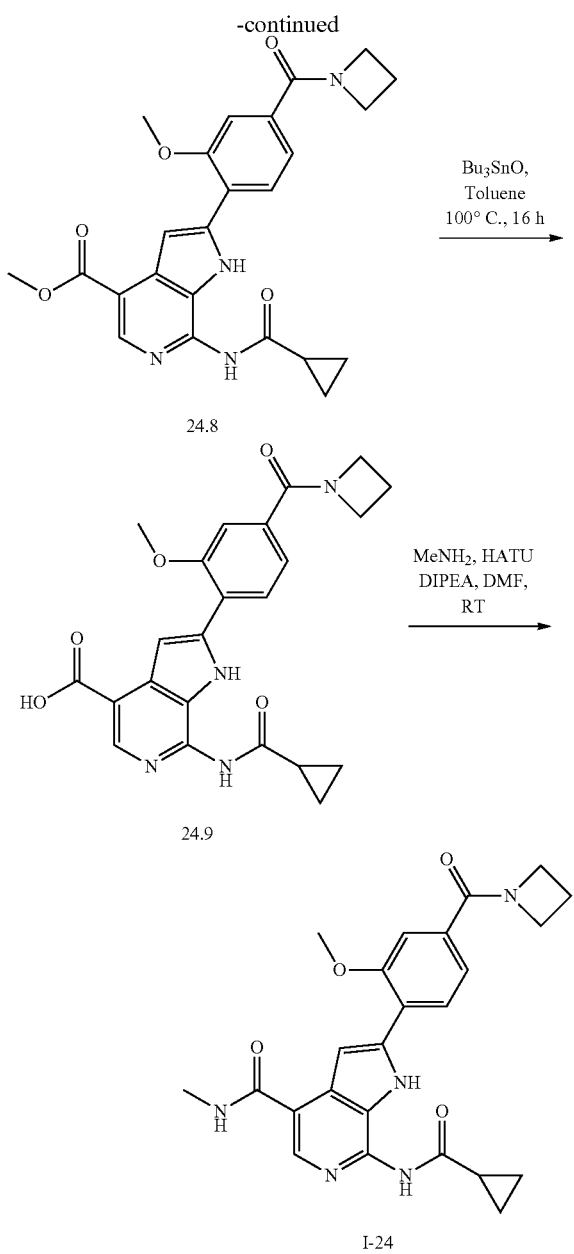

Synthesis of Compound 24.2

To a solution of compound 24.1 (10.0 g, 43.29 mmol, 1.0 eq) in dimethylformamide (100 mL), methyl iodide (6.7 g, 47.61 mmol, 1.1 eq) was added. The reaction mixture was degassed for 10 min under argon atmosphere followed by addition of potassium carbonate (17.9 g, 129.87 mmol, 3.0 eq). The reaction mixture was heated at 100° C. for 10 h. After completion of reaction, reaction mixture was transferred to ice cold water and product was extracted with ethylacetate. Organic layer was combined, washed with brine solution, dried over sodium sulfate and concentrated under reduced pressure to obtain crude material. This was further purified by column chromatography eluting with 5% methanol in dichloromethane to obtain 24.2. (7.2 g, Yield: 67.88%). MS (ES): m/z 244.98 [M+H]$^+$.

Synthesis of Compound 24.3

To a solution of compound 24.2 (7.2 g, 29.38 mmol, 1.0 eq), in tetrahydrofuran:methanol:water (80 mL, 2:2:1) was added lithium hydroxide (7.0 g, 293.8 mmol, 10 eq). The reaction was stirred at 60° C. for 16 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulfate and concentrated under reduced pressure to obtain crude material. This was further purified by column chromatography and compound was eluted in 2.1% methanol in dichloromethane to obtain pure 24.3. (5.0 g, Yield: 73.66%). MS (ES): m/z 231.96 [M+H]$^+$.

Synthesis of Compound 24.4

To a solution of compound 24.3 (1.0 g, 4.32 mmol, 1.0 eq) in dimethylformamide (10 mL) was added azetidine (0.270 g, 4.75 mmol, 1.1 eq) and 2-(1H-benzotriazole-1-yl)-1,1,3,3-tetramethylaminium tetrafluoroborate (2.77 g, 8.64 mmol, 2.0 eq). The reaction mixture was degassed for 10 min under argon atmosphere followed by addition of potassium carbonate (1.78 g, 12.96 mmol, 3.0 eq). The reaction mixture was heated at 100° C. for 10 h. After completion of reaction, reaction mixture was transferred to ice cold water and product was extracted with ethyl acetate. Organic layer was combined, washed with brine solution, dried over sodium sulfate and concentrated under reduced pressure to obtain crude material. This was further purified by column chromatography eluting with 5% methanol in dichloromethane to obtain 24.4. (0.8 g, Yield: 68.43%). MS (ES): m/z 271.00 [M+H]$^+$.

Synthesis of Compound 24.5

The compound was synthesized from compound 24.4 using General Procedure F, using 2-dicyclohexylphosphino-2',4',6'-triisopropylbiphenyl instead of 4,5-bis(diphenylphosphino)-9,9-dimethylxanthene, to obtain 24.5. (0.420 g, Yield: 44.71%). MS (ES): m/z 318.18 [M+H]$^+$.

Synthesis of Compound 24.6

The compound was synthesized from Core A and compound 24.5 using General Procedure A to obtain 24.6. (0.310 g, Yield: 33.41%), MS (ES): m/z 701.24 [M+H]$^+$.

Synthesis of Compound 24.7

The compound was synthesized from compound 24.6 using General Procedure B to obtain 24.7. (0.150 g, Yield: 89.14%), MS (ES): m/z 381.15 [M+H]$^+$.

Synthesis of Compound 24.8

The compound was synthesized from compound 24.7 using General Procedure C to obtain 24.8. (0.110 g, Yield: 62.20%), MS (ES): m/z 449.18 [M+H]$^+$.

Synthesis of Compound 24.9

To a suspension of compound 24.8 (0.110 g, 0.24 mmol, 1.0 eq) in toluene (2 mL) was added tributyltin oxide (0.286 g, 0.48 mmol, 2.0 eq) and reaction mixture was heated at 100° C. for 16 h. After completion of reaction, reaction mixture was concentrated under reduced pressure to obtain residue which was dissolved in saturated sodium bicarbonate solution and washed with hexane. Aqueous layer separated and acidified with 1N hydrochloric acid to pH~5-6 and extracted with ethyl acetate. Organic layer was combined, dried over sodium sulfate and concentrated under reduced pressure to obtain solid which was triturated with hexane to obtain pure 24.9. (0.060 g, Yield: 56.31%), MS (ES): m/z 435.16 [M+H]⁺.

Synthesis of Compound I-24

The compound was synthesized from compound 24.9 and methylamine using General Procedure H. The material was further purified by column chromatography and the compound was eluted in 40% ethyl acetate in hexane to obtain I-24 (0.030 g, Yield: 48.54%). MS(ES): m/z 448.37 [M+H]⁺ LCMS purity: 99.24%, HPLC purity: 95.14%, ¹H NMR (DMSO-d₆, 400 MHz): 12.53 (s, 1H), 11.34 (s, 1H), 8.34-8.32 (d, J=4.4 Hz, 1H), 8.06-8.04 (d, J=8.4 Hz, 1H), 7.51 (s, 1H), 7.35-7.33 (d, J=8 Hz, 1H), 7.10 (bs, 1H), 6.82 (bs, 1H), 4.41-4.37 (t, J=7.6 Hz, 2H), 4.13-4.08 (m, 2H), 4.05 (s, 3H), 2.86-2.85 (d, J=4.4 Hz, 3H), 2.33-2.26 (m, 2H), 1.56 (bs, 1H), 1.01-3.96 (m, 4H).

Example 25: 7-(cyclopropanecarboxamido)-2-(2-methoxy-4-(pyrrolidine-1-carbonyl) phenyl)-N-methyl-1H-pyrrolo[2,3-c]pyridine-4-carboxamide (I-25)

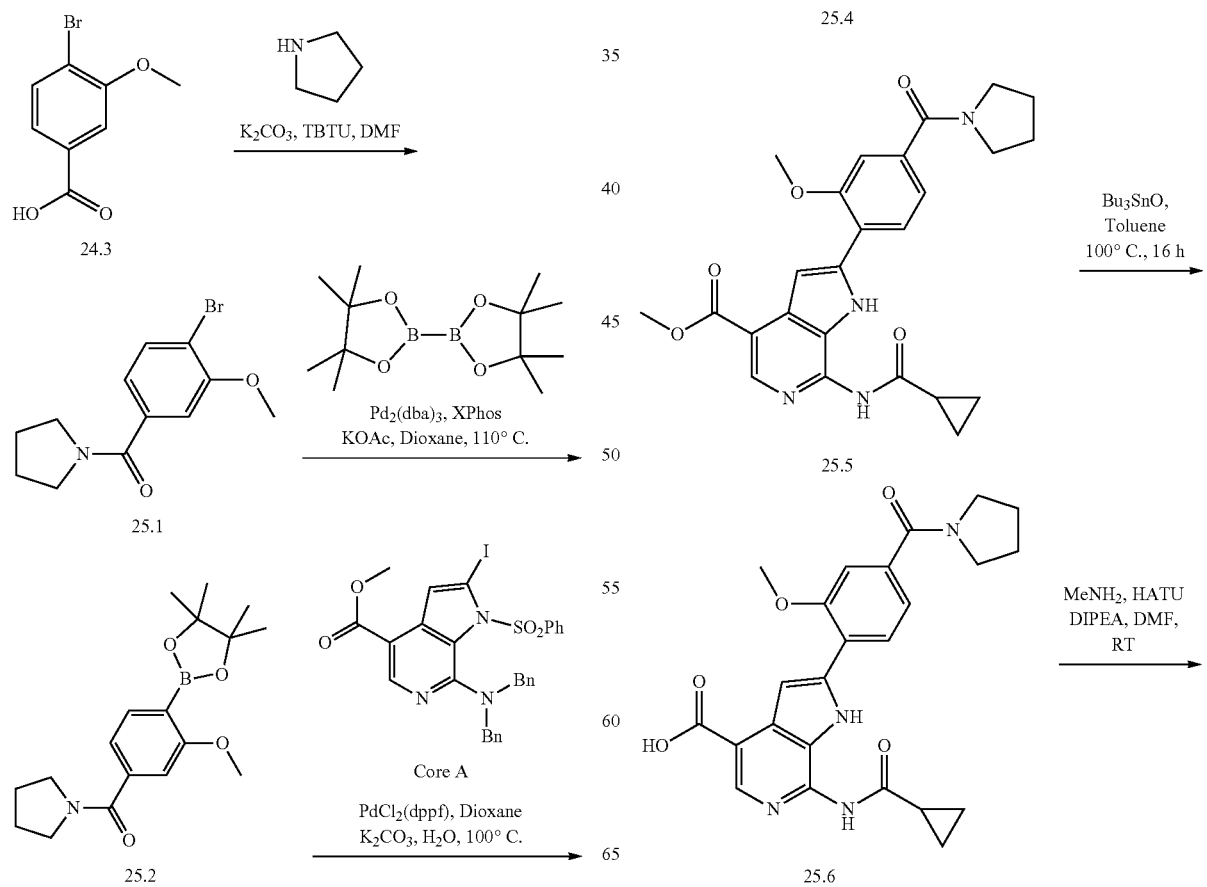

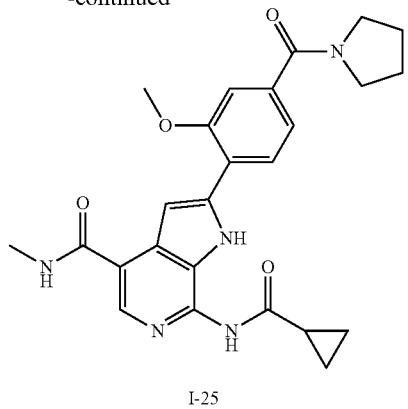

I-25

Synthesis of Compound 25.1

To a solution of compound 24.3 (1.0 g, 4.32 mmol, 1.0 eq) in dimethylformamide (10 mL) was added pyrrolidine (0.337 g, 4.75 mmol, 1.1 eq) and 2-(1H-benzotriazole-1-yl)-1,1,3,3-tetramethylaminium tetrafluoroborate (2.77 g, 8.64 mmol, 2.0 eq). The reaction mixture was degassed for 10 min under argon atmosphere followed by addition of potassium carbonate (1.78 g, 12.96 mmol, 3.0 eq). The reaction mixture was heated at 100° C. for 10 h. After completion of reaction, reaction mixture was transferred to ice cold water and product was extracted with ethyl acetate. Organic layer was combined, washed with brine solution, dried over sodium sulfate and concentrated under reduced pressure to obtain crude material. This was further purified by column chromatography eluting with 5% methanol in dichloromethane to obtain 25.1. (0.810 g, Yield: 65.86%). MS (ES): m/z 285.02 [M+H]$^+$.

Synthesis of Compound 25.2

The compound was synthesized from compound 25.1 using General Procedure F, using 2-dicyclohexylphosphino-2',4',6'-triisopropylbiphenyl instead of 4,5-bis(diphenylphosphino)-9,9-dimethylxanthene, to obtain 25.2. (0.430 g, Yield: 45.54%). MS (ES): m/z 332.20 [M+H]$^+$.

Synthesis of Compound 25.3

The compound was synthesized from Core A and compound 25.2 using General Procedure A to obtain 25.3. (0.4 g, Yield: 43.10%), MS (ES): m/z 715.25 [M+H]$^+$.

Synthesis of Compound 25.4

The compound was synthesized from compound 25.3 using General Procedure B to obtain 25.4. (0.180 g, Yield: 81.55%), MS (ES): m/z 395.17 [M+H]$^+$.

Synthesis of Compound 25.5

The compound was synthesized from compound 25.4 using General Procedure C to obtain 25.5. (0.140 g, Yield: 66.33%), MS (ES): m/z 463.19 [M+H]$^+$.

Synthesis of Compound 25.6

To a suspension of compound 25.5 (0.140 g, 0.30 mmol, 1.0 eq) in toluene (2 mL) was added tributyltin oxide (0.357 g, 0.6 mmol, 2.0) and reaction mixture was heated at 100° C. for 16 h. After completion of reaction, reaction mixture was concentrated under reduced pressure to obtain residue which was dissolved in saturated sodium bicarbonate solution and washed with hexane. Aqueous layer separated and acidified with 1N hydrochloric acid to pH~5-6 and extracted with ethyl acetate. Organic layer was combined, dried over sodium sulfate and concentrated under reduced pressure to obtain solid which was triturated with hexane to obtain pure 25.6. (0.080 g, Yield: 58.93%), MS (ES): m/z 449.18 [M+H]$^+$.

Synthesis of Compound I-25

The compound was synthesized from compound 25.6 and methylamine using General Procedure H. The material was further purified by column chromatography and the compound was eluted in 40% ethyl acetate in hexane to obtain I-25 (0.031 g, Yield: 37.65%). MS (ES): m/z 462.56 [M+H]$^+$ LCMS purity: 100%, HPLC purity: 98.72%, $^1$H NMR (DMSO-d$_6$, 400 MHz): 12.49 (s, 1H), 11.31 (s, 1H), 8.32 (s, 1H), 8.15 (s, 1H), 8.03-8.01 (d, J=8 Hz, 1H), 7.47 (s, 1H), 7.31 (s, 1H), 7.25-7.23 (d, J=7.6 Hz, 1H), 4.03 (s, 3H), 3.49-3.46 (m, 4H), 2.85 (s, 3H), 1.89-1.83 (m, 4H), 1.23 (bs, 1H), 1.00-0.95 (m, 4H).

Example 26: 7-(cyclopropanecarboxamido)-2-(2-methoxy-4-(2-oxopyrrolidin-1-yl)phenyl)-N-methyl-1H-pyrrolo[2,3-c]pyridine-4-carboxamide (I-26

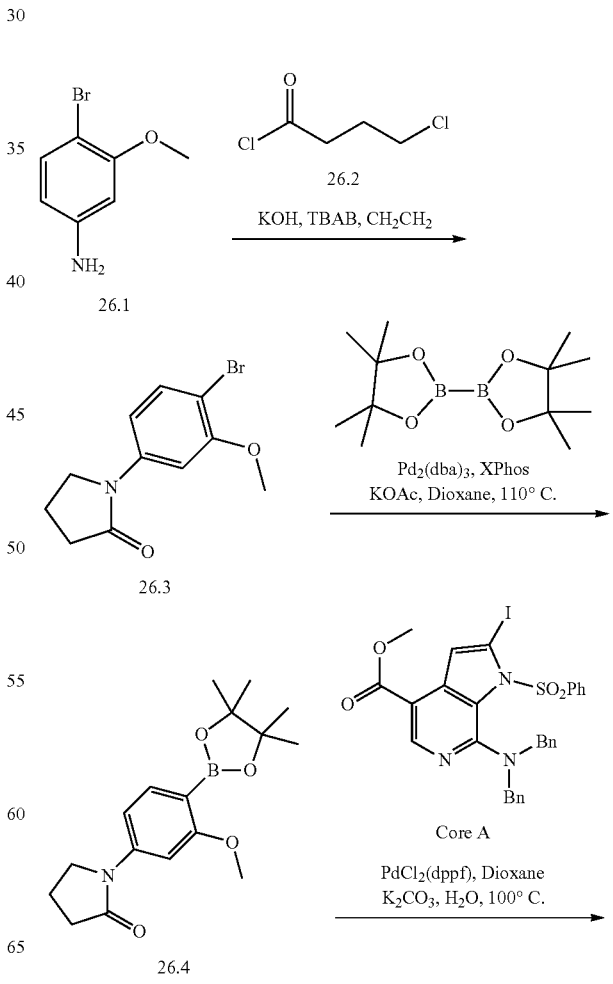

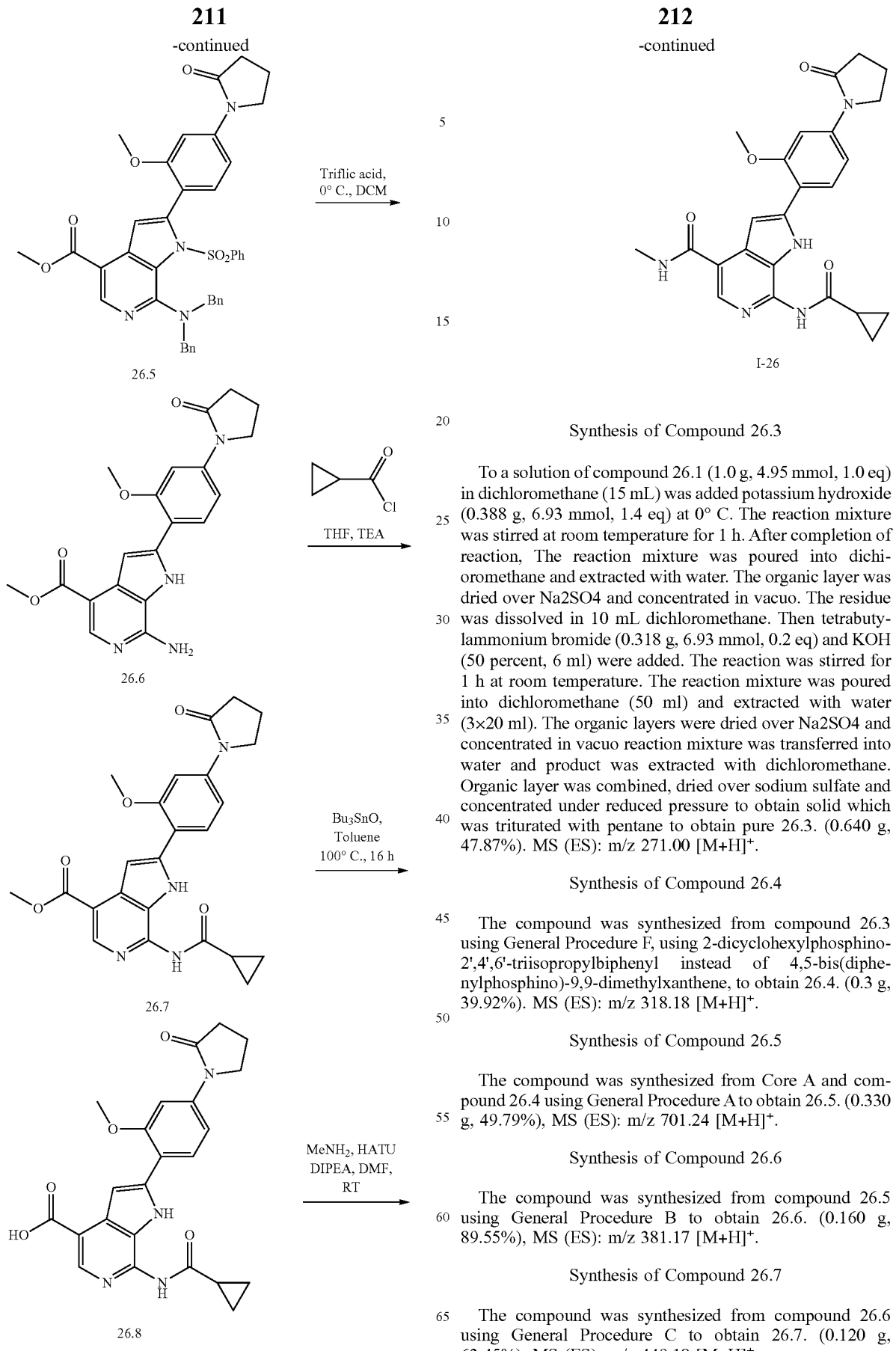

Synthesis of Compound 26.3

To a solution of compound 26.1 (1.0 g, 4.95 mmol, 1.0 eq) in dichloromethane (15 mL) was added potassium hydroxide (0.388 g, 6.93 mmol, 1.4 eq) at 0° C. The reaction mixture was stirred at room temperature for 1 h. After completion of reaction, The reaction mixture was poured into dichioromethane and extracted with water. The organic layer was dried over Na2SO4 and concentrated in vacuo. The residue was dissolved in 10 mL dichloromethane. Then tetrabutylammonium bromide (0.318 g, 6.93 mmol, 0.2 eq) and KOH (50 percent, 6 ml) were added. The reaction was stirred for 1 h at room temperature. The reaction mixture was poured into dichloromethane (50 ml) and extracted with water (3×20 ml). The organic layers were dried over Na2SO4 and concentrated in vacuo reaction mixture was transferred into water and product was extracted with dichloromethane. Organic layer was combined, dried over sodium sulfate and concentrated under reduced pressure to obtain solid which was triturated with pentane to obtain pure 26.3. (0.640 g, 47.87%). MS (ES): m/z 271.00 [M+H]$^+$.

Synthesis of Compound 26.4

The compound was synthesized from compound 26.3 using General Procedure F, using 2-dicyclohexylphosphino-2',4',6'-triisopropylbiphenyl instead of 4,5-bis(diphenylphosphino)-9,9-dimethylxanthene, to obtain 26.4. (0.3 g, 39.92%). MS (ES): m/z 318.18 [M+H]$^+$.

Synthesis of Compound 26.5

The compound was synthesized from Core A and compound 26.4 using General Procedure A to obtain 26.5. (0.330 g, 49.79%), MS (ES): m/z 701.24 [M+H]$^+$.

Synthesis of Compound 26.6

The compound was synthesized from compound 26.5 using General Procedure B to obtain 26.6. (0.160 g, 89.55%), MS (ES): m/z 381.17 [M+H]$^+$.

Synthesis of Compound 26.7

The compound was synthesized from compound 26.6 using General Procedure C to obtain 26.7. (0.120 g, 63.45%), MS (ES): m/z 449.18 [M+H]$^+$.

Synthesis of Compound 26.8

To a suspension of compound 26.7 (0.120 g, 0.26 mmol, 1.0 eq) in toluene (4 mL) was added tributyltin oxide (0.309 g, 0.52 mmol, 2.0 eq) and reaction mixture was heated at 100° C. for 16 h. After completion of reaction, reaction mixture was concentrated under reduced pressure to obtain residue which was dissolved in saturated sodium bicarbonate solution and washed with hexane. Aqueous layer separated and acidified with 1N hydrochloric acid to pH~5-6 and extracted with ethyl acetate. Organic layer was combined, dried over sodium sulfate and concentrated under reduced pressure to obtain solid which was triturated with hexane to obtain pure 26.8. (0.070 g, 60.22%), MS (ES): 435.36 [M+H]$^+$.

Synthesis of Compound I-26

The compound was synthesized from compound 26.8 and methylamine using General Procedure H. The material was further purified by column chromatography and the compound was eluted in 40% ethyl acetate in hexane to obtain I-26 (0.028 g, 38.83%). MS (ES): m/z 448.46 [M+H]$^+$ LCMS purity: 100%, HPLC purity: 96.91%, $^1$H NMR (DMSO-d$_6$, 400 MHz): 12.18 (s, 1H), 10.84 (s, 1H), 8.26 (s, 1H), 7.89 (bs, 1H), 7.70 (s, 1H), 7.32 (s, 1H), 7.11-7.09 (d, J=8.4 Hz, 1H), 6.85-6.83 (d, J=8.4 Hz, 1H), 4.01 (s, 3H), 3.95-3.92 (t, J=7.2 Hz, 2H), 3.21 (s, 2H), 2.89-2.88 (d, J=4.4 Hz, 3H), 2.17-2.09 (m, 1H), 1.59 (bs, 2H), 1.03-0.94 (m, 4H).

Example 27: 7-(cyclopropanecarboxamido)-N-methyl-2-(3-(5-methylpyrazin-2-yl)phenyl)-1H-pyrrolo[2,3-c]pyridine-4-carboxamide (I-27)

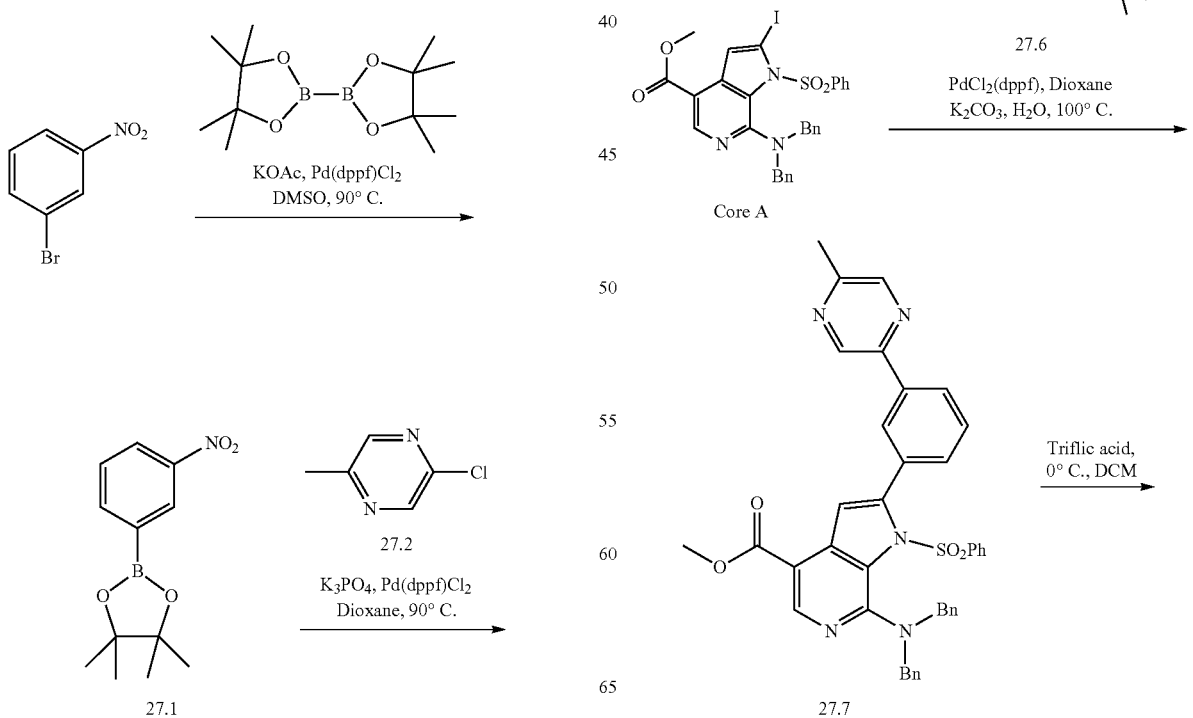

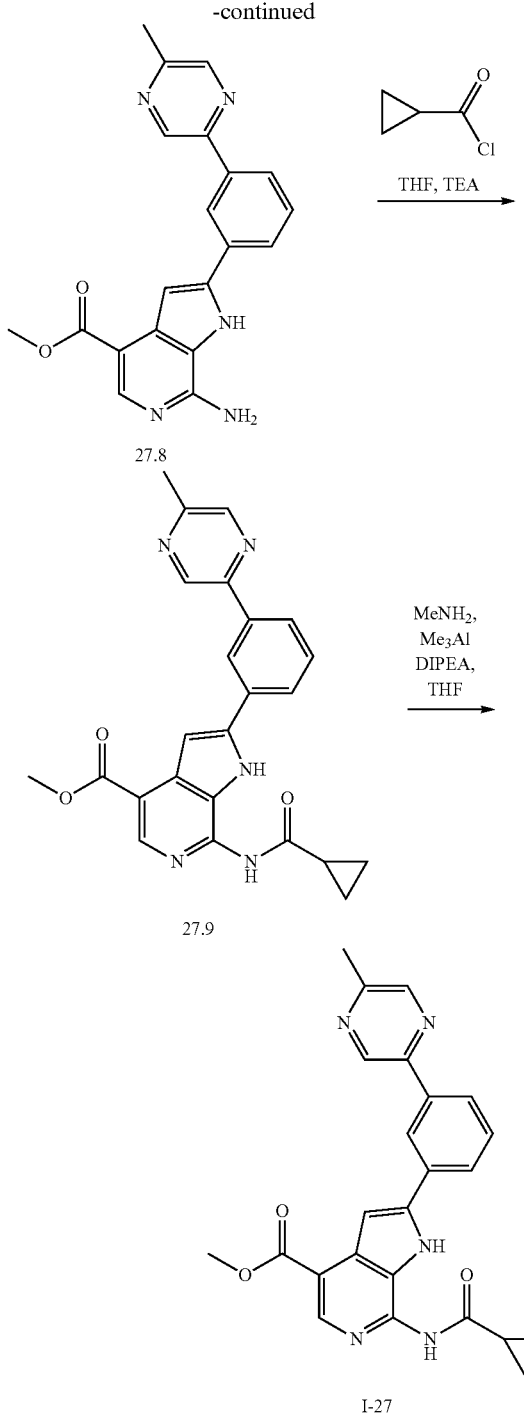

mmol, 2.5 eq) in 1,4-dioxane (60 mL). [1,1'-bis(diphenylphosphino)ferrocene]palladium(II) dichloride (0.877 mg, 1.2 mmol, 0.1 eq) was added to it and further purging done for 10 min. Reaction was stirred at 90° C. for 6 h. After completion of reaction, reaction mixture was poured over water and product was extracted with ethyl acetate. Organic layer was combined, washed with brine solution, dried over sodium sulfate and concentrated under reduced pressure to obtain 27.3. (1.5 g, Yield: 57.87%). MS (ES): m/z 216.07 [M+H]$^+$.

Synthesis of Compound 27.4

To a solution of compound 27.3 (1.5 g, 6.97 mmol, 1.0 eq) in ethanol (15 ml) was added tin(II) chloride (1.4 g, 7.6 mmol, 1.1 eq). The reaction was stirred at room temperature for 2 h. After completion of reaction, reaction mixture was transferred into water and product was extracted with ethyl acetate. Organic layer was combined, washed with brine solution, dried over sodium sulfate and concentrated under reduced pressure to obtain 27.4. (1.1 g, Yield: 85.20%). MS (ES): m/z 186.10 [M+H]$^+$.

Synthesis of Compound 27.5

To a solution of compound 27.4 (1.1 g, 5.91 mmol, 1.0 eq) in acetonitrile (15 ml) was added tert-butyl nitrite (0.669 g, 6.50 mmol, 1.1 eq) and copper(II) bromide (2.6 g, 11.82 mmol, 2.0 eq). The reaction was stirred at 4° C. for 2 h. After completion of reaction, reaction mixture was transferred into water and product was extracted with ethyl acetate. Organic layer was combined, washed with brine solution, dried over sodium sulfate and concentrated under reduced pressure to obtain 27.5. (0.7 g, Yield: 47.32%). MS (ES): m/z 249.00 [M+H]$^+$.

Synthesis of Compound 27.6

The compound was synthesized from compound 27.5 using General Procedure F, using 2-dicyclohexylphosphino-2',4',6'-triisopropylbiphenyl instead of 4,5-bis(diphenylphosphino)-9,9-dimethylxanthene, to obtain 27.6. (0.4 g, Yield: 48.06%). MS (ES): m/z 297.17 [M+H]$^+$.

Synthesis of Compound 27.7

The compound was synthesized from Core A and compound 27.6 using General Procedure A to obtain 27.7. (0.220 g, Yield: 45.85%), MS (ES): m/z 680.23 [M+H]$^+$.

Synthesis of Compound 27.8

The compound was synthesized from compound 27.7 using General Procedure B to obtain 27.8. (0.110 g, Yield: 94.58%), MS (ES): m/z 360.14 [M+H]$^+$.

Synthesis of Compound 27.9

The compound was synthesized from compound 27.8 using General Procedure C to obtain 27.9. (0.1 g, Yield: 76.43%), MS (ES): m/z 428.17 [M+H]$^+$.

Synthesis of Compound 27.1

The compound was synthesized from 1-bromo-3-nitrobenzene using General Procedure G to obtain 27.1. (3.2 g, Yield: 51.91%). MS (ES): m/z 250.12 [M+H]$^+$.

Synthesis of Compound 27.3

Argon was purged for 15 min through a stirred mixture of compounds 27.1 (3.0 g, 12.00 mmol, 1.0 eq), 27.2 (1.9 g, 15.6 mmol, 1.3 eq), and tripotassium phosphate (6.3 g, 30.0

Synthesis of Compound I-27

The compound was synthesized from compound 27.9 and methylamine using General Procedure D. The material was further purified by column chromatography eluting with 2.5% methanol in dichloromethane to obtain I-27 (0.027 g, Yield: 27.06%). MS (ES): m/z 427.17 [M+H]+ LCMS purity: 95.11%, HPLC purity: 96.25%, $^1$H NMR (DMSO-$d_6$, 400 MHz): 11.84 (s, 1H), 11.14 (s, 1H), 9.30 (s, 1H), 8.70 (s, 1H), 8.63 (s, 1H), 8.32 (s, 1H), 8.20-8.18 (d, J=8 Hz, 1H), 7.97-7.95 (d, J=7.6 Hz, 1H), 7.73-7.69 (m, 1H), 7.51 (s, 1H), 7.09-7.07 (m, 1H), 2.88-2.87 (d, J=4 Hz, 3H), 2.59 (s, 3H), 1.56 (bs, 1H), 1.01-0.87 (m, 4H).
Example 28: 7-(cyclopropanecarboxamido)-2-(3-(1,5-dimethyl-1H-1,2,4-triazol-3-yl) phenyl)-N-methyl-1H-pyrrolo[2,3-c]pyridine-4-carboxamide (I-28)
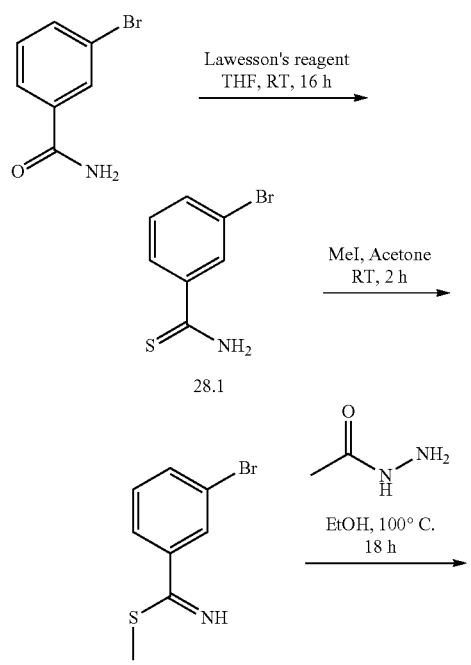
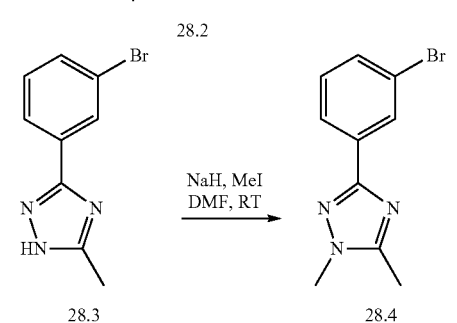
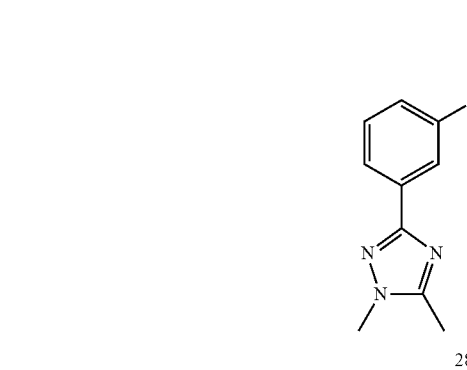
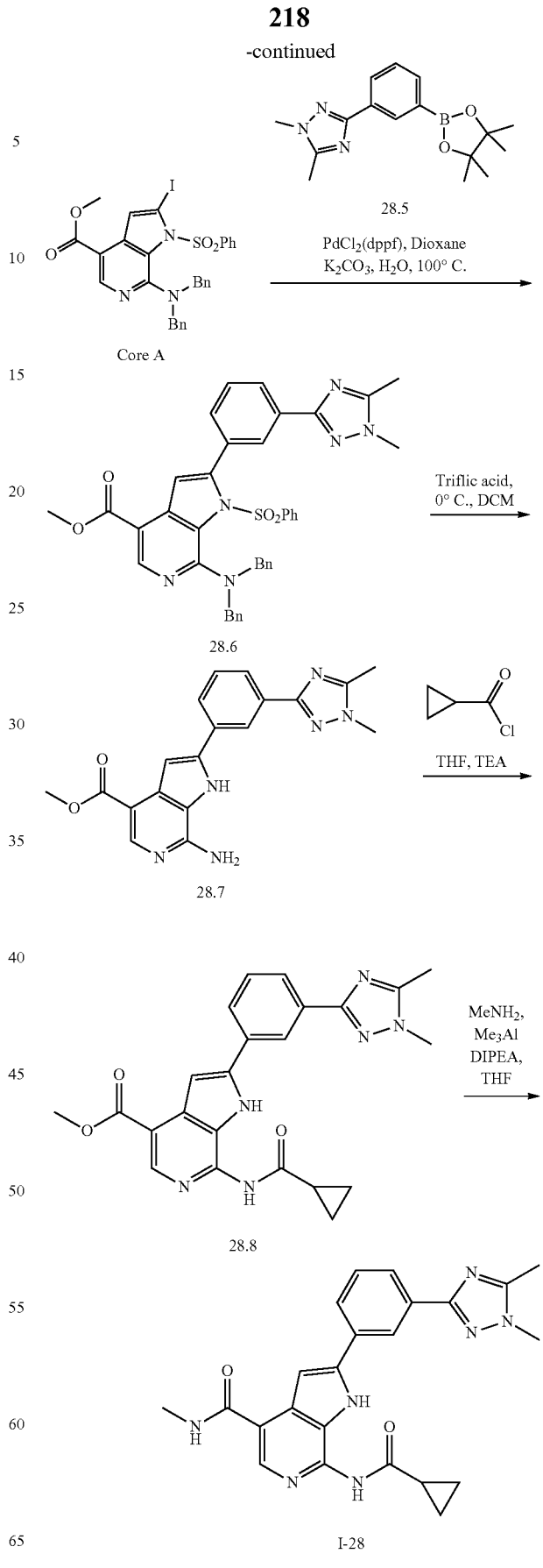

Synthesis of Compound 28.1

To a solution of 3-bromobenzamide (4.0 g, 20.0 mmol, 1.0 eq) in tetrahydrofuran (80 mL) was added Lawesson's reagent (8.8 g, 22.0 mmol, 1.1 eq) at 0° C. The reaction was stirred at room temperature for 16 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by combi flash using 3% methanol in dichloromethane as eluant to obtain pure 28.1. (3.0 g, Yield: 69.43%). MS (ES): m/z 215.94 [M+H]$^+$.

Synthesis of Compound 28.2

To a solution of compound 28.1 (3.0 g, 14.01 mmol, 1.0 eq) in acetone (30 mL) was added methyl iodide (2.1 g, 15.41 mmol, 1.1 eq) and reaction mixture was stirred at room temperature for 2 h. After completion of reaction, reaction mixture was transferred into ice, stirred and extracted with diethyl ether. Organic layer was combined, dried over sodium sulfate and concentrated under reduced pressure to obtain crude material. This was further purified by distillation to obtain pure 28.2. (2.5 g, Yield: 78.25%). MS (ES): m/z 230.95 [M+H]$^+$.

Synthesis of Compound 28.3

To a solution of compound 28.2 (2.5 g, 10.86 mmol, 1.0 eq) in ethanol (25 ml) was added acetohydrazide (1.2 g, 16.29 mmol, 1.5 eq). The reaction was stirred at 100° C. for 18 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by column chromatography and the compound was eluted in 20% ethyl acetate in hexane to obtain 28.3. (1.3 g, Yield: 50.26%). MS (ES): m/z 238.99 [M+H]$^+$.

Synthesis of Compound 28.4

To a solution of compound 28.3 (1.3 g, 5.46 mmol, 1.0 eq) in dimethylformamide (20 mL), was added sodium hydride (0.262 g, 10.92 mmol, 2 eq) at 0° C. and stirred for 20 min. Methyl iodide (0.852 g, 6.00 mmol, 1.1 eq) was added and reaction mixture was stirred at room temperature for 2 h. After completion of reaction, reaction mixture was transferred into ice, stirred and extracted with diethyl ether. Organic layer was combined, dried over sodium sulfate and concentrated under reduced pressure to obtain crude material. This was further purified by distillation to obtain pure 28.4. (0.7 g, Yield: 50.85%). MS (ES): m/z 253.00 [M+H]$^+$.

Synthesis of Compound 28.5

The compound was synthesized from compound 28.4 using General Procedure F, using 2-dicyclohexylphosphino-2',4',6'-triisopropylbiphenyl instead of 4,5-bis(diphenylphosphino)-9,9-dimethylxanthene, to obtain 28.5. (0.5 g, Yield: 60.19%). MS (ES): m/z 300.18 [M+H]$^+$.

Synthesis of Compound 28.6

The compound was synthesized from Core A and compound 28.5 using General Procedure A to obtain 28.6. (0.210 g, Yield: 43.57%), MS (ES): m/z 683.24 [M+H]$^+$.

Synthesis of Compound 28.7

The compound was synthesized from compound 28.6 using General Procedure B to obtain 28.7. (0.1 g, Yield: 89.72%), MS (ES): m/z 363.15 [M+H]$^+$.

Synthesis of Compound 28.8

The compound was synthesized from compound 28.7 using General Procedure C to obtain 28.8. (0.100 g, Yield: 84.19%), MS (ES): m/z 431.18 [M+H]$^+$.

Synthesis of Compound I-28

The compound was synthesized from 28.8 and methylamine using General Procedure D. The material was further purified by column chromatography eluting with 2.5% methanol in dichloromethane to obtain I-28 (0.027 g, Yield: 27.06%), MS (ES): m/z 430.32 [M+H]$^+$ LCMS purity: 100%, HPLC purity: 96.96%, $^1$H NMR (DMSO-d$_6$, 400 MHz): 11.87 (s, 1H), 11.11 (s, 1H), 8.42 (bs, 1H), 8.38-8.37 (d, J=4.4 Hz, 1H), 8.32 (s, 1H), 7.99 (bs, 1H), 7.87-7.85 (d, J=7.6 Hz, 1H), 7.64-7.60 (t, J=7.6 Hz, 1H), 7.40 (bs, 1H), 3.87 (s, 3H), 2.86-2.85 (d, J=4.4 Hz, 3H), 2.27 (bs, 1H), 1.23 (bs, 3H), 1.00-0.93 (m, 4H).

Example 29: 7-(cyclopropanecarboxamido)-2-(2-methoxy-4-(methylcarbamoyl)phenyl)-N-methyl-1H-pyrrolo[2,3-c]pyridine-4-carboxamide (I-29)

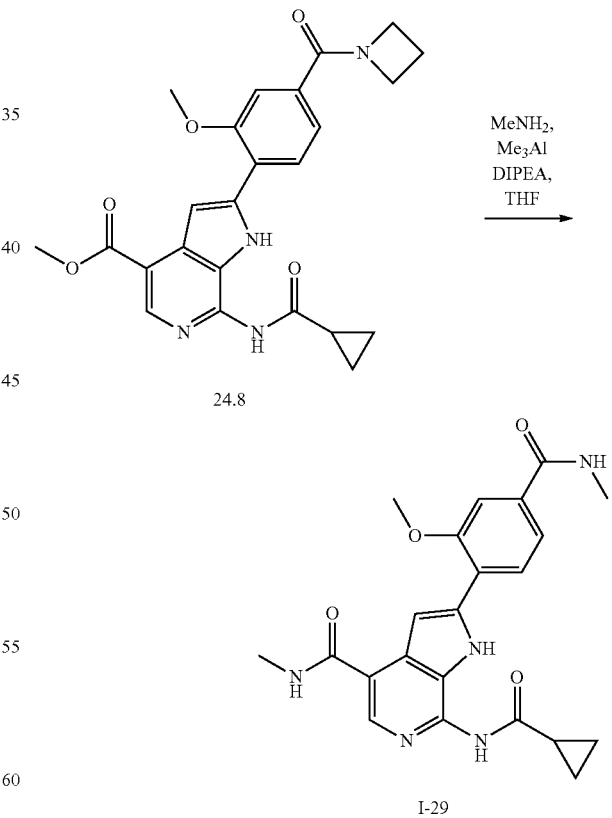

Synthesis of Compound I-29

The compound was synthesized from compound 24.8 and methylamine using General Procedure D. The material was further purified by column chromatography eluting with 2.5% methanol in dichloromethane to obtain I-29 (0.031 g, Yield: 37.65%), MS (ES): m/z 422.46 [M+H]+ LCMS purity: 96%, HPLC purity: 95.00%, $^1$H NMR (DMSO-$d_6$, 400 MHz): 12.15 (s, 1H), 11.17 (bs, 1H), 11.05 (s, 1H) 8.21 (s, 1H), 7.79-7.78 (d, J=4 Hz, 1H), 7.67-7.65 (d, J=8.8 Hz, 1H), 7.09-7.07 (d, J=6.8 Hz, 1H), 6.84-6.82 (d, J=7.6 Hz, 1H), 6.27 (s, 1H), 3.94 (s, 3H), 3.10-3.08 (d, J=5.2 Hz, 3H), 2.85-2.84 (d, J=4.4 Hz, 3H), 1.56 (bs, 1H), 0.99-0.95 (m, 4H).

Example 30: 7-(cyclopropanecarboxamido)-2-(2-methoxy-4-((4-(methylamino)-4-oxobutyl) amino) phenyl)-N-methyl-1H-pyrrolo[2,3-c]pyridine-4-carboxamide (I-30)

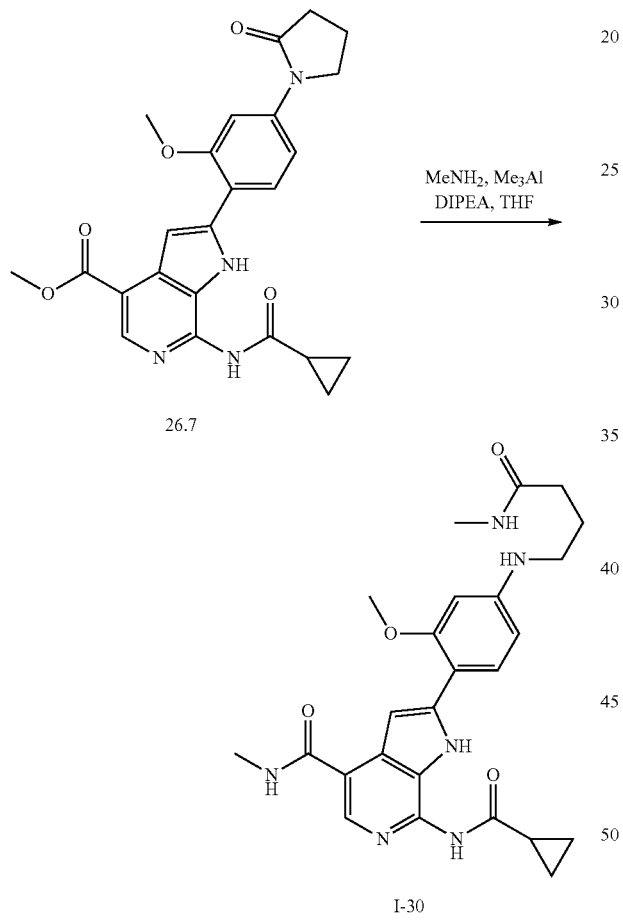

Synthesis of Compound I-30

The compound was synthesized from compound 26.7 and methylamine using General Procedure D. The material was further purified by column chromatography eluting with 2.5% methanol in dichloromethane to obtain I-30 (0.020 g, Yield: 18.74%), MS (ES): m/z 479.32 [M+H]+ LCMS purity: 100%, HPLC purity: 100%, $^1$H NMR (DMSO-$d_6$, 400 MHz): 12.15 (s, 1H), 11.17 (bs, 1H), 8.21 (s, 1H), 7.79-7.78 (d, J=4 Hz, 1H), 7.67-7.65 (d, J=8.8 Hz, 1H), 7.09-7.07 (d, J=6.8 Hz, 1H), 6.84-6.82 (d, J=7.6 Hz, 1H), 6.33-6.31 (t, J=6 Hz, 1H), 6.27 (s, 1H), 3.94 (s, 3H), 3.10-3.08 (d, J=5.2 Hz, 2H), 2.85-2.84 (d, J=4.4 Hz, 3H), 2.59-2.58 (d, J=4.4 Hz, 3H), 2.21-2.18 (t, J=7.2 Hz, 2H), 1.83-1.80 (t, J=7.2 Hz, 2H), 1.56 (bs, 1H), 1.24 (bs, 1H), 0.99-0.95 (m, 4H).

Example 31: 7-(cyclopropanecarboxamido)-2-(1-ethyl-6-oxo-1,6-dihydropyridin-3-yl)-N-methyl-1H-pyrrolo[2,3-c]pyridine-4-carboxamide (I-31)

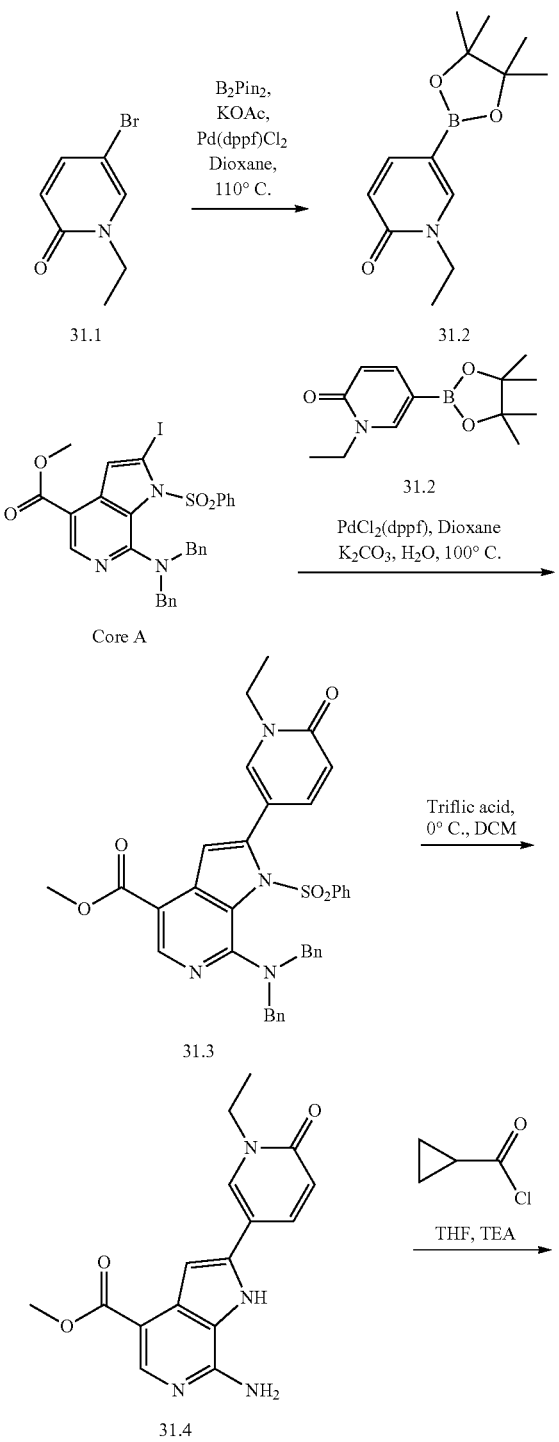

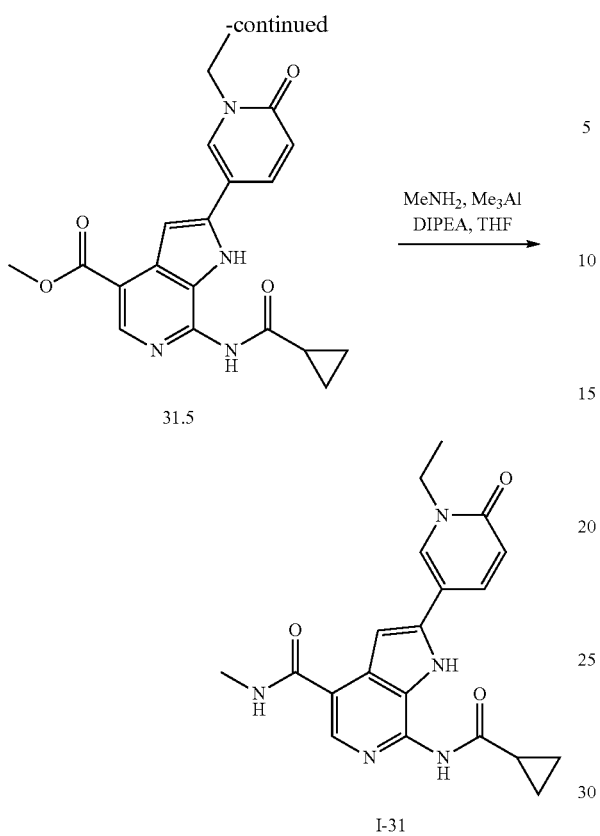

8.46 (bs, 1H), 8.25 (s, 1H), 8.04 (bs, 1H), 7.32 (s, 1H), 6.62-6.59 (d, J=9.6 Hz, 1H), 4.08-4.03 (m, 2H), 2.88-2.86 (d, J=4.4 Hz, 3H), 1.37-1.31 (m, 3H), 1.26 (s, 1H), 1.03 (bs, 4H).

Example 32: 7-(cyclopropanecarboxamido)-N-methyl-2-(6-(1-methyl-1H-1,2,4-triazol-3-yl)pyridin-2-yl)-1H-pyrrolo[2,3-c]pyridine-4-carboxamide (I-32)

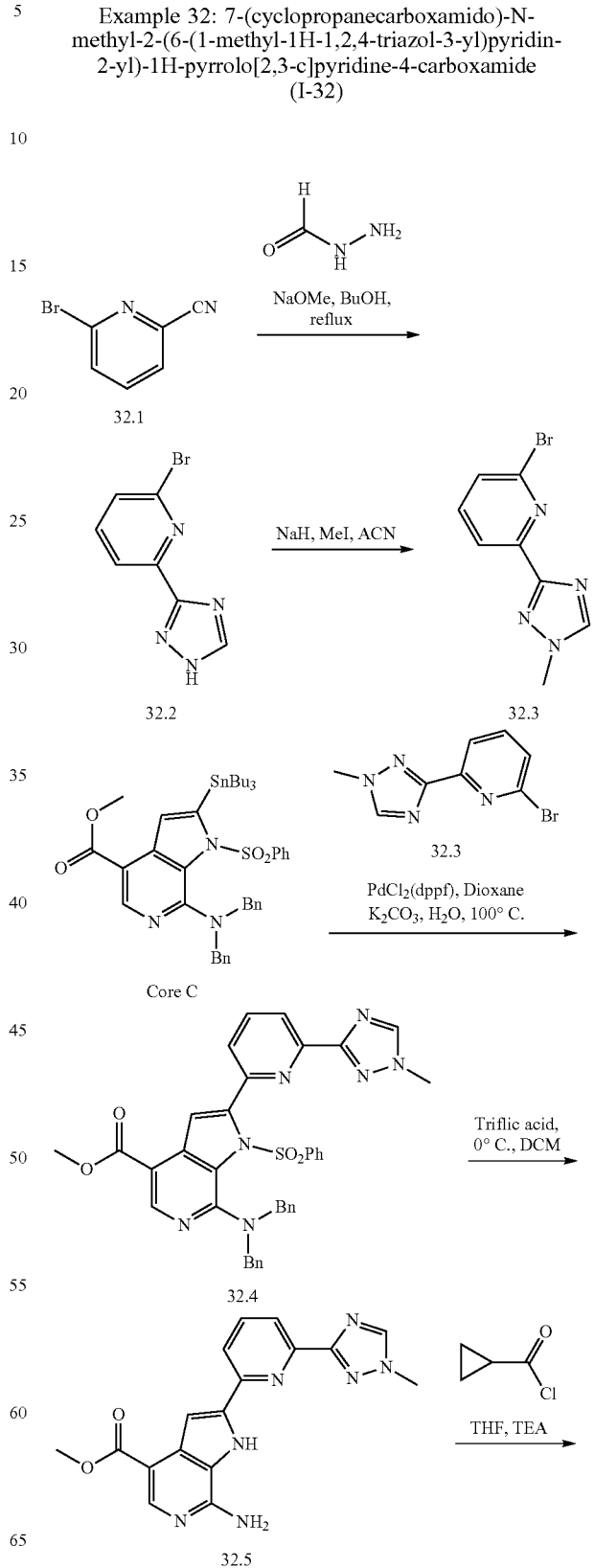

Synthesis of Compound 31.2

The compound was synthesized from compound 31.1 using General Procedure G to obtain 31.2. (0.5 g, Yield: 40.55%). MS (ES): m/z 250.16 [M+H]$^+$.

Synthesis of Compound 31.3

The compound was synthesized from Core A and compound 31.2 using General Procedure A to obtain 31.3. (0.220 g, Yield: 55.41%), MS (ES): m/z 633.21 [M+H]$^+$.

Synthesis of Compound 31.4

The compound was synthesized from compound 31.3 using General Procedure B to obtain 31.4. (0.1 g, Yield: 92.08%), MS (ES): m/z 313.13 [M+H]$^+$.

Synthesis of Compound 31.5

The compound was synthesized from compound 31.4 using General Procedure C to obtain 31.5. (0.060 g, Yield: 49.26%), MS (ES): m/z 381.15 [M+H]$^+$.

Synthesis of Compound I-31

The compound was synthesized from compound 1.3 and methylamine using General Procedure D. The material was further purified by column chromatography eluting with 2.5% methanol in dichloromethane to obtain I-31 (0.027 g, Yield: 27.06%), MS (ES): m/z 380.49 [M+H]$^+$ LCMS purity: 98.07%, HPLC purity: 99.07%, $^1$H NMR (DMSO-d$_6$, 400 MHz): 12.23 (bs, 1H), 11.33 (bs, 1H), 8.62 (bs, 1H),

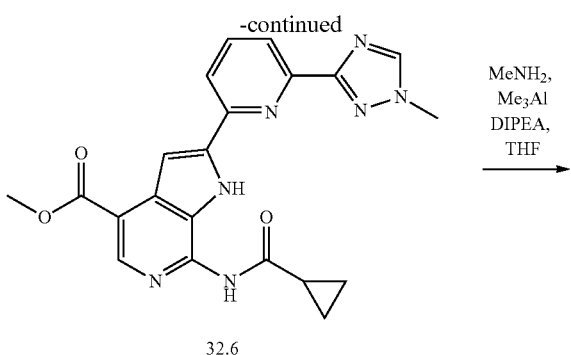

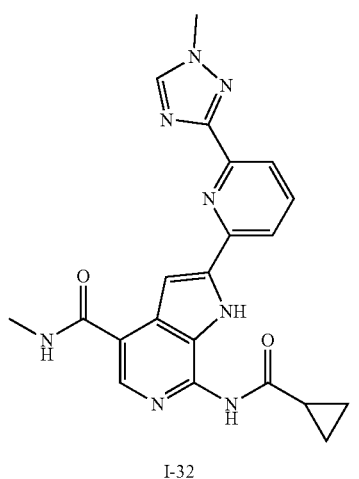

I-32

Synthesis of Compound 32.2

To a suspension of compound 32.1 (10 g, 54.64 mmol, 1.0 eq) in butanol (100 mL) was added formohydrazide (6.5 g, 109.28 mmol, 2.0) and reaction mixture was heated at 120° C. for 10 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by column chromatography and the compound was eluted in 40% ethyl acetate in hexane to obtain 32.2. (3.6 g, Yield: 29.27%). MS (ES): m/z 225.97 [M+H]$^+$.

Synthesis of Compound 32.3

To a solution of compound 32.2 (3.6 g, 16.00 mmol, 1.0 eq) in dimethylformamide (40 mL), was added sodium hydride (0.768 g, 32.00 mmol, 2 eq) at 0° C. and stirred for 20 min. Methyl iodide (2.4 g, 17.6 mmol, 1.1 eq) was added and reaction mixture was stirred at room temperature for 2 h. After completion of reaction, reaction mixture was transferred into ice, stirred and extracted with diethyl ether. Organic layer was combined, dried over sodium sulfate and concentrated under reduced pressure to obtain crude material. This was further purified by distillation to obtain pure 32.3. (1.4 g, Yield: 36.61%). MS (ES): m/z 238.99 [M+H]$^+$.

Synthesis of Compound 32.4

The compound was synthesized from Core C and compound 32.3 using General Procedure E to obtain 32.4. (0.190 g, Yield: 40.86%), MS (ES): m/z 670.22 [M+H]$^+$.

Synthesis of Compound 32.5

The compound was synthesized from compound 32.4 using General Procedure B to obtain 32.5. (0.090 g, Yield: 92.23%), MS (ES): m/z 350.13 [M+H]$^+$.

Synthesis of Compound 32.6

The compound was synthesized from compound 32.5 using General Procedure C to obtain 32.6. (0.80 g, Yield: 79.25%), MS (ES): m/z 418.16 [M+H]$^+$.

Synthesis of Compound I-32

The compound was synthesized from compound 32.6 and methylamine using General Procedure D. The material was further purified by column chromatography eluting with 2.5% methanol in dichloromethane to obtain I-32 (0.030 g, Yield: 33.41%), MS (ES): m/z 417.32 [M+H]$^+$ LCMS purity: 95.84%, HPLC purity: 95.00%, $^1$H NMR (DMSO-d$_6$, 400 MHz): 11.93 (s, 1H), 8.65 (s, 1H), 8.47 (bs, 1H), 8.28 (s, 1H), 8.19 (bs, 1H), 8.07 (bs, 1H), 7.71 (bs, 1H), 7.07 (bs, 1H), 6.82 (bs, 1H), 3.94 (s, 3H), 3.13 (bs, 3H), 1.54 (bs, 1H), 1.02 (bs, 4H).

Example 33: 7-(cyclopropanecarboxamido)-2-(2-ethoxypyridin-3-yl)-N-methyl-1H-pyrrolo[2,3-c]pyridine-4-carboxamide (I-33)

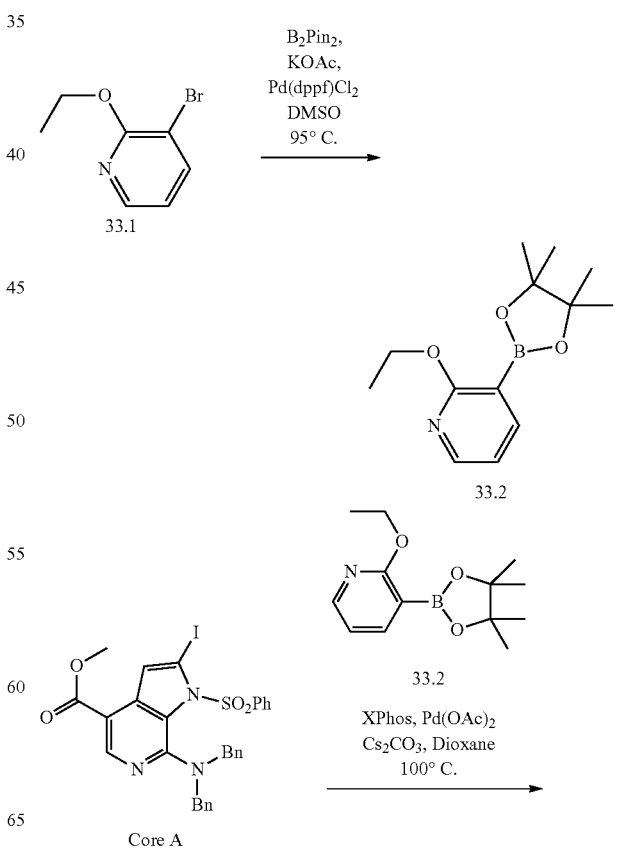

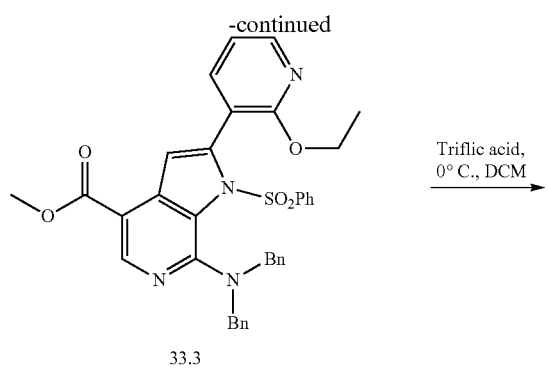

33.3

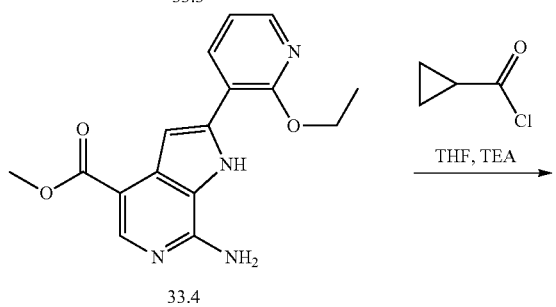

33.4

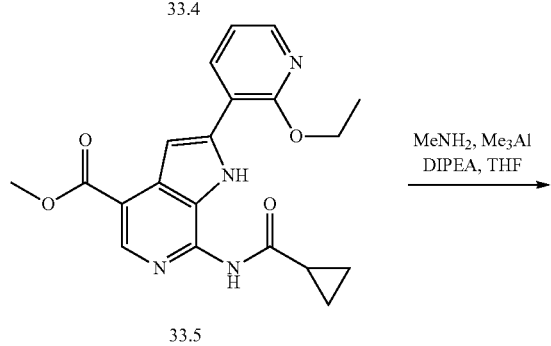

33.5

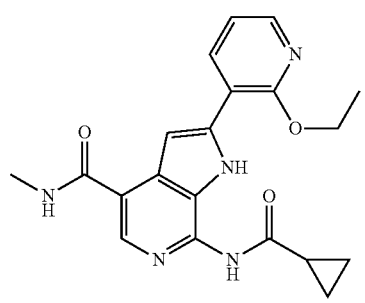

I-33

Synthesis of Compound 33.2

The compound was synthesized from compound 33.1 using General Procedure G to obtain 33.2. (0.450 g, Yield: 36.50%). MS (ES): m/z 250.16 [M+H]⁺.

Synthesis of Compound 33.3

To a solution of Core A (0.450 g, 0.70 mmol, 1.0 eq) in 1,4 dioxane (6 mL) was added compound 33.2 (0.210 g, 0.84 mmol, 1.2 eq) and cesium carbonate (0.455 g, 1.4 mmol, 2.0 eq). The reaction mixture was degassed for 10 min. under argon atmosphere, then palladium(II) acetate (0.235 g, 1.05 mmol, 1.5 eq) and 2-dicyclohexylphosphino-2',4',6'-triisopropylbiphenyl (0.033 g, 0.07 mmol, 0.1 eq) were added, again degassed for 5 min. The reaction was stirred at 100° C. for 4 h. After completion of reaction, reaction mixture was cooled to room temperature, transferred into water and product was extracted with ethyl acetate. Organic layer was combined, washed with brine solution, dried over sodium sulfate and concentrated under reduced pressure to obtain crude material. This was further purified by combi flash using 3% methanol in dichloromethane as eluant to obtain pure 33.3. (0.2 g, Yield: 44.78%). MS (ES): m/z 633.21 [M+H]⁺.

Synthesis of Compound 33.4

The compound was synthesized from compound 33.3 using General Procedure B to obtain 33.4. (0.098 g, Yield: 99.27%), MS (ES): m/z 313.13 [M+H]⁺.

Synthesis of Compound 33.5

The compound was synthesized from compound 33.4 using General Procedure C to obtain 33.5. (0.1 g, Yield: 74.64%), MS (ES): m/z 381.15 [M+H]⁺.

Synthesis of Compound I-33

The compound was synthesized from compound 33.5 and methylamine using General Procedure D. The material was further purified by column chromatography eluting with 2.5% methanol in dichloromethane to obtain I-33 (0.028 g, Yield: 28.07%), MS (ES): m/z 380.64 [M+H]⁺ LCMS purity: 97.05%, HPLC purity: 96.49%, ¹H NMR (DMSO-d₆, 400 MHz): 12.23 (bs, 1H), 11.33 (bs, 1H), 8.41-8.40 (d, J=7.2 Hz, 1H), 8.35 (bs, 1H), 8.29 (s, 1H), 8.23 (bs, 1H), 7.53 (bs, 1H), 7.18 (bs, 1H), 4.59-4.53 (m, 2H), 2.86-2.85 (d, J=3.6 Hz, 3H), 2.25 (bs, 1H), 1.51-1.47 (t, J=6.8 Hz, 3H), 0.97-0.95 (m, 4H).

Example 34: 7-(cyclopropanecarboxamido)-2-(2-cyclopropoxypyridin-3-yl)-N-methyl-1H-pyrrolo[2,3-c]pyridine-4-carboxamide (I-34)

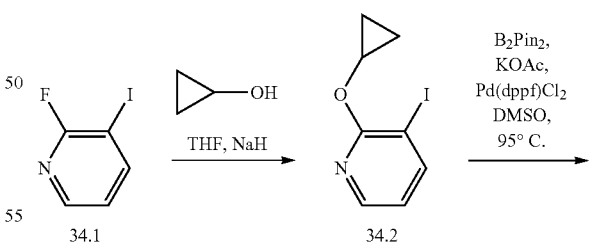

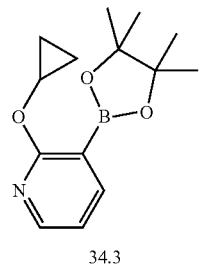

34.3

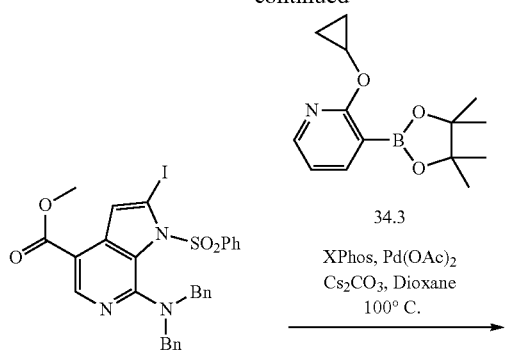

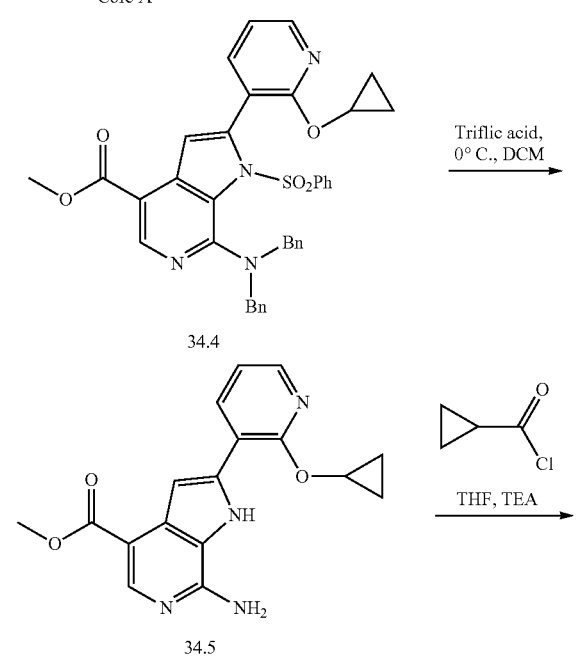

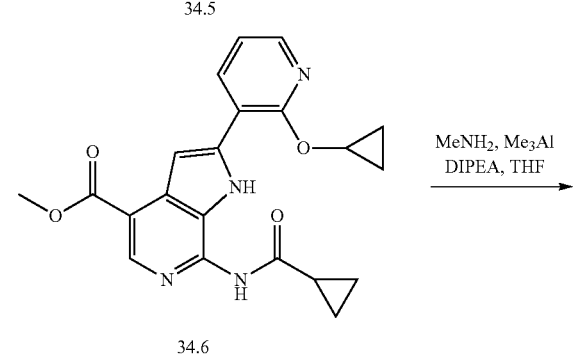

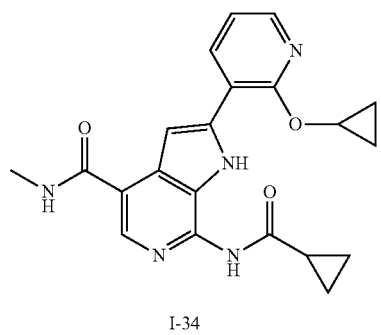

Synthesis of Compound 34.2

To a solution of compound 34.1 (2.0 g, 9.00 mmol, 1.0 eq) in tetrahydrofuran (20 mL), was added cyclopropanol (0.574 g, 9.9 mmol, 1.1 eq). Sodium hydride (0.432 g, 18.0 mmol, 2 eq) was added at 0° C. Reaction mixture was stirred at room temperature for 2 h. After completion of reaction, reaction mixture was transferred into ice-water, extracted with diethyl ether. Organic layer was combined, dried over sodium sulfate and concentrated under reduced pressure to obtain crude. This was further purified by distillation to obtain pure 34.2. (1.0 g, Yield: 42.71%). MS (ES): m/z 261.97 $[M+H]^+$.

Synthesis of Compound 34.3

The compound was synthesized from compound 34.2 using General Procedure G to obtain 34.3. (0.4 g, Yield: 39.99%). MS (ES): m/z 262.16 $[M+H]^+$.

Synthesis of Compound 34.4

To a solution of Core A (0.450 g, 0.70 mmol, 1.0 eq) in 1,4-dioxane (6 mL) was added compound 34.3 (0.219 g, 0.84 mmol, 1.2 eq) and cesium carbonate (0.455 g, 1.4 mmol, 2.0 eq). The reaction mixture was degassed for 10 min. under argon atmosphere, then palladium(II) acetate (0.235 g, 1.05 mmol, 1.5 eq) and 2-dicyclohexylphosphino-2',4',6'-triisopropylbiphenyl (0.033 g, 0.07 mmol, 0.1 eq) were added, again degassed for 5 min. The reaction was stirred at 100° C. for 4 h. After completion of reaction, reaction mixture was cooled to room temperature, transferred into water and product was extracted with ethyl acetate. Organic layer was combined, washed with brine solution, dried over sodium sulfate and concentrated under reduced pressure to obtain crude material. This was further purified by combi flash using 3% methanol in dichloromethane as eluant to obtain pure 34.4. (0.180 g, Yield: 39.55%). MS (ES): m/z 645.21 $[M+H]^+$.

Synthesis of Compound 34.5

The compound was synthesized from compound 34.4 using General Procedure B to obtain 34.5. (0.090 g, Yield: 99.39%), MS (ES): m/z 325.13 $[M+H]^+$.

Synthesis of Compound 34.6

The compound was synthesized from compound 34.5 using General Procedure C to obtain 34.6. (0.080 g, Yield: 64.83%), MS (ES): m/z 393.15 $[M+H]^+$.

Synthesis of Compound I-34

The compound was synthesized from compound 34.6 and methylamine using General Procedure D. The material was further purified by column chromatography eluting with 2.5% methanol in dichloromethane to obtain I-34 (0.026 g, Yield: 32.58%), MS (ES): m/z 392.57 $[M+H]^+$ LCMS purity: 99.56%, HPLC purity: 99.20%, $^1$H NMR (DMSO-$d_6$, 400 MHz): 12.03 (s, 1H), 11.63 (s, 1H), 8.43-8.42 (d, J=6 Hz, 1H), 8.35-8.34 (d, J=4.4 Hz, 1H), 8.29 (s, 2H), 7.53 (bs, 1H), 7.24-7.22 (m, 1H), 4.57-4.54 (m, 1H), 2.86-2.85 (d, J=3.6 Hz, 3H), 2.25 (bs, 1H), 1.06-0.97 (m, 6H), 0.86-0.80 (m, 2H).

Example 35: 7-(cyclopropanecarboxamido)-N-(methyl-d3)-2-(6-(1-methyl-1H-1,2,4-triazol-3-yl)pyridin-2-yl)-1H-pyrrolo[2,3-c]pyridine-4-carboxamide (I-35)

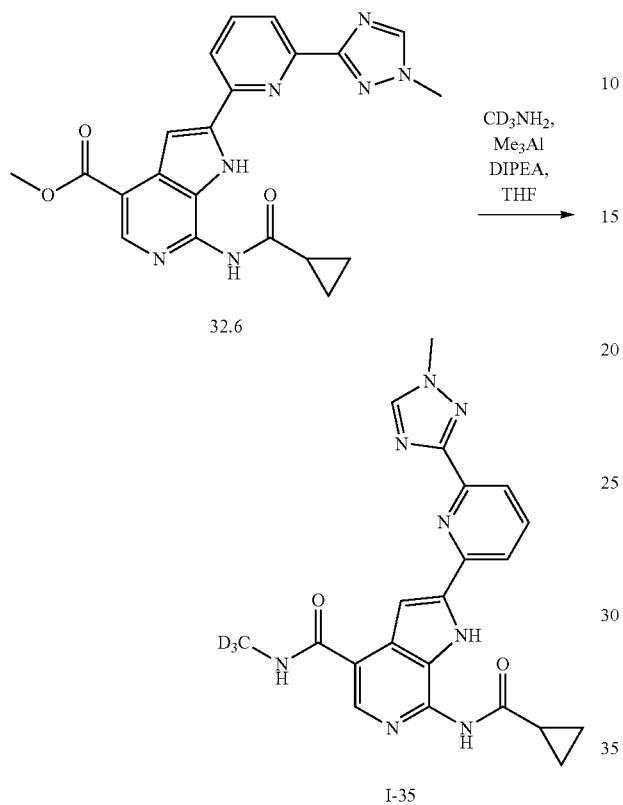

Synthesis of Compound I-35

The compound was synthesized from compound 32.6 and methyl-d₃-amine using General Procedure D. The material was further purified by column chromatography eluting with 2.5% methanol in dichloromethane to obtain I-35 (0.027 g, Yield: 22.39%), MS (ES): m/z 420.72 [M+H]⁺ LCMS purity: 96.23%, HPLC purity: 97.86%, $^1$H NMR (DMSO-d₆, 400 MHz): 11.79 (s, 1H), 11.32 (s, 1H), 8.65 (s, 1H), 8.38 (s, 1H), 8.31 (s, 1H), 8.15-8.12 (m, 1H), 8.05-8.04 (d, J=3.6 Hz, 2H), 7.67 (s, 1H), 4.01 (s, 3H), 2.27 (bs, 1H), 1.06-0.96 (m, 4H).

Example 36: 7-(cyclopropanecarboxamido)-2-(2-fluoro-3-(1-methyl-1H-1,2,4-triazol-3-yl)phenyl)-N-methyl-1H-pyrrolo[2,3-c]pyridine-4-carboxamide (I-36)

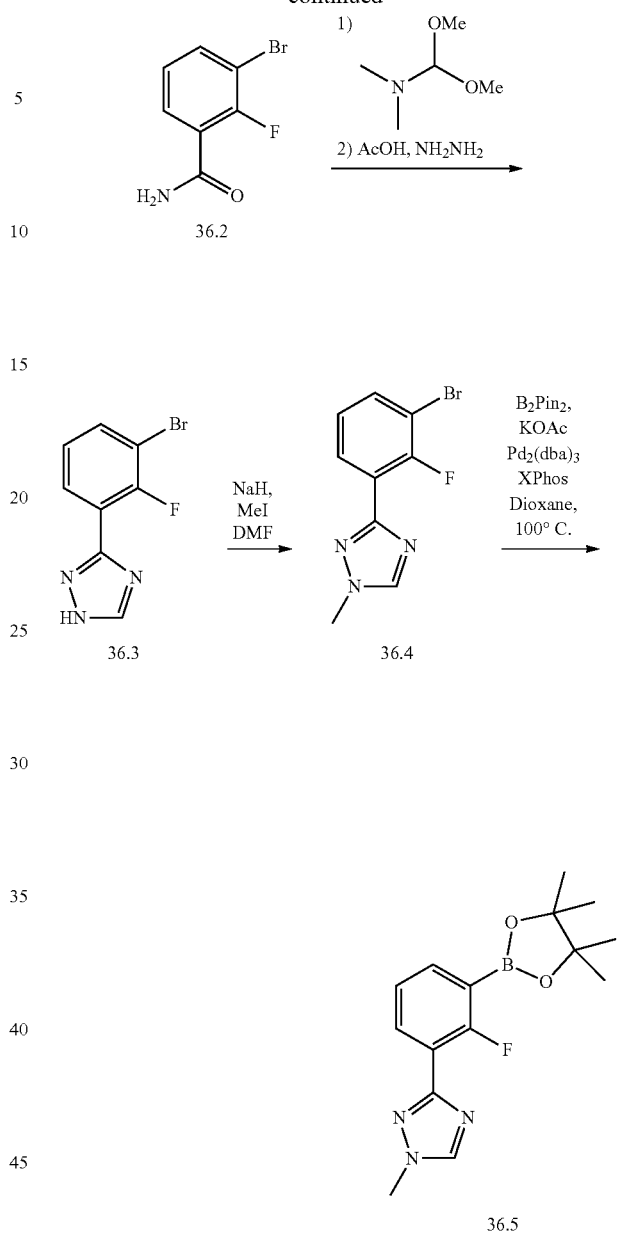

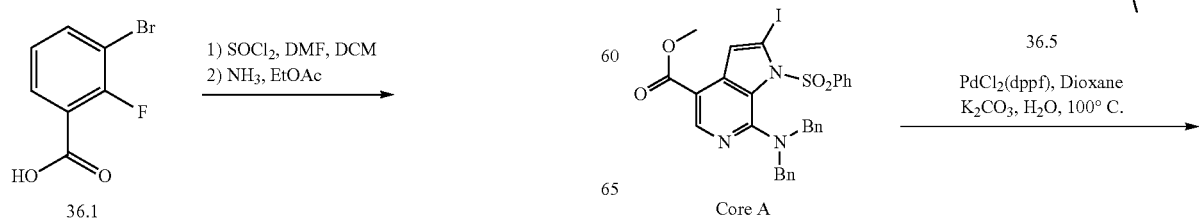

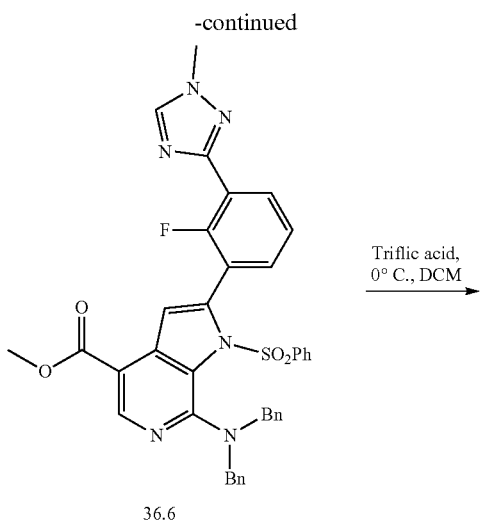

36.6

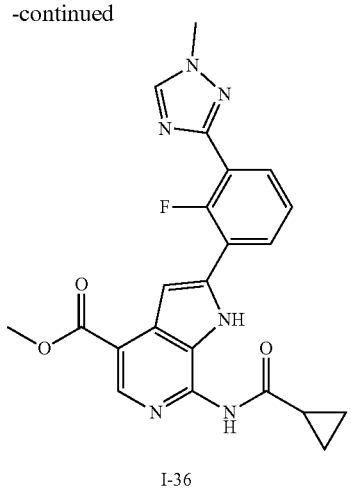

36.7

36.8

Triflic acid, 0° C., DCM

THF, TEA

MeNH₂, Me₃Al DIPEA, THF

I-36

Synthesis of Compound 36.2

To a solution of compound 36.1 (1.0 g, 4.56 mmol, 1.0 eq) in dichloromethane (15 mL) was added thionyl chloride (3.28 mL, 45.6 mmol, 10.0 eq) at 0° C. with catalytic dimethylformamide (0.5 mL). Reaction mixture was stirred at 70° C. for 2 h. After completion of reaction, reaction mixture was concentrated under reduced pressure to obtain crude material. To this crude material was added 20 ml ethyl acetate followed by 20 mL aqueous ammonia solution and stirred at room temperature for 1 h. The organic layer was separated, washed with brine solution, dried over sodium sulfate and concentrated under reduced pressure to obtain crude material. This was further purified by column chromatography using 30% ethyl acetate in hexane to obtain 36.2. (0.850 g, Yield: 85.38%), MS (ES): m/z 218.95 [M+H]⁺.

Synthesis of Compound 36.3

To a solution of compound 36.2 (0.850 g, 3.89 mmol, 1.0 eq) in dimethylformamide (10 mL) was added dimethylformamide dimethylacetal (0.555 g, 4.66 mmol, 1.2 eq). Reaction mixture was heated at 120° C. for 1 h. After completion of reaction, reaction mixture was cooled and was added acetic acid (8 mL) followed by hydrazine hydrate (0.972 g, 19.45 mmol, 5.0 eq) and again heated at 120° C. for 2 h. After completion of reaction, reaction mixture was transferred to ice cold water and product was extracted with ethyl acetate. Organic layer was combined, washed with brine solution, dried over sodium sulfate and concentrated under reduced pressure to obtain crude material. This was further purified by column chromatography eluting with 40% ethyl acetate in hexane to obtain 36.3. (0.7 g, Yield: 74.18%), MS (ES): m/z 242.96 [M+H]⁺.

Synthesis of Compound 36.4

To a solution of compound 36.3 (0.450 g, 1.85 mmol, 1.0 eq) in dimethylformamide (5 mL), was added methyl iodide (0.288 g, 2.03 mmol, 1.1 eq). Sodium hydride (0.088 g, 3.7 mmol, 2.0 eq) was added at 0° C. Reaction mixture was stirred at room temperature for 2 h. After completion of reaction, reaction mixture was transferred into ice, stirred and extracted with diethyl ether. Organic layer was combined, dried over sodium sulfate and concentrated under reduced pressure to obtain crude material. This was further purified by distillation to obtain pure 36.4. (0.472 g, Yield: 99.14%). MS (ES): m/z 256.98 [M+H]$^+$.

Synthesis of Compound 36.5

The compound was synthesized from compound 36.4 using General Procedure F, using 2-dicyclohexylphosphino-2',4',6'-triisopropylbiphenyl instead of 4,5-bis(diphenylphosphino)-9,9-dimethylxanthene, to obtain 36.5. (0.4 g, Yield: 67.58%). MS (ES): m/z 304.16 [M+H]$^+$.

Synthesis of Compound 36.6

The compound was synthesized from Core A and compound 36.5 using General Procedure A to obtain 36.6. (0.210 g, Yield: 43.32%), MS (ES): m/z 687.21 [M+H]$^+$.

Synthesis of Compound 36.7

The compound was synthesized from compound 36.6 using General Procedure B to obtain 36.7. (0.115 g, Yield: 98.19%), MS (ES): m/z 367.13 [M+H]$^+$.

Synthesis of Compound 36.8

The compound was synthesized from compound 36.7 using General Procedure C to obtain 36.8. (0.110 g, Yield: 77.30%), MS (ES): m/z 435.15 [M+H]$^+$.

Synthesis of Compound I-36

The compound was synthesized from compound 36.8 and methylamine using General Procedure D. The material was further purified by column chromatography eluting with 2.5% methanol in dichloromethane to obtain I-36 (0.025 g, Yield: 22.78%), MS (ES): m/z 434.56 [M+H]$^+$ LCMS purity: 97.82%, HPLC purity: 97.68%, $^1$H NMR (DMSO-d$_6$, 400 MHz): 12.10 (s, 1H), 11.32 (bs, 1H), 8.65 (bs, 1H), 8.39 (bs, 1H), 8.32 (bs, 1H), 8.05-8.03 (m, 2H), 7.51-7.48 (m, 2H), 3.99 (s, 3H), 2.85 (bs, 3H), 2.23 (bs, 1H), 0.99-0.95 (m, 4H).

Example 37: 7-(cyclopropanecarboxamido)-2-(2-ethoxy-5-(1-methyl-1H-pyrazol-3-yl) pyridin-3-yl)-N-methyl-1H-pyrrolo[2,3-c]pyridine-4-carboxamide (I-37)

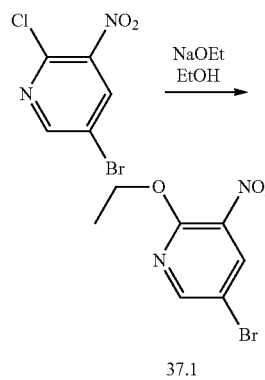

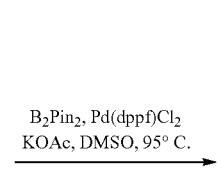

37.1

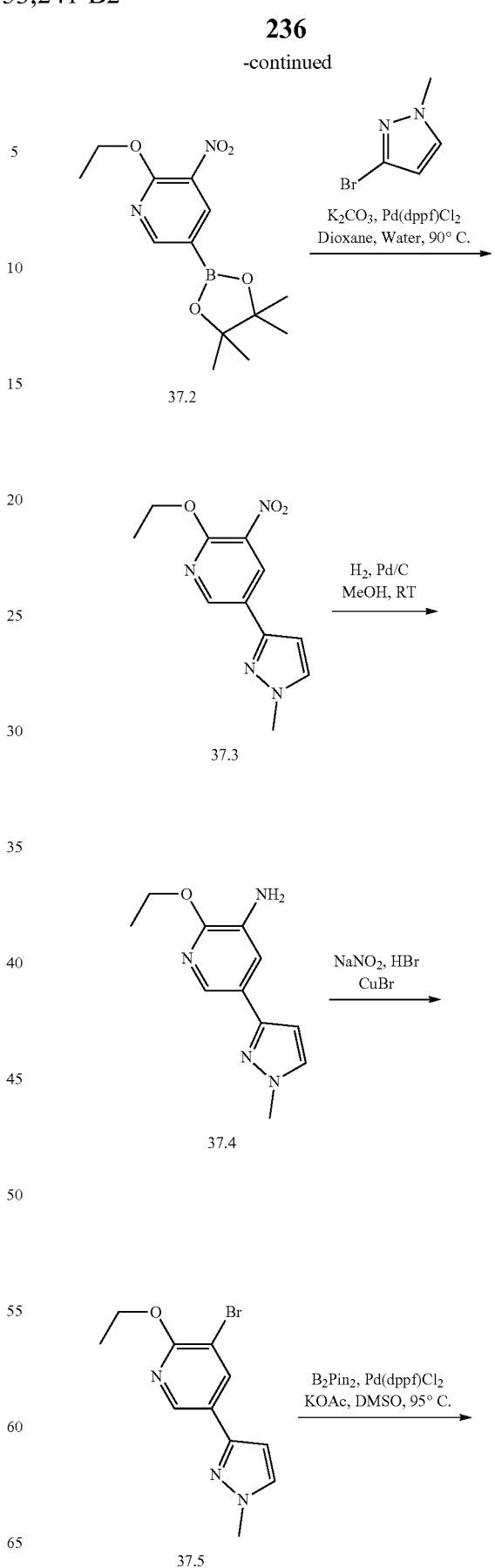

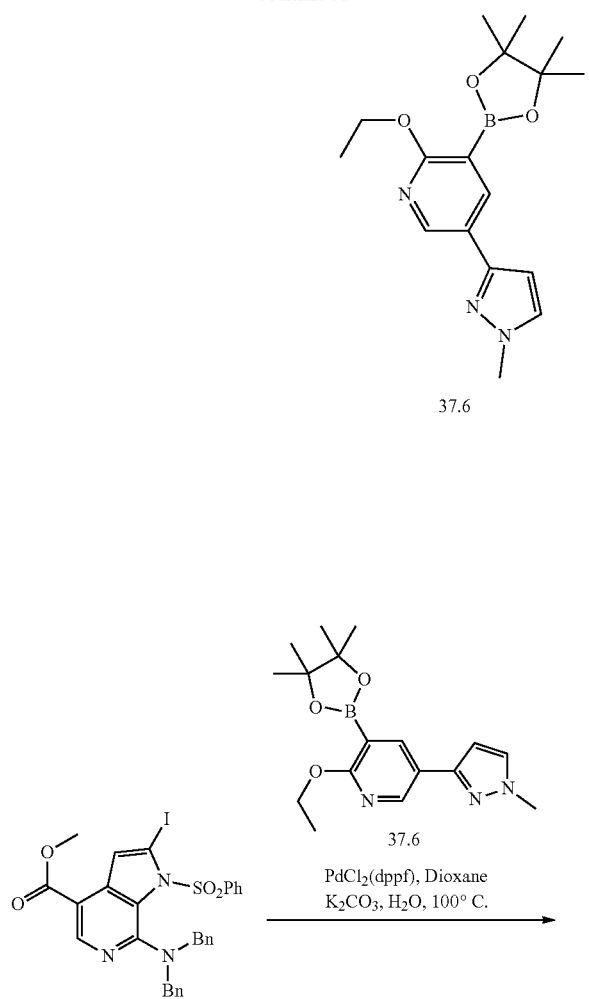

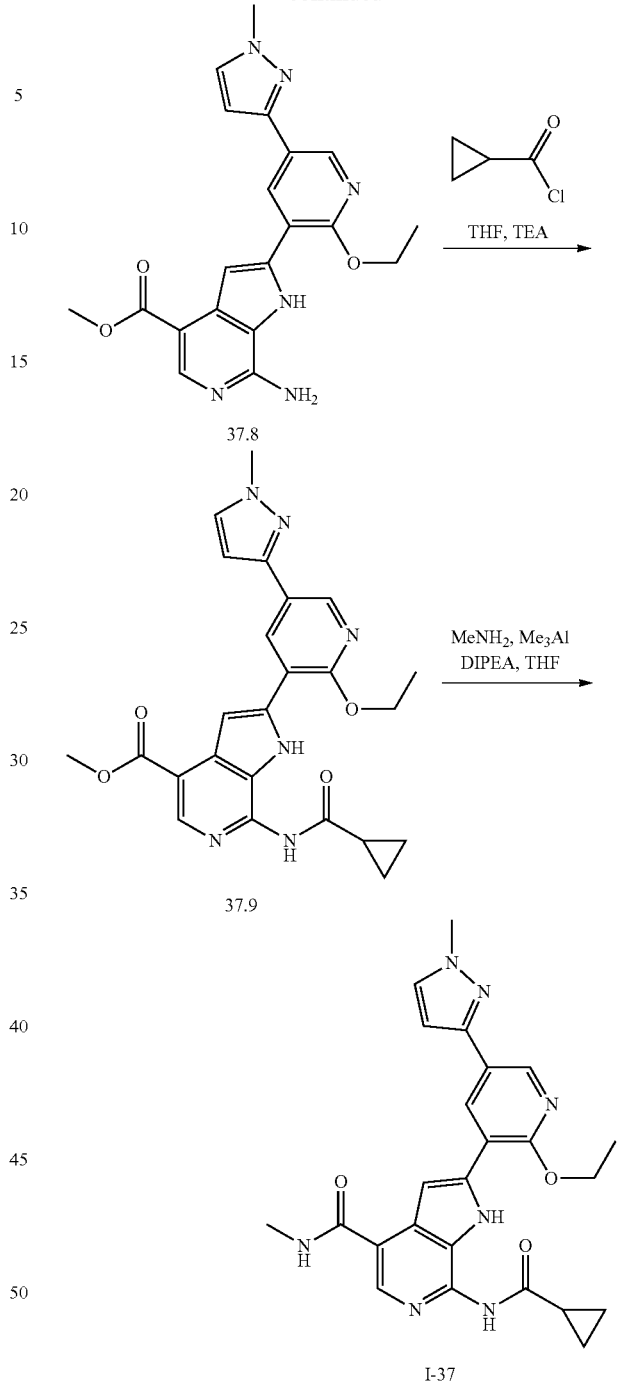

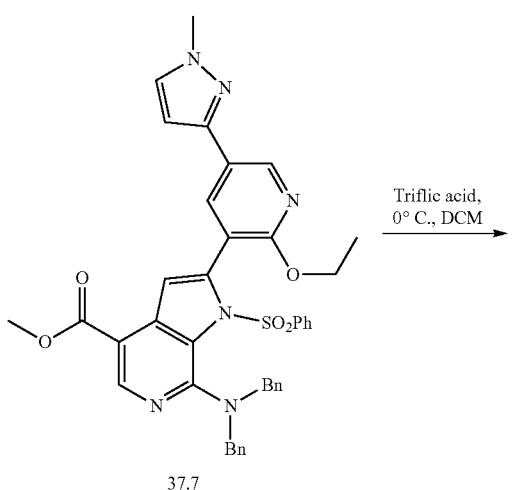

Synthesis of Compound 37.1

To a solution of 5-bromo-2-chloro-3-nitropyridine (5.0 g, 21.09 mmol, 1.0 eq) in ethanol (250 mL) was added dropwise sodium ethoxide (8.3 mL, 21% ethanol solution, 1.2 eq). Reaction mixture was stirred and heated at 80° C. for 1 h. After completion of reaction, reaction mixture was cooled to room temperature, transferred into water and product was extracted with ethyl acetate. Organic layer was combined, washed with brine solution, dried over sodium sulfate and concentrated under reduced pressure to obtain 37.1 (3.0 g, Yield: 57.67%). MS (ES): m/z 246.97 [M+H]+.

Synthesis of Compound 37.2

The compound was synthesized from compound 37.1 using General Procedure G to obtain 37.2. (2.3 g, Yield: 64.40%). MS (ES): m/z 295.14 [M+H]$^+$.

Synthesis of Compound 37.3

The compound was synthesized from compound 37.2 and 3-bromo-1-methyl-1H-pyrazole using General Procedure A to obtain 37.3. (1.5 g, Yield: 77.27%), MS (ES): m/z 249.09 [M+H]$^+$.

Synthesis of Compound 37.4

To a solution of compound 37.3 (1.5 g, 6.04 mmol, 1.0 eq) in methanol (30 ml), palladium on charcoal (0.8 g) was added. Hydrogen was purged through reaction mixture for 4 h at room temperature. After completion of reaction, reaction mixture was filtered through Celite bed and washed with methanol. Filtrate was concentrated under reduced pressure to obtain crude material. This was further purified by trituration with n-pentane to obtain pure 37.4. (1.1 g, 83.41%). MS (ES): m/z 219.11 [M+H]$^+$.

Synthesis of Compound 37.5

To the compound 37.4 (1.1 g, 5.02 mmol, 1.0 eq) was added 30% hydrobromic acid (2.2 mL) dropwise at 0° C. Sodium nitrite (0.692 g, 10.04 mmol, 2.0 eq) and acetone (8.8 mL) were added to this reaction mixture and stirred for 2 min. Then copper(I) bromide (1.4 g, 10.04 mmol, 2.0 eq) was added and reaction mixture was stirred for 15 min. After completion of reaction, reaction mixture was transferred into water and product was extracted with ethyl acetate. Organic layer was combined, washed with brine solution, dried over sodium sulfate and concentrated under reduced pressure to obtain 37.5. (0.7 g, Yield: 49.23%). MS (ES): m/z 282.02 [M+H]$^+$.

Synthesis of Compound 37.6

The compound was synthesized from compound 37.5 using General Procedure G to obtain 37.6. (0.4 g, Yield: 57.14%). MS (ES): m/z 330.19 [M+H]$^+$.

Synthesis of Compound 37.7

The compound was synthesized from Core A and compound 37.6 using General Procedure A to obtain 37.7. (0.2 g, Yield: 39.75%), MS (ES): m/z 713.25 [M+H]$^+$.

Synthesis of Compound 37.8

The compound was synthesized from compound 37.7 using General Procedure B to obtain 37.8. (0.1 g, Yield: 90.82%), MS (ES): m/z 393.16 [M+H]$^+$.

Synthesis of Compound 37.9

The compound was synthesized from compound 37.8 using General Procedure C to obtain 37.9. (0.095 g, Yield: 80.96%), MS (ES): m/z 461.19 [M+H]$^+$.

Synthesis of Compound I-37

The compound was synthesized from compound 37.9 and methylamine using General Procedure D. The material was further purified by column chromatography eluting with 2.5% methanol in dichloromethane to obtain I-37 (0.080 g, Yield: 84.39%), MS (ES): m/z 460.96 [M+H]$^+$ LCMS purity: 100%, HPLC purity: 99.73%, $^1$H NMR (DMSO-d$_6$, 400 MHz): 12.27 (s, 1H), 11.34 (s, 1H), 8.66 (bs, 1H), 8.64-8.63 (d, J=2 Hz, 1H), 8.39-8.38 (d, J=4.4 Hz, 1H), 8.30 (s, 1H), 7.80-7.80 (d, J=2 Hz, 1H), 7.60 (bs, 1H), 6.89 (bs, 1H), 4.61-4.55 (m, 2H), 3.93 (s, 3H), 2.86-2.85 (d, J=4.8 Hz, 3H), 2.24 (bs, 1H), 1.52-1.48 (t, J=7.2 Hz, 3H), 0.98-0.95 (m, 4H).

Example 38: 7-(cyclopropanecarboxamido)-2-(2-cyclopropoxy-5-(1-methyl-1H-pyrazol-3-yl)pyridin-3-yl)-N-methyl-1H-pyrrolo[2,3-c]pyridine-4-carboxamide (I-38)

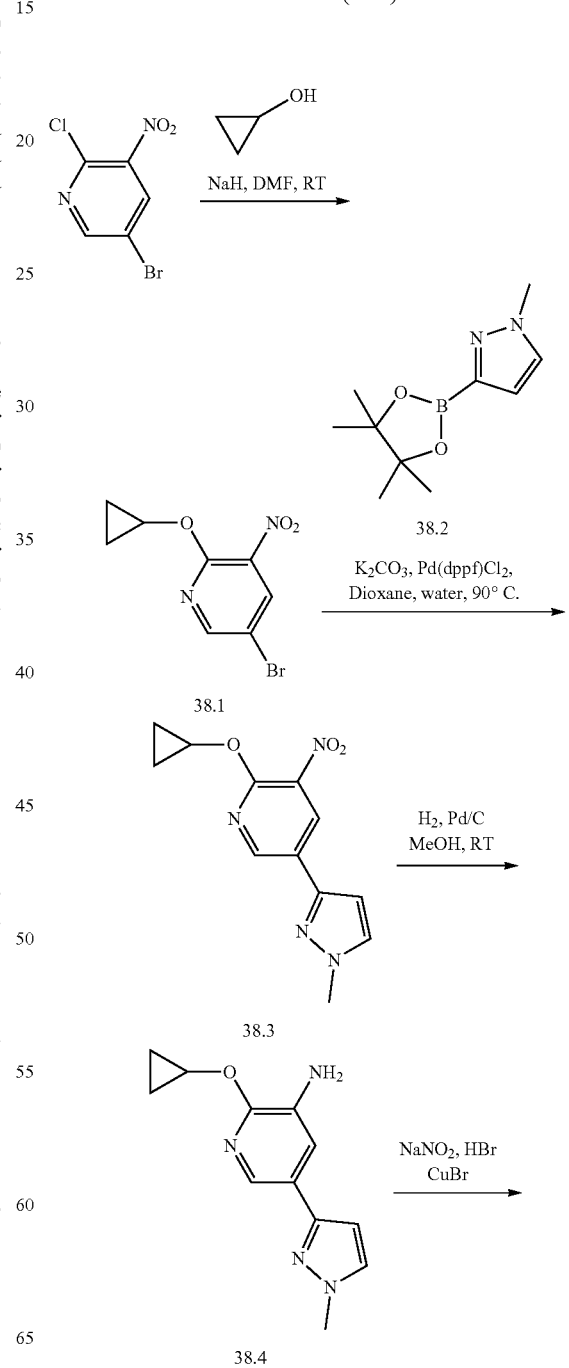

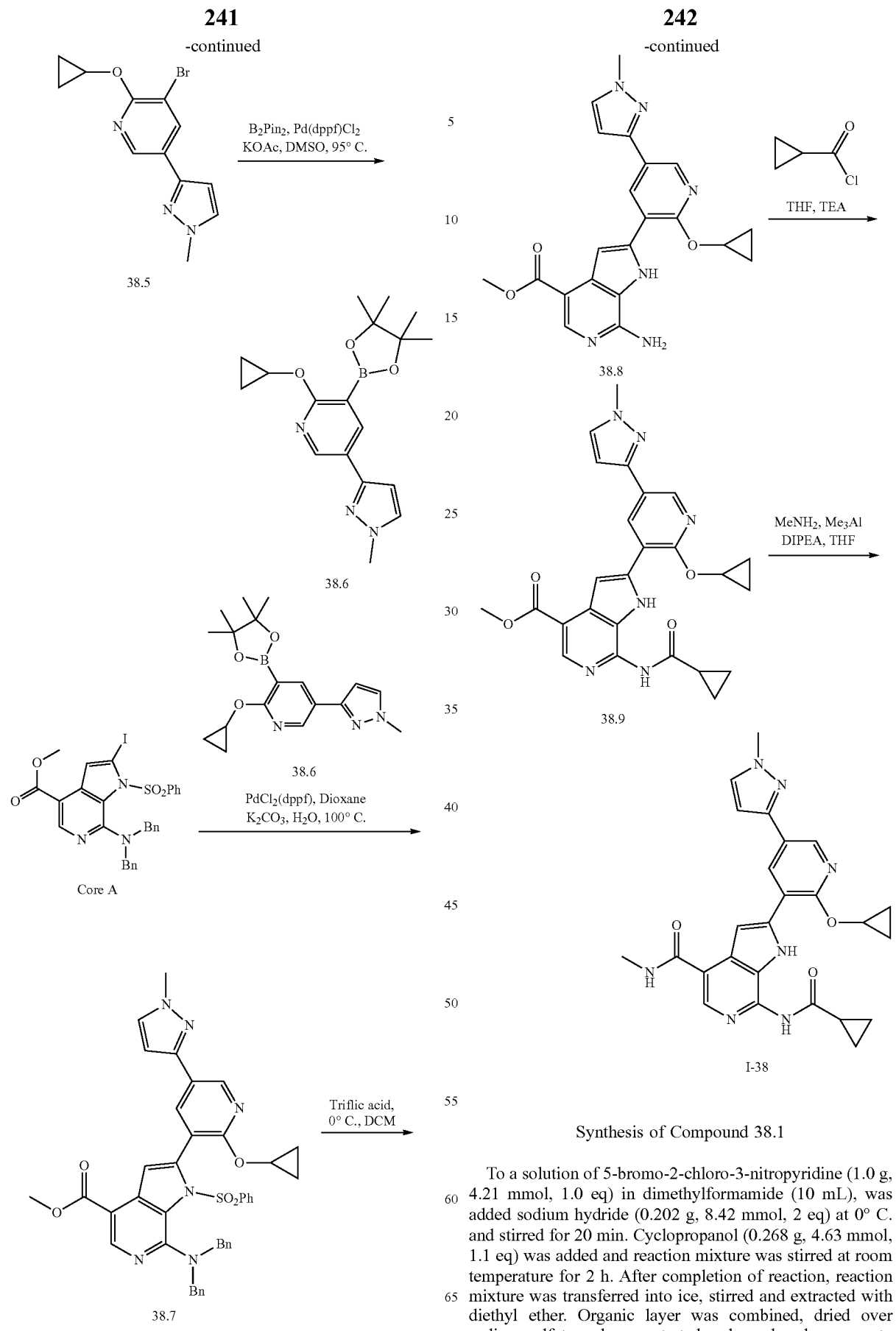

Synthesis of Compound 38.1

To a solution of 5-bromo-2-chloro-3-nitropyridine (1.0 g, 4.21 mmol, 1.0 eq) in dimethylformamide (10 mL), was added sodium hydride (0.202 g, 8.42 mmol, 2 eq) at 0° C. and stirred for 20 min. Cyclopropanol (0.268 g, 4.63 mmol, 1.1 eq) was added and reaction mixture was stirred at room temperature for 2 h. After completion of reaction, reaction mixture was transferred into ice, stirred and extracted with diethyl ether. Organic layer was combined, dried over sodium sulfate and concentrated under reduced pressure to obtain crude material. This was further purified by distillation to obtain pure 38.1. (0.34 g, Yield: 31.16%). MS (ES): m/z 259.96 [M+H]+.

Synthesis of Compound 38.3

The compound was synthesized from compounds 38.1 and 38.2 using General Procedure A to obtain 38.3. (1.2 g, Yield: 74.66%), MS (ES): m/z 261.09 [M+H]+.

Synthesis of Compound 38.4

To a solution of compound 38.3 (1.2 g, 4.61 mmol, 1.0 eq) in methanol (25 ml), palladium on charcoal (0.6 g) was added. Hydrogen was purged through reaction mixture for 4 h at room temperature. After completion of reaction, reaction mixture was filtered through Celite-bed and washed with methanol. Filtrate was concentrated under reduced pressure to obtain crude material. This was further purified by trituration with n-pentane to obtain pure 38.4. (0.9 g, Yield: 84.77%). MS (ES): m/z 231.12 [M+H]+.

Synthesis of Compound 38.5

To compound 38.4. (0.9 g, 3.89 mmol, 1.0 eq) was added 30% hydrobromic acid (1.8 mL) dropwise at 0° C. Sodium nitrite (0.536 g, 7.78 mmol, 2.0 eq) and acetone (7.2 mL) were added to this reaction mixture and stirred for 2 min. Then copper(I) bromide (1.1 g, 7.78 mmol, 2.0 eq) was added and reaction mixture was stirred for 15 min. After completion of reaction, reaction mixture was transferred into water and product was extracted with ethyl acetate. Organic layer was combined, washed with brine solution, dried over sodium sulfate and concentrated under reduced pressure to obtain 38.5. (0.540 g, Yield: 46.97%). MS (ES): m/z 295.01 [M+H]+.

Synthesis of Compound 38.6

The compound was synthesized from compound 38.5 using General Procedure G to obtain 38.6. (0.4 g, Yield: 63.86%). MS (ES): m/z 342.19 [M+H]+.

Synthesis of Compound 38.7

The compound was synthesized from Core A and compound 38.6 using General Procedure A to obtain 38.7. (0.230 g, Yield: 44.95%), MS (ES): m/z 725.25 [M+H]+.

Synthesis of Compound 38.8

The compound was synthesized from compound 38.7 using General Procedure B to obtain 38.8. (0.115 g, Yield: 89.61%), MS (ES): m/z 405.16 [M+H]+.

Synthesis of Compound 38.9

The compound was synthesized from compound 38.8 using General Procedure C to obtain 38.9. (0.1 g, Yield: 74.43%). MS (ES): m/z 473.19 [M+H]+.

Synthesis of Compound I-38

The compound was synthesized from compound 38.9 and methylamine using General Procedure D. The material was further purified by column chromatography eluting with 2.5% methanol in dichloromethane to obtain I-38 (0.074 g, Yield: 74.15%), MS (ES): m/z 472.82 [M+H]+ LCMS purity: 96.41%, HPLC purity: 95.48%, 1H NMR (DMSO-$d_6$, 400 MHz): 12.07 (s, 1H), 11.35 (s, 1H), 8.67 (bs, 2H), 8.38 (bs, 1H), 8.30 (s, 1H), 7.80 (bs, 1H), 7.60 (bs, 1H), 6.90 (bs, 1H), 4.59 (bs, 1H), 3.94 (s, 3H), 2.86-2.85 (d, J=4.8 Hz, 3H), 1.23 (bs, 2H), 1.08-1.02 (m, 5H), 0.83 (bs, 2H).

Example 39: 7-(cyclopropanecarboxamido)-2-(2-cyclopropoxy-5-(thiazol-2-yl)pyridin-3-yl)-N-methyl-1H-pyrrolo[2,3-c]pyridine-4-carboxamide (I-39)

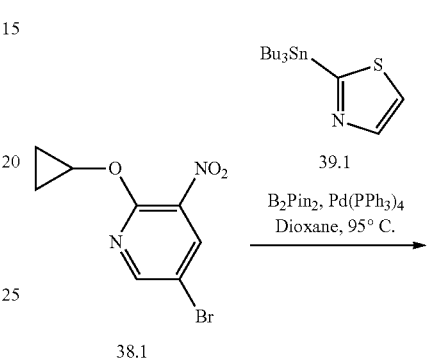

38.1

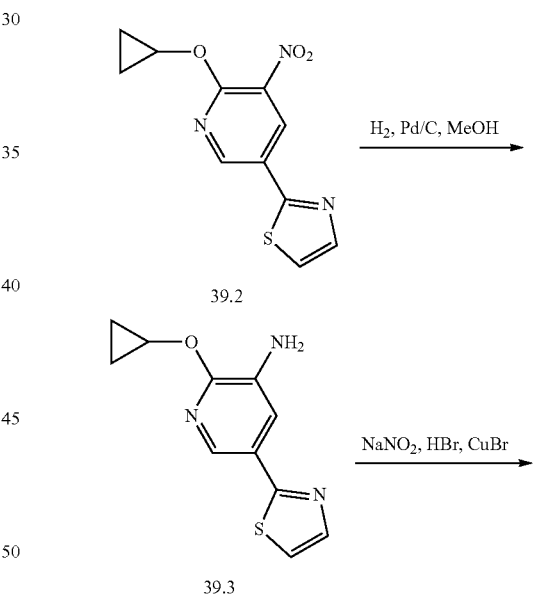

39.2

39.3

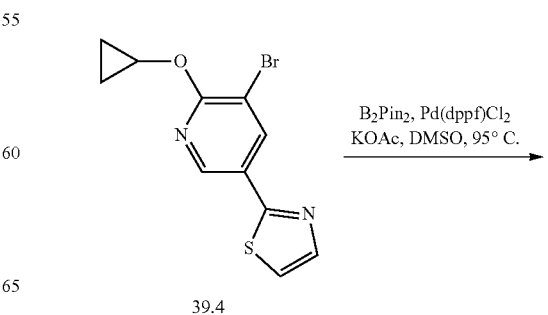

39.4

-continued

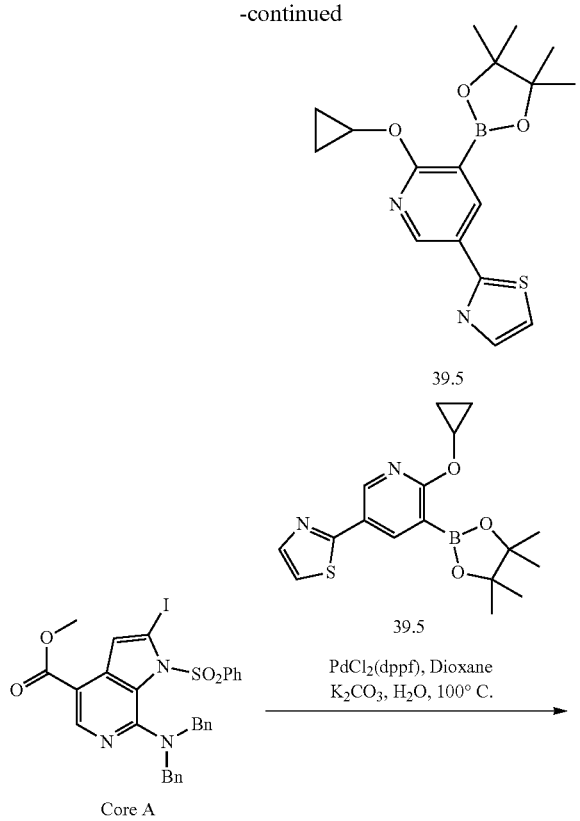

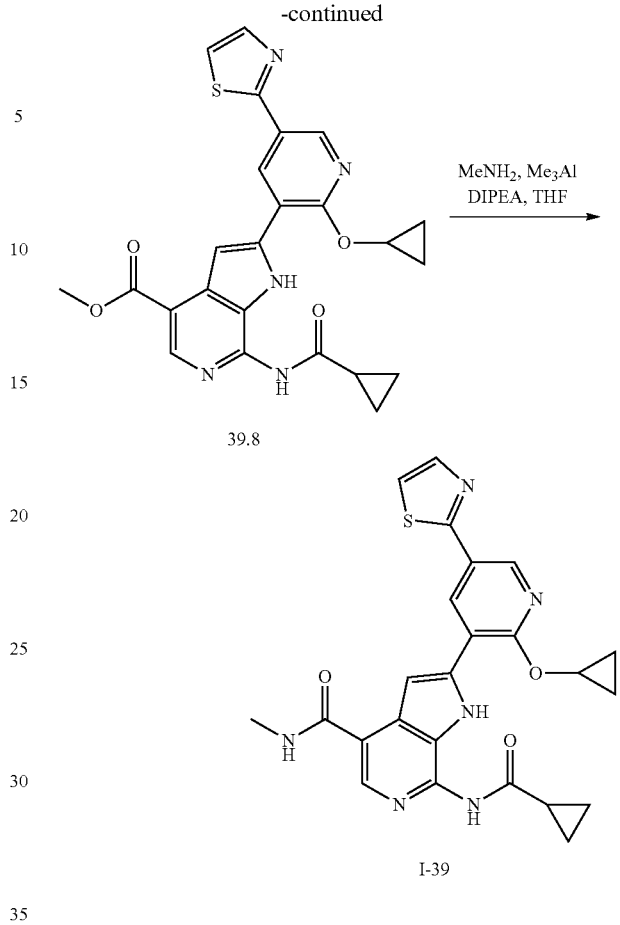

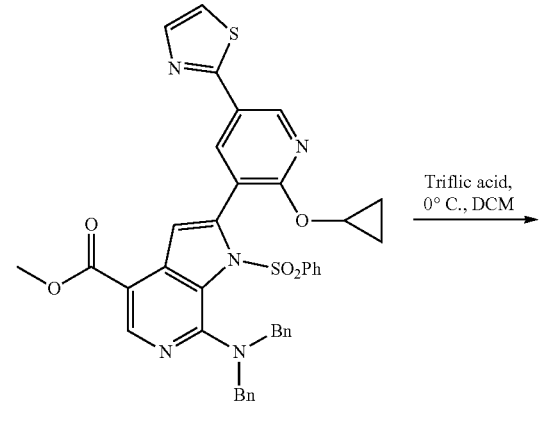

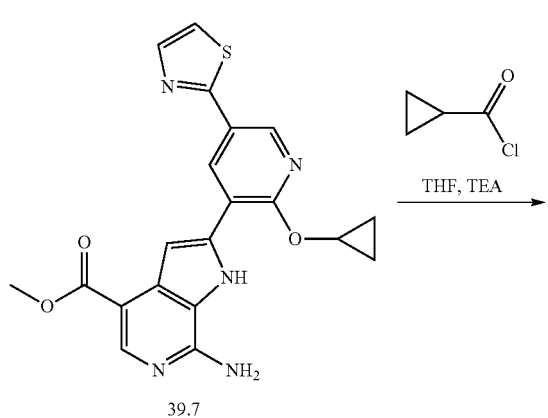

Synthesis of Compound 39.2

To a solution of 38.1 (1.1 g, 4.24 mmol, 1.0 eq) in 1,4-dioxane (15 mL) was added bis(pinacolato)diboron (1.2 g, 5.08 mmol, 1.2 eq). The reaction mixture was degassed for 10 min. under argon atmosphere, then tetrakis(triphenylphosphine)palladium(0) (0.489 g, 0.42 mmol, 0.1 eq) and compound 39.1 (1.5 g, 5.08 mmol, 1.0 eq) added, again degassed for 5 min. The reaction was stirred at 95° C. for 4 h. After completion of reaction, reaction mixture was cooled to room temperature, transferred into water and product was extracted with ethyl acetate. Organic layer was combined, washed with brine solution, dried over sodium sulfate and concentrated under reduced pressure to obtain crude material. This was further purified by combi flash using 3% methanol in dichloromethane as eluant to obtain pure 39.2. (1.1 g, Yield: 77.31%). MS (ES): m/z 264.04 [M+H]$^+$.

Synthesis of Compound 39.3

To a solution of compound 39.2 (1.1 g, 4.16 mmol, 1.0 eq) in methanol (15 ml), palladium on charcoal (0.4 g) was added. Hydrogen was purged through reaction mixture for 4 h at room temperature. After completion of reaction, reaction mixture was filtered through Celite-bed and washed with methanol. Filtrate was concentrated under reduced pressure to obtain crude material. This was further purified by trituration with n-pentane to obtain pure 39.3. (0.8 g, Yield: 82.07%). MS (ES): m/z 234.07 [M+H]$^+$.

Synthesis of Compound 39.4

To the compound 39.3. (0.8 g, 3.41 mmol, 1.0 eq) was added 30% hydrobromic acid (1.6 mL) dropwise at 0° C.

Sodium nitrite (0.536 g, 7.78 mmol, 2.0 eq) and acetone (6.4 mL) were added to this reaction mixture and stirred for 2 min. Then copper(I) bromide (0.975 g, 6.82 mmol, 2.0 eq) was added and reaction mixture was stirred for 15 min. After completion of reaction, reaction mixture was transferred into water and product was extracted with ethyl acetate. Organic layer was combined, washed with brine solution, dried over sodium sulfate and concentrated under reduced pressure to obtain 39.4. (0.5 g, Yield: 49.06%). MS (ES): m/z 296.97 [M+H]$^+$.

Synthesis of Compound 39.5

The compound was synthesized from compound 39.4 using General Procedure G to obtain 39.5. (0.4 g, Yield: 69.06%). MS (ES): m/z 345.14 [M+H]$^+$.

Synthesis of Compound 39.6

The compound was synthesized from Core A and compound 39.5 using General Procedure A to obtain 39.6. (0.180 g, Yield: 35.03%), MS (ES): m/z 728.20 [M+H]$^+$.

Synthesis of Compound 39.7

The compound was synthesized from compound 39.6 using General Procedure B to obtain 39.7. (0.090 g, Yield: 89.32%), MS (ES): m/z 408.11 [M+H]$^+$.

Synthesis of Compound 39.8

The compound was synthesized from compound 39.7 using General Procedure C to obtain 39.8. (0.080 g, Yield: 76.16%), MS (ES): m/z 476.13 [M+H]$^+$.

Synthesis of Compound I-39

The compound was synthesized from compound 39.8 and methylamine using General Procedure D. The material was further purified by column chromatography eluting with 2.5% methanol in dichloromethane to obtain I-39 (0.069 g, Yield: 86.43%), MS (ES): m/z 475.82 [M+H]$^+$ LCMS purity: 98.79%, HPLC purity: 96.44%, $^1$H NMR (DMSO-d$_6$, 400 MHz): 12.13 (s, 1H), 11.39 (s, 1H), 8.86 (bs, 1H), 8.80 (bs, 1H), 8.38 (bs, 1H), 8.32 (bs, 1H), 8.01 (bs, 1H), 7.90 (bs, 1H), 7.65 (bs, 1H), 4.64 (bs, 1H), 2.87-2.86 (d, J=4.8 Hz, 3H), 1.24 (bs, 4H), 1.12 (bs, 1H), 0.87-0.86 (m, 4H).

Example 40: 7-(cyclopropanecarboxamido)-2-(1-cyclopropyl-6-oxo-1,6-dihydropyridin-3-yl)-N-methyl-1H-pyrrolo[2,3-c]pyridine-4-carboxamide (I-40)

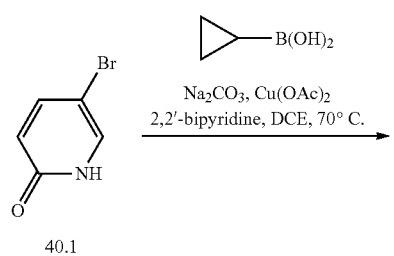
40.1

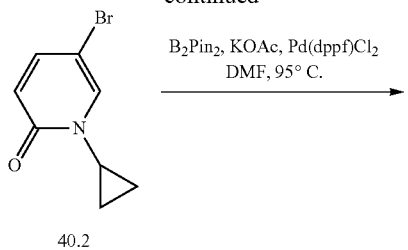
40.2

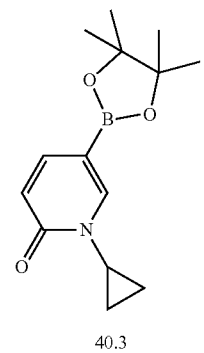
40.3

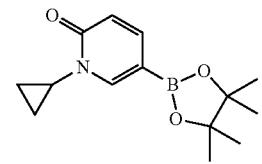
40.3

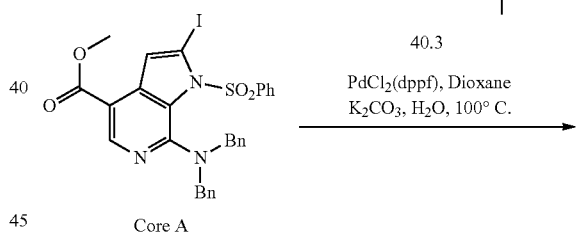
Core A

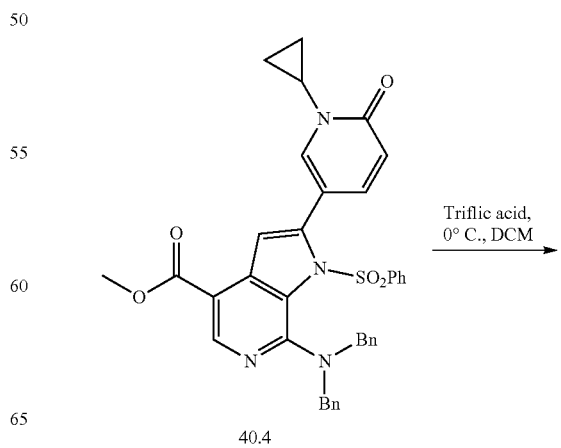
40.4

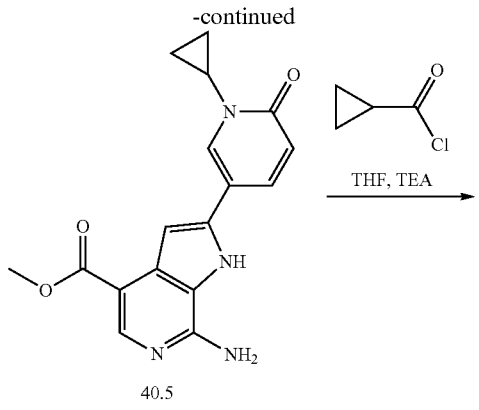

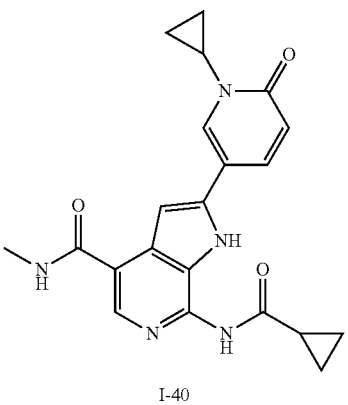

Synthesis of Compound 40.2

Argon was purged for 15 min through a stirred mixture of compound 40.1 (2.0 g, 11.49 mmol, 1.0 eq), sodium carbonate (3.6 g, 34.4 mmol, 3.0 eq), cyclopropyl boronic acid (1.2 g, 14.93 mmol, 1.3 eq) and cupric acetate (5.1 g, 28.72 mmol, 2.5 eq) in 1,2-dichloroethane (80 mL). 2,2'-Bipyridine (0.182 mg, 1.17 mmol, 0.5 eq) was added to it and further purging done for 10 min. Reaction was allowed to stir at 50° C. for 6 h. After completion of reaction, reaction mixture was poured over water and product was extracted with ethyl acetate. Organic layer was combined, washed with brine solution, dried over sodium sulfate and concentrated under reduced pressure to obtain 40.2. (1.0 g, Yield: 40.64%). MS (ES): m/z 213.98 [M+H]$^+$.

Synthesis of Compound 40.3

The compound was synthesized from compound 40.2 using General Procedure G to obtain 40.3. (0.4 g, Yield: 36.43%). MS (ES): m/z 262.16 [M+H]$^+$.

Synthesis of Compound 40.4

The compound was synthesized from Core A and compound 40.3 using General Procedure A to obtain 40.4. (0.2 g, Yield: 43.94%), MS (ES): m/z 645.21 [M+H]$^+$.

Synthesis of Compound 40.5

The compound was synthesized from compound 40.4 using General Procedure B to obtain 40.5. (0.1 g, Yield: 99.39%), MS (ES): m/z 325.13 [M+H]$^+$.

Synthesis of Compound 40.6

The compound was synthesized from compound 40.5 using General Procedure C to obtain 40.6. (0.090 g, Yield: 67.62%), MS (ES): m/z 393.15 [M+H]$^+$.

Synthesis of Compound I-40

The compound was synthesized from compound 40.6 and methylamine using General Procedure D. The material was further purified by column chromatography eluting with 2.5% methanol in dichloromethane to obtain I-40 (0.026 g, Yield: 32.58%), MS (ES): m/z 392.51 [M+H]$^+$ LCMS purity: 98.14%, HPLC purity: 98.14%, $^1$H NMR (DMSO-d$_6$, 400 MHz): 11.34 (s, 1H), 10.94 (s, 1H), 8.30-8.28 (d, J=4.4 Hz, 1H), 8.26 (s, 1H), 8.13 (s, 1H), 7.88-7.87 (d, J=2.4 Hz, 1H), 7.18 (s, 1H), 6.55-6.53 (d, J=9.6 Hz, 1H), 3.44-3.40 (m, 1H), 2.84-2.83 (d, J=4.4 Hz, 3H), 2.17 (bs, 1H), 1.07-1.03 (m, 2H), 1.00-0.97 (m, 4H), 0.90 (m, 2H).

Example 41: 2-(3-(azetidin-1-yl)-2-cyanophenyl)-7-(cyclopropanecarboxamido)-N-methyl-1H-pyrrolo[2,3-c]pyridine-4-carboxamide (I-41)

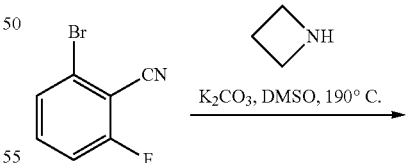

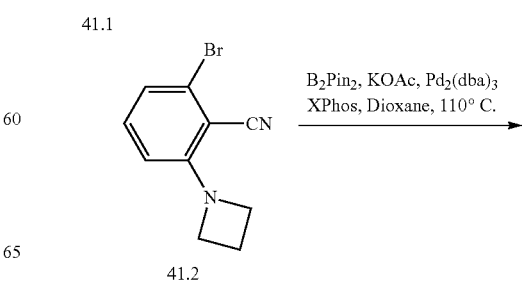

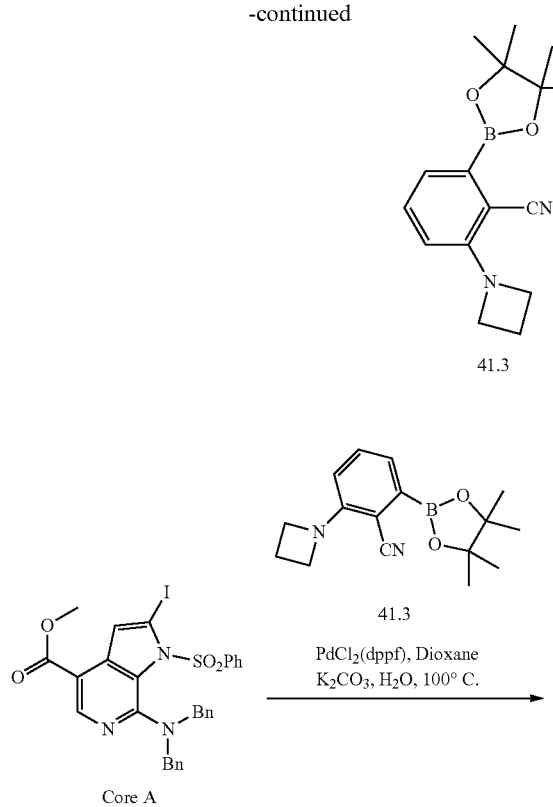

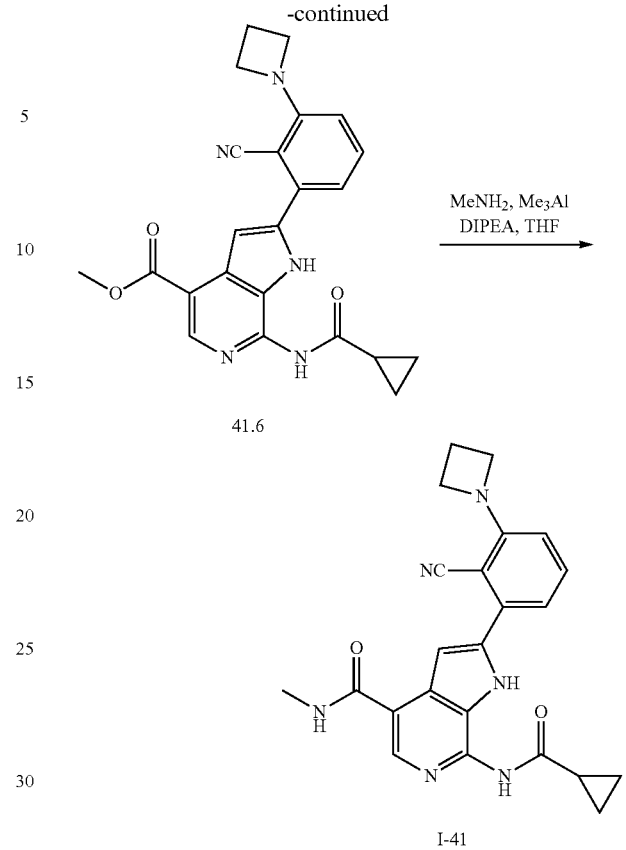

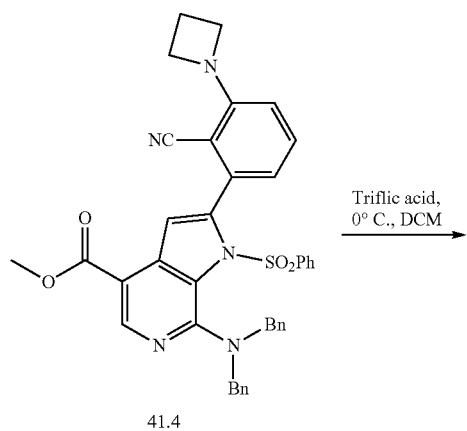

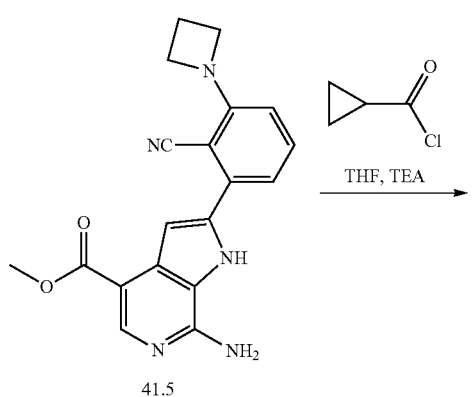

Synthesis of Compound 41.2

To a solution of 41.1 (1.0 g, 5.00 mmol, 1.0 eq) and azetidine (0.855 g, 15.00 mmol, 3.0 eq) in dimethyl sulphoxide (15 mL) was added potassium carbonate (1.3 g, 10.0 mmol, 2.0 eq) and reaction mixture heated at 190° C. for 10 h. After completion of reaction, reaction mixture was transferred into ice cold water and product was extracted with ethyl acetate. Organic layer was combined and dried over sodium sulfate and concentrated under reduced pressure to obtain crude material. This was further purified by column chromatography and compound was eluted in 25% ethyl acetate in hexane to obtain pure 41.2 (0.6 g, Yield: 50.61%). MS (ES): m/z 237.99 [M+H]$^+$.

Synthesis of Compound 41.3

The compound was synthesized from compound 41.2 using General Procedure F, using 2-dicyclohexylphosphino-2',4',6'-triisopropylbiphenyl instead of 4,5-bis(diphenylphosphino)-9,9-dimethylxanthene, to obtain 41.3. (0.5 g, Yield: 69.53%). MS (ES): m/z 285.17 [M+H]$^+$.

Synthesis of Compound 41.4

The compound was synthesized from Core A and compound 41.3 using General Procedure A to obtain 41.4. (0.3 g, Yield: 63.64%), MS (ES): m/z 668.23 [M+H]$^+$.

Synthesis of Compound 41.5

The compound was synthesized from compound 41.4 using General Procedure B to obtain 41.5. (0.130 g, Yield: 83.30%), MS (ES): m/z 348.14 [M+H]$^+$.

Synthesis of Compound 41.6

The compound was synthesized from compound 41.5 using General Procedure C to obtain 41.6. (0.110 g, Yield: 70.75%), MS (ES): m/z 416.17 [M+H]$^+$.

Synthesis of Compound I-41

The compound was synthesized from compound 41.6 and methylamine using General Procedure D. The material was further purified by column chromatography eluting with 2.5% methanol in dichloromethane to obtain I-41 (0.035 g, Yield: 31.89%), MS (ES): m/z 415.82 [M+H]$^+$ LCMS purity: 99.19%, HPLC purity: 99.50%, $^1$H NMR (DMSO-d$_6$, 400 MHz): 11.66 (s, 1H), 11.21 (s, 1H), 8.41-8.40 (d, J=4.4 Hz, 1H), 8.32 (s, 1H), 7.57-7.53 (t, J=7.6 Hz, 1H), 7.42-7.41 (d, J=2 Hz, 1H), 7.03-7.01 (d, J=7.2 Hz, 1H), 6.68-6.66 (d, J=8.4 Hz, 1H), 4.21-4.18 (t, J=7.2 Hz, 4H), 2.83-2.82 (d, J=4.4 Hz, 3H), 2.38-2.32 (m, 2H), 2.21 (bs, 1H), 0.95-0.90 (m, 4H).

Example 42: 2-(4-(azetidine-1-carbonyl)-2-fluorophenyl)-7-(cyclopropanecarboxamido)-N-methyl-1H-pyrrolo[2,3-c]pyridine-4-carboxamide (I-42)

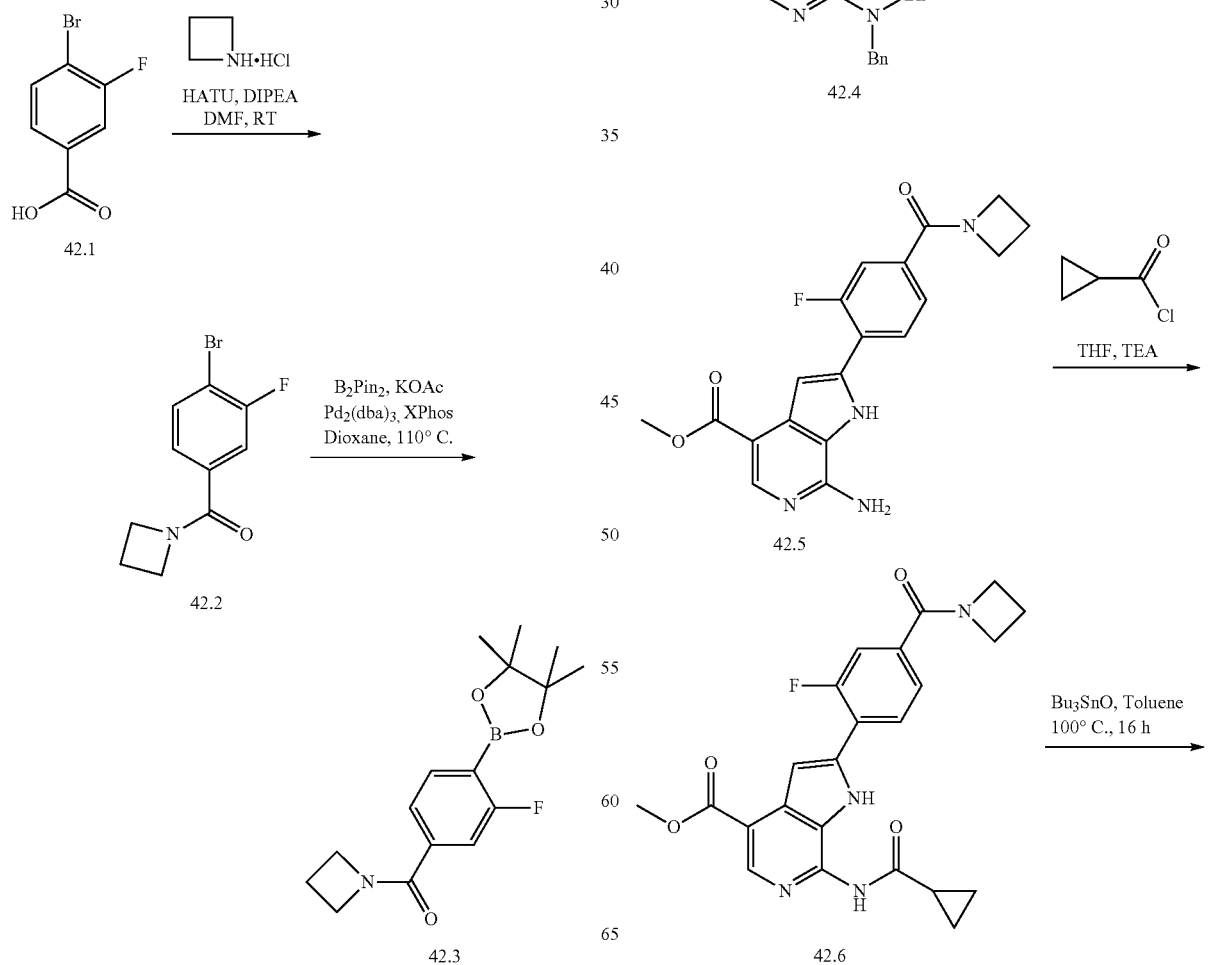

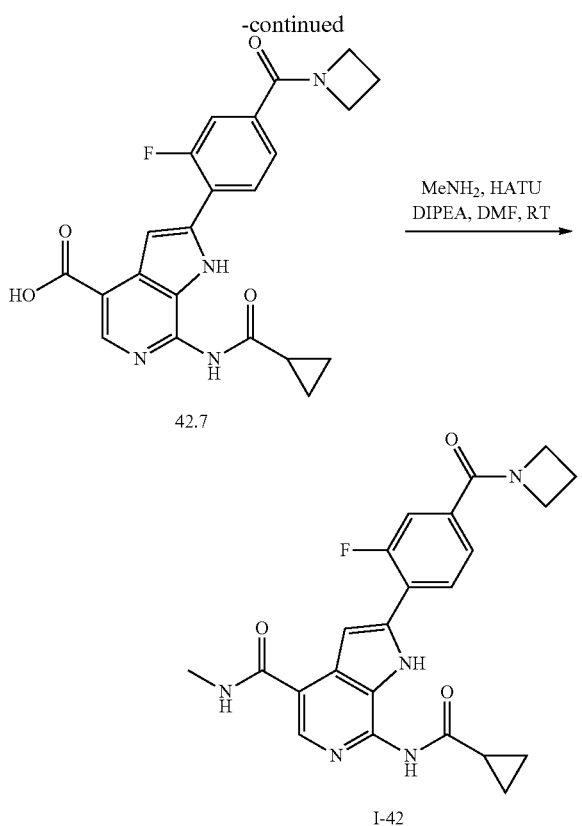

g, 0.58 mmol, 2.0 eq) and reaction mixture was heated at 100° C. for 16 h. After completion of reaction, reaction mixture was concentrated under reduced pressure to obtain residue which was dissolved in saturated sodium bicarbonate solution and washed with hexane. Aqueous layer separated and acidified with 1N hydrochloric acid to pH~5-6 and extracted with ethyl acetate. Organic layer was combined, dried over sodium sulfate and concentrated under reduced pressure to obtain solid which was triturated with hexane to obtain pure 42.7. (0.070 g, Yield: 55.63%), MS (ES): m/z 423.14 [M+H]$^+$.

Synthesis of Compound I-42

The compound was synthesized from compound 42.7 using General Procedure H to obtain I-42 (0.025 g, 34.64%), MS (ES): 436.82 [M+H]$^+$ LCMS purity: 100%, HPLC purity: 99.48%, $^1$H NMR (DMSO-d$_6$, 400 MHz): 12.15 (s, 1H), 11.33 (s, 1H), 8.40-8.39 (d, J=4.8 Hz, 1H), 8.32 (s, 1H), 8.07-8.03 (t, J=8 Hz, 2H), 7.64-7.60 (m, 1H), 7.53 (s, 1H), 4.40-4.37 (t, J=7.6 Hz, 2H), 4.09-4.05 (t, J=7.6 Hz, 2H), 2.84-2.83 (d, J=4.4 Hz, 3H), 2.32-2.24 (m, 3H), 0.98-0.93 (m, 4H).

Example 43: 7-(cyclopropanecarboxamido)-N-methyl-2-(2-oxo-1-(tetrahydro-2H-pyran-3-yl)-1,2-dihydropyridin-3-yl)-1H-pyrrolo[2,3-c]pyridine-4-carboxamide (I-43)

Synthesis of Compound 42.2

The compound was synthesized from compound 42.1 and azetidine hydrochloride using General Procedure H to obtain 42.2 (0.7 g, Yield: 59.40%). MS (ES): m/z 258.98 [M+H]$^+$.

Synthesis of Compound 42.3

The compound was synthesized from compound 42.2 using General Procedure F, using 2-dicyclohexylphosphino-2',4',6'-triisopropylbiphenyl instead of 4,5-bis(diphenylphosphino)-9,9-dimethylxanthene, to obtain 42.3. (0.4 g, Yield: 56.38%). MS (ES): m/z 306.16 [M+H]$^+$.

Synthesis of Compound 42.4

The compound was synthesized from Core A and compound 42.3 using General Procedure A to obtain 42.4. (0.280 g, Yield: 57.59%), MS (ES): m/z 689.22 [M+H]$^+$.

Synthesis of Compound 42.5

The compound was synthesized from compound 42.4 using General Procedure B to obtain 42.5. (0.149 g, Yield: 99.50%), MS (ES): m/z 369.13 [M+H]$^+$.

Synthesis of Compound 42.6

The compound was synthesized from compound 42.5 using General Procedure C to obtain 42.6. (0.130 g, Yield: 73.15%), MS (ES): m/z 437.16 [M+H]$^+$.

Synthesis of Compound 42.7

To a suspension of compound 42.6 (0.130 g, 0.29 mmol, 1.0 eq) in toluene (2 mL) was added tributyltin oxide (0.345

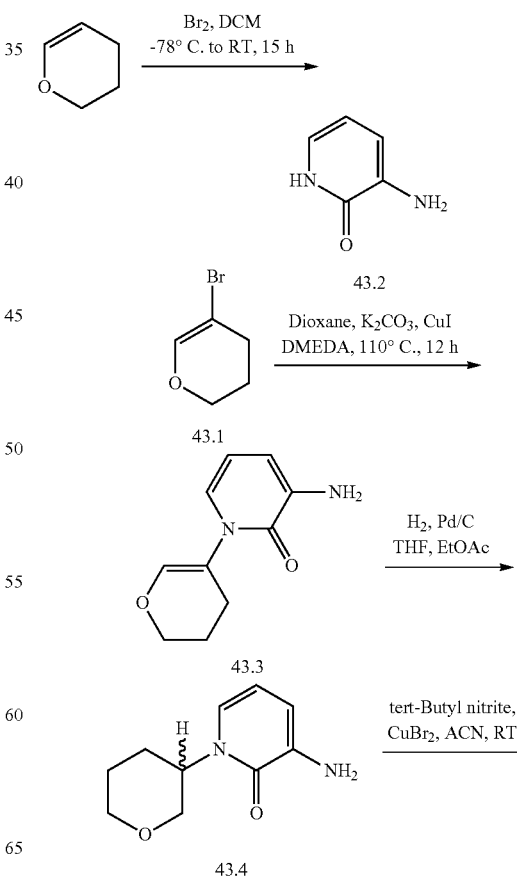

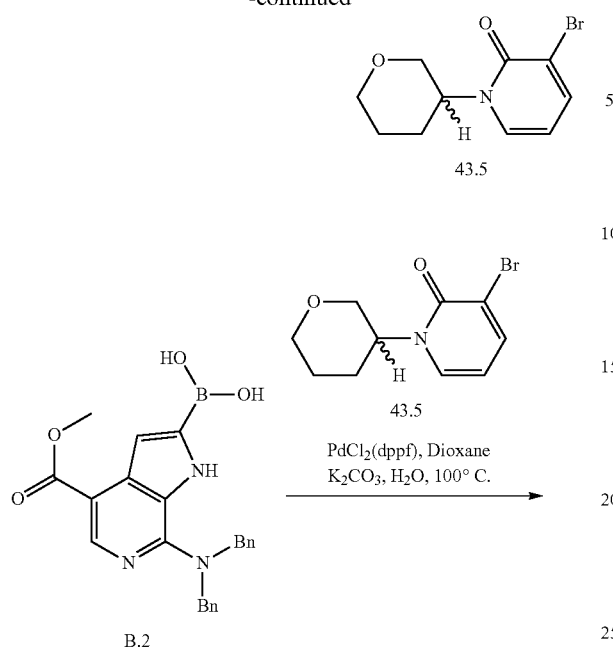

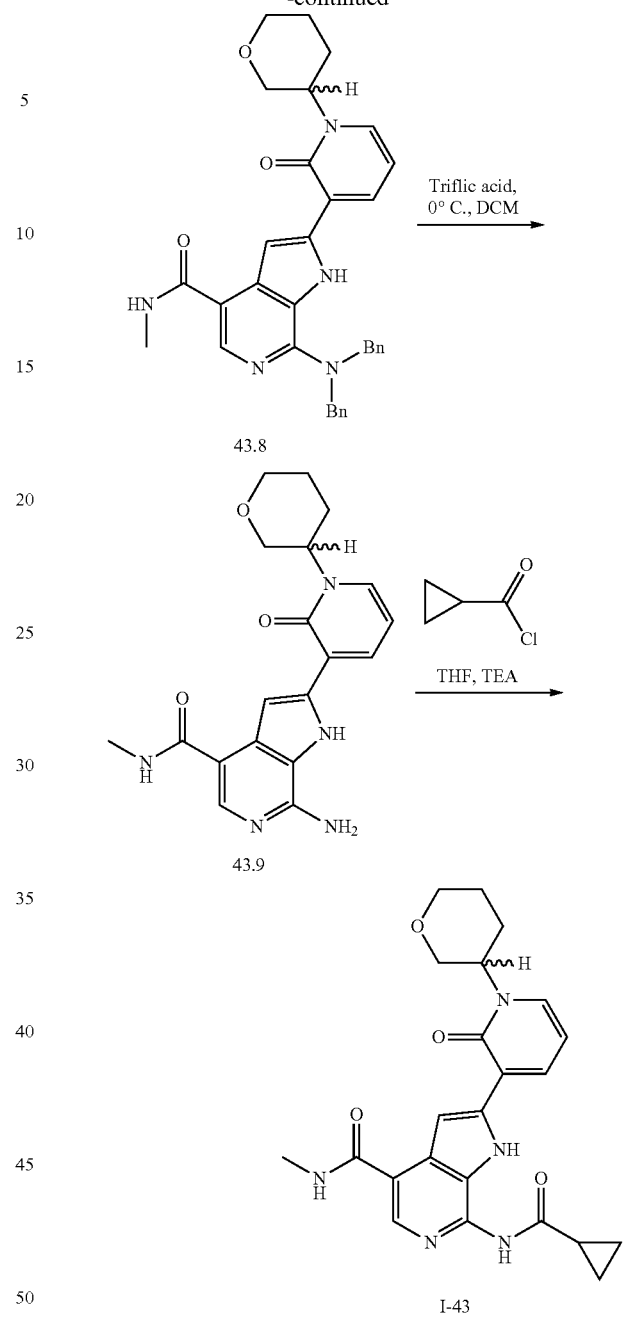

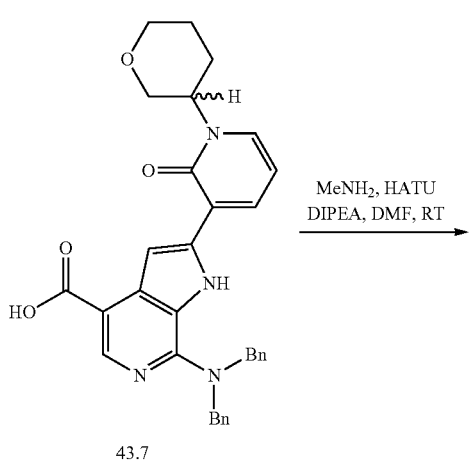

Synthesis of Compound 43.1

To a solution of 3,4-dihydro-2H-pyran (20.0 g, 238.09 mmol, 1.0 eq) in dichloromethane (200 mL) was added dropwise bromine in dichloromethane (37.8 g, 11.90 mmol, 1.0 eq) at −78° C. The reaction was stirred at room temperature for 10 h. After completion of reaction, reaction mixture was concentrated under reduced pressure and added diethyl ether and filtered. Filtrate was concentrated under reduced pressure to obtain crude material. This was further purified by vacuum distillation to obtain pure 43.1. (16.0 g, Yield: 41.28%). MS (ES): m/z 163.97 [M+H]$^+$.

Synthesis of Compound 43.3

To a solution of compound 43.1 (16.0 g, 98.15 mmol, 1 eq) and compound 43.2 (12.9 g, 117.78 mmol, 1.2 eq) in 1,4-dioxane (250 mL) was added potassium carbonate (27.0 g, 196.3 mmol, 2.0 eq) and degassed with argon for 15 min. Copper iodide (3.7 g, 19.63 mmol, 0.2 eq) and 1,2-dimethylethylenediamine (3.4 g, 39.26 mmol, 0.4 eq) was added and reaction mixture again degassed with argon for 5 min followed by heating at 110° C. for 12 h. After completion of reaction, reaction mixture was cooled to room temperature, transferred into water and product was extracted with ethyl acetate. Organic layer was combined, washed with brine solution, dried over sodium sulfate and concentrated under reduced pressure to obtain crude material. This was further purified by column chromatography and compound was eluted in 1.2% methanol in dichloromethane to obtain pure 43.3. (7.0 g, Yield: 37.10%). MS (ES): m/z 193.09 [M+H]$^+$.

Synthesis of Compound 43.4

To a solution of compound 43.3 (7.0 g, 36.26 mmol, 1.0 eq) in ethyl acetate and tetrahydrofuran (1:1.70 mL), 10% palladium on charcoal (1.8 g) was added. Hydrogen was purged through reaction mixture for 4 h at room temperature. After completion of reaction, reaction mixture was filtered through Celite-bed and washed with methanol. Filtrate was concentrated under reduced pressure to obtain crude material. This was further purified by trituration with n-pentane to obtain pure 43.4. (4.1 g, Yield: 57.96%). MS (ES): m/z 195.11 [M+H]$^+$.

Synthesis of Compound 43.5

To a solution of compound 43.4 (4.1 g, 21.13 mmol, 1.0 eq) in acetonitrile (70 mL) were added tert-butyl nitrite (2.3 g, 23.24 mmol, 1.1 eq) and copper(II) bromide (4.7 g, 21.13 mmol, 1.0 eq) under nitrogen atmosphere. The reaction mixture was stirred at room temperature for 10 min. After completion of reaction, reaction mixture was transferred into water and product was extracted with ethyl acetate. Organic layer was combined, washed with brine solution, dried over sodium sulfate and concentrated under reduced pressure to obtain crude material. This was further purified by column chromatography and compound was eluted in 20% ethyl acetate in hexane to obtain pure 43.5. (1.1 g, Yield: 20.19%). MS (ES): m/z 259.00 [M+H]$^+$.

Synthesis of Compound 43.6

The compound was synthesized from compounds B.2 and 43.5 using General Procedure A to obtain 43.6. (0.380 g, Yield: 38.35%), MS (ES): m/z 549.25 [M+H]$^+$.

Synthesis of Compound 43.7

To a solution of compound 43.6 (0.380 g, 0.69 mmol, 1.0 eq), in methanol (5 mL) was added sodium hydroxide (0.138 g, 3.45 mmol, 5.0 eq). The reaction mixture was stirred at 60° C. for 1 h. After completion of reaction, reaction mixture was concentrated under reduced pressure to obtain residue. To this added water and acidified with 1N hydrochloric acid to adjust pH~6 at 10° C. Product was extracted with dichloromethane. Organic layer was combined, washed with brine solution, dried over sodium sulfate and concentrated under reduced pressure to obtain crude material. This was further purified by column chromatography and compound was eluted in 2.1% methanol in dichloromethane to obtain pure 43.7. (0.3 g, Yield: 81.02%). MS (ES): m/z 535.23 [M+H]$^+$.

Synthesis of Compound 43.8

The compound was synthesized from compound 43.7 and methylamine using General Procedure H to obtain 43.8. (0.250 g, Yield: 81.35%). MS (ES): m/z 548.26 [M+H]$^+$.

Synthesis of Compound 43.9

The compound was synthesized from compound 43.8 using General Procedure B to obtain 43.9. (0.130 g, Yield: 77.51%), MS (ES): m/z 368.17 [M+H]$^+$.

Synthesis of Compound I-43

The compound was synthesized from compound 43.9 using General Procedure C to obtain I-43. (0.090 g, Yield: 58.41%), MS (ES): m/z 436.77 [M+H]$^+$ LCMS purity: 100%, HPLC purity: 98.75%, CHIRAL HPLC: 48.42%, 51.58%, $^1$H NMR (DMSO-d$_6$, 400 MHz): 12.63 (s, 1H), 11.15 (s, 1H), 8.30-8.26 (m, 2H), 8.03-8.02 (d, J=5.2 Hz, 1H), 7.45 (bs, 1H), 6.55-6.54 (d, J=6.8 Hz, 1H), 5.03 (bs, 1H), 3.87 (bs, 2H), 3.59-3.49 (m, 3H), 2.85-2.84 (d, J=4.4 Hz, 2H), 2.21 (bs, 1H), 2.01 (bs, 2H), 1.91 (s, 1H), 1.79 (bs, 2H), 0.97-0.93 (m, 4H).

Example 44: 7-(cyclopropanecarboxamido)-2-(4-cyclopropoxypyridin-3-yl)-N-methyl-1H-pyrrolo[2,3-c]pyridine-4-carboxamide (I-44)

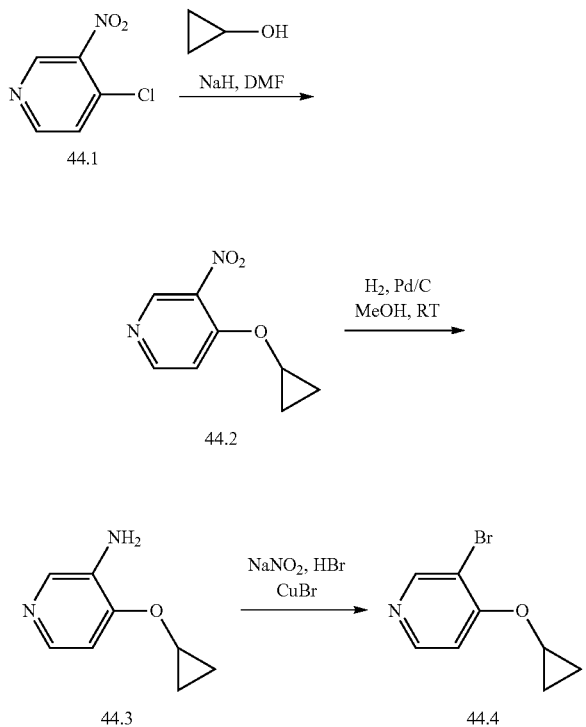

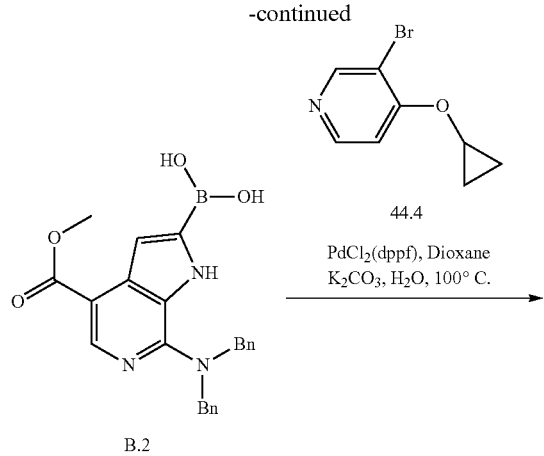

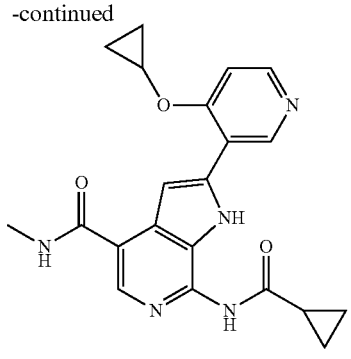

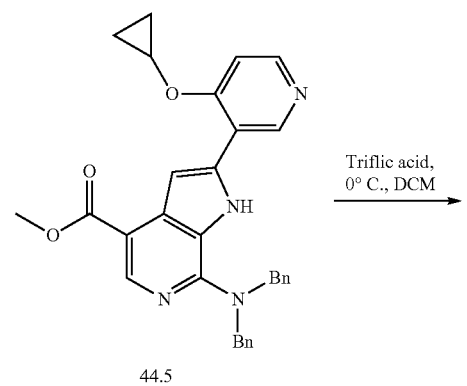

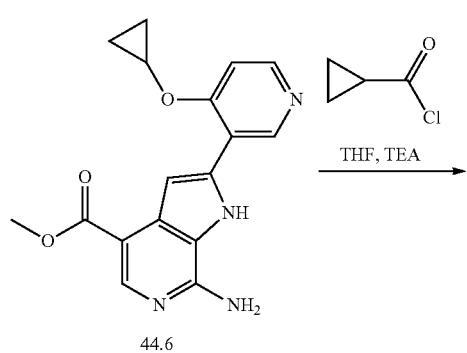

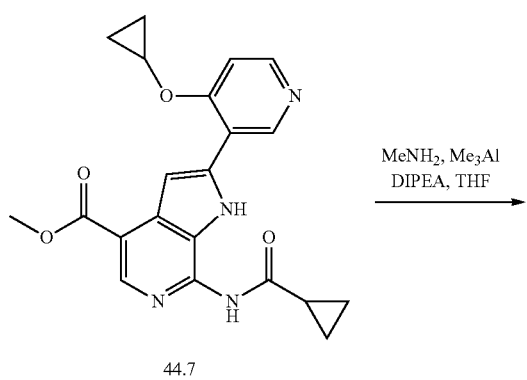

Synthesis of Compound 44.2

To a solution of compound 44.1 (6.0 g, 37.97 mmol, 1.0 eq) in dimethylformamide (80 mL), was added sodium hydride (1.8 g, 75.94 mmol, 2 eq) at 0° C. and stirred for 20 min. Cyclopropanol (2.4 g, 41.76 mmol, 1.1 eq) was added and reaction mixture was stirred at room temperature for 2 h. After completion of reaction, reaction mixture was transferred into ice, stirred and extracted with diethyl ether. Organic layer was combined, dried over sodium sulfate and concentrated under reduced pressure to obtain crude material. This was further purified by distillation to obtain pure 44.2. (4.3 g, Yield: 63.07%). MS (ES): m/z 181.06 [M+H]$^+$.

Synthesis of Compound 44.3

To a solution of compound 44.2 (4.3 g, 23.88 mmol, 1.0 eq) in methanol (45 ml), palladium on charcoal (1.9 g) was added. Hydrogen was purged through reaction mixture for 4 h at room temperature. After completion of reaction, reaction mixture was filtered through Celite-bed and washed with methanol. Filtrate was concentrated under reduced pressure to obtain crude material. This was further purified by trituration with n-pentane to obtain pure 44.3. (3.5 g, Yield: 97.65%). MS (ES): m/z 151.08 [M+H]$^+$.

Synthesis of Compound 44.4

To the compound 44.3 (3.5 g, 23.17 mmol, 1.0 eq) was added 30% hydrobromic acid (6.0 mL) dropwise at 0° C. Sodium nitrite (3.1 g, 46.34 mmol, 2.0 eq) and acetone (25 mL) were added to this reaction mixture and stirred for 2 min. Then copper(I) bromide (6.6 g, 46.34 mmol, 2.0 eq) was added and reaction mixture was stirred for 15 min. After completion of reaction, reaction mixture was transferred into water and product was extracted with ethyl acetate. Organic layer was combined, washed with brine solution, dried over sodium sulfate and concentrated under reduced pressure to obtain 44.4. (2.1 g, Yield: 38.77%). MS (ES): m/z 214.98 [M+H]$^+$.

Synthesis of Compound 44.5

The compound was synthesized from compounds B.2 and 44.4 using General Procedure A to obtain 44.5. (0.2 g, Yield: 41.15%), MS (ES): m/z 505.22 [M+H]$^+$.

Synthesis of Compound 44.6

The compound was synthesized from compound 44.5 using General Procedure B to obtain 44.6. (0.110 g, Yield: 85.57%), MS (ES): m/z 325.13 [M+H]$^+$.

Synthesis of Compound 44.7

The compound was synthesized from compound 44.6 using General Procedure C to obtain 44.7. (0.090 g, Yield: 67.62%), MS (ES): m/z 393.15 [M+H]⁺.

Synthesis of Compound I-44

The compound was synthesized from compound 44.7 and methylamine using General Procedure D. The material was further purified by column chromatography eluting with 2.5% methanol in dichloromethane to obtain I-44 (0.025 g, Yield: 27.85%), MS (ES): m/z 392.70 [M+H]⁺ LCMS purity: 100%, HPLC purity: 98.81%, $^1$H NMR (DMSO-d$_6$, 400 MHz): 12.07 (s, 1H), 11.35 (s, 1H), 9.07 (bs, 1H), 8.53-8.52 (d, J=5.6 Hz, 1H), 8.31-8.30 (d, J=6 Hz, 2H), 7.56-7.53 (m, 2H), 4.20 (bs, 1H), 2.86-2.85 (d, J=4.4 Hz, 3H), 2.25 (bs, 1H), 1.08 (bs, 2H), 0.99 (bs, 2H), 0.97-0.92 (m, 4H).

Example 45: 2-(2-cyano-3-(1-methyl-1H-pyrazol-4-yl)phenyl)-7-(cyclopropane-carboxamido)-N-methyl-1H-pyrrolo[2,3-c]pyridine-4-carboxamide (I-45)

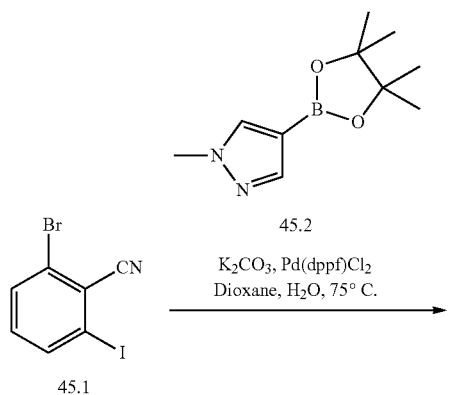

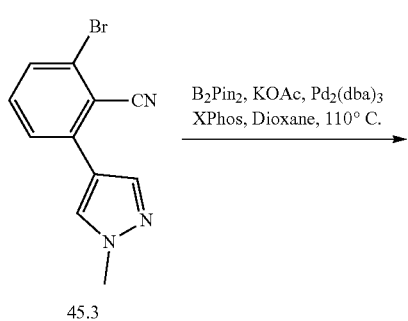

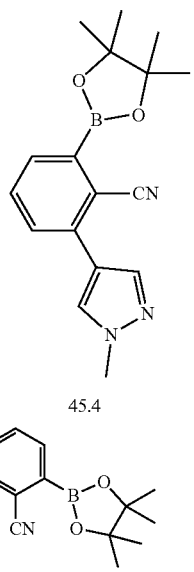

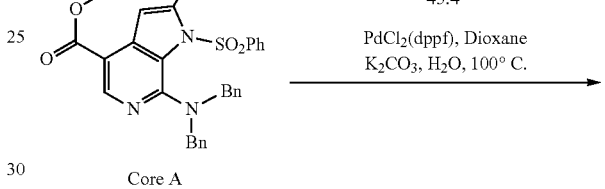

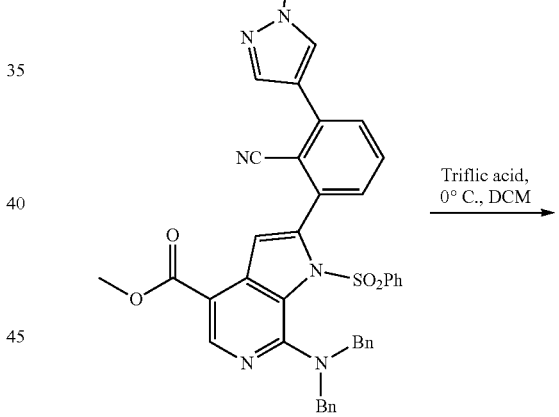

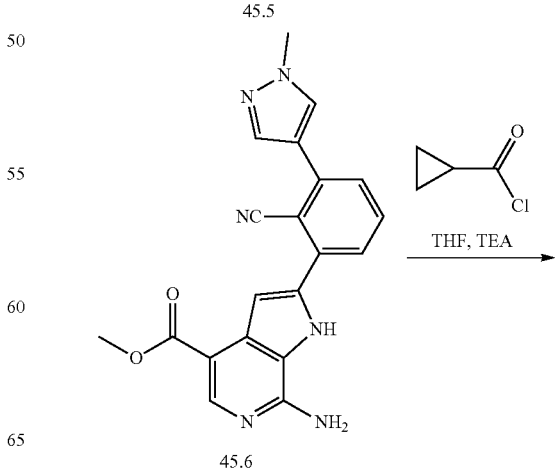

265
-continued

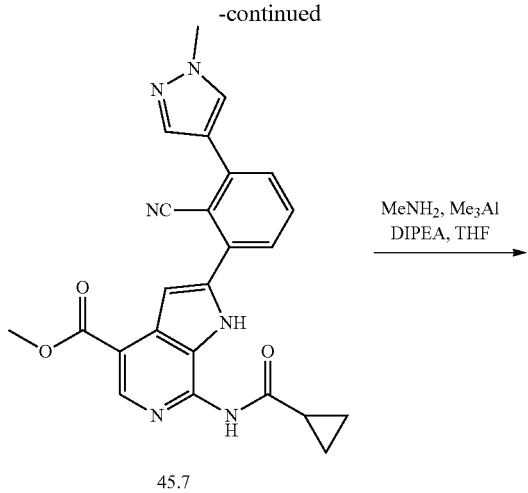

45.7

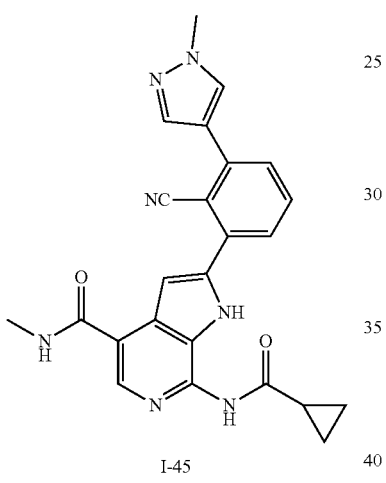

I-45

Synthesis of Compound 45.3

The compound was synthesized from compounds 45.1 and 45.2 using General Procedure A to obtain 45.3. (0.650 g, Yield: 76.36%), MS (ES): m/z 262.99 [M+H]$^+$.

Synthesis of Compound 45.4

The compound was synthesized from compound 45.3 using General Procedure F, using 2-dicyclohexylphosphino-2',4',6'-triisopropylbiphenyl instead of 4,5-bis(diphenylphosphino)-9,9-dimethylxanthene, to obtain 45.4. (0.5 g, Yield: 84.78%). MS (ES): m/z 310.17 [M+H]$^+$.

Synthesis of Compound 45.5

The compound was synthesized from Core A and compound 45.4 using General Procedure A to obtain 45.5. (0.3 g, Yield: 61.35%), MS (ES): m/z 693.22 [M+H]$^+$.

266

Synthesis of Compound 45.6

The compound was synthesized from compound 45.5 using General Procedure B to obtain 45.6. (0.150 g, Yield: 93.02%), MS (ES): m/z 373.14 [M+H]$^+$.

Synthesis of Compound 45.7

The compound was synthesized from compound 45.6 using General Procedure C to obtain 45.7. (0.110 g, Yield: 62.00%), MS (ES): m/z 441.16 [M+H]$^+$.

Synthesis of Compound I-45

The compound was synthesized from compound 45.7 and methylamine using General Procedure D. The material was further purified by column chromatography eluting with 2.5% methanol in dichloromethane to obtain I-45 (0.030 g, Yield: 27.33%), MS (ES): m/z 440.42 [M+H]$^+$ LCMS purity: 96.41%, HPLC purity: 97.91%, $^1$H NMR (DMSO-d$_6$, 400 MHz): 11.77 (s, 1H), 11.22 (s, 1H), 8.43-8.42 (d, J=4 Hz, 1H), 8.35 (s, 1H), 8.32 (s, 1H), 8.00 (s, 1H), 7.86-7.82 (m, 1H), 7.77-7.75 (d, J=7.6 Hz, 1H), 7.71-7.69 (d, J=7.6 Hz, 1H), 7.52 (bs, 1H), 3.94 (s, 3H), 2.84-2.83 (d, J=4.4 Hz, 3H), 2.21 (bs, 1H), 0.96-0.91 (m, 4H).

Example 46: 7-(cyclopropanecarboxamido)-2-(2-(4-hydroxypiperidin-1-yl)phenyl)-N-methyl-1H-pyrrolo[2,3-c]pyridine-4-carboxamide (I-46)

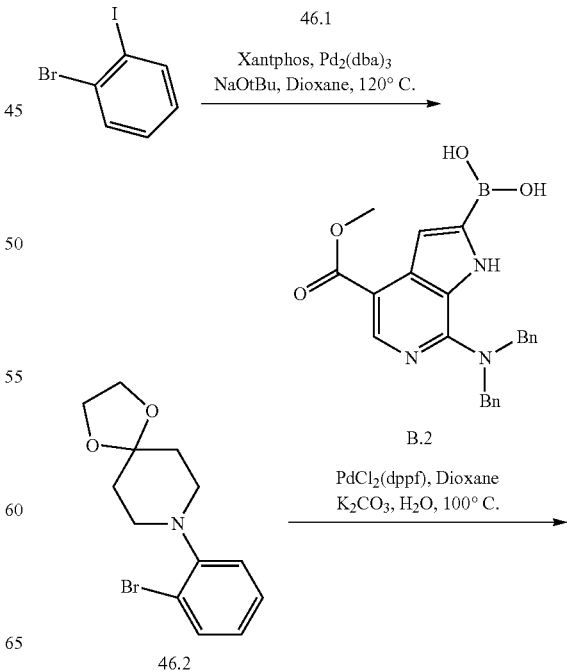

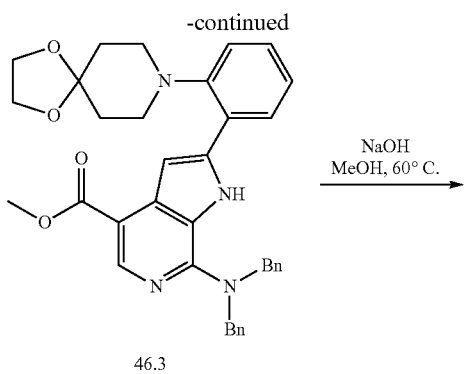

46.3

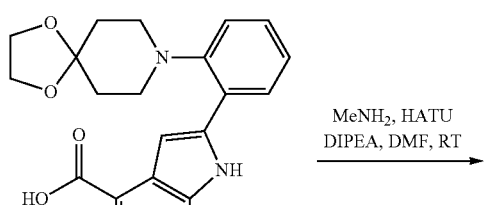

46.4

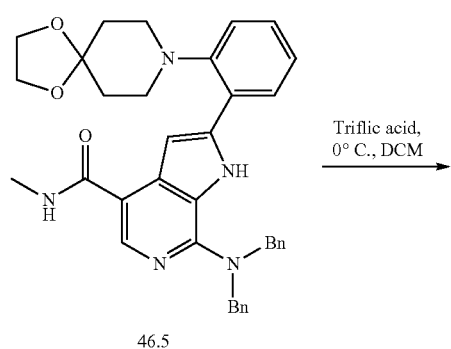

46.5

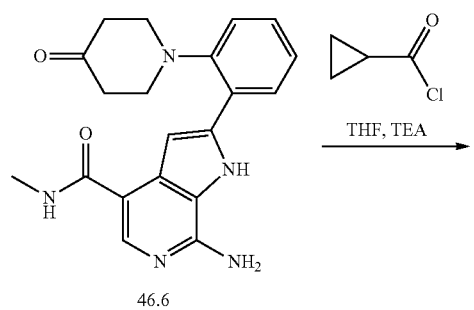

46.6

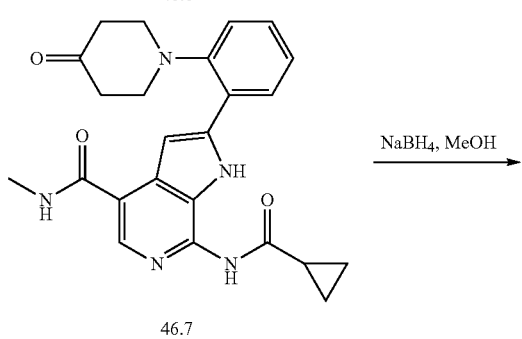

46.7

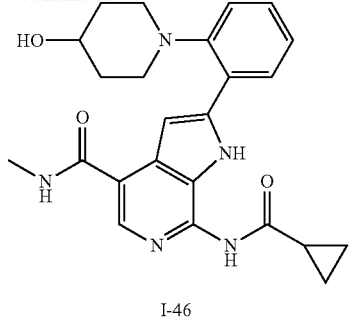

I-46

Synthesis of Compound 46.2

To a solution of 1-bromo-2-iodobenzene (5.0 g, 17.66 mmol, 1.0 eq) in 1,4-dioxane (80 mL) was added compound 46.1 (3.0 g, 21.19 mmol, 1.2 eq) and sodium tert-butoxide (3.3 g, 35.32 mmol, 2.0 eq). The reaction mixture was degassed for 10 min. under argon atmosphere, then tris(dibenzylideneacetone)dipalladium(0) (0.807 g, 0.88 mmol, 0.05 eq) and 4,5-bis(diphenylphosphino)-9,9-dimethylxanthene (1.0 g, 1.76 mmol, 0.1 eq) were added, again degassed for 5 min. The reaction was stirred at 120° C. for 4 h. After completion of reaction, reaction mixture was cooled to room temperature, transferred into water and product was extracted with ethyl acetate. Organic layer was combined, washed with brine solution, dried over sodium sulfate and concentrated under reduced pressure to obtain crude material. This was further purified by combi flash using 3% methanol in dichloromethane as eluant to obtain pure 46.2. (1.2 g, Yield: 22.77%). MS (ES): m/z 299.03 [M+H]⁺.

Synthesis of Compound 46.3

The compound was synthesized from compounds B.2 and 46.2 using General Procedure A to obtain 46.3. (0.250 g, Yield: 31.66%), MS (ES): m/z 589.28 [M+H]⁺.

Synthesis of Compound 46.4

To a solution of compound 46.3 (0.250 g, 0.60 mmol, 1.0 eq), in methanol (3 mL) was added sodium hydroxide (0.120 g, 3.0 mmol, 5.0 eq). The reaction mixture was stirred at 60° C. for 1 h. After completion of reaction, reaction mixture was concentrated under reduced pressure to obtain residue. To this added water and acidified with 1N hydrochloric acid to adjust pH~6 at 10° C. Product was extracted with dichloromethane. Organic layer was combined, washed with brine solution, dried over sodium sulfate and concentrated under reduced pressure to obtain crude material. This was further purified by column chromatography and compound was eluted in 2.1% methanol in dichloromethane to obtain pure 46.4. (0.2 g, Yield: 81.95%). MS (ES): m/z 575.26 [M+H]⁺.

Synthesis of Compound 46.5

The compound was synthesized from compound 46.4 and methylamine using General Procedure H to obtain 46.5. (0.180 g, Yield: 88%). MS (ES): m/z 588.29 [M+H]⁺.

Synthesis of Compound 46.6

The compound was synthesized from compound 46.5 using General Procedure B to obtain 46.6. (0.090 g, Yield: 80.86%), MS (ES): m/z 364.17 [M+H]⁺.

Synthesis of Compound 46.7

The compound was synthesized from compound 46.6 using General Procedure C to obtain 46.7. (0.080 g, Yield: 74.87%), MS (ES): m/z 432.20 [M+H]$^+$.

Synthesis of Compound I-46

To a solution of compound 46.7 (0.080 g, 0.18 mmol, 1.0 eq) in methanol (2 mL) was added sodium borohydride (0.027 g, 0.72 mmol, 4.0 eq) portionwise at 0° C. Reaction mixture was stirred at room temperature for 16 h. After completion of reaction, reaction mixture was concentrated under reduced pressure. To this was added water and product was extracted with ethyl acetate. Organic layer was combined, washed with brine solution, dried over sodium sulfate and concentrated under reduced pressure to obtain I-46 (0.038 g, Yield: 47.28%). MS (ES): m/z 434.71 [M+H]$^+$ LCMS purity: 95.29%, HPLC purity: 95.00%, $^1$H NMR (DMSO-d$_6$, 400 MHz): 12.40 (s, 1H), 11.28 (s, 1H), 8.33-8.32 (d, J=4.4 Hz, 1H), 8.27 (s, 1H), 7.78-7.76 (s, J=7.2 Hz, 1H), 7.39-7.36 (t, J=6.8 Hz, 1H), 7.28 (bs, 2H), 7.18-7.15 (t, J=7.6 Hz, 1H), 4.69 (s, 1H), 3.60 (bs, 1H), 2.97 (bs, 2H), 2.86-2.85 (d, J=4 Hz, 3H), 2.61 (bs, 3H), 1.77 (bs, 2H), 1.65 (bs, 2H), 1.05 (bs, 2H), 0.90 (bs, 2H).

Example 47: 7-(cyclopropanecarboxamido)-2-(2-fluoro-3-(3-methyl-1H-1,2,4-triazol-1-yl)phenyl)-N-methyl-1H-pyrrolo[2,3-c]pyridine-4-carboxamide (I-47)

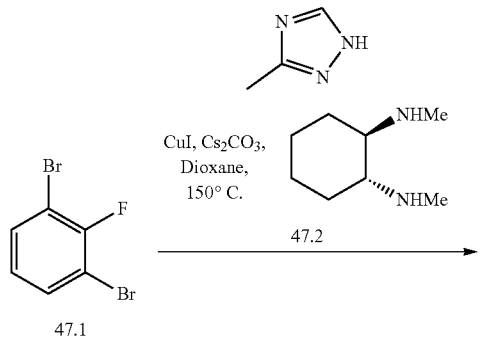

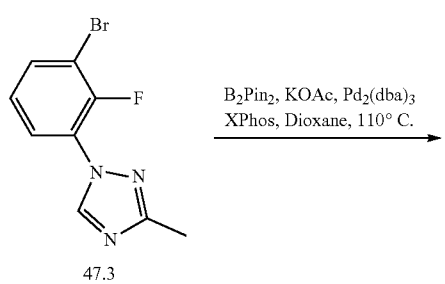

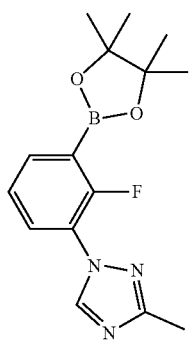

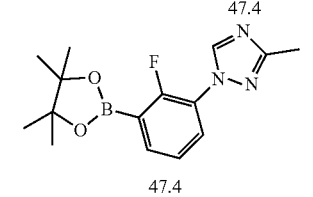

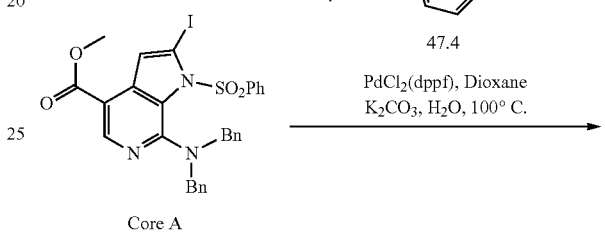

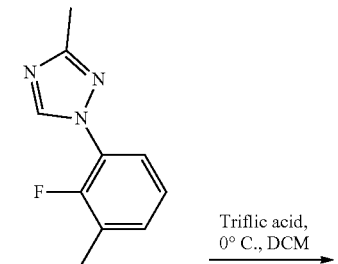

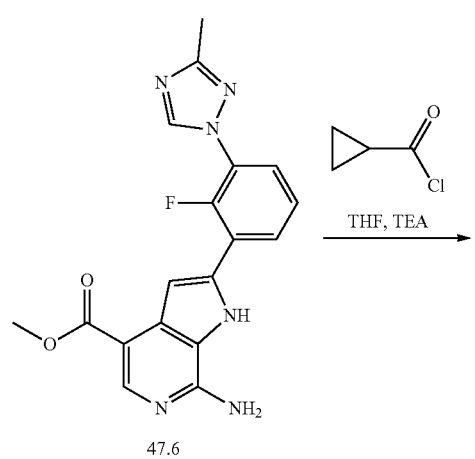

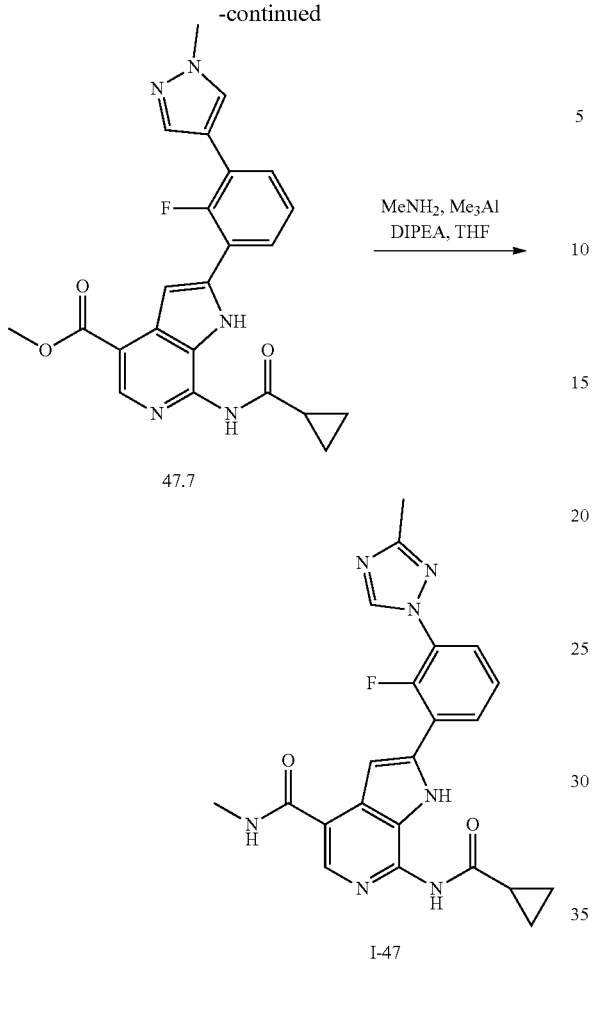

47.7

Synthesis of Compound 47.3

To a solution of compounds 47.1 (1.0 g, 3.93 mmol, 1 eq) and 47.2 (0.391 g, 4.71 mmol, 1.2 eq) in 1,4-dioxane (20 mL) was added cesium carbonate (2.5 g, 7.86 mmol, 2.0 eq) and degassed with argon for 15 min. Copper iodide (0.149 g, 0.78 mmol, 0.2 eq) and (1R,2R)—N,N'-dimethylcyclohexane-1,2-diamine (0.279 g, 1.96 mmol, 0.5 eq) was added and reaction mixture again degassed with argon for 5 min followed by heating at 150° C. for 16 h. After completion of reaction, reaction mixture was cooled to room temperature, transferred into water and product was extracted with ethyl acetate. Organic layer was combined, washed with brine solution, dried over sodium sulfate and concentrated under reduced pressure to obtain crude material. This was further purified by column chromatography and compound was eluted in 1.2% methanol in dichloromethane to obtain pure 47.3 (0.4 g, Yield: 39.66%). MS (ES): m/z 256.98 [M+H]$^+$.

Synthesis of Compound 47.4

The compound was synthesized from compound 47.3 using General Procedure F, using 2-dicyclohexylphosphino-2',4',6'-triisopropylbiphenyl instead of 4,5-bis(diphenylphosphino)-9,9-dimethylxanthene, to obtain 47.4. (0.3 g, Yield: 63.36%). MS (ES): m/z 304.16 [M+H]$^+$.

Synthesis of Compound 47.5

The compound was synthesized from Core A and compound 47.4 using General Procedure A to obtain 47.5. (0.240 g, Yield: 49.51%), MS (ES): m/z 687.21 [M+H]$^+$.

Synthesis of Compound 47.6

The compound was synthesized from compound 47.5 using General Procedure B to obtain 47.6. (0.120 g, Yield: 93.73%), MS (ES): m/z 367.13 [M+H]$^+$.

Synthesis of Compound 47.7

The compound was synthesized from compound 47.6 using General Procedure C to obtain 47.7. (0.090 g, Yield: 63.25%), MS (ES): m/z 435.15 [M+H]$^+$.

Synthesis of Compound I-47

The compound was synthesized from compound 47.7 and methylamine using General Procedure D. The material was further purified by column chromatography eluting with 2.5% methanol in dichloromethane to obtain I-47 (0.027 g, Yield: 30.07%), MS (ES): m/z 434.66 [M+H]$^+$ LCMS purity: 96.76%, HPLC purity: 95.35%, $^1$H NMR (DMSO-$d_6$, 400 MHz): 12.06 (s, 1H), 11.31 (s, 1H), 8.97 (s, 1H), 8.33 (s, 1H), 8.05-8.01 (t, J=6.8 Hz, 1H), 7.82-7.78 (t, J=7.2 Hz, 1H), 7.56 (s, 1H), 7.08-7.06 (d, J=7.6 Hz, 1H), 6.83-6.81 (d, J=6.4 Hz, 1H), 2.84-2.83 (d, J=4.4 Hz, 3H), 2.40 (s, 3H), 2.24 (bs, 1H), 0.97-0.92 (m, 4H).

Example 48: 7-(cyclopropanecarboxamido)-2-(2-fluoro-3-(1-methyl-1H-imidazol-4-yl) phenyl)-N-methyl-1H-pyrrolo[2,3-c]pyridine-4-carboxamide (I-48)

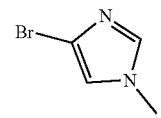

48.2

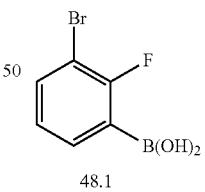

48.1

PdCl$_2$(PPh$_3$)$_2$, K$_2$CO$_3$, Dioxane, H$_2$O, 95° C.

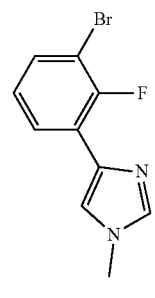

48.3

-continued

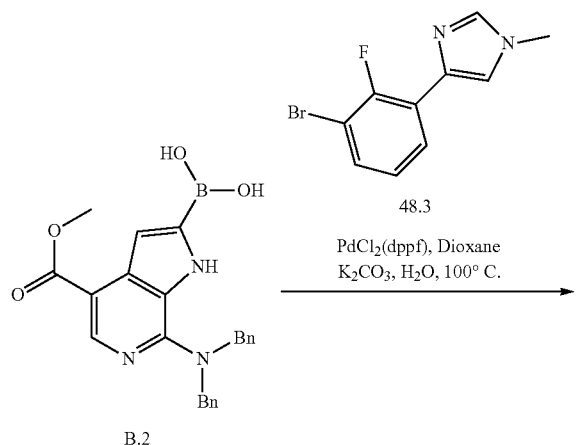

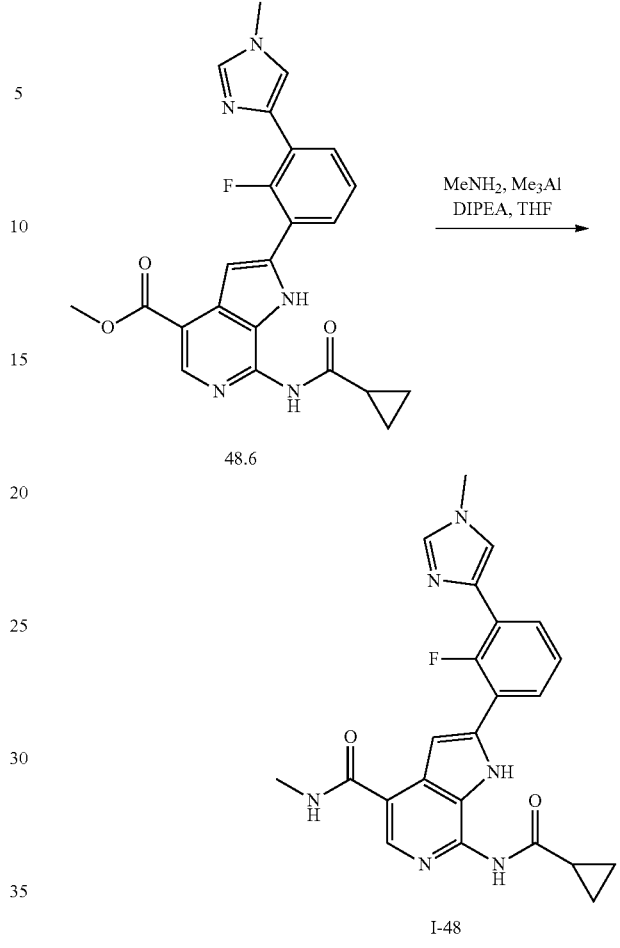

Synthesis of Compound 48.3

Argon was purged for 15 min through a stirred solution of compounds 48.1 (1.0 g, 4.58 mmol, 1.0 eq), 48.2 (0.958 g, 5.95 mmol, 1.3 eq) and potassium carbonate (1.5 g, 11.45 mmol, 2.5 eq) in 1,4-dioxane:water (20 mL, 9:1). Bis (triphenylphosphine)palladium(II) dichloride (0.321 g, 0.45 mmol, 0.1 eq) was added to it and further purging done for 10 min. Reaction was allowed to stir at 95° C. for 5 h. After completion of reaction, reaction mixture was transferred into water and product was extracted with ethyl acetate. Organic layer was combined, washed with brine solution, dried over sodium sulfate and concentrated under reduced pressure to obtain 48.3. (0.220 g, Yield: 18.87%). MS (ES): m/z 254.99 [M+H]$^+$.

Synthesis of Compound 48.4

The compound was synthesized from compounds B.2 and 48.3 using General Procedure A to obtain 48.4. (0.180 g, Yield: 45.66%), MS (ES): m/z 546.23 [M+H]$^+$.

Synthesis of Compound 48.5

The compound was synthesized from compound 48.4 using General Procedure B to obtain 48.5. (0.1 g, Yield: 82.96%), MS (ES): m/z 366.13[M+H]$^+$.

Synthesis of Compound 48.6

The compound was synthesized from compound 48.5 using General Procedure C to obtain 48.6. (0.080 g, Yield: 67.44%), MS (ES): m/z 434.16 [M+H]$^+$.

Synthesis of Compound I-48

The compound was synthesized from compound 48.6 and methylamine using General Procedure D. The material was further purified by column chromatography eluting with 2.5% methanol in dichloromethane to obtain I-48 (0.025 g, Yield: 31.32%), MS (ES): m/z 433.25 [M+H]$^+$ LCMS purity: 95.71%, HPLC purity: 96.83%, $^1$H NMR (DMSO-d$_6$, 400 MHz): 12.08 (s, 1H), 11.39 (s, 1H), 8.46 (bs, 1H), 8.33 (s, 1H), 8.16 (bs, 1H), 8.09 (bs, 1H), 7.84-7.82 (m, 2H), 7.53-7.47 (m, 2H), 3.82 (bs, 3H), 2.87 (bs, 3H), 2.25 (bs, 1H), 1.03-1.01 (m, 4H).

Example 49: 7-(cyclopropanecarboxamido)-2-(6-(1,4-dimethyl-1H-imidazol-2-yl)pyridin-2-yl)-N-methyl-1H-pyrrolo[2,3-c]pyridine-4-carboxamide (I-49)

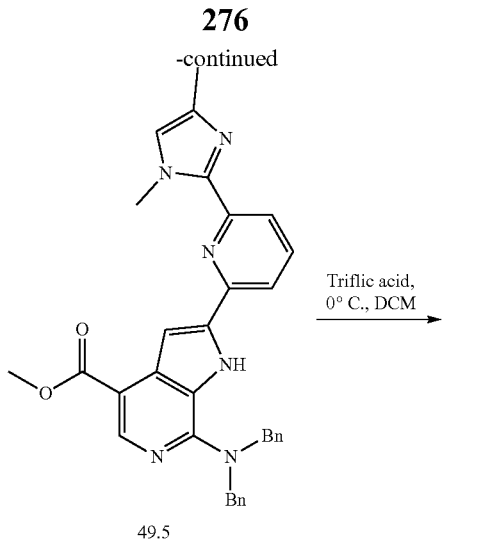

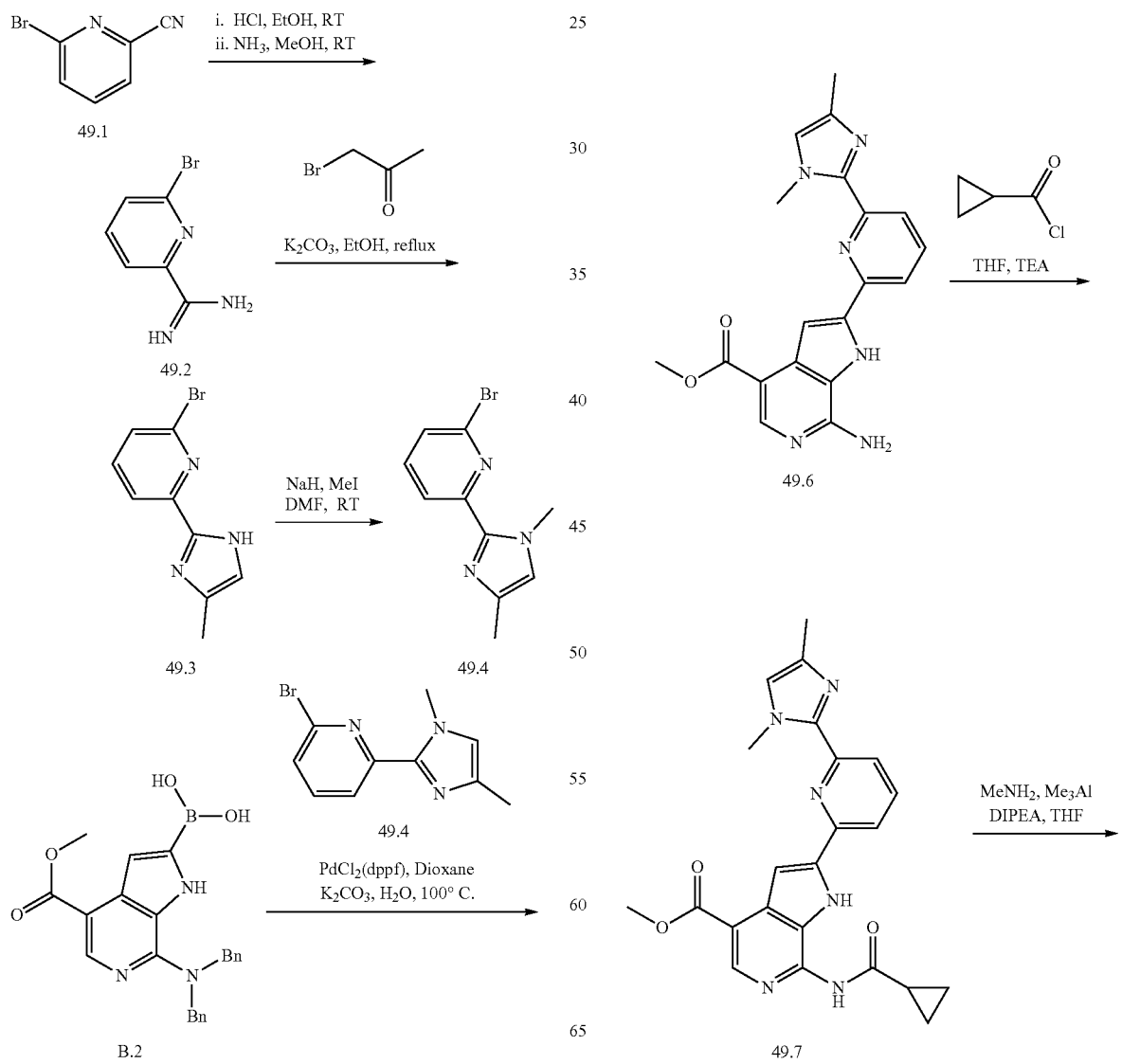

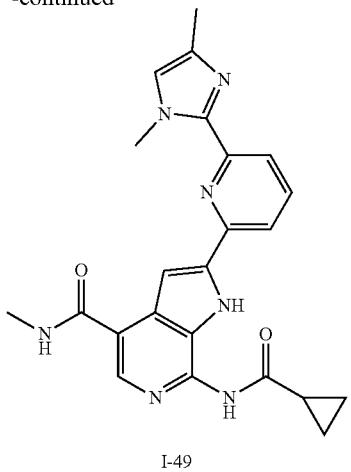

I-49

Synthesis of Compound 49.2

To a solution of compound 49.1 (5.0 g, 27.32 mmol, 1.0 eq) in ethanol (10 mL) was added hydrochloric acid (2.2 mL, 27.32 mmol, 1.0 eq). The reaction mixture was stirred at room temperature for 15 min. After completion of reaction, reaction mixture was concentrated under reduced pressure to obtain residue. To this added 30% aqueous ammonia solution and was extracted with dichloromethane. Organic layer was combined, washed with brine solution, dried over sodium sulfate and concentrated under reduced pressure to obtain crude material. This was further purified by combi flash using 7% ethyl acetate in hexane as eluant to obtain pure 49.2. (3.5 g, Yield: 64.04%). MS (ES): m/z 200.04 $[M+H]^+$.

Synthesis of Compound 49.3

To a solution of compound 49.2 (3.5 g, 17.5 mmol, 1.0 eq) in ethanol (35 mL) was added potassium carbonate (2.4 g, 17.5 mmol, 1.0 eq) at 0° C. followed by 1-bromopropan-2-one (2.5 g, 18.37 mmol, 1.05 eq) and reaction mixture was refluxed for 1 h. After completion of reaction; reaction mixture was concentrated under reduced pressure to obtain residue which was transferred into ice cold water. Precipitated solid was filtered, washed with water and dried under vacuum to obtain 49.3. (1.0 g, Yield: 24.01%). MS (ES): m/z 238.99 $[M+H]^+$.

Synthesis of Compound 49.4

To a solution of compound 49.3 (1.0 g, 4.20 mmol, 1.0 eq) in dimethylformamide (10 mL), was added sodium hydride (0.201 g, 8.4 mmol, 2 eq) at 0° C. and stirred for 20 min. Methyl iodide (0.656 g, 4.62 mmol, 1.1 eq) was added and reaction mixture was stirred at room temperature for 2 h. After completion of reaction, reaction mixture was transferred into ice, stirred and extracted with diethyl ether. Organic layer was combined, dried over sodium sulfate and concentrated under reduced pressure to obtain crude material. This was further purified by distillation to obtain pure 49.4. (0.7 g, Yield: 66.11%). MS (ES): m/z 253.00 $[M+H]^+$.

Synthesis of Compound 49.5

The compound was synthesized from compounds B.2 and 49.4 using General Procedure A to obtain 49.5. (0.250 g, Yield: 63.77%), MS (ES): m/z 543.25 $[M+H]^+$.

Synthesis of Compound 49.6

The compound was synthesized from compound 49.5 using General Procedure B to obtain 49.6. (0.130 g, Yield: 77.86%), MS (ES): m/z 363.15 $[M+H]^+$.

Synthesis of Compound 49.7

The compound was synthesized from compound 49.6 using General Procedure C to obtain 49.7. (0.1 g, Yield: 64.76%), MS (ES): m/z 431.18 $[M+H]^+$.

Synthesis of Compound I-49

The compound was synthesized from compound 49.7 and methylamine using General Procedure D. The material was further purified by column chromatography eluting with 2.5% methanol in dichloromethane to obtain I-49 (0.030 g, Yield: 30.07%), MS (ES): m/z 430.72 $[M+H]^+$ LCMS purity: 100%, HPLC purity: 96.66%, $^1$H NMR (DMSO-$d_6$, 400 MHz): 12.12 (s, 1H), 11.44 (s, 1H), 8.42 (bs, 1H), 8.32 (s, 1H), 8.09-8.07 (d, J=8 Hz, 1H), 7.68 (s, 1H), 7.17 (s, 1H), 7.08 (bs, 1H), 6.85 (s, 1H), 4.18 (s, 3H), 2.88-2.87 (d, J=4.4 Hz, 3H), 2.19 (s, 3H), 1.57 (bs, 1H), 0.99-0.97 (m, 4H).

Example 50: 7-(cyclopropanecarboxamido)-N-methyl-2-(3-(2-methyl-2H-tetrazol-5-yl) phenyl)-1H-pyrrolo[2,3-c]pyridine-4-carboxamide (I-50)

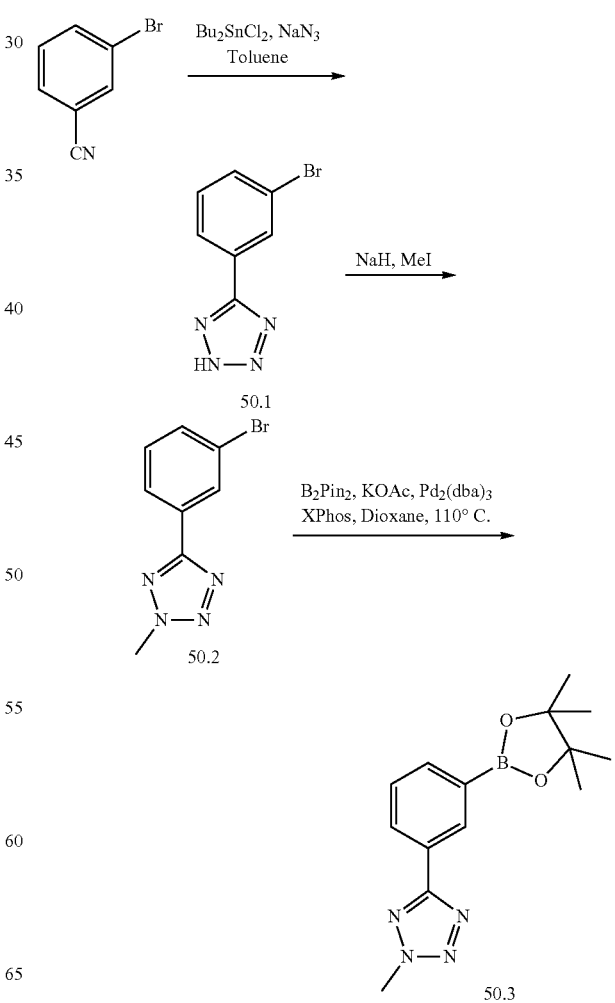

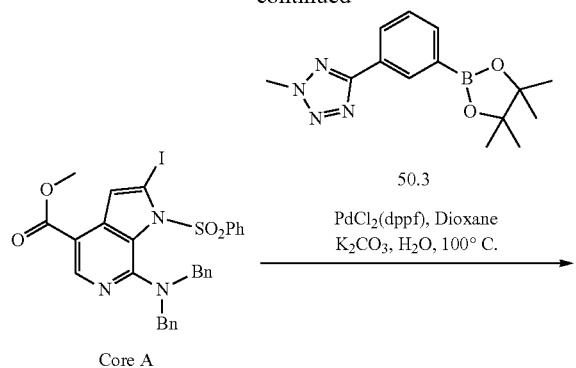

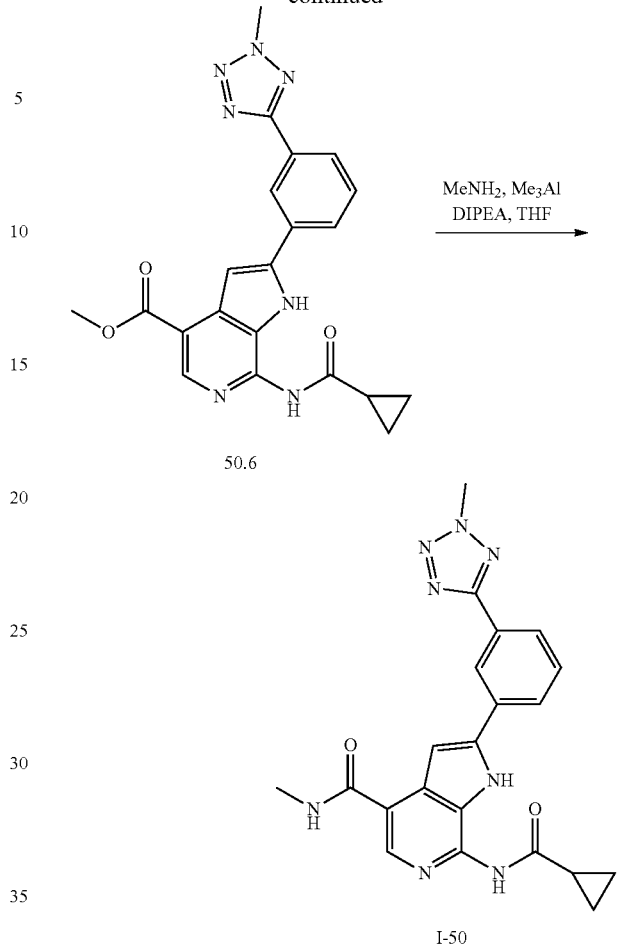

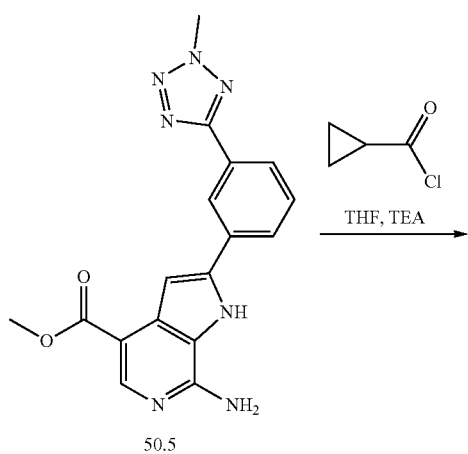

Synthesis of Compound 50.1

To a solution of 3-bromobenzonitrile (5.0 g, 5.49 mmol, 1.0 eq) in toluene (50 mL) was added dibutyltin chloride (3.3 g, 10.98 mmol, 2.0 eq) and sodium azide (0.535 g, 8.23 mmol, 1.5 eq) The reaction was stirred at room temperature for 4 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by combi flash using 3% methanol in dichloromethane as eluant to obtain pure 50.1. (2.5 g, Yield: 40.44%). MS (ES): m/z 225.97 [M+H]$^+$.

Synthesis of Compound 50.2

To a solution of compound 50.1 (1.0 g, 4.44 mmol, 1.0 eq) in dimethylformamide (10 mL), was added sodium hydride (0.213 g, 8.88 mmol, 2 eq) at 0° C. and stirred for 20 min. Methyl iodide (0.693 g, 4.88 mmol, 1.1 eq) was added and reaction mixture was stirred at room temperature for 2 h. After completion of reaction, reaction mixture was transferred into ice, stirred and extracted with diethyl ether. Organic layer was combined, dried over sodium sulfate and concentrated under reduced pressure to obtain crude material. This was further purified by distillation to obtain pure 50.2. (0.7 g, Yield: 65.89%). MS (ES): m/z 239.98 [M+H]$^+$.

Synthesis of Compound 50.3

The compound was synthesized from compound 50.2 using General Procedure F, using 2-dicyclohexylphosphino-2',4',6'-triisopropylbiphenyl instead of 4,5-bis(diphenylphosphino)-9,9-dimethylxanthene, to obtain 50.3. (0.5 g, Yield: 59.68%). MS (ES): m/z 287.16 [M+H]$^+$.

Synthesis of Compound 50.4

The compound was synthesized from Core A and compound 50.3 using General Procedure A to obtain 50.4. (0.280 g, Yield: 59.22%), MS (ES): m/z 670.22 [M+H]$^+$.

Synthesis of Compound 50.5

The compound was synthesized from compound 50.4 using General Procedure B to obtain 50.5. (0.120 g, Yield: 82.16%), MS (ES): m/z 350.13 [M+H]$^+$.

Synthesis of Compound 50.6

The compound was synthesized from compound 50.5 using General Procedure C to obtain 50.6. (0.090 g, Yield: 62.77%), MS (ES): m/z 418.16 [M+H]$^+$.

Synthesis of Compound I-50

The compound was synthesized from compound 50.6 and methylamine using General Procedure D. The material was further purified by column chromatography eluting with 2.5% methanol in dichloromethane to obtain I-50 (0.026 g, Yield: 28.96%), MS (ES): m/z 417.60 [M+H]$^+$ LCMS purity: 95.02%, HPLC purity: 95.00%, $^1$H NMR (DMSO-d$_6$, 400 MHz): 12.20 (s, 1H), 11.24 (s, 1H), 8.55 (bs, 1H), 8.42-8.41 (d, J=4.4 Hz, 1H), 8.34 (s, 1H), 8.12-8.11 (d, J=7.2 Hz, 2H), 7.77-7.73 (t, J=7.6 Hz, 1H), 7.47 (bs, 1H), 4.49 (s, 3H), 2.87-2.86 (d, J=4.4 Hz, 3H), 2.21 (bs, 1H), 0.99-0.96 (m, 4H).

Example 51: 7-(cyclopropanecarboxamido)-2-(5-(dimethylcarbamoyl)-3-fluoropyridin-2-yl)-N-methyl-1H-pyrrolo[2,3-c]pyridine-4-carboxamide (I-51)

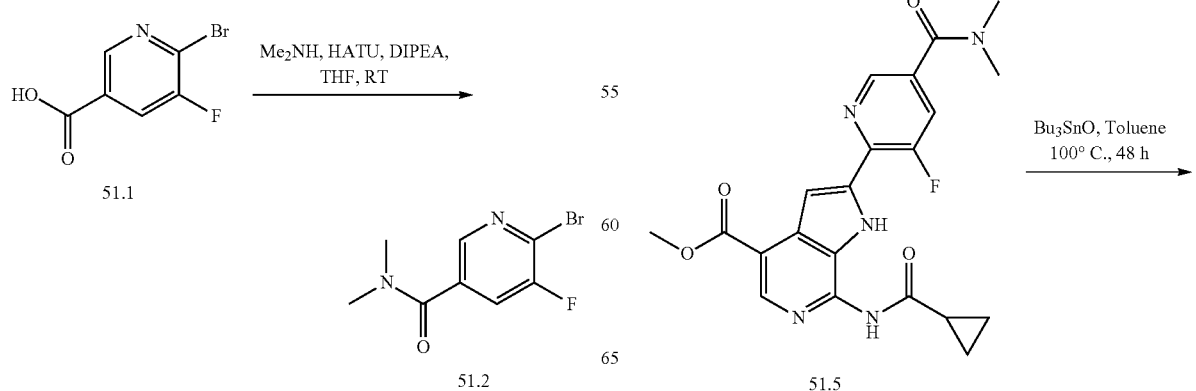

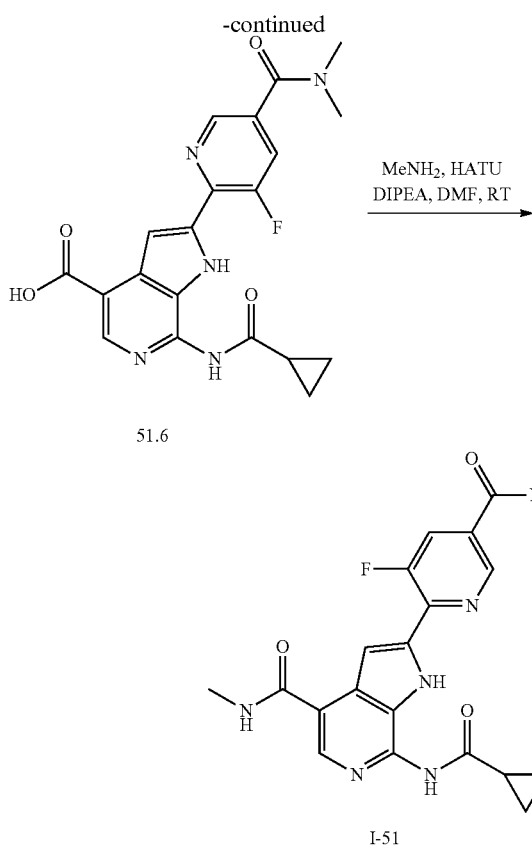

51.6

I-51

Synthesis of Compound 51.2

The compound was synthesized from compound 51.1 and dimethylamine using General Procedure H to obtain 51.2 (0.7 g, Yield: 62.33%). MS (ES): m/z 246.98 [M+H]$^+$.

Synthesis of Compound 51.3

The compound was synthesized from compounds B.2 and 51.2 using General Procedure A to obtain 51.3. (0.180 g, Yield: 46.35%), MS (ES): m/z 538.22 [M+H]$^+$.

Synthesis of Compound 51.4

The compound was synthesized from compound 51.3 using General Procedure B to obtain 51.4. (0.110 g, Yield: 61.11%), MS (ES): m/z 358.22 [M+H]$^+$.

Synthesis of Compound 51.5

The compound was synthesized from compound 51.4 using General Procedure C to obtain 51.5. (0.085 g, Yield: 97.65%), MS (ES): m/z 426.15[M+H]$^+$.

Synthesis of Compound 51.6

To a suspension of compound 51.5 (0.075 g, 0.17 mmol, 1.0 eq) in toluene (2 mL) was added tributyltin oxide (0.202 g, 0.34 mmol, 2.0 eq) and reaction mixture was heated at 100° C. for 48 h. After completion of reaction, reaction mixture was concentrated under reduced pressure to obtain residue which was dissolved in saturated sodium bicarbonate solution and washed with hexane. Aqueous layer separated and acidified with 1N hydrochloric acid to pH~5-6 and extracted with ethyl acetate. Organic layer was combined, dried over sodium sulfate and concentrated under reduced pressure to obtain solid which was triturated with hexane to obtain pure 51.6. (0.040 g, Yield: 55.15%), MS (ES): m/z 412.14 [M+H]$^+$.

Synthesis of Compound I-51

The compound was synthesized from compound 51.6 and methylamine using General Procedure H. The material was further purified by column chromatography and the compound was eluted in 40% ethyl acetate in hexane to obtain I-51 (0.012 g, Yield: 77.54%). MS (ES): m/z 425.65 [M+H]$^+$ LCMS purity: 100%, HPLC purity: 95.71%, $^1$H NMR (DMSO-d$_6$, 400 MHz): 12.39 (s, 1H), 9.11 (s, 1H), 8.64 (bs, 1H), 8.27 (s, 1H), 7.70 (bs, 1H), 7.67 (bs, 1H), 7.17-7.15 (d, J=8 Hz, 1H), 4.38 (bs, 3H), 3.15 (bs, 6H), 1.37 (bs, 1H), 0.92-0.90 (m, 4H).

Example 52: 7-(cyclopropanecarboxamido)-2-(2-fluoro-3-(2-methyl-2H-tetrazol-5-yl)phenyl)-N-methyl-1H-pyrrolo[2,3-c]pyridine-4-carboxamide (I-52)

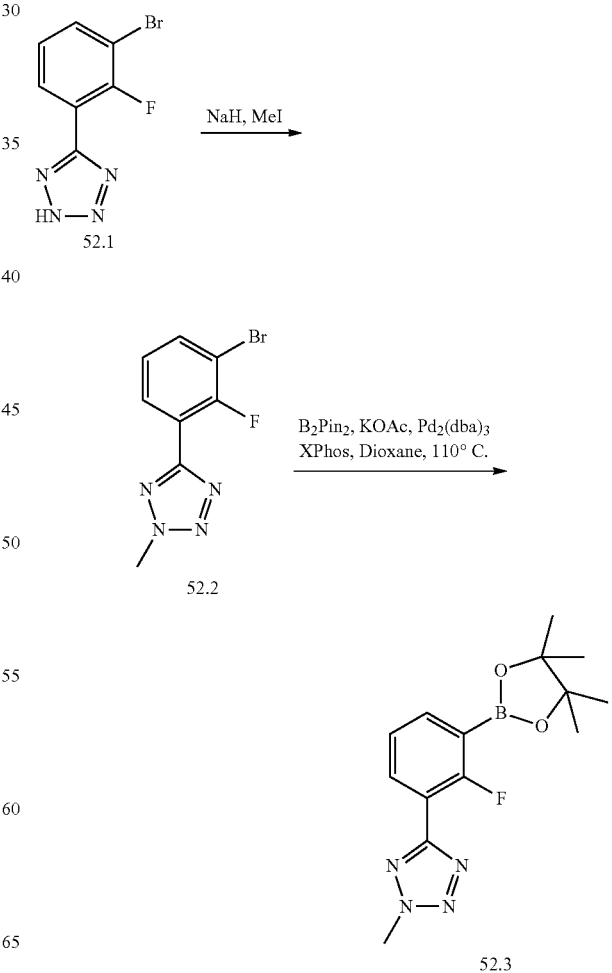

285

-continued

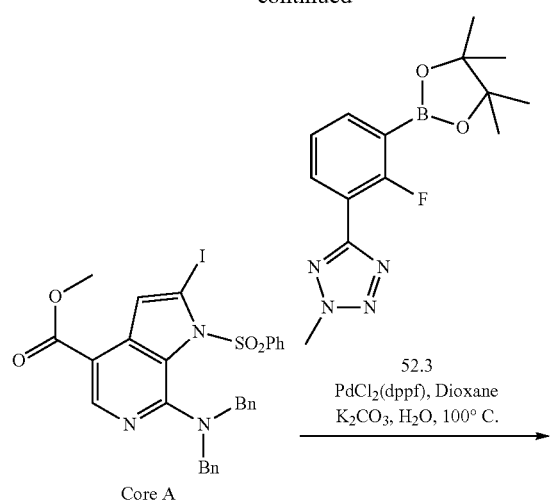

286

-continued

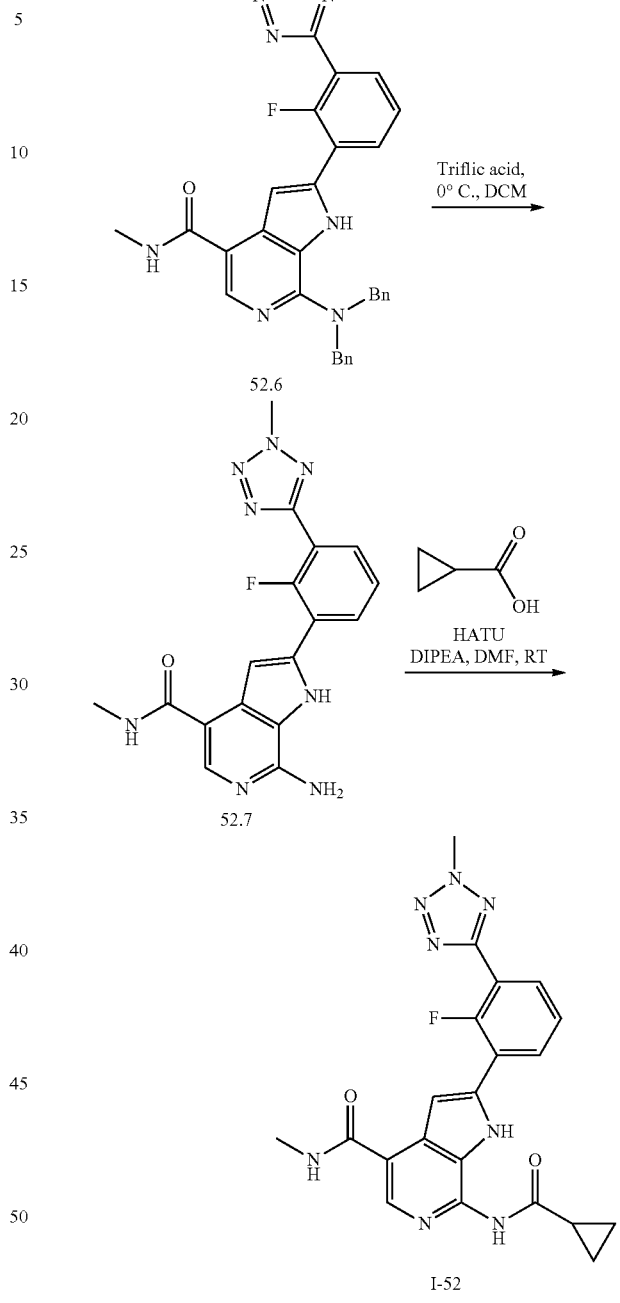

Synthesis of Compound 52.2

To a solution of compound 52.1 (1.2 g, 4.93 mmol, 1.0 eq) in dimethylformamide (12 mL), was added sodium hydride (0.236 g, 9.86 mmol, 2 eq) at 0° C. and stirred for 20 min. Methyl iodide (0.770 g, 5.42 mmol, 1.1 eq) was added and reaction mixture was stirred at room temperature for 2 h. After completion of reaction, reaction mixture was transferred into ice, stirred and extracted with diethyl ether. Organic layer was combined, dried over sodium sulfate and concentrated under reduced pressure to obtain crude mate-

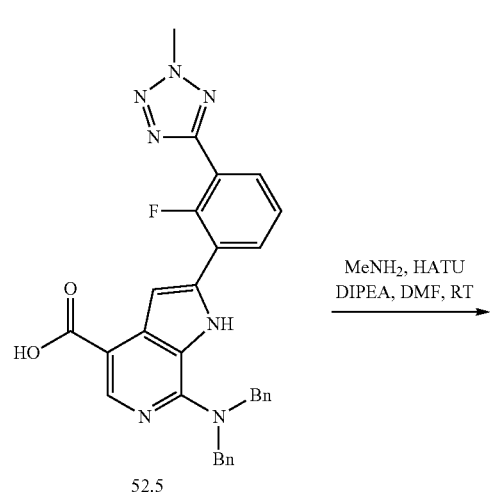

rial. This was further purified by distillation to obtain pure 52.2. (0.8 g, Yield: 63.03%). MS (ES): m/z 256.98 [M+H]⁺.

Synthesis of Compound 52.3

The compound was synthesized from compound 52.2 using General Procedure F, using 2-dicyclohexylphosphino-2',4',6'-triisopropylbiphenyl instead of 4,5-bis(diphenylphosphino)-9,9-dimethylxanthene, to obtain 52.3. (0.640 g, Yield: 67.62%). MS (ES): m/z 305.15 [M+H]⁺.

Synthesis of Compound 52.4

The compound was synthesized from Core A and compound 52.3 using General Procedure A to obtain 52.4. (0.260 g, Yield: 53.56%), MS (ES): m/z 688.21 [M+H]⁺.

Synthesis of Compound 52.5

To a solution of compound 52.4 (0.260 g, 0.37 mmol, 1.0 eq), in methanol (5 mL) was added sodium hydroxide (0.074 g, 1.85 mmol, 5 eq). The reaction was stirred at 60° C. for 6 h. After completion of reaction, reaction mixture was concentrated under reduced pressure to obtain residue. To this added water and acidified with 1N hydrochloric acid to adjust pH~6-6.5 at 10° C. Product was extracted with dichloromethane. Organic layer was combined, washed with brine solution, dried over sodium sulfate and concentrated under reduced pressure to obtain crude material. This was further purified by column chromatography and compound was eluted in 2.1% methanol in dichloromethane to obtain pure 52.5. (0.160 g, Yield: 79.32%). MS (ES): m/z 534.20 [M+H]⁺.

Synthesis of Compound 52.6

The compound was synthesized from compound 52.5 and methylamine using General Procedure H to obtain 52.6. (0.140 g, Yield: 85.41%). MS (ES): m/z 547.23 [M+H]⁺.

Synthesis of Compound 52.7

The compound was synthesized from compound 52.6 using General Procedure B to obtain 52.7. (0.093 g, Yield: 99.11%), MS (ES): m/z 367.14 [M+H]⁺.

Synthesis of Compound I-52

To a solution of compound cyclopropanecarboxylic acid (0.027 g, 0.32 mmol, 1.0 eq), in N,N-dimethylformamide (2 mL) was added 1-[bis(dimethylamino)methylene]-1H-1,2,3-triazolo[4,5-b]pyridinium 3-oxid hexafluorophosphate (0.243 g, 0.64 mmol, 2.0 eq) and stirred at room temperature for 15 min. To this added diisopropylethylamine (0.123 g, 0.96 mmol, 3.0 eq) followed by addition of 52.7 (0.120 g, 0.32 mmol, 1.0 eq), The reaction mixture was stirred at room temperature for 5 min. After completion of reaction, reaction mixture was transferred into water and product was extracted with ethyl acetate. Organic layer was combined, washed with brine solution, dried over sodium sulfate and concentrated under reduced pressure to obtain crude material. The material was further purified by column chromatography and the compound was eluted in 40% ethyl acetate in hexane to obtain I-52 (0.045 g, Yield: 31.62%). MS (ES): m/z 435.72 [M+H]⁺ LCMS purity: 100%, HPLC purity: 98.65%, ¹H NMR (DMSO-d₆, 400 MHz): 12.13 (s, 1H), 11.33 (s, 1H), 8.42 (bs, 1H), 8.35 (s, 1H), 8.17-8.13 (m, 2H), 7.56 (bs, 2H), 4.52 (bs, 3H), 2.87 (bs, 3H), 1.24 (bs, 1H), 1.00-0.97 (m, 4H).

Example 53: 7-(cyclopropanecarboxamido)-2-(5-(3,3-difluoroazetidine-1-carbonyl)pyridin-2-yl)-N-methyl-1H-pyrrolo[2,3-c]pyridine-4-carboxamide (I-53)

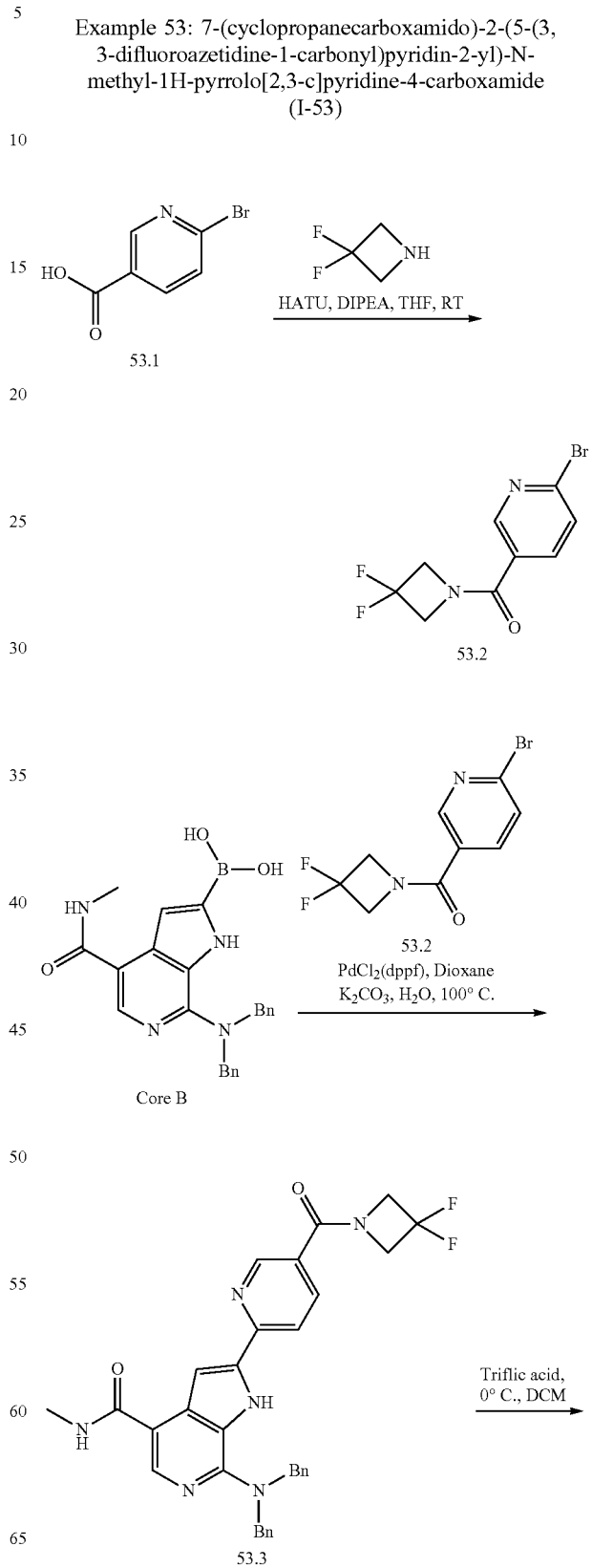

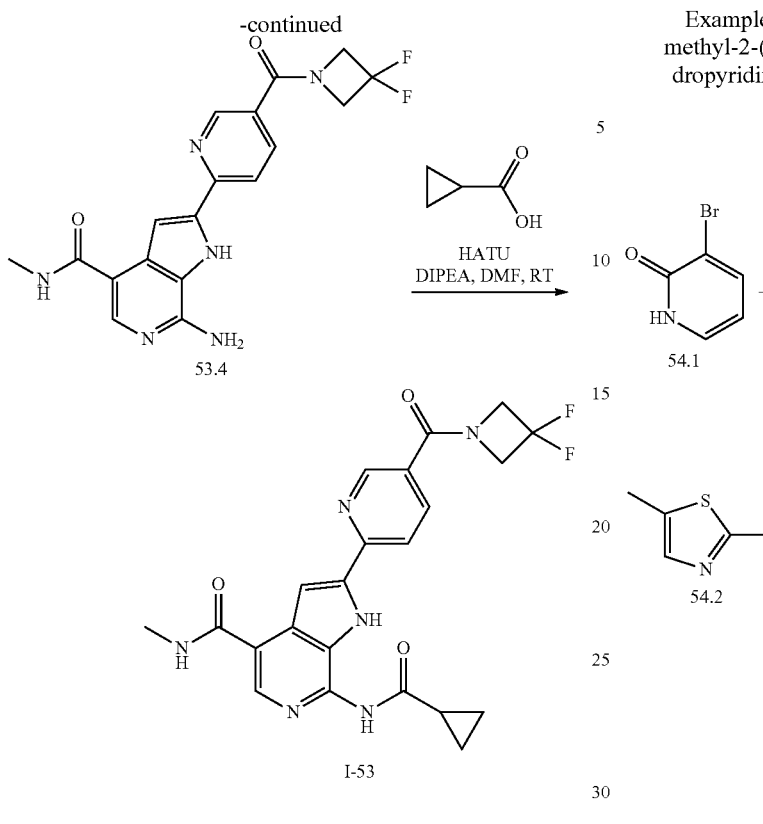

I-53

Synthesis of Compound 53.2

The compound was synthesized from compound 53.1 and 3,3-difluoroazetidine using General Procedure H to obtain 53.2 (0.5 g, Yield: 36.45%), MS (ES): m/z 276.97 [M+H]$^+$.

Synthesis of Compound 53.3

The compound was synthesized from Core B and compound 53.2 using General Procedure A to obtain 53.3. (0.120 g, Yield: 58.49%), MS (ES): m/z 567.23 [M+H]$^+$.

Synthesis of Compound 53.4

The compound was synthesized from compound 53.3 using General Procedure B to obtain 53.4. (0.070 g, Yield: 85.55%), MS (ES): m/z 387.13 [M+H]$^+$.

Synthesis of Compound I-53

The compound was synthesized from compound 53.4 and cyclopropanecarboxylic acid using General Procedure H. The material was further purified by column chromatography and the compound was eluted in 40% ethyl acetate in hexane to obtain I-53 (0.026 g, Yield: 31.58%). MS(ES): m/z 455.76 [M+H]$^+$ LCMS purity: 96%, HPLC purity: 95.77%, $^1$H NMR (DMSO-d$_6$, 400 MHz): 12.19 (s, 1H), 11.35 (s, 1H), 8.96 (bs, 1H), 8.39 (s, 1H), 8.30 (s, 1H), 8.25-8.19 (m, 2H), 7.74 (s, 1H), 4.94 (bs, 2H), 4.53 (bs, 2H), 2.85-2.84 (d, J=4.4 Hz, 3H), 2.26 (bs, 1H), 0.98-0.94 (m, 4H).

Example 54: 7-(cyclopropanecarboxamido)-N-methyl-2-(1-(5-methylthiazol-2-yl)-2-oxo-1,2-dihydropyridin-3-yl)-1H-pyrrolo[2,3-c]pyridine-4-carboxamide (I-54)

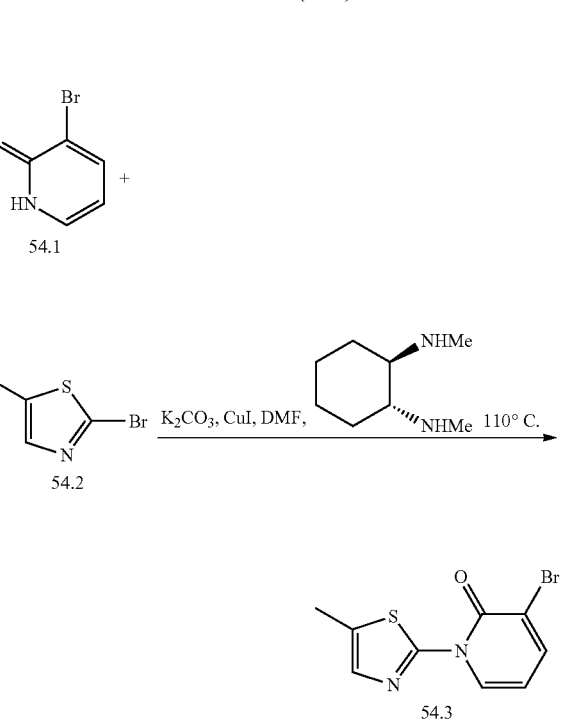

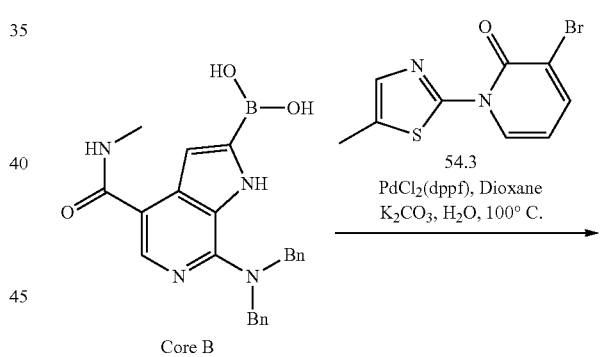

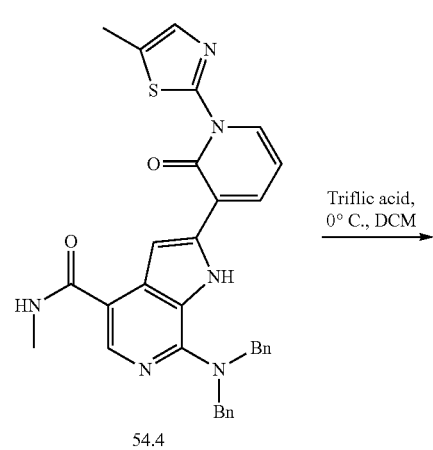

291

-continued

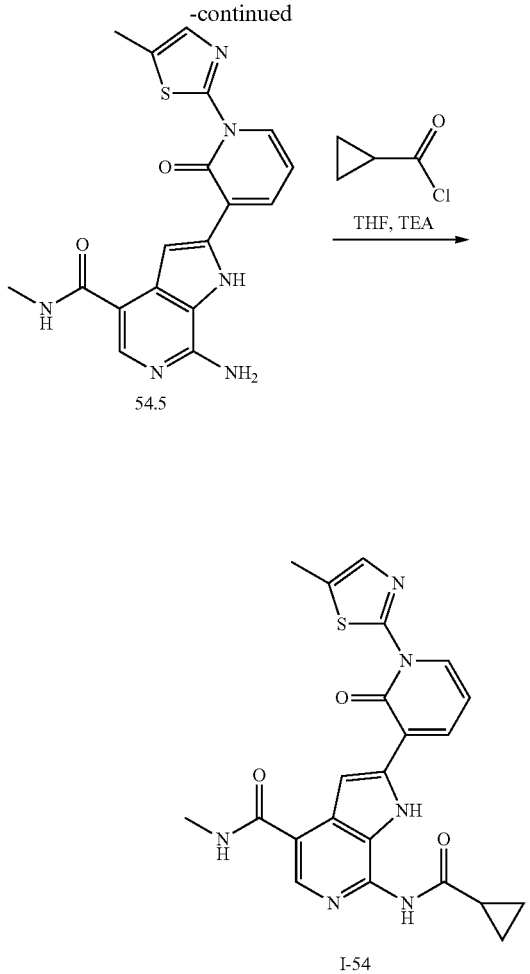

54.5

I-54

Synthesis of Compound 54.3

To a solution of compounds 54.1 (1.0 g, 5.74 mmol, 1 eq) and 54.2 (1.2 g, 6.88 mmol, 1.2 eq) in dimethylformamide (15 mL) was added potassium carbonate (1.5 g, 11.48 mmol, 2.0 eq) and degassed with argon for 15 min. Copper iodide (0.262 g, 1.37 mmol, 0.2 eq) and (1R,2R)—N,N'-dimethyl-cyclohexane-1,2-diamine (0.326 g, 2.29 mmol, 0.4 eq) was added and reaction mixture again degassed with argon for 5 min followed by heating at 100° C. for 16 h. After completion of reaction, reaction mixture was cooled to room temperature, transferred into water and product was extracted with ethyl acetate. Organic layer was combined, washed with brine solution, dried over sodium sulfate and concentrated under reduced pressure to obtain crude material. This was further purified by column chromatography and compound was eluted in 1.2% methanol in dichloromethane to obtain pure 52.3. (0.5 g, Yield: 32.09%). MS (ES): m/z 270.95 [M+H]$^+$.

Synthesis of Compound 54.4

The compound was synthesized from Core B and compound 54.3 using General Procedure A to obtain 54.4. (0.110 g, Yield: 54.18%), MS (ES): m/z 561.20 [M+H]$^+$.

292

Synthesis of Compound 54.5

The compound was synthesized from compound 54.4 using General Procedure B to obtain 54.5. (0.065 g, Yield: 87.09%), MS (ES): m/z 381.11 [M+H]$^+$.

Synthesis of Compound I-54

The compound was synthesized from compound 54.5 using General Procedure C to obtain I-54 (0.028 g, Yield: 36.54%). MS(ES): m/z 449.72 [M+H]$^+$ LCMS purity: 96.15%, HPLC purity: 95.00%, $^1$H NMR (DMSO-d$_6$, 400 MHz): 12.33 (s, 1H), 11.23 (s, 1H), 8.86-8.85 (bs, J=6 Hz, 1H), 8.43-8.41 (d, J=6.8 Hz, 1H), 8.35 (bs, 1H), 8.28 (bs, 1H), 8.59-8.55 (d, J=12.4 Hz, 1H), 6.83-6.81 (t, J=7.2 Hz, 1H), 5.76 (s, 1H), 2.85-2.84 (d, J=4 Hz, 3H), 2.32 (bs, 3H), 2.23 (bs, 1H), 0.99-0.96 (m, 4H).

Examples 55 and 56: (S)-7-(cyclopropanecarboxamido)-N-methyl-2-(2-oxo-1-(tetrahydro-2H-pyran-3-yl)-1,2-dihydropyridin-3-yl)-1H-pyrrolo[2,3-c]pyridine-4-carboxamide (I-55) and (R)-7-(cyclopropanecarboxamido)-N-methyl-2-(2-oxo-1-(tetrahydro-2H-pyran-3-yl)-1,2-dihydropyridin-3-yl)-1H-pyrrolo[2,3-c]pyridine-4-carboxamide (I-56)

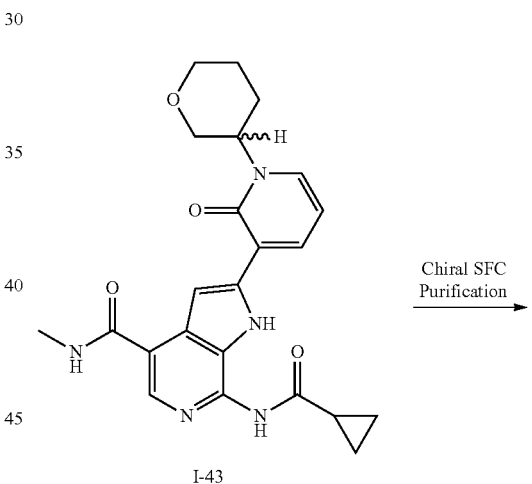

I-43

Chiral SFC Purification →

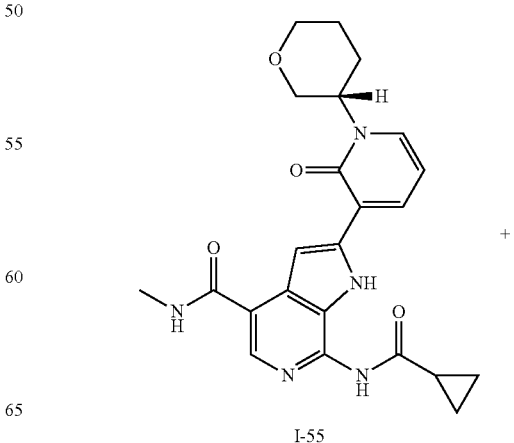

I-55

293
-continued

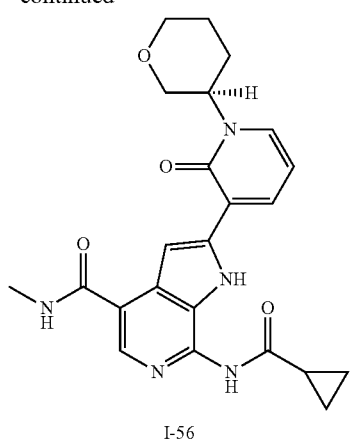

I-56

Synthesis of Compounds I-55 and I-56

Enantiomers of compound I-43 were separated by on Shimadzu LC-20AP and UV detector. The column used was CHIRALPAK AD-H (250*21.0) mm, 5 micron, column flow was 18.0 ml/min. Mobile phase used was 0.1% Diethylamine in Methanol. The UV spectra were recorded at 240 nm Lambdamax.

Isocratic ratio was, as described below.

| Time (min) | Mobile phase % (0.1% DEA in MeOH) |
| --- | --- |
| 0.01 | 100 |
| 25 | 100 | to provide pure fraction-1 and fraction-2.

Fraction-1 was concentrated under reduced pressure at 30° C. to afford pure I-55 (0.025 g). MS (ES): m/z 436.62 [M+H]+, LCMS purity: 97.01%, HPLC purity: 97.00%, CHIRAL HPLC purity: 97.54%, $^1$H NMR (DMSO-$d_6$, 400 MHz): 12.63 (s, 1H), 11.63 (s, 1H), 8.30-8.29 (d, J=5.6 Hz, 2H), 8.26 (s, 1H), 8.03-8.02 (d, J=6 Hz, 1H), 7.45 (s, 1H), 6.57-6.53 (t, J=6.8 Hz, 1H), 5.03 (bs, 1H), 3.89-3.84 (t, J=8.4 Hz, 2H), 3.59-3.54 (t, J=10 Hz, 1H), 3.51-3.47 (t, J=9.6 Hz, 1H), 2.85-2.84 (d, J=4.4 Hz, 3H), 2.21 (bs, 1H), 2.01 (bs, 2H), 1.79 (bs, 1H), 1.24 (bs, 1H), 0.97-0.93 (m, 4H).

Fraction-2 was concentrated under reduced pressure at 30° C. to afford pure I-56 (0.026 g). MS (ES): m/z 436.67 [M+H]+, LCMS purity: 97.11%, HPLC purity: 96.75%, CHIRAL HPLC purity: 98.40%, $^1$H NMR (DMSO-$d_6$, 400 MHz): 12.63 (s, 1H), 11.15 (s, 1H), 8.30-8.29 (d, J=5.6 Hz, 2H), 8.26 (s, 1H), 8.03-8.02 (d, J=6 Hz, 1H), 7.45 (s, 1H), 6.57-6.53 (t, J=6.8 Hz, 1H), 5.03 (bs, 1H), 3.89-3.84 (t, J=8.4 Hz, 2H), 3.59-3.54 (t, J=10 Hz, 1H), 3.51-3.47 (t, J=9.6 Hz, 1H), 2.85-2.84 (d, J=4.4 Hz, 3H), 2.21 (bs, 1H), 2.03 (bs, 2H), 1.79 (bs, 1H), 1.24 (bs, 1H), 0.97-0.93 (m, 4H).

294

Example 57: 7-(cyclopropanecarboxamido)-2-(2-cyclopropoxy-4-(1-methyl-1H-imidazol-2-yl)phenyl)-N-methyl-1H-pyrrolo[2,3-c]pyridine-4-carboxamide (I-57)

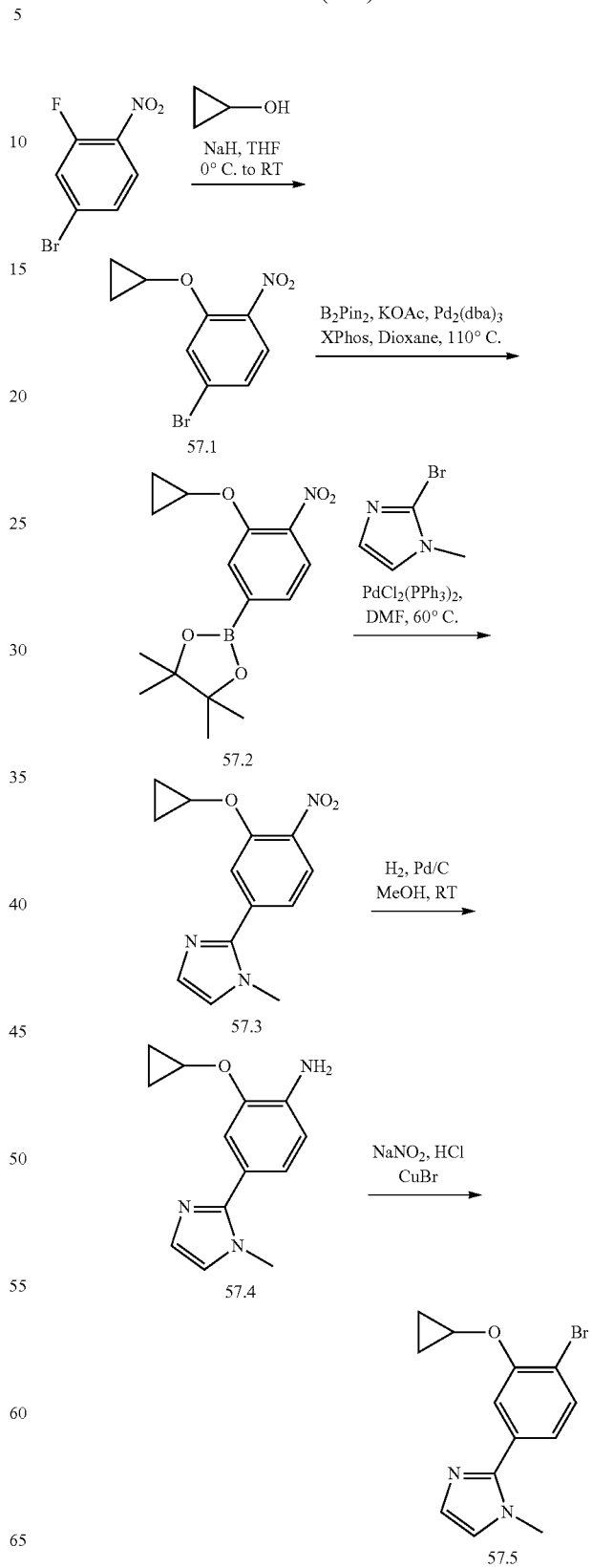

-continued

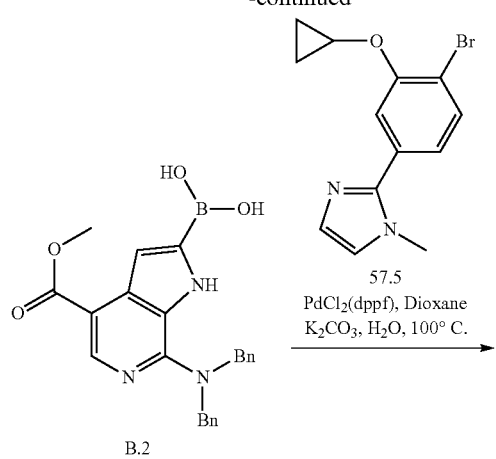

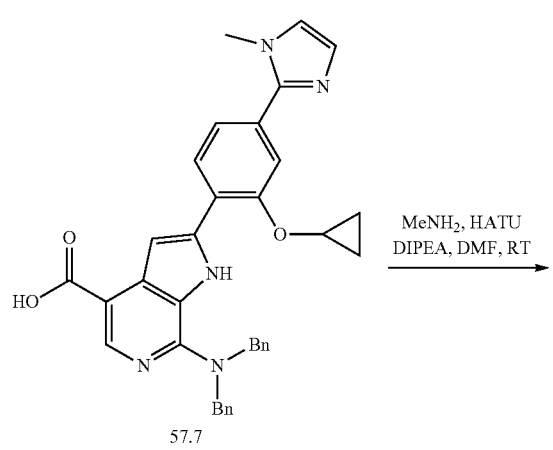

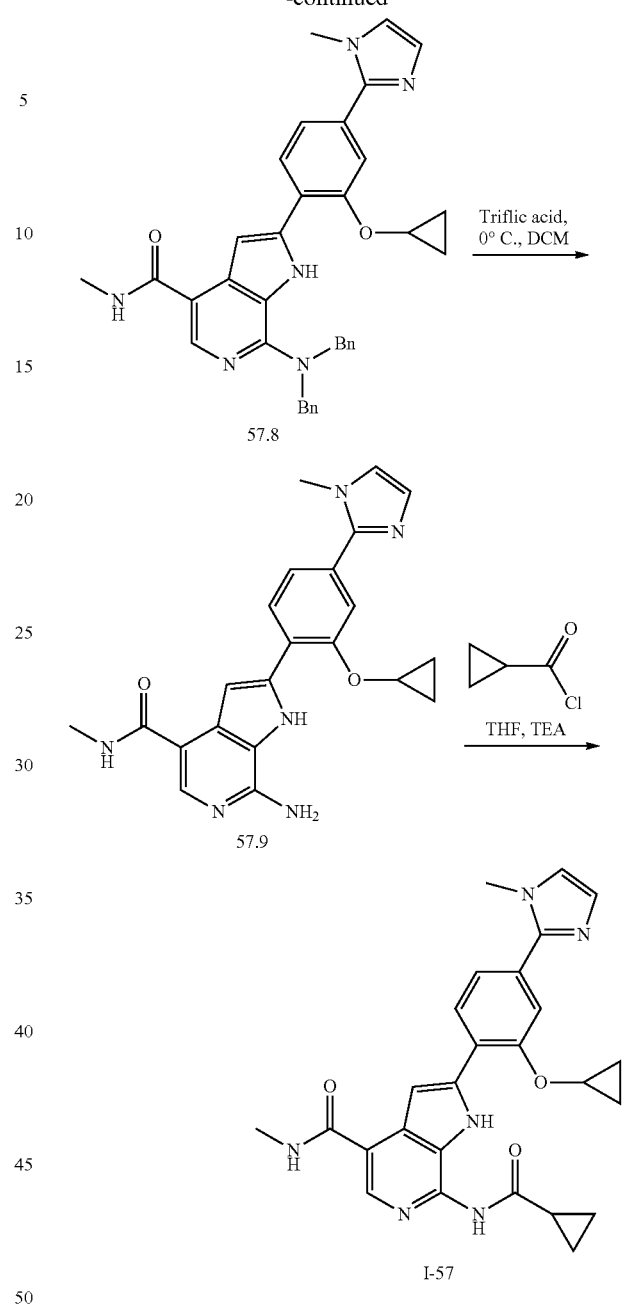

Synthesis of Compound 57.1

To a solution of 4-bromo-2-fluoro-1-nitrobenzene (3.0 g, 13.63 mmol, 1.0 eq) in tetrahydrofuran (30 mL), was added sodium hydride (0.654 g, 27.26 mmol, 2 eq) at 0° C. and stirred for 20 min. Cyclopropanol (0.869 g, 14.99 mmol, 1.1 eq) was added and reaction mixture was stirred at room temperature for 2 h. After completion of reaction, reaction mixture was transferred into ice, stirred and extracted with diethyl ether. Organic layer was combined, dried over sodium sulfate and concentrated under reduced pressure to obtain crude material. This was further purified by distillation to obtain pure 57.1. (2.7 g, Yield: 76.72%). MS (ES): m/z 257.97 [M+H]+.

Synthesis of Compound 57.2

The compound was synthesized from compound 57.1 using General Procedure F, using 2-dicyclohexylphosphino-2',4',6'-triisopropylbiphenyl instead of 4,5-bis(diphenylphosphino)-9,9-dimethylxanthene, to obtain 57.2. (1.3 g, Yield: 40.72%). MS (ES): m/z 306.15 [M+H]$^+$.

Synthesis of Compound 57.3

Argon was purged for 15 min through a stirred solution of compound 57.2 (1.3 g, 4.26 mmol, 1.0 eq) and 2-bromo-1-methyl-1H-imidazole (0.891 g, 5.53 mmol, 1.3 eq) in dimethylformamide (10 mL). Bis(triphenylphosphine)palladium(II) dichloride (0.298 g, 0.42 mmol, 0.1 eq) was added to it and further purging done for 10 min. Reaction was allowed to stir at 100° C. for 5 h. After completion of reaction, reaction mixture was transferred into water and product was extracted with ethyl acetate. Organic layer was combined, washed with brine solution, dried over sodium sulfate and concentrated under reduced pressure to obtain 57.3. (0.7 g, Yield: 63.37%). MS (ES): m/z 260.09 [M+H]$^+$.

Synthesis of Compound 57.4

To a solution of compound 57.3 (0.7 g, 2.70 mmol, 1.0 eq) in methanol (14 ml), palladium on charcoal (0.36 g) was added. Hydrogen was purged through reaction mixture for 4 h at room temperature. After completion of reaction, reaction mixture was filtered through Celite-bed and washed with methanol. Filtrate was concentrated under reduced pressure to obtain crude material. This was further purified by trituration with n-pentane to obtain pure 57.4. (0.6 g, Yield: 96.92%). MS (ES): m/z 230.12 [M+H]$^+$.

Synthesis of Compound 57.5

To the compound 57.4 (0.6 g, 2.60 mmol, 1.0 eq) was added 30% hydrobromic acid (1.2 mL) dropwise at 0° C. Sodium nitrite (0.358 g, 5.2 mmol, 2.0 eq) and acetone (4.8 mL) were added to this reaction mixture and stirred for 2 min. Then copper(I) bromide (0.743 g, 5.2 mmol, 2.0 eq) was added and reaction mixture was stirred for 15 min. After completion of reaction, reaction mixture was transferred into water and product was extracted with ethyl acetate. Organic layer was combined, washed with brine solution, dried over sodium sulfate and concentrated under reduced pressure to obtain 57.5. (0.3 g, Yield: 39.10%). MS (ES): m/z 293.02 [M+H]$^+$.

Synthesis of Compound 57.6

The compound was synthesized from compounds B.2 and 57.5 using General Procedure A to obtain 57.6. (0.180 g, Yield: 51.22%), MS (ES): m/z 584.26 [M+H]$^+$.

Synthesis of Compound 57.7

To a solution of compound 57.6 (0.180 g, 0.30 mmol, 1.0 eq), in methanol (2 mL) was added sodium hydroxide (0.06 g, 1.5 mmol, 5.0 eq). The reaction mixture was stirred at 60° C. for 1 h. After completion of reaction, reaction mixture was concentrated under reduced pressure to obtain residue. To this added water and acidified with 1N hydrochloric acid to adjust pH~6 at 10° C. Product was extracted with dichloromethane. Organic layer was combined, washed with brine solution, dried over sodium sulfate and concentrated under reduced pressure to obtain crude material. This was further purified by column chromatography and compound was eluted in 2.1% methanol in dichloromethane to obtain pure 57.7. (0.140 g, Yield: 79.69%). MS (ES): m/z 570.25 [M+H]$^+$.

Synthesis of Compound 57.8

The compound was synthesized from compound 57.7 and methylamine using General Procedure H to obtain 57.8. (0.120 g, Yield: 83.80%). MS (ES): m/z 583.28 [M+H]$^+$.

Synthesis of Compound 57.9

The compound was synthesized from compound 57.8 using General Procedure B to obtain 57.9. (0.070 g, Yield: 84.46%), MS (ES): m/z 403.18 [M+H]$^+$.

Synthesis of Compound I-57

The compound was synthesized from compound 57.9 using General Procedure C to obtain I-57 (0.028 g, Yield: 34.21%). MS (ES): m/z 471.30 [M+H]$^+$ LCMS purity: 95.37%, HPLC purity: 96.11%, $^1$H NMR (DMSO-d$_6$, 400 MHz): 12.27 (s, 1H), 11.54 (s, 1H), 8.71-8.69 (d, J=8 Hz, 2H), 8.55 (s, 1H), 7.83 (s, 1H), 7.63 (s, 1H), 6.94 (s, 2H), 5.77 (s, 1H), 4.6 (bs, 1H), 3.96 (s, 3H), 2.62 (s, 3H), 2.21 (bs, 1H), 1.09-1.00 (m, 4H), 0.86-0.83 (m, 4H).

Example 58: 7-(cyclopropanecarboxamido)-2-(2-fluoro-4-(1-methyl-1H-imidazol-2-yl)phenyl)-N-methyl-11H-pyrrolo[2,3-c]pyridine-4-carboxamide (I-58)

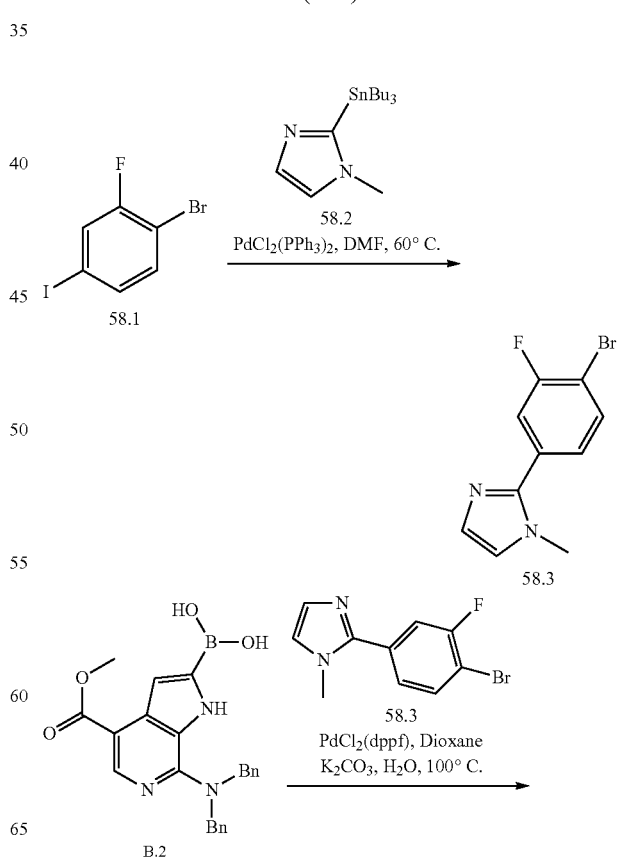

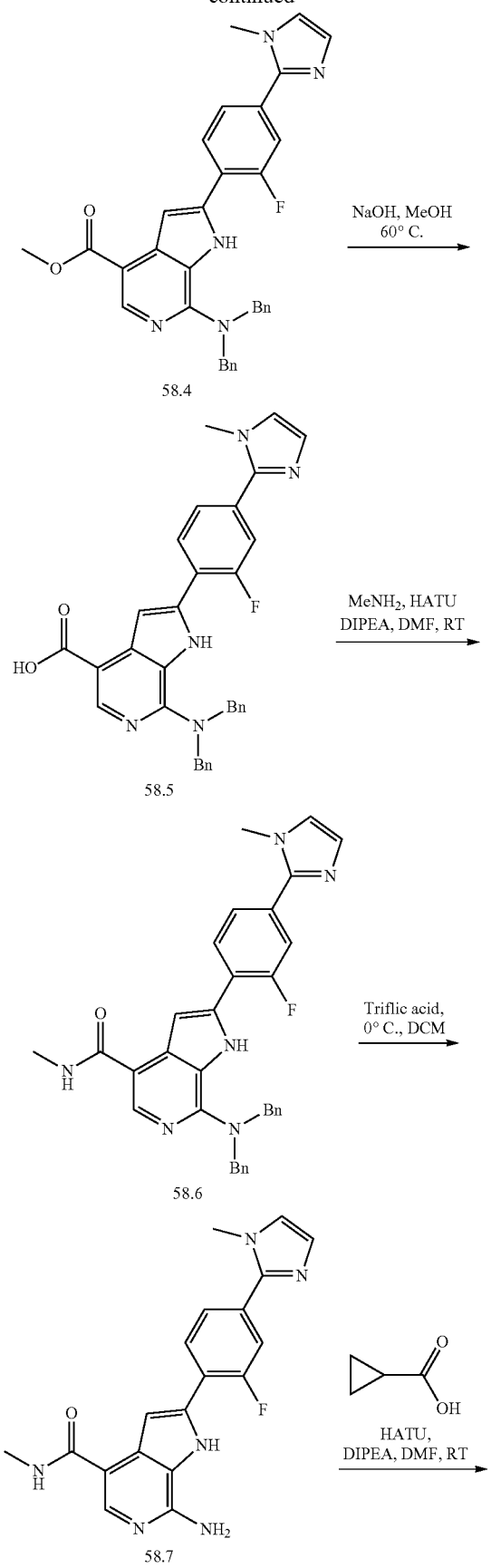

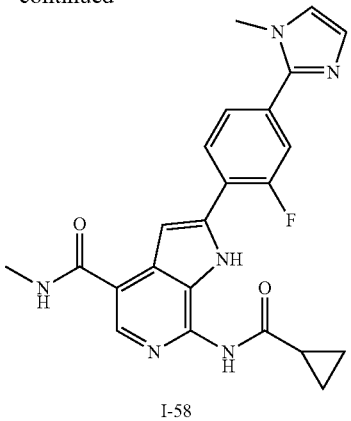

I-58

Synthesis of Compound 58.3

Argon was purged for 15 min through a stirred solution of compounds 58.1 (2.0 g, 6.66 mmol, 1.0 eq) and 58.2 (3.2 g, 8.65 mmol, 1.3 eq) in dimethylformamide (50 mL). Bis(triphenylphosphine)palladium(II) dichloride (0.466 g, 0.66 mmol, 0.1 eq) was added to it and further purging done for 10 min. Reaction was allowed to stir at 60° C. for 5 h. After completion of reaction, reaction mixture was transferred into water and product was extracted with ethyl acetate. Organic layer was combined, washed with brine solution, dried over sodium sulfate and concentrated under reduced pressure to obtain 58.3. (0.160 g, Yield: 10.44%). MS (ES): m/z 254.99 [M+H]$^+$.

Synthesis of Compound 58.4

The compound was synthesized from compounds B.2 and 58.3 using General Procedure A to obtain 58.4. (0.180 g, Yield: 54.80%), MS (ES): m/z 546.23 [M+H]$^+$.

Synthesis of Compound 58.5

To a solution of compound 58.4 (0.180 g, 0.33 mmol, 1.0 eq), in methanol (2 mL) was added sodium hydroxide (0.066 g, 1.65 mmol, 5.0 eq). The reaction mixture was stirred at 60° C. for 1 h. After completion of reaction, reaction mixture was concentrated under reduced pressure to obtain residue. To this added water and acidified with 1N hydrochloric acid to adjust pH~6 at 10° C. Product was extracted with dichloromethane. Organic layer was combined, washed with brine solution, dried over sodium sulfate and concentrated under reduced pressure to obtain crude material. This was further purified by column chromatography and compound was eluted in 2.1% methanol in dichloromethane to obtain pure 58.5. (0.120 g, Yield: 68.43%). MS (ES): m/z 532.21 [M+H]$^+$.

Synthesis of Compound 58.6

The compound was synthesized from compound 58.5 and methylamine using General Procedure H to obtain 58.6. (0.1 g, Yield: 81.34%), MS (ES): m/z 545.24 [M+H]$^+$.

Synthesis of Compound 58.7

The compound was synthesized from compound 58.6 using General Procedure B to obtain 58.7. (0.050 g, Yield: 74.73%), MS (ES): m/z 365.15 [M+H]$^+$.

Synthesis of Compound I-58

The compound was synthesized from compound 58.7 and cyclopropanecarboxylic acid using General Procedure H. The material was further purified by column chromatography and the compound was eluted in 40% ethyl acetate in hexane to obtain I-58 (0.030 g, Yield: 50.56%), MS (ES): m/z 433.72 [M+H]+ LCMS purity: 99.02%, HPLC purity: 96.75%, $^1$H NMR (DMSO-$d_6$, 400 MHz): 12.16 (s, 1H), 11.35 (s, 1H), 9.06 (bs, 1H), 8.42 (s, 1H), 8.40 (s, 1H), 8.12-8.08 (t, J=8 Hz, 1H), 7.81-7.76 (t, J=13.2 Hz, 2H), 7.55 (s, 1H), 7.40 (s, 1H), 3.88 (s, 3H), 2.87-2.86 (d, J=4.4 Hz, 3H), 1.35 (bs, 1H), 1.00-0.95 (m, 4H).

Example 59: 7-(cyclopropanecarboxamido)-2-(2-methoxy-3-(2-methyl-2H-tetrazol-5-yl)phenyl)-N-methyl-1H-pyrrolo[2,3-c]pyridine-4-carboxamide (I-59)

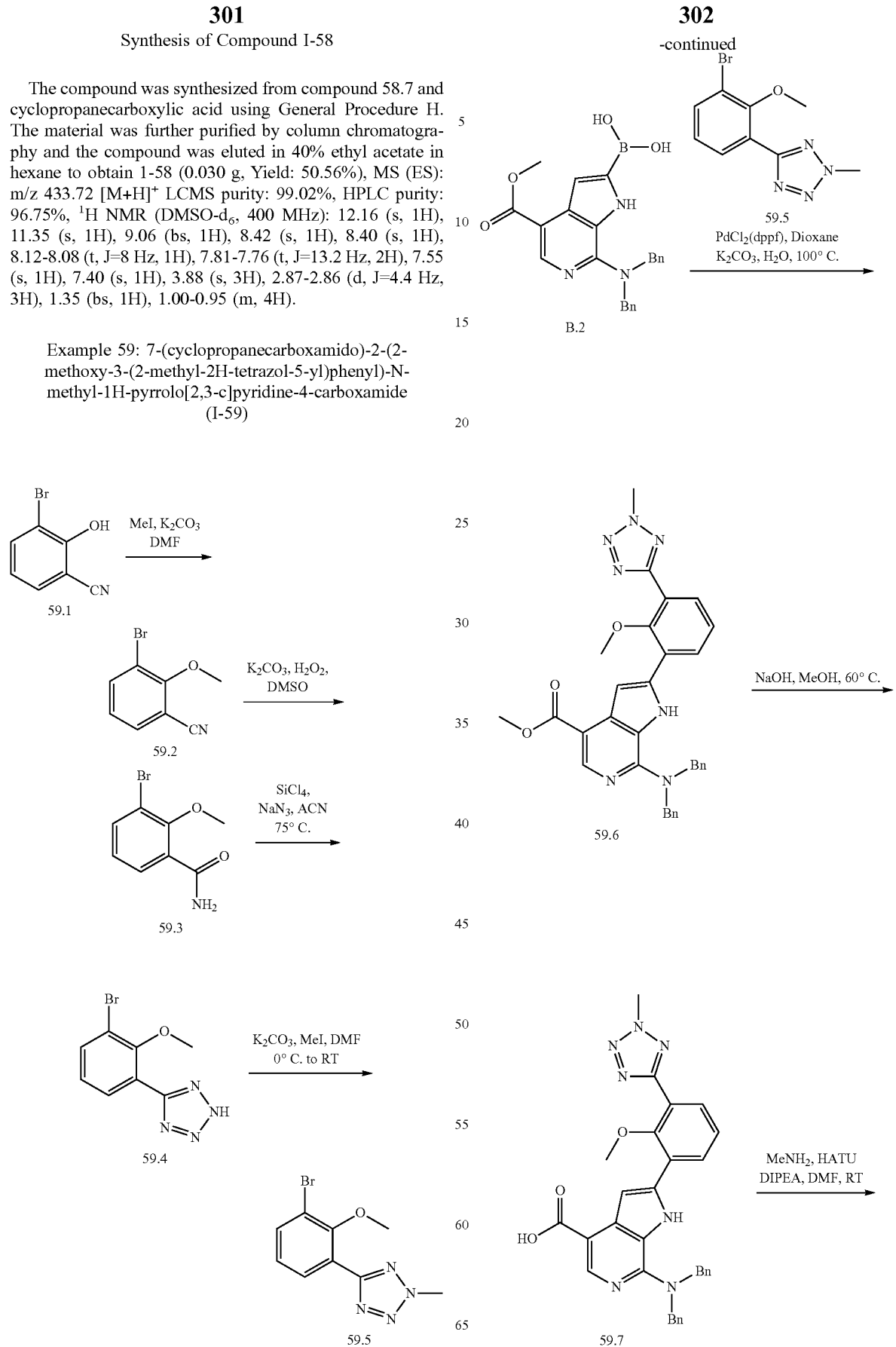

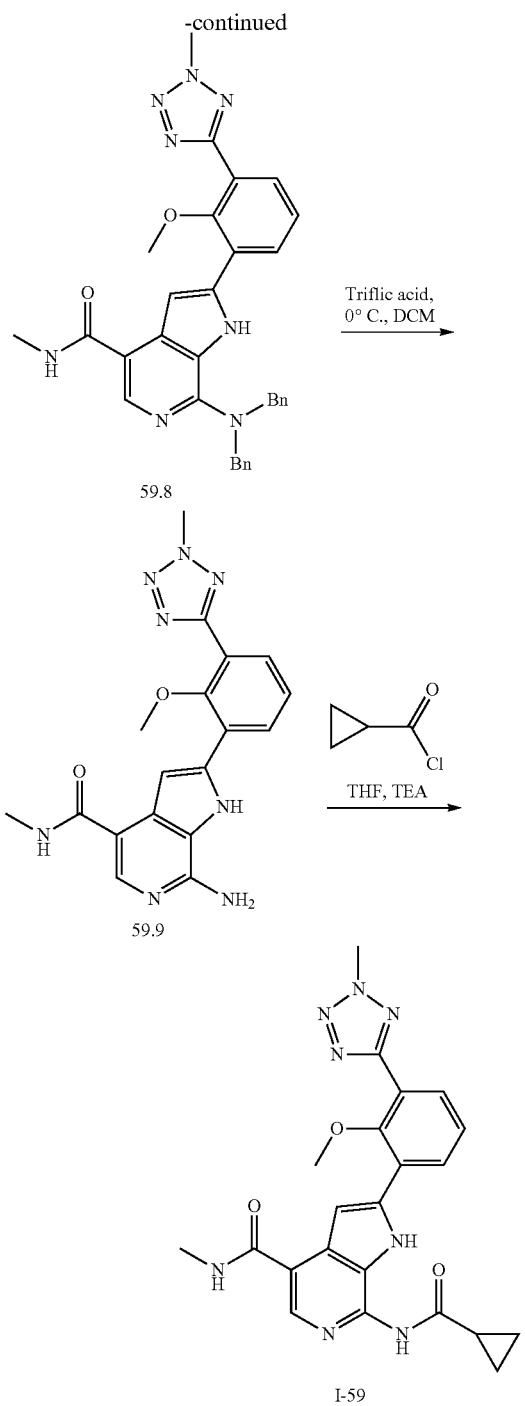

Synthesis of Compound 59.2

To a solution of compound 59.1 (1.0 g, 5.05 mmol, 1.0 eq) in N,N-dimethylformamide (10 mL), was added potassium carbonate (1.3 g, 10.1 mmol, 2.0 eq) at 0° C. and stirred for 15 min. To this added methyl iodide (1.4 g, 10.1 mmol, 2 eq) dropwise and reaction mixture was stirred at 60° C. for 2 h. After completion of reaction, reaction mixture was transferred in ice-water and precipitated product was filtered and dried to obtain 59.2 (0.9 g, Yield: 84.05%). MS (ES): m/z 212.96 [M+H]$^+$.

Synthesis of Compound 59.3

To a solution of compound 59.2 (0.9 g, 4.26 mmol, 1.0 eq) in dimethyl sulfoxide (10 mL), was added potassium carbonate (0.293 g, 2.13 mmol, 0.5 eq) and hydrogen peroxide (0.159 g, 4.68 mmol, 1.1 eq) dropwise and reaction mixture was stirred at 60° C. for 2 h. After completion of reaction, reaction mixture was transferred in ice-water and precipitated product was filtered and dried to obtain 59.3. (0.85 g, Yield: 87.05%). MS (ES): m/z 230.97 [M+H]$^+$.

Synthesis of Compound 59.4

To a suspension of sodium azide (0.719 g, 11.07 mmol, 3.0 eq) in acetonitrile (10 mL) was added silicon tetrachloride (0.689 g, 4.05 mmol, 1.1 eq) and reaction mixture was stirred. To this added compound 59.3 (0.850 g, 3.69 mmol, 1.0 eq) and reaction mixture was stirred at 75° C. for 16 h. Reaction mixture was cooled to room temperature and water was added. A solid precipitated, which was filtered and dried to obtain 59.4. (0.7 g, Yield: 74.28%). MS (ES): m/z 255.98 [M+H]$^+$.

Synthesis of Compound 59.5

To a solution of 59.4 (0.7 g, 2.74 mmol, 1.0 eq) in N,N-dimethylformamide (7 mL) was added potassium carbonate (1.1 g, 8.22 mmol, 3.0 eq) at 0° C. To this added dropwise methyl iodide (0.505 g, 3.56 mmol, 1.3 eq). Reaction mixture was stirred at room temperature for 24 h. After completion of reaction, reaction mixture was transferred into water and extracted with ethyl acetate. Organic layer was combined, washed with brine solution, dried over sodium sulfate and concentrated under reduced pressure to obtain crude material. This was further purified by column chromatography and the depicted regioisomer was eluted in 10% ethyl acetate in hexane to obtain pure 59.5 (0.250 g, Yield: 33.85%). MS (ES): m/z 269.99 [M+H]$^+$.

Synthesis of Compound 59.6

The compound was synthesized from compounds B.2 and 59.35 using General Procedure A to obtain 59.6. (0.180 g, Yield: 53.43%), MS (ES): m/z 560.24 [M+H]$^+$.

Synthesis of Compound 59.7

To a solution of 59.6 (0.180 g, 0.33 mmol, 1.0 eq), in methanol (2 mL) was added sodium hydroxide (0.066 g, 1.65 mmol, 5.0 eq). The reaction mixture was stirred at 60° C. for 1 h. After completion of reaction, reaction mixture was concentrated under reduced pressure to obtain residue. To this added water and acidified with 1N hydrochloric acid to adjust pH~6 at 10° C. Product was extracted with dichloromethane. Organic layer was combined, washed with brine solution, dried over sodium sulfate and concentrated under reduced pressure to obtain crude material. This was further purified by column chromatography and compound was eluted in 2.1% methanol in dichloromethane to obtain pure 59.7. (0.110 g, Yield: 62.68%). MS (ES): m/z 546.22 [M+H]$^+$.

Synthesis of Compound 59.8

The compound was synthesized from compound 59.7 and methylamine using General Procedure H to obtain 59.8. (0.1 g, Yield: 88.79%). MS (ES): m/z 559.25 [M+H]$^+$.

305

Synthesis of Compound 59.9

The compound was synthesized from compound 59.8 using General Procedure B to obtain 59.9. (0.060 g, Yield: 88.58%), MS (ES): m/z 379.16 [M+H]$^+$.

Synthesis of Compound I-59

The compound was synthesized from compound 59.9 using General Procedure C to obtain I-59 (0.030 g, Yield: 42.38%), MS (ES): m/z 447.46 [M+H]$^+$ LCMS purity: 100%, HPLC purity: 95.77%, $^1$H NMR (DMSO-d$_6$, 400 MHz): 12.30 (s, 1H), 11.30 (s, 1H), 8.61 (s, 1H), 8.34-8.33 (d, J=4 Hz, 1H), 8.04-8.02 (d, J=7.6 Hz, 1H), 7.81-7.87-7.85 (d, J=7.6 Hz, 1H), 7.38-7.34 (t, J=7.6 Hz, 1H), 7.07-7.06 (bs, 1H), 3.98 (s, 3H), 3.64 (s, 3H), 2.85-0.84 (d, J=4.4 Hz, 3H), 2.25 (bs, 1H), 0.97-0.92 (m, 4H).

Example 60: 7-(cyclopropanecarboxamido)-2-(2-methoxy-4-(thiazol-2-yl)phenyl)-N-methyl-1H-pyrrolo[2,3-c]pyridine-4-carboxamide (I-60)

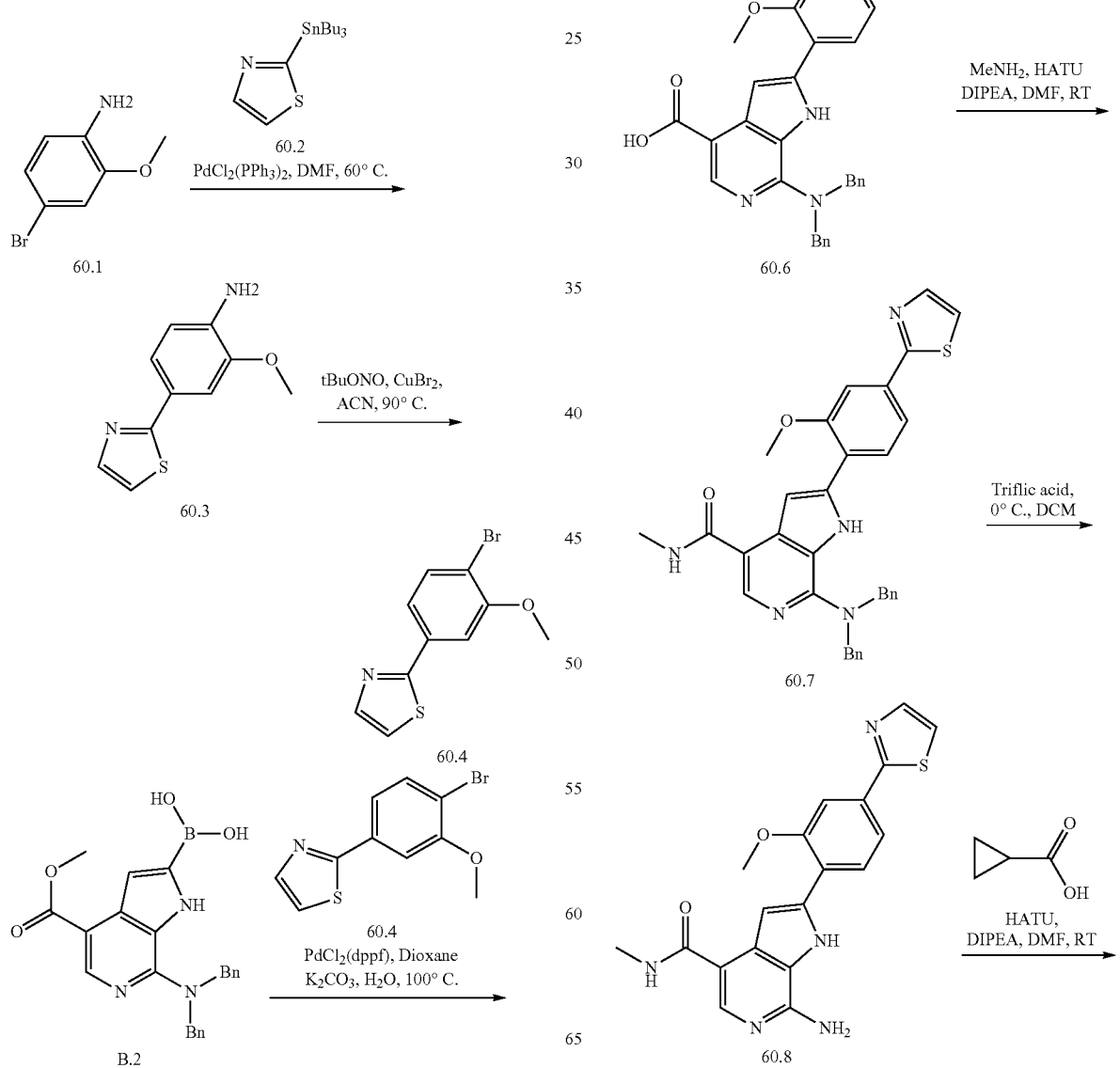

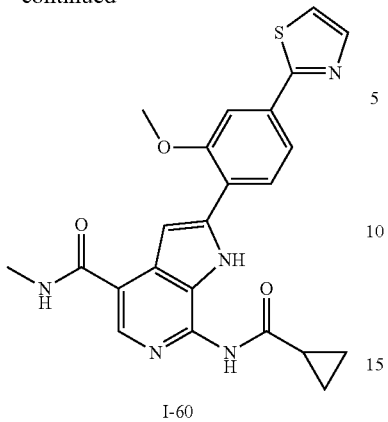

I-60

Synthesis of Compound 60.3

Argon was purged for 15 min through a stirred solution of compounds 60.1 (2.0 g, 9.90 mmol, 1.0 eq) and 60.2 (4.8 g, 12.87 mmol, 1.3 eq) in dimethylformamide (30 mL). Bis(triphenylphosphine)palladium(II) dichloride (0.694 g, 0.99 mmol, 0.1 eq) was added to it and further purging done for 10 min. Reaction was allowed to stir at 60° C. for 5 h. After completion of reaction, reaction mixture was transferred into water and product was extracted with ethyl acetate. Organic layer was combined, washed with brine solution, dried over sodium sulfate and concentrated under reduced pressure to obtain 60.3. (1.1 g, Yield: 53.88%). MS (ES): m/z 207.05 [M+H]$^+$.

Synthesis of Compound 60.4

To a solution of compound 60.3 (1.0 g, 4.85 mmol, 1.0 eq) in acetonitrile (15 mL) was added tert-butyl nitrite (0.549 g, 5.33 mmol, 1.1 eq) and copper(II) bromide (2.1 g, 9.7 mmol, 2.0 eq). Reaction was allowed to stir at 90° C. for 5 h. After completion of reaction, reaction mixture was transferred into water and product was extracted with ethyl acetate. Organic layer was combined, washed with brine solution, dried over sodium sulfate and concentrated under reduced pressure. This was further purified by column chromatography and compound was eluted in 40% ethyl acetate in hexane to obtain 60.4. (0.4 g, Yield: 30.54%). MS (ES): m/z 270.95 [M+H]$^+$.

Synthesis of Compound 60.5

The compound was synthesized from compounds B.2 and 60.4 using General Procedure A to obtain 60.5. (0.210 g, Yield: 62.21%), MS (ES): m/z 561.19 [M+H]$^+$.

Synthesis of Compound 60.6

To a solution of compound 60.5 (0.210 g, 0.37 mmol, 1.0 eq), in methanol (2 mL) was added sodium hydroxide (0.074 g, 1.85 mmol, 5.0 eq). The reaction mixture was stirred at 60° C. for 1 h. After completion of reaction, reaction mixture was concentrated under reduced pressure to obtain residue. To this added water and acidified with 1N hydrochloric acid to adjust pH~6 at 10° C. Product was extracted with dichloromethane. Organic layer was combined, washed with brine solution, dried over sodium sulfate and concentrated under reduced pressure to obtain crude material. This was further purified by column chromatography and compound was eluted in 2.1% methanol in dichloromethane to obtain pure 60.6. (0.180 g, Yield: 87.91%). MS (ES): m/z 547.18 [M+H]$^+$.

Synthesis of Compound 60.7

The compound was synthesized from compound 60.6 and methylamine using General Procedure H to obtain 60.7. (0.140 g, Yield: 75.97%). MS (ES): m/z 560.21 [M+H]$^+$.

Synthesis of Compound 60.8

The compound was synthesized from compound 60.7 using General Procedure B to obtain 60.8. (0.090 g, Yield: 94.82%), MS (ES): m/z 380.11 [M+H]$^+$.

Synthesis of Compound I-60

The compound was synthesized from compound 60.8 and cyclopropanecarboxylic acid using General Procedure H. The material was further purified by column chromatography and the compound was eluted in 40% ethyl acetate in hexane to obtain 1-60 (0.032 g, Yield: 30.15%), MS (ES): m/z 448.8 [M+H]$^+$ LCMS purity: 100%, HPLC purity: 98.43%, $^1$H NMR (DMSO-d$_6$, 400 MHz): 12.55 (s, 1H), 11.33 (s, 1H), 8.34 (bs, 1H), 8.29 (s, 1H), 8.14-8.12 (d, J=8 Hz, 1H), 8.00 (bs, 1H), 7.89 (bs, 1H), 7.76 (bs, 1H), 7.69-7.67 (d, J=8 Hz, 1H), 7.52 (bs, 1H), 4.12 (s, 3H), 2.87 (bs, 3H), 2.26 (bs, 1H), 1.03-0.97 (m, 4H).

Example 61: 2-(4-(1,4-dioxan-2-yl)-2-methoxyphenyl)-7-(cyclopropanecarboxamido)-N-methyl-1H-pyrrolo[2,3-c]pyridine-4-carboxamide (I-61)

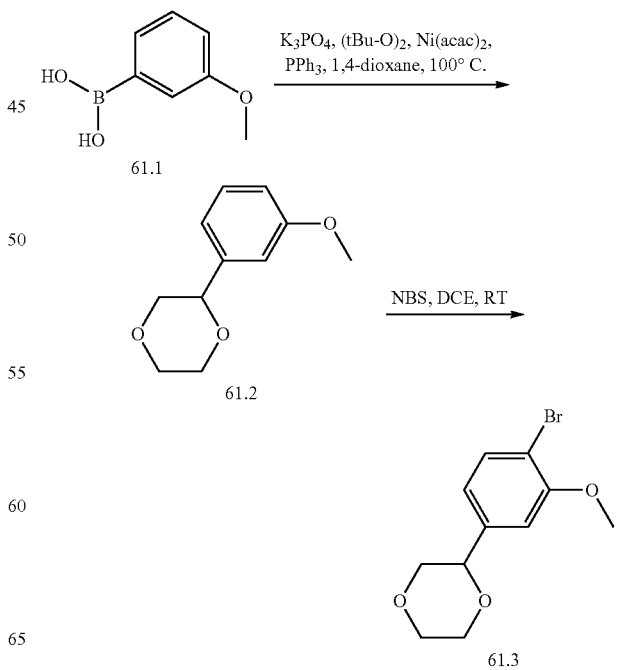

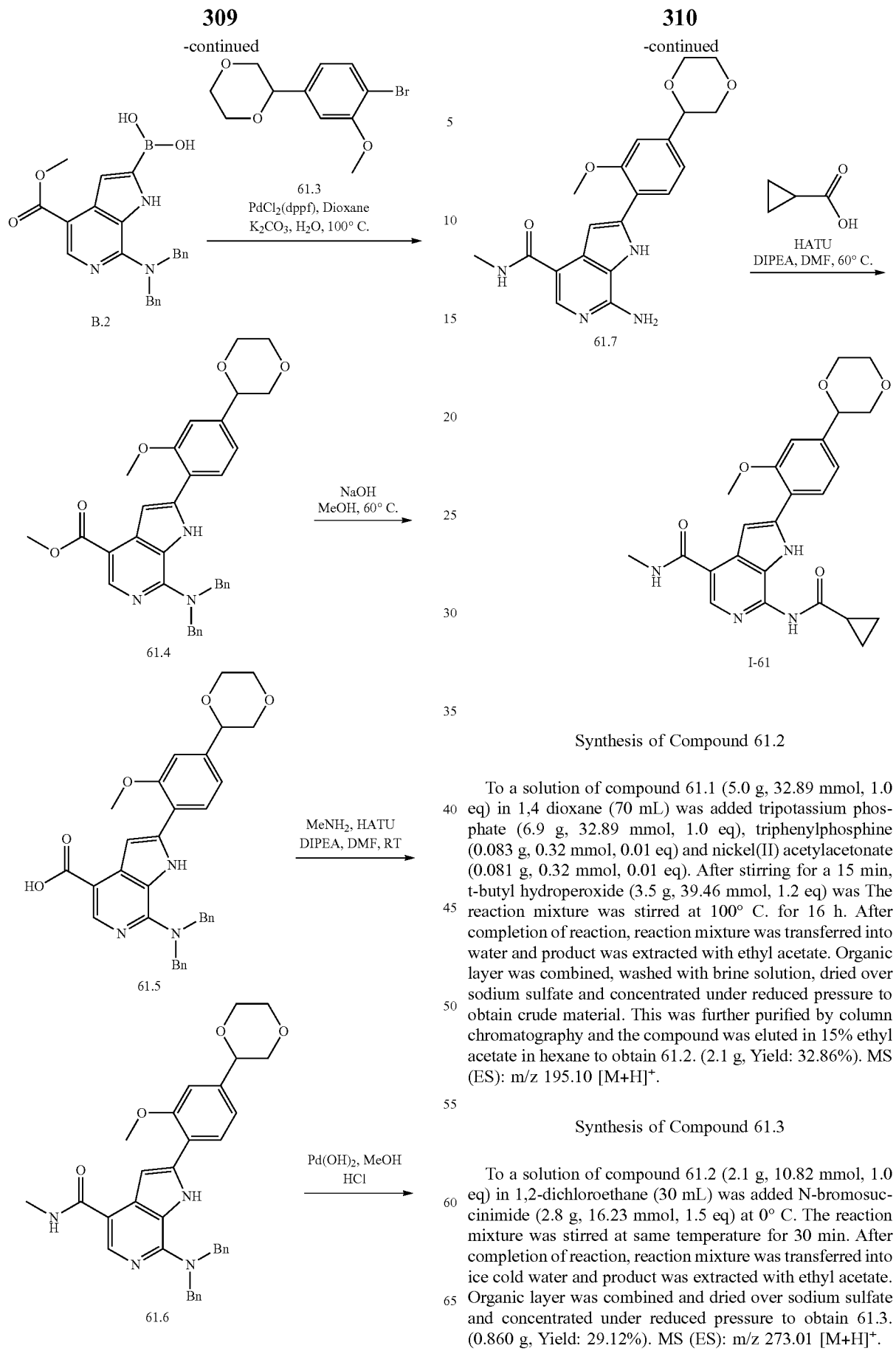

Synthesis of Compound 61.2

To a solution of compound 61.1 (5.0 g, 32.89 mmol, 1.0 eq) in 1,4 dioxane (70 mL) was added tripotassium phosphate (6.9 g, 32.89 mmol, 1.0 eq), triphenylphosphine (0.083 g, 0.32 mmol, 0.01 eq) and nickel(II) acetylacetonate (0.081 g, 0.32 mmol, 0.01 eq). After stirring for a 15 min, t-butyl hydroperoxide (3.5 g, 39.46 mmol, 1.2 eq) was The reaction mixture was stirred at 100° C. for 16 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by column chromatography and the compound was eluted in 15% ethyl acetate in hexane to obtain 61.2. (2.1 g, Yield: 32.86%). MS (ES): m/z 195.10 [M+H]$^+$.

Synthesis of Compound 61.3

To a solution of compound 61.2 (2.1 g, 10.82 mmol, 1.0 eq) in 1,2-dichloroethane (30 mL) was added N-bromosuccinimide (2.8 g, 16.23 mmol, 1.5 eq) at 0° C. The reaction mixture was stirred at same temperature for 30 min. After completion of reaction, reaction mixture was transferred into ice cold water and product was extracted with ethyl acetate. Organic layer was combined and dried over sodium sulfate and concentrated under reduced pressure to obtain 61.3. (0.860 g, Yield: 29.12%). MS (ES): m/z 273.01 [M+H]$^+$.

Synthesis of Compound 61.4

The compound was synthesized from compounds B.2 and 61.3 using General Procedure A to obtain 61.4. (0.320 g, Yield: 42.86%), MS (ES): m/z 564.25 [M+H]$^+$.

Synthesis of Compound 61.5

To a solution of compound 61.4 (0.320 g, 0.56 mmol, 1.0 eq), in methanol (4 mL) was added sodium hydroxide (0.112 g, 2.8 mmol, 5.0 eq). The reaction mixture was stirred at 60° C. for 1 h. After completion of reaction, reaction mixture was concentrated under reduced pressure to obtain residue. To this added water and acidified with 1N hydrochloric acid to adjust pH~6 at 10° C. Product was extracted with dichloromethane. Organic layer was combined, washed with brine solution, dried over sodium sulfate and concentrated under reduced pressure to obtain crude material. This was further purified by column chromatography and compound was eluted in 2.1% methanol in dichloromethane to obtain pure 61.5. (0.280 g, Yield: 89.73%). MS (ES): m/z 550.23 [M+H]$^+$.

Synthesis of Compound 61.6

The compound was synthesized from compound 61.5 and methylamine using General Procedure H to obtain 61.6. (0.250 g, Yield: 87.22%), MS (ES): m/z 563.24 [M+H]$^+$.

Synthesis of Compound 61.7

To a solution of 61.6 (0.250 g, 0.44 mmol, 1.0 eq) in methanol (5 ml), 10% palladium hydroxide charcoal (0.2 g) was added. Hydrogen was purged through reaction mixture for 6 h at room temperature. After completion of reaction, reaction mixture was filtered through Celite-bed and washed with methanol. Filtrate was concentrated under reduced pressure to obtain crude material. This was further purified by trituration with n-pentane to obtain pure 61.7. (0.080 g, Yield: 47.08%). MS (ES): m/z 451.19 [M+H]$^+$.

Synthesis of Compound I-61

The compound was synthesized from compound 61.7 and cyclopropanecarboxylic acid using General Procedure H. The material was further purified by column chromatography and the compound was eluted in 40% ethyl acetate in hexane to obtain I-61 (0.025 g, Yield: 35.37%). MS (ES): m/z 451.62 [M+H]$^+$ LCMS purity: 100%, HPLC purity: 100%, $^1$H NMR (DMSO-d$_6$, 400 MHz): 11.47 (s, 1H), 11.18 (s, 1H), 8.37 (bs, 1H), 8.34 (bs, 1H), 7.49-7.47 (d, J=8 Hz, 1H), 7.17 (bs, 1H), 7.10-7.08 (d, J=8.4 Hz, 1H), 7.00 (bs, 1H), 4.75-4.72 (d, J=10.4 Hz, 1H), 3.85 (s, 3H), 3.71-3.68 (d, J=10 Hz, 3H), 3.55-3.50 (s, 2H), 2.87-2.85 (d, J=4 Hz, 3H), 2.19 (s, 1H), 1.25 (bs, 1H), 1.00-0.92 (bs, 4H).

Example 62: 7-(cyclopropanecarboxamido)-2-(2-fluoro-4-(4-methyl-4H-1,2,4-triazol-3-yl)phenyl)-N-methyl-1H-pyrrolo[2,3-c]pyridine-4-carboxamide (I-62)

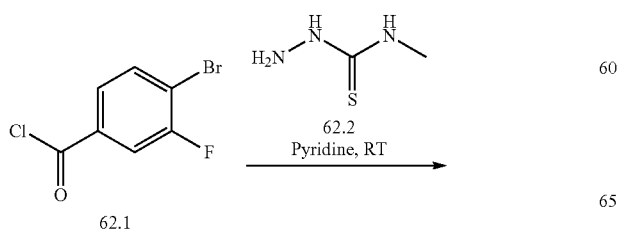

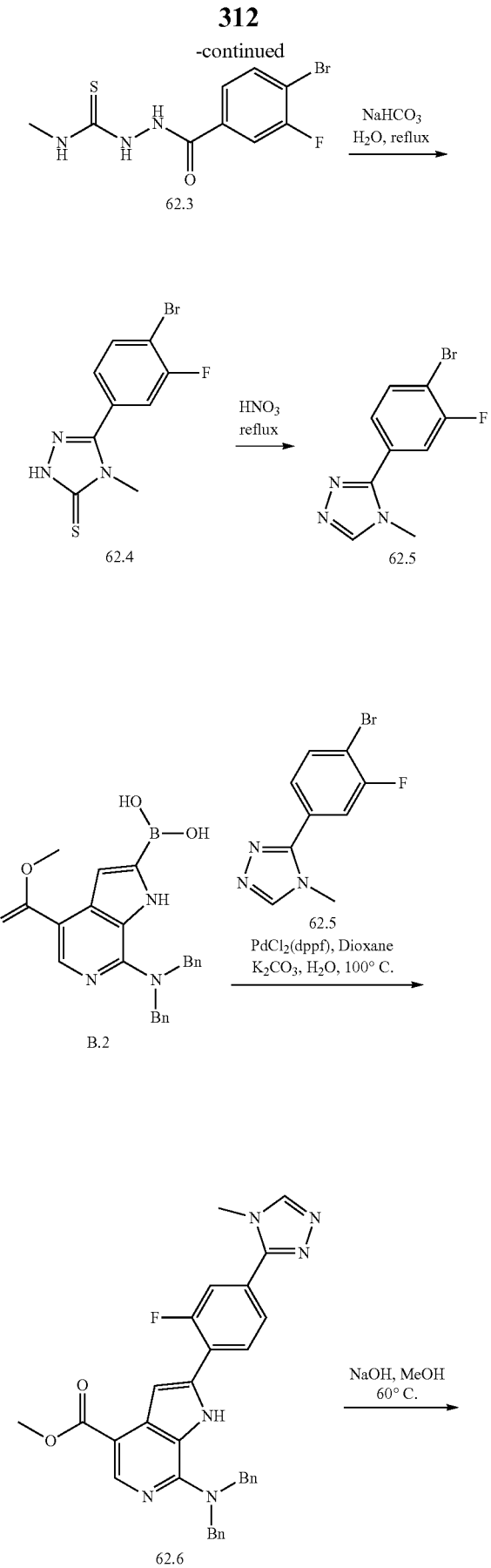

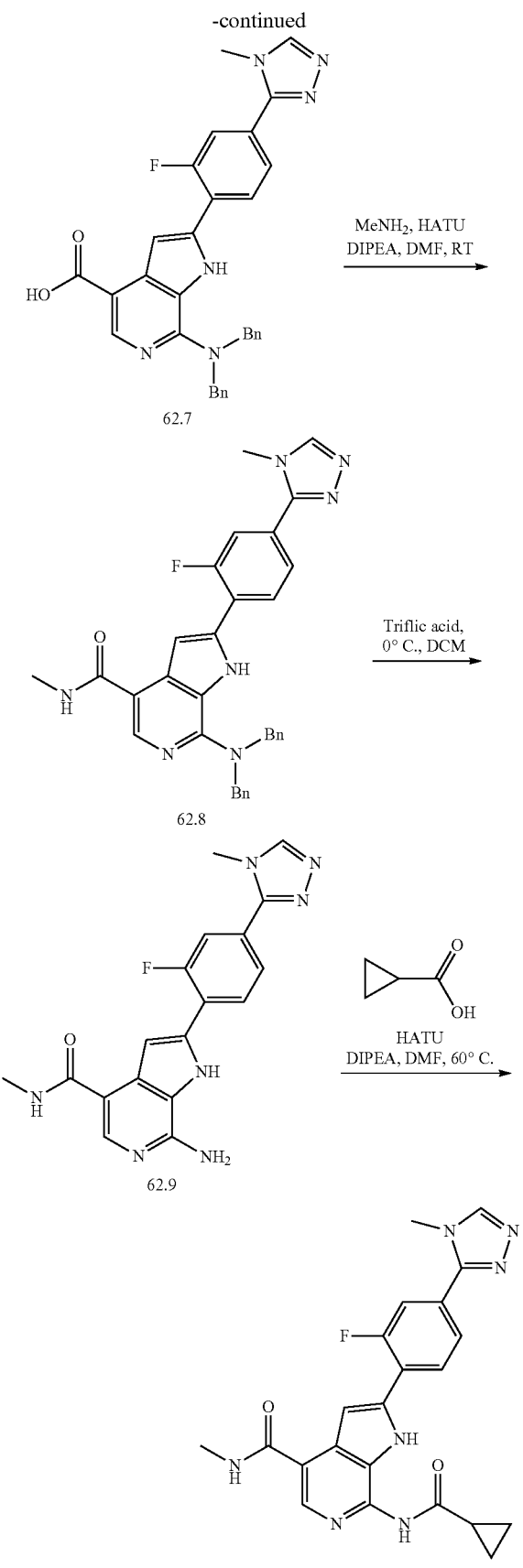

Synthesis of Compound 62.3

To a solution of compound 62.1 (4.0 g, 16.87 mmol, 1.0 eq) in pyridine (20 mL) was added compound 62.2 (1.7 g, 16.87 mmol, 1.0 eq). The reaction mixture was stirred at room temperature for 1 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by trituration using hexane to obtain 62.3. (4.0 g, Yield: 77.56%). MS (ES): m/z 306.96 [M+H]$^+$.

Synthesis of Compound 62.4

A solution of compound 62.3 (4.0 g, 13.07 mmol, 1.0 eq) in 50% aqueous sodium bicarbonate (120 mL) was refluxed at 100° C. for 2 h. After completion of reaction, reaction mixture was filtered. Filtrate was cooled to room temperature and acidified with dilute hydrochloric acid. Filtrate was extracted with ethyl acetate. Organic layer was combined, dried over sodium sulfate and concentrated under reduced pressure to obtain crude material. This was further purified by column chromatography and compound was eluted in 12% ethyl acetate in hexane to obtain pure 62.4. (2.0 g, Yield: 53.13%). MS (ES): m/z 288.95 [M+H]$^+$.

Synthesis of Compound 62.5

A solution of compound 62.4 (2.0 g, 6.94 mmol, 1.0 eq) in 69% aqueous nitric acid (10 mL) and water (30 mL) was warmed gently. The reaction was completed by slowly increasing temperature and refluxed for 1 h. After completion of reaction, reaction mixture was cooled to 0° C., basified by aqueous sodium hydroxide solution and extracted with dichloromethane. Organic layer was combined, dried over sodium sulfate and concentrated under reduced pressure to obtain crude material. This was further purified by column chromatography and compound was eluted in 20% ethyl acetate in hexane to obtain pure 62.5. (0.7 g, Yield: 39.38%), MS (ES): m/z 255.98 [M+H]$^+$.

Synthesis of Compound 62.6

The compound was synthesized from compounds B.2 and 62.5 using General Procedure A to obtain 62.6. (0.210 g, Yield: 53.18%), MS (ES): m/z 547.22 [M+H]$^+$.

Synthesis of Compound 62.7

To a solution of compound 62.6 (0.210 g, 0.38 mmol, 1.0 eq), in methanol (2 mL) was added sodium hydroxide (0.076 g, 1.9 mmol, 5.0 eq). The reaction mixture was stirred at 60° C. for 1 h. After completion of reaction, reaction mixture was concentrated under reduced pressure to obtain residue. To this added water and acidified with 1N hydrochloric acid to adjust pH~6 at 10° C. Product was extracted with dichloromethane. Organic layer was combined, washed with brine solution, dried over sodium sulfate and concentrated under reduced pressure to obtain crude material. This was further purified by column chromatography and compound was eluted in 2.1% methanol in dichloromethane to obtain pure 62.7. (0.160 g, Yield: 78.20%). MS (ES): m/z 534.21 [M+H]$^+$.

315

Synthesis of Compound 62.8

The compound was synthesized from compound 62.7 and methylamine using General Procedure H to obtain 62.8. (0.130 g, Yield: 79.31%), MS (ES): m/z 546.24 [M+H]$^+$.

Synthesis of Compound 62.9

The compound was synthesized from compound 62.8 using General Procedure B to obtain 62.9. (0.060 g, Yield: 68.92%), MS (ES): m/z 366.14 [M+H]$^+$.

Synthesis of Compound I-62

The compound was synthesized from compound 62.9 and cyclopropanecarboxylic acid using General Procedure H. The material was further purified by column chromatography and the compound was eluted in 40% ethyl acetate in hexane to obtain I-62 (0.027 g, Yield: 38.35%), MS (ES): m/z 434.6 [M+H]$^+$ LCMS purity: 97.82%, HPLC purity: 95.77%, $^1$H NMR (DMSO-d$_6$, 400 MHz): 12.22 (s, 1H), 11.37 (s, 1H), 8.66 (bs, 1H), 8.43 (bs, 1H), 8.35 (s, 1H), 8.19-8.15 (t, J=7.6 Hz, 1H), 7.89-7.80 (m, 2H), 7.58 (bs, 1H), 3.86 (s, 3H), 2.87-2.86 (d, J=4 Hz, 3H), 1.56 (bs, 1H), 1.00-0.97 (bs, 4H).

Example 63: 7-(cyclopropanecarboxamido)-2-(2-fluoro-3-(2H-1,2,3-triazol-2-yl)phenyl)-N-methyl-1H-pyrrolo[2,3-c]pyridine-4-carboxamide (I-63)

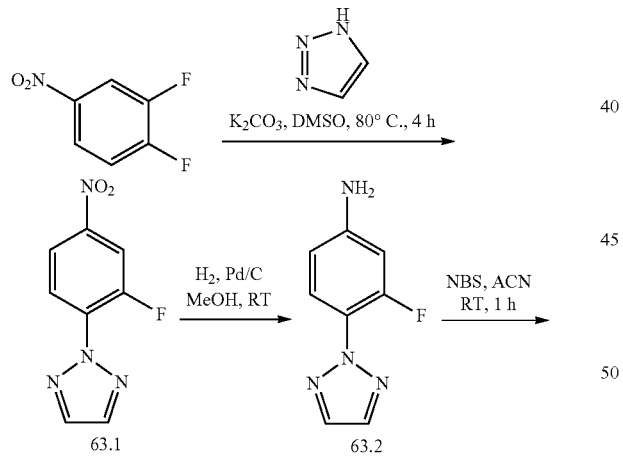

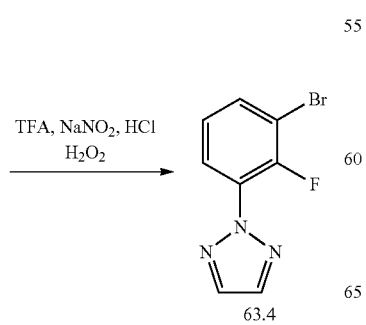

-continued

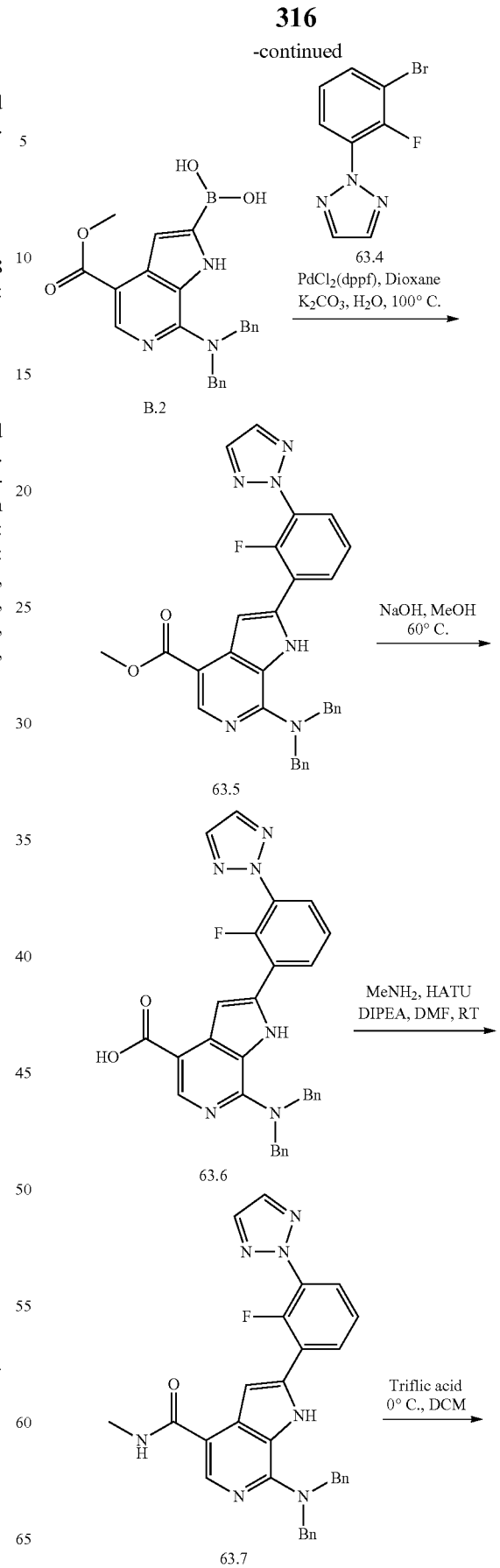

-continued

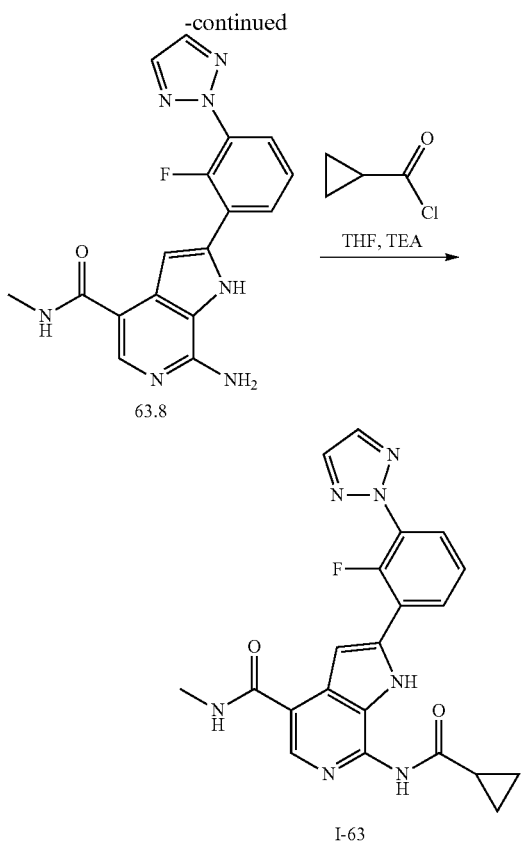

Synthesis of Compound 63.1

To a solution of 1,2-difluoro-4-nitrobenzene (5.0 g, 31.25 mmol, 1.0 eq) and 1H-1,2,3-triazole (4.3 g, 62.5 mmol, 2.0 eq) in dimethyl sulphoxide (60 mL) was added potassium carbonate (8.6 g, 11.56 mmol, 2.0 eq) and reaction mixture heated at 80° C. for 4 h. After completion of reaction, reaction mixture was transferred into ice cold water and product was extracted with ethyl acetate. Organic layer was combined and dried over sodium sulfate and concentrated under reduced pressure to obtain crude material. This was further purified by column chromatography and compound was eluted in 25% ethyl acetate in hexane to obtain pure 63.1. (1.5 g, Yield: 22.93%). MS (ES): m/z 209.04 [M+H]$^+$.

Synthesis of Compound 63.2

To a solution of compound 63.1 (1.5 g, 7.21 mmol, 1.0 eq) in methanol (25 ml), palladium on charcoal (0.7 g) was added. Hydrogen was purged through reaction mixture for 4 h at room temperature. After completion of reaction, reaction mixture was filtered through Celite-bed and washed with methanol. Filtrate was concentrated under reduced pressure to obtain crude material. This was further purified by trituration with n-pentane to obtain pure 63.2. (1.25 g, 97.36%). MS (ES): m/z 179.07 [M+H]$^+$.

Synthesis of Compound 63.3

To a solution of compound 63.2 (0.9 g, 5.02 mmol, 1.0 eq) in acetonitrile (15 mL) was added N-bromosuccinimide (1.3 g, 7.53 mmol, 1.5 eq) at 0° C. The reaction mixture was stirred at 0° C. for 30 min. After completion of reaction, reaction mixture was transferred into ice cold water and product was extracted with ethyl acetate. Organic layer was combined and dried over sodium sulfate and concentrated under reduced pressure to obtain 63.3. (0.650 g, Yield: 50.06%). MS (ES): m/z 257.97 [M+H]$^+$.

Synthesis of Compound 63.4

To a cooled solution of compound 63.3 (0.650 g, 2.52 mmol, 1.0 eq) in tetrahydrofuran (7 mL) was added trifluoroacetic acid (0.6 mL) at 0° C. Then added 2N hydrochloric acid (6.5 mL) and stirred reaction mixture for 5 min. Then added solution of sodium nitrite (0.173 g, 2.52 mmol, 1.0 eq) in 5 mL water followed by 3% hydrogen peroxide (6.5 mL) and reaction mixture was stirred at 0° C. for 30 min and then at room temperature for 1 h. After completion of reaction, reaction mixture was transferred into ice cold water and product was extracted with ethyl acetate. Organic layer was combined and dried over sodium sulfate and concentrated under reduced pressure to obtain crude material. This was further purified by column chromatography and the compound was eluted in 7% ethyl acetate in hexane to obtain 63.4. (0.3 g, Yield: 49.02%). MS (ES): m/z 242.96 [M+H]$^+$.

Synthesis of Compound 63.5

The compound was synthesized from compounds B.2 and 63.4 using General Procedure A to obtain 63.5. (0.220 g, Yield: 57.18%), MS (ES): m/z 533.21 [M+H]$^+$.

Synthesis of Compound 63.6

To a solution of compound 63.5 (0.220 g, 0.40 mmol, 1.0 eq), in methanol (2 mL) was added sodium hydroxide (0.080 g, 2.0 mmol, 5.0 eq). The reaction mixture was stirred at 60° C. for 1 h. After completion of reaction, reaction mixture was concentrated under reduced pressure to obtain residue. To this added water and acidified with 1N hydrochloric acid to adjust pH~6 at 10° C. Product was extracted with dichloromethane. Organic layer was combined, washed with brine solution, dried over sodium sulfate and concentrated under reduced pressure to obtain crude material. This was further purified by column chromatography and compound was eluted in 2.1% methanol in dichloromethane to obtain pure 63.6. (0.160 g, Yield: 74.69%). MS (ES): m/z 519.19 [M+H]$^+$.

Synthesis of Compound 63.7

The compound was synthesized from compound 63.6 and methylamine using General Procedure H to obtain 63.7. (0.140 g, Yield: 85.35%), MS (ES): m/z 532.22[M+H]$^+$.

Synthesis of Compound 63.8

The compound was synthesized from compound 63.7 using General Procedure B to obtain 63.8. (0.070 g, Yield: 75.65%), MS (ES): m/z 352.01 [M+H]$^+$.

Synthesis of Compound I-63

The compound was synthesized from compound 63.8 using General Procedure C to obtain I-63 (0.030 g, Yield: 37.14%), MS (ES): m/z 420.75 [M+H]$^+$ LCMS purity: 100%, HPLC purity: 99.49%, $^1$H NMR (DMSO-d$_6$, 400 MHz): 11.78 (s, 1H), 11.03 (s, 1H), 8.35-8.34 (d, J=5.2 Hz, 2H), 8.26 (bs, 3H), 8.06-8.04 (m, 1H), 7.74-7.69 (t, J=10.4 Hz, 1H), 7.44 (s, 1H), 2.85-2.84 (d, J=4.4 Hz, 3H), 2.21 (bs, 1H), 0.96-0.91 (m, 4H).

Example 64: 7-(cyclopropanecarboxamido)-2-(2-methoxy-4-(1-methyl-1H-1,2,3-triazol-4-yl)phenyl)-N-methyl-1H-pyrrolo[2,3-c]pyridine-4-carboxamide (I-64)

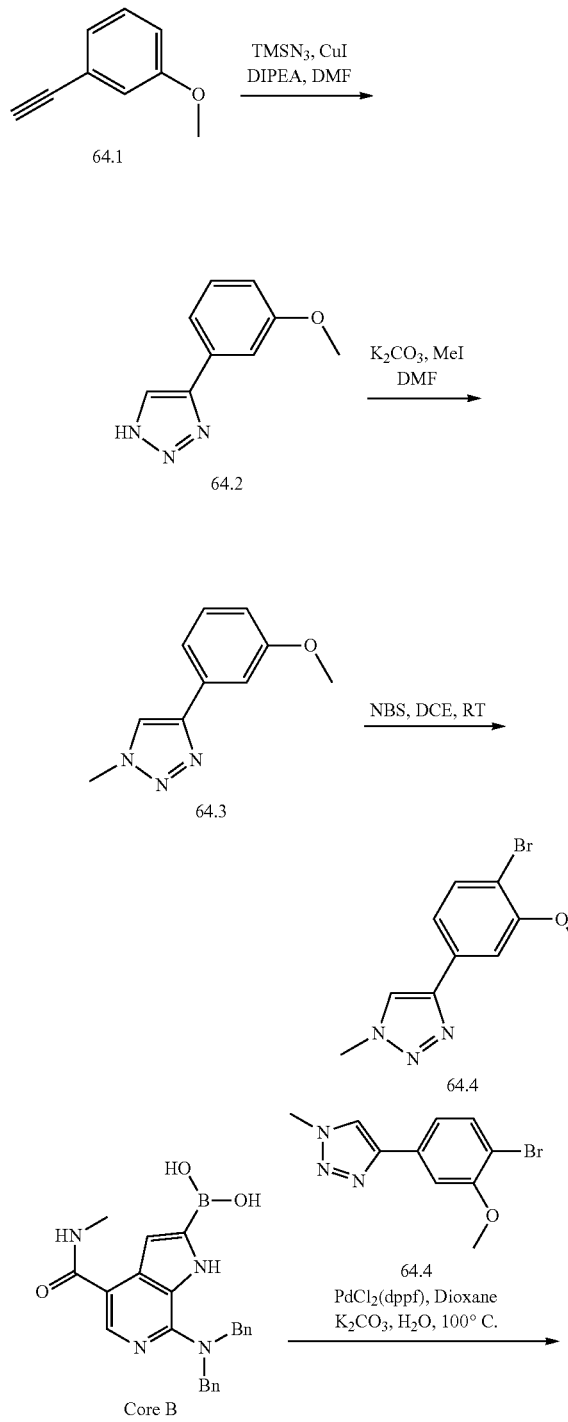

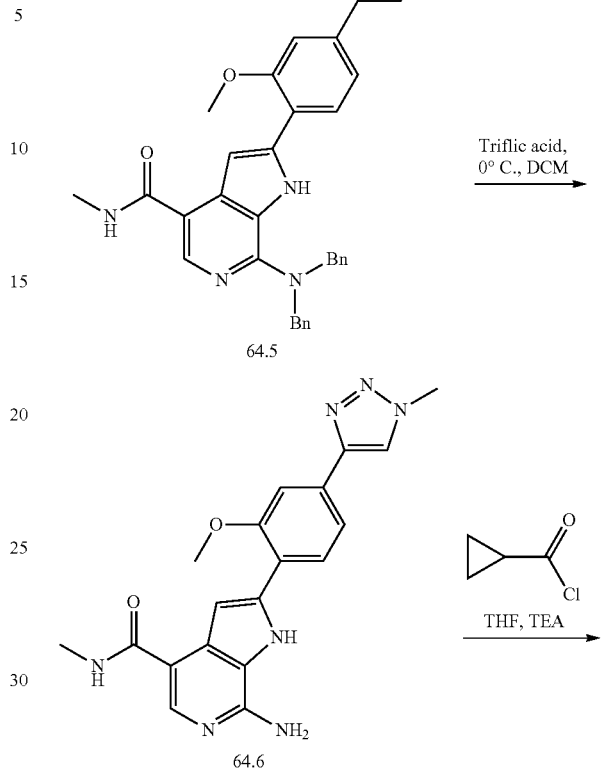

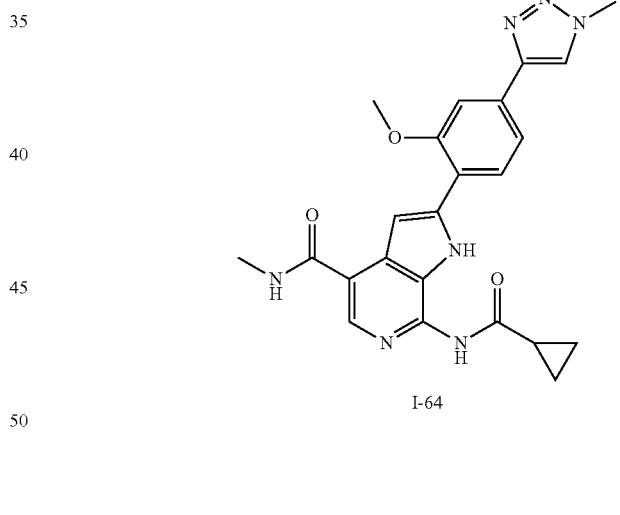

Synthesis of Compound 64.2

To a solution of compound 64.1 (1.0 g, 7.57 mmol, 1.0 eq) in N,N-dimethylformamide (15 mL), was added trimethylsilyl azide (1.7 g, 15.14 mmol, 2.0 eq), copper(I) iodide (1.5 g, 7.94 mmol, 1.05 eq) and diisopropylethylamine (2.9 g, 22.71 mmol, 3.0 eq). The reaction mixture was stirred at 60° C. for 10 h. After completion of reaction, reaction mixture was transferred into water and product was extracted with ethyl acetate. Organic layer was combined, washed with brine solution, dried over sodium sulfate and concentrated under reduced pressure to obtain 64.2 (0.74 g, Yield: 55.82%). MS (ES): m/z 176.08 [M+H]$^+$.

Synthesis of Compound 64.3

To a solution of compound 64.2 (2.2 g, 12.57 mmol, 1.0 eq) in N,N-dimethylformamide (25 mL), was added potassium carbonate (3.4 g, 25.14 mmol, 2.0 eq) at 0° C. and stirred for 15 min. To this added methyl iodide (3.5 g, 25.14 mmol, 2 eq) dropwise and reaction mixture was stirred at 60° C. for 2 h. After completion of reaction, reaction mixture was transferred in ice-water and precipitated product was filtered and dried to obtain 64.3 (0.700 g, Yield: 29.46%). MS (ES): m/z 190.09 [M+H]$^+$.

Synthesis of Compound 64.4

To a solution of compound 64.3 (0.550 g, 2.91 mmol, 1.0 eq) in 1,2-dichloroethane (6 mL) was added N-bromosuccinimide (0.776 g, 4.36 mmol, 1.5 eq). The reaction mixture was stirred at room temperature for 20 min. After completion of reaction, reaction mixture was transferred to ice cold water and product was extracted with ethyl acetate. Organic layer was combined, washed with brine solution, dried over sodium sulfate and concentrated under reduced pressure to obtain 64.4. (0.25 g, Yield: 32.08%). MS (ES): m/z 269.00 [M+H]$^+$.

Synthesis of Compound 64.5

The compound was synthesized from Core B and compound 64.4 using General Procedure A to obtain 64.5. (0.120 g, Yield: 44.57%), MS (ES): m/z 558.26 [M+H]$^+$.

Synthesis of Compound 64.6

The compound was synthesized from compound 64.5 using General Procedure B to obtain 64.6. (0.060 g, Yield: 73.88%), MS (ES): m/z 378.16 [M+H]$^+$.

Synthesis of Compound I-64

The compound was synthesized from compound 64.6 using General Procedure C to obtain I-64 (0.025 g, Yield: 35.30%), MS (ES): m/z 446.76 [M+H]$^+$ LCMS purity: 95.2%, HPLC purity: 95.4%, $^1$H NMR (DMSO-d$_6$, 400 MHz): 12.21 (s, 1H), 11.14 (s, 1H), 8.29 (s, 1H), 7.77 (s, 1H), 7.65-7.63 (d, J=8 Hz, 1H), 7.52 (bs, 1H), 7.31 (s, 1H), 7.09 (bs, 2H), 3.98 (s, 3H), 3.89 (s, 3H), 2.32 (bs, 1H), 1.25 (bs, 4H).

Example 65: 7-(cyclopropanecarboxamido)-2-(2-fluoro-4-(5-methyl-1H-1,2,4-triazol-1-yl)phenyl)-N-methyl-1H-pyrrolo[2,3-c]pyridine-4-carboxamide (I-65)

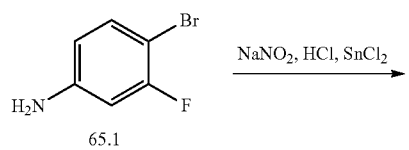

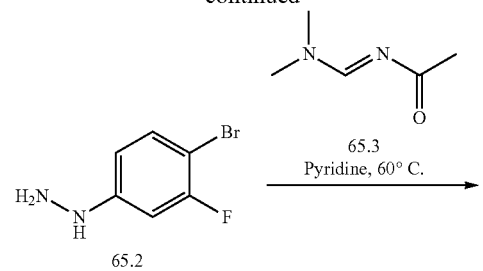

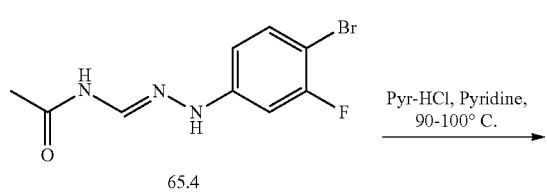

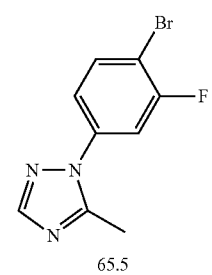

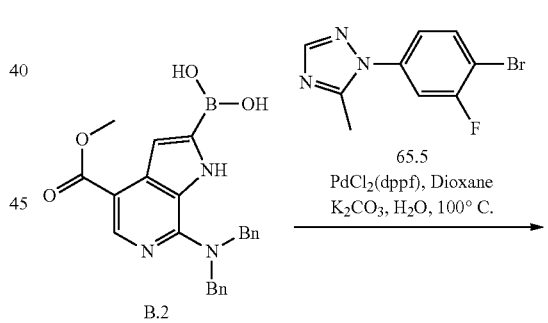

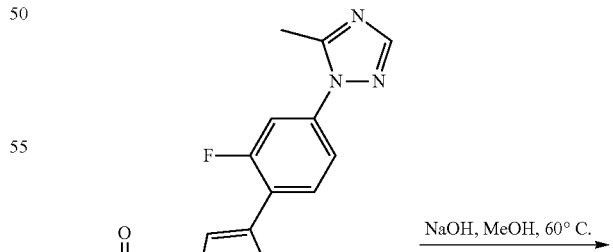

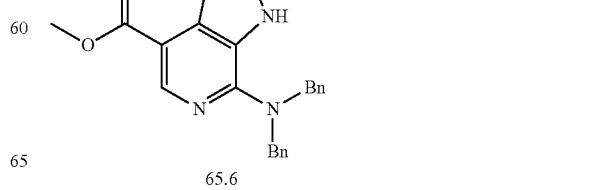

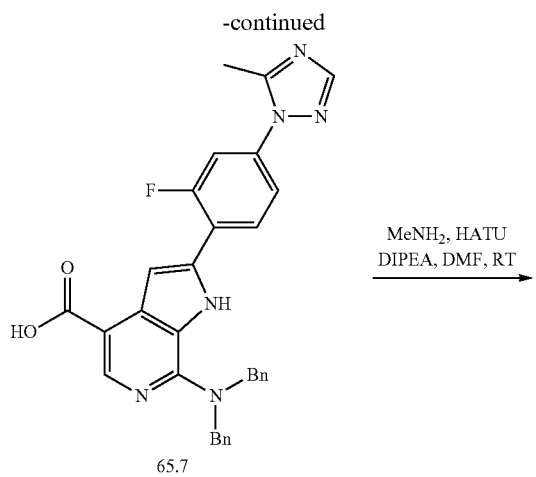

65.7

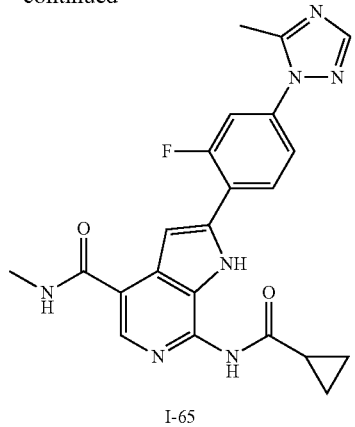

I-65

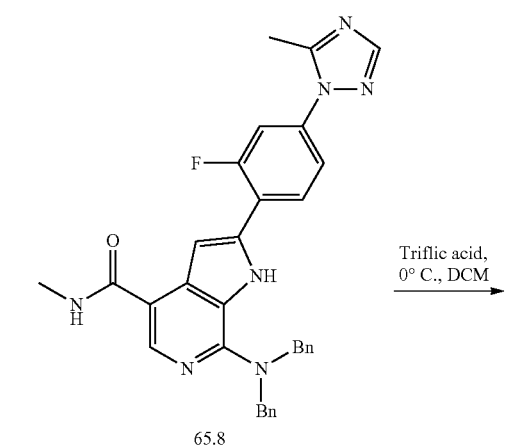

65.8

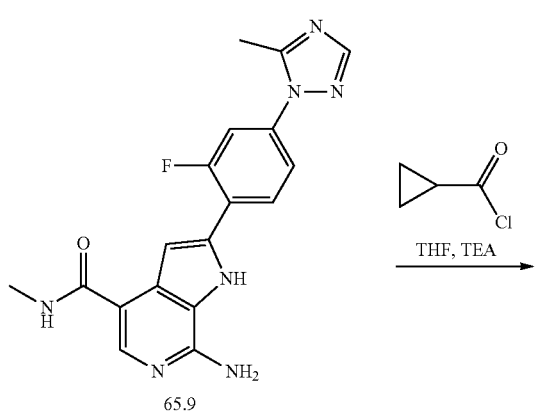

65.9

Synthesis of Compound 65.2

To a solution of compound 65.1 (2.0 g, 10.52 mmol, 1.0 eq) in 12M hydrochloric acid in water (20 mL) was added ethanol (10 mL) and cooled to −20° C. and stirred for 10 min. Then added sodium nitrite (5 mL in water) (1.0 g, 14.72 mmol, 1.4 eq) dropwise and stirred for 30 min at same temperature. Then added tin(II) chloride (3.9 g, 21.04 mmol, 2.0 eq). The reaction mixture was stirred at same temperature for 30 min. After completion of reaction, solid material was filtered and wash with water dried under vacuum to obtain 65.2. (0.4 g, Yield: 18.54%). MS (ES): m/z 204.97 [M+H]$^+$.

Synthesis of Compound 65.4

To a solution of compound 65.2 (1.0 g, 4.87 mmol, 1.0 eq) in pyridine (10 mL) was added compound 65.3 (0.555 g, 4.87 mmol, 1.0 eq). The reaction mixture was stirred at 60° C. for 1 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by trituration using hexane to obtain 65.4. (0.5 g, Yield: 37.40%). MS (ES): m/z 273.99 [M+H]$^+$.

Synthesis of Compound 65.5

To a solution of compound 65.4 (0.5 g, 1.83 mmol, 1.0 eq) in pyridine (5 mL) was added pyridine hydrochloride (0.105 g, 0.91 mmol, 1.0 eq). The reaction mixture was stirred at 90° C.-100° C. for 10 h. After completion of reaction, reaction mixture was transferred into water and product was extracted with ethyl acetate. Organic layer was combined, washed with brine solution, dried over sodium sulfate and concentrated under reduced pressure to obtain 65.5. (0.250 g, Yield: 53.52%). MS (ES): m/z 255.98 [M+H]$^+$.

Synthesis of Compound 65.6

The compound was synthesized from compounds B.2 and 65.5 using General Procedure A to obtain 65.6. (0.210 g, Yield: 53.18%), MS (ES): m/z 547.22 [M+H]$^+$.

Synthesis of Compound 65.7

To a solution of compound 65.6 (0.210 g, 0.38 mmol, 1.0 eq), in methanol (2 mL) was added sodium hydroxide (0.076 g, 1.9 mmol, 5.0 eq). The reaction mixture was stirred at 60° C. for 1 h. After completion of reaction, reaction mixture was concentrated under reduced pressure to obtain residue. To this added water and acidified with 1N hydrochloric acid to adjust pH~6 at 10° C. Product was extracted with dichloromethane. Organic layer was combined, washed with brine solution, dried over sodium sulfate and concentrated under reduced pressure to obtain crude material. This was further purified by column chromatography and compound was eluted in 2.1% methanol in dichloromethane to obtain pure 65.7. (0.150 g, Yield: 73.31%). MS (ES): m/z 533.21 [M+H]$^+$.

Synthesis of Compound 65.8

The compound was synthesized from compound 65.7 and methylamine using General Procedure H to obtain 65.8. (0.120 g, Yield: 78.09%), MS (ES): m/z 546.24 [M+H]$^+$.

Synthesis of Compound 65.9. The compound was synthesized from compound 65.8 using General Procedure B to obtain 65.9. (0.060 g, Yield: 74.67%), MS (ES): m/z 366.14 [M+H]$^+$ Synthesis of Compound I-65

The compound was synthesized from compound 65.9 using General Procedure C to obtain I-65 (0.030 g, Yield: 42.15%), MS (ES): m/z 434.25 [M+H]$^+$ LCMS purity: 100%, HPLC purity: 96.11%, $^1$H NMR (DMSO-d$_6$, 400 MHz): 12.15 (s, 1H), 11.35 (s, 1H), 8.40 (bs, 1H), 8.32 (s, 1H), 8.16 (s, 1H), 7.81-7.78 (d, J=12 Hz, 2H), 8.10 (s, 1H), 7.57 (s, 1H), 3.92 (s 3H), 2.60 (s, 3H), 2.20 (bs, 1H), 0.95-0.90 (m, 4H).

Example 66: 7-(cyclopropanecarboxamido)-2-(2-fluoro-4-(pyrazin-2-yl)phenyl)-N-methyl-1H-pyrrolo[2,3-c]pyridine-4-carboxamide (I-66)

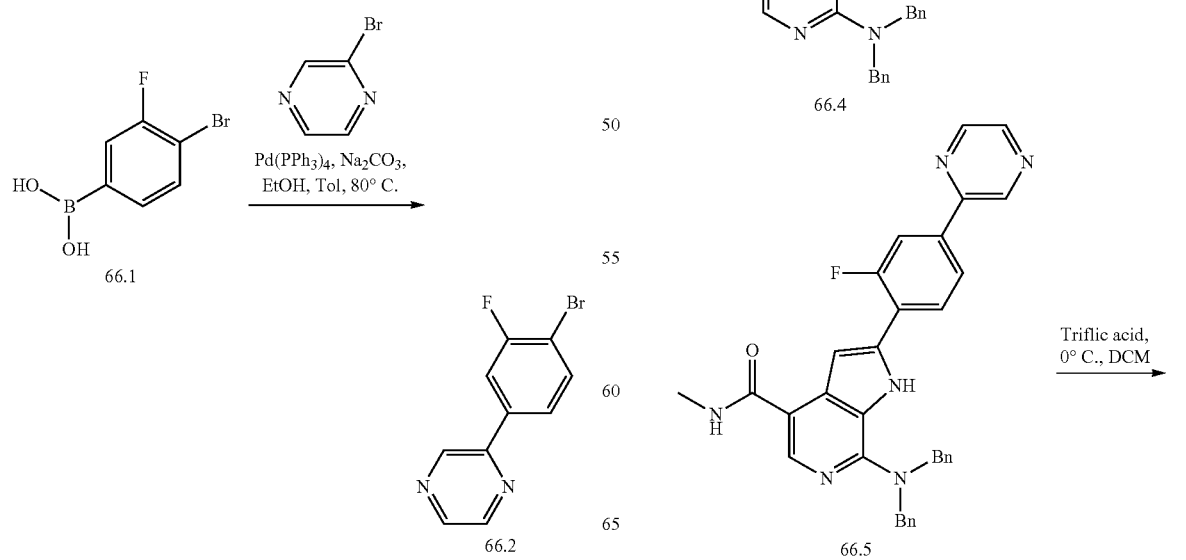

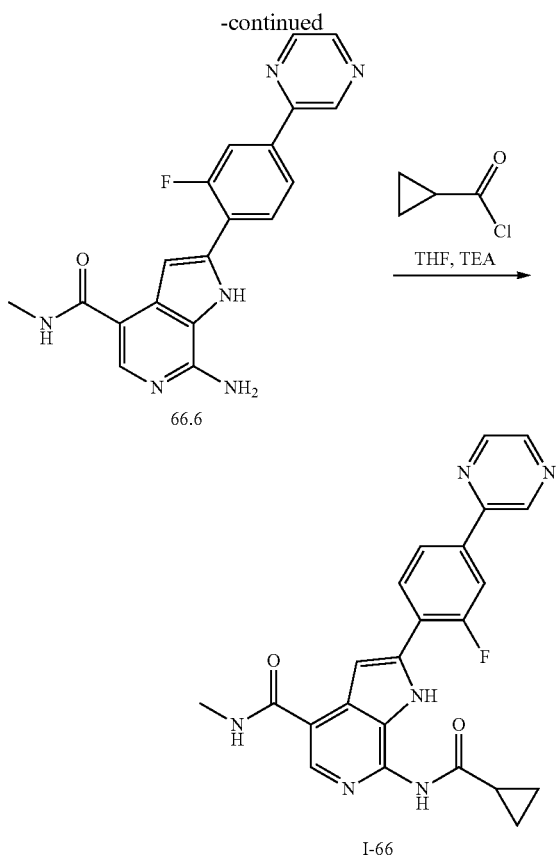

Synthesis of Compound 66.2

To a degassed solution of compound 66.1 (1.0 g, 4.58 mmol, 1.0 eq) and 2-bromopyrazine (0.952 g, 5.95 mmol, 1.3 eq) in ethanol and toluene (1:1, 20 mL), potassium carbonate (1.2 g, 9.16 mmol, 2.0 eq) and tetrakis(triphenylphosphine)palladium(0) (0.528 g, 0.45 mmol, 0.1 eq) were added to it and further purging done for 10 min. Reaction was allowed to stir at 80° C. for 5 h. After completion of reaction, reaction mixture was transferred into water and product was extracted with ethyl acetate. Organic layer was combined, washed with brine solution, dried over sodium sulfate and concentrated under reduced pressure to obtain 66.2. (0.350 g, Yield: 30.26%). MS (ES): m/z 253.97 [M+H]$^+$.

Synthesis of Compound 66.3

The compound was synthesized from compounds B.2 and 66.2 using General Procedure A to obtain 66.3. (0.220 g, Yield: 56.02%), MS (ES): m/z 544.21 [M+H]$^+$.

Synthesis of Compound 66.4

To a solution of compound 66.3 (0.220 g, 0.40 mmol, 1.0 eq), in methanol (2 mL) was added sodium hydroxide (0.080 g, 2.0 mmol, 5.0 eq). The reaction mixture was stirred at 60° C. for 1 h. After completion of reaction, reaction mixture was concentrated under reduced pressure to obtain residue. To this added water and acidified with 1N hydrochloric acid to adjust pH~6 at 10° C. Product was extracted with dichloromethane. Organic layer was combined, washed with brine solution, dried over sodium sulfate and concentrated under reduced pressure to obtain crude material. This was further purified by column chromatography and compound was eluted in 2.1% methanol in dichloromethane to obtain pure 66.4. (0.180 g, Yield: 83.99%). MS (ES): m/z 530.19 [M+H]$^+$.

Synthesis of Compound 66.5

The compound was synthesized from compound 66.4 and methylamine using General Procedure H to obtain 66.5. (0.150 g, Yield: 81.33%), MS (ES): m/z 543.23 [M+H]$^+$.

Synthesis of Compound 66.6

The compound was synthesized from compound 66.5 using General Procedure B to obtain 66.6. (0.070 g, Yield: 69.88%), MS (ES): m/z 363.13 [M+H]$^+$.

Synthesis of Compound I-66

The compound was synthesized from compound 66.6 using General Procedure C to obtain I-66 (0.028 g, Yield: 33.67%), MS (ES): m/z 431.25 [M+H]$^+$ LCMS purity: 96.59%, HPLC purity: 95.77%, $^1$H NMR (DMSO-d$_6$, 400 MHz): 12.16 (s, 1H), 11.32 (s, 1H), 9.41 (bs, 1H), 8.78 (s, 1H), 8.69 (s, 1H), 8.40-8.39 (d, J=4 Hz, 1H), 8.23-8.14 (m, 2H), 7.57 (s, 1H), 7.07-7.06 (d, J=6.8 Hz, 1H), 6.82-6.81 (d, J=6.8 Hz, 1H), 2.86-2.85 (d, J=4.4 Hz, 3H), 2.26 (bs, 1H), 1.00-0.94 (m, 4H).

Example 67: 7-(cyclopropanecarboxamido)-2-(4-ethylthiazol-2-yl)-N-methyl-1H-pyrrolo[2,3-c]pyridine-4-carboxamide (I-70)

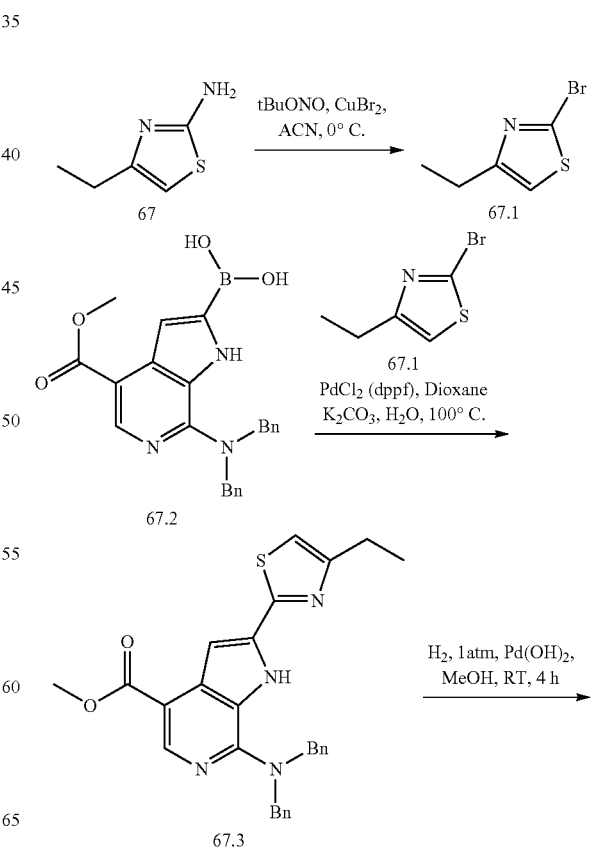

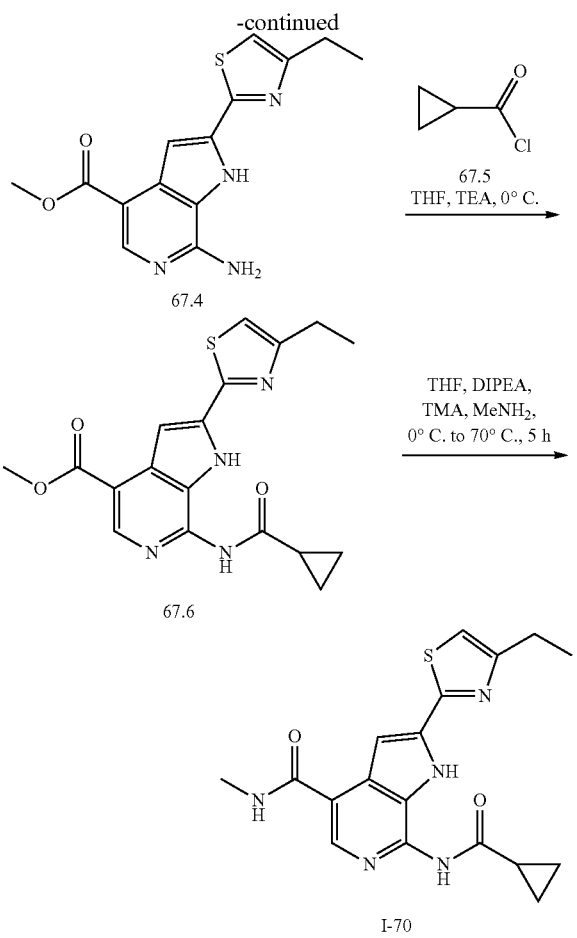

Synthesis of Compound 67.4

To a solution of 67.3 (0.2 g, 0.41 mmol, 1.0 eq) in methanol (4 mL), was added palladium hydroxide on carbon (20%, 0.150 g). Hydrogen was purged through reaction mixture for 4 h at room temperature. After completion of reaction, reaction mixture was filtered through Celite-bed and washed with methanol. Filtrate was concentrated under reduced pressure to obtain crude material. This was further purified by trituration with n-pentane to obtain pure 67.4. (0.120 g, Yield: 95.77%), MS (ES): m/z 303.09 [M+H]$^+$.

Synthesis of Compound 67.6

Compound was synthesized using general procedure C to obtain 67.6. (0.080 g, Yield: 48.37%), MS (ES): m/z 371.11 [M+H]$^+$.

Synthesis of Compound I-70

To a solution of compound 67.6 (0.080 g, 0.21 mmol, 1.0 eq) in tetrahydrofuran (2 mL) were added N,N-Diisopropylethylamine (0.1 mL, 0.63 mmol, 3.0 eq), Trimethylaluminium (2M in hexane, 0.52 mL, 1.05 mmol, 5.0 eq) and Methylamine (2M in tetrahydrofuran, 0.031 mL, 0.63 mmol, 3.0 eq) at 0° C. Reaction mixture was stirred at 70° C. for 5 h. After completion of reaction, reaction mixture was transferred into ice cold water and product was extracted with ethyl acetate. Organic layer was combined, washed with brine solution, dried over sodium sulfate and concentrated under reduced pressure to obtain crude material. This was further purified by 2.5% methanol in dichloromethane to obtain I-70 (0.034 g, Yield: 42.61%), MS (ES): 370.26 [M+H]$^+$ LCMS purity: 100%, HPLC purity: 99.14%, $^1$H NMR (DMSO-d$_6$, 400 MHZ): 8.41 (bs, 3H), 8.33 (bs, 1H), 7.47-7.44 (d, J=13.2 Hz, 2H), 2.83-2.82 (m, 3H), 2.81-2.77 (m, 2H), 2.18 (bs, 1H), 1.30-1.26 (t, J=7.6 Hz, 3H), 0.97-0.92 (m, 4H).

Synthesis of Compound 67.1

To a solution of compound 67 (0.5 g, 3.90 mmol, 1.0 eq) in acetonitrile (10 ml) was added tert-Butyl nitrite (0.5 mL, 4.29 mmol, 1.1 eq) at 0° C. and stirred for 10 min. Copper (II) bromide (0.608 g, 2.73 mmol, 0.7 eq) was added and reaction mixture was stirred at 0° C. for 30 min. After completion of reaction, reaction mixture was transferred into water and product was extracted with ethyl acetate. Organic layer was combined, washed with brine solution, dried over sodium sulfate and concentrated under reduced pressure to obtain crude material. This was further purified by column chromatography and compound was eluted in 2.0% ethyl acetate in hexane to obtain pure 67.1. (0.3 g, Yield: 40.04%). MS(ES): m/z 191.94 [M+H]$^+$.

Synthesis of Compound 67.2

Compound was synthesized as per experimental protocol of core synthesis B to obtain 67.2. (Yield: 66.51%), MS (ES): m/z 416.17 [M+H]$^+$.

Synthesis of Compound 67.3

Compound was synthesized using general procedure A to obtain 67.3. (0.2 g, Yield: 49.17%), MS (ES): m/z 483.18 [M+H]$^+$.

Example 68: 7-(cyclopropanecarboxamido)-2-(4-(1,5-dimethyl-1H-imidazol-2-yl)-2-fluorophenyl)-N-methyl-1H-pyrrolo[2,3-c]pyridine-4-carboxamide (I-68)

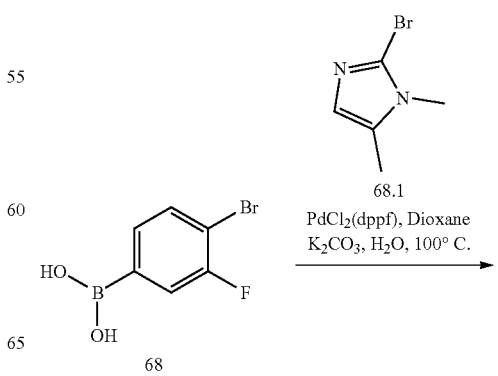

331
-continued

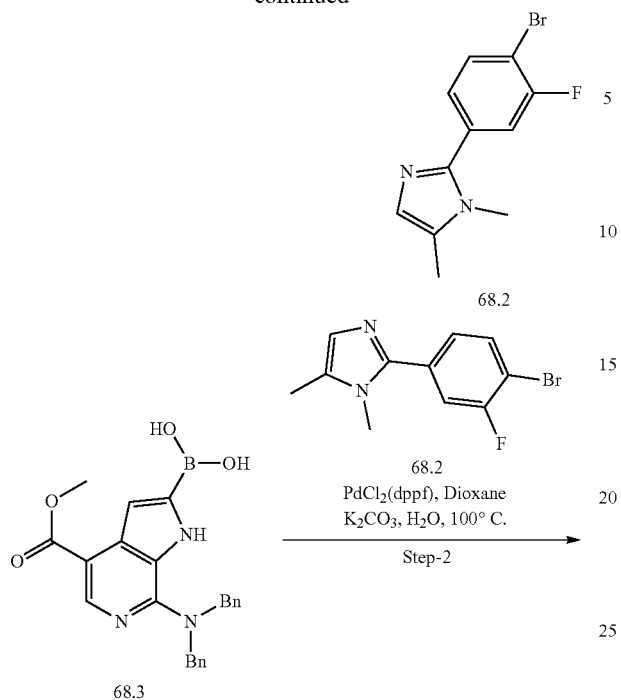

332
-continued

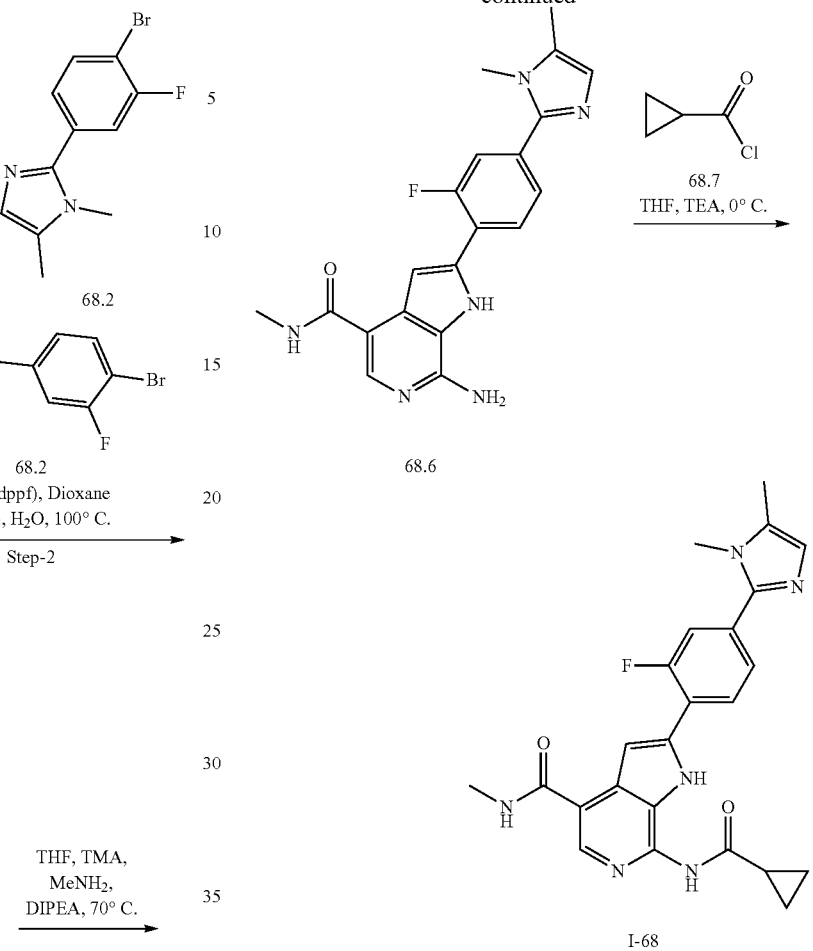

Synthesis of Compound 68.2

Compound was synthesized using general procedure A to obtain 68.2. (0.8 g, Yield: 65.05%), MS (ES): m/z 270.00 [M+H]$^+$.

Synthesis of Compound 68.3

Compound was synthesized as per experimental protocol of core synthesis B to obtain 68.3. (Yield: 66.51%), MS (ES): m/z 416.17 [M+H]$^+$.

Synthesis of Compound 68.4

Compound was synthesized using general procedure A to obtain 68.4. (0.250 g, Yield: 61.83%), MS (ES): m/z 560.24 [M+H]$^+$.

Synthesis of Compound 68.5

To a solution of compound 68.4 (0.250 g, 0.44 mmol, 1.0 eq) in tetrahydrofuran (5 mL) were added N,N-Diisopropylethylamine (0.24 mL, 1.32 mmol, 3.0 eq), Trimethylaluminium (2M in hexane, 1.1 mL, 2.2 mmol, 5.0 eq) and Methylamine (2M in tetrahydrofuran, 0.66 mL, 1.32 mmol, 3.0 eq) at 0° C. Reaction mixture was stirred at 70° C. for 5 h. After completion of reaction, reaction mixture was transferred to ice cold water and product was extracted with ethyl acetate. Organic layer was combined, washed with brine solution, dried over sodium sulfate and concentrated under reduced pressure to obtain crude material. This was further purified by 2.5% methanol in dichloromethane to obtain 68.5. (0.180 g, Yield: 72.13%), MS (ES): m/z 559.26 [M+H]+.

Synthesis of Compound 68.6

Compound was synthesized using general procedure B to obtain 68.6. (0.120 g, Yield: 98.42%), MS (ES): m/z 379.16 [M+H]+.

Synthesis of Compound I-68

Compound was synthesized using general procedure C to obtain I-68 (0.060 g, Yield: 42.38%), MS (ES): 447.52 [M+H]+ LCMS purity: 98.45%, HPLC purity: 97.76%, $^1$H NMR (DMSO-$d_6$, 400 MHZ): 12.14 (s, 1H), 11.33 (s, 1H), 8.40-8.39 (d, J=4.4 Hz, 1H), 8.33 (s, 1H), 8.09-8.05 (t, J=8 Hz, 1H), 7.71-7.70 (d, J=6 Hz, 1H), 7.68 (s, 1H), 7.53 (s, 1H), 6.85 (s, 1H), 3.69 (s, 3H), 2.87-2.86 (d, J=4.4 Hz, 3H), 2.26 (s, 3H), 1.24 (bs, 1H), 1.00-0.95 (m, 4H).

Example 69: 7-(cyclopropanecarboxamido)-2-(3-(6,7-dihydro-5H-pyrrolo[1,2-a]imidazol-2-yl)-2-fluorophenyl)-N-methyl-1H-pyrrolo[2,3-c]pyridine-4-carboxamide (I-69)

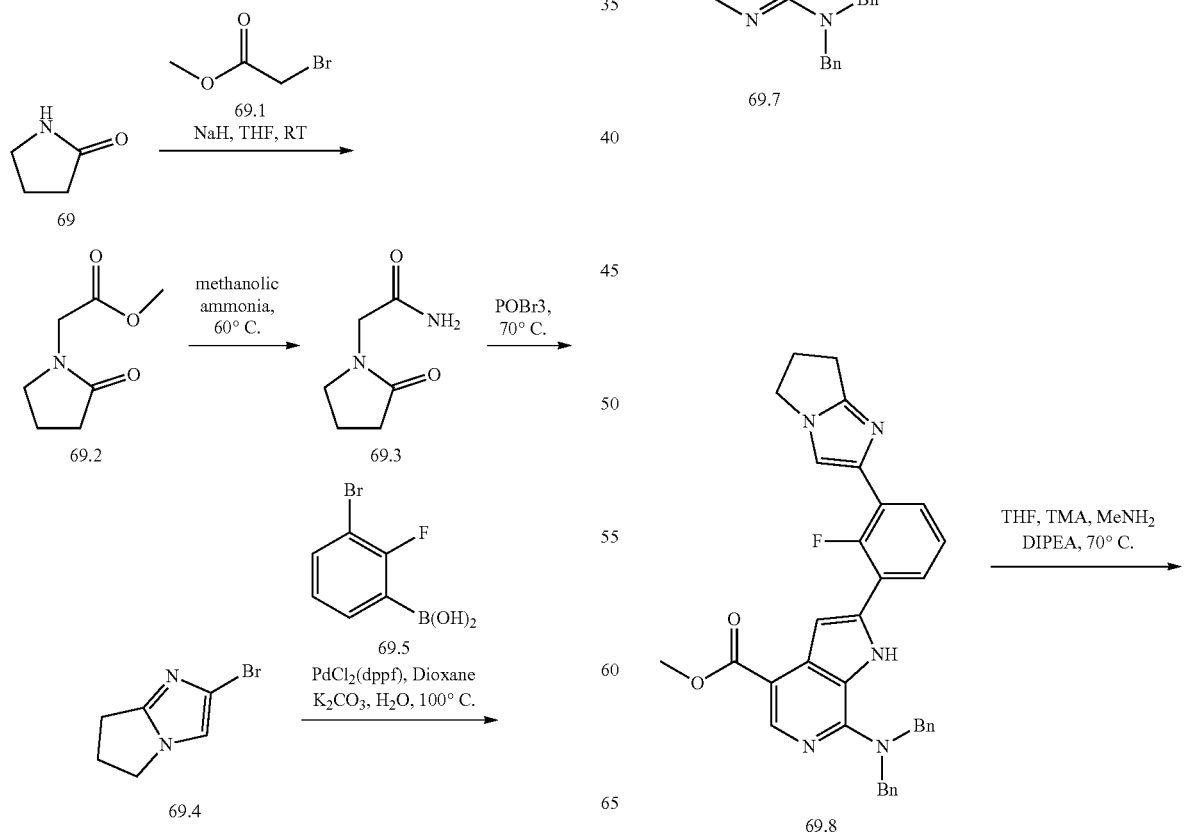

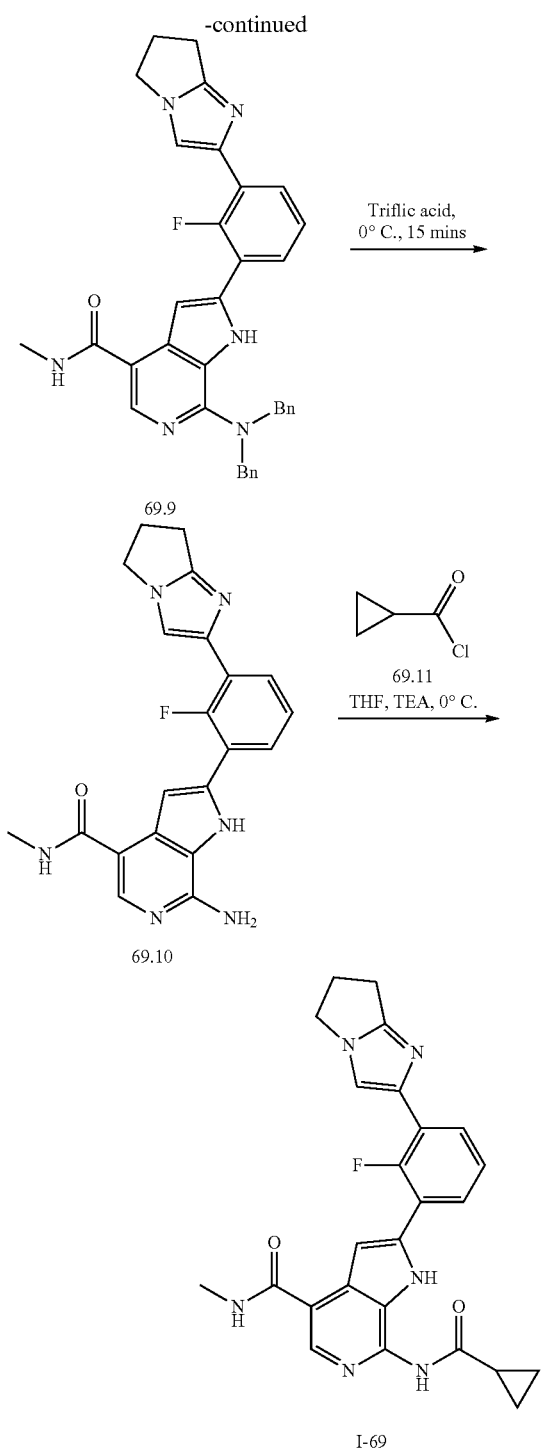

Synthesis of Compound 69.2

To the suspension of sodium hydride (1.69 g, 70.58 mmol, 1.2 eq) in tetrahydrofuran (25 mL) at 0° C. was added solution of 69 (5.0 g, 58.82 mmol, 1.0 eq) in tetrahydrofuran (25 mL) dropwise. Reaction mixture was stirred at room temperature for 30 min. Then 69.1 (10.7 g, 70.58 mmol, 1.2 eq) was added in to reaction mixture and stirred at room temperature for 2 h. After completion of reaction, reaction mixture was transferred into ice cold water and product was extracted with ethyl acetate. Organic layer was combined, washed with brine solution, dried over sodium sulfate and concentrated under reduced pressure to obtain 69.2. (5.0 g, Yield: 54.15%). MS(ES): m/z 157.07 [M+H]$^+$.

Synthesis of Compound 69.3

Mixture of compound 69.2 (4.5 g, 28.66 mmol, 1.0 eq) and methanolic ammonia (50 ml) was stirred at 60° C. for 4 h. After completion of reaction, reaction mixture was concentrated under reduced pressure and triturated with diethyl ether to obtain 69.3. (1.87 g, Yield: 45.94%). MS(ES): m/z 143.08 [M+H]$^+$.

Synthesis of Compound 69.4

The mixture of compound 69.3 (1.87 g, 13.16 mmol, 1.0 eq) and Phosphoryl bromide (0.9 g) was heated at 70° C. for 3 h. After completion of reaction, reaction mixture was quenched with saturated sodium bicarbonate solution and extracted with ethyl acetate. Organic layer was combined, washed with brine solution, dried over sodium sulfate and concentrated under reduced pressure to obtain crude material. This was further purified by trituration using n-pentane to obtain pure 69.4. (0.970 g, Yield: 39.42%). MS(ES): m/z 185.9 [M+H]$^+$.

Synthesis of Compound 69.6

Compound was synthesized using general procedure A to obtain 69.6. (1.1 g, Yield: 75.45%). MS (ES): m/z 280.0 [M+H]$^+$.

Synthesis of Compound 69.7

Compound was synthesized as per experimental protocol of core synthesis B to obtain 69.7. (Yield: 66.51%), MS (ES): m/z 416.17 [M+H]$^+$.

Synthesis of Compound 69.8

Compound was synthesized using general procedure A to obtain 69.8. (0.180 g, Yield: 56.85%), MS (ES): m/z 572.24 [M+H]$^+$.

Synthesis of Compound 69.9

To a solution of compound 69.8 (0.180 g, 0.31 mmol, 1.0 eq) in tetrahydrofuran (3 mL) were added N,N-Diisopropylethylamine (0.17 mL, 0.93 mmol, 3.0 eq), Trimethylaluminium (2M in hexane, 0.7 mL, 1.55 mmol, 5.0 eq) and Methylamine (2M in tetrahydrofuran, 0.46 mL, 0.93 mmol, 3.0 eq) at 0° C. Reaction mixture was stirred at 70° C. for 5 h. After completion of reaction, reaction mixture was transferred into ice cold water and product was extracted with ethyl acetate. Organic layer was combined, washed with brine solution, dried over sodium sulfate and concentrated under reduced pressure to obtain crude material. This was further purified by 2.5% methanol in dichloromethane to obtain 69.9. (0.110 g, Yield: 61.22%), MS (ES): m/z 571.26 [M+H]$^+$.

Synthesis of Compound 69.10

Compound was synthesized using general procedure B to obtain 69.10. (0.070 g, Yield: 93.02%), MS (ES): m/z 391.16 [M+H]$^+$.

Synthesis of Compound I-69
Compound was synthesized using general procedure C to obtain I-69 (0.040 g, Yield: 48.66%), MS (ES): 459.60 [M+H]+ LCMS purity: 100%, HPLC purity: 97.45%, $^1$H NMR (DMSO-d$_6$, 400 MHZ): 11.99 (s, 1H), 11.28 (s, 1H), 8.39-8.38 (d, J=4 Hz, 1H), 8.31 (s, 1H), 8.09-8.06 (t, J=7.2 Hz, 1H), 7.74-7.71 (t, J=6.4 Hz, 1H), 7.60-7.59 (d, J=4.4 Hz, 1H), 7.46 (s, 1H), 7.40-7.36 (d, J=7.6 Hz, 1H), 4.07-4.03 (m, 3H), 2.85-2.84 (d, J=4 Hz, 3H), 1.55 (s, 4H), 1.00-0.93 (m, 4H).
Example 70: 7-(cyclopropanecarboxamido)-2-(3-(1,5-dimethyl-1H-1,2,4-triazol-3-yl)-2-fluorophenyl)-N-methyl-1H-pyrrolo[2,3-c]pyridine-4-carboxamide (I-73)
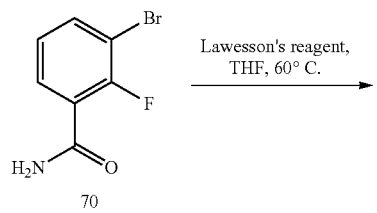
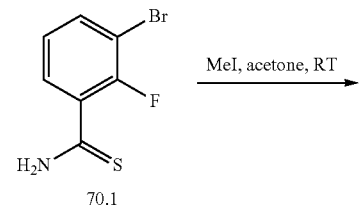
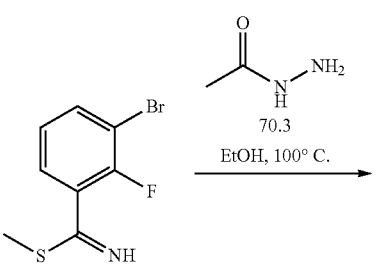
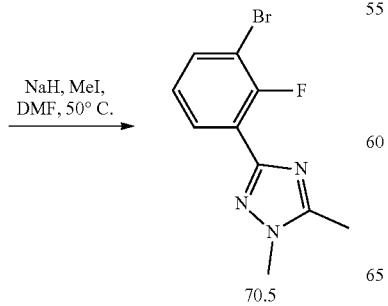
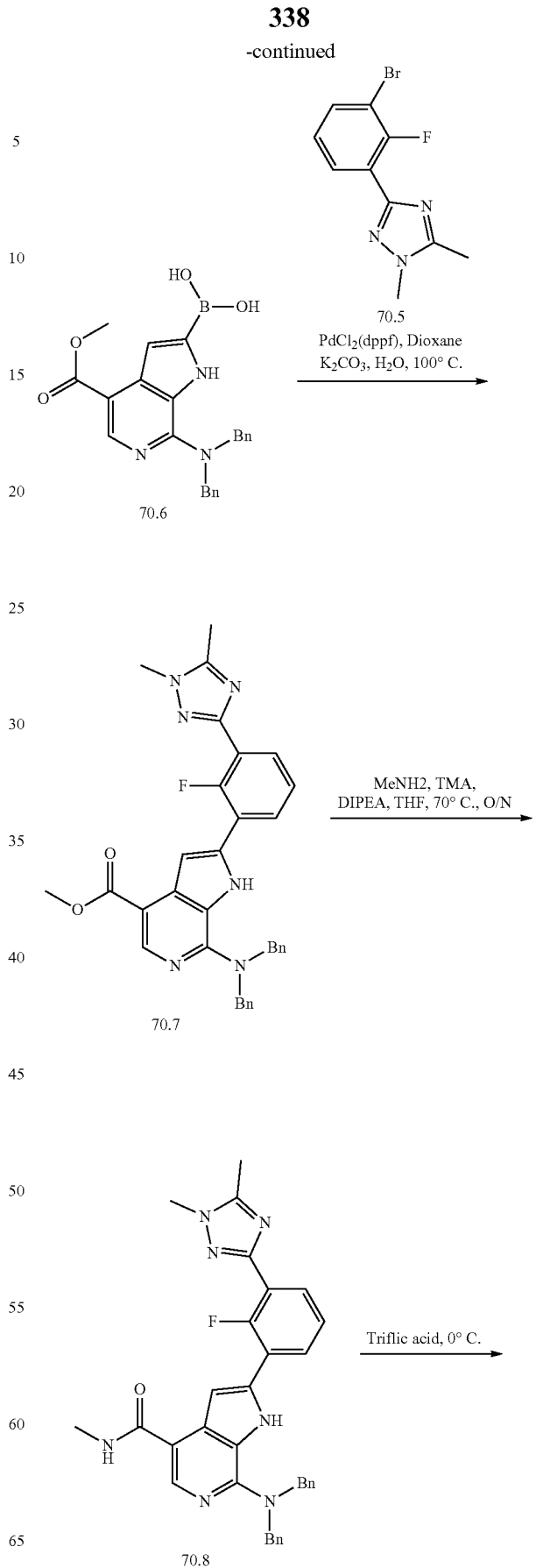

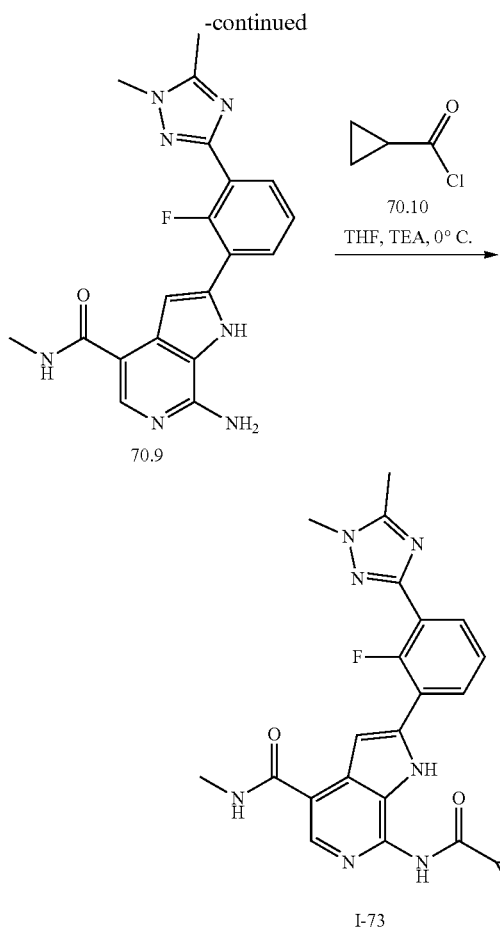

Synthesis of Compound 70

Compound was synthesized as per experimental protocol of I-36 to obtain 70. (Yield: 85.38%), MS (ES): m/z 218.95 [M+H]⁺.

Synthesis of Compound 70.1

To the solution of compound 70 (0.2 g, 0.91 mmol, 1.0 eq) in tetrahydrofuran (4 mL) was added Lawesson's reagent (0.183 g, 0.45 mmol, 0.5 eq). Reaction mixture was refluxed at 60° C. for 16 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by column chromatography and the compound was eluted in 15% ethyl acetate in hexane to obtain 70.1. (0.160 g, Yield: 74.51%). MS(ES): m/z 234.9 [M+H]⁺.

Synthesis of Compound 70.2

To the solution of compound 70.1 (0.160 g, 0.68 mmol, 1.0 eq) in acetone (4 mL) was added methyl iodide (0.106 g, 0.74 mmol, 1.1 eq). Reaction mixture was stirred at room temperature for 15 h. After completion of reaction, reaction mixture was filtered and solid was washed with dichloromethane. The obtained solid material was stirred with 50% aqueous potassium carbonate solution (15 mL) and extracted with dichloromethane. Organic layer was combined, dried over sodium sulfate and concentrated under reduced pressure to obtain 70.2. (0.120 g, Yield: 70.76%). MS(ES): m/z 248.9 M+H]⁺.

Synthesis of Compound 70.4

To the solution of compound 70.2 (0.120 g, 0.48 mmol, 1.0 eq) in ethanol (2 mL) was added 70.3. (0.035 g, 0.48 mmol, 1.0 eq). Reaction mixture was refluxed at 100° C. for 1 h. After completion of reaction, reaction mixture was filtered through millipore and concentrated under reduced pressure to obtain 70.4. (0.082 g, Yield: 66.21%). MS(ES): m/z 255.9 [M+H]⁺.

Synthesis of Compound 70.5

To a solution of 70.4 (0.082 g, 0.32 mmol, 1.0 eq) in N,N-dimethylformamide (2 mL), was added sodium hydride (0.015 g, 0.64 mmol, 2.0 eq) at 0° C. and stirred for 20 min. Methyl iodide (0.049 g, 0.35 mmol, 1.1 eq) was added and reaction mixture was stirred at 50° C. for 2 h. After completion of reaction, reaction mixture was transferred into ice, stirred and extracted with ethyl acetate. Organic layer was combined, dried over sodium sulfate and concentrated under reduced pressure to obtain 70.5. (0.022 g, Yield: 25.44%). MS (ES): m/z 270.9[M+H]⁺.

Synthesis of Compound 70.6

Compound was synthesized as per experimental protocol of core synthesis B to obtain 70.6. (Yield: 66.51%), MS (ES): m/z 416.17 [M+H]⁺.

Synthesis of Compound 70.7

Compound was synthesized using general procedure A to obtain 70.7. (0.190 g, Yield: 43.30%), MS (ES): m/z 561.24 [M+H]⁺.

Synthesis of Compound 70.8

To a solution of compound 70.7 (0.190 g, 0.33 mmol, 1.0 eq) in tetrahydrofuran (3 mL) were added N,N-Diisopropylethylamine (0.18 mL, 0.99 mmol, 3.0 eq), Trimethylaluminium (2M in hexane, 0.82 mL, 1.65 mmol, 5.0 eq) and Methylamine (2M in tetrahydrofuran, 0.49 mL, 0.99 mmol, 3.0 eq) at 0° C. Reaction mixture was stirred at 70° C. for 16 h. After completion of reaction, reaction mixture was transferred to ice cold water and product was extracted with ethyl acetate. Organic layer was combined, washed with brine solution, dried over sodium sulfate and concentrated under reduced pressure to obtain crude material. This was further purified by 2.5% methanol in dichloromethane to obtain 70.8. (0.150 g, Yield: 79.09%), MS (ES): m/z 560.25 [M+H]⁺.

Synthesis of Compound 70.9

Compound was synthesized using general procedure B to obtain 70.9. (0.090 g, Yield: 88.51%), MS (ES): m/z 380.16 [M+H]⁺.

Synthesis of Compound I-73

Compound was synthesized using general procedure C to obtain I-73 (0.050 g, Yield: 47.10%), MS (ES): 448.72

[M+H]+ LCMS purity: 98.58%, HPLC purity: 98.17%, ¹H NMR (DMSO-d₆, 400 MHZ): 12.25 (s, 1H), 11.41 (s, 1H), 8.39 (s, 1H), 8.32 (bs, 1H), 8.03-8.01 (d, J=6.8 Hz, 2H), 7.50-7.44 (m, 2H), 3.89 (s, 3H), 2.86-2.85 (d, J=4.8 Hz, 3H), 2.84 (s, 3H), 1.65 (s, 1H), 0.99-0.94 (m, 4H).
Example 71: 7-(cyclopropanecarboxamido)-2-(2-fluoro-4-(1,4,5-trimethyl-1H-imidazol-2-yl)phenyl)-N-methyl-1H-pyrrolo[2,3-c]pyridine-4-carboxamide (I-74)
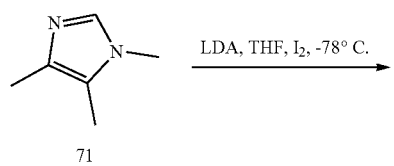
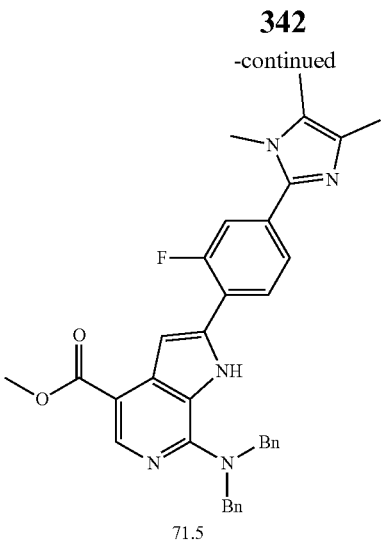
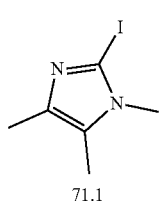
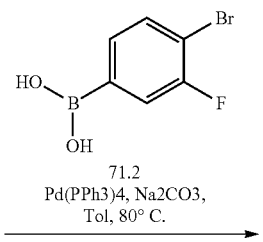
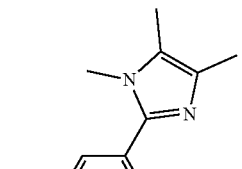
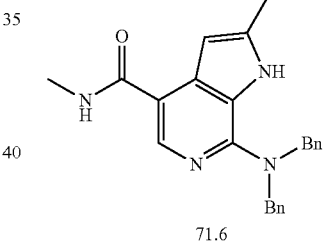
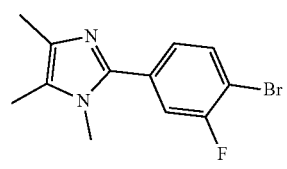
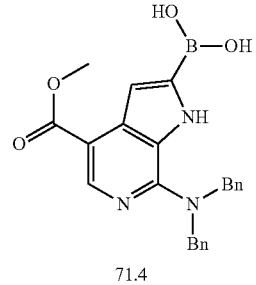
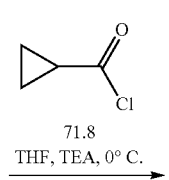

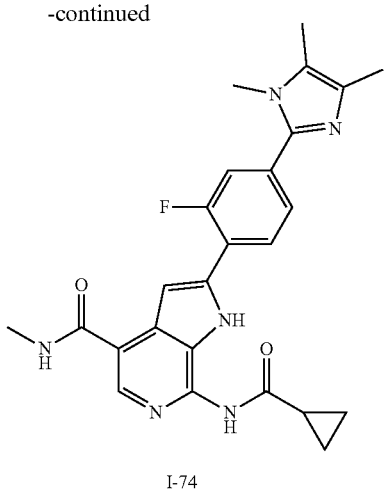

I-74

Synthesis of Compound 71.1

To the solution of compound 71 (4.2 g, 38.18 mmol, 1.0 eq) in tetrahydrofuran (42 mL) was added dropwise Lithium diisopropylamide (2M in tetrahydrofuran), (57 mL, 114.54 mmol, 3.0 eq) at −78° C. The reaction mixture was stirred at −78° C. for 1 h. Then a solution of iodine (9.6 g, 76.36 mmol, 2.0 eq) in tetrahydrofuran (20 mL) was added to reaction mixture and stirred for 2 h at same temperature. After completion of reaction, reaction mixture was transferred into ice cold water and product was extracted with ethyl acetate. Organic layer was combined, washed with brine solution, dried over sodium sulfate and concentrated under reduced pressure to obtain crude material. This was further purified by 7% ethyl acetate in hexane to obtain 71.1. (1.6 g, Yield: 17.78%). MS (ES): m/z 236.9 [M+H]$^+$.

Synthesis of Compound 71.3

Argon was purged for 15 min through a stirred mixture of 71.1 (1.6 g, 6.77 mmol, 1.0 eq), 71.2 (1.9 g, 8.80 mmol, 1.3 eq) and sodium carbonate (1.7 g, 16.92 mmol, 2.5 eq) in toluene (30 mL). Tetrakis(triphenylphosphine)palladium(0) (0.781 g, 0.67 mmol, 0.1 eq) was added to it and further purging done for 10 min. Reaction was allowed to stir at 80° C. for 5 h. After completion of reaction, reaction mixture was transferred into water and product was extracted with ethyl acetate. Organic layer was combined, washed with brine solution, dried over sodium sulfate and concentrated under reduced pressure to obtain 71.3. (0.7 g, Yield: 36.47%). MS (ES): m/z 284.01 [M+H]$^+$.

Synthesis of Compound 71.4

Compound was synthesized as per experimental protocol of core synthesis B to obtain 71.4. (Yield: 66.51%), MS (ES): m/z 416.17 [M+H]$^+$.

Synthesis of Compound 71.5

Compound was synthesized using general procedure A to obtain 71.5. (0.160 g, Yield: 45.42%), MS (ES): m/z 574.26 [M+H]$^+$.

Synthesis of Compound 71.6

To a solution of compound 71.5 (0.160 g, 0.27 mmol, 1.0 eq) in tetrahydrofuran (2 mL) were added N,N-Diisopropylethylamine (0.14 mL, 0.81 mmol, 3.0 eq), Trimethylaluminium (2M in hexane, 0.6 mL, 1.35 mmol, 5.0 eq) and Methylamine (2M in tetrahydrofuran, 0.4 mL, 0.81 mmol, 3.0 eq) at 0° C. Reaction mixture was stirred at 70° C. for 5 h. After completion of reaction, reaction mixture was transferred to ice cold water and product was extracted with ethyl acetate. Organic layer was combined, washed with brine solution, dried over sodium sulfate and concentrated under reduced pressure to obtain crude material. This was further purified by 2.5% methanol in dichloromethane to obtain 71.6. (0.127 g, Yield: 79.51%), MS (ES): m/z 573.27 [M+H]$^+$.

Synthesis of Compound 71.7

Compound was synthesized using general procedure B to obtain 71.7. (0.067 g, Yield: 76.99%), MS (ES): m/z 393.18 [M+H]$^+$.

Synthesis of Compound I-74

Compound was synthesized using general procedure C to obtain I-74 (0.032 g, Yield: 40.70%), MS (ES): 461.67 [M+H]$^+$ LCMS purity: 97.11%, HPLC purity: 96.81%, $^1$H NMR (DMSO-$d_6$, 400 MHZ): 12.13 (s, 1H), 11.33 (s, 1H), 8.40-8.39 (d, J=4.4 Hz, 1H), 8.33 (s, 1H), 8.06-8.02 (t, J=8 Hz, 1H), 7.67 (bs, 1H), 7.65 (bs, 1H), 7.52 (bs, 1H), 3.66 (s, 3H), 2.87-2.86 (d, J=4.4 Hz, 3H), 2.27 (bs, 1H), 2.19 (s, 3H), 2.12 (s, 3H), 1.00-0.95 (m, 4H).

Example 72: 7-(cyclopropanecarboxamido)-2-(2-fluoro-4-(5,6,7,8-tetrahydroimidazo[1,5-a]pyridin-3-yl)phenyl)-N-methyl-1H-pyrrolo[2,3-c]pyridine-4-carboxamide (I-75)

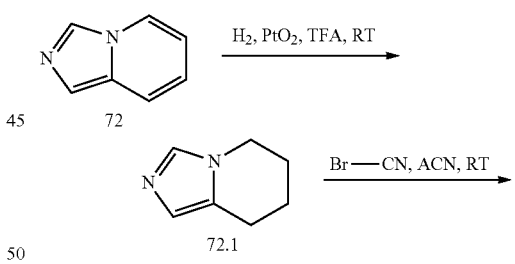

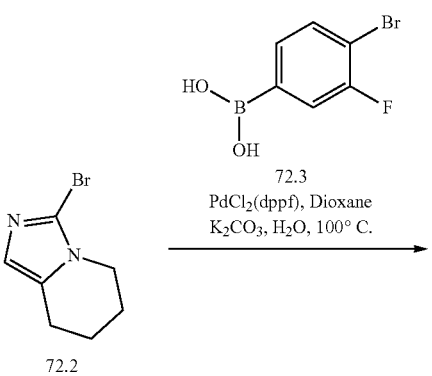

345
-continued

346
-continued

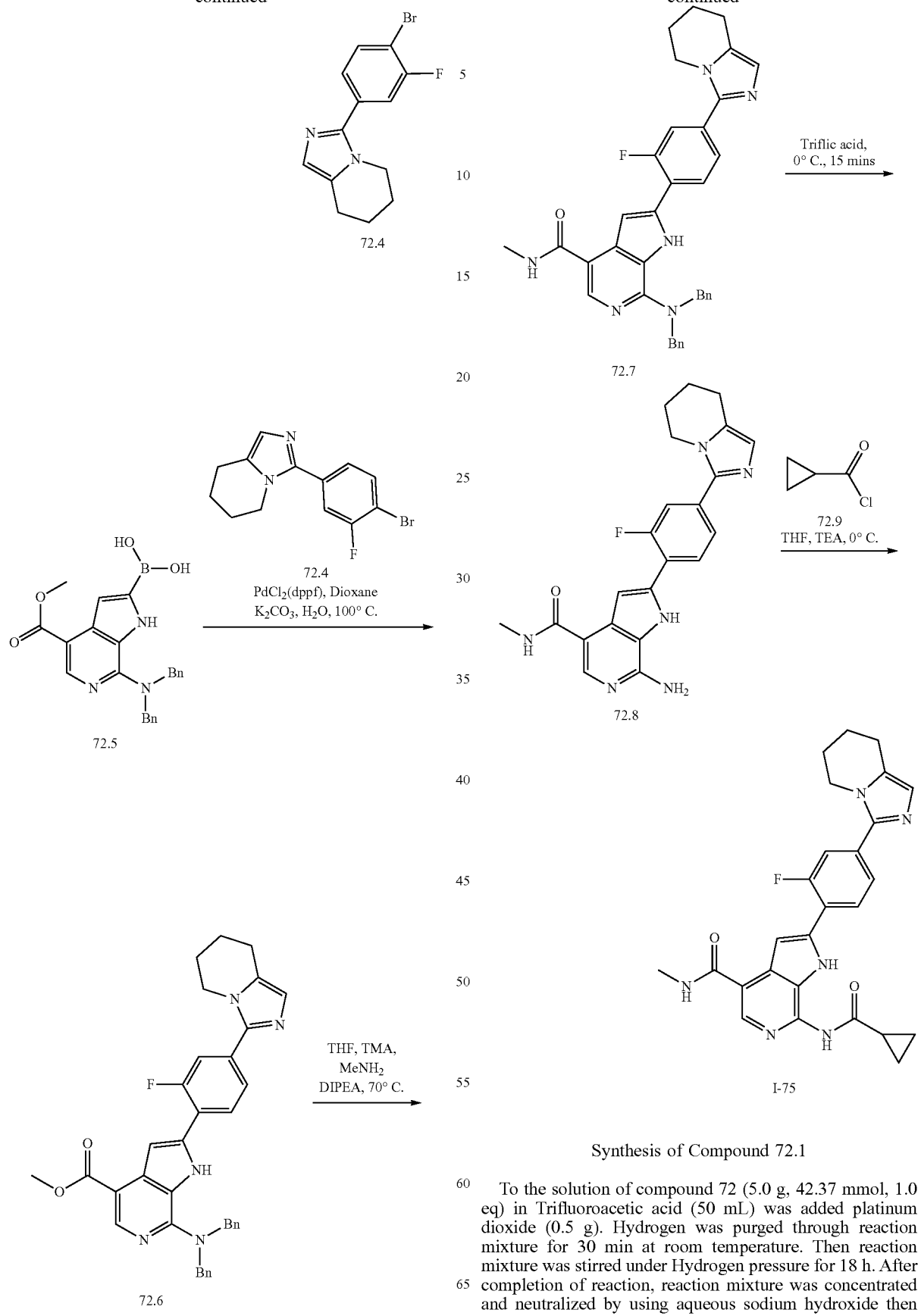

Synthesis of Compound 72.1

To the solution of compound 72 (5.0 g, 42.37 mmol, 1.0 eq) in Trifluoroacetic acid (50 mL) was added platinum dioxide (0.5 g). Hydrogen was purged through reaction mixture for 30 min at room temperature. Then reaction mixture was stirred under Hydrogen pressure for 18 h. After completion of reaction, reaction mixture was concentrated and neutralized by using aqueous sodium hydroxide then extracted with 5% methanol in dichloromethane. Organic layer was combined, dried over sodium sulfate and concentrated under reduced pressure to obtain 72.1. (2.73 g, Yield: 52.80%). MS (ES): m/z 123.09 [M+H]+.

Synthesis of Compound 72.2

To a solution of compound 72.1 (2.73 g, 22.37 mmol, 1.0 eq) in Acetonitrile (30 mL) was added Cyanogen bromide (2.3 g, 22.37 mmol, 1.0 eq). Reaction mixture was stirred at room temperature for 18 h. After completion of reaction, reaction mixture was transferred into aqueous sodium bicarbonate solution and extracted with ethyl acetate. Organic layer was combined, washed with brine solution, dried over sodium sulfate and concentrated under reduced pressure to obtain crude material. This was further purified by 20% ethyl acetate in hexane to obtain 72.2. (2.0 g, Yield: 44.51%), MS (ES): m/z 201.9 [M+H]+.

Synthesis of Compound 72.4

Compound was synthesized using general procedure A to obtain 72.4. (0.210 g, Yield: 7.15%), MS (ES): m/z 295.16 [M+H]+.

Synthesis of Compound 72.5

Compound was synthesized as per experimental protocol of core synthesis B to obtain 72.5. (Yield: 66.51%), MS (ES): m/z 416.17 [M+H]+.

Synthesis of Compound 72.6

Compound was synthesized using general procedure A to obtain 72.6. (0.170 g, Yield: 48.21%), MS (ES): m/z 586.26 [M+H]+.

Synthesis of Compound 72.7

To a solution of compound 72.6 (0.170 g, 0.29 mmol, 1.0 eq) in tetrahydrofuran (2 mL) were added N,N-diisopropylethylamine (0.16 mL, 0.87 mmol, 3.0 eq), Trimethylaluminium (2M in hexane, 0.72 mL, 1.45 mmol, 5.0 eq) and Methylamine (2M in tetrahydrofuran, 0.43 mL, 0.87 mmol, 3.0 eq) at 0° C. Reaction mixture was stirred at 70° C. for 5 h. After completion of reaction, reaction mixture was transferred into ice cold water and product was extracted with ethyl acetate. Organic layer was combined, washed with brine solution, dried over sodium sulfate and concentrated under reduced pressure to obtain crude material. This was further purified by 2.5% methanol in dichloromethane to obtain 72.7. (0.150 g, Yield: 88.38%), MS (ES): m/z 585.27 [M+H]+.

Synthesis of Compound 72.8

Compound was synthesized using general procedure B to obtain 72.8. (0.080 g, Yield: 77.10%), MS (ES): m/z 405.18 [M+H]+.

Synthesis of Compound I-75

Compound was synthesized using general procedure C to obtain I-75 (0.042 g, Yield: 44.94%), MS (ES): 473.67 [M+H]+ LCMS purity: 100%, HPLC purity: 97.95%, 1H NMR (DMSO-$d_6$, 400 MHZ): 12.12 (s, 1H), 11.33 (s, 1H), 8.40-8.39 (d, J=4 Hz, 1H), 8.33 (s, 1H), 8.07-8.03 (t, J=8.4 Hz, 1H), 7.75 (bs, 1H), 7.72-7.71 (d, J=3.2 Hz, 1H), 7.52 (s, 1H), 6.85 (s, 1H), 4.23-4.20 (t, J=5.6 Hz, 2H), 2.87-2.86 (d, J=4.4 Hz, 3H), 2.27 (bs, 1H), 1.90 (bs, 3H), 1.79 (bs, 3H), 1.00-0.95 (m, 4H).

Example 73: 7-(cyclopropanecarboxamido)-2-(3-(6,7-dihydro-5H-imidazo[2,1-b][1,3]oxazin-2-yl)-2-fluorophenyl)-N-methyl-1H-pyrrolo[2,3-c]pyridine-4-carboxamide (I-76)

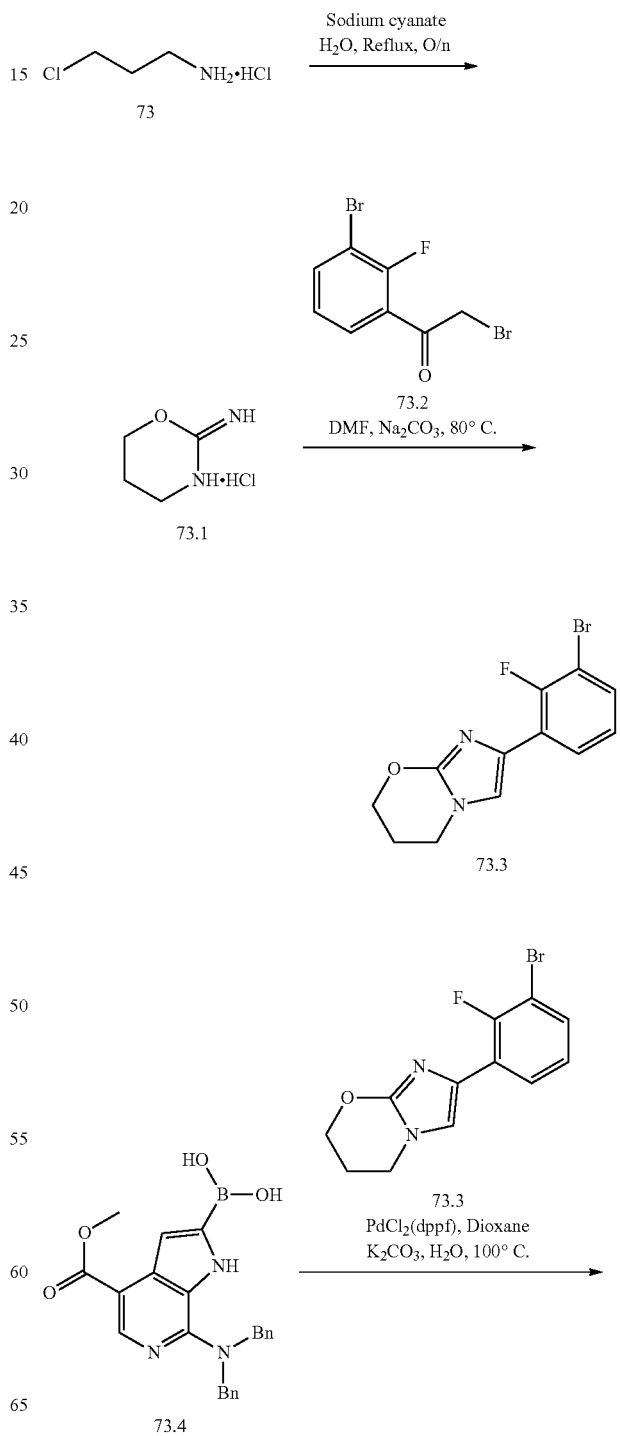

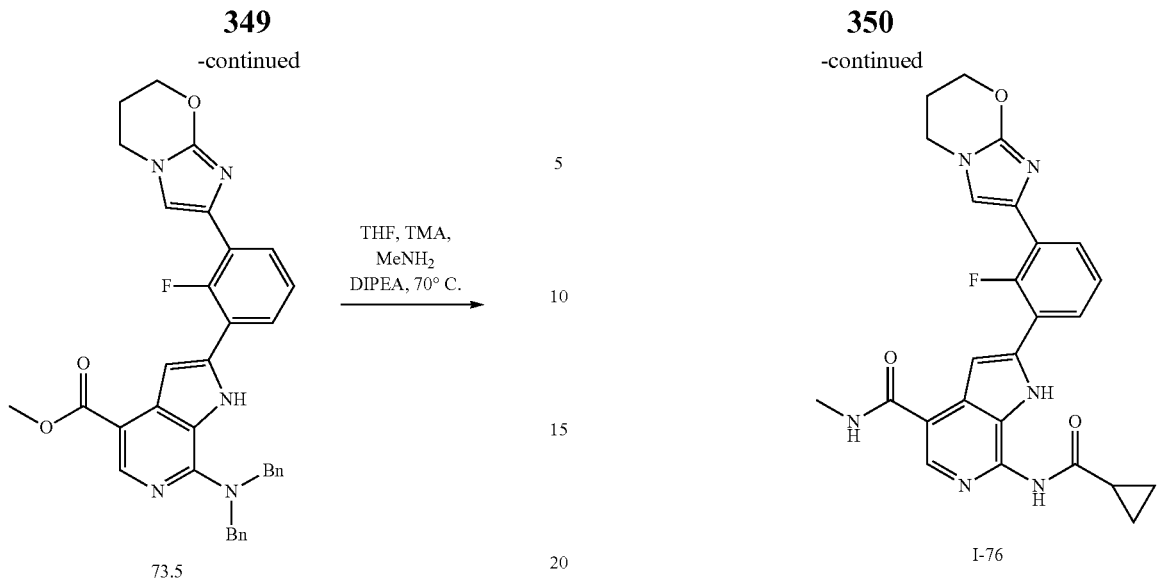

Synthesis of Compound 73.1

Mixture of compound 73 (4.0 g, 30.76 mmol, 1.0 eq) and sodium cyanate (1.9 g, 30.76 mmol, 1.0 eq) in water (10 mL) was stirred at 90° C. for 2 h. After completion of reaction, reaction mixture was concentrated under reduced pressure to obtained semi solid material which was treated with hot ethanol. Ethanol layer was cooled and diethyl ether was added. Precipitated solid was filtered and dried to obtain 73.1. (2.2 g, Yield: 71.42%). MS(ES): m/z 136.04 [M+H]$^+$.

Synthesis of Compound 73.3

To the solution of compound 73.1 (0.3 g, 2.22 mmol, 1.0 eq) and 73.2 (0.654 g, 2.22 mmol, 1.0 eq) in Dimethylformamide (10 mL) was added Sodium carbonate (1.1 g, 11.1 mmol, 5.0 eq). Reaction mixture was heated at 80° C. for 16 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by column chromatography and the compound was eluted in 20% ethyl acetate in hexane to obtain 73.3. (0.150 g, Yield: 16.85%). MS(ES): m/z 297.9 [M+H]$^+$.

Synthesis of Compound 73.4

Compound was synthesized as per experimental protocol of core synthesis B to obtain 73.4. (Yield: 66.51%), MS (ES): m/z 416.17 [M+H]$^+$.

Synthesis of Compound 73.5

Compound was synthesized using general procedure A to obtain 73.5. (0.170 g, Yield: 48.05%), MS (ES): m/z 588.24 [M+H]$^+$.

Synthesis of Compound 73.6

To a solution of compound 73.5 (0.170 g, 0.28 mmol, 1.0 eq) in tetrahydrofuran (3 mL) were added N,N-Diisopropylethylamine (0.15 mL, 0.84 mmol, 3.0 eq), Trimethylaluminium (2M in hexane, 0.7 mL, 1.4 mmol, 5.0 eq) and Methylamine (2M in tetrahydrofuran, 0.42 mL, 0.84 mmol, 3.0 eq) at 0° C. Reaction mixture was stirred at 70° C. for 5 h. After completion of reaction, reaction mixture was transferred to ice cold water and product was extracted with ethyl acetate. Organic layer was combined, washed with brine solution, dried over sodium sulfate and concentrated under reduced pressure to obtain crude material. This was further purified by 2.5% methanol in dichloromethane to obtain 73.6. (0.123 g, Yield: 72.47%), MS (ES): m/z 587.25 [M+H]$^+$.

Synthesis of Compound 73.7

Compound was synthesized using general procedure B to obtain 73.7. (0.075 g, Yield: 88.02%), MS (ES): m/z 407.16 [M+H]$^+$.

Synthesis of Compound I-76

Compound was synthesized using general procedure C to obtain I-76 (0.030 g, Yield: 34.26%), MS (ES): 475.62 [M+H]$^+$ LCMS purity: 99.35%, HPLC purity: 97.36%, $^1$H NMR (DMSO-d$_6$, 400 MHZ): 11.97 (s, 1H), 11.29 (s, 1H), 8.40-8.39 (d, J=4.4 Hz, 1H), 8.33 (s, 1H), 7.98-7.95 (t, J=6.8 Hz, 1H), 7.73-7.69 (t, J=7.6 Hz, 1H), 7.47 (s, 1H), 7.39-7.35 (d, J=7.6 Hz, 1H), 7.31-7.29 (d, J=4.4 Hz, 1H), 4.40 (bs, 1H), 4.08-3.97 (m, 4H), 2.86-2.85 (d, J=4.4 Hz, 3H), 1.56 (bs, 2H), 1.02-0.95 (m, 4H).

Example 74: 7-(cyclopropanecarboxamido)-2-(2,6-difluoro-4-(1-methyl-1H-imidazol-2-yl)phenyl)-N-methyl-1H-pyrrolo[2,3-c]pyridine-4-carboxamide (I-77)

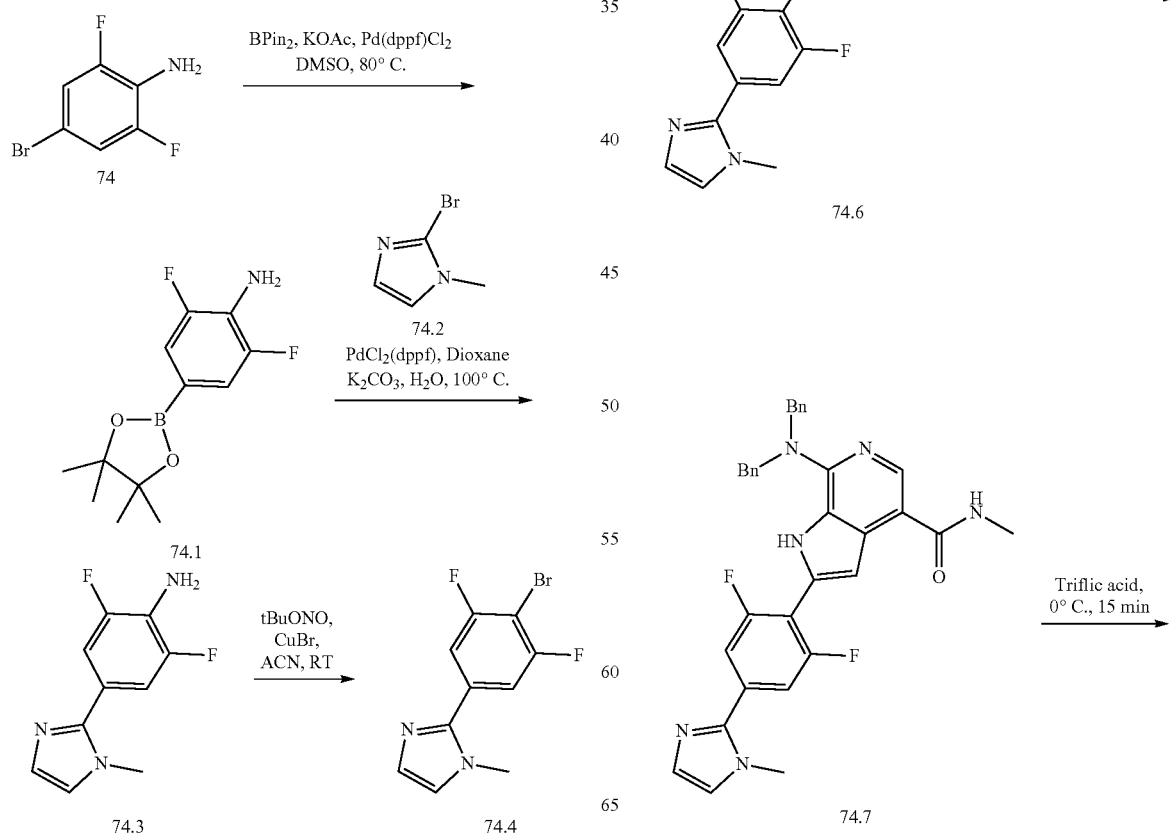

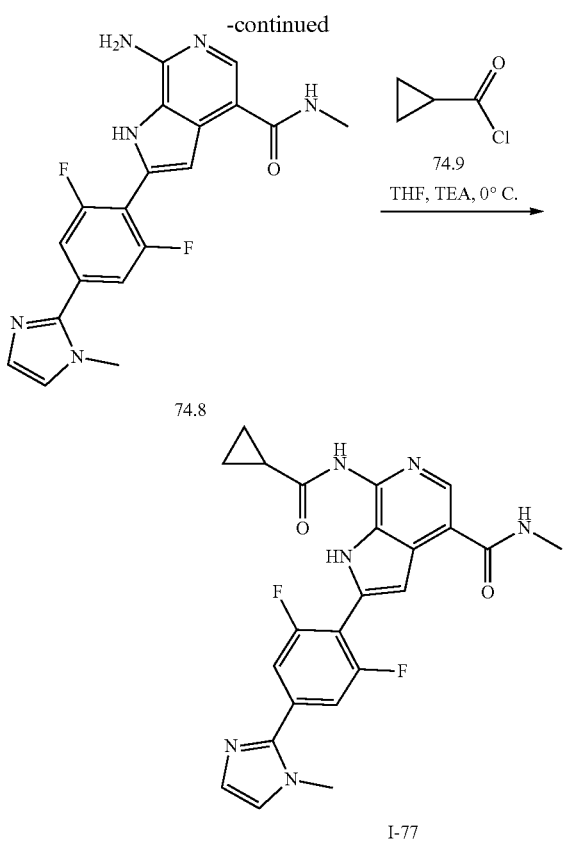

Synthesis of Compound 74.1

To a solution of 74 (3.0 g, 14.42 mmol, 1.0 eq) in dimethyl sulfoxide (60 mL) was added Bis(pinacolato)diboron (4.0 g, 15.86 mmol, 1.1 eq), and potassium acetate (4.2 g, 43.26 mmol, 3.0 eq). The reaction mixture was degassed for 10 min. under argon atmosphere, then [1,1'-Bis(diphenylphosphino)ferrocene]dichloropalladium(II) (0.171 g, 0.21 mmol, 0.015 eq) was added, and degassed for 5 min. The reaction mixture was stirred at 80° C. for 1 h. After completion of reaction, reaction mixture was cooled to room temperature, transferred into water and product was extracted with ethyl acetate. Organic layer was combined, washed with brine solution, dried over sodium sulfate and concentrated under reduced pressure to obtain crude material. This was further purified by combi flash using 3% methanol in dichloromethane as eluant to obtain pure 74.1. (1.8 g, Yield: 48.93%). MS(ES): m/z 254.13 [M+H]$^+$.

Synthesis of Compound 74.3

Compound was synthesized using general procedure A to obtain 74.3. (0.6 g, Yield: 40.64%). MS (ES): m/z 210.08 [M+H]$^+$.

Synthesis of Compound 74.4

To a solution of compound 74.3 (0.550 g, 2.63 mmol, 1.0 eq) in acetonitrile (10 mL) was added tert-Butyl nitrite (0.541 g, 5.26 mmol, 2.0 eq) and reaction mixture was cooled to 0° C. Then Copper (II) bromide (1.1 g, 5.26 mmol, 2.0 eq) was added to reaction mixture and stirred at room temperature for 2 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by combi flash using 20% ethyl acetate in hexane as eluant to obtain pure 74.4. (0.260 g, Yield: 36.21%). MS(ES): m/z 271.9 [M+H]$^+$.

Synthesis of Compound 74.5

Compound was synthesized as per experimental protocol of core synthesis B to obtain 74.5. (Yield: 66.51%), MS (ES): m/z 416.17 [M+H]$^+$.

Synthesis of Compound 74.6

Compound was synthesized using general procedure A to obtain 74.6. (0.180 g, Yield: 53.05%), MS (ES): m/z 564.22 [M+H]$^+$.

Synthesis of Compound 74.7

To a solution of compound 74.6 (0.180 g, 0.31 mmol, 1.0 eq) in tetrahydrofuran (3 mL) were added N,N-Diisopropylethylamine (0.17 mL, 0.93 mmol, 3.0 eq), Trimethylaluminium (2M in hexane, 0.7 mL, 1.55 mmol, 5.0 eq) and Methylamine (2M in tetrahydrofuran, 0.46 mL, 0.93 mmol, 3.0 eq) at 0° C. Reaction mixture was stirred at 70° C. for 5 h. After completion of reaction, reaction mixture was transferred to ice cold water and product was extracted with ethyl acetate. Organic layer was combined, washed with brine solution, dried over sodium sulfate and concentrated under reduced pressure to obtain crude material. This was further purified by 2.5% methanol in dichloromethane to obtain 74.7. (0.110 g, Yield: 61.22%), MS (ES): m/z 563.23 [M+H]$^+$.

Synthesis of Compound 74.8

Compound was synthesized using general procedure B to obtain 74.8. (0.070 g, Yield: 93.63%), MS (ES): m/z 383.14 [M+H]$^+$.

Synthesis of Compound I-77

Compound was synthesized using general procedure C to obtain I-77 (0.040 g, Yield: 48.51%), MS (ES): 451.37 [M+H]$^+$ LCMS purity: 100%, HPLC purity: 97.24%, $^1$H NMR (DMSO-d$_6$, 400 MHZ): 12.29 (s, 1H), 11.42 (s, 1H), 8.46 (s, 1H), 8.34 (s, 1H), 7.71-7.68 (t, J=10.8 Hz, 2H), 7.55 (bs, 1H), 7.38 (bs, 1H), 6.82 (bs, 1H), 3.89 (bs, 3H), 2.84 (bs, 3H), 1.54 (bs, 1H), 0.96-0.85 (m, 4H).

Example 75: 7-(cyclopropanecarboxamido)-2-(2-ethoxy-6-fluoro-4-(1-methyl-1H-imidazol-2-yl)phenyl)-N-methyl-1H-pyrrolo[2,3-c]pyridine-4-carboxamide (I-78)

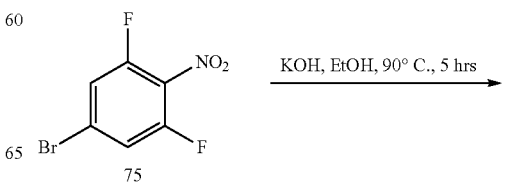

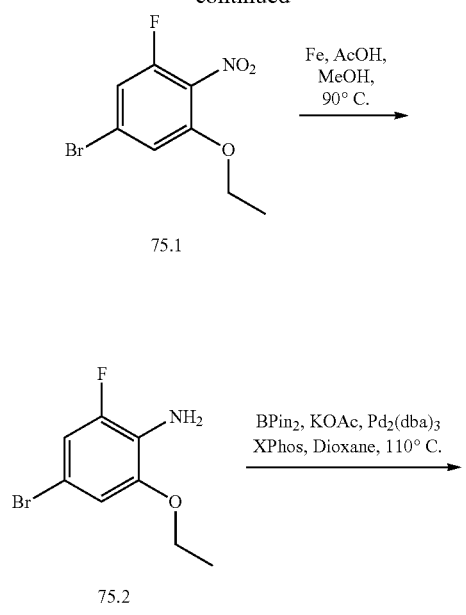
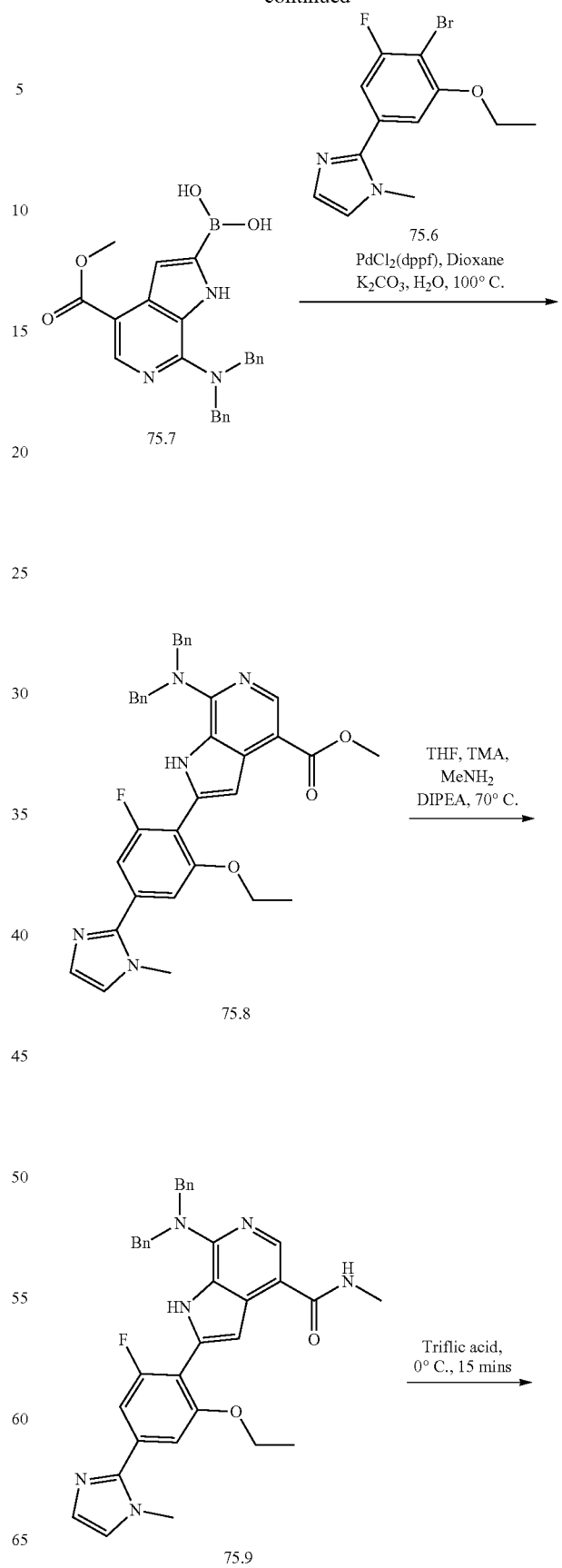

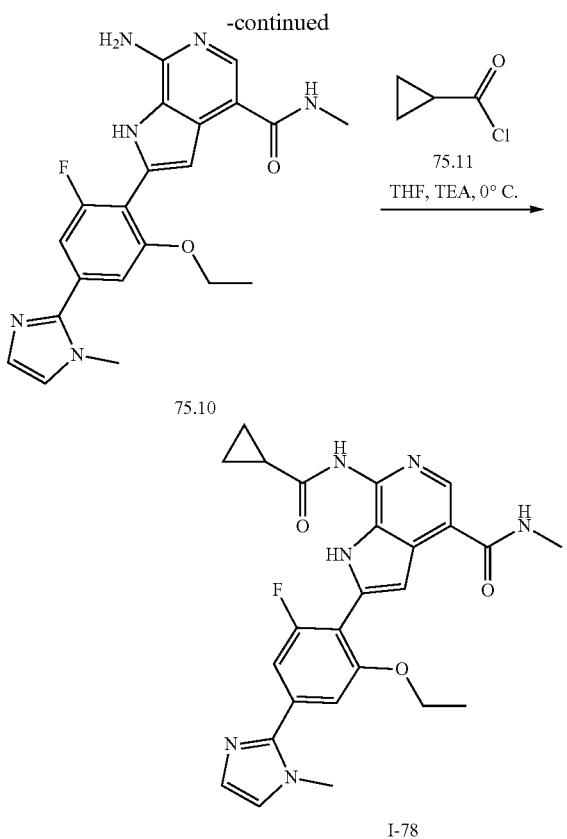

75.10

I-78

Synthesis of Compound 75.1

To a solution of 75 (5.0 g, 21 mmol, 1.0 eq) in ethanol (50 mL) was added Potassium hydroxide (2.3 g, 42 mmol, 2.0 eq). The reaction mixture was stirred at 90° C. for 5 h. After completion of reaction, reaction mixture was cooled to room temperature, transferred into water and product was extracted with ethyl acetate. Organic layer was combined, washed with brine solution, dried over sodium sulfate and concentrated under reduced pressure to obtain crude material. This was further purified by combi flash using 10% ethyl acetate in hexane as eluant to obtain pure 75.1. (3.2 g, Yield: 57.68%). MS (ES): m/z 264.9 [M+H]$^+$.

Synthesis of Compound 75.2

To a solution of 75.1 (1.0 g, 3.78 mmol, 1.0 eq) in Acetic acid (2.1 mL, 37.8 mmol, 10.0 eq) was added Iron powder (1.0 g, 18.9 mmol, 5.0 eq). Reaction mixture was stirred at 90° C. for 30 min. After completion of reaction, reaction mixture was cooled to room temperature and filtered through Celite-bed. Filtrate was concentrated under reduced pressure to obtain crude material. This was further purified by column chromatography and the compound was eluted in 5% ethyl acetate in hexane to obtain 75.2. (0.7 g, Yield: 78.97%), MS (ES): m/z 234.9 [M+H]$^+$.

Synthesis of Compound 75.3

To a solution of 75.2 (0.7 g, 2.99 mmol, 1.0 eq) in 1,4-dioxane (15 mL) was added Bis(pinacolato)diboron (0.835 g, 3.28 mmol, 1.1 eq), and Potassium acetate (0.880 g, 8.97 mmol, 3.0 eq). The reaction mixture was degassed for 15 min under argon atmosphere, then Tris(dibenzylideneacetone)dipalladium(0) (0.190 g, 0.20 mmol, 0.07 eq) and 2-Dicyclohexylphosphino-2',4',6'-triisopropylbiphenyl (0.142 g, 0.29 mmol, 0.1 eq) were added and again degassed for 5 min. The reaction mixture was stirred at 110° C. for 4 h. After completion of reaction, reaction mixture was cooled to room temperature, transferred into water and product was extracted with ethyl acetate. Organic layer was combined, washed with brine solution, dried over sodium sulfate and concentrated under reduced pressure to obtain crude material. This was further purified by combi flash using 4% ethyl acetate in hexane as eluant to obtain pure 75.3. (0.560 g, Yield: 66.61%). MS(ES): m/z 281.1 [M+H]$^+$.

Synthesis of Compound 75.5

Argon was purged for 15 min through a stirred solution of 75.3 (0.560 g, 1.99 mmol, 1.0 eq), and 75.4 (0.416 g, 2.58 mmol, 1.3 eq) in dimethylformamide (8 mL). Bis(triphenylphosphine)palladium(II) dichloride (0.139 g, 0.19 mmol, 0.1 eq) was added to it and the mixture was further purged for 10 min. Reaction was stirred at 60° C. for 5 h. After completion of reaction, reaction mixture was transferred into water and product was extracted with ethyl acetate. Organic layer was combined, washed with brine solution, dried over sodium sulfate and concentrated under reduced pressure to obtain 75.5. (0.362 g, Yield: 77.25%). MS (ES): m/z 236.1 [M+H]$^+$.

Synthesis of Compound 75.6

To a solution of compound 75.5 (0.3 g, 1.27 mmol, 1.0 eq) in acetonitrile (6 ml) was added tert-Butyl nitrite (0.261 g, 2.54 mmol, 2.0 eq) and the reaction mixture was cooled to 0° C. Copper (II) bromide (0.566 g, 2.54 mmol, 2.0 eq) was added to reaction mixture and stirred at room temperature for 2 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by combi flash using 20% ethyl acetate in hexane as eluant to obtain pure 75.6. (0.150 g, Yield: 39.32%). MS(ES): m/z 299.1 [M+H]$^+$.

Synthesis of Compound 75.7

Compound was synthesized as per experimental protocol of core synthesis B to obtain 75.7. (Yield: 66.51%), MS (ES): m/z 416.17 [M+H]$^+$.

Synthesis of Compound 75.8

Compound was synthesized using general procedure A to obtain 75.8. (0.120 g, Yield: 33.80%), MS (ES): m/z 590.25 [M+H]$^+$.

Synthesis of Compound 75.9

To a solution of compound 75.8 (0.120 g, 0.20 mmol, 1.0 eq) in tetrahydrofuran (3 mL) were added N,N-Diisopropylethylamine (0.11 mL, 0.6 mmol, 3.0 eq), Trimethylaluminium (2M in hexane, 0.5 mL, 1.0 mmol, 5.0 eq) and Methylamine (2M in tetrahydrofuran, 0.3 mL, 0.6 mmol, 3.0 eq) at 0° C. Reaction mixture was stirred at 70° C. for 5 h. After completion of reaction, reaction mixture was transferred to ice cold water and product was extracted with ethyl acetate. Organic layer was combined, washed with brine solution, dried over sodium sulfate and concentrated under reduced pressure to obtain crude material. This was further purified by 2.5% methanol in dichloromethane to obtain 75.9. (0.060 g, Yield: 50.08%), MS (ES): m/z 589.2 [M+H]+.

Synthesis of Compound 75.10

Compound was synthesized using general procedure B to obtain 75.10. (0.033 g, Yield: 79.27%), MS (ES): m/z 409.1 [M+H]+.

Synthesis of Compound I-78

Compound was synthesized using general procedure C to obtain I-78 (0.025 g, Yield: 64.93%), MS (ES): 477.67 [M+H]+ LCMS purity: 100%, HPLC purity: 99.72%, $^1$H NMR (DMSO-$d_6$, 400 MHZ): 12.20 (s, 1H), 11.34 (s, 1H), 8.40-8.39 (d, J=4.4 Hz, 1H), 7.53 (s, 1H), 7.38-7.34 (d, J=12.6 Hz, 1H), 7.07-7.04 (d, J=11.6 Hz, 2H), 6.82 (bs, 2H), 4.36-4.32 (m, 1H), 3.84 (bs, 3H), 2.83-2.82 (d, J=4 Hz, 3H), 2.23 (bs, 1H), 1.48-1.44 (t, J=6.8 Hz, 3H), 1.22 (bs, 1H), 0.95-0.85 (m, 4H).

Example 76: 7-(cyclopropanecarboxamido)-2-(3-(5,6-dihydro-8H-imidazo[2,1-c][1,4]oxazin-2-yl)-2-fluorophenyl)-N-methyl-1H-pyrrolo[2,3-c]pyridine-4-carboxamide (I-79)

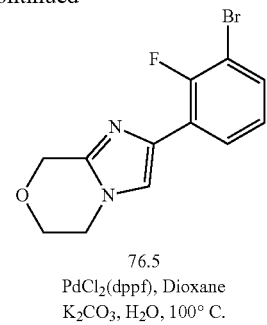

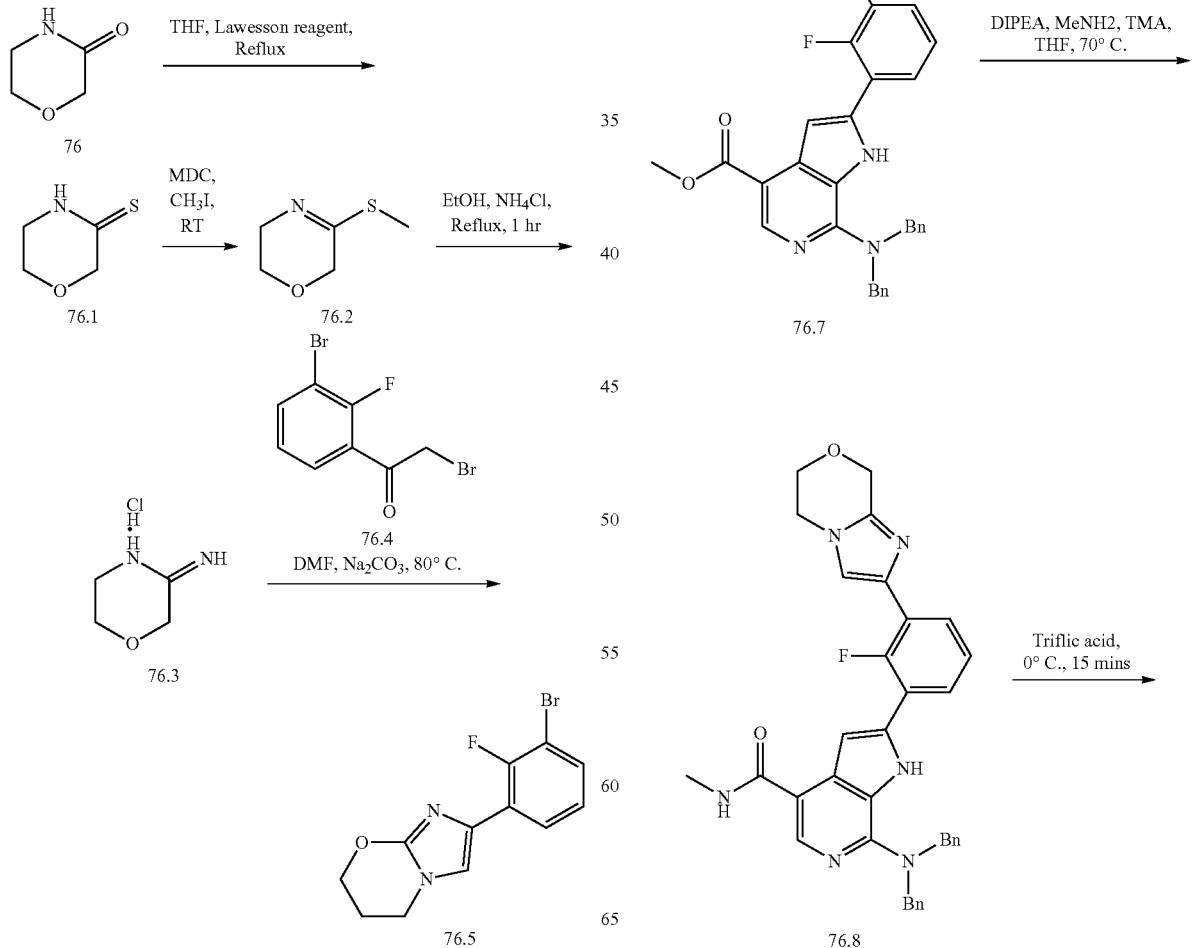

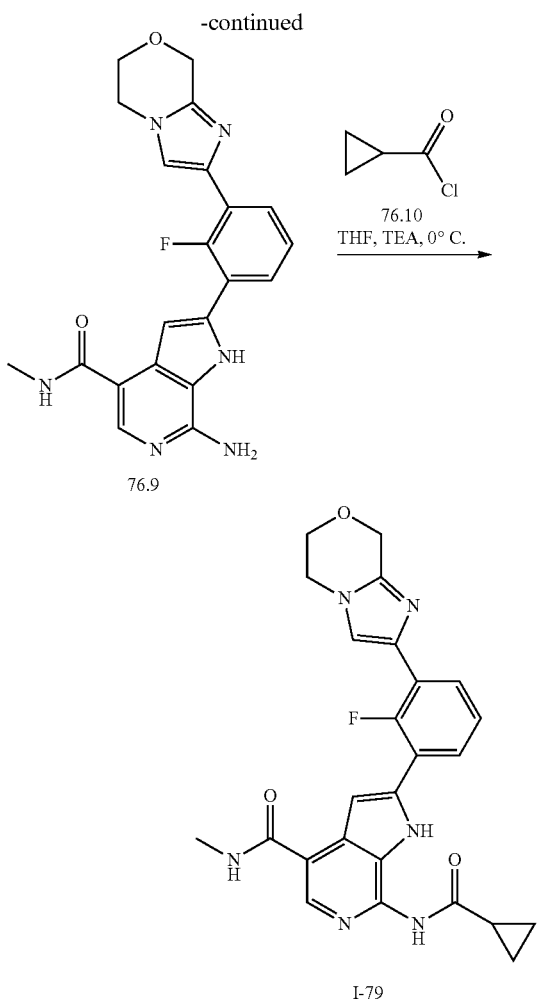

Synthesis of Compound 76.1

To the solution of compound 76 (1.8 g, 17.82 mmol, 1.0 eq) in tetrahydrofuran (30 mL) was added Lawesson's reagent (3.59 g, 8.91 mmol, 0.5 eq) Reaction mixture was refluxed for 16 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by column chromatography and the compound was eluted in 15% ethyl acetate in hexane to obtain 76.1. (1.0 g, Yield: 47.94%). MS(ES): m/z 119.02 [M+H]+.

Synthesis of Compound 76.2

To the solution of compound 76.1 (1.5 g, 12.71 mmol, 1.0 eq) in dichloromethane (25 mL) was added methyl iodide (1.9 g, 13.98 mmol, 1.1 eq). Reaction mixture was stirred at room temperature for 15 h. After completion of reaction, reaction mixture was filtered and solid was washed with dichloromethane. The obtained solid material was dissolved with 50% aqueous potassium carbonate solution (15 mL) and extracted with dichloromethane. Organic layer was combined, dried over sodium sulfate and concentrated under reduced pressure to obtain 76.2. (0.8 g, Yield: 47.63%). MS(ES): m/z 131.04 [M+H]+.

Synthesis of Compound 76.3

To the solution of compound 76.2 (0.8 g, 6.15 mmol, 1.0 eq) in ethanol (15 mL) was added ammonium chloride (0.332 g, 6.15 mmol, 1.0 eq). Reaction mixture was refluxed for 1 h. After completion of reaction, reaction mixture was filtered through millipore and concentrated under reduced pressure to obtain 76.3. (0.7 g, Yield: 84.05%). MS(ES): m/z 136.04 [M+H]+.

Synthesis of Compound 76.5

To the solution of compound 76.3 (0.3 g, 2.22 mmol, 1.0 eq) and 76.4 (0.654 g, 2.22 mmol, 1.0 eq) in Dimethylformamide (10 mL) was added Sodium carbonate (1.1 g, 11.1 mmol, 5.0 eq). Reaction mixture was heated at 80° C. for 16 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by column chromatography and the compound was eluted in 20% ethyl acetate in hexane to obtain 76.5. (0.190 g, Yield: 29.11%). MS(ES): m/z 297.9 [M+H]+.

Synthesis of Compound 76.6

Compound was synthesized as per experimental protocol of core synthesis B to obtain 76.6. (Yield: 66.51%), MS (ES): m/z 416.17 [M+H]+.

Synthesis of Compound 76.7. Compound was synthesized using general procedure A to obtain 76.7. (0.170 g, Yield: 48.05%), MS (ES): m/z 588.24 [M+H]+

Synthesis of Compound 76.8

To a solution of compound 76.7 (0.170 g, 0.28 mmol, 1.0 eq) in tetrahydrofuran (3 mL) were added N,N-Diisopropylethylamine (0.15 mL, 0.84 mmol, 3.0 eq), Trimethylaluminium (2M in hexane, 0.7 mL, 1.4 mmol, 5.0 eq) and Methylamine (2M in tetrahydrofuran, 0.42 mL, 0.84 mmol, 3.0 eq) at 0° C. Reaction mixture was stirred at 70° C. for 5 h. After completion of reaction, reaction mixture was transferred to ice cold water and product was extracted with ethyl acetate. Organic layer was combined, washed with brine solution, dried over sodium sulfate and concentrated under reduced pressure to obtain crude material. This was further purified by 2.5% methanol in dichloromethane to obtain 76.8. (0.120 g, Yield: 70.71%), MS (ES): m/z 587.25 [M+H]+.

Synthesis of Compound 76.9

Compound was synthesized using general procedure B to obtain 76.9. (0.070 g, Yield: 84.20%), MS (ES): m/z 407.16 [M+H]+.

Synthesis of Compound I-79

Compound was synthesized using general procedure C to obtain I-79 (0.028 g, Yield: 34.26%), MS (ES): 475.66 [M+H]+ LCMS purity: 98.48%, HPLC purity: 98.20%, 1H NMR (DMSO-d$_6$, 400 MHZ): 11.97 (s, 1H), 11.29 (s, 1H), 8.40-8.39 (d, J=4.4 Hz, 1H), 8.31 (s, 1H), 8.09-8.05 (t, J=7.2 Hz, 1H), 7.76-7.73 (t, J=7.2 Hz, 1H), 7.66-7.65 (d, J=4.4 Hz, 1H), 7.47 (s, 1H), 7.41-7.37 (d, J=8 Hz, 1H), 4.82 (s, 1H), 4.13-4.05 (m, 4H), 2.85-2.84 (d, J=4.4 Hz, 3H), 1.54 (bs, 2H), 1.00-0.94 (m, 4H).
Example 77: 7-(cyclopropanecarboxamido)-N-methyl-2-(1'-methyl-1'H-[1,4'-bipyrazol]-3-yl)-1H-pyrrolo[2,3-c]pyridine-4-carboxamide (I-80)
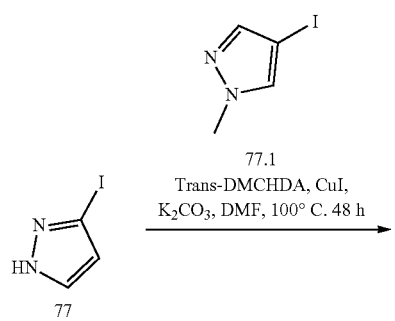
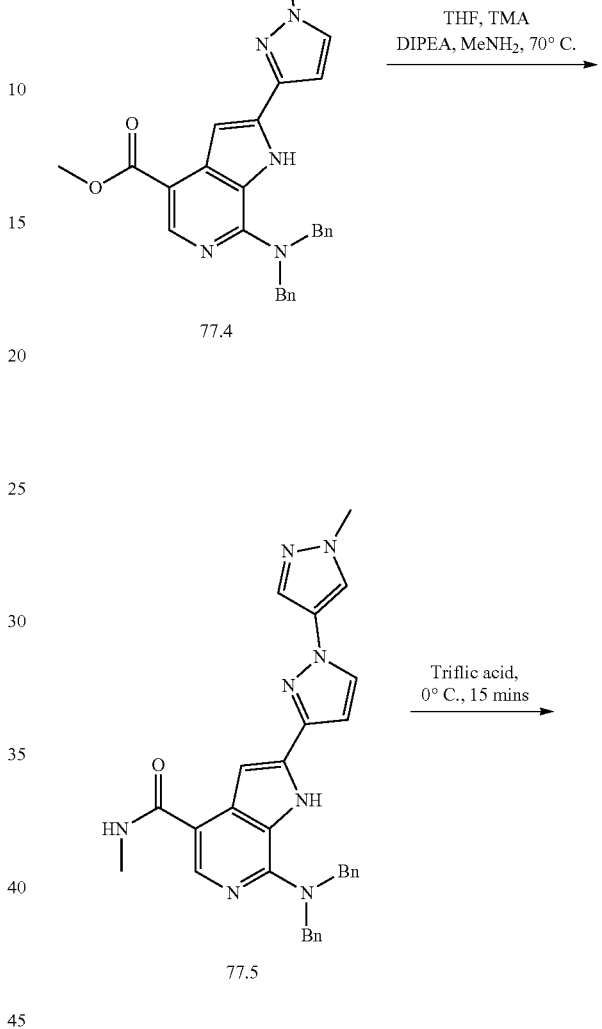
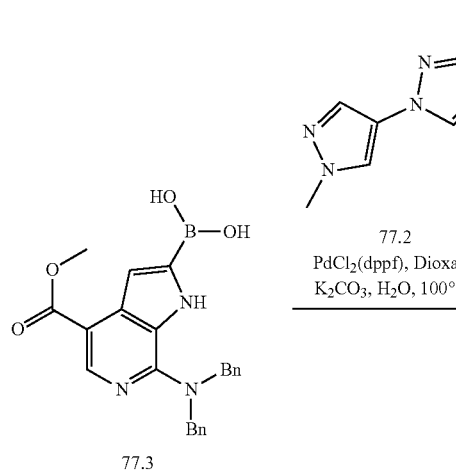

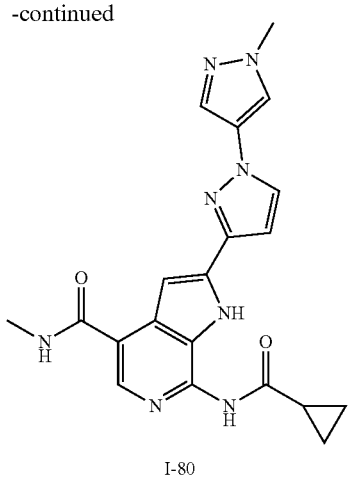

I-80

Synthesis of Compound 77.2

To a solution of 77 (3.0 g, 15.46 mmol, 1.0 eq) and 77.1 (3.8 g, 18.55 mmol, 1.2 eq) in 1,4-dioxane (60 mL) was added potassium carbonate (4.2 g, 30.92 mmol, 2.0 eq) and the reaction mixture was degassed with argon for 15 min. Copper iodide (0.588 g, 3.09 mmol, 0.2 eq) and trans-N,N'-Dimethylcyclohexane-1,2-diamine (0.878 g, 6.18 mmol, 0.4 eq) were added and reaction mixture again was degassed with argon for 5 min followed by heating at 100° C. for 48 h. After completion of reaction, reaction mixture was cooled to room temperature, transferred into water and product was extracted with ethyl acetate. Organic layer was combined, washed with brine solution, dried over sodium sulfate and concentrated under reduced pressure to obtain crude material. This was further purified by column chromatography and compound was eluted in 1.2% methanol in dichloromethane to obtain pure 77.2. (0.859 g, Yield: 20.27%). MS(ES): m/z 274.9 [M+H]$^+$.

Synthesis of Compound 77.3

Compound was synthesized as per experimental protocol of core synthesis B to obtain 77.3. (Yield: 66.51%), MS (ES): m/z 416.17 [M+H]$^+$.

Synthesis of Compound 77.4

Compound was synthesized using general procedure A to obtain 77.4. (0.190 g, Yield: 50.81%), MS (ES): m/z 518.23 [M+H]$^+$.

Synthesis of Compound 77.5

To a solution of compound 77.4 (0.190 g, 0.36 mmol, 1.0 eq) in tetrahydrofuran (2 mL) were added N,N-Diisopropylethylamine (0.19 mL, 1.08 mmol, 3.0 eq), Trimethylaluminium (2M in hexane, 0.9 mL, 1.8 mmol, 5.0 eq) and Methylamine (2M in tetrahydrofuran, 0.54 mL, 1.08 mmol, 3.0 eq) at 0° C. Reaction mixture was stirred at 70° C. for 5 h. After completion of reaction, reaction mixture was transferred to ice cold water and product was extracted with ethyl acetate. Organic layer was combined, washed with brine solution, dried over sodium sulfate and concentrated under reduced pressure to obtain crude material. This was further purified by 2.5% methanol in dichloromethane to obtain 77.5. (0.148 g, Yield: 78.07%), MS (ES): m/z 517.24 [M+H]$^+$.

Synthesis of Compound 77.6

Compound was synthesized using general procedure B to obtain 77.6. (0.052 g, Yield: 53.96%), MS (ES): m/z 337.15 [M+H]$^+$.

Synthesis of Compound I-80

Compound was synthesized using general procedure C to obtain I-80 (0.022 g, Yield: 35.19%), MS (ES): 405.67 [M+H]$^+$ LCMS purity: 97.82%, HPLC purity: 96.75%, $^1$H NMR (DMSO-d$_6$, 400 MHZ): 12.01 (s, 1H), 11.51 (s, 1H), 8.41-8.40 (d, J=4 Hz, 1H), 8.31 (bs, 1H), 8.27 (bs, 2H), 7.92 (s, 1H), 7.39 (s, 1H), 7.13 (bs, 1H), 3.92 (bs, 3H), 2.85-2.86 (d, J=4.4 Hz, 3H), 2.28 (s, 1H), 1.02-0.92 (m, 4H).

Example 78: 7-(cyclopropanecarboxamido)-2-(2-fluoro-3-(2-methyloxazol-5-yl)phenyl)-N-methyl-1H-pyrrolo[2,3-c]pyridine-4-carboxamide (I-81)

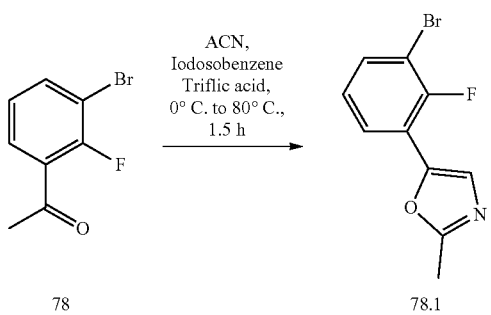

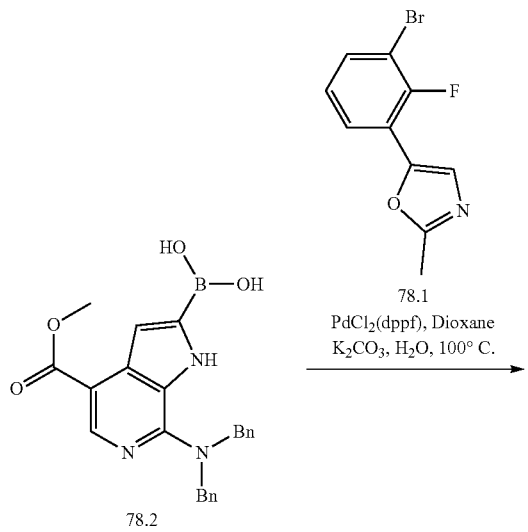

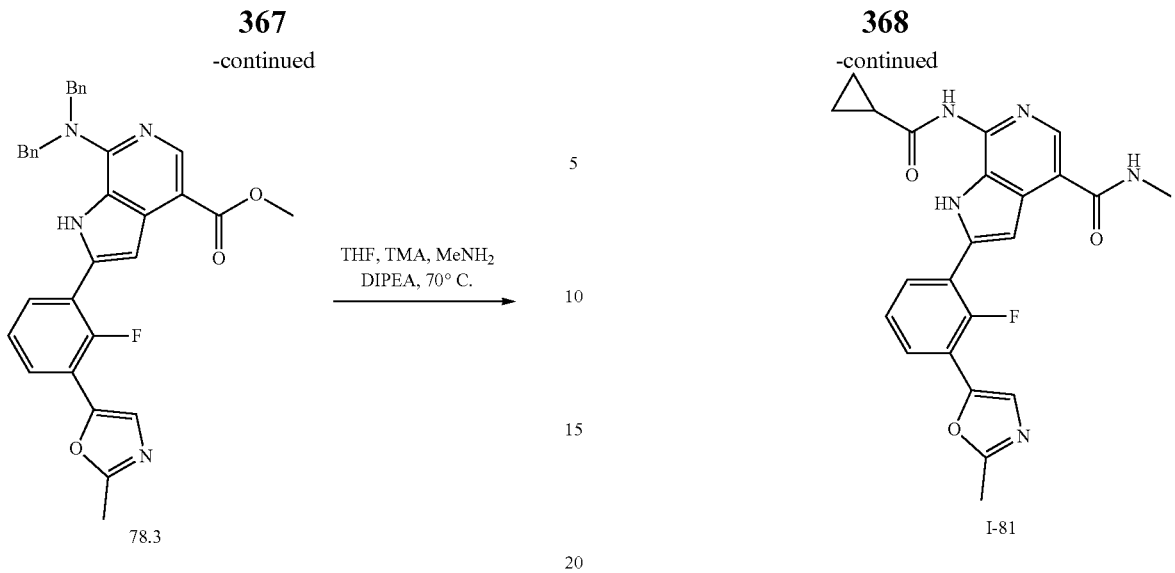

Synthesis of Compound 78.1

To the solution of Iodosobenzene (0.765 g, 3.48 mmol, 1.5 eq) and triflic acid (0.5 g, 2.31 mmol, 3.0 eq) in Acetonitrile (10 mL) was added 78 (1.0 g, 6.96 mmol, 1.0 eq) at 0° C. Reaction mixture was stirred at 80° C. for 1.5 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by 15% ethyl acetate in hexane to obtain 78.1. (0.2 g, Yield: 33.90%), MS (ES): m/z 254.9 [M+H]$^+$.

Synthesis of Compound 78.2

Compound was synthesized as per experimental protocol of core synthesis B to obtain 78.2. (Yield: 66.51%), MS (ES): m/z 416.17 [M+H]$^+$.

Synthesis of Compound 78.3

Compound was synthesized using general procedure A to obtain 78.3. (0.180 g, Yield: 45.58%), MS (ES): m/z 546.21 [M+H]$^+$.

Synthesis of Compound 78.4

To a solution of compound 78.3 (0.180 g, 0.32 mmol, 1.0 eq) in tetrahydrofuran (3 mL) were added N,N-Diisopropylethylamine (0.17 mL, 0.96 mmol, 3.0 eq), Trimethylaluminium (2M in hexane, 0.8 mL, 1.6 mmol, 5.0 eq) and Methylamine (2M in tetrahydrofuran, 0.48 mL, 0.96 mmol, 3.0 eq) at 0° C. Reaction mixture was stirred at 70° C. for 5 h. After completion of reaction, reaction mixture was transferred into ice cold water and product was extracted with ethyl acetate. Organic layer was combined, washed with brine solution, dried over sodium sulfate and concentrated under reduced pressure to obtain crude material. This was further purified by 2.5% methanol in dichloromethane to obtain 78.4. (0.110 g, Yield: 61.22%), MS (ES): m/z 546.23 [M+H]$^+$.

Synthesis of Compound 78.5

Compound was synthesized using general procedure B to obtain 78.5. (0.055 g, Yield: 74.67%), MS (ES): m/z 366.13 [M+H]$^+$.

Synthesis of Compound I-81
Compound was synthesized using general procedure C to obtain I-81 (0.025 g, Yield: 38.32%), MS (ES): 434.67 [M+H]$^+$ LCMS purity: 96.41%, HPLC purity: 95.31%, $^1$H NMR (DMSO-d$_6$, 400 MHZ): 12.01 (s, 1H), 11.29 (s, 1H), 8.42-8.41 (d, J=4.4 Hz, 1H), 8.34 (s, 1H), 7.94-7.91 (t, J=7.2 Hz, 1H), 7.84-7.80 (t, J=7.2 Hz, 1H), 7.56-7.55 (d, J=3.6 Hz, 1H), 7.50 (s, 1H), 7.08 (bs, 1H), 2.89-2.88 (d, J=4.4 Hz, 3H), 2.54 (s, 3H), 1.58 (bs, 1H), 0.95-0.86 (m, 4H).
Example 79: 7-(cyclopropanecarboxamido)-2-(2-cyclopropoxy-6-fluoro-4-(2H-1,2,3-triazol-2-yl)phenyl)-N-methyl-1H-pyrrolo[2,3-c]pyridine-4-carboxamide (I-82)
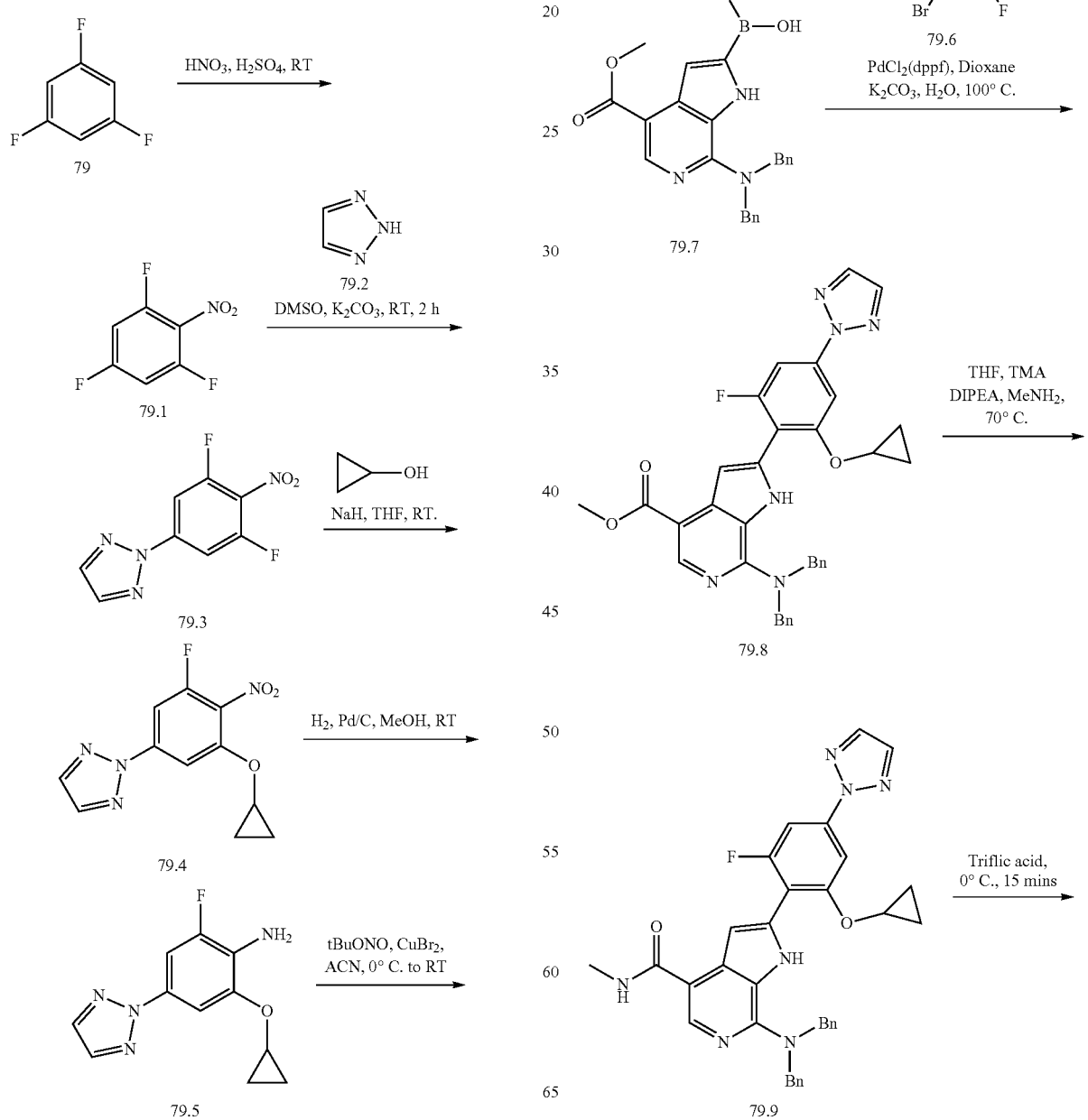

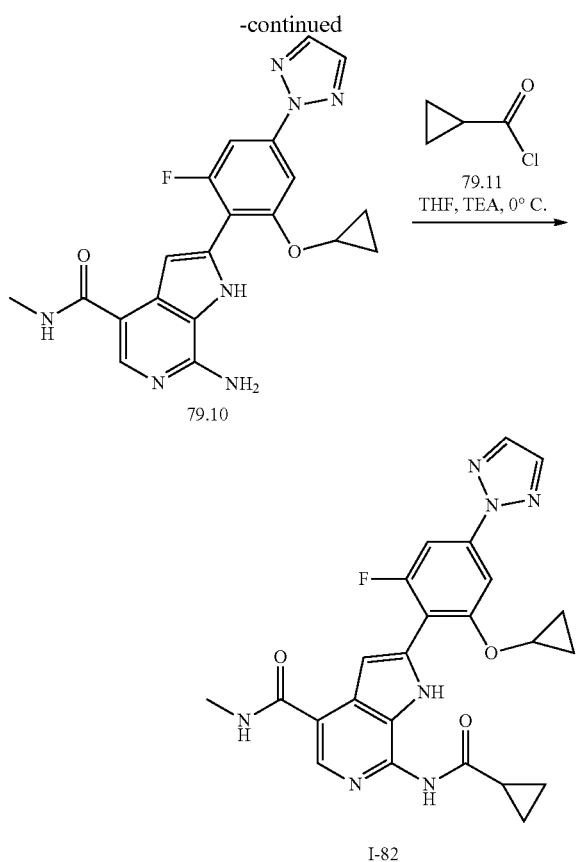

Synthesis of Compound 79.1

To a solution of 79 (5.0 g, 37.87 mmol, 1.5 eq) in sulfuric acid (17 mL) was added nitric acid (23 mL) dropwise at 0° C. Reaction mixture was stirred at 0° C. for 2 h. After completion of reaction, reaction mixture was transferred to ice and product was extracted with ethyl acetate. Organic layer was combined, dried over sodium sulfate and concentrated under reduced pressure to obtain 79.1. (3.2 g, Yield: 47.74%), MS (ES): m/z 178.01 [M+H]$^+$.

Synthesis of Compound 79.3

To a solution of 79.1 (3.2 g, 18.07 mmol, 1.0 eq) and 79.2 (1.3 g, 19.87 mmol, 1.1 eq) in dimethyl sulphoxide (35 mL) was added potassium carbonate (4.9 g, 36.14 mmol, 2.0 eq) and reaction mixture was stirred at 90° C. for 1 h. After completion of reaction, reaction mixture was cooled to room temperature, transferred into ice cold water and product was extracted with ethyl acetate. Organic layer was combined, dried over sodium sulfate and concentrated under reduced pressure to obtain 79.3 (2.05 g, Yield: 50.15%). MS(ES): m/z 227.03 [M+H]$^+$.

Synthesis of Compound 79.4

To a solution of cyclopropanol (0.526 g, 9.07 mmol, 1.0 eq) in tetrahydrofuran (40 mL) was added Sodium hydride (60%) (1.0 g, 45.35 mmol, 5.0 eq) slowly at 0° C. under nitrogen atmosphere. After 10 min, 79.3 (2.05 g, 9.07 mmol, 1.0 eq) was added to the reaction mixture which was stirred at room temperature for 2 h. After completion of reaction, reaction mixture was transferred into ice cold water and product was extracted with ethyl acetate. Organic layer was combined, dried over sodium sulfate and concentrated under reduced pressure to obtain crude material. This was further purified by column chromatography and the compound was eluted in 10% ethyl acetate in hexane to obtain 79.4. (1.72 g, Yield: 71.81%). MS(ES): m/z 265.07 [M+H]$^+$.

Synthesis of Compound 79.5

To a solution of 79.4 (1.72 g, 6.51 mmol, 1.0 eq) in methanol (25 mL), was added 10% palladium on charcoal (0.8 g). Hydrogen was purged through reaction mixture for 4 h at room temperature. After completion of reaction, reaction mixture was filtered through Celite-bed and washed with methanol. Filtrate was concentrated under reduced pressure to obtain crude material. This was further purified by trituration with n-pentane to obtain pure 79.5. (0.4 g, Yield: 26.23%). MS (ES): m/z 235.10 [M+H]$^+$.

Synthesis of Compound 79.6

To a solution of 79.5 (0.5 g, 2.13 mmol, 1.0 eq) in Acetonitrile (5 mL) was added Copper (II) bromide (0.9 g, 4.04 mmol, 1.9 eq) at 0° C. Then tert-Butyl nitrite (0.5 mL, 4.26 mmol, 2.0 eq) was added dropwise to reaction mixture at 0° C. and stirred at room temperature for 1 h. After completion of reaction, reaction mixture was transferred into water and product was extracted with dichloromethane. Organic layer was combined, washed with brine solution, dried over sodium sulfate and concentrated under reduced pressure to obtain crude material. This was further purified by column chromatography and the compound was eluted in 3% ethyl acetate in hexane to obtain 79.6. (0.280 g, Yield: 44.00%), MS (ES): m/z 298.9 [M+H]$^+$.

Synthesis of Compound 79.7

Compound was synthesized as per experimental protocol of core synthesis B to obtain 79.7. (Yield: 66.51%), MS (ES): m/z 416.17 [M+H]$^+$.

Synthesis of Compound 79.8

Compound was synthesized using general procedure A to obtain 79.8. (0.195 g, Yield: 34.39%), MS (ES): m/z 589.2 [M+H]$^+$.

Synthesis of Compound 79.9

To a solution of compound 79.8 (0.195 g, 0.33 mmol, 1.0 eq) in tetrahydrofuran (3 mL) were added N,N-Diisopropylethylamine (0.18 mL, 0.99 mmol, 3.0 eq), Trimethylaluminium (2M in hexane, 0.82 mL, 1.65 mmol, 5.0 eq) and Methylamine (2M in tetrahydrofuran, 0.49 mL, 0.99 mmol, 3.0 eq) at 0° C. Reaction mixture was stirred at 70° C. for 5 h. After completion of reaction, reaction mixture was transferred to ice cold water and product was extracted with ethyl acetate. Organic layer was combined, washed with brine solution, dried over sodium sulfate and concentrated under reduced pressure to obtain crude material. This was further purified by 2.5% methanol in dichloromethane to obtain 79.9. (0.110 g, Yield: 56.50%), MS (ES): m/z 588.25 [M+H]$^+$.

373

Synthesis of Compound 79.10

Compound was synthesized using general procedure B to obtain 79.10. (0.045 g, Yield: 59.01%), MS (ES): m/z 408.15 [M+H]$^+$.

Synthesis of Compound I-82

Compound was synthesized using general procedure C to obtain I-82 (0.024 g, Yield: 45.70%), MS (ES): 476.41 [M+H]$^+$ LCMS purity: 96.69%, HPLC purity: 97.28%, $^1$H NMR (DMSO-d$_6$, 400 MHZ): 11.26 (s, 1H), 10.68 (s, 1H), 8.54-8.53 (d, J=4.4 Hz, 1H), 8.10 (s, 1H), 7.70-7.68 (d, J=6.8 Hz, 1H), 7.24-7.22 (d, J=7.6 Hz, 1H), 7.11-7.09 (d, J=9.2 Hz, 2H), 6.81 (s, 1H), 3.98 (bs, 3H), 2.81-2.80 (d, J=4.4 Hz, 3H), 1.99 (bs, 1H), 1.77-1.74 (t, J=6.8 Hz, 2H), 1.55 (bs, 1H), 1.23 (bs, 3H).

Example 80: 7-(cyclopropanecarboxamido)-2-(2-(3,3-difluoropyrrolidin-1-yl)-6-fluoro-4-(1-methyl-1H-imidazol-2-yl)phenyl)-N-methyl-1H-pyrrolo[2,3-c]pyridine-4-carboxamide (I-83)

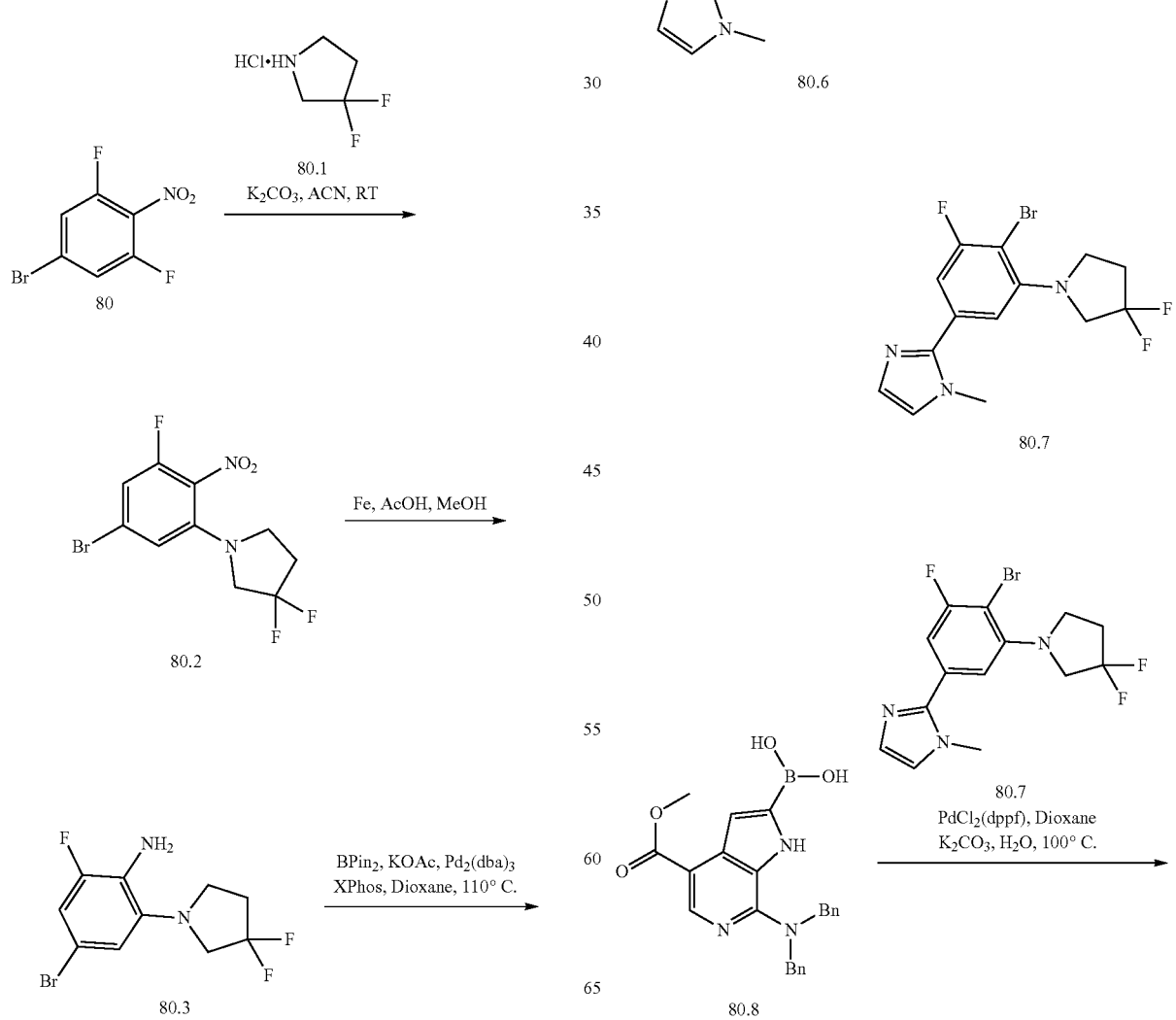

-continued

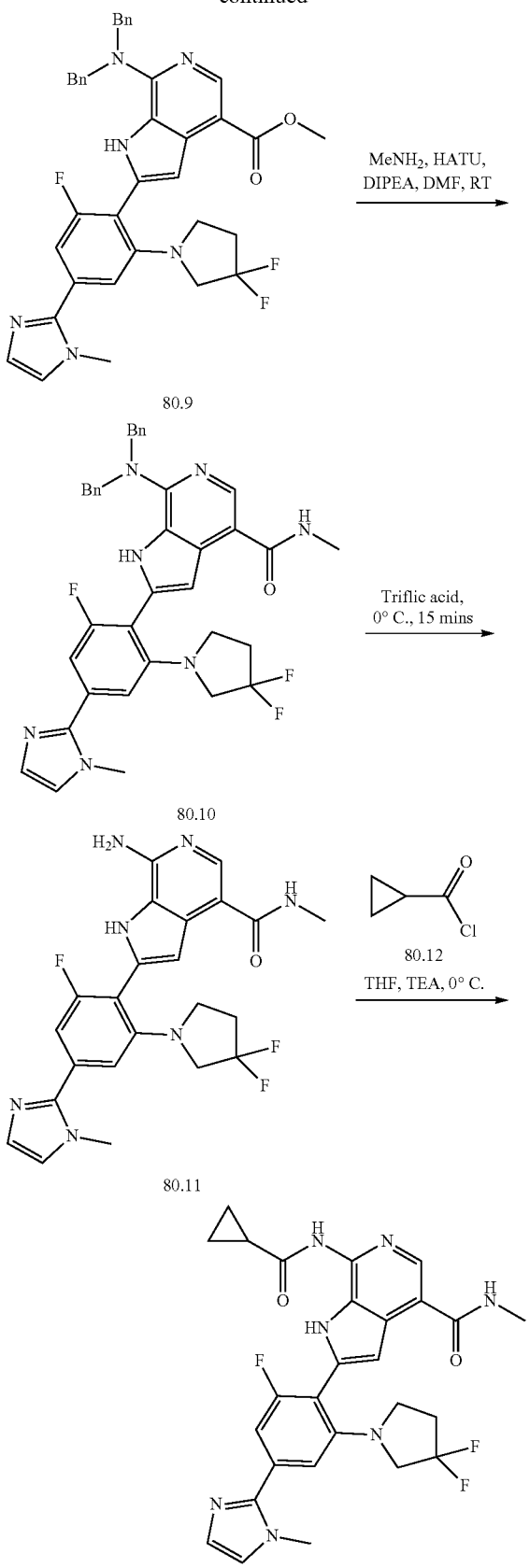

Synthesis of Compound 80.2

To a solution of 80 (10 g, 42.01 mmol, 1.5 eq) and 80.1 (7.2 g, 50.41 mmol, 1.2 eq) in Acetonitrile (300 mL) was added Potassium carbonate (14.0 g, 105.02 mmol, 2.5 eq). Reaction mixture was stirred at room temperature for 16 h. After completion, reaction mixture was transferred into water and product was extracted with ethyl acetate. Organic layer was combined, washed with brine solution, dried over sodium sulfate and concentrated under reduced pressure to obtain crude material. This was further purified by column chromatography and the compound was eluted in 2% ethyl acetate in hexane to obtain 80.2. (6 g, Yield: 43.92%), MS (ES): m/z 325.9 [M+H]$^+$.

Synthesis of Compound 80.3

To a solution of 80.2 (2.0 g, 6.15 mmol, 1.5 eq) in Acetic acid (3.5 mL, 61.5 mmol, 10.0 eq) was added Iron powder (1.7 g, 30.75 mmol, 5.0 eq). Reaction mixture was stirred at 90° C. for 30 min. After completion of reaction, reaction mixture was cooled to room temperature and filtered through Celite-bed. Filtrate was concentrated under reduced pressure to obtain crude material. This was further purified by column chromatography and the compound was eluted in 5% ethyl acetate in hexane to obtain 80.3. (1.12 g, Yield: 61.69%), MS (ES): m/z 296.0 [M+H]$^+$.

Synthesis of Compound 80.4

To a solution of 80.3 (1.12 g, 3.79 mmol, 1.0 eq) in 1,4-dioxane (22 mL) was added Bis(pinacolato)diboron (1.0 g, 4.16 mmol, 1.1 eq), and Potassium acetate (1.1 g, 11.37 mmol, 3.0 eq). The reaction mixture was degassed for 15 min under argon atmosphere, then Tris(dibenzylideneacetone)dipalladium(0) (0.237 g, 0.26 mmol, 0.07 eq) and 2-Dicyclohexylphosphino-2',4',6'-triisopropylbiphenyl (0.180 g, 0.37 mmol, 0.1 eq) were added and again degassed for 5 min. The reaction mixture was stirred at 110° C. for 4 h. After completion of reaction, reaction mixture was cooled to room temperature, transferred into water and product was extracted with ethyl acetate. Organic layer was combined, washed with brine solution, dried over sodium sulfate and concentrated under reduced pressure to obtain crude material. This was further purified by combi flash using 4% ethyl acetate in hexane as eluant to obtain pure 80.4. (0.620 g, Yield: 47.74%). MS(ES): m/z 342.1 [M+H]$^+$.

Synthesis of Compound 80.6

To a solution of 80.4 (0.5 g, 1.46 mmol, 1.0 eq) in 1,4-dioxane (5 mL) were added 80.5 (0.164 g, 1.022 mmol, 0.7 eq) and 2M Sodium carbonate solution (3.8 mL). The reaction mixture was degassed for 15 min under argon atmosphere, then [1,1'-Bis(diphenylphosphino)ferrocene]dichloropalladium(II), complex with dichloromethane (0.119 g, 0.14 mmol, 0.1 eq) was added and again degassed for 5 min. The reaction mixture was stirred at 100° C. for 1 h. After completion of reaction, reaction mixture was cooled to room temperature, transferred into water and product was extracted with ethyl acetate. Organic layer was combined, washed with brine solution, dried over sodium sulfate and concentrated under reduced pressure to obtain crude material. This was further purified by combi flash using 7% ethyl acetate in hexane as eluant to obtain pure 80.6 (0.310 g, Yield: 71.60%). MS(ES): m/z 297.13 [M+H]$^+$.

Synthesis of Compound 80.7

To a solution of 80.6 (0.260 g, 0.87 mmol, 1.0 eq) in Acetonitrile (3 mL) was added Copper (II) bromide (0.368 g, 1.65 mmol, 1.9 eq) at 0° C. Then tert-Butyl nitrite (0.20 g, 1.74 mmol, 2.0 eq) was added dropwise to reaction mixture at 0° C. and stirred for 1 h. After completion of reaction, reaction mixture was transferred into water and product was extracted with dichloromethane. Organic layer was combined, washed with brine solution, dried over sodium sulfate and concentrated under reduced pressure to obtain crude material. This was further purified by column chromatography and the compound was eluted in 3% ethyl acetate in hexane to obtain 80.7 (0.178 g, Yield: 56.32%), MS (ES): m/z 360.1 [M+H]$^+$.

Synthesis of Compound 80.8

Compound was synthesized as per experimental protocol of core synthesis B to obtain 80.8. (Yield: 66.51%), MS (ES): m/z 416.17 [M+H]$^+$.

Synthesis of Compound 80.9

Compound was synthesized using general procedure A to obtain 80.9. (0.192 g, Yield: 49.01%), MS (ES): m/z 651.27 [M+H]$^+$.

Synthesis of Compound 80.10

To a solution of compound 80.9 (0.192 g, 0.29 mmol, 1.0 eq) in tetrahydrofuran (2 mL) were added N,N-diisopropylethylamine (0.16 mL, 0.87 mmol, 3.0 eq), Trimethylaluminium (2M in hexane, 0.72 mL, 1.45 mmol, 5.0 eq) and Methylamine (2M in tetrahydrofuran, 0.43 mL, 0.87 mmol, 3.0 eq) at 0° C. Reaction mixture was stirred at 70° C. for 5 h. After completion of reaction, reaction mixture was transferred into ice cold water and product was extracted with ethyl acetate. Organic layer was combined, washed with brine solution, dried over sodium sulfate and concentrated under reduced pressure to obtain crude material. This was further purified by 2.5% methanol in dichloromethane to obtain 80.10 (0.110 g, Yield: 57.38%), MS (ES): m/z 650.28 [M+H]$^+$.

Synthesis of Compound 80.11 Compound was synthesized using general procedure B to obtain 80.11

(0.070 g, Yield: 88.07%), MS (ES): m/z 470.19 [M+H]$^+$.

Synthesis of Compound I-83

Compound was synthesized using general procedure C to obtain I-83 (0.050 g, Yield: 62.38%), MS (ES): 538.68 [M+H]$^+$ LCMS purity: 97.72%, HPLC purity: 97.02%, $^1$H NMR (DMSO-d$_6$, 400 MHZ): 11.87 (s, 1H), 11.24 (s, 1H), 8.41-8.40 (d, J=4.4 Hz, 1H), 8.34 (s, 1H), 7.36 (s, 1H), 7.27-7.24 (t, J=10.8 Hz, 1H), 7.19 (bs, 2H), 6.84 (bs, 1H), 3.87 (s, 3H), 3.28-3.27 (d, J=2.8 Hz, 3H), 2.85-2.84 (d, J=4.4 Hz, 3H), 2.43-2.35 (m, 2H), 1.24 (bs, 2H), 0.94-0.86 (m, 4H).

Example 81: 7-(cyclopropanecarboxamido)-2-(3-(8,8-dimethyl-5,6-dihydro-8H-imidazo[2,1-c][1,4]oxazin-2-yl)-2-fluorophenyl)-N-methyl-1H-pyrrolo[2,3-c]pyridine-4-carboxamide (I-84)

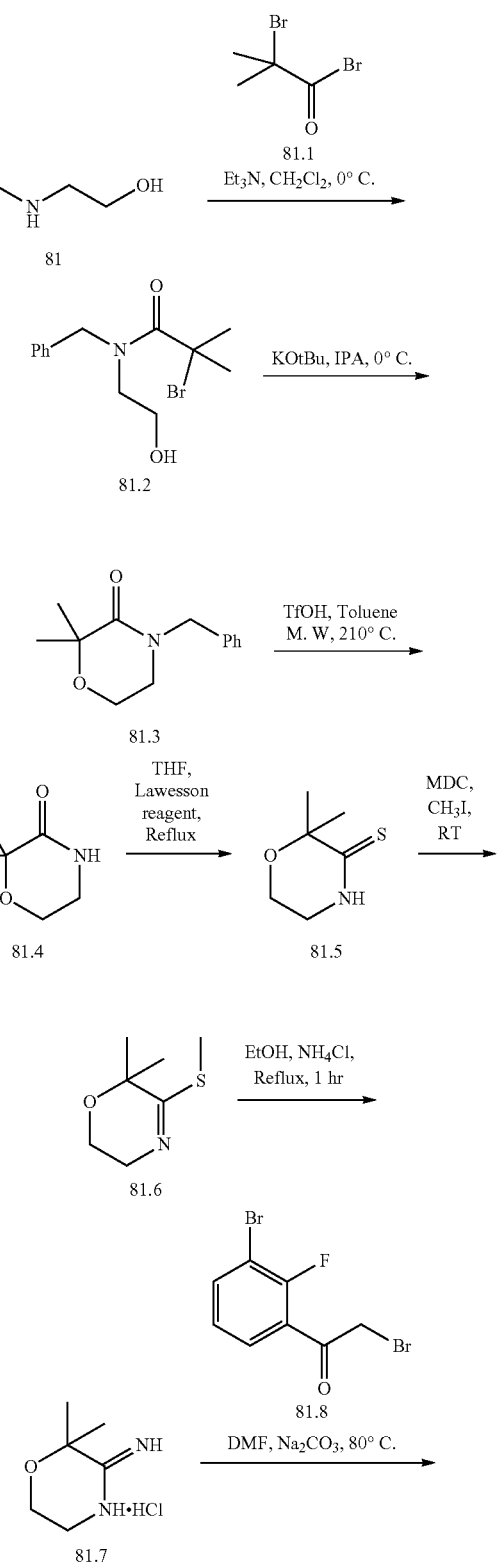

379
-continued
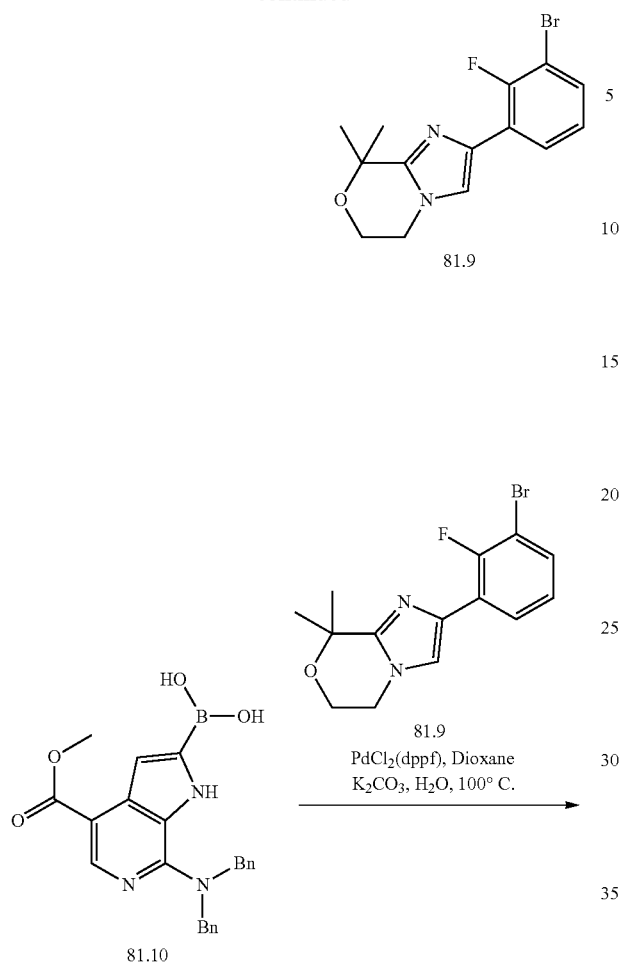
380
-continued
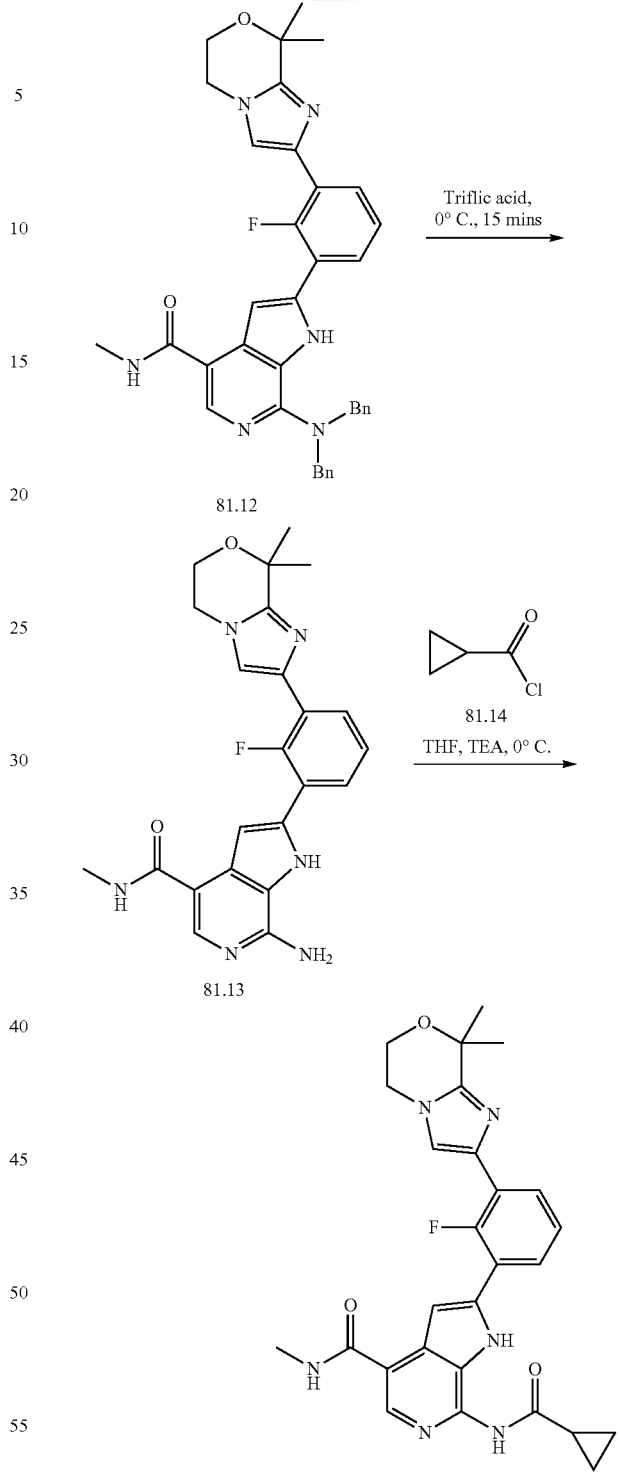
Synthesis of Compound 81.2
To the solution of compound 81 (25.0 g, 165.56 mmol, 1.0 eq) in dichloromethane (250 mL) was added triethylamine (35 mL, 248.34 mmol, 1.5 eq) at 0° C. Reaction mixture was stirred at 0° C. for 15 min. Then compound 81.1 (37.9 g, 165.56 mmol, 1.0 eq) was added dropwise at 0° C. and reaction mixture was stirred at 0° C. for 14 h. After completion of reaction, reaction mixture was transferred into water and product was extracted with dichloromethane. Organic layer was combined, washed with brine solution, dried over sodium sulfate and concentrated under reduced pressure to obtain crude material. This was further purified by column chromatography and the compound was eluted in 27% ethyl acetate in hexane to obtain 81.2. (10.0 g, Yield: 20.15%). MS(ES): m/z 301.05 $[M+H]^+$.

Synthesis of Compound 81.3

To the solution of compound 81.2 (25.0 g, 83.33 mmol, 1.0 eq) in Isopropyl alcohol (250 mL) was added Potassium tert-butoxide solution (1M in tetrahydrofuran, 249 mL, 249.99 mmol, 3.0 eq) at 0° C. Reaction mixture was stirred at 0° C. for 30 min. After completion of reaction, reaction mixture was transferred into water and product was extracted with ethyl acetate. Organic layer was combined, washed with brine solution, dried over sodium sulfate and concentrated under reduced pressure to obtain crude material. This was further purified by column chromatography and the compound was eluted in 25% ethyl acetate in hexane to obtain 81.3 (8.0 g, Yield: 43.81%). MS(ES): m/z 220.13 $[M+H]^+$.

Synthesis of Compound 81.4

To the solution of compound 81.3 (8.0 g, 36.52 mmol, 1.0 eq) in toluene (80 mL) was added Triflic acid (12.8 mL, 146.08 mmol, 4.0 eq). Reaction mixture was irradiated at 210° C. in microwave for 15 min. After completion of reaction, reaction mixture was neutralized with methanolic ammonia and concentrated to obtain crude material which was purified by column chromatography and the compound was eluted in 2.0% methanol in dichloromethane to obtain 81.4. (2.0 g, Yield: 42.44%). MS(ES): m/z 130.08 $[M+H]^+$.

Synthesis of Compound 81.5

To the solution of compound 81.4 (1.0 g, 7.75 mmol, 1.0 eq) in tetrahydrofuran (30 mL) was added Lawesson's reagent (1.56 g, 3.87 mmol, 0.5 eq). Reaction mixture was refluxed at 70° C. for 16 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by column chromatography and the compound was eluted in 15% ethyl acetate in hexane to obtain 81.5. (0.640 g, Yield: 56.92%). MS(ES): m/z 146.06 $[M+H]^+$.

Synthesis of Compound 81.6

To the solution of compound 81.5 (0.640 g, 4.41 mmol, 1.0 eq) in dichloromethane (15 mL) was added methyl iodide (0.688 g, 4.85 mmol, 1.1 eq). Reaction mixture was stirred at room temperature for 15 h. After completion of reaction, reaction mixture was filtered and solid was washed with dichloromethane. The obtained solid material was dissolved with 50% aqueous potassium carbonate solution (15 mL) and extracted with dichloromethane. Organic layer was combined, dried over sodium sulfate and concentrated under reduced pressure to obtain 81.6 (0.280 g, Yield: 39.90%). MS(ES): m/z 160.08 $[M+H]^+$.

Synthesis of Compound 81.7

To the solution of compound 81.6 (0.280 g, 1.76 mmol, 1.0 eq) in ethanol (9 mL) was added ammonium chloride (0.095 g, 1.76 mmol, 1.0 eq). Reaction mixture was refluxed for 1 h. After completion of reaction, reaction mixture was filtered through millipore and concentrated under reduced pressure to obtain 81.7 (0.265 g, Yield: 91.55%). MS(ES): m/z 165.07 $[M+H]^+$.

Synthesis of Compound 81.9

To the solution of compound 81.7 (0.265 g, 1.61 mmol, 1.0 eq) and 81.8 (0.474 g, 1.61 mmol, 1.0 eq) in Dimethylformamide (15 mL) was added Sodium carbonate (0.853 g, 8.05 mmol, 5.0 eq). Reaction mixture was heated at 80° C. for 16 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by column chromatography and the compound was eluted in 20% ethyl acetate in hexane to obtain 81.9. (0.2 g, Yield: 38.21%). MS(ES): m/z 324.03 $[M+H]^+$.

Synthesis of Compound 81.10

Compound was synthesized as per experimental protocol of core synthesis B to obtain 81.10 (Yield: 66.51%), MS (ES): m/z 416.17 $[M+H]^+$.

Synthesis of Compound 81.11

Compound was synthesized using general procedure A to obtain 81.11 (0.250 g, Yield: 56.20%), MS (ES): m/z 616.27 $[M+H]^+$.

Synthesis of Compound 81.12

To a solution of compound 81.11 (0.250 g, 0.40 mmol, 1.0 eq) in tetrahydrofuran (4 mL) were added N,N-Diisopropylethylamine (0.22 mL, 1.2 mmol, 3.0 eq), Trimethylaluminium (2M in hexane, 1.0 mL, 2.0 mmol, 5.0 eq) and Methylamine (2M in tetrahydrofuran, 0.6 mL, 1.2 mmol, 3.0 eq) at 0° C. Reaction mixture was stirred at 70° C. for 5 h. After completion of reaction, reaction mixture was transferred to ice cold water and product was extracted with ethyl acetate. Organic layer was combined, washed with brine solution, dried over sodium sulfate and concentrated under reduced pressure to obtain crude material. This was further purified by 2.5% methanol in dichloromethane to obtain 81.12 (0.180 g, Yield: 72.12%), MS (ES): m/z 614.28 $[M+H]^+$.

Synthesis of Compound 81.13

Compound was synthesized using general procedure B to obtain 81.13 (0.096 g, Yield: 75.46%), MS (ES): m/z 435.19 $[M+H]^+$.

Synthesis of Compound I-84

Compound was synthesized using general procedure C to obtain I-84 (0.050 g, Yield: 45.03%), MS (ES): 503.46 $[M+H]^+$ LCMS purity: 100%, HPLC purity: 97.20%, $^1$H NMR (DMSO-$d_6$, 400 MHZ): 11.98 (s, 1H), 11.30 (s, 1H), 8.40-8.39 (d, J=4 Hz, 1H), 8.33 (s, 1H), 8.12-8.08 (t, J=6.8

Hz, 1H), 7.78-7.74 (m, 1H), 7.60-7.59 (d, J=4.4 Hz, 1H), 7.49 (s, 1H), 7.42-7.38 (d, J=7.6 Hz, 1H), 4.16-4.01 (m, 4H), 2.87-2.86 (d, J=4.4 Hz, 3H), 2.27 (bs, 1H), 1.57 (s, 6H), 0.90-0.80 (m, 4H).

Example 82: 7-(cyclopropanecarboxamido)-2-(2-fluoro-3-((tetrahydro-2H-pyran-4-yl)oxy)phenyl)-N-methyl-1H-pyrrolo[2,3-c]pyridine-4-carboxamide (I-85)

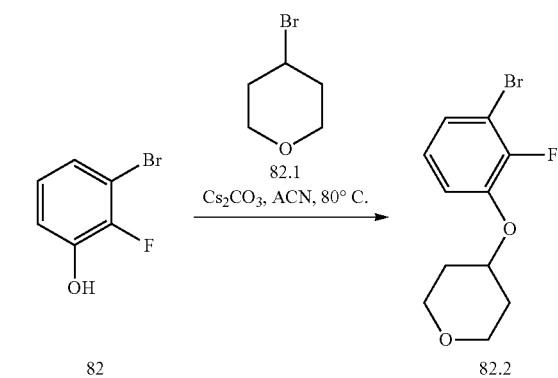

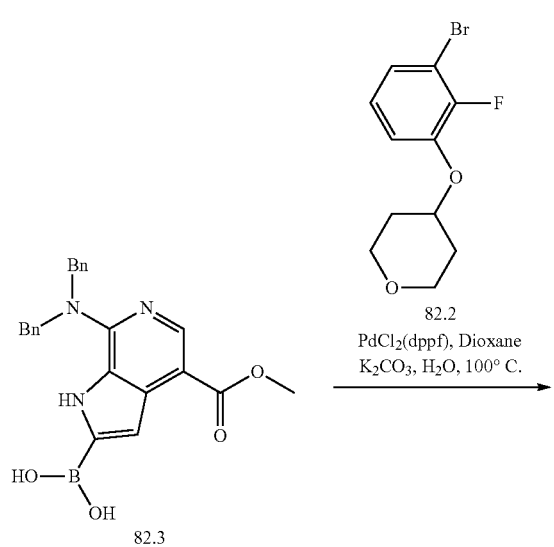

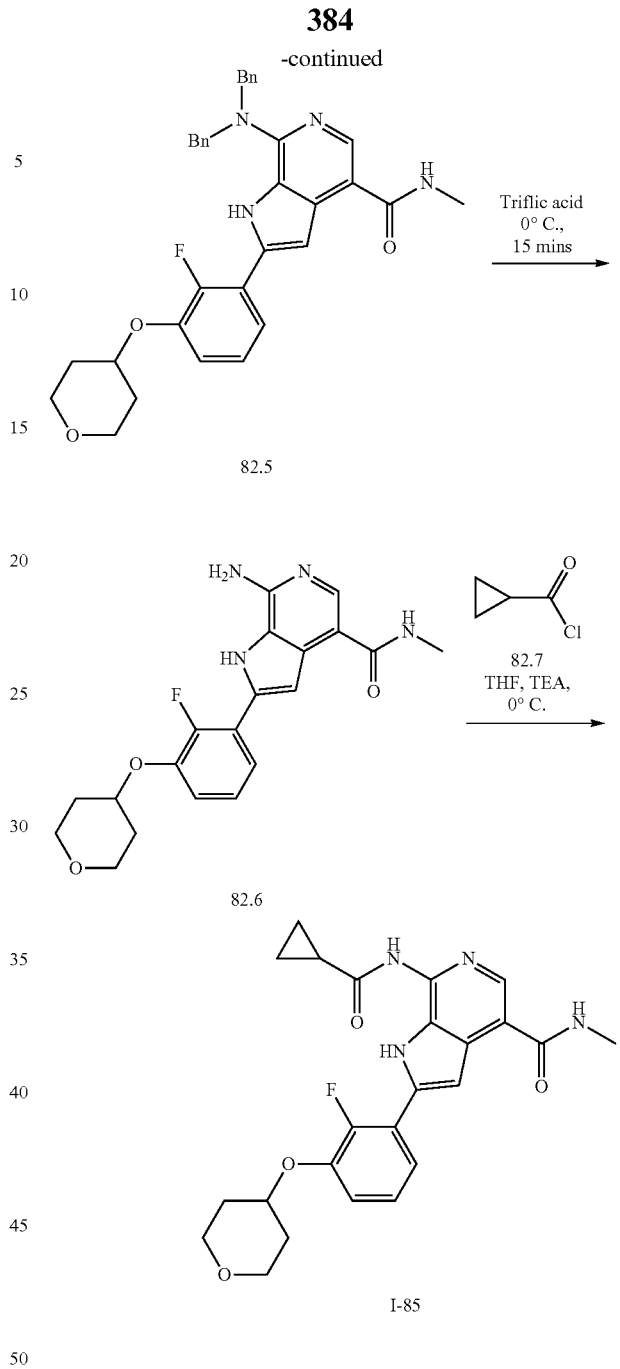

Synthesis of Compound 82.2

To a solution of 82 (1.0 g, 5.23 mmol, 1.0 eq) and 82.1 (3.4 g, 20.92 mmol, 4.0 eq) in Acetonitrile (25 mL) was added cesium carbonate (6.7 g, 20.92 mmol, 4.0 eq). Reaction mixture was heated to refluxed at 80° C. for 18 h. After completion of reaction, reaction mixture was cooled to room temperature, transferred into water and product was extracted with ethyl acetate. Organic layer was combined, washed with brine solution, dried over sodium sulfate and concentrated under reduced pressure to obtain crude material. This was further purified by column chromatography and the compound was eluted in 9% ethyl acetate in hexane to obtain 82.2. (0.450 g, Yield: 31.24%), MS (ES): m/z 275.1 [M+H]$^+$.

Synthesis of Compound 82.3

Compound was synthesized as per experimental protocol of core synthesis B to obtain 82.3 (Yield: 66.51%), MS (ES): m/z 416.17 [M+H]$^+$.

Synthesis of Compound 82.4

Compound was synthesized using general procedure A to obtain 82.4 (0.190 g, Yield: 46.49%), MS (ES): m/z 566.2 [M+H]$^+$.

Synthesis of Compound 82.5

To a solution of compound 82.4 (0.190 g, 0.33 mmol, 1.0 eq) in tetrahydrofuran (2 mL) were added N,N-Diisopropylethylamine (0.18 mL, 0.99 mmol, 3.0 eq), Trimethylaluminium (2M in hexane, 0.82 mL, 1.65 mmol, 5.0 eq) and Methylamine (2M in tetrahydrofuran, 0.49 mL, 0.99 mmol, 3.0 eq) at 0° C. Reaction mixture was stirred at 70° C. for 5 h. After completion of reaction, reaction mixture was transferred to ice cold water and product was extracted with ethyl acetate. Organic layer was combined, washed with brine solution, dried over sodium sulfate and concentrated under reduced pressure to obtain crude material. This was further purified by 2.5% methanol in dichloromethane to obtain 82.5 (0.160 g, Yield: 84.36%), MS (ES): m/z 565.26 [M+H]$^+$.

Synthesis of Compound 82.6

Compound was synthesized using general procedure B to obtain 82.6 (0.083 g, Yield: 76.20%), MS (ES): m/z 385.16 [M+H]$^+$.

Synthesis of Compound I-85

Compound was synthesized using general procedure C to obtain I-85 (0.030 g, Yield: 30.71%), MS (ES): 453.47 [M+H]$^+$ LCMS purity: 96.20%, HPLC purity: 95.70%, $^1$H NMR (DMSO-d$_6$, 400 MHZ): 12.06 (s, 1H), 11.30 (s, 1H), 8.37-8.36 (d, J=4 Hz, 1H), 8.30 (s, 1H), 7.50-7.47 (t, J=6.8 Hz, 1H), 7.43 (s, 1H), 7.36-7.32 (t, J=8 Hz, 1H), 7.28-7.24 (t, J=8 Hz, 1H), 4.69-4.67 (m, 1H), 3.89-3.87 (m, 2H), 3.51-3.47 (t, J=9.6 Hz, 2H), 2.84-2.83 (d, J=4 Hz, 3H), 2.24 (bs, 1H), 2.03-2.00 (m, 2H), 1.67-1.64 (m, 2H), 0.98-0.93 (m, 4H).

Example 83: 7-(cyclopropanecarboxamido)-2-(2-fluoro-4-(1-methyl-1H-imidazol-2-yl)-6-morpholinophenyl)-N-methyl-1H-pyrrolo[2,3-c]pyridine-4-carboxamide (I-86)

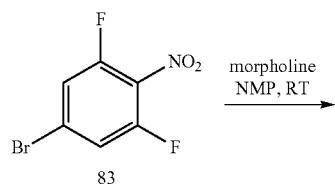
83 morpholine
NMP, RT

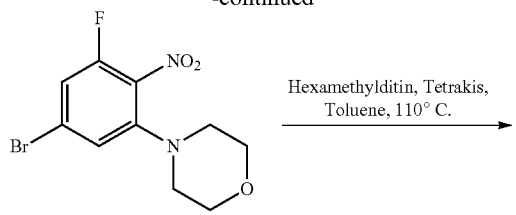
83.1

Hexamethylditin, Tetrakis, Toluene, 110° C.

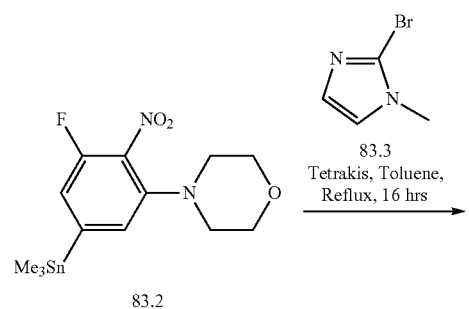
83.2

83.3
Tetrakis, Toluene, Reflux, 16 hrs

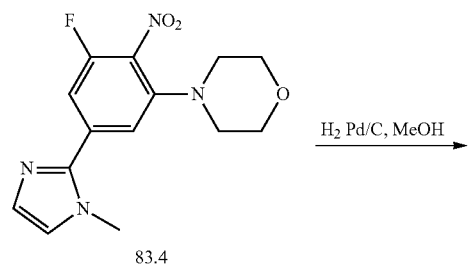
83.4

H$_2$ Pd/C, MeOH

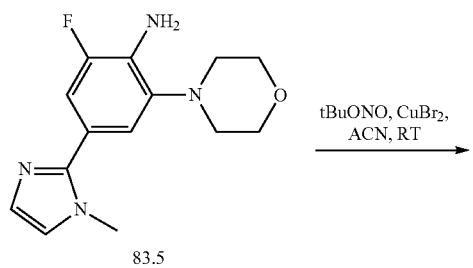
83.5 tBuONO, CuBr$_2$, ACN, RT

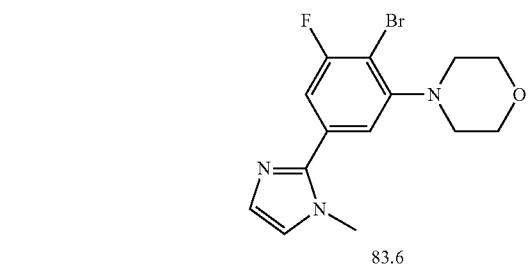
83.6

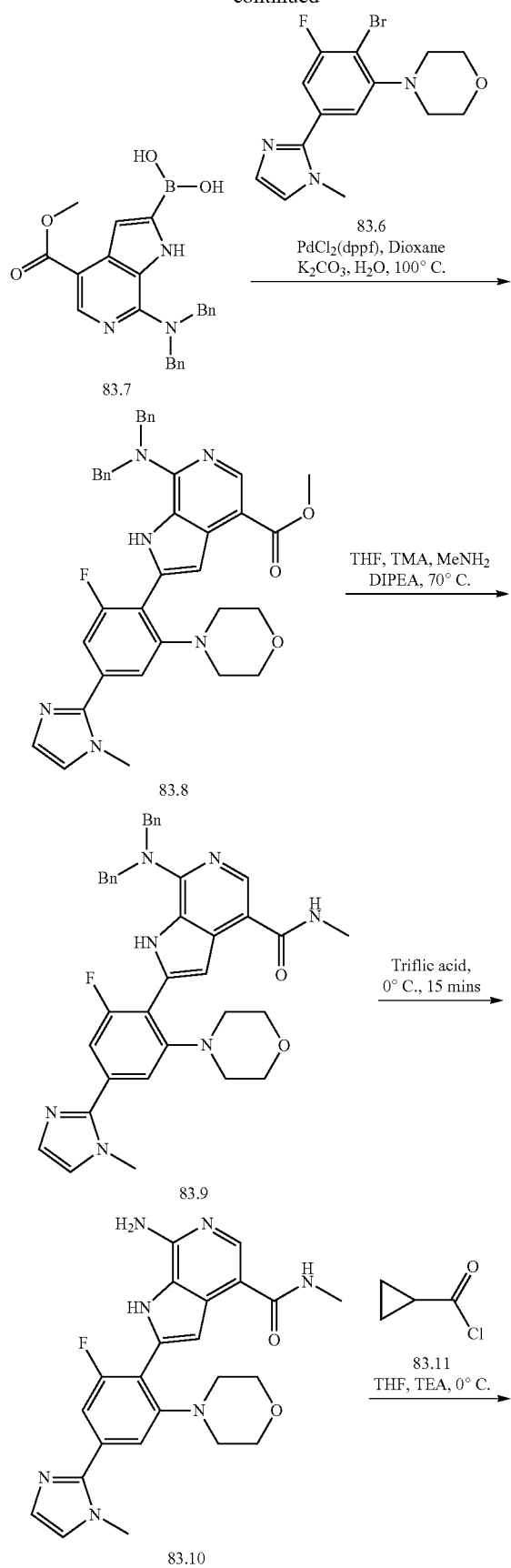

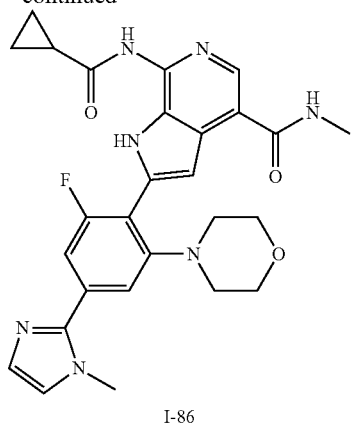

I-86

Synthesis of Compound 83.1

To a solution of 83 (2.0 g, 8.47 mmol, 1.0 eq) in N-Methyl-2-pyrrolidone (20 mL) was added Morpholine (0.884 g, 10.16 mmol, 1.2 eq). Reaction mixture was stirred at room temperature for 16 h. After completion of reaction, reaction mixture was cooled to room temperature, transferred into water and product was extracted with ethyl acetate. Organic layer was combined, washed with brine solution, dried over sodium sulfate and concentrated under reduced pressure to obtain crude material. This was further purified by column chromatography and the compound was eluted in 20% ethyl acetate in hexane to obtain 83.1. (1.6 g, Yield: 62.40%), MS (ES): m/z 305.1 [M+H]$^+$.

Synthesis of Compound 83.2

To a degassed solution of 83.1 (1.4 g, 4.59 mmol, 1.0 eq) and hexamethylditin (6.0 g, 18.36 mmol, 4.0 eq) in toluene (15 mL) was added Tetrakis(triphenylphosphine)palladium (0) (0.530 g, 0.45 mmol, 0.1 eq) and the reaction mixture was heated at 110° C. for 1 h under $N_2$. After completion of reaction, reaction mixture was concentrated under reduced pressure to obtain crude residue which was purified by column chromatography using 5% ethyl acetate in hexane as eluant to obtain pure 83.2. (0.7 g, Yield: 39.21%). MS(ES): m/z 390.0 [M+H]$^+$.

Synthesis of Compound 83.4

To a degassed solution of 83.2 (0.7 g, 1.79 mmol, 1.0 eq) in toluene (14 mL) was added 83.3 (0.344 g, 2.14 mmol, 1.2 eq). The reaction mixture was degassed for 15 min under argon atmosphere, then Tetrakis(triphenylphosphine)palladium(0) (0.103 g, 0.089 mmol, 0.05 eq) was added and again degassed for 5 min. Reaction mixture was heated to refluxed at 110° C. for 16 h under $N_2$. After completion of reaction, reaction mixture was concentrated under reduced pressure to obtain crude residue which was purified by column chromatography using 6% ethyl acetate in hexane as eluant to obtain pure 83.4. (0.320 g, Yield: 58.06%). MS(ES): m/z 307.12 [M+H]$^+$.

Synthesis of Compound 83.5

To a solution of 83.4 (0.320 g, 1.04 mmol, 1.0 eq) in methanol (6 ml), was added 10% palladium on charcoal (0.2 g). Hydrogen was purged through reaction mixture for 4 h at room temperature. After completion of reaction, reaction mixture was filtered through Celite-bed and washed with methanol. Filtrate was concentrated under reduced pressure to obtain crude material. This was further purified by trituration with n-pentane to obtain pure 83.5 (0.260 g, Yield: 90.07%). MS (ES): m/z 277.14 [M+H]$^+$.

Synthesis of Compound 83.6

To a solution of compound 83.5 (0.520 g, 1.88 mmol, 1.0 eq) in acetonitrile (6 mL) was added tert-Butyl nitrite (0.387 g, 3.76 mmol, 2.0 eq) and reaction mixture was cooled to 0° C. Then Copper (II) bromide (0.838 g, 3.76 mmol, 2.0 eq) was added dropwise into the reaction mixture. The reaction was stirred at room temperature for 2 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by combi flash using 20% ethyl acetate in hexane as eluant to obtain pure 83.6. (0.280 g, Yield: 43.74%). MS(ES): m/z 340.2 [M+H]$^+$.

Synthesis of Compound 83.7

Compound was synthesized as per experimental protocol of core synthesis B to obtain 83.7 (Yield: 66.51%), MS (ES): m/z 416.17 [M+H]$^+$.

Synthesis of Compound 83.8

Compound was synthesized using general procedure A to obtain 83.8 (0.142 g, Yield: 46.74%), MS (ES): m/z 631.28 [M+H]$^+$.

Synthesis of Compound 83.9

To a solution of compound 83.8 (0.142 g, 0.22 mmol, 1.0 eq) in tetrahydrofuran (2 mL) were added N,N-Diisopropylethylamine (0.12 mL, 0.66 mmol, 3.0 eq), Trimethylaluminium (2M in hexane, 0.55 mL, 1.1 mmol, 5.0 eq) and Methylamine (2M in tetrahydrofuran, 0.33 mL, 0.66 mmol, 3.0 eq) at 0° C. Reaction mixture was stirred at 70° C. for 5 h. After completion of reaction, reaction mixture was transferred to ice cold water and product was extracted with ethyl acetate. Organic layer was combined, washed with brine solution, dried over sodium sulfate and concentrated under reduced pressure to obtain crude material. This was further purified by 2.5% methanol in dichloromethane to obtain 83.9 (0.102 g, Yield: 71.94%), MS (ES): m/z 630.29 [M+H]$^+$.

Synthesis of Compound 83.10

Compound was synthesized using general procedure B to obtain 83.10 (0.070 g, Yield: 96.15%), MS (ES): m/z 450.20 [M+H]$^+$.

Synthesis of Compound I-86

Compound was synthesized using general procedure C to obtain I-86 (0.032 g, Yield: 39.70%), MS (ES): 518.51 [M+H]$^+$ LCMS purity: 99.07%, HPLC purity: 98.16%, $^1$H NMR (DMSO-d$_6$, 400 MHZ): 12.29 (s, 1H), 11.41 (s, 1H), 8.41-8.40 (d, J=4.4 Hz, 1H), 8.30 (s, 1H), 7.42 (bs, 2H), 7.34 (bs, 1H), 7.05 (s, 1H), 6.82 (s, 1H), 3.86 (bs, 3H), 3.67 (bs, 3H), 2.83-2.82 (d, J=3.6 Hz, 3H), 1.54 (bs, 3H), 1.22 (bs, 3H), 1.00-0.95 (m, 4H).

Example 84: 7-(cyclopropanecarboxamido)-2-(3-(4,4-dimethyl-4,5-dihydrooxazol-2-yl)-2-fluorophenyl)-N-methyl-1H-pyrrolo[2,3-c]pyridine-4-carboxamide (I-87)

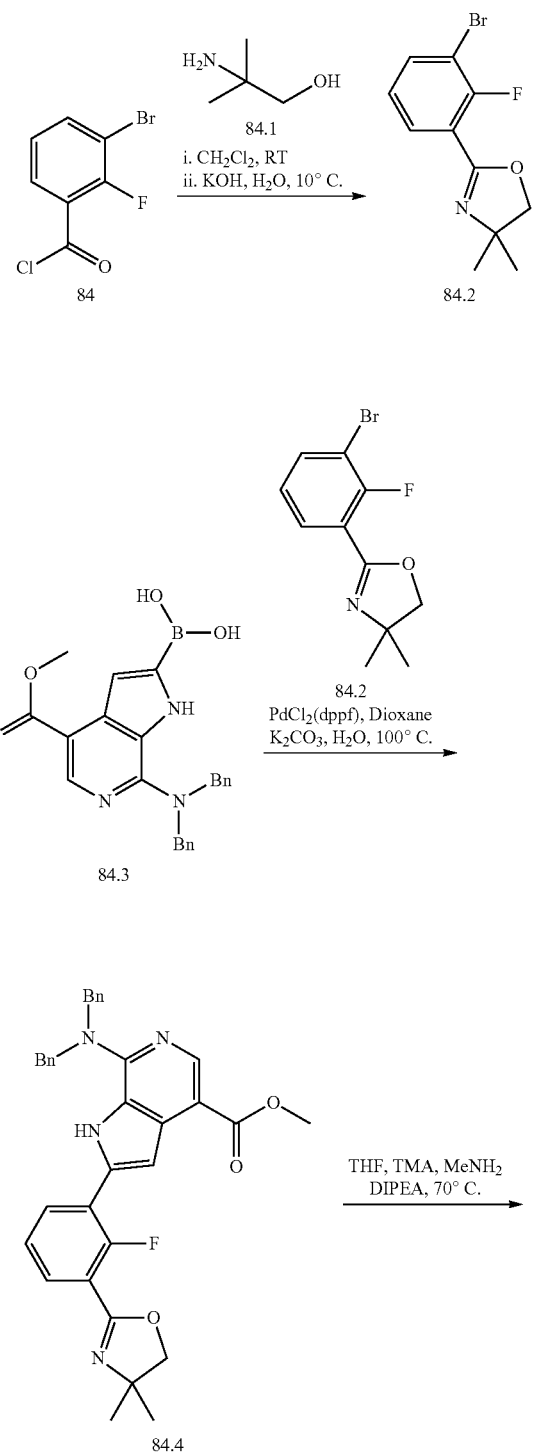

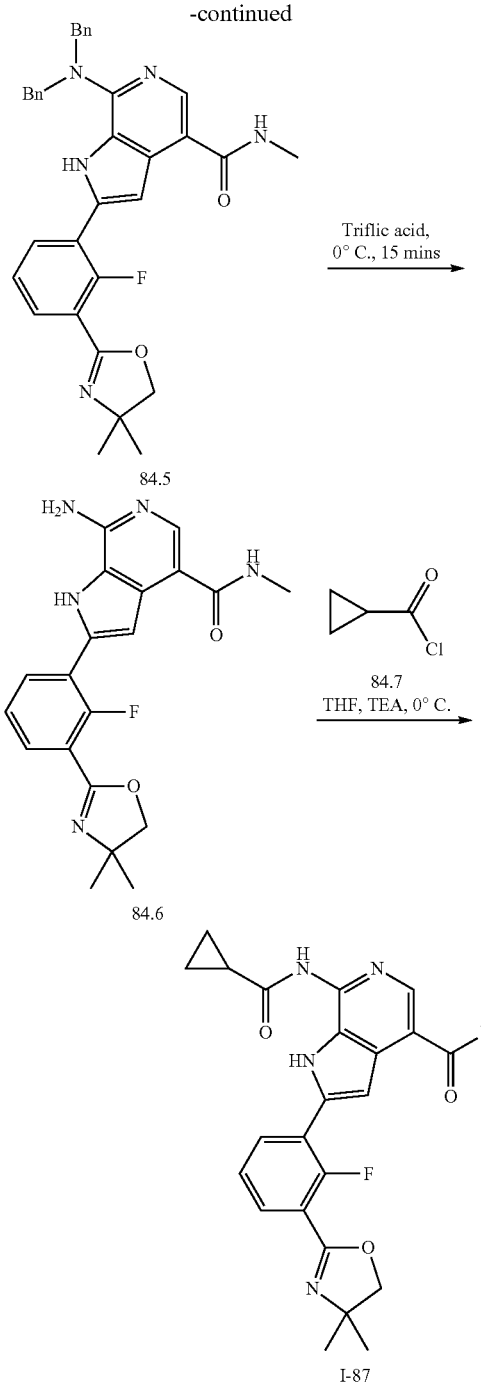

Synthesis of Compound 84.2

To a cooled solution of 84 (2.0 g, 8.43 mmol, 1.0 eq) in dichloromethane (20 mL) was added dropwise 84.1 (1.8 g, 21.07 mmol, 2.5 eq) dissolved in dichloromethane (20 mL) over 30 min. Reaction mixture was stirred at room temperature for 16 h. After completion of reaction, reaction mixture was concentrated under reduced pressure, basified with 5M Potassium hydroxide solution and extracted with dichloromethane. Organic layer was combined, dried over sodium sulfate and concentrated under reduced pressure to obtain crude material. This was further purified by column chromatography and the compound was eluted in 5% ethyl acetate in hexane to obtain 84.2 (0.172 g, Yield: 7.50%), MS (ES): m/z 273.0[M+H]$^+$.

Synthesis of Compound 84.3

Compound was synthesized as per experimental protocol of core synthesis B to obtain 84.3 (Yield: 66.51%), MS (ES): m/z 416.17 [M+H]$^+$.

Synthesis of Compound 84.4

Compound was synthesized using general procedure A to obtain 84.4 (0.142 g, Yield: 52.40%), MS (ES): m/z 563.2 [M+H]$^+$.

Synthesis of Compound 84.5

To a solution of compound 84.4 (0.142 g, 0.25 mmol, 1.0 eq) in tetrahydrofuran (2 mL) were added N,N-Diisopropylethylamine (0.13 mL, 0.75 mmol, 3.0 eq), Trimethylaluminium (2M in hexane, 0.62 mL, 1.25 mmol, 5.0 eq) and Methylamine (2M in tetrahydrofuran, 0.37 mL, 0.75 mmol, 3.0 eq) at 0° C. Reaction mixture was stirred at 70° C. for 5 h. After completion of reaction, reaction mixture was transferred into ice cold water and product was extracted with ethyl acetate. Organic layer was combined, washed with brine solution, dried over sodium sulfate and concentrated under reduced pressure to obtain crude material. This was further purified by 2.5% methanol in dichloromethane to obtain 84.5 (0.088 g, Yield: 62.08%), MS (ES): m/z 562.26 [M+H]$^+$.

Synthesis of Compound 84.6

Compound was synthesized using general procedure B to obtain 84.6 (0.040 g, Yield: 98.17%), MS (ES): m/z 382.16 [M+H]$^+$.

Synthesis of Compound I-87

Compound was synthesized using general procedure C to obtain I-87 (0.025 g, Yield: 51.74%), MS (ES): 450.66 [M+H]$^+$ LCMS purity: 95.00%, HPLC purity: 98.19%, $^1$H NMR (DMSO-d$_6$, 400 MHZ): 12.21 (s, 1H), 11.44 (s, 1H), 8.42-8.41 (d, J=4 Hz, 1H), 8.30 (s, 1H), 7.89 (bs, 1H), 7.51 (bs, 1H), 7.07 (bs, 1H), 6.82 (bs, 1H), 4.14 (bs, 2H), 2.85-2.84 (d, J=4 Hz, 3H), 1.54 (bs, 1H), 1.33 (s, 6H), 1.00-0.93 (m, 4H).

Example 85: (S)-7-(cyclopropanecarboxamido)-2-(2-fluoro-4-(((tetrahydrofuran-2-yl)methoxy)phenyl)-N-methyl-1H-pyrrolo[2,3-c]pyridine-4-carboxamide (I-88)

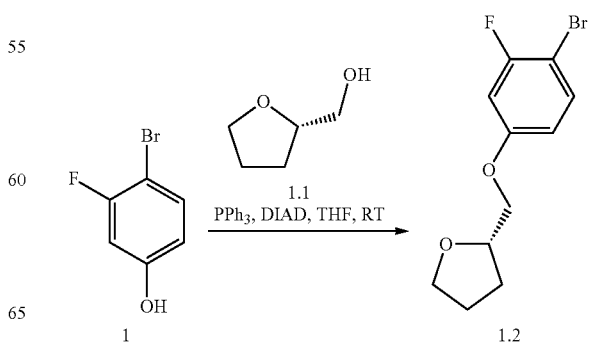

393
-continued

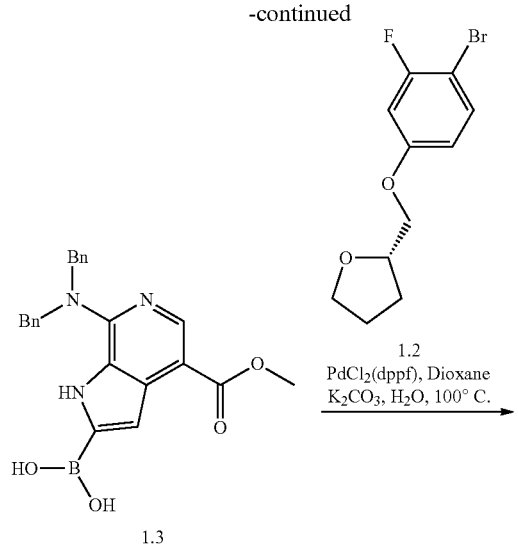

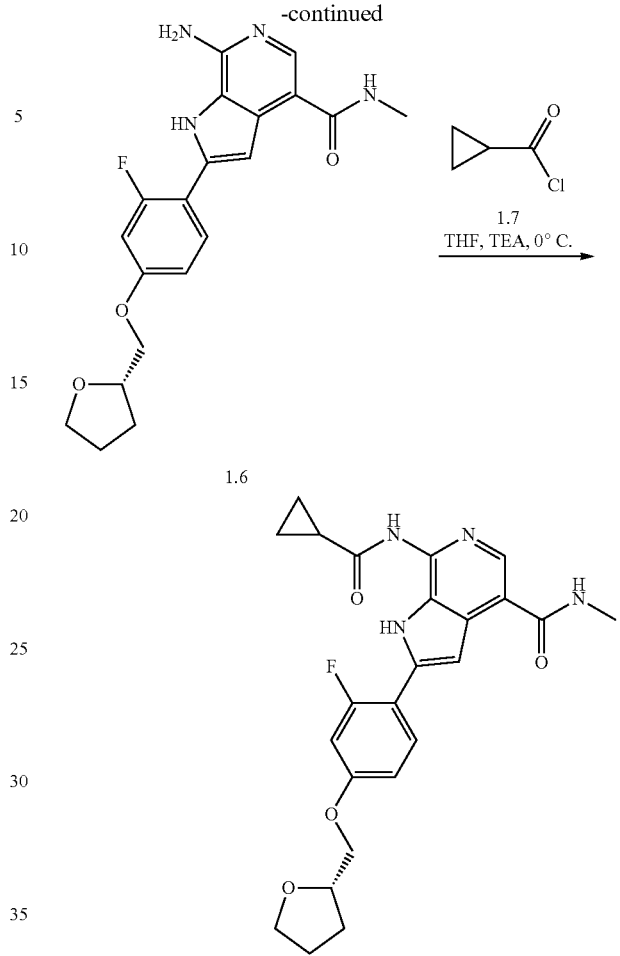

Synthesis of Compound 85.2

To a solution of 85 (2.0 g, 10.47 mmol, 1.0 eq) and 85.1 (1.3 mL, 12.56 mmol, 1.2 eq) in tetrahydrofuran (25 mL) was added Triphenylphosphine (3.4 g, 13.08 mmol, 1.25 eq) and the reaction mixture was stirred for 5 min. Then Diisopropyl azodicarboxylate (2.4 mL, 12.56 mmol, 1.2 eq) was added dropwise and the reaction mixture was stirred at room temperature for 16 h. After completion of reaction, reaction mixture was concentrated under reduced pressure, 1N Sodium hydroxide solution was added, and extracted with dichloromethane. Organic layer was combined, washed with brine solution, dried over sodium sulfate and concentrated under reduced pressure to obtain crude material. This was further purified by 6% ethyl acetate in hexane to obtain 85.2. (0.9 g, Yield: 31.24%), MS (ES): m/z 276.0 [M+H]$^+$.

Synthesis of Compound 85.3

Compound was synthesized as per experimental protocol of core synthesis B to obtain 85.3 (Yield: 66.51%), MS (ES): m/z 416.17 [M+H]$^+$.

Synthesis of Compound 85.4

Compound was synthesized using general procedure A to obtain 85.4 (0.190 g, Yield: 39.85%), MS (ES): m/z 566.24 [M+H]$^+$.

Synthesis of Compound 85.5

To a solution of compound 85.4 (0.190 g, 0.33 mmol, 1.0 eq) in tetrahydrofuran (3 mL) were added N,N-Diisopropylethylamine (0.18 mL, 0.99 mmol, 3.0 eq), Trimethylaluminium (2M in hexane, 0.82 mL, 1.65 mmol, 5.0 eq) and Methylamine (2M in tetrahydrofuran, 0.49 mL, 0.99 mmol, 3.0 eq) at 0° C. Reaction mixture was stirred at 70° C. for 5 h. After completion of reaction, reaction mixture was transferred into ice cold water and product was extracted with ethyl acetate. Organic layer was combined, washed with brine solution, dried over sodium sulfate and concentrated under reduced pressure to obtain crude material. This was further purified by 2.5% methanol in dichloromethane to obtain 85.5 (0.132 g, Yield: 69.59%), MS (ES): m/z 565.26 [M+H]$^+$.

Synthesis of Compound 85.6

Compound was synthesized using general procedure B to obtain 85.6 (0.070 g, Yield: 77.90%), MS (ES): m/z 385.16 [M+H]$^+$.

Synthesis of Compound I-88

Compound was synthesized using general procedure C to obtain I-88 (0.029 g, Yield: 35.20%), MS (ES): 453.47 [M+H]$^+$ LCMS purity: 100%, HPLC purity: 100%, CHIRAL HPLC: 100%, $^1$H NMR (DMSO-d$_6$, 400 MHZ): 11.96 (s, 1H), 11.27 (s, 1H), 8.35 (bs, 1H), 8.30 (bs, 1H), 7.90-7.85 (t, J=8.4 Hz, 1H), 7.34 (bs, 1H), 7.09-7.06 (d, J=12.5 Hz, 1H), 6.98 (bs, 1H), 4.19 (bs, 1H), 4.07-3.98 (m, 2H), 3.80 (bs, 1H), 3.69 (bs, 1H), 2.85-2.84 (d, J=3.8 Hz, 3H), 2.25 (bs, 1H), 2.02-2.00 (m, 1H), 1.86 (bs, 2H), 1.69 (bs, 1H), 0.98-0.93 (m, 4H).

Example 86: 2-(4-(1,4-dioxan-2-yl)-2-methoxyphenyl)-7-(cyclopropanecarboxamido)-N-methyl-1H-pyrrolo[2,3-c]pyridine-4-carboxamide (I-89)

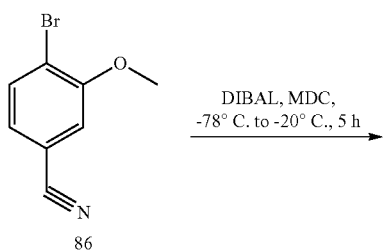

86

DIBAL, MDC,
-78° C. to -20° C., 5 h
→

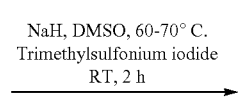

86.1

NaH, DMSO, 60-70° C.
Trimethylsulfonium iodide
RT, 2 h
→

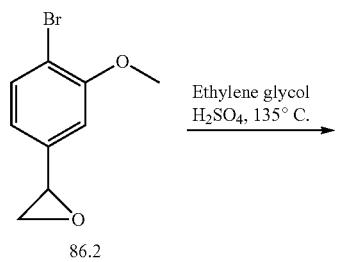

86.2

Ethylene glycol
H$_2$SO$_4$, 135° C.
→

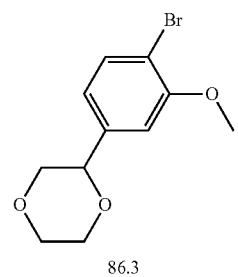

86.3

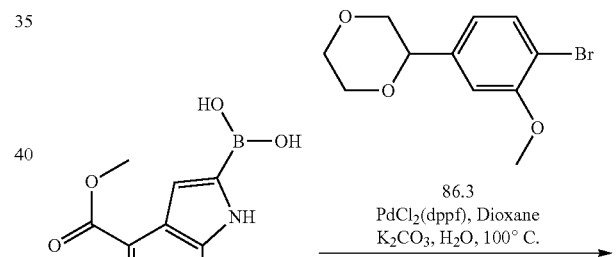

86.4

86.3
PdCl$_2$(dppf), Dioxane
K$_2$CO$_3$, H$_2$O, 100° C.
→

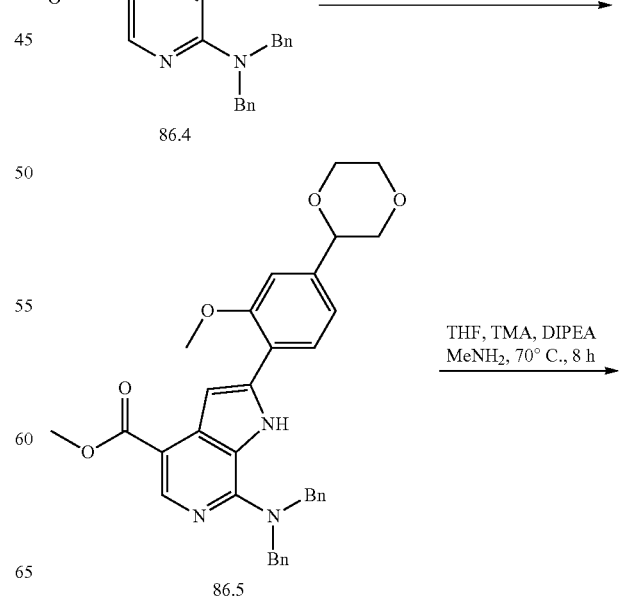

86.5

THF, TMA, DIPEA
MeNH$_2$, 70° C., 8 h
→

-continued

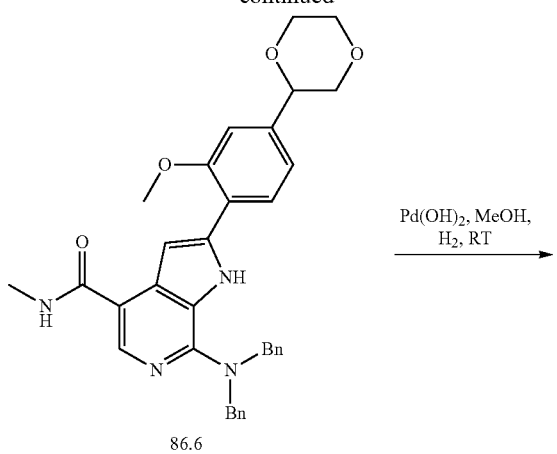

86.6

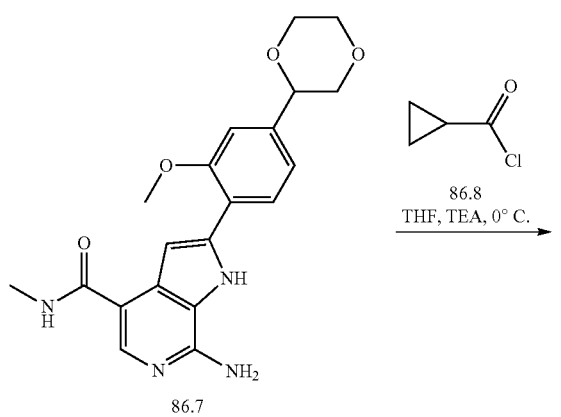

86.7

I-89

Synthesis of Compound 86.1

To a solution of 86 (3.0 g, 14.15 mmol, 1.0 eq) in dichloromethane (35 mL) was added Diisobutylaluminium hydride (1M in toluene, 28 mL, 28.3 mmol, 2.0 eq) dropwise at −78° C. Reaction mixture was stirred at room temperature for 5 h. After completion of reaction, methanol and 1N hydrochloric acid were added to it, stirred at 0° C. for 15 min and extracted with dichlromethane. Organic layer was combined, dried over sodium sulfate and concentrated under reduced pressure to obtain crude material, which was purified by 12% ethyl acetate in hexane to obtain 86.1. (1.6 g, Yield: 52.59%), MS (ES): m/z 215.9 [M+H]$^+$.

Synthesis of Compound 86.2

A solution of Sodium hydride (0.267 g, 11.16 mmol, 1.5 eq) in Dimethyl sulfoxide (15 mL) was heated at 70° C. for 2 h. The reaction mixture was cooled to 0° C. and tetrahydrofuran (16 mL) and Trimethylsulfonium iodide (2.2 g, 11.16 mmol, 1.5 eq) were added. The reaction mixture was stirred at 0° C. for 10 min. After 10 min, 86.1 (1.6 g, 7.44 mmol, 1.0 eq) was added and stirred at room temperature for 5 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by 15% ethyl acetate in hexane to obtain 86.2 (0.950 g, Yield: 55.74%), MS (ES): m/z 229.9 [M+H]$^+$.

Synthesis of Compound 86.3

To the solution of 86.2 (0.950 g, 4.14 mmol, 1.0 eq) in Ethylene glycol (10 mL) was added concentrated sulfuric acid (1 mL), and the reaction was heated at 135° C. for 2 h. After completion, reaction mixture was transferred into water and product was extracted with ethyl acetate. Organic layer was combined, washed with brine solution, dried over sodium sulfate and concentrated under reduced pressure to obtain crude material. This was further purified by 20% ethyl acetate in hexane to obtain 86.3 (0.160 g, Yield: 14.13%), MS (ES): m/z 273.1 [M+H]$^+$.

Synthesis of Compound 86.4

Compound was synthesized as per experimental protocol of core synthesis B to obtain 86.4 (Yield: 66.51%), MS (ES): m/z 416.17 [M+H]$^+$.

Synthesis of Compound 86.5

Compound was synthesized using general procedure A to obtain 86.5 (0.470 g, Yield: 57.71%), MS (ES): m/z 563.2 [M+H]$^+$.

Synthesis of Compound 86.6

To a solution of compound 86.5 (0.470 g, 0.83 mmol, 1.0 eq) in tetrahydrofuran (5 mL) were added N,N-Diisopropylethylamine (0.45 mL, 2.49 mmol, 3.0 eq), Trimethylaluminium (2M in hexane, 2.07 mL, 4.15 mmol, 5.0 eq) and Methylamine (2M in tetrahydrofuran, 1.24 mL, 2.49 mmol, 3.0 eq) at 0° C. Reaction mixture was stirred at 70° C. for 5 h. After completion of reaction, reaction mixture was transferred into ice cold water and product was extracted with ethyl acetate. Organic layer was combined, washed with brine solution, dried over sodium sulfate and concentrated under reduced pressure to obtain crude material. This was further purified by 2.5% methanol in dichloromethane to obtain 86.6 (0.370 g, Yield: 78.86%), MS (ES): m/z 562.2 [M+H]$^+$.

Synthesis of Compound 86.7

To a solution of 86.6 (0.370 g, 0.65 mmol, 1.0 eq) in methanol (10 mL) was added 20% palladium hydroxide on carbon (0.4 g). Hydrogen was purged through reaction mixture for 12 h at room temperature. After completion, reaction mixture was filtered through Celite-bed and washed with methanol. Filtrate was concentrated under reduced pressure to obtain crude material. This was further purified by trituration with n-pentane to obtain pure 86.7 (0.140 g, Yield: 55.67%), MS (ES): m/z 383.1 [M+H]⁺.

Synthesis of Compound I-89

Compound was synthesized using general procedure C to obtain I-89 (0.030 g, Yield: 38.32%), MS (ES): 451.47 [M+H]⁺ LCMS purity: 97.44%, HPLC purity: 95.11%, ¹H NMR (DMSO-d₆, 400 MHZ): 12.58 (s, 1H), 11.39 (s, 1H), 8.38 (bs, 1H), 8.22 (s, 1H), 7.91-7.89 (d, J=8 Hz, 1H), 7.42 (bs, 1H), 7.14 (bs, 1H), 7.03-7.01 (d, J=7.6 Hz, 1H), 5.07-5.04 (d, J=5.2 Hz, 1H), 3.93 (s, 2H), 3.83 (s, 2H), 3.80-3.77 (m, 2H), 2.96-2.94 (d, J=4.8 Hz, 2H), 2.84-2.83 (d, J=4.4 Hz, 3H), 2.26 (bs, 1H), 1.22 (s, 1H), 1.01-0.93 (m, 4H).

Example 87: (R)-7-(cyclopropanecarboxamido)-2-(2-fluoro-6-(3-methoxypyrrolidin-1-yl)-4-(1-methyl-1H-imidazol-2-yl)phenyl)-N-methyl-1H-pyrrolo[2,3-c]pyridine-4-carboxamide (I-90)

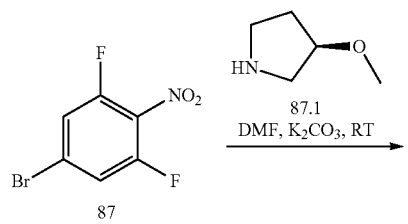

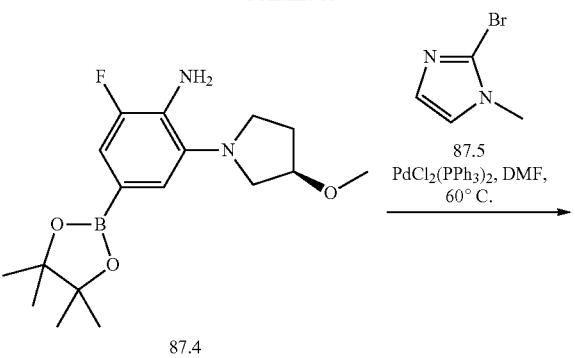

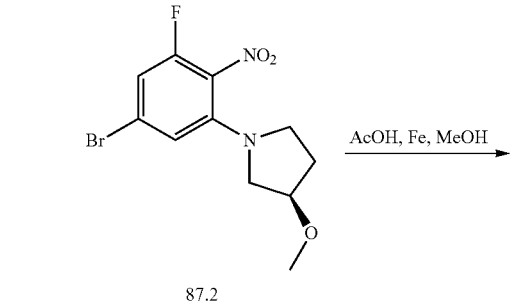

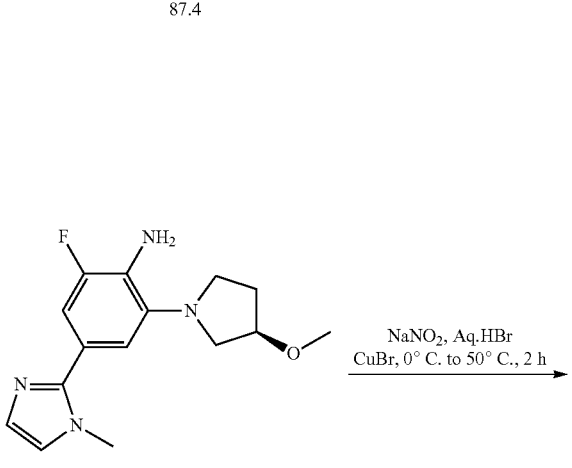

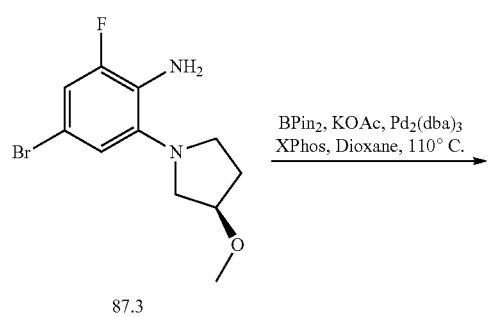

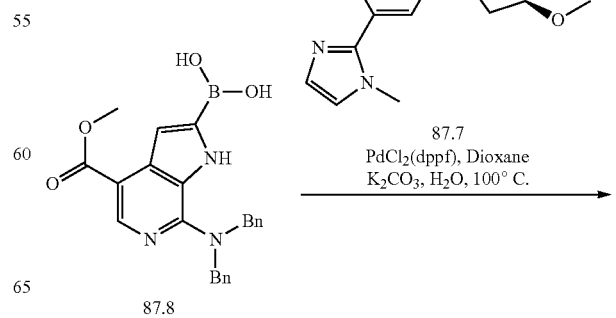

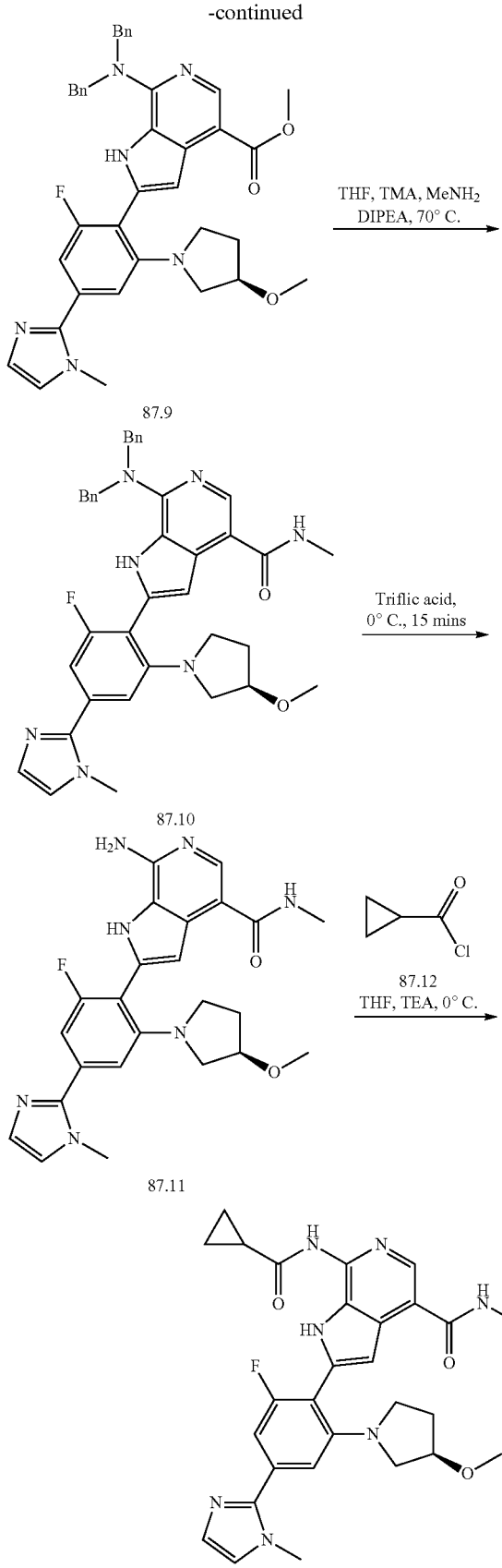

Synthesis of Compound 87.2

To a solution of 87 (5.0 g, 21.00 mmol, 1.0 eq) in dimethylformamide (70 mL), was added 87.1 (2.3 g, 23.1 mmol, 1.1 eq). The reaction mixture was degassed for 10 min under argon atmosphere followed by addition of potassium carbonate (8.6 g, 63.0 mmol, 3.0 eq). The reaction mixture was stirred at room temperature for 10 h. After completion of reaction, reaction mixture was transferred into ice cold water and product was extracted with ethyl acetate. Organic layer was combined, washed with brine solution, dried over sodium sulfate and concentrated under reduced pressure to obtain crude material. This was further purified by 5% ethyl acetate in hexane to obtain 87.2 (4.2 g, Yield: 62.64%). MS (ES): m/z 318.0 [M+H]$^+$.

Synthesis of Compound 87.3

To a solution of 87.2 (4.2 g, 13.16 mmol, 1.0 eq) in methanol were added Acetic acid (7.5 mL, 131.6 mmol, 10.0 eq) and Iron powder (3.6 g, 65.8 mmol, 5.0 eq) Reaction mixture was stirred at 90° C. for 30 min. After completion of reaction, reaction mixture was cooled to room temperature and filtered through Celite-bed. Filtrate was concentrated under reduced pressure to obtain crude material. This was further purified by column chromatography and the compound was eluted in 10% ethyl acetate in hexane to obtain 87.3 (3.6 g, Yield: 94.60%), MS (ES): m/z 289.15 [M+H]$^+$.

Synthesis of Compound 87.4

To a solution of 87.3 (3.6 g, 12.45 mmol, 1.0 eq) in 1,4-dioxane (60 mL) was added Bis(pinacolato)diboron (3.4 g, 13.69 mmol, 1.1 eq), and Potassium acetate (3.6 g, 37.35 mmol, 3.0 eq). The reaction mixture was degassed for 15 min under argon atmosphere, then Tris(dibenzylideneacetone)dipalladium(0) (0.796 g, 0.87 mmol, 0.07 eq) and 2-Dicyclohexylphosphino-2',4',6'-triisopropylbiphenyl (0.592 g, 1.24 mmol, 0.1 eq) were added, and degassed for 5 min. The reaction mixture was stirred at 110° C. for 4 h. After completion of reaction, reaction mixture was cooled to room temperature, transferred into water and product was extracted with ethyl acetate. Organic layer was combined, washed with brine solution, dried over sodium sulfate and concentrated under reduced pressure to obtain crude material. This was further purified by combi flash using 12% ethyl acetate in hexane as eluant to obtain pure 87.4. (2.9 g, Yield: 69.28%). MS(ES): m/z 336.2 [M+H]$^+$.

Synthesis of Compound 87.6

Argon was purged for 15 min through a stirred solution of 87.4 (2.9 g, 8.63 mmol, 1.0 eq) and 87.5 (1.8 g, 11.21 mmol, 1.3 eq) in dimethylformamide (30 mL). Bis(triphenylphosphine)palladium(II) dichloride (0.605 g, 0.86 mmol, 0.1 eq) was added and was further purged for 10 min. Reaction was allowed to stir at 60° C. for 5 h. After completion, reaction mixture was transferred into water and product was extracted with ethyl acetate. Organic layer was combined, washed with brine solution, dried over sodium sulfate and concentrated under reduced pressure to obtain 87.6 (1.67 g, Yield: 66.68%). MS (ES): m/z 291.15 [M+H]$^+$.

Synthesis of Compound 87.7

To compound 87.6 (0.6 g, 2.06 mmol, 1.0 eq) was added 30% Hydrobromic acid (1.2 mL) dropwise at 0° C. Sodium nitrite (0.284 g, 4.12 mmol, 2.0 eq) and acetone (4.8 mL) were added and the reaction mixture was stirred for 2 min. Copper(I) bromide (0.589 g, 4.12 mmol, 2.0 eq) was added and reaction mixture stirred for 2 h. After completion of reaction, reaction mixture was cooled to room temperature, transferred into water and product was extracted with ethyl acetate. Organic layer was combined, washed with brine solution, dried over sodium sulfate and concentrated under reduced pressure to obtain 87.7. (0.090 g, Yield: 12.29%). MS(ES): m/z 354.2 [M+H]$^+$.

Synthesis of Compound 87.8

Compound was synthesized as per experimental protocol of core synthesis B to obtain 87.8 (Yield: 66.51%), MS (ES): m/z 416.17 [M+H]$^+$.

Synthesis of Compound 87.9 Compound was synthesized using general procedure A to obtain 87.9

(0.055 g, Yield: 35.42%), MS (ES): m/z 645.29 [M+H]$^+$.

Synthesis of Compound 87.10

To a solution of compound 87.9 (0.055 g, 0.085 mmol, 1.0 eq) in tetrahydrofuran (5 mL) were added N,N-Diisopropylethylamine (0.046 mL, 0.25 mmol, 3.0 eq), Trimethylaluminium (2M in hexane, 0.21 mL, 0.42 mmol, 5.0 eq) and Methylamine (2M in tetrahydrofuran, 0.12 mL, 0.25 mmol, 3.0 eq) at 0° C. Reaction mixture was stirred at 70° C. for 5 h. After completion of reaction, reaction mixture was transferred into ice cold water and product was extracted with ethyl acetate. Organic layer was combined, washed with brine solution, dried over sodium sulfate and concentrated under reduced pressure to obtain crude material. This was further purified by 2.5% methanol in dichloromethane to obtain 87.10 (0.047 g, Yield: 85.59%), MS (ES): m/z 643.7 [M+H]$^+$.

Synthesis of Compound 87.11

Compound was synthesized using general procedure B to obtain 87.11 (0.033 g, Yield: 97.52%), MS (ES): m/z 464.2 [M+H]$^+$.

Synthesis of Compound I-90

Compound was synthesized using general procedure C to obtain I-90 (0.028 g, Yield: 62.60%), MS (ES): 532.52 [M+H]$^+$ LCMS purity: 99.64%, HPLC purity: 98.04%, $^1$H NMR (DMSO-d$_6$, 400 MHZ): 11.67 (s, 1H), 11.16 (s, 1H), 8.36 (bs, 1H), 8.32 (s, 1H), 7.46 (s, 1H), 7.23 (bs, 1H), 7.06-7.03 (d, J=7.6 Hz, 2H), 6.82-6.81 (d, J=6.8 Hz, 1H), 5.34 (bs, 2H), 4.45 (bs, 2H), 4.09 (bs, 2H), 3.99-3.94 (m, 3H), 3.86 (s, 3H), 2.83-2.82 (d, J=4.4 Hz, 3H), 1.85 (bs, 1H), 1.54 (bs, 1H), 0.90-0.88 (m, 4H).

Example 88: 7-(cyclopropanecarboxamido)-2-(2-fluoro-3-((1s,3s)-3-methoxycyclobutyl)phenyl)-N-methyl-1H-pyrrolo[2,3-c]pyridine-4-carboxamide (I-91)

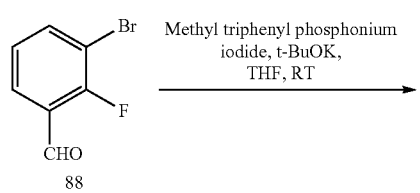

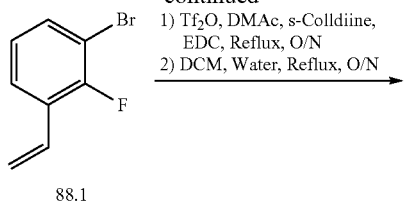

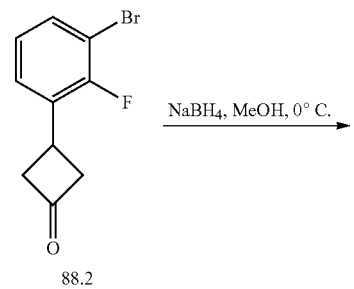

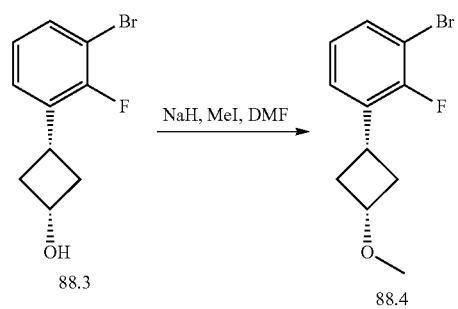

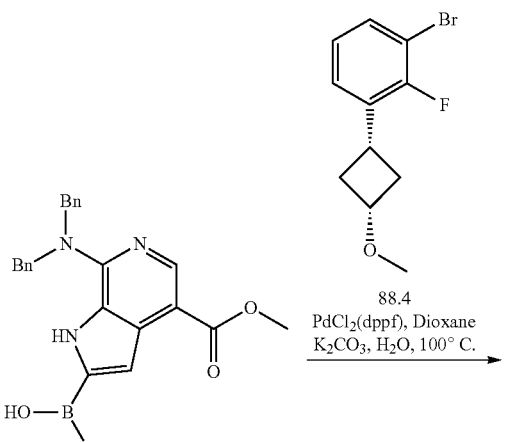

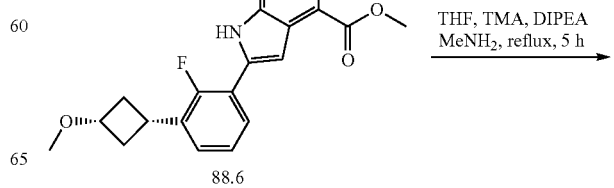

-continued

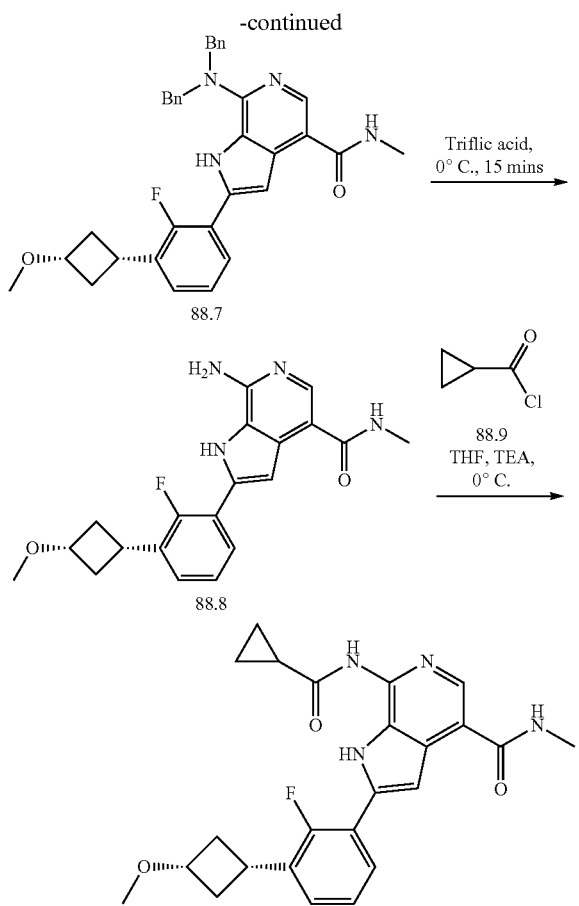

Synthesis of Compound 88.1

A solution of Methyl triphenyl phosphonium iodide (24.8 g, 61.57 mmol, 2.5 eq) in tetrahydrofuran (150 mL) was cooled to 0° C. Potassium tert-butoxide (6.8 g, 61.57 mmol, 2.5 eq) was added portionwise over 15 min. After 10 min, 88 (5.0 g, 24.63 mmol, 1.0 eq) was dissolved in tetrahydrofuran (20 mL) and added dropwise over 15 min. Reaction mixture was stirred at room temperature for 1 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by 2% ethyl acetate in hexane to obtain 88.1 (2.6 g, Yield: 52.51%), MS (ES): m/z 201.04 [M+H]$^+$.

Synthesis of Compound 88.2

A solution of Dimethylacetamide (1.2 g, 14.22 mmol, 1.1 eq) in 1,2-Dichloroethane (26 mL) was cooled to −12° C. Triflic anhydride (5.0 g, 14.22 mmol, 1.1 eq) was added over 30 min. After 15 min, 88.1 (2.6 g, 12.93 mmol, 1.0 eq) dissolved in 1,2-Dichloroethane (15 mL) was added slowly. Then 2,4,6-Collidine (2.6 mL) was added to reaction mixture at −12° C. and stirred at 150° C. for 4 h. Then reaction mixture was cooled to room temperature, water was added and again heated to 80° C. for 16 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by 6% ethyl acetate in hexane to obtain 88.2 (0.7 g, Yield: 22.27%), MS (ES): m/z 243.08 [M+H]$^+$.

Synthesis of Compound 88.3

A solution of 88.2 (0.7 g, 2.88 mmol, 1.0 eq) in methanol (10 mL) was cooled to 0° C. and sodium borohydride (0.119 g, 3.16 mmol, 1.1 eq) was added portiowise. Reaction mixture was stirred at room temperature for 1 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by 10% ethyl acetate in hexane to obtain 88.3 (0.630 g, Yield: 89.26%), MS (ES): m/z 245.9 [M+H]$^+$.

Synthesis of Compound 88.4

To a cooled suspension of sodium hydride (60%) (0.032 g, 1.33 mmol, 1.5 eq) in N,N-Dimethylformamide (4.4 mL) at 0° C. was added 88.3 (0.220 g, 0.89 mmol, 1.0 eq) and Methyl iodide (0.150 g, 1.06 mmol, 1.2 eq). Reaction mixture was stirred at room temperature for 1 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by 10% ethyl acetate in hexane to obtain 88.4 (0.180 g, Yield: 77.39%), MS (ES): m/z 259.12 [M+H]$^+$.

Synthesis of Compound 88.5

Compound was synthesized as per experimental protocol of core synthesis B to obtain 88.5 (Yield: 66.51%), MS (ES): m/z 416.17 [M+H]$^+$.

Synthesis of Compound 88.6

Compound was synthesized using general procedure A to obtain 88.6 (0.120 g, Yield: 60.44%), MS (ES): m/z 550.2 [M+H]$^+$.

Synthesis of Compound 88.7

To a solution of compound 88.6 (0.120 g, 0.21 mmol, 1.0 eq) in tetrahydrofuran (2 mL) were added N,N-Diisopropylethylamine (0.11 mL, 0.63 mmol, 3.0 eq), Trimethylaluminium (2M in hexane, 0.52 mL, 1.05 mmol, 5.0 eq) and Methylamine (2M in tetrahydrofuran, 0.31 mL, 0.63 mmol, 3.0 eq) at 0° C. Reaction mixture was stirred at 70° C. for 5 h. After completion of reaction, reaction mixture was transferred into ice cold water and product was extracted with ethyl acetate. Organic layer was combined, washed with brine solution, dried over sodium sulfate and concentrated under reduced pressure to obtain crude material. This was further purified by 2.5% methanol in dichloromethane to obtain 88.7 (0.087 g, Yield: 72.63%), MS (ES): m/z 549.26 [M+H]$^+$.

Synthesis of Compound 88.8

Compound was synthesized using general procedure B to obtain 88.8 (0.047 g, Yield: 80.45%), MS (ES): m/z 369.1 [M+H]$^+$.

Synthesis of Compound I-91

Compound was synthesized using general procedure C to obtain I-91 (0.025 g, Yield: 44.90%), MS (ES): 437.46 [M+H]$^+$ LCMS purity: 98.50%, HPLC purity: 95.00%, $^1$H NMR (DMSO-d$_6$, 400 MHZ): 12.11 (s, 1H), 11.32 (s, 1H), 8.43 (bs, 1H), 8.30 (s, 1H), 7.83 (bs, 1H), 7.38-7.35 (t, J=7.6 Hz, 1H), 7.09-7.07 (d, J=7.2 Hz, 1H), 6.84 (s, 1H), 4.05-3.90 (m, 2H), 3.20 (s, 3H), 2.86-2.85 (d, J=4.4 Hz, 3H), 2.00-1.97 (m, 2H), 1.56 (bs, 1H), 1.24 (bs, 1H), 1.20-1.17 (t, J=7.2 Hz, 1H), 1.00-0.96 (m, 4H).

Example 89: 7-(cyclopropanecarboxamido)-2-(7-fluoro-1,2-dimethyl-1H-benzo[d]imidazol-6-yl)-N-methyl-1H-pyrrolo[2,3-c]pyridine-4-carboxamide (I-92)

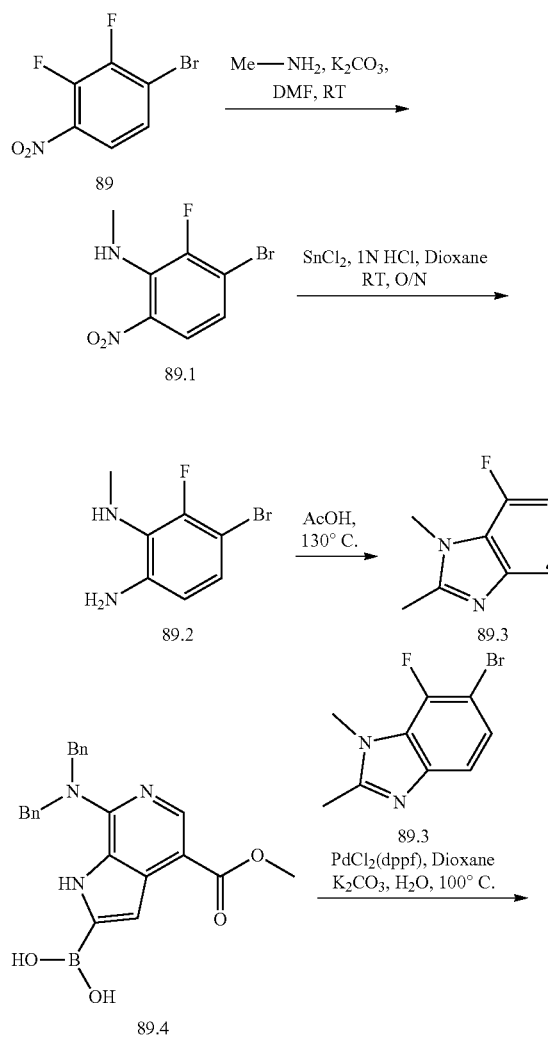

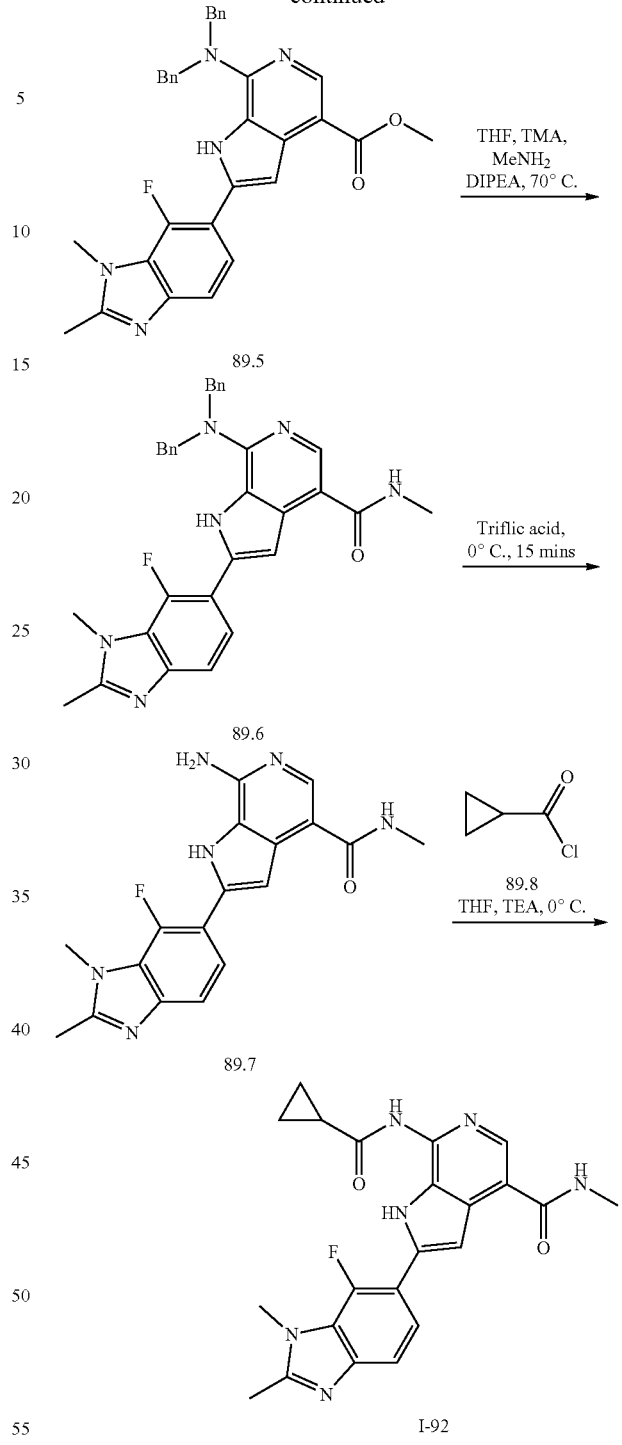

Synthesis of Compound 89.1

To a solution of 89 (2.0 g, 8.40 mmol, 1.0 eq) in N,N-dimethylformamide (20 mL) was added Potassium carbonate (2.3 g, 16.8 mmol, 2.0 eq). Then Methylamine (2M in tetrahydrofuran, 5.04 mL, 10.08 mmol, 1.2 eq) was added and stirred at room temperature for 5 h. After completion of reaction, reaction mixture was filtered and concentrated under reduced pressure to obtain 89.1 (1.2 g, Yield: 57.34%), MS (ES): m/z 249.0 [M+H]$^+$.

Synthesis of Compound 89.2

To a solution of 89.1 (1.2 g, 4.81 mmol, 1.0 eq) in 1,4 Dioxane (15 mL) was added stannous chloride dihydrate (5.4 g, 24.05 mmol, 5.0 eq). Then hydrochloric acid (1.2 mL) was added to the reaction mixture and stirred at room temperature for 16 h. After completion of reaction, reaction mixture was transferred into water, added 1N sodium hydroxide solution and product was extracted with ethyl acetate. Organic layer was combined, washed with brine solution, dried over sodium sulfate and concentrated under reduced pressure to obtain crude material. This was further purified by trituration with n-pentane to obtain 89.2 (0.7 g, Yield: 66.32%), MS (ES): m/z 219.06 [M+H]$^+$.

Synthesis of Compound 89.3

A solution of 89.2 (0.7 g, 3.19 mmol, 1.0 eq) in Acetic acid (10 mL) was heated at 130° C. for 4 h. After completion of reaction, reaction mixture was transferred into saturated Sodium bicarbonate solution, filtered and concentrated under reduced pressure to obtain 89.3 (0.350 g, Yield: 45.06%), MS (ES): m/z 243.0 [M+H]$^+$.

Synthesis of Compound 89.4

Compound was synthesized as per experimental protocol of core synthesis B to obtain 89.4 (Yield: 66.51%), MS (ES): m/z 416.17 [M+H]$^+$.

Synthesis of Compound 89.5

Compound was synthesized using general procedure A to obtain 89.5 (0.2 g, Yield: 51.88%), MS (ES): m/z 534.2 [M+H]$^+$.

Synthesis of Compound 89.6

To a solution of compound 89.5 (0.2 g, 0.37 mmol, 1.0 eq) in tetrahydrofuran (2 mL) were added N,N-diisopropylethylamine (0.2 mL, 1.1 mmol, 3.0 eq), Trimethylaluminium (2M in hexane, 0.92 mL, 1.85 mmol, 5.0 eq) and Methylamine (2M in tetrahydrofuran, 0.55 mL, 1.1 mmol, 3.0 eq) at 0° C. Reaction mixture was stirred at 70° C. for 5 h. After completion of reaction, reaction mixture was transferred into ice cold water and product was extracted with ethyl acetate. Organic layer was combined, washed with brine solution, dried over sodium sulfate and concentrated under reduced pressure to obtain crude material. This was further purified by 2.5% methanol in dichloromethane to obtain 89.6. (0.122 g, Yield: 61.11%), MS (ES): m/z 533.2 [M+H]$^+$.

Synthesis of Compound 89.7

Compound was synthesized using general procedure B to obtain 89.7 (0.052 g, Yield: 64.63%), MS (ES): m/z 353.15 [M+H]$^+$.

Synthesis of Compound I-92

Compound was synthesized using general procedure C to obtain I-92 (0.025 g, Yield: 40.29%), MS (ES): 421.51 [M+H]$^+$ LCMS purity: 95.65%, HPLC purity: 95.00%, $^1$H NMR (DMSO-d$_6$, 400 MHZ): 12.10 (s, 1H), 11.35 (s, 1H), 8.35 (bs, 1H), 8.29 (s, 1H), 7.67-7.65 (d, J=7.6 Hz, 1H), 7.50-7.48 (d, J=8.4 Hz, 1H), 7.41 (s, 1H), 3.96 (s, 3H), 2.85-2.83 (d, J=4.4 Hz, 3H), 2.55 (s, 3H), 1.14-1.11 (t, J=7.2 Hz, 1H), 0.98-0.86 (m, 4H).

Example 90: N-methyl-7-((1-methyl-1H-pyrazol-3-yl)amino)-2-phenyl-1H-pyrrolo[2,3-c]pyridine-4-carboxamide (I-93)

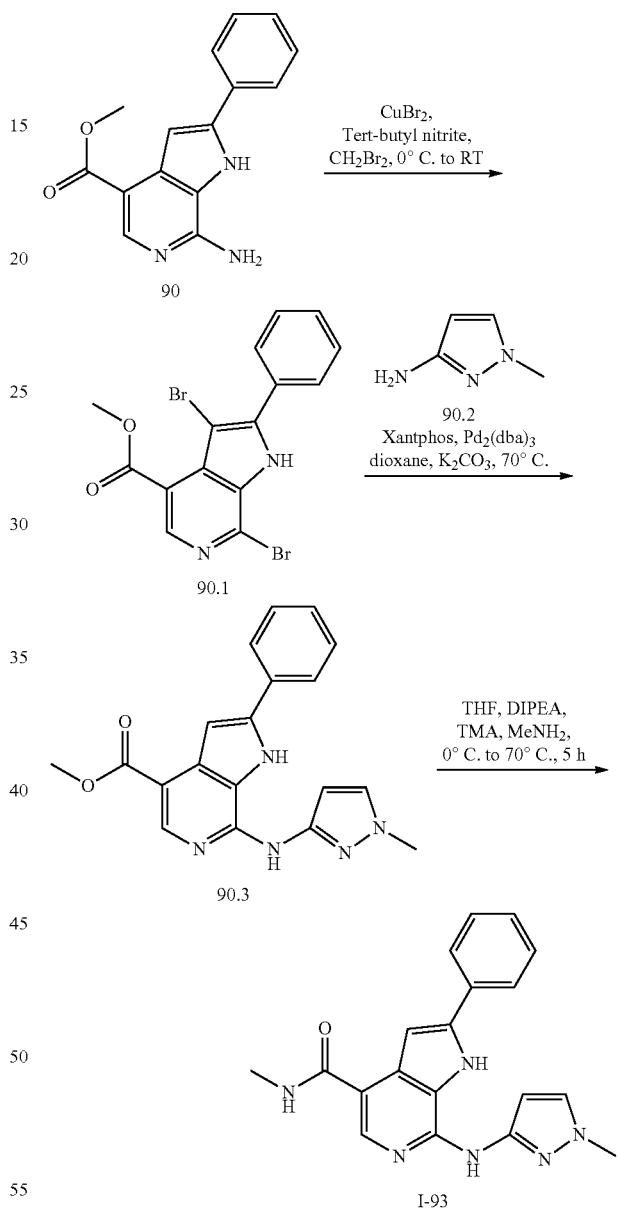

Synthesis of Compound 90

Compound was synthesized as per experimental protocol I-1 to obtain 90. MS (ES): m/z 268.10 [M+H]$^+$.

Synthesis of Compound 90.1

To a solution of compound 90 (0.4 g, 1.49 mmol, 1.0 eq) in dichloromethane (5 mL) was added tert-Butyl nitrite (0.168 g, 1.63 mmol, 1.1 eq) and Copper(II) bromide (0.166 g, 0.74 mmol, 0.5 eq). The reaction mixture was stirred at room temperature for 2 h. After completion of reaction, reaction mixture was transferred into water and product was extracted with ethyl acetate. Organic layer was combined, washed with brine solution, dried over sodium sulfate and concentrated under reduced pressure to obtain 90.1. (0.150 g, Yield: 24.44%). MS(ES): m/z 410.07 [M+H]$^+$.

Synthesis of Compound 90.3

To a solution of 90.1 (0.150 g, 0.36 mmol, 1.0 eq) in 1,4-dioxane (5 mL) was added 90.2 (0.042 g, 0.43 mmol, 1.2 eq), and potassium carbonate (0.1 g, 0.73 mmol, 2.0 eq). The reaction mixture was degassed for 10 min. under argon atmosphere, then tris(dibenzylideneacetone)dipalladium(0) (0.016 g, 0.018 mmol, 0.05 eq) and 4,5-Bis(diphenylphosphino)-9,9-dimethylxanthene (0.021 g, 0.036 mmol, 0.1 eq) were added, and degassed for 5 min. The reaction was stirred at 70° C. for 4 h. After completion of reaction, reaction mixture was cooled to room temperature, transferred into water and product was extracted with ethyl acetate. Organic layer was combined, washed with brine solution, dried over sodium sulfate and concentrated under reduced pressure to obtain crude material. This was further purified by combi flash using 2.3% methanol in dichloromethane as eluant to obtain pure 90.2 (0.064 g, Yield: 50.37%). MS(ES): m/z 348.14 [M+H]$^+$.

Synthesis of Compound I-93

To a solution of compound 90.2 (0.064 g, 0.18 mmol, 1.0 eq) in tetrahydrofuran (3 mL) were added N,N-Diisopropylethylamine (0.09 mL, 0.54 mmol, 3.0 eq), Trimethylaluminium (2M in hexane, 0.45 mL, 0.9 mmol, 5.0 eq) and Methylamine (2M in tetrahydrofuran, 0.27 mL, 0.54 mmol, 3.0 eq) at 0° C. Reaction mixture was stirred at 70° C. for 5 h. After completion of reaction, reaction mixture was transferred into ice cold water and product was extracted with ethyl acetate. Organic layer was combined, washed with brine solution, dried over sodium sulfate and concentrated under reduced pressure to obtain crude material. This was further purified by combi flash using 2.5% methanol in dichloromethane to obtain I-93 (0.028 g, Yield: 43.87%), MS (ES): m/z 347.39 [M+H]$^+$, LCMS purity: 99.38%, HPLC purity: 98.44%, $^1$H NMR (DMSO-d$_6$, 400 MHZ): 11.79 (s, 1H), 9.60 (bs, 1H), 8.19 (s, 1H), 8.08-8.07 (d, J=4.4 Hz, 1H), 7.87-7.86 (d, J=7.2 Hz, 2H), 7.59-7.52 (m, 3H), 7.42-7.39 (m, 1H), 7.31 (s, 1H), 6.84 (s, 1H), 3.79 (s, 3H), 2.82-2.81 (d, J=4 Hz, 3H).

Example 91: 7-(cyclopropanecarboxamido)-2-(2-fluoro-3-((1r,3r)-3-methoxycyclobutyl)phenyl)-N-methyl-1H-pyrrolo[2,3-c]pyridine-4-carboxamide (I-94)

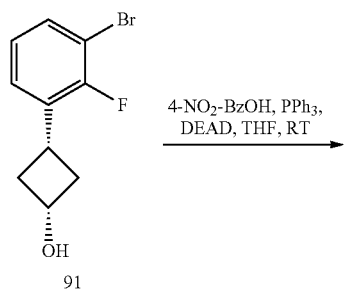

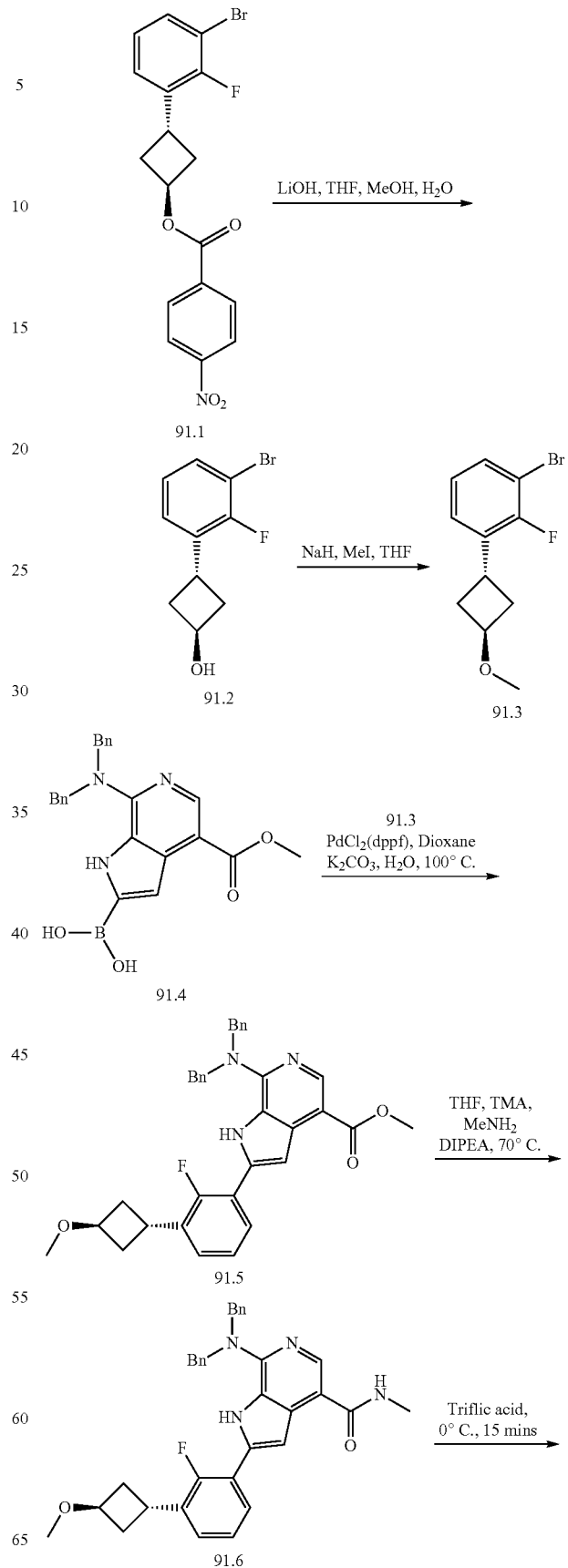

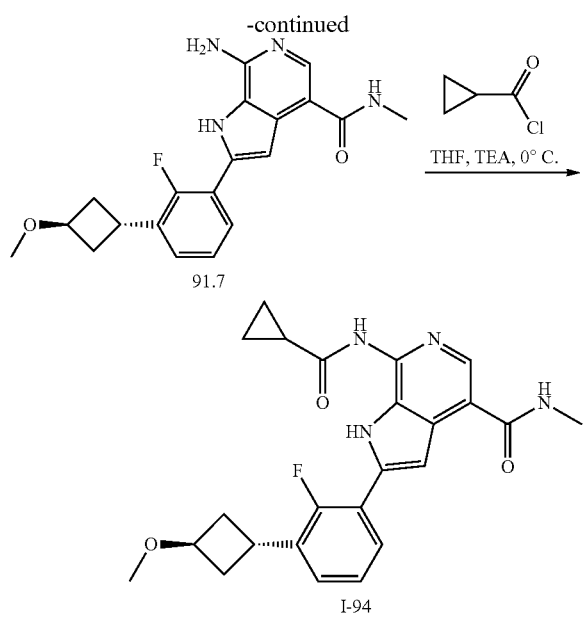

Synthesis of Compound 91

Compound was synthesized as per experimental protocol 1-91 to obtain 91 (Yield: 89.26%). MS (ES): m/z 245.9 [M+H]⁺.

Synthesis of Compound 91.1

To a solution of 91 (0.5 g, 2.04 mmol, 1.0 eq) and 4-nitrobenzoic acid (0.681 g, 4.08 mmol, 2.0 eq) in tetrahydrofuran (10 mL) was added triphenylphosphine (1.6 g, 6.12 mmol, 3.0 eq) and Diisopropyl azodicarboxylate (1.2 g, 6.12 mmol, 3.0 eq) at 0° C. The reaction mixture was stirred at room temperature for 6 h. After completion of reaction, reaction mixture was transferred into water and product was extracted with ethyl acetate. Organic layer was combined, washed with brine solution, dried over sodium sulfate and concentrated under reduced pressure to obtain crude material. This was further purified by column chromatography and the compound was eluted in 20% ethyl acetate in hexane to obtain 91.1 (0.5 g, Yield: 90.08%). MS(ES): m/z 394.2 [M+H]⁺.

Synthesis of Compound 91.2

To a solution of 91.1 (0.5 g, 1.26 mmol, 1.0 eq), in tetrahydrofuran:methanol:water (16 mL, 2:1) was added lithium hydroxide (0.264 g, 6.3 mmol, 5.0 eq). The reaction was stirred at room temperature for 16 h. After completion of reaction, reaction mixture was concentrated under reduced pressure to obtain residue. To this was added water and was acidified with 1N hydrochloric acid to adjust pH~6-6.5 at 10° C. Product was extracted with dichloromethane. Organic layer was combined, washed with brine solution, dried over sodium sulfate and concentrated under reduced pressure to obtain crude material. This was further purified by column chromatography and compound was eluted in 2.1% methanol in dichloromethane to obtain pure 91.2 (0.230 g, Yield: 73.98%). MS(ES): m/z 245.09 [M+H]⁺.

Synthesis of Compound 91.3

To a solution of 91.2 (0.205 g, 0.83 mmol, 1.0 eq) in N,N-Dimethylformamide (4 mL), was added portionwise sodium hydride (0.04 g, 1.66 mmol, 2 eq) at 0° C. and stirred for 20 min. Methyl iodide (0.130 g, 0.91 mmol, 1.1 eq) was added and reaction mixture was stirred at room temperature for 2 h. After completion of reaction, reaction mixture was transferred into ice, stirred and extracted with diethyl ether. Organic layer was combined, dried over sodium sulfate and concentrated under reduced pressure to obtain crude material. This was further purified by column chromatography and compound was eluted in 1.2% methanol in dichloromethane to obtain pure 91.3 (0.143 g, Yield: 65.98%). MS (ES): m/z 259.1 [M+H]⁺.

Synthesis of Compound 91.4

Compound was synthesized as per experimental protocol of core synthesis to obtain 91.4 (Yield: 66.51%). MS (ES): m/z 416.1 [M+H]⁺.

Synthesis of Compound 91.5

Compound was synthesized using general procedure A to obtain 91.5 (0.122 g, Yield: 36.87%), MS (ES): m/z 550.2 [M+H]⁺.

Synthesis of Compound 91.6

To a solution of compound 91.5 (0.122 g, 0.22 mmol, 1.0 eq) in tetrahydrofuran (3 mL) were added N,N-Diisopropylethylamine (0.12 mL, 0.66 mmol, 3.0 eq), Trimethylaluminium (2M in hexane, 0.55 mL, 1.1 mmol, 5.0 eq) and Methylamine (2M in tetrahydrofuran, 0.33 mL, 0.66 mmol, 3.0 eq) at 0° C. Reaction mixture was stirred at 70° C. for 5 h. After completion of reaction, reaction mixture was transferred into ice cold water and product was extracted with ethyl acetate. Organic layer was combined, washed with brine solution, dried over sodium sulfate and concentrated under reduced pressure to obtain crude material. This was further purified by 2.2% methanol in dichloromethane to obtain 91.6 (0.106 g, Yield: 87.04%), MS (ES): m/z 549.2 [M+H]⁺.

Synthesis of Compound 91.7

Compound was synthesized using general procedure B to obtain 91.7 (0.070 g, Yield: 98.35%), MS (ES): m/z 369.1 [M+H]⁺.

Synthesis of Compound I-94

Compound was synthesized using general procedure C to obtain I-94 (0.025 g, Yield: 30.14%), MS (ES): m/z 437.52 [M+H]⁺, LCMS purity 96.87%, HPLC purity: 97.70%, ¹H NMR (DMSO-d₆, 400 MHZ): 11.99 (s, 1H), 11.29 (s, 1H), 8.38-8.37 (d, J=4.8 Hz, 1H), 8.31 (s, 1H), 7.82-7.78 (t, J=6.8 Hz, 1H), 7.54-7.50 (t, J=7.2 Hz, 1H), 7.44 (bs, 1H), 7.38-7.34 (t, J=8 Hz, 1H), 4.07-4.04 (m, 1H), 3.86-3.82 (m, 1H), 3.21 (s, 3H), 3.85-3.84 (d, J=4 Hz, 3H), 2.44-2.40 (m, 3H), 2.26 (bs, 1H), 0.99-0.94 (m, 3H), 0.87 (bs, 2H).

Example 92: 7-(cyclopropanecarboxamido)-2-(2-fluoro-3-(tetrahydrofuran-2-yl)phenyl)-N-methyl-1H-pyrrolo[2,3-c]pyridine-4-carboxamide (I-95)

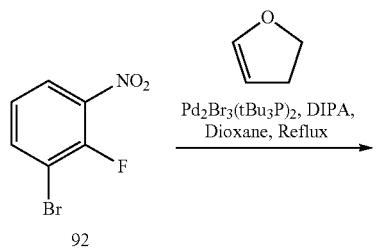

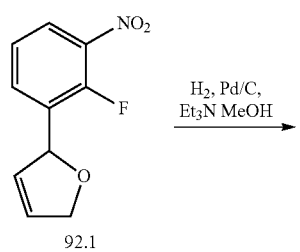

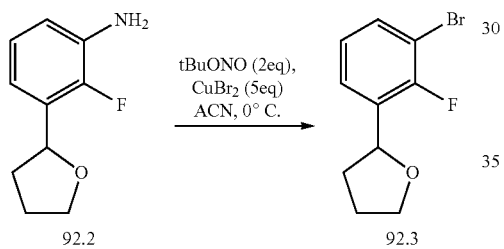

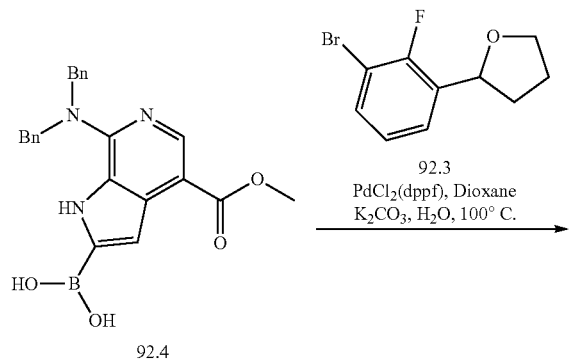

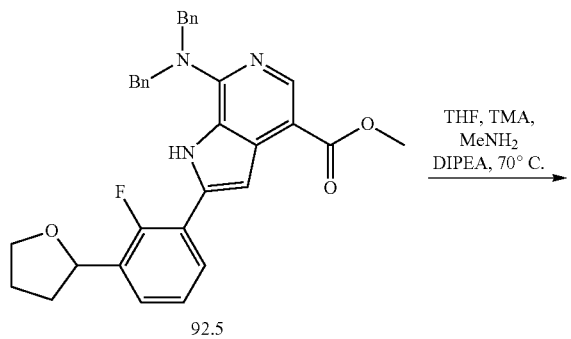

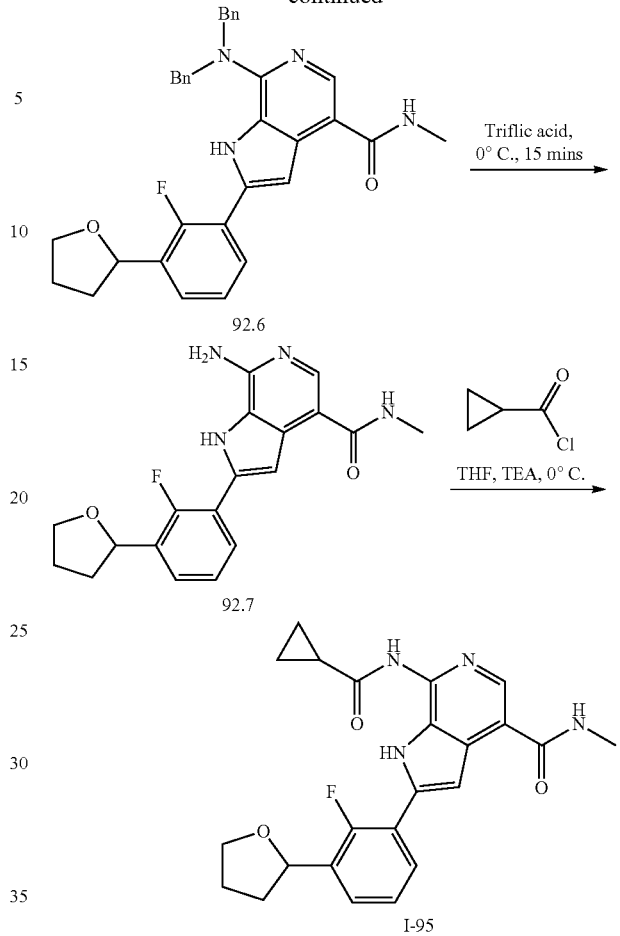

Synthesis of Compound 92.1

To a solution of compound 92 (5.0 g, 22.72 mmol, 1.0 eq) in 1,4-dioxane (25 ml) was added 2,3-dihydrofuran (7.9 g, 113.6 mmol, 5.0 eq) and N,N-Diisopropylethylamine (4.1 mL, 22.72 mmol, 1.0 eq). The reaction mixture was degassed for 10 min under argon atmosphere, then Bromo (tri-tert-butylphosphine)palladium(I) dimer (0.176 g, 0.22 mmol, 0.01 eq) was added, and degassed for 5 min. The reaction was refluxed at 120° C. for 6 h. After completion of reaction, reaction mixture was filtered through Celite-bed and washed with ethyl acetate. Filtrate was concentrated under reduced pressure to obtain crude material. This was further purified by combi flash using 5% ethyl acetate in hexane as eluant to obtain pure 92.1 (2.7 g, Yield: 56.79%). MS(ES): m/z 209.05[M+H]$^+$.

Synthesis of Compound 92.2

Palladium hydroxide on carbon (20%, 0.6 g) was added to a solution of 92.1 (2.7 g, 12.91 mmol, 1.0 eq) in methanol (30 mL). Then Triethylamine (1.86 mL, 12.91 mmol, 1.0 eq) was added to the reaction mixture and hydrogen was purged through reaction mixture for 5 h at room temperature. After completion of reaction, reaction mixture was filtered through Celite-bed and washed with methanol. Filtrate was concentrated under reduced pressure to obtain crude material. This was further purified by trituration with n-pentane to obtain pure 92.2 (0.8 g, Yield: 34.20%). MS (ES): m/z 181.09 [M+H]$^+$.

Synthesis of Compound 92.3

To a solution of compound 92.2 (0.8 g, 4.41 mmol, 1.0 eq) in acetonitrile (10 ml) was added copper(II) bromide (4.9 g, 22.05 mmol, 5.0 eq) and tert-butyl nitrite (0.908 g, 8.82 mmol, 2.0 eq). The reaction was stirred at room temperature for 2 h. After completion of reaction, reaction mixture was transferred into water and product was extracted with ethyl acetate. Organic layer was combined, washed with brine solution, dried over sodium sulfate and concentrated under reduced pressure to obtain 92.3 (0.730 g, Yield: 67.47%). MS(ES): m/z 245.09 [M+H]$^+$.

Synthesis of Compound 92.4

Compound was synthesized as per experimental protocol of core synthesis B to obtain 92.4 (Yield: 66.51%). MS (ES): m/z 416.1 [M+H]$^+$.

Synthesis of Compound 92.5

Compound was synthesized using general procedure A to obtain 92.5 (0.165 g, Yield: 25.58%), MS (ES): m/z 535.2 [M+H]$^+$.

Synthesis of Compound 92.6

To a solution of compound 92.5 (0.165 g, 0.30 mmol, 1.0 eq) in tetrahydrofuran (5 mL) were added N,N-Diisopropylethylamine (0.16 mL, 0.9 mmol, 3.0 eq), Trimethylaluminium (2M in hexane, 0.75 mL, 1.5 mmol, 5.0 eq) and Methylamine (2M in tetrahydrofuran, 0.45 mL, 0.9 mmol, 3.0 eq) at 0° C. Reaction mixture was stirred at 70° C. for 5 h. After completion of reaction, reaction mixture was transferred into ice cold water and product was extracted with ethyl acetate. Organic layer was combined, washed with brine solution, dried over sodium sulfate and concentrated under reduced pressure to obtain crude material. This was further purified by 2.3% methanol in dichloromethane to obtain 92.6 (0.135 g, Yield: 81.97%). MS(ES): m/z 534.2 [M+H]$^+$.

Synthesis of Compound 92.7

Compound was synthesized using general procedure B to obtain 92.7 (0.085 g, Yield: 84.99%), MS (ES): m/z 355.1 [M+H]$^+$.

Synthesis of Compound I-95

Compound was synthesized using general procedure C to obtain I-95 (0.013 g, Yield: 12.83%), MS (ES): m/z 423.31 [M+H]$^+$, LCMS purity: 96.60%, HPLC purity: 97.82%, $^1$H NMR (DMSO-d$_6$, 400 MHZ): 12.01 (s, 1H), 11.29 (s, 1H), 8.38-8.37 (d, J=4.8 Hz, 1H), 8.31 (s, 1H), 7.88-7.84 (t, J=7.2 Hz, 1H), 7.53-7.49 (m, 1H), 7.45 (s, 1H), 7.38-7.34 (t, J=7.6 Hz, 1H), 5.18-5.15 (t, J=6.8 Hz, 1H), 4.06-4.03 (m, 1H), 3.89-3.86 (m, 1H), 2.85-2.84 (d, J=4.4 Hz, 3H), 2.26 (bs, 1H), 2.01-1.96 (m, 2H), 1.79-1.74 (m, 1H), 1.24 (s, 1H), 0.96-0.94 (m, 4H).

Example 93: 7-(cyclopropanecarboxamido)-N-methyl-2-(piperidin-1-yl)-1H-pyrrolo[2,3-c]pyridine-4-carboxamide (I-96)

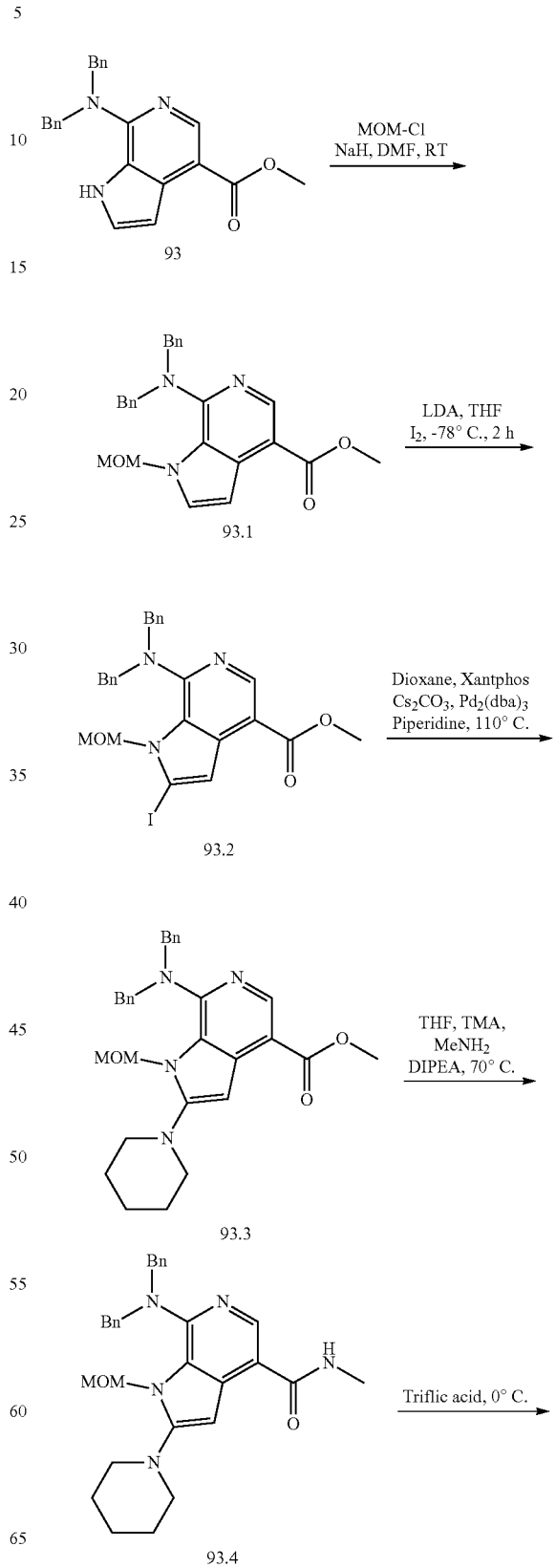

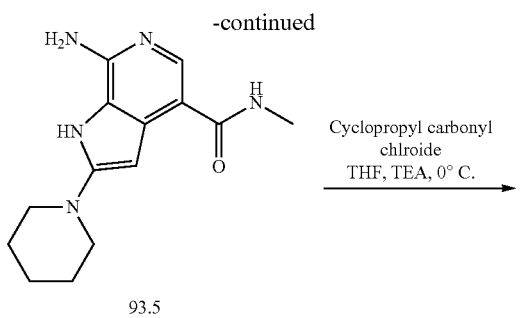

Cyclopropyl carbonyl chlroide
THF, TEA, 0° C.

93.5

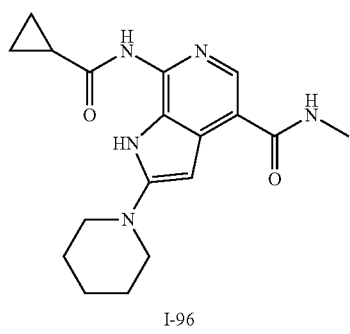

I-96

Synthesis of Compound 93

Compound was synthesized as per experimental protocol of core synthesis A to obtain 93. (Yield: 79.93%). MS (ES): m/z 372.17 [M+H]$^+$.

Synthesis of Compound 93.1

To a solution of 93 (2.0 g, 5.39 mmol, 1.0 eq) in N,N-Dimethylformamide (30 mL), was added portionwise sodium hydride (0.258 g, 10.78 mmol, 2 eq) at 0° C. and stirred for 30 min. Chloromethyl methyl ether (0.646 g, 8.08 mmol, 1.5 eq) dissolved in N,N-Dimethylformamide (1 mL) was added dropwise into the reaction mixture and stirred at 50° C. for 16 h. After completion of reaction, reaction mixture was transferred into cold water, stirred and extracted with ethyl acetate. Organic layer was combined, dried over sodium sulfate and concentrated under reduced pressure to obtain crude material. This was further purified by column chromatography and compound was eluted in 12% ethyl acetate in hexane to obtain pure 93.1 (1.9 g, Yield: 84.93%). MS (ES): m/z 416.1 [M+H]$^+$.

Synthesis of Compound 93.2

A solution of compound 93.1 (1.9 g, 4.57 mmol, 1.0 eq) in tetrahydrofuran (30 mL) was cooled at −78° C. and Lithium diisopropylamide (2.0 mL, 13.71 mmol, 3.0 eq) was added dropwise, and stirred for 2 h at same temperature. Then iodine in tetrahydrofuran (4.6 g, 18.28 mmol, 4.0 eq) was added and stirred for 2 h at same temperature. After completion of reaction, reaction mixture was transferred into cold water, stirred and extracted with ethyl acetate. Organic layer was combined, dried over sodium sulfate and concentrated under reduced pressure to obtain crude material. This was further purified by column chromatography and compound was eluted in 8% ethyl acetate in hexane to obtain pure 93.2 (0.8 g, Yield: 32.31%). MS (ES): m/z 541.09 [M+H]$^+$.

Synthesis of Compound 93.3

To a solution of 93.2 (0.8 g, 1.47 mmol, 1.0 eq) in 1,4-dioxane (20 mL) was added Piperidine (0.252 g, 2.94 mmol, 2.0 eq), and cesium carbonate (1.1 g, 3.67 mmol, 2.5 eq). The reaction mixture was degassed for 10 min. under argon atmosphere, then tris(dibenzylideneacetone)dipalladium(0) (0.134 g, 0.14 mmol, 0.1 eq) and 4,5-Bis(diphenylphosphino)-9,9-dimethylxanthene (0.169 g, 0.29 mmol, 0.2 eq) were added, and degassed for 5 min. The reaction was stirred at 110° C. for 4 h. After completion of reaction, reaction mixture was cooled to room temperature, transferred into water and product was extracted with ethyl acetate. Organic layer was combined, washed with brine solution, dried over sodium sulfate and concentrated under reduced pressure to obtain crude material. This was further purified by combi flash using 25% ethyl acetate in hexane as eluant to obtain pure 93.3 (0.127 g, Yield: 17.24%). MS(ES): m/z 498.2 [M+H]$^+$.

Synthesis of Compound 93.4

To a solution of compound 93.3 (0.127 g, 0.25 mmol, 1.0 eq) in tetrahydrofuran (3 mL) were added N,N-Diisopropylethylamine (0.13 mL, 0.75 mmol, 3.0 eq), Trimethylaluminium (2M in hexane, 0.62 mL, 1.25 mmol, 5.0 eq) and Methylamine (2M in tetrahydrofuran, 0.37 mL, 0.75 mmol, 3.0 eq) at 0° C. Reaction mixture was stirred at 70° C. for 5 h. After completion of reaction, reaction mixture was transferred into ice cold water and product was extracted with ethyl acetate. Organic layer was combined, washed with brine solution, dried over sodium sulfate and concentrated under reduced pressure to obtain crude material. This was further purified by 2.4% methanol in dichloromethane to obtain 93.4 (0.099 g, Yield: 78.11%), MS (ES): m/z 497.2 [M+H]$^+$.

Synthesis of Compound 93.5

Compound was synthesized using general procedure B to obtain 93.5 (0.045 g, Yield: 82.75%), MS (ES): m/z 273.16 [M+H]$^+$.

Synthesis of Compound I-96

Compound was synthesized using general procedure C to obtain I-96 (0.031 g, Yield: 55.15%), MS (ES): m/z 342.50 [M+H]$^+$, LCMS purity: 100%, HPLC purity: 99.02%, $^1$H NMR (DMSO-d$_6$, 400 MHZ): 10.88 (bs, 1H), 10.77 (s, 1H), 8.14 (s, 1H), 8.04-8.03 (d, J=4.4 Hz, 1H), 6.01 (s, 1H), 3.25 (bs, 4H), 2.78-2.77 (d, J=4.4 Hz, 3H), 2.16 (bs, 1H), 1.62 (bs, 6H), 0.91 (bs, 1H), 0.88-0.86 (m, 3H).

Example 94: 2-(2-fluoro-3-(1-methyl-1H-pyrazol-4-yl)phenyl)-N-methyl-7-((1-methyl-1H-pyrazol-3-yl)amino)-1H-pyrrolo[2,3-c]pyridine-4-carboxamide (I-97)
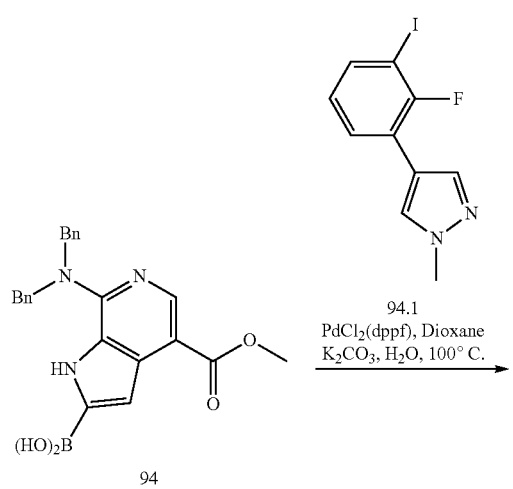
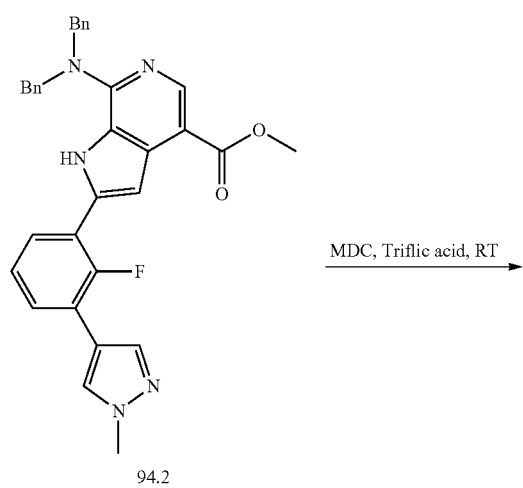
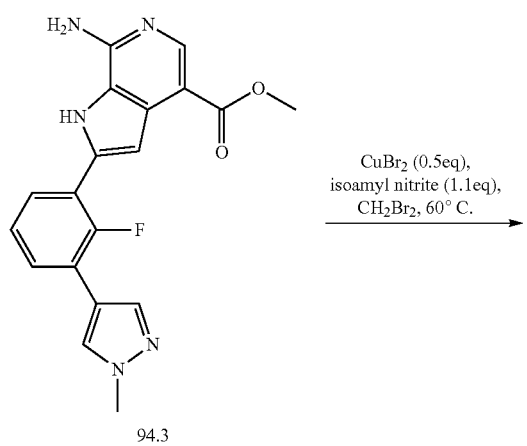
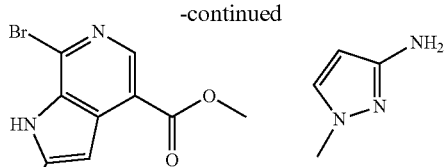
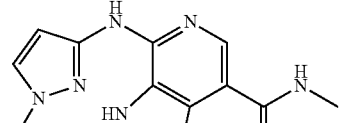
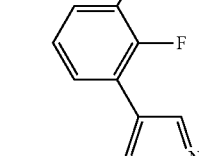
Synthesis of Compound 94
Compound was synthesized as per experimental protocol of core synthesis B to obtain 94 (Yield: 66.51%). MS (ES): m/z 416.1 [M+H]$^+$.
Synthesis of Compound 94.1
Compound was synthesized as per experimental protocol 1-19 to obtain 94.1 (Yield: 46.79%). MS (ES): m/z 302.9 [M+H]$^+$.

Synthesis of Compound 94.2

Compound was synthesized using general procedure A to obtain 94.2 (0.272 g, Yield: 60.89%), MS (ES): m/z 545.2 [M+H]$^+$.

Synthesis of Compound 94.3

Compound was synthesized using general procedure B to obtain 94.3 (0.170 g, Yield: 93.33%), MS (ES): m/z 365.1 [M+H]$^+$.

Synthesis of Compound 94.4

To a solution of compound 94.3 (0.120 g, 0.32 mmol, 1.0 eq) in Dibromomethane (3 mL) was added Isoamyl nitrite (0.041 g, 0.35 mmol, 1.1 eq) and Copper(II) bromide (0.035 g, 0.16 mmol, 0.5 eq) The reaction was stirred at room temperature for 2 h. After completion of reaction, reaction mixture was transferred into water and product was extracted with ethyl acetate. Organic layer was combined, washed with brine solution, dried over sodium sulfate and concentrated under reduced pressure to obtain 94.4. (0.055 g, Yield: 39.01%). MS(ES): m/z 430.03 [M+H]$^+$.

Synthesis of Compound 94.6

To a solution of 94.4 (0.055 g, 0.12 mmol, 1.0 eq) in 1,4-dioxane (2 mL) was added 94.5 (0.023 g, 0.24 mmol, 2.0 eq), and Potassium carbonate (0.041 g, 0.3 mmol, 2.5 eq). The reaction mixture was degassed for 10 min. under argon atmosphere, then tris(dibenzylideneacetone)dipalladium(0) (0.010 g, 0.012 mmol, 0.1 eq) and 4,5-Bis(diphenylphosphino)-9,9-dimethylxanthene (0.013 g, 0.02 mmol, 0.2 eq) were added, and degassed for 5 min. The reaction was stirred at 100° C. for 4 h. After completion of reaction, reaction mixture was cooled to room temperature, transferred into water and product was extracted with ethyl acetate. Organic layer was combined, washed with brine solution, dried over sodium sulfate and concentrated under reduced pressure to obtain crude material. This was further purified by combi flash using 28% ethyl acetate in hexane as eluant to obtain pure 94.6. (0.037 g, Yield: 64.82%). MS(ES): m/z 446.17 [M+H]$^+$.

Synthesis of Compound I-97

To a solution of compound 94.6 (0.037 g, 0.083 mmol, 1.0 eq) in tetrahydrofuran (54 mL) were added N,N-Diisopropylethylamine (0.045 mL, 0.24 mmol, 3.0 eq), Trimethylaluminium (2M in hexane, 0.2 mL, 0.41 mmol, 5.0 eq) and Methylamine (2M in tetrahydrofuran, 0.12 mL, 0.24 mmol, 3.0 eq) at 0° C. Reaction mixture was stirred at 70° C. for 8 h. After completion of reaction, reaction mixture was transferred into ice cold water and product was extracted with ethyl acetate. Organic layer was combined, washed with brine solution, dried over sodium sulfate and concentrated under reduced pressure to obtain crude material. This was further purified by 2.2% methanol in dichloromethane to obtain I-97 (0.019 g, Yield: 51.47%), MS (ES): m/z 445.35 [M+H]$^+$, LCMS purity: 100%, HPLC purity: 99.76%, $^1$H NMR (DMSO-d$_6$, 400 MHZ): 11.81 (s, 1H), 9.79 (s, 1H), 8.28 (s, 1H), 8.21 (s, 1H), 8.15 (bs, 1H), 8.00 (s, 1H), 7.76-7.74 (d, J=8.4 Hz, 2H), 7.59 (bs, 1H), 7.42-7.37 (m, 2H), 6.85 (s, 1H), 3.93 (s, 3H), 3.79 (s, 3H), 2.81-2.80 (d, J=3.2 Hz, 3H).

Example 95: 7-(cyclopropanecarboxamido)-2-(4-(3,3-difluoroazetidine-1-carbonyl)-2-fluorophenyl)-N-methyl-1H-pyrrolo[2,3-c]pyridine-4-carboxamide (I-98)

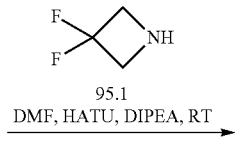

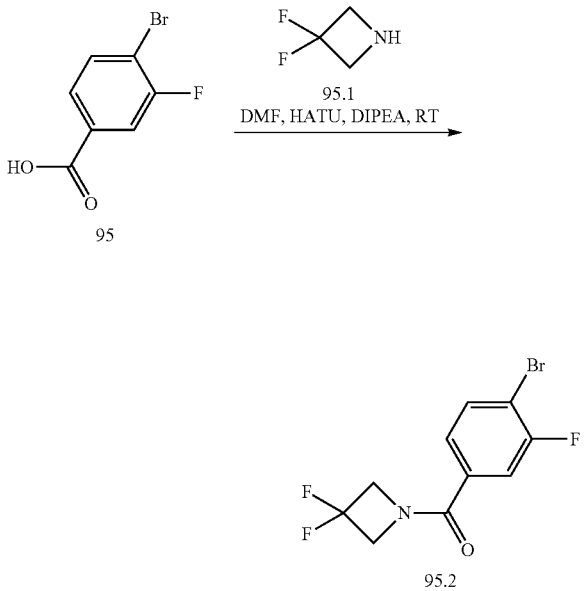

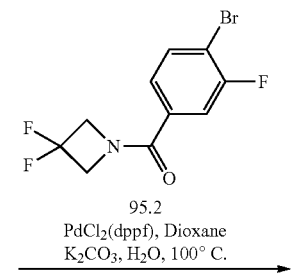

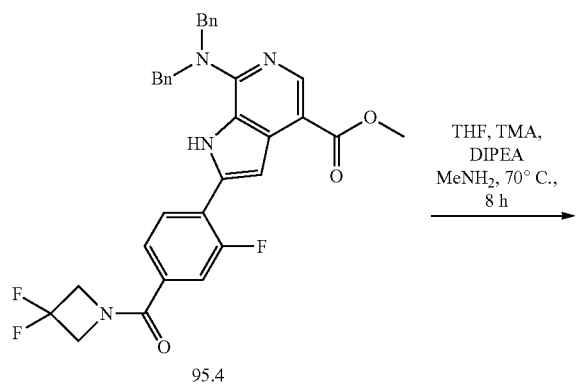

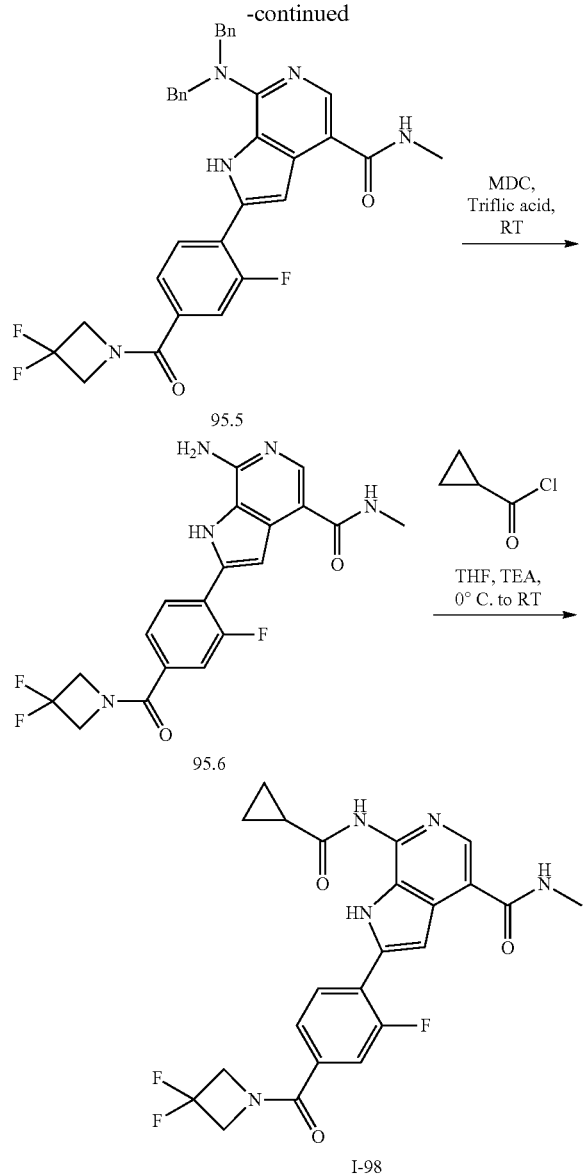

Synthesis of Compound 95.2

To a solution of 95 (1.0 g, 4.60 mmol, 1.0 eq), in N,N-dimethylformamide (20 mL) was added 1-[Bis(dimethylamino)methylene]-1H-1,2,3-triazolo[4,5-b]pyridinium 3-oxid hexafluorophosphate (3.4 g, 9.2 mmol, 2.0 eq) and the reaction was stirred at room temperature for 15 min. To this added was added diisopropylethylamine (2.54 mL, 13.8 mmol, 3.0 eq) followed by addition of 95.1 (0.593 g, 4.60 mmol, 1.0 eq). The reaction mixture was stirred at room temperature for 5 min. After completion of reaction, reaction mixture was transferred into water and product was extracted with ethyl acetate. Organic layer was combined, washed with brine solution, dried over sodium sulfate and concentrated under reduced pressure to obtain crude material. This was further purified by column chromatography and the compound was eluted in 40% ethyl acetate in hexane to obtain 95.2 (0.640 g, Yield: 47.66%). MS(ES): m/z 294.07 [M+H]$^+$.

Synthesis of Compound 95.3

Compound was synthesized as per experimental protocol of core synthesis B to obtain 95.3 (Yield: 66.51%). MS (ES): m/z 416.1 [M+H]$^+$.

Synthesis of Compound 95.4

Compound was synthesized using general procedure A to obtain 95.4 (0.150 g, Yield: 26.64%), MS (ES): m/z 585.2 [M+H]$^+$.

Synthesis of Compound 95.5

To a solution of compound 95.4 (0.150 g, 0.25 mmol, 1.0 eq) in tetrahydrofuran (5 mL) were added N,N-Diisopropylethylamine (0.096 mL, 0.75 mmol, 3.0 eq), Trimethylaluminium (2M in hexane, 0.62 mL, 1.25 mmol, 5.0 eq) and Methylamine (2M in tetrahydrofuran, 0.37 mL, 0.75 mmol, 3.0 eq) at 0° C. Reaction mixture was stirred at 70° C. for 8 h. After completion of reaction, reaction mixture was transferred into ice cold water and product was extracted with ethyl acetate. Organic layer was combined, washed with brine solution, dried over sodium sulfate and concentrated under reduced pressure to obtain crude material. This was further purified by 2.2% methanol in dichloromethane to obtain 95.5 (0.095 g, Yield: 63.44%). MS(ES): m/z 583.2 [M+H]$^+$.

Synthesis of Compound 95.6

Compound was synthesized using general procedure B to obtain 95.6 (0.060 g, Yield: 91.38%), MS (ES): m/z 403.13 [M+H]$^+$.

Synthesis of Compound I-98

Compound was synthesized using general procedure C to obtain I-98 (0.030 g, Yield: 42.78%), MS (ES): m/z 472.61 [M+H]$^+$, LCMS purity: 100%, HPLC purity: 98.25%, $^1$H NMR (DMSO-d$_6$, 400 MHZ): 12.20 (s, 1H), 11.37 (s, 1H), 8.43 (s, 1H), 8.34 (bs, 1H), 8.11-8.08 (t, J=7.6 Hz, 1H), 7.76-7.70 (m, 2H), 7.58 (s, 1H), 4.91 (bs, 2H), 4.54 (bs, 2H), 2.86-2.85 (d, J=3.2 Hz, 3H), 2.26 (bs, 2H), 1.06-0.96 (m, 3H).

Example 96: 2-(2-fluoro-3-(2-methyloxazol-5-yl)phenyl)-N-methyl-7-((1-methyl-1H-pyrazol-3-yl)amino)-1H-pyrrolo[2,3-c]pyridine-4-carboxamide (I-99)

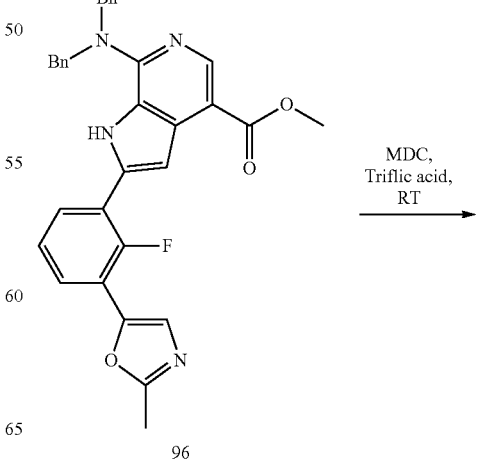

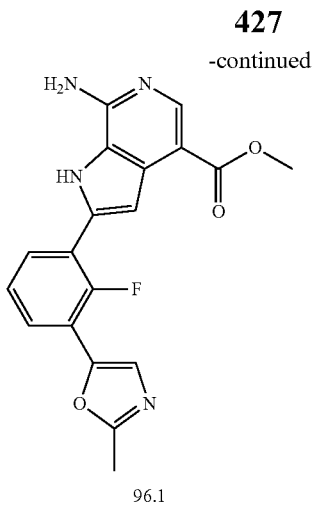

96.1

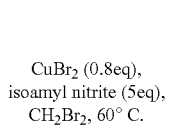

CuBr₂ (0.8eq), isoamyl nitrite (5eq), CH₂Br₂, 60° C.

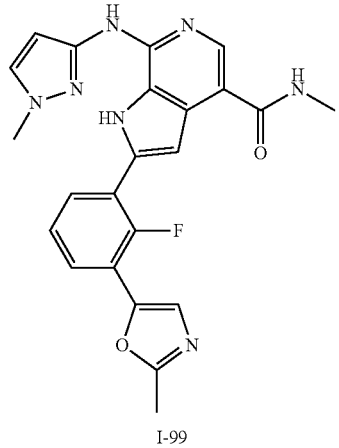

I-99

Synthesis of Compound 96

Compound was synthesized as per experimental protocol 1-81 to obtain 96 (Yield: 45.58%). MS (ES): m/z 546.21 [M+H]⁺.

Synthesis of Compound 96.1

Compound was synthesized using general procedure B to obtain 96.1 (0.2 g, Yield: 45.91%), MS (ES): m/z 366.11 [M+H]⁺.

Synthesis of Compound 96.2

To a solution of compound 96.1 (0.2 g, 0.54 mmol, 1.0 eq) in Dibromomethane (6 mL) was added Isoamyl nitrite (0.315 g, 2.7 mmol, 5.0 eq) and Copper(II) bromide (0.096 g, 0.43 mmol, 0.8 eq) The reaction was stirred at room temperature for 2 h. After completion of reaction, reaction mixture was transferred into water and product was extracted with ethyl acetate. Organic layer was combined, washed with brine solution, dried over sodium sulfate and concentrated under reduced pressure to obtain 96.2 (0.047 g, Yield: 20.01%). MS(ES): m/z 430.01 [M+H]⁺.

Synthesis of Compound 96.4

To a solution of 96.2 (0.047 g, 0.10 mmol, 1.0 eq) in 1,4-dioxane (2 mL) was added 96.3 (0.019 g, 0.2 mmol, 2.0 eq) and Potassium carbonate (0.034 g, 0.25 mmol, 2.5 eq). The reaction mixture was degassed for 10 min. under argon atmosphere, then tris(dibenzylideneacetone)dipalladium(0) (0.010 g, 0.01 mmol, 0.1 eq) and 4,5-Bis(diphenylphosphino)-9,9-dimethylxanthene (0.012 g, 0.02 mmol, 0.2 eq) were added, and degassed for 5 min. The reaction was stirred at 100° C. for 4 h. After completion of reaction, reaction mixture was cooled to room temperature, transferred into water and product was extracted with ethyl acetate. Organic layer was combined, washed with brine solution, dried over sodium sulfate and concentrated under reduced pressure to obtain crude material. This was further purified by combi flash using 28% ethyl acetate in hexane as eluant to obtain pure 96.4. (0.026 g, Yield: 53.31%). MS(ES): m/z 446.15 [M+H]⁺.

Synthesis of Compound I-99

To a solution of compound 96.4 (0.026 g, 0.058 mmol, 1.0 eq) in tetrahydrofuran (5 mL) were added N,N-Diisopropylethylamine (0.032 mL, 0.17 mmol, 3.0 eq), Trimethylaluminium (2M in hexane, 0.14 mL, 0.29 mmol, 5.0 eq) and Methylamine (2M in tetrahydrofuran, 0.08 mL, 0.17 mmol, 3.0 eq) at 0° C. Reaction mixture was stirred at 70° C. for 5 h. After completion of reaction, reaction mixture was transferred into ice cold water and product was extracted with ethyl acetate. Organic layer was combined, washed with brine solution, dried over sodium sulfate and concentrated under reduced pressure to obtain crude material. This was further purified by 2.2% methanol in dichloromethane to obtain I-99 (0.025 g, Yield: 96.37%), MS (ES): m/z 446.61 [M+H]$^+$, LCMS purity: 100%, HPLC purity: 99.05%, $^1$H NMR (DMSO-d$_6$, 400 MHZ): 12.05 (s, 1H), 10.15 (s, 1H), 8.47 (s, 1H), 7.94-7.91 (t, J=7.2 Hz, 1H), 7.83-7.79 (t, J=6.8 Hz, 1H), 7.64-7.63 (d, J=2 Hz, 1H), 7.59-7.58 (d, J=4 Hz, 1H), 7.55-7.51 (t, J=8 Hz, 1H), 7.42 (bs, 1H), 7.09-7.08 (d, J=6.8 Hz, 1H), 6.83 (s, 1H), 3.89 (s, 3H), 3.83 (s, 3H), 2.56 (s, 3H).

Example 97: 2-(3-(5,6-dihydro-8H-imidazo[2,1-c][1,4]oxazin-2-yl)-2-fluorophenyl)-N-methyl-7-((1-methyl-1H-pyrazol-3-yl)amino)-1H-pyrrolo[2,3-c]pyridine-4-carboxamide (I-100)

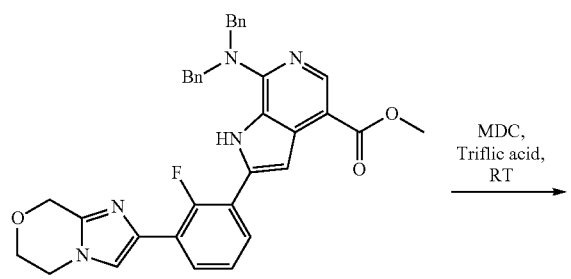

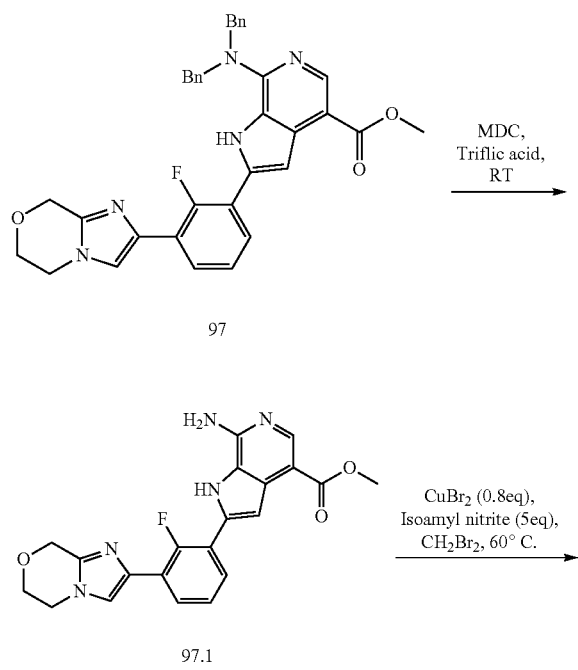

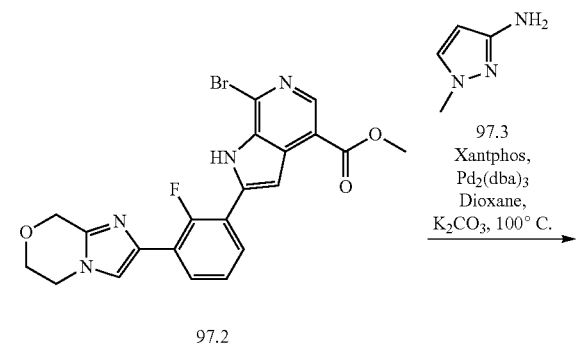

Synthesis of Compound 97

Compound was synthesized as per experimental protocol 1-79 to obtain 97 (Yield: 48.05%). MS (ES): m/z 588.24 [M+H]$^+$.

Synthesis of Compound 97.1

Compound was synthesized using general procedure B to obtain 97.1 (0.310 g, Yield: 85.99%), MS (ES): m/z 408.1 [M+H]$^+$.

Synthesis of Compound 97.2

To a solution of compound 97.1 (0.310 g, 0.76 mmol, 1.0 eq) in Dibromomethane (6 ml) was added Isoamyl nitrite (0.444 g, 3.8 mmol, 5.0 eq) and Copper(II) bromide (0.135 g, 0.60 mmol, 0.8 eq) The reaction was stirred at room temperature for 2 h. After completion of reaction, reaction mixture was transferred into water and product was extracted with ethyl acetate. Organic layer was combined, washed with brine solution, dried over sodium sulfate and concentrated under reduced pressure to obtain 97.2 (0.150 g, Yield: 41.83%). MS(ES): m/z 472.04 [M+H]$^+$.

Synthesis of Compound 97.4

To a solution of 97.2 (0.113 g, 0.23 mmol, 1.0 eq) in 1,4-dioxane (3 mL) was added 97.3 (0.044 g, 0.46 mmol, 2.0 eq), and Potassium carbonate (0.079 g, 0.57 mmol, 2.5 eq). The reaction mixture was degassed for 10 min. under argon atmosphere, then tris(dibenzylideneacetone)dipalladium(0) (0.021 g, 0.023 mmol, 0.1 eq) and 4,5-Bis(diphenylphosphino)-9,9-dimethylxanthene (0.026 g, 0.046 mmol, 0.2 eq) were added, and degassed for 5 min. The reaction was stirred at 100° C. for 4 h. After completion of reaction, reaction mixture was cooled to room temperature, transferred into water and product was extracted with ethyl acetate. Organic layer was combined, washed with brine solution, dried over sodium sulfate and concentrated under reduced pressure to obtain crude material. This was further purified by combi flash using 28% ethyl acetate in hexane as eluant to obtain pure 97.4. (0.057 g, Yield 48.77%). MS(ES): m/z 487.1 [M+H]$^+$.

Synthesis of Compound I-100

To a solution of compound 97.4 (0.057 g, 0.11 mmol, 1.0 eq) in tetrahydrofuran (3 mL) were added N,N-Diisopropylethylamine (0.06 mL, 0.33 mmol, 3.0 eq), Trimethylaluminium (2M in hexane, 0.27 mL, 0.55 mmol, 5.0 eq) and Methylamine (2M in tetrahydrofuran, 0.16 mL, 0.33 mmol, 3.0 eq) at 0° C. Reaction mixture was stirred at 70° C. for 8 h. After completion of reaction, reaction mixture was transferred into ice cold water and product was extracted with ethyl acetate. Organic layer was combined, washed with brine solution, dried over sodium sulfate and concentrated under reduced pressure to obtain crude material. This was further purified by 2.5% methanol in dichloromethane to obtain I-100 (0.025 g, Yield: 43.95%), MS (ES): m/z 487.66 [M+H]$^+$, LCMS purity: 98.80%, HPLC purity: 95.61%, $^1$H NMR (DMSO-d$_6$, 400 MHZ): 11.82 (s, 1H), 9.78 (s, 1H), 8.23 (s, 1H), 8.15 (s, 1H), 78.07-8.05 (d, J=6.4 Hz, 1H), 7.76-7.71 (m, 2H), 7.61 (s, 1H), 7.44-7.40 (m, 2H), 6.86 (s, 1H), 4.84 (s, 2H), 3.81 (s, 3H), 2.83-2.82 (d, J=4.4 Hz, 3H), 1.36-1.34 (d, J=7.6 Hz, 2H), 1.24 (bs, 2H).

Example 98. TYK2 JH2 Domain Binding Assay

Binding constants for compounds of the present invention against the JH2 domain were determined by the following protocol for a KINOMEscan® assay (DiscoveRx). A fusion protein of a partial length construct of human TYK2 (JH2domain-pseudokinase) (amino acids G556 to D888 based on reference sequence NP_003322.3) and the DNA binding domain of NFkB was expressed in transiently transfected HEK293 cells. From these HEK 293 cells, extracts were prepared in M-PER extraction buffer (Pierce) in the presence of Protease Inhibitor Cocktail Complete (Roche) and Phosphatase Inhibitor Cocktail Set II (Merck) per manufacturers' instructions. The TYK2(JH2domain-pseudokinase) fusion protein was labeled with a chimeric double-stranded DNA tag containing the NFkB binding site (5'-GGGAATTCCC-3') fused to an amplicon for qPCR readout, which was added directly to the expression extract (the final concentration of DNA-tag in the binding reaction is 0.1 nM).

Streptavidin-coated magnetic beads (Dynal M280) were treated with a biotinylated small molecule ligand for 30 minutes at room temperature to generate affinity resins for the binding assays. The liganded beads were blocked with excess biotin and washed with blocking buffer (SeaBlock (Pierce), 1% BSA, 0.05% Tween 20, 1 mM DTT) to remove unbound ligand and to reduce nonspecific binding.

The binding reaction was assembled by combining 16 µl of DNA-tagged kinase extract, 3.8 µl liganded affinity beads, and 0.18 µl test compound (PBS/0.05% Tween 20/10 mM DTT/0.1% BSA/2 µg/ml sonicated salmon sperm DNA). Extracts were used directly in binding assays without any enzyme purification steps at a ≥10,000-fold overall stock dilution (final DNA-tagged enzyme concentration <0.1 nM). Extracts were loaded with DNA-tag and diluted into the binding reaction in a two step process. First extracts were diluted 1:100 in 1× binding buffer (PBS/0.05% Tween 20/10 mM DTT/0.1% BSA/2 µg/ml sonicated salmon sperm DNA) containing 10 nM DNA-tag. This dilution was allowed to equilibrate at room temperature for 15 minutes and then subsequently diluted 1:100 in 1× binding buffer. All reactions were performed in polypropylene 384-well plates. Each was a final volume of 0.02 mL. Assays were incubated with shaking for 1 hour at room temperature. Then the beads were pelleted and washed with wash buffer (1×PBS, 0.05% Tween 20) to remove displaced kinase and test compound. The washed based were re-suspended in elution buffer (1×PBS, 0.05% Tween 20, 0.5 µM non-biotinylated affinity ligand) and incubated at room temperature with shaking for 30 minutes. The kinase concentration in the eluates was measured by qPCR. qPCR reactions were assembled by adding 2.5 µL of kinase eluate to 7.5 µL of qPCR master mix containing 0.15 µM amplicon primers and 0.15 µM amplicon probe. The qPCR protocol consisted of a 10 minute hot start at 95° C., followed by 35 cycles of 95° C. for 15 seconds, 60° C. for 1 minute.

Test compounds were prepared as 111× stocks in 100% DMSO. K$_d$ values were determined using an 11-point 3-fold compound dilution series with three DMSO control points. All compounds for K$_d$ measurements are distributed by acoustic transfer (non-contact dispensing) in 100% DMSO. The compounds were then diluted directly into the assays such that the final concentration of DMSO was 0.9%. The K$_d$ values were determined using a compound top concentration of 30,000 nM. K$_d$ measurements were performed in duplicate.

Binding constants (K$_d$s) were calculated with a standard dose-response curve using the Hill equation:

$$\text{Response} = \text{Background} + \frac{(\text{Signal} - \text{Background})}{\left(1 + \left(\frac{Kd^{Hill\ Slope}}{Dose^{Hill\ Slope}}\right)\right)}$$

The Hill Slope was set to −1. Curves were fitted using a non-linear least square fit with the Levenberg-Marquardt algorithm (Levenberg, K., A method for the solution of certain non-linear problems in least squares, *Q. Appl. Math.* 2, 164-168 (1944)).

Results of the TYK2 JH2 Domain Binding Assay are presented in Table 2. Compounds denoted as "A" had a Kd lower than 200 pM; compounds denoted as "B" had a Kd between 200 pM and 1 nM; compounds denoted as "C" had a Kd between 1 nM and 10 nM; and compounds denoted as "D" had a Kd greater than 10 nM.

TABLE 2

Results of Tyk2 JH2 Domain Binding Assay

| Compound | Tyk2 JH2 Kd |
|---|---|
| I-1 | C |
| I-2 | A |
| I-3 | B |
| I-4 | A |
| I-5 | C |
| I-6 | A |
| I-7 | B |
| I-8 | C |
| I-9 | B |
| I-10 | B |
| I-11 | B |
| I-12 | A |
| I-13 | A |
| I-14 | B |
| I-15 | B |
| I-16 | A |

TABLE 2-continued

Results of Tyk2 JH2 Domain Binding Assay

| Compound | Tyk2 JH2 Kd |
|---|---|
| I-17 | B |
| I-18 | B |
| I-19 | A |
| I-20 | B |
| I-21 | A |
| I-22 | A |
| I-23 | A |
| I-24 | A |
| I-25 | A |
| I-26 | A |
| I-27 | A |
| I-28 | B |
| I-29 | B |
| I-30 | A |
| I-31 | C |
| I-32 | B |
| I-33 | B |
| I-34 | A |
| I-35 | B |
| I-36 | A |
| I-37 | C |
| I-38 | C |
| I-39 | C |
| I-40 | C |
| I-41 | C |
| I-42 | A |
| I-43 | B |
| I-44 | A |
| I-45 | B |
| I-46 | B |
| I-47 | A |
| I-48 | A |
| I-49 | A |
| I-50 | B |
| I-51 | B |
| I-52 | A |
| I-53 | B |
| I-54 | A |
| I-55 | B |
| I-56 | B |
| I-57 | C |
| I-58 | A |
| I-59 | B |
| I-60 | A |
| I-61 | D |
| I-62 | A |
| I-63 | B |
| I-64 | D |
| I-65 | A |
| I-66 | A |
| I-67 | A |
| I-68 | A |
| I-69 | A |
| I-70 | B |
| I-71 | D |
| I-72 | D |
| I-73 | A |
| I-74 | A |
| I-75 | A |
| I-76 | A |
| I-77 | A |
| I-78 | A |
| I-79 | A |
| I-80 | A |
| I-81 | A |
| I-82 | D |
| I-83 | A |
| I-84 | A |
| I-85 | B |
| I-86 | A |
| I-87 | A |
| I-88 | A |
| I-89 | B |
| I-90 | A |
| I-91 | A |
| I-92 | A |
| I-93 | B |
| I-94 | A |
| I-95 | A |
| I-96 | D |
| I-97 | A |
| I-98 | A |
| I-99 | A |
| I-100 | A |
| I-101 | B |

Example 99. TYK2 & JAK2 Radioactive Kinase Assay

Peptide substrate, [KKSRGDYMTMQIG], (20 μM) was prepared in reaction buffer (20 mM Hepes pH 7.5, 10 mM $MgCl_2$, 1 mM EGTA, 0.02% Brij35, 0.02 mg/mL BSA, 0.1 mM $Na_3PO_4$, 2 mM DTT, 1% DMSO). TYK2 (Invitrogen) kinase was added, followed by compounds in DMSO. $^{33}$PATP was added to initiate the reaction in ATP at 10 μM. The kinase reaction was incubated for 120 min at room temp and reactions were spotted onto P81 ion exchange paper (Whatman #3698-915), and then washed extensively in 0.75% phosphoric acid, prior to reading the radioactivity counts. For JAK2 (Invitrogen) kinase assay the peptide substrate poly[Glu:Tyr](4:1), 0.2 mg/ml was used, in the reaction carried out the same as for TYK2.

The TYK2 and JAK2 radioactive kinase assay measures the percent inhibition at the TYK2 kinase domain (JH1) and the percent inhibition at the JAK2 kinase domain (JH1). Results of the assay are expressed as percent inhibition at 10 μM.

Results of the TYK2 and JAK2 Radioactive Kinase Assay are presented in Table 3. Compounds denoted as "A" had a percent inhibition at 10 μM lower than 50; compounds denoted as "B" had a percent inhibition at 10 μM between 50 and 70; compounds denoted as "C" had a percent inhibition at 10 μM between 70 and 90; and compounds denoted as "D" had a percent inhibition at 10 μM greater than 90.

TABLE 3

TYK2 & JAK2 Radioactive Kinase Assay

| Compound | TYK2 JH1 % Inhibition @ 10 μM | JAK2 JH1 % Inhibition @ 10 μM |
|---|---|---|
| I-1 | A | A |
| I-2 | A | A |
| I-3 | A | A |
| I-4 | A | A |
| I-5 | A | A |
| I-6 | A | A |
| I-7 | A | A |
| I-8 | A | A |
| I-9 | A | A |
| I-10 | A | A |
| I-11 | A | A |
| I-12 | D | D |
| I-13 | A | A |
| I-14 | A | A |
| I-15 | A | A |
| I-16 | A | A |
| I-17 | A | A |
| I-18 | A | A |

TABLE 3-continued

TYK2 & JAK2 Radioactive Kinase Assay

| Compound | TYK2 JH1 % Inhibition @ 10 μM | JAK2 JH1 % Inhibition @ 10 μM |
|---|---|---|
| I-19 | A | A |
| I-20 | A | A |
| I-21 | A | A |
| I-22 | A | A |
| I-23 | A | A |
| I-24 | A | A |
| I-25 | A | A |
| I-26 | A | A |
| I-27 | A | A |
| I-28 | A | A |
| I-29 | A | A |
| I-30 | A | A |
| I-31 | A | A |
| I-32 | A | A |
| I-33 | A | A |
| I-34 | A | A |
| I-35 | A | A |
| I-36 | A | A |
| I-37 | A | A |
| I-38 | A | A |
| I-39 | A | A |
| I-40 | A | A |

Example 100. TYK2 & JAK2 Caliper Assay

The caliper machine employs an off chip mobility shift assay to detect phosphorylated peptide substrates from kinase assays, using microfluidics technology. The assays were carried out at ATP concentration equivalent to the ATP Km, and at 1 mM ATP. Compounds were serially diluted in DMSO then further diluted in assay buffer (25 mM HEPES, pH 7.5, 0.01% Brij-35, 0.01% Triton, 0.5 mM EGTA). 5 ul of diluted compound was added into wells first, then 10 ul of enzyme mix was added into wells, followed by 10 uL of substrate mix (peptide and ATP in 10 mM $MgCl_2$) to start reaction. Reaction was incubated at 28° C. for 25 min and then added 25 ul stop buffer (100 mM HEPES, 0.015% Brij-35, 50 mM EDTA), followed by reading with Caliper. JAK2 at 1 nM final concentration and TYK2 at 9.75 nM are from Carna, and substrates used are ATP at 20 and 16 uM, respectively. JAK2 assay uses peptide 22 and TYK2 uses peptide 30 (Caliper), each at 3 uM.

Example 101. IL-12 Induced pSTAT4 in Human PBMC

Human PBMC were isolated from buffy coat and were stored frozen for assays as needed. Cells for assay were thawed and resuspended in complete media containing serum, then cells were diluted to 1.67 E6 cells/mL so that 120 μl per well is 200,000 cells. 15 μl of compound or DMSO was added to the well at the desired concentrations and incubated at 1 hr at 37 C. 15 μl of stimulus (final concentration of 1.7 ng/mL IL-12) was added for 30 minutes prior to pSTAT4 and total STAT4 analysis using cell lysates prepared and analyzed by MSD reagents as per manufacturer protocol. The final DMSO concentration of compound in the assay was 0.1%.

The IL-12 Induced pSTAT4 assay evaluates the inhibition of IL-12 induced STAT4 phophorylation mediated by TYK2/JAK2 (heterodimeric complex).

Results of the IL-12 Induced pSTAT4 in human PBMC are presented in Table 4. Compounds denoted as "A" had an $IC_{50}$ lower than 0.1 μM; compounds denoted as "B" had an $IC_{50}$ between 0.1 and 0.5 μM; compounds denoted as "C" had an $IC_{50}$ between 0.5 and 1.0 μM; and compounds denoted as "D" had an $IC_{50}$ greater than 1.0 μM.

TABLE 4

IL-12 Induced pSTAT4 in human PBMC assay results.

| Compound | IL-12-pSTAT4 $IC_{50}$ (μM) |
|---|---|
| I-1 | C |
| I-2 | A |
| I-4 | A |
| I-12 | A |
| I-19 | A |
| I-23 | A |
| I-24 | A |
| I-42 | A |
| I-48 | A |
| I-52 | A |
| I-54 | B |

Example 102. GM-CSF Induced pSTAT5 in Human PBMC

Cells were prepared for analysis as in the above procedure and 15 μl of GM-CSF (final concentration 5 ng/mL) was added for 20 minutes prior to pSTAT5 and total STAT5 analysis using cell lysates prepared and analyzed by MSD reagents as per manufacturer protocol. The final DMSO concentration of compound in the assay was 0.1%.

The GM-CSF Induced pSTAT5 assay is a JAK2 cellular selectivity assay which evaluates inhibition of GM-CSF induced STAT5 phopsphorylation mediated by the JAK2/JAK2 homodimeric complex.

Results of the GM-CSF Induced pSTAT5 assay are presented in Table 5. Compounds denoted as "A" had an $IC_{50}$>50 μM; compounds denoted as "B" had an $IC_{50}$ result of >12.5, >20, >25, or >30 μM; compounds denoted as "C" had an $IC_{50}$ result of >2.5 or >10 μM; and compounds denoted as "D" had an $IC_{50}$ result of >0.3, >0.5, or >1.0 μM.

TABLE 5

GM-CSF Induced pSTAT5 assay results.

| Compound | PBMC_GMCSF_pSTAT5 $IC_{50}$ (μM) |
|---|---|
| I-1 | A |
| I-2 | A |
| I-4 | B |
| I-12 | D |
| I-19 | D |
| I-23 | A |

Example 103. Ex Vivo Mouse IL-12 Induced IFNγ Studies

C57/BL6 mice are given a single oral dose of either vehicle or different doses of compound at a volume of 10 mL/kg. 30 minutes to 1 hour after dosing, animals are euthanized and blood was collected via vena cava into sodium heparin blood collection tubes and inverted several times. Blood is then plated on anti-CD3 coated plates and stimulated with 2 ng/ml of mouse IL-12 in RPMI media for 24 hours at 37° C. in humidified incubator with 5% $CO_2$. At the end of the incubation, blood is centrifuged at 260 g for 5 minutes to collect supernatant. IFNγ concentration in the supernatant is determined with mouse IFNγ MSD kit per manufacture's instruction (Meso Scale Discovery). At the time of the blood collection, plasma is collected for drug level analysis by LC-MS/MS.

Example 104. T-ALL Cell Proliferation Assay

T-ALL cell lines KOPT-K1, HPB-ALL, DND-41, PEER, and CCRF-CEM are cultured in RPMI-1640 medium with 10% fetal bovine serum and penicillin/streptomycin. Cells are plated in triplicate at $1\times10^4$ cells per well in 96-well plates. T-ALL cell lines DU.528, LOUCY, and SUP-T13 are cultured in the same medium and plated at a density of $1.5\times10^4$ cells per well. The cells are treated with DMSO or different concentrations of each compound of the invention. Cell viability at 72 hour exposure to the drug is assessed by CellTiter-Glo Luminescent Cell Viability Assay (Promega). CellTiter-Glo Reagent is added into the well and incubated for 10 minutes. Luminescence is measured subsequently using a 96-well plate luminescence reader. Cell viability is calculated by using the DMSO treated samples as 100%. $IC_{50}$ value is calculated by nonlinear regression using GraphPad Prism software.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:
1. A compound of formula I':

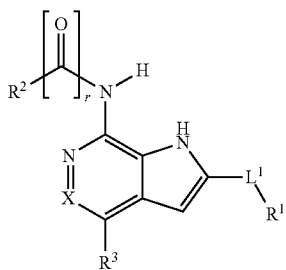

or a pharmaceutically acceptable salt thereof, wherein:
X is N or CH;
$L^1$ is a covalent bond or a $C_{1-4}$ bivalent saturated or unsaturated, straight or branched hydrocarbon chain wherein one or two methylene units of the chain are optionally and independently replaced by —C($R^4$)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—;
$R^4$ is independently $R^A$ or $R^B$;
each instance of $R^A$ is independently halogen, —CN, —NO$_2$, —OR, —SR, —NR$_2$, —S(O)$_2$R, —S(O)(NR)R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, or —P(O)R$_2$; or two instances of $R^A$ are optionally taken together to form an oxo;

each instance of $R^B$ is independently $C_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by q instances of $R^C$;
each instance of $R^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR or —P(O)R$_2$ or an optionally substituted group selected from $C_{1-6}$ aliphatic; phenyl; naphthalenyl; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; a 6-11 membered saturated or partially unsaturated bicyclic heterocyclic ring having 1-2 heteroatoms independently selected from nitrogen, oxygen, and sulfur; a 3-7 membered saturated or partially unsaturated monocyclic heterocyclic ring having 1-2 heteroatoms independently selected from nitrogen, oxygen, phosphorous, silicon and sulfur; and a 5-6 membered monocyclic heteroaryl ring having 1-4 heteroatoms independently selected from nitrogen, oxygen, and sulfur; or for each instance of $R^B$, optionally:
two $R^C$ groups on the same atom are taken together with the atom to form an optionally substituted 4-7 membered saturated, spirocyclic heterocyclic ring having 1-2 heteroatoms, independently selected from nitrogen, oxygen, and sulfur;
two $R^C$ groups are taken together with their intervening atoms to form an optionally substituted 4-7 membered saturated or partially unsaturated, fused ring having 0-2 heteroatoms, independently selected from nitrogen, oxygen, and sulfur; or
two $R^C$ groups are taken together with their intervening atoms to form an optionally substituted 5-6 membered fused aryl ring having 0-3 heteroatoms, independently selected from nitrogen, oxygen, and sulfur;
each R is independently hydrogen, or an optionally substituted group selected from $C_{1-6}$ aliphatic; phenyl; naphthalenyl; an 8-10 membered bicyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur; and a 5-6 membered monocyclic heteroaryl ring having 1-4 heteroatoms independently selected from nitrogen, oxygen, and sulfur; or:

two R groups on the same nitrogen are taken together with the nitrogen to form an optionally substituted 4-7 membered monocyclic saturated, partially unsaturated, or heteroaryl ring having, in addition to the nitrogen, 0-3 heteroatoms independently selected from nitrogen, oxygen, and sulfur;

$R^1$ is $Cy^1$;

$Cy^1$ is phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; a 3-7 membered saturated or partially unsaturated monocyclic carbocyclic ring; or a 7-12 membered saturated or partially unsaturated bicyclic heterocyclic ring having 1-4 heteroatoms independently selected from nitrogen, oxygen, and sulfur; wherein $Cy^1$ is substituted with p instances of $R^{14}$;

each instance of $R^{14}$, is independently $R^A$ or $R^B$;

$R^2$ is $C_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by q instances of $R^C$;

$R^3$ is —C(O)NH$_2$, —C(O)NHCH$_3$, or —C(O)NHCD$_3$;

each of p and q is independently 0, 1, 2, 3, or 4; and r is 0 or 1.

2. The compound of claim 1, wherein the compound is of formula II:

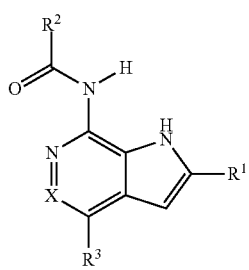

or a pharmaceutically acceptable salt thereof.

3. The compound of claim 1, wherein the compound is of formula III:

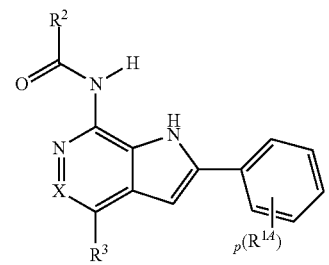

or a pharmaceutically acceptable salt thereof.

4. The compound of claim 1, wherein the compound is of formula IV:

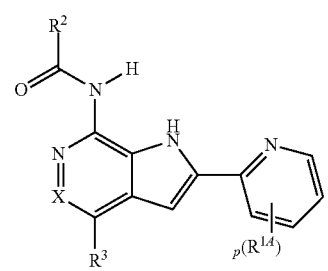

or a pharmaceutically acceptable salt thereof.

5. The compound of claim 1, wherein the compound is of formula VI:

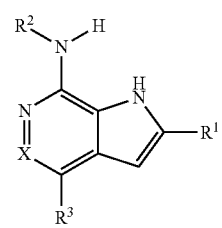

or a pharmaceutically acceptable salt thereof.

6. The compound of claim 1, wherein the compound is one of formulae VII, VIII, or IX

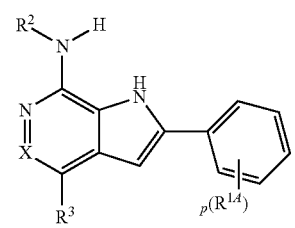

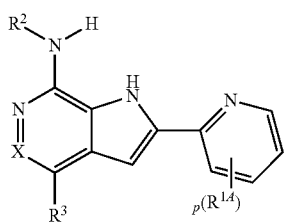

VIII

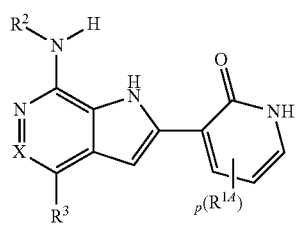

IX or a pharmaceutically acceptable salt thereof.

7. The compound of claim 1, wherein the compound is of formula X:

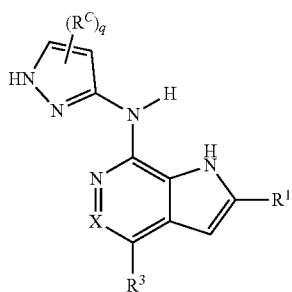

X or a pharmaceutically acceptable salt thereof.

8. The compound of claim 1, wherein the compound is one of formulae XI, XII, or XIII:

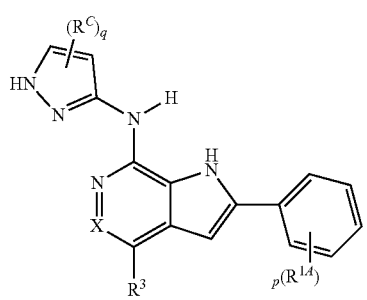

XI

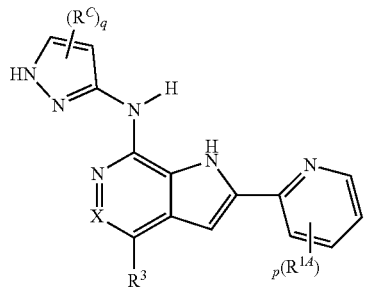

XII

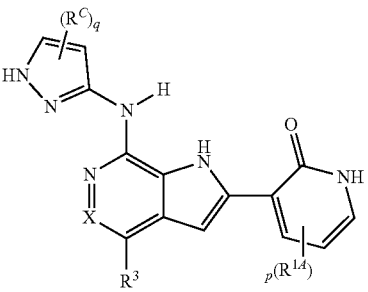

XIII or a pharmaceutically acceptable salt thereof.

9. The compound of claim 1, wherein $Cy^1$ is phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; or a 3-7 membered saturated or partially unsaturated monocyclic heterocyclic ring having 1-2 heteroatoms independently selected from nitrogen, oxygen, and sulfur; wherein $Cy^1$ is substituted with p instances of R.

10. The compound of claim 1, wherein $Cy^1$ is phenyl or a 6 membered monocyclic heteroaryl ring having 1-2 nitrogen atoms; wherein $Cy^1$ is substituted with p instances of R.

11. The compound of claim 10, wherein X is CH.

12. The compound of claim 11, wherein $R^2$ is a 3-7 membered saturated or partially unsaturated monocyclic carbocyclic ring or a 5-6 membered monocyclic heteroaryl ring having 1-4 heteroatoms independently selected from nitrogen, oxygen, and sulfur, substituted by q instances of $R^C$.

13. The compound of claim 1, wherein $R^2$ is cyclopropyl or pyrazolyl.

14. The compound of claim 13, wherein at least one instance of $R^{14}$ is $R^B$.

15. The compound of claim 14, wherein $R^B$ is a 5-6 membered monocyclic heteroaryl ring having 1-4 heteroatoms independently selected from nitrogen, oxygen, and sulfur; a 3-7 membered saturated or partially unsaturated monocyclic carbocyclic ring; or a 3-7 membered saturated or partially unsaturated monocyclic heterocyclic ring having 1-2 heteroatoms independently selected from nitrogen, oxygen, and sulfur; each of which is substituted with q instances of $R^C$.

16. The compound of claim 15, wherein p is 1, 2, or 3.

17. The compound of claim 16, wherein q is 0, 1, or 2.

18. The compound of claim 1, wherein the compound is selected from

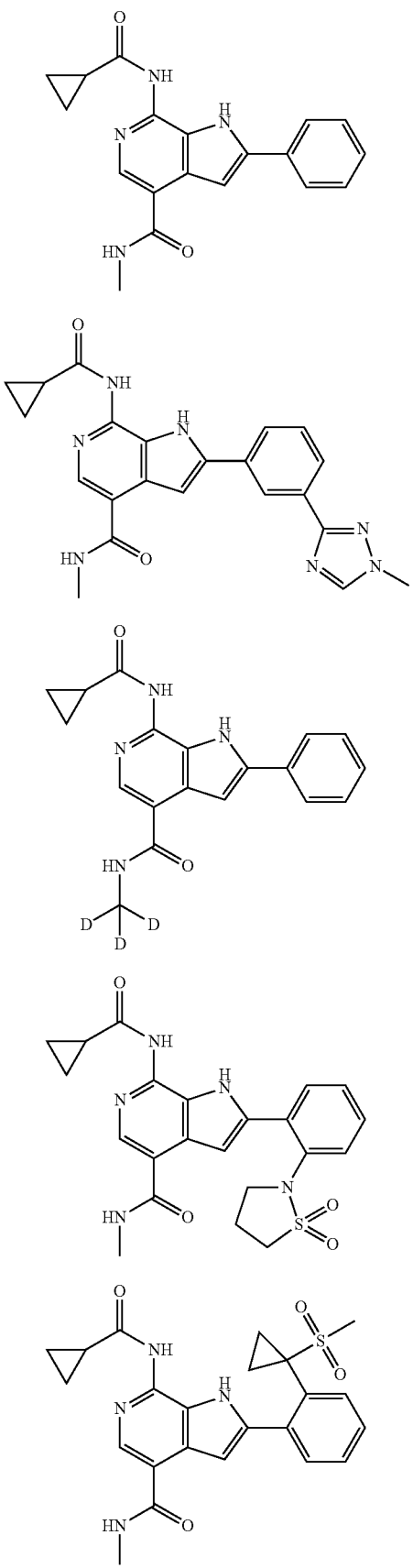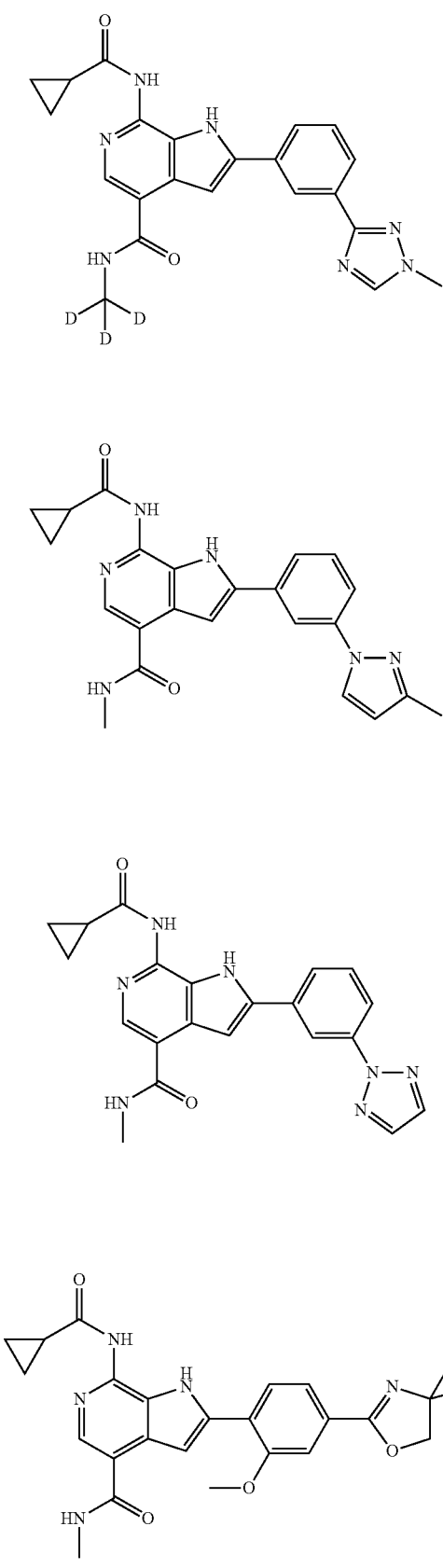

| 445 -continued | 446 -continued |
|---|---|
| I-10 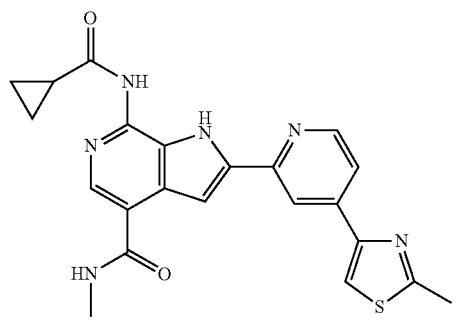 [SMILES: CNC(=O)c1cnc(NC(=O)C2CC2)c2[nH]c(-c3cc(-c4csc(C)n4)ccn3)cc12] | I-15 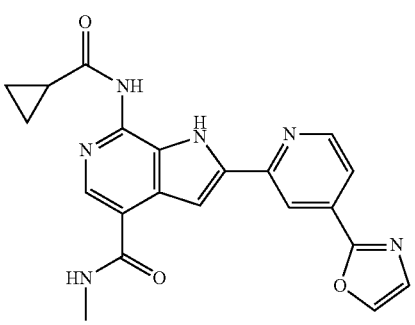 |
| I-11 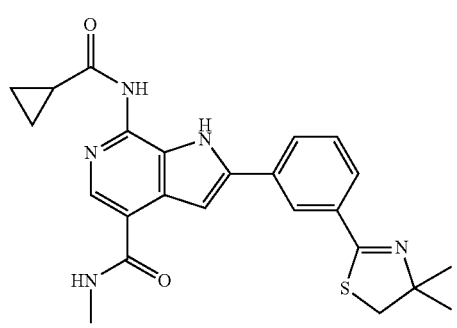 [SMILES: CNC(=O)c1cnc(NC(=O)C2CC2)c2[nH]c(-c3cccc(C4=NC(C)(C)CS4)c3)cc12] | I-16 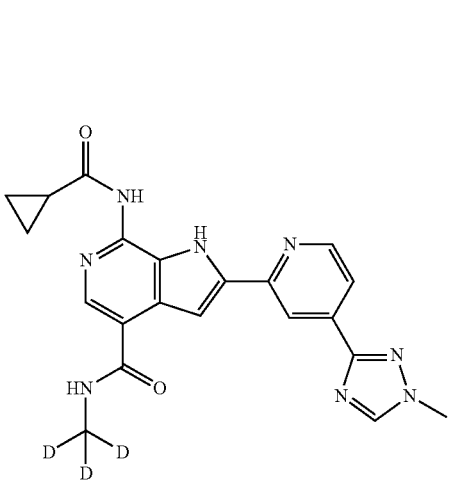 |
| I-12 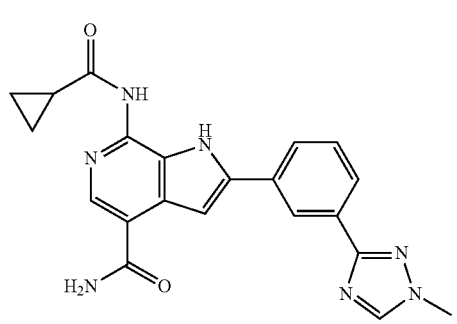 [SMILES: Cn1cnc(-c2cccc(-c3cc4c(C(N)=O)cnc(NC(=O)C5CC5)c4[nH]3)c2)n1] | |
| I-13 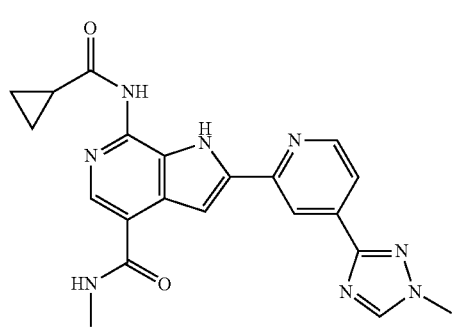 [SMILES: CNC(=O)c1cnc(NC(=O)C2CC2)c2[nH]c(-c3cc(-c4ncn(C)n4)ccn3)cc12] | I-17 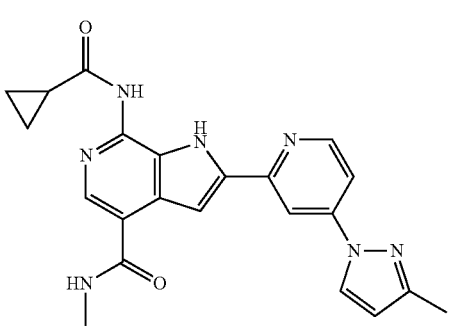 |
| I-14 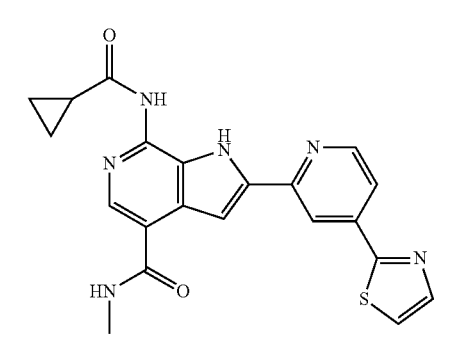 [SMILES: CNC(=O)c1cnc(NC(=O)C2CC2)c2[nH]c(-c3cc(-c4nccs4)ccn3)cc12] | I-18 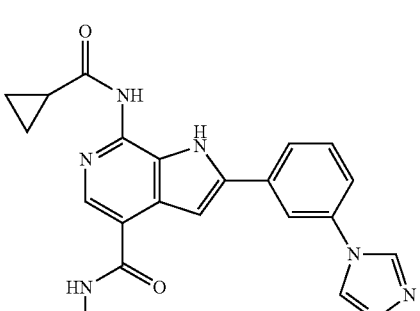 |

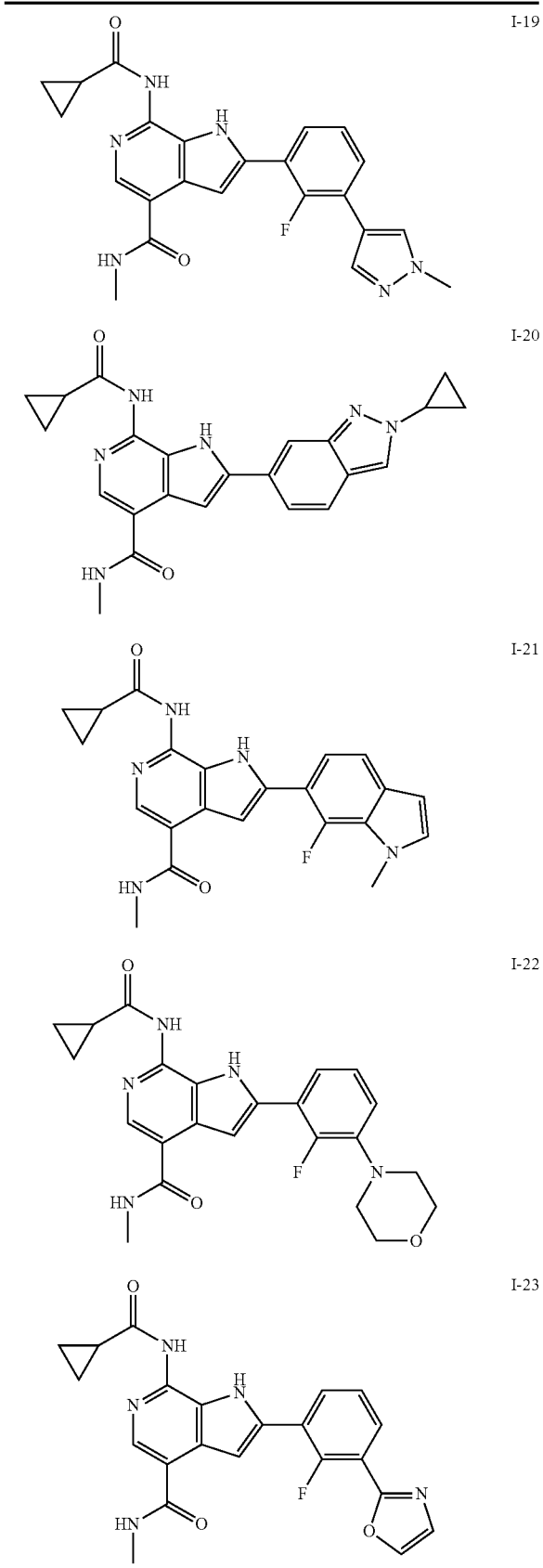
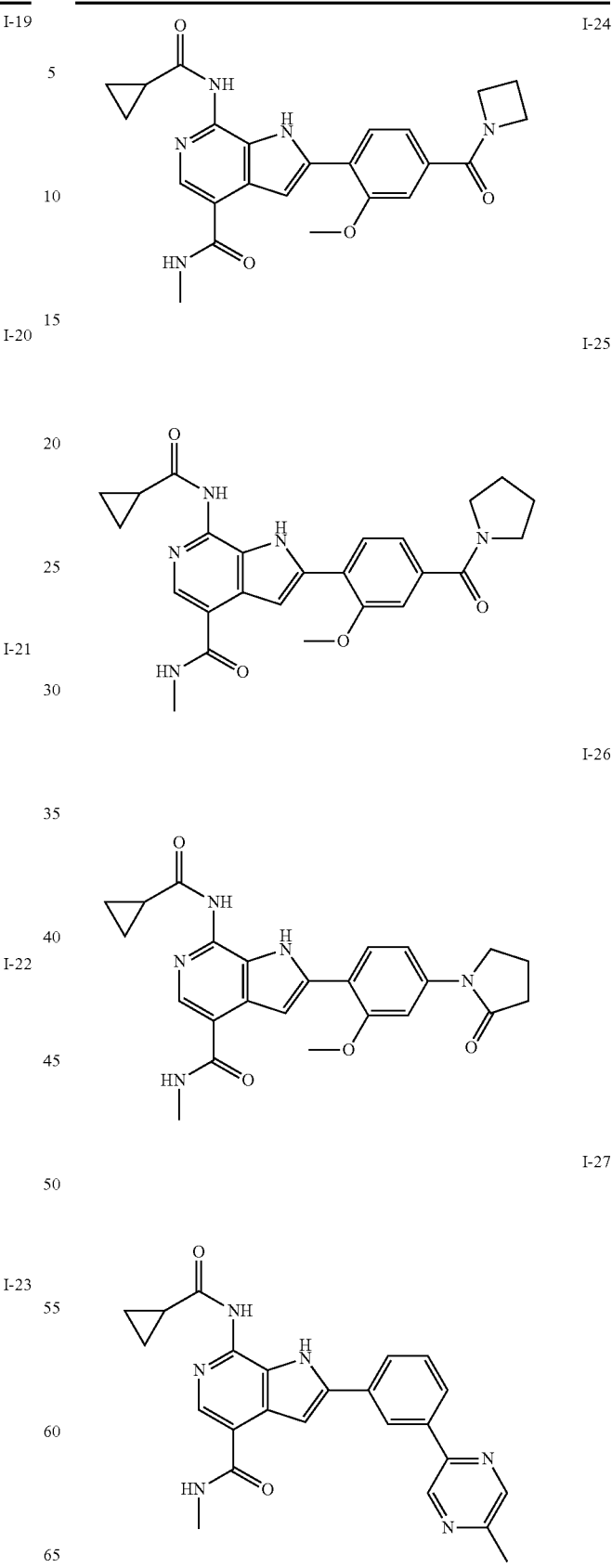

| 449 -continued | 450 -continued |
|---|---|
| I-28 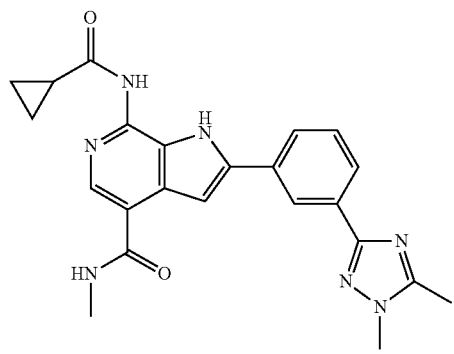 [SMILES: CNC(=O)c1cnc(NC(=O)C2CC2)c2[nH]c(-c3cccc(-c4nc(C)n(C)n4)c3)cc12] | I-33 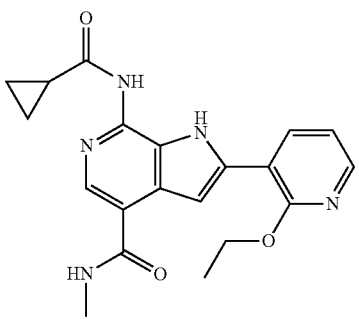 |
| I-29 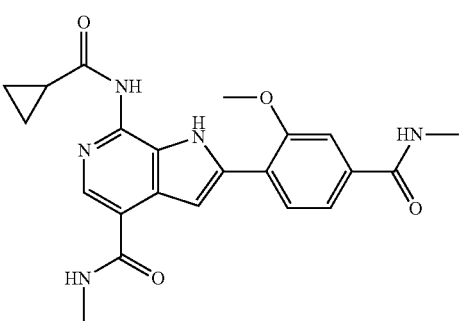 [SMILES: CNC(=O)c1ccc(-c2cc3c(C(=O)NC)cnc(NC(=O)C4CC4)c3[nH]2)c(OC)c1] | I-34 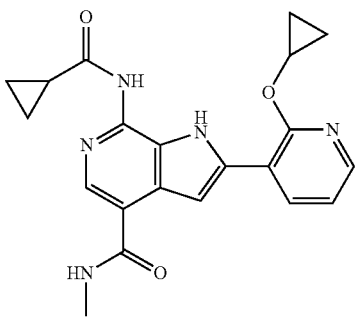 |
| I-30 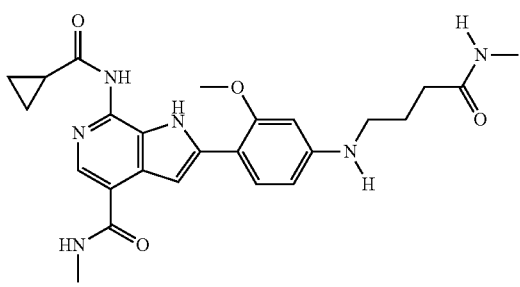 [SMILES: CNC(=O)CCCNc1ccc(-c2cc3c(C(=O)NC)cnc(NC(=O)C4CC4)c3[nH]2)c(OC)c1] | I-35 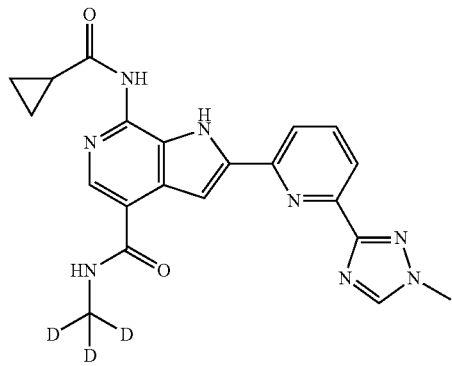 |
| I-31 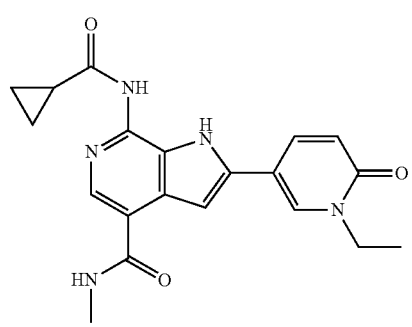 [SMILES: CCn1cc(-c2cc3c(C(=O)NC)cnc(NC(=O)C4CC4)c3[nH]2)ccc1=O] | I-36 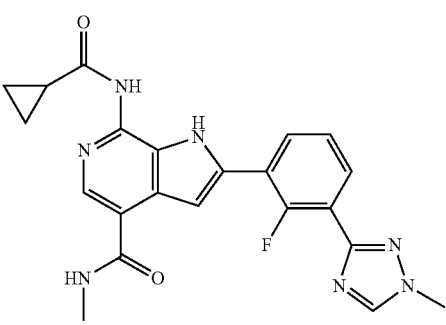 |
| I-32 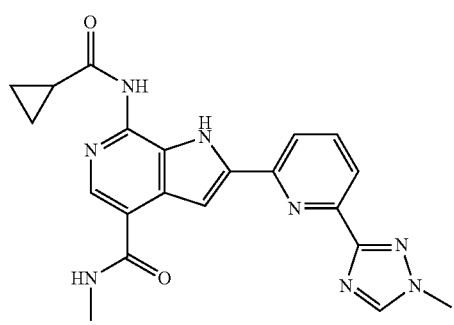 [SMILES: CNC(=O)c1cnc(NC(=O)C2CC2)c2[nH]c(-c3cccc(-c4ncn(C)n4)n3)cc12] | |

| 451 -continued | | 452 -continued | |
|---|---|---|---|
| 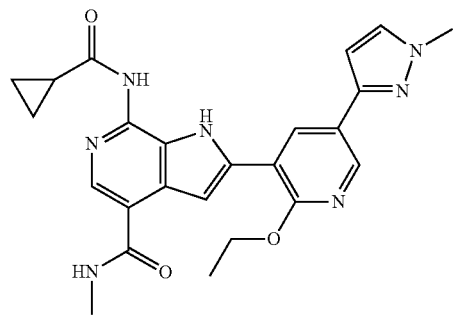 [SMILES: CCOc1ncc(-c2ccn(C)n2)cc1-c1cc2c(C(=O)NC)cnc(NC(=O)C3CC3)c2[nH]1] | I-37 | 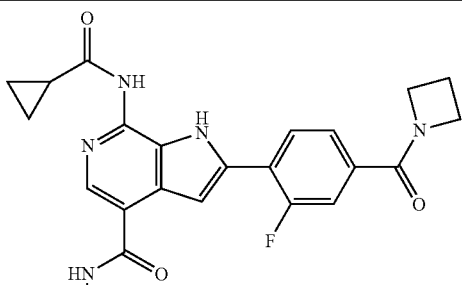 | I-42 |
| 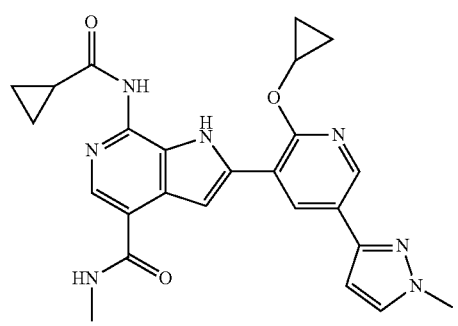 [SMILES: CNC(=O)c1cnc(NC(=O)C2CC2)c2[nH]c(-c3cc(-c4ccn(C)n4)cnc3OC3CC3)cc12] | I-38 | 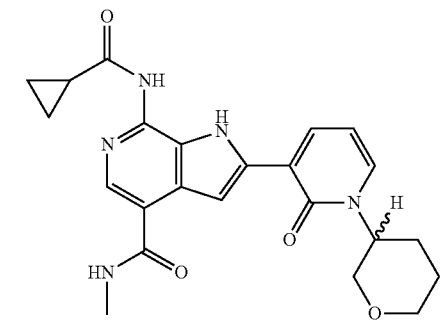 | I-43 |
| 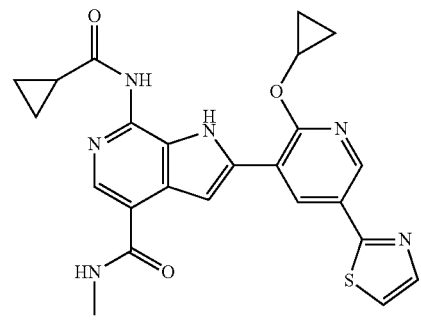 [SMILES: CNC(=O)c1cnc(NC(=O)C2CC2)c2[nH]c(-c3cc(-c4nccs4)cnc3OC3CC3)cc12] | I-39 | 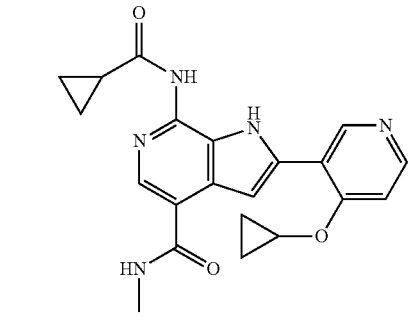 | I-44 |
| 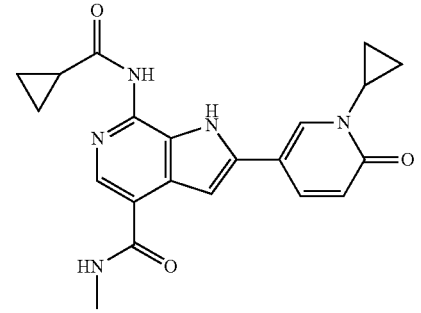 [SMILES: CNC(=O)c1cnc(NC(=O)C2CC2)c2[nH]c(-c3ccc(=O)n(C4CC4)c3)cc12] | I-40 | 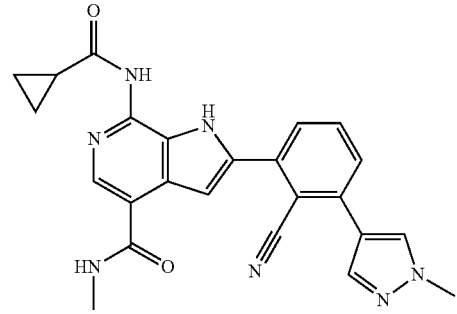 | I-45 |
| 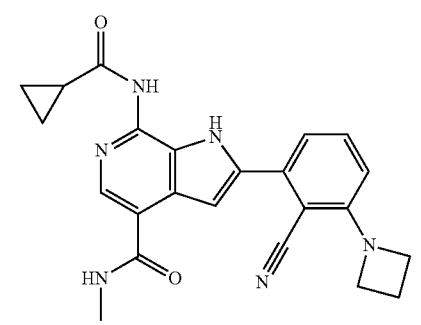 [SMILES: CNC(=O)c1cnc(NC(=O)C2CC2)c2[nH]c(-c3cccc(N4CCC4)c3C#N)cc12] | I-41 | 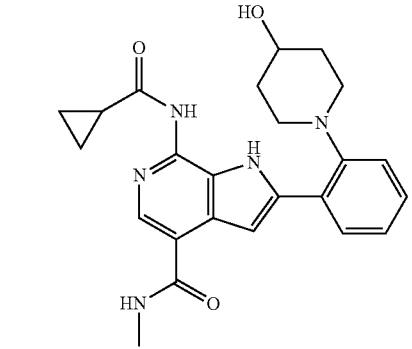 [SMILES: CNC(=O)c1cnc(NC(=O)C2CC2)c2[nH]c(-c3ccccc3N3CCC(O)CC3)cc12] | I-46 |

453
-continued
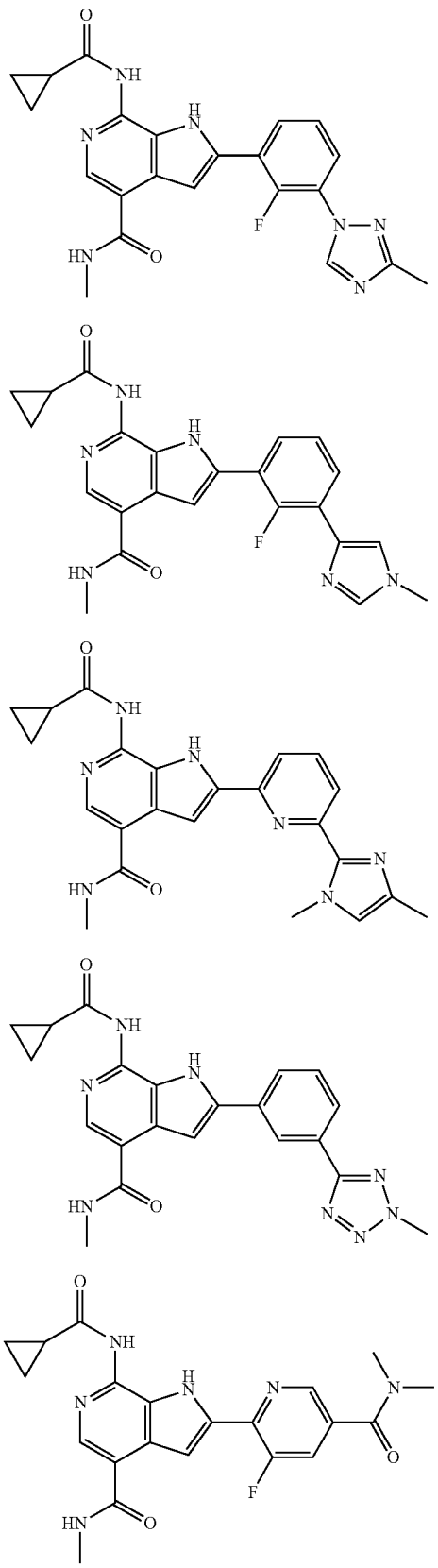
I-47
I-48
I-49
I-50
I-51
454
-continued
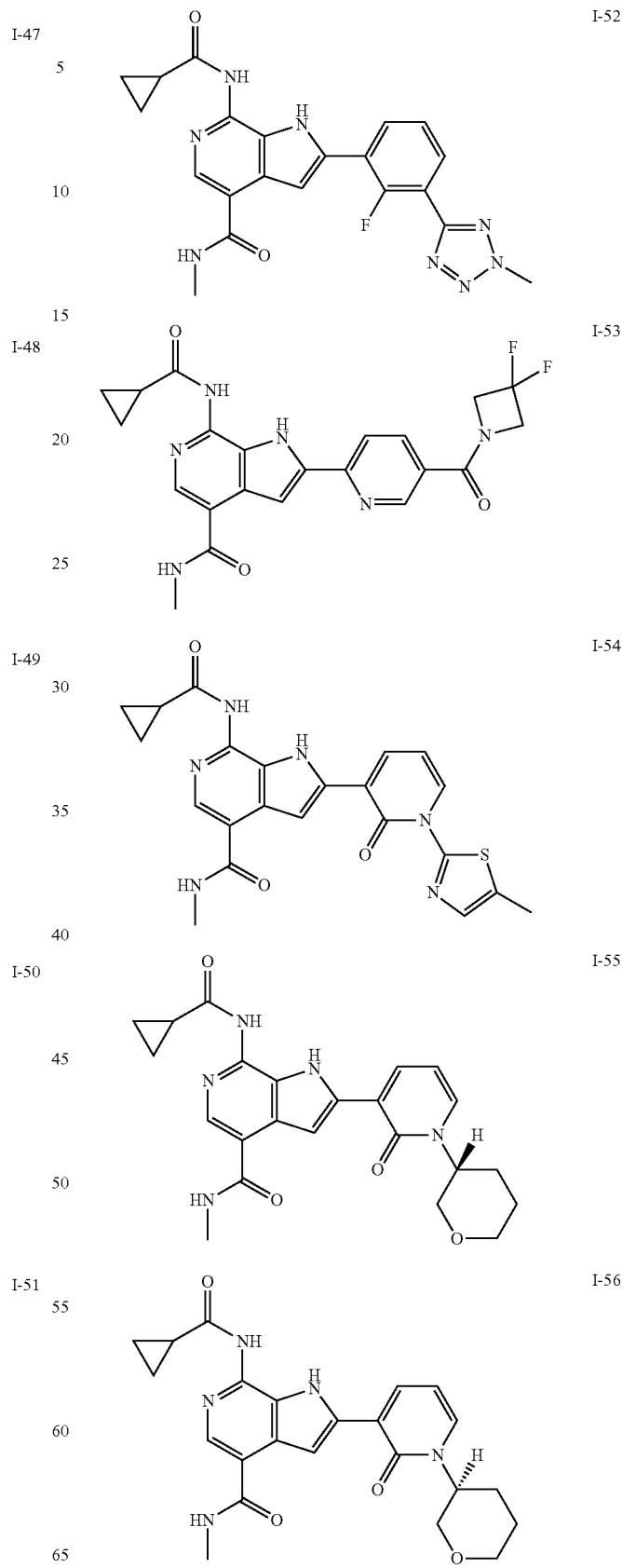
I-52
I-53
I-54
I-55
I-56

| 455 -continued | 456 -continued |
|---|---|
| 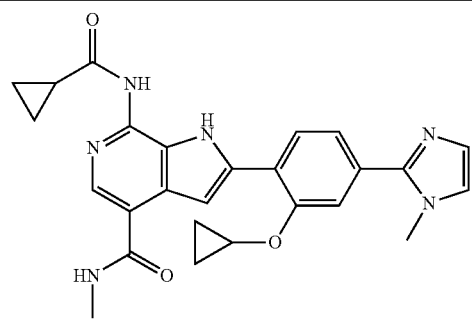 I-57 | 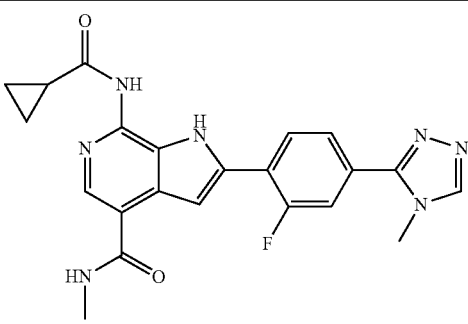 I-62 |
| 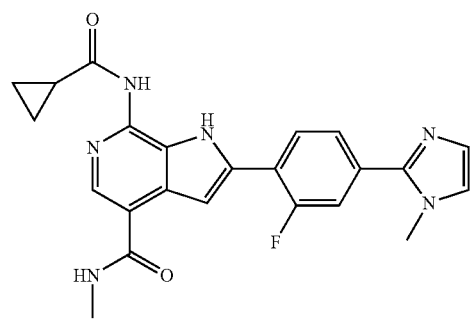 [SMILES: CNC(=O)c1cnc(NC(=O)C2CC2)c2[nH]c(-c3ccc(-c4nccn4C)cc3F)cc12] I-58 | 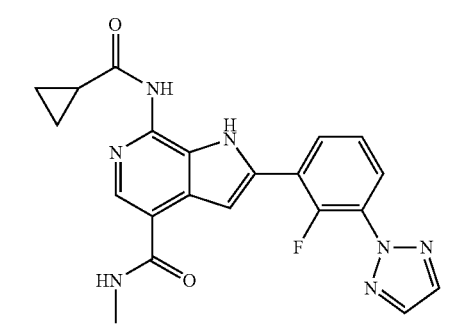 I-63 |
| 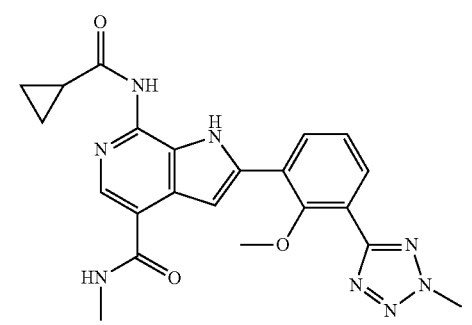 [SMILES: CNC(=O)c1cnc(NC(=O)C2CC2)c2[nH]c(-c3cccc(-c4nnn(C)n4)c3OC)cc12] I-59 | 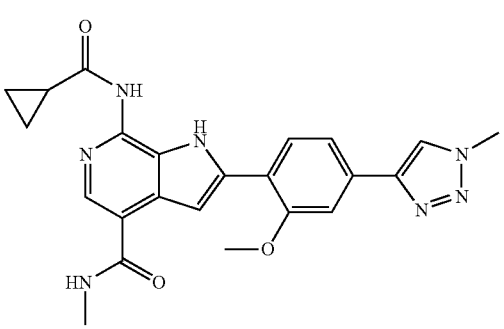 I-64 |
| 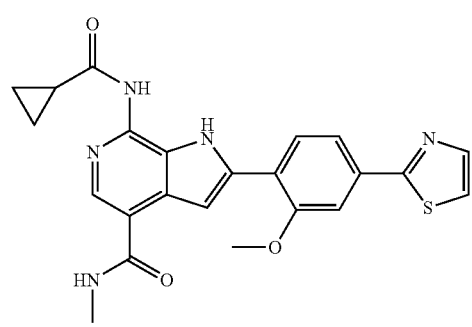 [SMILES: CNC(=O)c1cnc(NC(=O)C2CC2)c2[nH]c(-c3ccc(-c4nccs4)cc3OC)cc12] I-60 | 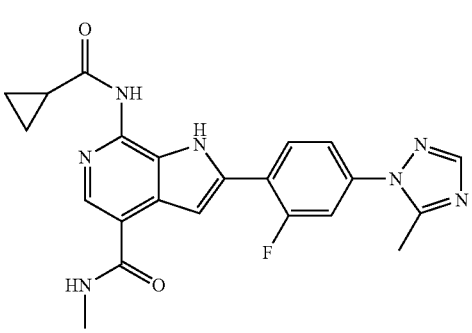 I-65 |
| 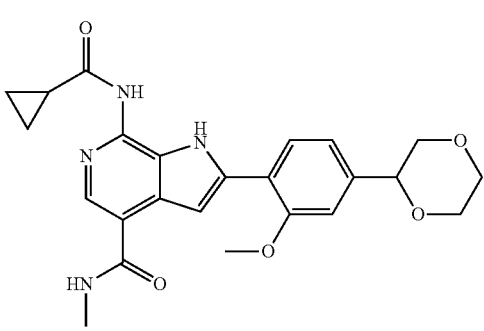 [SMILES: CNC(=O)c1cnc(NC(=O)C2CC2)c2[nH]c(-c3ccc(C4COCCO4)cc3OC)cc12] I-61 | 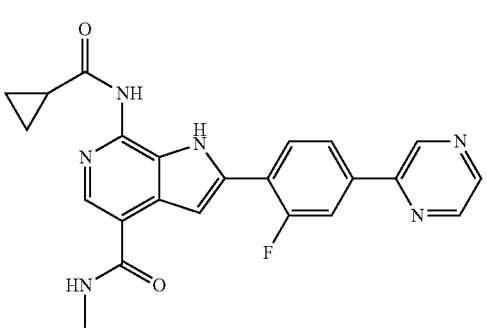 [SMILES: CNC(=O)c1cnc(NC(=O)C2CC2)c2[nH]c(-c3ccc(-c4cnccn4)cc3F)cc12] I-66 |

457
-continued
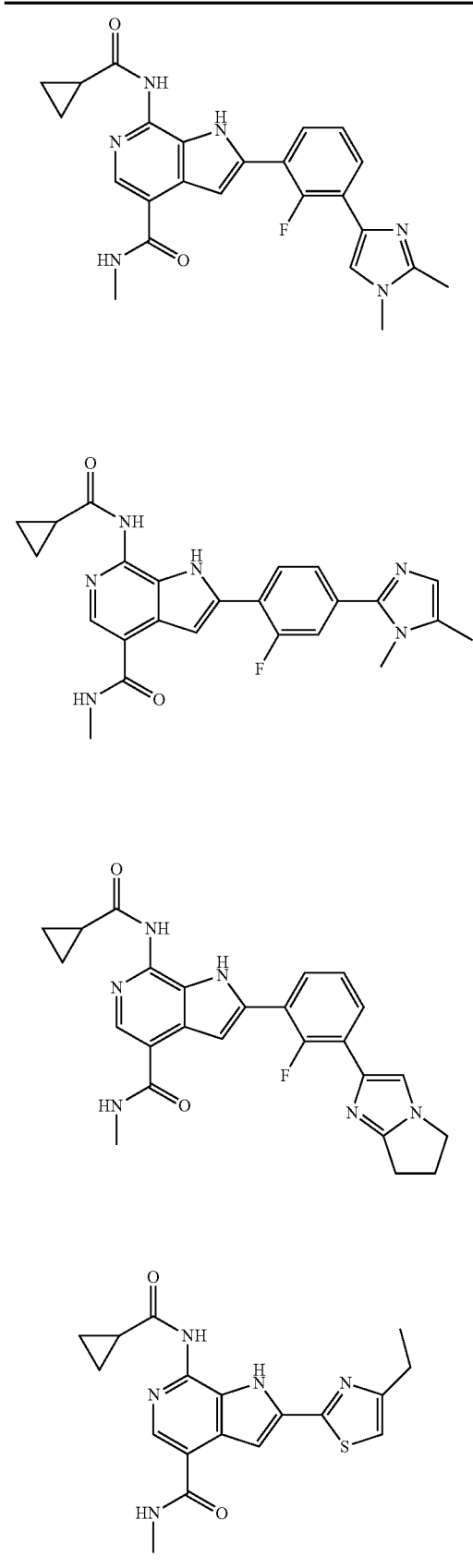
458
-continued
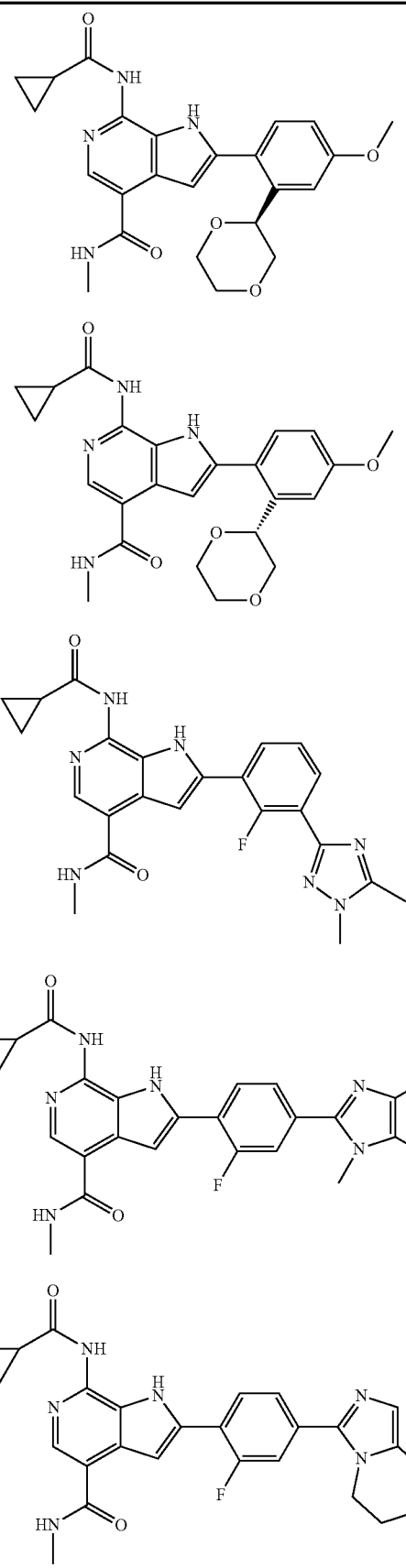

I-76
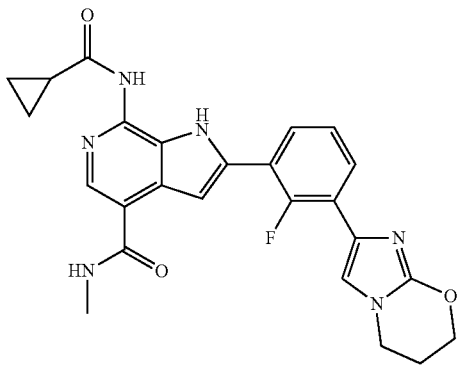 [SMILES: CNC(=O)c1cnc(NC(=O)C2CC2)c2[nH]c(-c3cccc(-c4cn5c(n4)OCCC5)c3F)cc12]
I-77
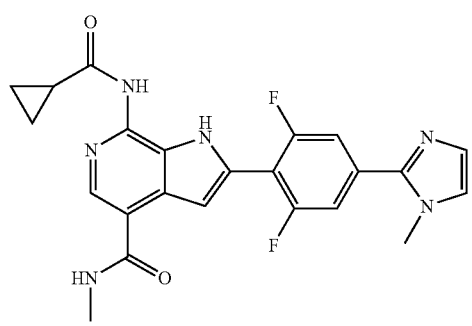 [SMILES: CNC(=O)c1cnc(NC(=O)C2CC2)c2[nH]c(-c3c(F)cc(-c4nccn4C)cc3F)cc12]
I-78
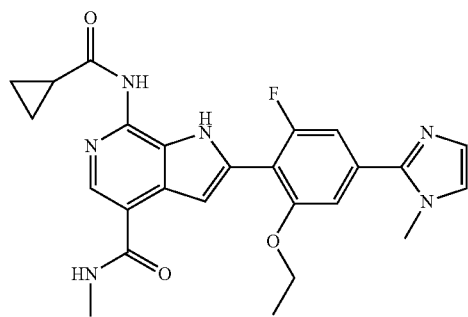 [SMILES: CCOc1cc(-c2nccn2C)cc(F)c1-c1cc2c(C(=O)NC)cnc(NC(=O)C3CC3)c2[nH]1]
I-79
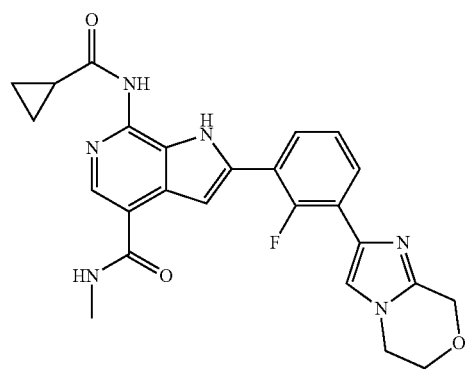 [SMILES: CNC(=O)c1cnc(NC(=O)C2CC2)c2[nH]c(-c3cccc(-c4cn5c(n4)COCC5)c3F)cc12]
I-80
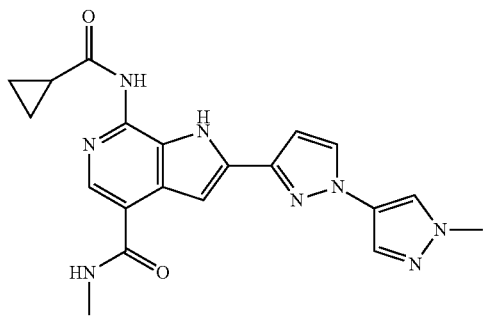 [SMILES: CNC(=O)c1cnc(NC(=O)C2CC2)c2[nH]c(-c3ccn(-c4cnn(C)c4)n3)cc12]
I-81
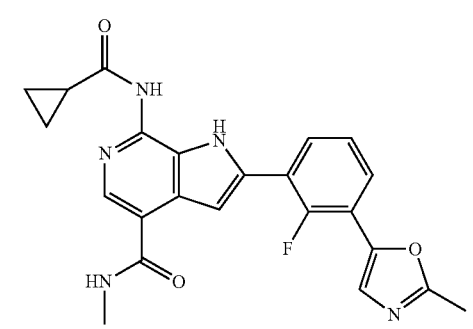 [SMILES: CNC(=O)c1cnc(NC(=O)C2CC2)c2[nH]c(-c3cccc(-c4cnc(C)o4)c3F)cc12]
I-82
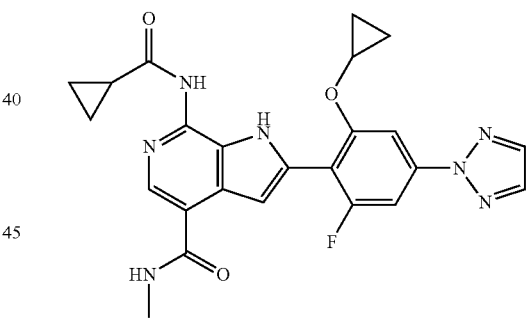
I-83
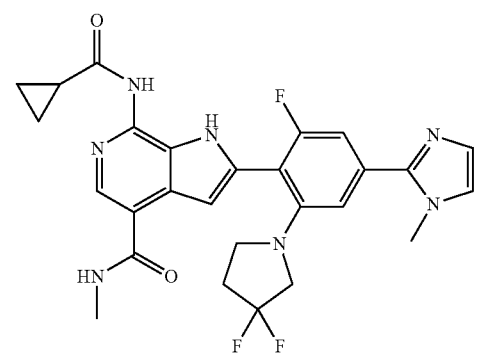 [SMILES: CNC(=O)c1cnc(NC(=O)C2CC2)c2[nH]c(-c3c(F)cc(-c4nccn4C)cc3N3CCC(F)(F)C3)cc12]

| 461 -continued | 462 -continued |
|---|---|
| 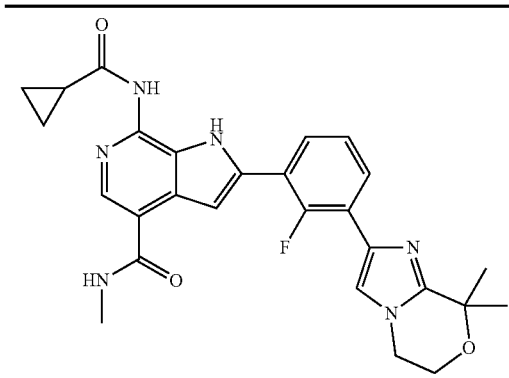 I-84 | 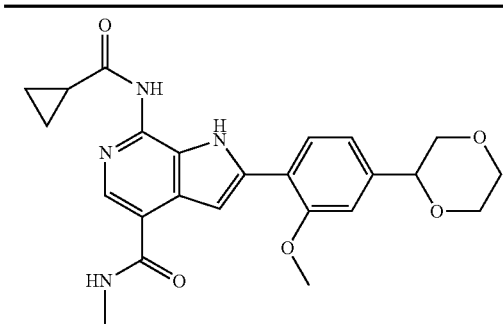 I-89 |
| 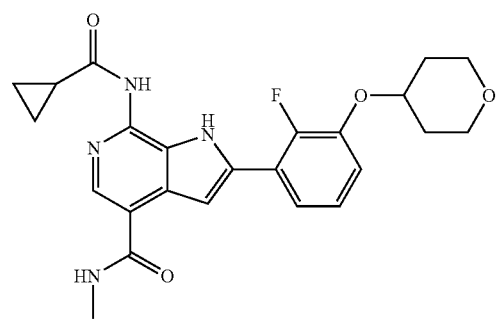 [SMILES: CNC(=O)c1cnc(NC(=O)C2CC2)c2[nH]c(-c3cccc(OC4CCOCC4)c3F)cc12] I-85 | 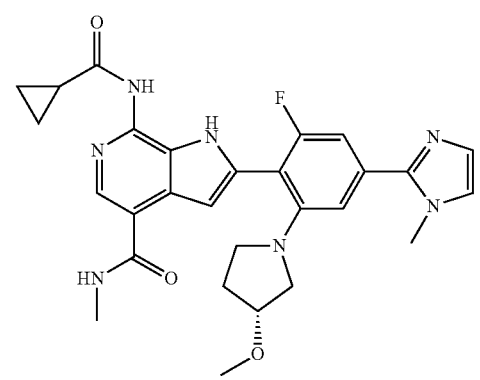 I-90 |
| 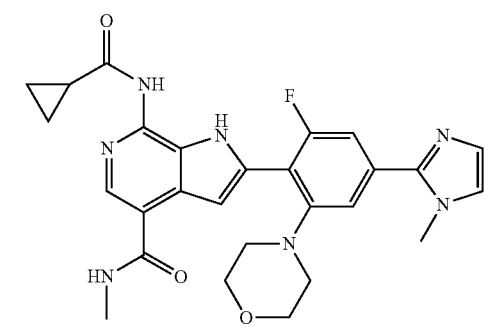 [SMILES: CNC(=O)c1cnc(NC(=O)C2CC2)c2[nH]c(-c3c(F)cc(-c4nccn4C)cc3N3CCOCC3)cc12] I-86 | 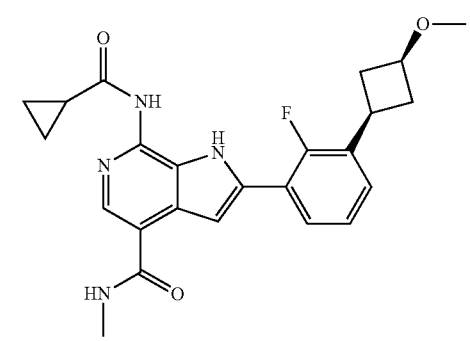 I-91 |
| 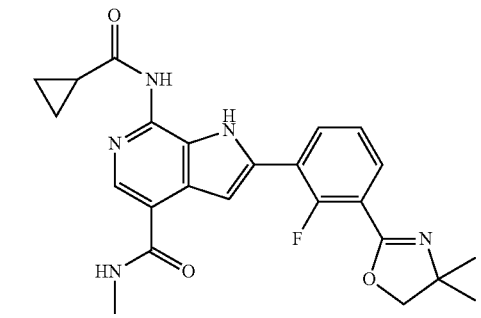 [SMILES: CNC(=O)c1cnc(NC(=O)C2CC2)c2[nH]c(-c3cccc(C4=NC(C)(C)CO4)c3F)cc12] I-87 | 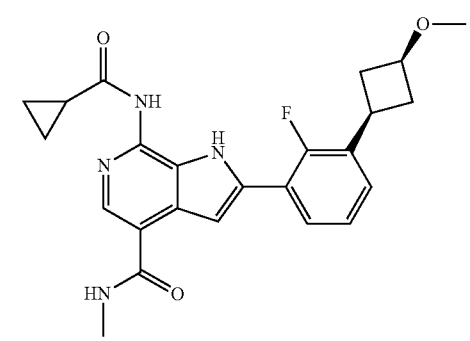 I-92 |
| 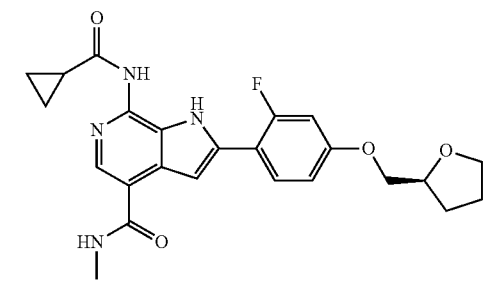 [SMILES: CNC(=O)c1cnc(NC(=O)C2CC2)c2[nH]c(-c3ccc(OC[C@@H]4CCCO4)cc3F)cc12] I-88 | 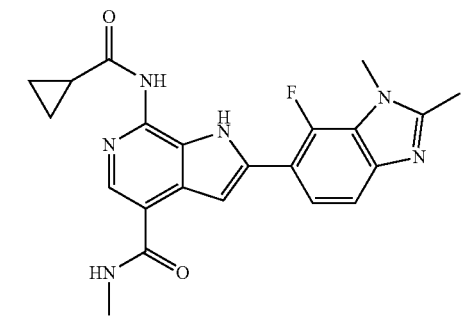 [SMILES: CNC(=O)c1cnc(NC(=O)C2CC2)c2[nH]c(-c3ccc4nc(C)n(C)c4c3F)cc12] |

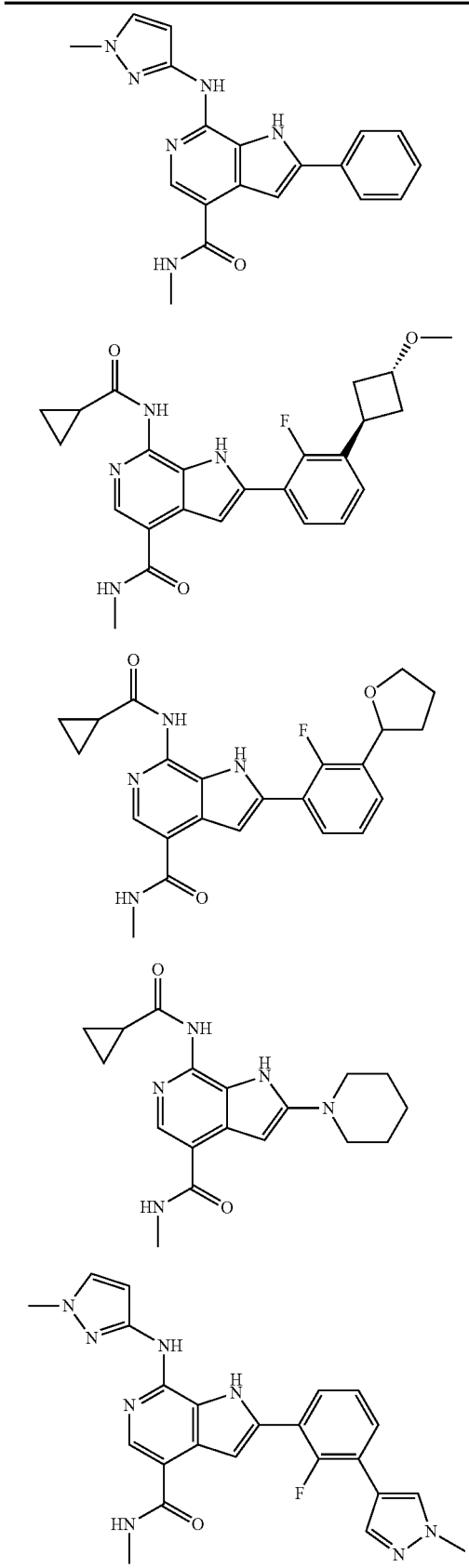

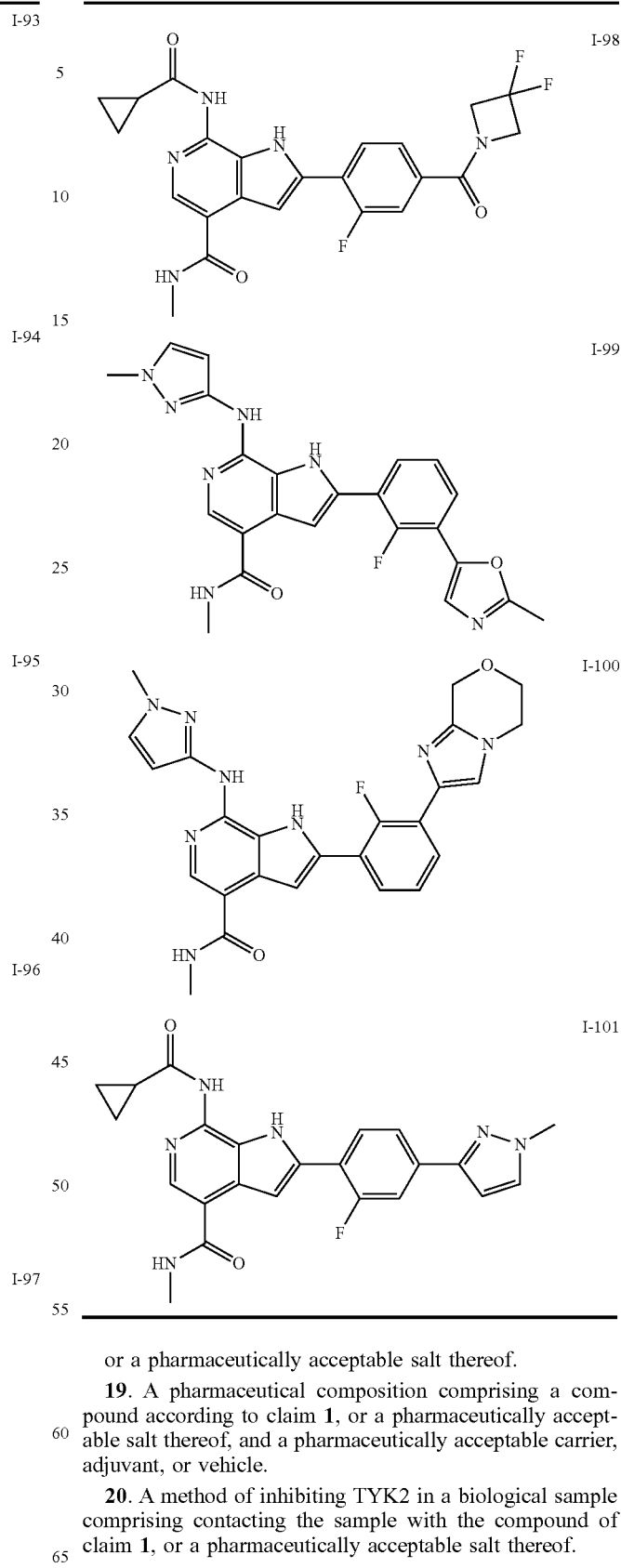

or a pharmaceutically acceptable salt thereof.

19. A pharmaceutical composition comprising a compound according to claim 1, or a pharmaceutically acceptable salt thereof, and a pharmaceutically acceptable carrier, adjuvant, or vehicle.

20. A method of inhibiting TYK2 in a biological sample comprising contacting the sample with the compound of claim 1, or a pharmaceutically acceptable salt thereof.

* * * * *